US011072787B2

(12) United States Patent
Wu et al.

(10) Patent No.: US 11,072,787 B2

(45) **Date of Patent: *Jul. 27, 2021**

(54) HISTIDYL-TRNA SYNTHETASE-FC CONJUGATES

(71) Applicant: aTyr Pharma Inc., San Diego, CA (US)

(72) Inventors: Chi-Fang Wu, San Diego, CA (US); Darin Lee, San Diego, CA (US); Jeffry D. Watkins, Encinitas, CA (US); Kristi Piehl, San Diego, CA (US); Kyle P. Chiang, Cardiff, CA (US); Marc Thomas, Vista, CA (US); Minh-Ha Do, San Diego, CA (US); Ying Buechler, Carlsbad, CA (US); John D. Mendlein, Encinitas, CA (US)

(73) Assignee: aTyr Pharma Inc., San Diego, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 16/842,200

(22) Filed: Apr. 7, 2020

(65) Prior Publication Data

US 2020/0283751 A1 Sep. 10, 2020

Related U.S. Application Data

(63) Continuation of application No. 16/577,992, filed on Sep. 20, 2019, now Pat. No. 10,711,260, which is a continuation of application No. 16/122,231, filed on Sep. 5, 2018, now Pat. No. 10,472,618, which is a continuation of application No. 15/415,369, filed on Jan. 25, 2017, now Pat. No. 10,093,915, which is a continuation of application No. 14/214,491, filed on Mar. 14, 2014, now Pat. No. 9,587,235.

(60) Provisional application No. 61/789,011, filed on Mar. 15, 2013.

(51) Int. Cl.

| | |
|---|---|
| ***C12N 9/00*** | (2006.01) |
| ***C12N 9/96*** | (2006.01) |
| ***A61P 37/00*** | (2006.01) |
| ***A61P 11/00*** | (2006.01) |
| ***A61P 29/00*** | (2006.01) |

(52) U.S. Cl.

CPC ................ *C12N 9/93* (2013.01); *A61P 11/00* (2018.01); *A61P 29/00* (2018.01); *A61P 37/00* (2018.01); *C12N 9/96* (2013.01); *C12Y 601/01021* (2013.01); *C07K 2319/30* (2013.01)

(58) Field of Classification Search

None

See application file for complete search history.

(56) References Cited

U.S. PATENT DOCUMENTS

| | | | |
|---|---|---|---|
| 5,155,214 | A | 10/1992 | Baird et al. |
| 5,370,995 | A | 12/1994 | Hennecke et al. |
| 5,484,703 | A | 1/1996 | Raben et al. |
| 5,556,645 | A | 9/1996 | Bockman et al. |
| 5,641,867 | A | 6/1997 | Stern et al. |
| 5,663,066 | A | 9/1997 | Raben et al. |
| 5,665,066 | A | 9/1997 | Fisher |
| 5,750,387 | A | 5/1998 | Hodgson et al. |
| 5,753,480 | A | 5/1998 | Lawlor |
| 5,756,327 | A | 5/1998 | Sassanfar et al. |
| 5,759,833 | A | 6/1998 | Shiba et al. |
| 5,776,749 | A | 7/1998 | Hodgson et al. |
| 5,795,757 | A | 8/1998 | Hodgson et al. |
| 5,798,240 | A | 8/1998 | Martinis et al. |
| 5,801,013 | A | 9/1998 | Tao et al. |
| 5,817,528 | A | 10/1998 | Bohm et al. |
| 5,866,390 | A | 2/1999 | Lawlor |
| 5,885,815 | A | 3/1999 | Sassanfar et al. |
| 5,928,920 | A | 7/1999 | Hodgson et al. |
| 5,939,298 | A | 8/1999 | Brown et al. |
| 5,977,079 | A | 11/1999 | Good et al. |
| 5,981,606 | A | 11/1999 | Martin |
| 6,013,483 | A | 1/2000 | Coleman et al. |
| 6,225,060 | B1 | 5/2001 | Clark et al. |
| 6,228,837 | B1 | 5/2001 | Stern et al. |
| 6,428,960 | B1 | 8/2002 | Clark et al. |
| 6,548,060 | B1 | 4/2003 | Kim |
| 6,696,619 | B1 | 2/2004 | Famodu et al. |
| 6,712,978 | B2 | 3/2004 | Leinenbach et al. |
| 6,723,318 | B1 | 4/2004 | Sandberg et al. |

(Continued)

FOREIGN PATENT DOCUMENTS

| | | |
|---|---|---|
| CA | 2531146 | 3/2005 |
| CN | 1314486 A | 9/2001 |

(Continued)

OTHER PUBLICATIONS

International Preliminary Report on Patentability for International Application No. PCT/US2009/048915, dated Jan. 5, 2011.

(Continued)

*Primary Examiner* — Kagnew H Gebreyesus

(74) *Attorney, Agent, or Firm* — Cooley LLP

(57) ABSTRACT

The present invention provides histidyl-tRNA synthetase and Fc region conjugate polypeptides (HRS-Fc conjugates), such as HRS-Fc fusion polypeptides, compositions comprising the same, and methods of using such conjugates and compositions for treating or diagnosing a variety of conditions. The HRS-Fc conjugates of the invention have improved controlled release properties, stability, half-life, and other pharmacokinetic and biological properties relative to corresponding, unmodified HRS polypeptides.

12 Claims, 34 Drawing Sheets

Specification includes a Sequence Listing.

(56) References Cited

U.S. PATENT DOCUMENTS 6,743,619 B1 6/2004 Tang et al.
6,800,286 B1 10/2004 Olwin et al.
6,812,339 B1 11/2004 Venter et al.
6,864,226 B1 3/2005 Coleman et al.
6,875,749 B2 4/2005 Schwarz et al.
6,903,189 B2 6/2005 Schimmel et al.
6,916,648 B2 7/2005 Goddard et al.
7,037,505 B2 5/2006 Kim et al.
7,045,301 B2 5/2006 Coleman et al.
7,067,126 B2 6/2006 Schimmel et al.
7,144,984 B2 12/2006 Schimmel et al.
7,196,068 B2 3/2007 Kim et al.
7,273,844 B2 9/2007 Schimmel et al.
7,282,208 B2 10/2007 Kim
7,413,885 B2 8/2008 Schimmel et al.
7,459,529 B2 12/2008 Kim
7,476,651 B2 1/2009 Schimmel et al.
7,482,326 B2 1/2009 Coleman et al.
7,521,215 B2 4/2009 Schimmel et al.
7,528,106 B2 5/2009 Friedlander et al.
7,572,452 B2 8/2009 Kim
7,842,467 B1 11/2010 Heidbrink et al.
7,901,917 B2 3/2011 Schimmel et al.
7,902,165 B2 3/2011 Kim
7,981,426 B2 7/2011 Kim
8,003,780 B2 8/2011 Kim et al.
8,014,957 B2 9/2011 Radich et al.
8,017,593 B2 9/2011 Schimmel et al.
8,026,088 B2 9/2011 Yang
8,101,566 B2 1/2012 Schimmel et al.
8,148,125 B2 4/2012 Schimmel et al.
8,182,686 B2 5/2012 Witthaus et al.
8,318,163 B2 11/2012 Appleton et al.
8,404,242 B2 3/2013 Zhou et al.
8,404,471 B2 3/2013 Greene et al.
8,466,264 B2 6/2013 Appleton et al.
8,481,296 B2 7/2013 Yang
8,648,173 B2 2/2014 Wu et al.
8,722,043 B2 5/2014 Borg et al.
8,753,638 B2 6/2014 Zhou et al.
8,828,395 B2 9/2014 Watkins et al.
8,835,387 B2 9/2014 Chiang et al.
8,920,805 B2 12/2014 Wu et al.
9,127,268 B2 9/2015 Watkins et al.
9,273,302 B2 3/2016 Chiang et al.
9,296,803 B2 3/2016 Kozbar
9,328,340 B2 5/2016 Watkins et al.
9,422,539 B2 8/2016 Greene et al.
9,453,214 B2 9/2016 Greene
9,540,628 B2 1/2017 Watkins et al.
9,587,235 B2 3/2017 Buechler et al.
9,605,265 B2 3/2017 Zhou et al.
9,637,730 B2 5/2017 Greene et al.
9,943,577 B2 4/2018 Watkins et al.
10,017,582 B2 7/2018 Zhou et al.
10,093,915 B2 10/2018 Wu et al.
10,196,628 B2 2/2019 Greene et al.
10,472,618 B2 11/2019 Wu et al.
10,526,419 B2 1/2020 Zhou et al.
10,669,533 B2 6/2020 Greene et al.
10,711,260 B2 7/2020 Wu et al.
2002/0128187 A1 9/2002 Tang et al.
2002/0160957 A1 10/2002 Stern et al.
2002/0182666 A1 12/2002 Schimmel et al.
2003/0004309 A1 1/2003 Kim et al.
2003/0017564 A1 1/2003 Schimmel et al.
2003/0018985 A1 1/2003 Falco et al.
2003/0158400 A1 8/2003 Tang et al.
2003/0165921 A1 9/2003 Tang et al.
2003/0215827 A1 11/2003 Yue et al.
2004/0009163 A1 1/2004 Schimmel et al.
2004/0018505 A1 1/2004 Lee et al.
2004/0048290 A1 3/2004 Lee et al.
2004/0101879 A1 5/2004 Seidel-Dugan et al.
2004/0152079 A1 8/2004 Schimmel et al.
2004/0203094 A1 10/2004 Martinis et al.
2004/0214216 A1 10/2004 Famodu et al.
2004/0224981 A1 11/2004 Janjic et al.
2005/0119175 A1 6/2005 Kim
2005/0136513 A1 6/2005 Zhang
2005/0181375 A1 8/2005 Aziz et al.
2005/0196754 A1 9/2005 Drmanac et al.
2005/0208536 A1 9/2005 Schultz et al.
2006/0024288 A1 2/2006 Glidden
2006/0035232 A1 2/2006 McGregor et al.
2006/0046250 A1 3/2006 Kim
2006/0078553 A1 4/2006 Glidden
2006/0134663 A1 6/2006 Harkin et al.
2006/0160175 A1 7/2006 Anderson et al.
2006/0204508 A1 9/2006 Champion et al.
2006/0228715 A1 10/2006 Shiffman et al.
2006/0248617 A1 11/2006 Imanaka et al.
2006/0275794 A1 12/2006 Carrino et al.
2007/0037165 A1 2/2007 Venter et al.
2007/0042392 A1 2/2007 Tang et al.
2007/0048322 A1 3/2007 Schimmel et al.
2007/0054278 A1 3/2007 Cargill
2007/0061916 A1 3/2007 Kovalic et al.
2007/0072175 A1 3/2007 Cooper et al.
2007/0083334 A1 4/2007 Mintz et al.
2007/0093440 A1 4/2007 Champion et al.
2007/0111238 A1 5/2007 Jamieson et al.
2007/0154931 A1 7/2007 Radich et al.
2008/0044854 A1 2/2008 Wang et al.
2008/0113914 A1 5/2008 Hays et al.
2008/0153745 A1 6/2008 Tian
2009/0123971 A1 5/2009 Paulsel et al.
2009/0202539 A1 8/2009 You et al.
2009/0221437 A1 9/2009 Harkin et al.
2009/0221794 A1 9/2009 Kim et al.
2009/0226966 A1 9/2009 Yokoyama et al.
2009/0227002 A1 9/2009 Schultz et al.
2009/0227662 A1 9/2009 Schimmel et al.
2009/0264453 A1 10/2009 Shiffman et al.
2009/0285792 A1 11/2009 Friedlander et al.
2009/0305973 A1 12/2009 Kim et al.
2010/0003230 A1 1/2010 Glidden
2010/0028352 A1 2/2010 Greene et al.
2010/0041608 A1 2/2010 Kim
2010/0048413 A1 2/2010 Arcus et al.
2010/0092434 A1 4/2010 Belani et al.
2010/0093082 A1 4/2010 Tian et al.
2010/0130904 A1 5/2010 Kirber
2010/0138941 A1 6/2010 Kim et al.
2010/0167997 A1 7/2010 Kim
2010/0172921 A1 7/2010 Wu et al.
2010/0209445 A1 8/2010 Jahns et al.
2010/0297149 A1 11/2010 Zhou et al.
2010/0310576 A1 12/2010 Adams et al.
2011/0086058 A1 4/2011 Jiang et al.
2011/0091377 A1 4/2011 Alani et al.
2011/0104139 A1 5/2011 Faber
2011/0110917 A1 5/2011 Schimmel et al.
2011/0117572 A1 5/2011 Kim et al.
2011/0124582 A1 5/2011 Kim et al.
2011/0136119 A1 6/2011 Kim et al.
2011/0150885 A1 6/2011 Watkins et al.
2011/0183924 A1 7/2011 Beck et al.
2011/0189195 A1 8/2011 Kim et al.
2011/0250701 A1 10/2011 Kim et al.
2011/0256119 A1 10/2011 Kim et al.
2012/0004185 A1 1/2012 Greene
2012/0015383 A1 1/2012 Park et al.
2012/0058133 A1 3/2012 Whitman et al.
2012/0064082 A1 3/2012 Watkins et al.
2013/0052177 A1 2/2013 Schimmel et al.
2013/0108630 A1 5/2013 Watkins et al.
2013/0129703 A1 5/2013 Chiang et al.
2013/0129704 A1 5/2013 Greene et al.
2013/0129705 A1 5/2013 Greene et al.
2013/0142774 A1 6/2013 Greene et al.
2013/0195832 A1 8/2013 Greene et al.
2013/0202574 A1 8/2013 Greene et al.
2013/0202575 A1 8/2013 Greene et al.

(56) References Cited

U.S. PATENT DOCUMENTS

| | | | |
|---|---|---|---|
| 2013/0202576 | A1 | 8/2013 | Greene et al. |
| 2013/0209434 | A1 | 8/2013 | Greene et al. |
| 2013/0209472 | A1 | 8/2013 | Greene et al. |
| 2013/0224173 | A1 | 8/2013 | Greene et al. |
| 2013/0224174 | A1 | 8/2013 | Greene et al. |
| 2013/0230505 | A1 | 9/2013 | Greene et al. |
| 2013/0230507 | A1 | 9/2013 | Greene et al. |
| 2013/0230508 | A1 | 9/2013 | Greene et al. |
| 2013/0236440 | A1 | 9/2013 | Greene et al. |
| 2013/0236455 | A1 | 9/2013 | Greene et al. |
| 2013/0243745 | A1 | 9/2013 | Greene et al. |
| 2013/0243766 | A1 | 9/2013 | Zhou et al. |
| 2013/0273045 | A1 | 10/2013 | Watkins et al. |
| 2013/0280230 | A1 | 10/2013 | Greene et al. |
| 2013/0287755 | A1 | 10/2013 | Greene et al. |
| 2013/0315887 | A1 | 11/2013 | Greene et al. |
| 2013/0330312 | A1 | 12/2013 | Greene et al. |
| 2013/0344096 | A1 | 12/2013 | Chiang et al. |
| 2014/0066321 | A1 | 3/2014 | Xu et al. |
| 2014/0141994 | A1 | 5/2014 | Wu et al. |
| 2014/0349369 | A1 | 11/2014 | Buechler et al. |
| 2014/0371294 | A1 | 12/2014 | Zhou et al. |
| 2015/0064188 | A1 | 3/2015 | Greene |
| 2015/0093799 | A1 | 4/2015 | Chiang et al. |
| 2015/0140072 | A1 | 5/2015 | Watkins et al. |
| 2015/0344866 | A1 | 12/2015 | Greene et al. |
| 2016/0175458 | A1 | 6/2016 | Alvarez et al. |
| 2016/0369259 | A1 | 12/2016 | Chiang et al. |
| 2017/0100456 | A1 | 4/2017 | Briscoe et al. |
| 2017/0114148 | A1 | 4/2017 | Zhou et al. |
| 2017/0202933 | A1 | 7/2017 | Watkins et al. |
| 2017/0267990 | A1 | 9/2017 | Wu et al. |
| 2017/0321206 | A1 | 11/2017 | Greene et al. |
| 2018/0282402 | A1 | 10/2018 | Adams et al. |
| 2019/0031775 | A1 | 1/2019 | Zhou et al. |
| 2019/0062720 | A1 | 2/2019 | Wu et al. |
| 2019/0264190 | A1 | 8/2019 | Greene et al. |
| 2019/0309076 | A1 | 10/2019 | Burman et al. |
| 2020/0085925 | A1 | 3/2020 | Burkart et al. |
| 2020/0149028 | A1 | 5/2020 | Wu et al. |
| 2020/0216564 | A1 | 7/2020 | Zhou et al. |
| 2020/0231704 | A1 | 7/2020 | Zhou et al. |

FOREIGN PATENT DOCUMENTS

| | | | |
|---|---|---|---|
| CN | 1331293 | | 1/2002 |
| CN | 1341725 | | 3/2002 |
| CN | 1341727 | | 3/2002 |
| CN | 1352242 | | 6/2002 |
| CN | 1352252 | | 6/2002 |
| CN | 1519315 | A | 8/2004 |
| CN | 101528914 | | 9/2009 |
| EP | 0313378 | | 10/1988 |
| EP | 0307247 | | 3/1989 |
| EP | 0893494 | | 1/1999 |
| EP | 0893496 | | 1/1999 |
| EP | 0897004 | | 2/1999 |
| EP | 0575484 | | 9/2000 |
| EP | 1275720 | | 1/2003 |
| EP | 1300468 | | 4/2003 |
| EP | 1384486 | | 1/2004 |
| EP | 1748063 | | 1/2007 |
| EP | 1377305 | | 1/2009 |
| EP | 1776138 | | 10/2009 |
| EP | 2177610 | | 4/2010 |
| EP | 1274834 | | 7/2010 |
| EP | 2084190 | | 3/2011 |
| JP | 2003-514510 | A | 4/2003 |
| JP | 2012-520681 | | 9/2012 |
| JP | 2013-513390 | | 4/2013 |
| JP | 55-90540 | | 9/2014 |
| KR | 10-2002-0092596 | | 12/2002 |
| KR | 101067816 | | 9/2011 |
| KR | 2015/0077770 | A | 7/2015 |
| WO | WO 1991/008291 | | 6/1991 |
| WO | WO 1996/039506 | | 12/1996 |
| WO | WO 1997/025426 | | 7/1997 |
| WO | WO 1997/026351 | | 7/1997 |
| WO | WO 1997/039017 | | 10/1997 |
| WO | WO 1998/014591 | | 4/1998 |
| WO | WO 1998/050554 | | 11/1998 |
| WO | WO 1999/029729 | | 6/1999 |
| WO | WO 1999/029858 | | 6/1999 |
| WO | WO 1999/045130 | | 9/1999 |
| WO | WO 2000/055320 | | 9/2000 |
| WO | WO 2000/073801 | | 12/2000 |
| WO | WO 2001/007628 | | 2/2001 |
| WO | WO 2001/019999 | | 3/2001 |
| WO | WO 2001/057190 | | 8/2001 |
| WO | WO 2001/064892 | | 9/2001 |
| WO | WO 2001/074841 | | 10/2001 |
| WO | WO 2001/075067 | | 10/2001 |
| WO | WO 2001/075078 | | 10/2001 |
| WO | WO 2001/088188 | | 11/2001 |
| WO | WO 2001/090330 | | 11/2001 |
| WO | WO 2001/094568 | | 12/2001 |
| WO | WO 2001/095927 | | 12/2001 |
| WO | WO 2002/044349 | | 6/2002 |
| WO | WO 2002/055663 | | 7/2002 |
| WO | WO 2002/059323 | | 8/2002 |
| WO | WO 2002/067970 | | 9/2002 |
| WO | WO 2002/068579 | | 9/2002 |
| WO | WO 2003/009813 | | 2/2003 |
| WO | WO 2003/051388 | | 6/2003 |
| WO | WO 2003/080648 | | 10/2003 |
| WO | WO 2003/094848 | | 11/2003 |
| WO | WO 2003/094862 | | 11/2003 |
| WO | WO 2004/023973 | | 3/2004 |
| WO | WO 2004/030615 | | 4/2004 |
| WO | WO 2004/060262 | | 7/2004 |
| WO | WO 2004/063355 | | 7/2004 |
| WO | WO 2004/064863 | | 8/2004 |
| WO | WO 2004/087875 | | 10/2004 |
| WO | WO 2005/019258 | | 3/2005 |
| WO | WO 2005/019415 | | 3/2005 |
| WO | WO 2005/073250 | | 8/2005 |
| WO | WO 2005/087953 | | 9/2005 |
| WO | WO 2005/102395 | | 11/2005 |
| WO | WO 2005/113812 | | 12/2005 |
| WO | WO 2005/117954 | | 12/2005 |
| WO | WO 2006/016217 | | 2/2006 |
| WO | WO 2006/048219 | | 5/2006 |
| WO | WO 2006/057500 | | 6/2006 |
| WO | WO 2006/083087 | | 8/2006 |
| WO | WO 2007/020075 | | 2/2007 |
| WO | WO 2007/064941 | | 6/2007 |
| WO | WO 2007/083853 | | 7/2007 |
| WO | WO 2007/091106 | | 8/2007 |
| WO | WO 2007/139397 | | 12/2007 |
| WO | WO 2008/007818 | | 1/2008 |
| WO | WO 2008/016356 | | 2/2008 |
| WO | WO 2008/021290 | | 2/2008 |
| WO | WO 2008/030558 | | 3/2008 |
| WO | WO 2008/094012 | | 8/2008 |
| WO | WO 2008/133359 | | 11/2008 |
| WO | WO 2009/059056 | | 5/2009 |
| WO | WO 2009/114623 | | 9/2009 |
| WO | WO 2009/152247 | | 12/2009 |
| WO | WO 2009/158649 | | 12/2009 |
| WO | WO 2010/021415 | | 2/2010 |
| WO | WO 2010/041892 | | 4/2010 |
| WO | WO 2010/041913 | | 4/2010 |
| WO | WO 2010/090471 | | 8/2010 |
| WO | WO 2010/096170 | | 8/2010 |
| WO | WO 2010/099477 | | 9/2010 |
| WO | WO 2010/107825 | | 9/2010 |
| WO | WO 2010/120509 | | 10/2010 |
| WO | WO 2011/032013 | | 3/2011 |
| WO | WO 2011/035335 | | 3/2011 |
| WO | WO 2011/072265 | | 6/2011 |
| WO | WO 2011/072266 | | 6/2011 |
| WO | WO 2011/097031 | | 8/2011 |
| WO | WO 2011/139714 | | 11/2011 |
| WO | WO 2011/139799 | | 11/2011 |

(56) References Cited

FOREIGN PATENT DOCUMENTS

| | | |
|---|---|---|
| WO | WO 2011/139801 | 11/2011 |
| WO | WO 2011/139853 | 11/2011 |
| WO | WO 2011/139854 | 11/2011 |
| WO | WO 2011/139907 | 11/2011 |
| WO | WO 2011/139986 | 11/2011 |
| WO | WO 2011/139988 | 11/2011 |
| WO | WO 2011/140132 | 11/2011 |
| WO | WO 2011/140135 | 11/2011 |
| WO | WO 2011/140266 | 11/2011 |
| WO | WO 2011/140267 | 11/2011 |
| WO | WO 2011/143482 | 11/2011 |
| WO | WO 2011/146410 | 11/2011 |
| WO | WO 2011/150279 | 12/2011 |
| WO | WO 2011/153277 | 12/2011 |
| WO | WO 2012/009289 | 1/2012 |
| WO | WO 2012/021247 | 2/2012 |
| WO | WO 2012/021249 | 2/2012 |
| WO | WO 2012/027611 | 3/2012 |
| WO | WO 2012/048125 | 4/2012 |
| WO | WO 2012/149247 | 11/2012 |
| WO | WO 2012/149252 | 11/2012 |
| WO | WO 2012/149259 | 11/2012 |
| WO | WO 2012/149265 | 11/2012 |
| WO | WO 2012/149282 | 11/2012 |
| WO | WO 2012/149301 | 11/2012 |
| WO | WO 2012/149405 | 11/2012 |
| WO | WO 2012/149411 | 11/2012 |
| WO | WO 2012/158945 | 11/2012 |
| WO | WO 2013/022982 | 2/2013 |
| WO | WO 2013/036293 | 3/2013 |
| WO | WO 2013/036294 | 3/2013 |
| WO | WO 2013/036295 | 3/2013 |
| WO | WO 2013/036296 | 3/2013 |
| WO | WO 2013/036299 | 3/2013 |
| WO | WO 2013/036300 | 3/2013 |
| WO | WO 2013/036301 | 3/2013 |
| WO | WO 2013/036302 | 3/2013 |
| WO | WO 2013/086216 | 6/2013 |
| WO | WO 2013/086228 | 6/2013 |
| WO | WO 2013/115926 | 8/2013 |
| WO | WO 2013/123432 | 8/2013 |
| WO | WO 2014/145050 | 9/2014 |
| WO | WO 2016/172722 | 10/2016 |
| WO | WO 2018/102589 | 6/2018 |

OTHER PUBLICATIONS

International Search Report and Written Opinion for International Application No. PCT/US2009/048915, dated Nov. 2, 2009.
Office Action for U.S. Appl. No. 12/482,151, dated Oct. 11, 2011, 43 pages.
Office Action for U.S. Appl. No. 12/482,151, dated Mar. 18, 2011, 11 pages.
Office Action for U.S. Appl. No. 12/482,151, dated Aug. 13, 2013, 33 pages.
International Preliminary Report on Patentability for International Application No. PCT/US2009/046910, dated Dec. 13, 2010.
International Search Report and Written Opinion for International Application No. PCT/US2009/046910, dated Mar. 4, 2010.
Supplementary European Search Report for European Application No. 06838844.6, dated Apr. 9, 2009, 10 pages.
Office Action for U.S. Appl. No. 12/085,884, dated Jan. 20, 2011.
International Preliminary Report on Patentability for International Application No. PCT/US2006/046106, dated Jun. 4, 2008.
International Search Report and Written Opinion for International Application No. PCT/US2006/046106, dated Aug. 9, 2007.
Supplementary European Search Report for European Application No. 10746935.5, dated Oct. 26, 2012.
International Preliminary Report on Patentability for International Application No. PCT/US2010/025642, dated Aug. 30, 2011.
International Search Report and Written Opinion for International Application No. PCT/US2010/025642, dated Oct. 29, 2010.
Supplementary European Search Report for European Application No. 10764856.0, dated Sep. 5, 2012.
Office Action for U.S. Appl. No. 12/751,358, dated Dec. 2, 2014.
Office Action for U.S. Appl. No. 12/751,358, dated Jun. 11, 2014.
Office Action for U.S. Appl. No. 12/751,358, dated Oct. 3, 2011.
Office Action for U.S. Appl. No. 12/751,358, dated Mar. 3, 2011.
International Preliminary Report on Patentability for International Application No. PCT/US2010/029377, dated Oct. 4, 2011.
International Search Report and Written Opinion for International Application No. PCT/US2010/029377, dated Jan. 26, 2011.
Supplementary European Search Report for European Application No. 10753998.3, dated Nov. 21, 2012.
Office Action for U.S. Appl. No. 12/725,272, dated Jul. 13, 2012, 9 pages.
Restriction Requirement for U.S. Appl. No. 12/725,272, dated Apr. 27, 2012.
International Preliminary Report on Patentability for International Application No. PCT/US2010/027525, dated Sep. 20, 2011.
International Search Report and Written Opinion for International Application No. PCT/US2010/027525, dated Jan. 10, 2011.
Office Action for U.S. Appl. No. 13/766,659, dated Nov. 19, 2013.
Office Action for U.S. Appl. No. 13/766,659, dated Sep. 16, 2013.
International Search Report and Written Opinion for International Application No. PCT/US2010/059964, dated Aug. 25, 2011.
International Preliminary Report on Patentability for International Application No. PCT/US2010/059964, dated Jun. 12, 2012.
Communication Pursuant to Article 94(3) EPC for European Application No. 10793402.8, dated Mar. 27, 2013.
Office Action for U.S. Appl. No. 13/514,952, dated Jul. 18, 2014, 11 pages.
Office Action for U.S. Appl. No. 13/514,952, dated Nov. 14, 2014, 8 pages.
International Preliminary Report on Patentability for International Application No. PCT/US2010/059963, dated Jun. 12, 2012, 18 pages.
International Search Report and Written Opinion for International Application No. PCT/US2010/059963, dated May 12, 2011.
Office Action for U.S. Appl. No. 13/762,151, dated Sep. 10, 2014, 12 pages.
Office Action for U.S. Appl. No. 13/762,151, dated Jan. 2, 2015, 14 pages.
Office Action for U.S. Appl. No. 13/762,151, dated Aug. 3, 2015, 12 pages.
International Search Report and Written Opinion for International Application No. PCT/US2011/000210, dated Aug. 12, 2011.
International Preliminary Report on Patentabiltity for International Application No. PCT/US2011/000210, dated Aug. 7, 2012.
Supplementary European Search Report for European Application No. 11778025.4, dated Nov. 6, 2013.
International Search Report and Written Opinion for International Application No. PCT/US2011/034387, dated Mar. 23, 2012.
International Preliminary Report on Patentability for International Application No. PCT/US2011/034387, dated Oct. 30, 2012.
Supplementary European Search Report for European Application No. 11778026.2, dated Oct. 22, 2013.
International Search Report and Written Opinion for International Application No. PCT/US2011/034388, dated Mar. 23, 2012.
International Preliminary Report on Patentability for International Application No. PCT/US2011/034388, dated Oct. 30, 2012.
International Search Report and Written Opinion for International Application No. PCT/US2011/043596, dated Feb. 29, 2012.
International Preliminary Report on Patentability for International Application No. PCT/US2011/043596, dated Jan. 15, 2013.
Supplementary European Search Report for European Application No. 11778118.7, dated Aug. 19, 2013.
International Search Report and Written Opinion for International Application No. PCT/US2011/034838, dated Jan. 9, 2012.
International Preliminary Report on Patentability for International Application No. PCT/US2011/034838, dated Nov. 6, 2012.
International Search Report and Written Opinion for International Application No. PCT/US2011/033988, dated Feb. 9, 2012.
International Preliminary Report on Patentability for International Application No. PCT/US2011/033988, dated Oct. 30, 2012.

(56) References Cited

OTHER PUBLICATIONS

International Search Report and Written Opinion for International Application No. PCT/US2011/038240, dated Feb. 9, 2012.
International Preliminary Report on Patentability for International Application No. PCT/US2011/038240, dated Nov. 27, 2012.
Supplementary European Search Report for European Application No. 11778296.1, dated Nov. 12, 2013.
International Search Report and Written Opinion for International Application No. PCT/US2011/035250, dated Jan. 19, 2012.
International Preliminary Report on Patentability for International Application No. PCT/2011/035250, dated Nov. 6, 2012.
International Search Report and Written Opinion for International Application No. PCT/US2011/043756, dated Mar. 2, 2012.
International Preliminary Report on Patentability for International Application No. PCT/US2011/043756, dated Jan. 15, 2013.
Supplementary European Search Report for European Application No. 11816760.0, dated Jul. 7, 2014.
Office Action for U.S. Appl. No. 13/809,757, dated Oct. 31, 2014, 10 pages.
International Search Report and Written Opinion for International Application No. PCT/US2011/043758, dated Mar. 2, 2012.
International Preliminary Report on Patentability for International Application No. PCT/US2011/043758, dated Jan. 15, 2013.
International Search Report and Written Opinion for International Application No. PCT/US2011/034205, dated Feb. 8, 2012.
International Preliminary Report on Patentability for International Application No. PCT/US2011/034205, dated Oct. 30, 2012.
International Search Report and Written Opinion for International Application No. PCT/US2011/036684, dated Feb. 9, 2012.
International Preliminary Report on Patentability for International Application No. PCT/US2011/036684, dated Nov. 20, 2012.
International Search Report and Written Opinion for International Application No. PCT/US2011/038813, dated Mar. 28, 2012.
International Preliminary Report on Patentability for International Application No. PCT/US2011/038813, dated Dec. 4, 2012.
International Search Report and Written Opinion for International Application No. PCT/US2011/035056, dated Mar. 23, 2012.
International Preliminary Report on Patentability for International Application No. PCT/US2011/035056, dated Nov. 6, 2012.
International Search Report and Written Opinion for International Application No. PCT/US2011/035053, dated Mar. 23, 2012.
International Preliminary Report on Patentability for International Application No. PCT/US2011/035053, dated Nov. 6, 2012.
Supplementary European Search Report for European Application No. 11778120.3, dated Nov. 15, 2013.
International Search Report and Written Opinion for International Application No. PCT/US2011/034840, dated Feb. 10, 2012.
International Preliminary Report on Patentability for International Application No. PCT/US2011/034840, dated Nov. 6, 2012.
Supplementary European Search Report for European Application No. 11777984.3, dated Oct. 18, 2013.
International Search Report and Written Opinion for International Application No. PCT/US2011/034207, dated Feb. 8, 2012.
International Preliminary Report on Patentability for International Application No. PCT/US2011/034207, dated Oct. 30, 2012.
International Search Report and Written Opinion for International Application No. PCT/US2011/055130, dated May 14, 2012.
International Preliminary Report on Patentability for International Application No. PCT/US2011/055130, dated Apr. 9, 2013.
International Search Report and Written Opinion for International Application No. PCT/US2011/049223, dated Mar. 27, 2012.
International Preliminary Report on Patentability for International Application No. PCT/US2011/049223, dated Feb. 26, 2013.
International Search Report and Written Opinion for International Application No. PCT/US2011/034626, dated Jan. 19, 2012.
International Preliminary Report on Patentability for International Application No. PCT/US2011/034626, dated Oct. 30, 2012.
Supplementary European Search Report for European Application No. 11781304.8, dated Oct. 23, 2013.
International Search Report and Written Opinion for International Application No. PCT/US2011/036326, dated Feb. 9, 2012.
International Preliminary Report on Patentability for International Application No. PCT/US2011/036326, dated Nov. 20, 2012.
International Search Report and Written Opinion for International Application No. PCT/US2011/035251, dated Feb. 8, 2012.
International Preliminary Report on Patentability for International Application No. PCT/US2011/035251, dated Nov. 6, 2012.
International Search Report and Written Opinion for International Application No. PCT/US2012/068282, dated Apr. 1, 2013.
International Search Report and Written Opinion for International Application No. PCT/US2012/068296, dated Apr. 19, 2013.
Supplementary European Search Report and Written Opinion for European Application No. 13749967.9, dated Sep. 4, 2015, 11 pages.
International Search Report and Written Opinion for International Application No. PCT/US2013/026494, dated Aug. 21, 2013, 21 pages.
International Preliminary Report on Patentability for International Application No. PCT/US2013/026494, dated Aug. 19, 2014, 15 pages.
International Search Report and Written Opinion for International Application No. PCT/US2014/029699, dated Aug. 19, 2014, 16 pages.
International Preliminary Report on Patentability for International Application No. PCT/US2014/029699, dated Sep. 15, 2015, 11 pages.
Adams, M. D. et al., "The genome sequence of *Drosophila melanogaster*," Science, 287(5961):2185-2195 (2000).
Aderem, A. et al., "Toll-like receptors in the induction of the innate immune response," Nature, 406:782-787 (2000).
Amaar, Y. G. et al., "Cloning and characterization of the C.elegans histidyl-tRNA synthetase gene," Nucleic Acids Research, 21(18):4344-4347 (1993).
Antonellis, A. et al., "The Role of Aminoacyl-tRNA Synthetases in Genetic Diseases," Annual Review of Genomics and Human Genetics, 9(1):87-107 (2008).
Ascherman, D. P. et al., "Critical Requirement for Professional APCs in Eliciting T Cell Responses to Novel Fragments of Histidyl-tRNA Synthetase (Jo-1) in Jo-1 Antibody-Positive Polymyositis," J. Immunol., 169:7127-7134 (2002).
Ascherman, D. P., "The Role of Jo-1 in the Immunopathogenesis of Polymyositis: Current Hypotheses," Current Rheumatology Reports, 5:425-430 (2003).
Barbasso, S. et al., "Sera From Anti-Jo-1-Positive Patients with Polymyositis and Interstitial Lung Disease Induce Expression of Intercellular Adhesion Molecule 1 in Human Lung Endothelial Cells," Arthritis & Rheumatism, 60(8):2524-2530 (2009).
Berger, T., "Is there a rationale for therapeutic immunoadsorption in multiple sclerosis?" Eur. J. Clin. Invest. 35(8):467-468 (2005).
Bernstein, R. M. et al., "Anti-Jo-1 antibody: a marker for myositis with interstitial lung disease," British Medical Journal, 289:151-152 (1984).
Biesenbach, P. et al., "Immunoadsorption in SLE: Three different high affinity columns are adequately effective in removing autoantibodies and controlling disease activity," Atherosclerosis Supplements, 10:114-121 (2009).
Blechynden, L. M. et al., "Sequence and polymorphism analysis of the murine gene encoding histidyl-tRNA synthetase," Gene, 178:151-156 (1996).
Blechynden, L. M. et al., "Myositis Induced by Naked DNA Immunization with the Gene for Histidyl-tRNA Synthetase," Human Gene Therapy, 8:1469-1480 (Aug. 10, 1997).
Blum, D. et al., "Extracellular toxicity of 6-hydroxydopamine on PC12 cells," Neuroscience Letters, 283(3):193-196 (2000).
Bohm, M. et al., "Longlasting effects of immunoadsorption in severe Sjögren's syndrome," Ann. Rheum. Dis., 63:214-215 (2004).
Braun, N. et al., "Immunoadsorption onto protein A induces remission in severe systemic lupus erythematosus," Nephrol. Dial. Transplant, 15(9):1367-1372 (2000).
Braun, N. et al., "Immunoglobulin and circulating immune complex kinetics during immunoadsorption onto protein A sepharose," Transfus. Sci., 19(Suppl):25-31 (1998).

(56) References Cited

OTHER PUBLICATIONS

Brenner et al., "IG-therasorb immunoapheresis in orthotopic xenotransplantation of baboons with landrace pig hearts," Transplantation, 69:208-214 (2000) [Abstract].
Brightbill, H. D. et al., "Toll-like receptors: molecular mechanisms of the mammalian immune response," Immunology, 101:1-10 (2000).
Broun, P. et al., "Catalytic plasticity of fatty acid modification enzymes underlying chemical diversity of plant lipids," Science, 282:1315-1317 (1998).
Brown, M. V. et al., "Mammalian aminoacyl-tRNA synthetases: Cell signaling functions of the protein translation machinery," Vascular Pharmacology, 52(1-2):21-26 (2010).
Carter, P. J., "Introduction to current and future protein therapeutics: A protein engineering perspective," Experimental Cell Research, 317(9):1261-1269 (2011).
Casciola-Rosen, L. et al., "Cleavage by Granzyme B Is Strongly Predictive of Autoantigen Status: Implications for Initiation of Autoimmunity," J. Exp. Med., 190(6):815-825 (1999).
Casciola-Rosen, L., "Histidyl-Transfer RNA Synthetase: A Key Participant in Idiopathic Inflammatory Myopathies," Arthritis and Rheumatism, 63(2):331-333 (2011).
Chica, R. A. et al., "Semi-rational approaches to engineering enzyme activity: combining the benefits of directed evolution and rational design," Curr. Opin. Biotechnol., 16:378-384 (2005).
Choi, W. S. et al., "Two Distinct Mechanisms Are Involved in 6-Hydroxydopamine-and MPP+-Induced Dopaminergic Neuronal Cell Death: Role of Caspases, ROS, and JNK," Journal of Neuroscience Research, 57(1):86-94 (1999).
Deiters, A. et al., "Site-specific PEGylation of proteins containing unnatural amino acids," Bioorg Med Chem Lett, 14(23):5743-5745 (2004).
Delgado, C. et al., "The uses and properties of PEG-linked proteins," Critical Reviews in Therapeutic Drug Carrier Systems, 9(3,4):249-304 (1992).
Devos, D. et al., "Practical limits of function prediction," Proteins: Structure, Function, and Genetics, 41:98-107 (2000).
Dittrich et al., "Immunoadsorption and plasma exchange in pregnancy," Kidney Blood Press. Res., 25:232-239 (2002) [Abstract].
Dorffel et al., "Immunoadsorption in idiopathic dilated cardiomyopathy, a 3-year follow-up," Int. J. Cardiol., 97(3):529-534 (2004) [Abstract].
Eming, R. et al., "Prolonged clinical remission of patients with severe pemphigus upon rapid removal of desmoglein-reactive autoantibodies by immunoadsorption," Dermatology, 212(2):177-187 (2006).
Esnault, V. L. M. et al., "Influence of immunoadsorption on the removal of immunoglobulin G autoantibodies in crescentic glomerulonephritis," Nephron, 65(2):180-184 (1993).
Ewalt, K. L. et al., "Activation of Angiogenic Signaling Pathways by Two Human tRNA Synthetases," Biochemistry, 41(45):13344-13349 (2002).
Felden, B. et al., "Resected RNA pseudoknots and their recognition by histidyl-tRNA synthetase," Proc. Natl. Acad. Sci. USA, 95:10431-10436 (1998).
Felix et al., "Hemodynamic effects of immunoadsorption and subsequent immunoglobulin substitution in dilated cardiomyopathy: three-month results from a randomized study," J. Am. Coll. Cardiol., 35:1590-1598 (2000) [Abstract].
Francklyn, C. et al., "Histidyl-tRNA Synthetase," Eurekah Bioscience, 1(3):265-277 (2005).
Fresenius Medical Care Deutschland GmbH, "Globaffin, First Synthetic Broadband-Immunoadsorber," (2006), 2 pages.
Fresenius Medical Care Deutschland GmbH, "Immunosorba, Protein A Column for Immunoadsorption," Therapeutic Apheresis, (2006), 12 pages.
Frommhold, D. et al., "Sialyltransferase ST3Gal-IV controls CXCR2-mediated firm leukocyte arrest during inflammation," Journal of Experimental Medicine, 205(6):1435-1446 (2008).
Frost, N. et al., "Treatment of pemphigus vulgaris with protein a immunoadsorption: case report of long-term history showing favorable outcome," Ann. N.Y. Acad. Sci., 1051:591-596 (2005).
GenBank Accession No. AA984229, published May 27, 1998.
GenBank Accession No. AK055917, published Jan. 19, 2008.
GenBank Accession No. AK124831, published Jul. 3, 2008.
GenBank Accession No. AK225776, published Jul. 22, 2006.
GenBank Accession No. AK293154, published Jul. 24, 2008.
GenBank Accession No. AK293531, published Jul. 24, 2008.
GenBank Accession No. AK295219, published Jul. 24, 2008.
GenBank Accession No. AK302295, published Jul. 24, 2008.
GenBank Accession No. AK303778, published Jul. 24, 2008.
GenBank Accession No. AU129836, published Feb. 18, 2011.
GenBank Accession No. BE872272, published Jan. 13, 2011.
GenBank Accession No. BF791754, published Jan. 13, 2011.
GenBank Accession No. BG108830, published Jun. 1, 2001.
GenBank Accession No. BP268250, published Feb. 10, 2011.
GenBank Accession No. DA083923, published Feb. 17, 2011.
GenBank Accession No. DB146646, published Feb. 16, 2011.
GenBank Accession No. Q7QD89, Anopheles gambiae Sequence Committee, submitted Apr. 2002, [Retrieved from the Internet Apr. 24, 2007], <URL: http://www.ncbi.nlm.nih.gov/entrez/viewer.fcgi?db=protein&val=74803944>.
GenBank Accession No. Q9VV60, published May 1, 2000.
GenBank Accession No. Z11518, published Oct. 7, 2008.
GenBank Accession No. BC080514, "*Homo sapiens* histidyl-tRNA synthetase, mRNA (cDNA clone MGC:99562 IMAGE:2821065), complete cds," Jul. 15, 2006.
Goldgur, Y. et al., "The crystal structure of phenylalanyl-tRNA synthetase from Thermus thermophilus complexed with cognate tRNA," Structure, 5(1):59-68 (1997).
Graninger et al., "Immunoadsorption therapy (therasorb) in patients with severe lupus erythematosus," Acta Med. Austriaca, 29:26-29 (2002) [Abstract].
Greenberg, Y. et al., "The novel fragment of tyrosyl tRNA synthetase, mini-TyrRS, is secreted to induce an angiogenic response in endothelial cells," FASEB Journal, 22(5):1597-1605 (2008).
Grundtman, C. et al., "Immune mechanisms in the pathogenesis of idiopathic inflammatory myopathies," Arthritis Research & Therapy, 9:208 (2007).
Guijarro, J. I. et al., "Structure and Dynamics of the Anticodon Arm Binding Domain of Bacillus stearothermophilus Tyrosyl-tRNA Synthetase," Structure, 10(3):311-317 (2002).
Gunther et al., Successful therapy of pemphigus vulgaris with immunoadsorption using the TheraSorb adsorber, J. Dtsch. Dermatol. Ges., 6:661-663 (2008) [Abstract].
Guo, R-T. et al., "Crystal structures and biochemical analyses suggest a unique mechanism and role for human glycyl-tRNA synthetase in Ap4A homeostasis," Journal of Biological Chemistry, 284(42):28968-28976 (2009).
Guo, M. et al., "Functional expansion of human tRNA synthetases achieved by structural inventions," FEBS Letters, 584(2):434-442 (2010).
Guo, M. et al., "New functions of aminoacyl-tRNA synthetases beyond translation," Nature Reviews Molecular Cell Biology, 11:668-674 (2010).
Guzzo, C. M. et al., "Systematic analysis of fusion and affinity tags using human aspartyl-tRNA synthetase expressed in *E. coli*," Protein Expression and Purification, 54(1):166-175 (2007).
Haas et al., "Long-term treatment of myasthenia gravis with immunoadsorption," J. Clin. Apher., 17:84-87 (2002) [Abstract].
Hanrott, K. et al., "6-Hydroxydopamine-induced Apoptosis Is Mediated via Extracellular Auto-oxidation and Caspase 3-dependent Activation of Protein Kinase C8," The Journal of Biological Chemistry, 281(9):5373-5382 (2006).
Hartl, D. et al., "Infiltrated neutrophils acquire novel chemokine receptor expression and chemokine responsiveness in chronic inflammatory lung diseases," J. Immunol., 181:8053-8067 (2008).
Hausmann, C. D. et al., "Aminoacyl-tRNA synthetase complexes: molecular multitasking revealed," FEMS Microbiol. Rev., 32(4):705-721 (2008).
Haussermann, A. et al., "Das anti-Jo-1-Syndrom—eine Sonderform der Myositis mit interstitieller Lungenerkrankung," Pneumologie, 64(08):496-503 (2010).

(56) References Cited

OTHER PUBLICATIONS

Hengstman, G. J. D. et al., "Anti-Jo-1 positive inclusion body myositis with a marked and sustained clinical improvement after oral prednisone," J. Neurol. Neurosurg. Psychiatry, 70(5):706 (2001).
Hessel et al., "Economic evaluation and survival analysis of immunoglobulin adsorption in patients with idiopathic dilated cardiomyopathy," Eur. J. Health Econ., 5:58-63 (2004) [Abstract].
Hou, Y-M. et al., "Sequence determination and modeling of structural motifs for the smallest monomeric aminoacyl-tRNA synthetase," Proc. Nat. Acad. Sci., 88(3):976-980 (1991).
Howard, O. M. Z. et al., "Histidyl-tRNA Synthetase and Asparaginyl-tRNA Synthetase, Autoantigens in Myositis, Activate Chemokine Receptors on T Lymphocytes and Immature Dendritic Cells," The Journal of Experimental Medicine, 196(6):781-791 (2002).
Howard, O. M. Z. et al., "Autoantigens signal through cheokine receptors: uveitis antigens induce CXCR3-and CRCR5-expressing lymphocytes and immature dendritic cells to migrate", Blood, 105(11) 4207-4214 (2005).
Huang, C. et al., "Receptor-Fc fusion therapeutics, traps, and MIMETIBODY technology," Current Opinion in Biotechnology, 20(6):692-699 (2009).
Ivakhno, S. S. et al., "Cytokine-Like Activities of Some Aminoacyl-tRNA Synthetases and Auxiliary p43 Cofactor of Aminoacylation Reaction and Their Role in Oncogenesis," Exp. Oncol., 26(4):250-255 (2004).
Ivanov, K. A. et al., "Non-canonical Functions of Aminoacyl-tRNA Synthetases," Biochemistry (Moscow), 65(8):888-897 (2000).
Izumi, Y. et al., "p-Quinone Mediates 6-Hydroxydopamine-Induced Dopaminergic Neuronal Death and Ferrous Iron Accelerates the conversion of p-Quinone Into Melanin Extracellularly," Journal of Neuroscience Research, 79(6):849-860 (2005).
Jacobo-Molina, A. et al., "cDNA Sequence, Predicted Primary Structure, and Evolving Amphiphilic Helix of Human Aspartyl-tRNA Synthetase," Journal of Biological Chemistry, 264(28):16608-16612 (1989).
Jahns et al., "Direct evidence for a beta 1-adrenergic receptor-directed autoimmune attack as a cause of idiopathic dilated cardiomyopathy," J. Clin. Invest., 113:1419-1429 (2004) [Abstract].
Jansen et al., "Treatment of coagulation inhibitors with extracorporeal immunoadsorption (Ig-Therasorb)," Br. J. Haematol., 112:91-97 (2001) [Abstract].
Junemann, A. G. et al., "Stimulatory Autoantibodies against β2-adrenergic Receptors in Open-angle Glaucoma—Effect of Immunoadsorption on Antibody Level and Intraocular Pressure," Glaucoma Genetics and Proteomics, ARVO2011 Visionary Genomics, Fort Lauderdale, FL, May 2, 2011 3 pages.
Jura, M. et al., "Comprehensive insight into human aminoacyl-tRNA synthetases as autoantigens in idiopathic inflammatory myopathies," Critical Reviews in Immunology, 27(6):559-572 (2007).
Kaczmarek et al., "Successful management of antibody-mediated cardiac allograft rejection with combined immunoadsorption and anti-CD20 monoclonal antibody treatment: case report and literature review," J. Heart Lung Transplant., 26:511-515 (2007) [Abstract].
Kapoor, M. et al., "Mutational separation of aminoacylation and cytokine activities of human tyrosyl-tRNA synthetase," Chemistry & Biology, 16(5):531-539 (2009).
Katsumata, Y. et al., "Species-specific immune responses generated by histidyl-tRNA synthetase immunization are associated with muscle and lung inflammation," Journal of Autoimmunity, 29(2-3):174-186 (2007).
Katsumata, Y. et al., "Animal models in myositis," Current Opinion in Rheumatology, 20:681-685 (2008).
Katsumata, Y. et al., "Attenuation of experimental autoimmune myositis by blocking ICOS-ICOS ligand interaction," J. Immunol., 179:3772-3779 (2007).
Kimchi-Sarfaty, C. et al., "A 'Silent' polymorphism in the MDR1 gene changes substrate specificty," Science, 315:525-528 (2007).
Kise, Y. et al., "A short peptide insertion crucial for angiostatic activity of human tryptophanyl-tRNA synthetase," Nature Structural & Molecular Biology, 11(2):149-156 (2004).
Klingel, R. et al., "Plasma exchange and immunoadsorption for autoimmune neurologic diseases—current guidelines and future perspectives," Atherosclerosis Supplements, 10:129-132 (2009).
Knebel et al., "Reduction of morbidity by immunoadsorption therapy in patients with dilated cardiomyopathy," Int. J. Cardiol., 97:517-520 (2004) [Abstract].
Knobl et al., "Extracorporeal immunoadsorption for the treatment of haemophilic patients with inhibitors to factor VIII or IX," Vox Sang. 77 (suppl 1): 57-64 (1999) [Abstract].
Knobl, P. et al., "Immunoadsorption for the treatment of a patient with severe thrombotic thrombocytopenic purpura resistant to plasma exchange: kinetics of an inhibitor of ADAMTS13," J. Thromb. Haemost., 1:187-189 (2003).
Kochendoerfer, G. G., "Site-specific polymer modification of therapeutic proteins," Current Opinion in Chemical Biology, 9:555-560 (2005).
Kohler, W. et al., "A randomized and controlled study comparing immunoadsorption and plasma exchange in myasthenic crisis," Journal of Clinical Apheresis, 26(6):347-355 (2011).
Koll, "Ig-TheraSorb immunoadsorption for selective removal of human immunoglobulins in diseases associated with pathogenic antibodies of all classes and IgG subclasses, immune complexes, and fragments of immunoglobulins," Ther. Apher., 2:147-152 (1998) [Abstract].
Koller et al., "Clearance of C4d deposition after successful treatment of acute humoral rejection in follow-up biopsies: a report of three cases," Transpl. Int., 17:177-181 (2004) [Abstract].
Kovaleski, B. J. et al.,"In vitro characterization of the interaction between HIV-1 Gag and human lysyl-tRNA synthetase," J. Bio. Chem., 281(28):19449-19456 (2006).
Kucharzik, T. et al., "Neutrophil transmigration in inflammatory bowel disease is associated with differential expression of epithelial intercellular junction proteins," American Journal of Pathology, 159(6):2001-2009 (2001).
Laczika et al., "Immunoadsorption in Goodpasture's syndrome," Am. J. Kidney Dis., 36:392-395 (2000) [Abstract].
Lagoumintzis, G. et al., "Recent approaches to the development of antigen-specific immunotherapies for myasthenia gravis," Autoimmunity, 43(5-6):436-445 (2010).
Levine, S. M. et al., "Anti-aminoacyl tRNA synthetase immune responses: insights into the pathogenesis of the idiopathic inflammatory myopathies," Current Opinion in Rheumatology, 15(6):708-713 (2003).
Levine, S. M., et al., "Novel Conformation of Histidyl-Transfer RNA Synthetase in the Lung", Arthritis & Rheumatism, 56(8): 2729-2739 (2007).
Link, A. J. et al., "Discovery of aminoacyl-tRNA synthetase activity through cell-surface display of noncanonical amino acids, " Proc. Nat. Acad. Sci., 103(27):10180-10185 (2006).
Magalhaes, P. O. et al., "Methods of endotoxin removal from biological preparations: a review," J. Pharm. Pharmaceut. Sci., 10(3):388-404 (2007).
Martin, A. et al., "Epitope studies indicate that histidyl-tRNA synthetase is a stimulating antigen in idiopathic myositis," The FASEB Journal, 9:1226-1233 (1995).
Matic et al., "Three cases of C-ANCA-positive vasculitis treated with immunoadsorption: possible benefit in early treatment," Ther. Aph., 5:68-72 (2001) [Abstract].
Miller, F. W., et al., "Origin and Regulation of a Disease-specific Autoantibody Response, Antigenic Epitopes, Spectrotype Stability, and Isotype Restriction of Anti-Jo-1 Autoantibodies," J. Clin. Invest., 85:468-475 (1990).
Miller, F. W. et al., "The role of an autoantigen, histidyl-tRNA synthetase, in the induction and maintenance of autoimmunity," Proc. Natl. Acad. Sci. USA, 87:9933-9937 (1990).
Moldenhauer et al., "Immunoadsorption patients with multiple sclerosis: an open-label pilot study," Eur. J. Clin. Invest., 35:523-530 (2005) [Abstract].
Moldoveanu, B. et al., "Inflammatory mechanisms in the lung," Journal of Inflammation Research, 2:1-11 (2009).

(56) References Cited

OTHER PUBLICATIONS

Molecular Modeling Database (MMDB), "Solution Structures of the Whep-trs domain of human histidyl-trna synthetase," MMDB ID No. 35920, available for www.ncbi.nlm.nih.gov/Structure/mmdb, accessed Aug. 24, 2012.
Mozaffar, T. et al., "Myopathy with anti-Jo-1 antibodies: pathology in perimysium and neighbouring muscle fibres," J. Neurol. Neurosurg. Psychiatry, 68:472-478 (2000).
Mueller et al., "Immunoglobulin adsorption in patients with idiopathic dilated cardiomyopathy," Circulation, 101:385-391 (2000) [Abstract].
Mukhopadhyay, R. et al., "The GAIT System: a gatekeeper of inflammatory gene expression," Trends in Biochemical Sciences, 34(7):324-331 (2009).
Nackley, A. G. et al., "Human Caechol-O-Methytransferase haplotypes modulate protein expression by altering mRNA secondary structure," Science, 314:1930-1933 (2006).
Naito, Y. et al., "Neutrophil-dependent oxidative stress in ulcerative colitis," J. Clin. Biochem. Nutr., 41:18-26 (2007).
Ngo, J. T. et al., "Computational complexity, protein structure prediction, and the Levinthal paradox," In The Protein Folding Problem and Tertiary Structure Prediction, Merz et al. (ed.), Birkhauser, Boston, MA, pp. 433 and 492-495 (1994).
Nichols, R. C. et al., "Human isoleucyl-tRNA synthetase: sequence of the cDNA, alternative mRNA splicing, and the characteristics of an unusually long C-terminal extension," Gene, 155(2):299-304 (1995).
Nishikai, M. et al., "Heterogeneity of Precipitating Antibodies in Polymyositis and Dermatomyositis," Arthritis and Rheumatism, 23(8):881-888 (1980).
O'Hanlon, T. P. et al., "Genomic organization, transcriptional mapping, and evolutionary implications of the human bi-directional histidyl-tRNA synthetase locus (HARS/HARSL)," Biochemical and Biophysical Research Communications, 294:609-614 (2002).
Omotoso, B. A. et al., "Therapeutic Plasma Exchange in Antisynthetase Syndrome With Severe Interstitial Lung Disease," Journal of Clinical Apheresis (2015), 5 pages.
Oppenheim, J. J. et al., "Chemokine receptors on dendritic cells promote autoimmune reactions," Arthritis Res., 4(3):S183-S188 (2002).
Oppenheim, J. J. et al., "Autoantigens act as tissue-specific chemoattractants," Journal of Leukocyte Biology, 77:854-861 (2005).
Palmer, A. et al., "Treatment of rapidly progressive glomerulonephritis by extracorporeal immunoadsorption, prednisolone and cyclophosphamide," Nephrol Dial Transplant., 6(8):536-542 (1991).
Palmer, A. et al., "Treatment of systemic lupus erythematosus by extracorporeal immunoadsorption," Lancet, 2(8605):272 (1988).
Park, S. G., et al., "Aminoacyl tRNA synthetases and their connections to disease," PNAS, 105(32):11043-11049 (2008).
Park, C-K. et al., "Development of antisynthetase syndrome in a patient with rheumatoid arthritis," Rheumatol. Int., 31:529-532 (2011).
Park, S. G. et al., "Dose-dependent biphasic activity of tRNA synthetase-associating factor, p43, in angiogenesis," The Journal of Biological Chemistry, 277(47):45243-45248 (2002).
Park, S. G. et al., "Is there an answer? Do aminoacyl-tRNA synthetases have biological functions other than in protein biosynthesis?" IUBMB Life, 58(9):556-558 (2006).
Parker, L. C. et al., "Toll-Like Receptor (TLR)2 and TLR4 Agonists Regulate CCR Expression in Human Monocytic Cells," The Journal of Immunology, 172:4977-4986 (2004).
Pierce, S. B. et al., "Mutations in mitochondrial histidyl tRNA synthetase HARS2 cause ovarian dysgenesis and sensorineural hearing loss of Perrault syndrome," PNAS, 108(16):6543-6548 (2011).
Prophet et al., "Two cases of refractory endocrine ophthalmopathy successfully treated with extracorporeal immunoadsorption," Ther. Apher., 5:142-146 (2001) [Abstract].
Puffenberger, E. G. et al., "Genetic mapping and exome sequencing identify variants associated with five novel diseases," PLoS, 7(1):e28936 (2012).
Quesniaux, V. F.J. et al., "Hematopoiesis, including lymphocyte developmet and maturation," Principles of Immunopharmacology, pp. 3-17 (2005).
Raben, N. et al., "A Motif in Human Histidyl-tRNA Synthetase Which Is Shared among Several Aminoacyl-tRNA Synthetases Is a Coiled-coil That is Essential for Enzymatic Activity and Contains the Major Autoantigenic Epitope," The Journal of Biological Chemistry, 269(39):24277-24283 (1994).
Rabitsch et al., "Prolonged red cell aplasia after major ABO-incompatible allogeneic hematopoietic stem cell transplantation: removal of persisting isohemagglutinins with Ig-Therasorb immunoadsorption," Bone Marrow Transplant,. 32:1015-1019 (2003) [Abstract].
Rech, J. et al., "Immunoadsorption and CD20 antibody treatment in a patient with treatment resistant systemic lupus erythematosus and preterminal renal insufficiency," Ann Rheum Dis., 65(4):552-553 (2006).
Reed, V. S. et al., "Characterization of a Novel N-terminal Peptide in Human Aspartyl-tRNA Synthetase," Journal of Biological Chemistry, 269(52):32937-32941 (1994).
Rho, S. B. et al., "Interaction between human tRNA synthetases involves repeated sequence elements," Proc. Natl. Acad. Sci. USA, 93(19):10128-10133 (1996).
Rho, S. B. et al., "A multifunctional repeated motif is present in human bifunctional tRNA synthetase," Journal of Biological Chemistry, 273(18):11267-11273 (1998).
Ribas de Pouplana, L. et al., "Not Just Because it is There: Aminoacyl-tRNA Synthetases Gain Control of the Cell," Molecular Cell, 30:3-4 (2008).
Richardson, R. M. et al., "Role of the cytoplasmic tails of CXCR1 and CXCR2 in mediating leukocyte migration, activation, and regulation," Journal of Immunology, 170(6):2904-2911 (2003).
Rosenberg, N. L. et al., "Experimental autoimmune myositis in SJL/J mice," Clin. Exp. Immunol., 68:117-129 (1987).
Sanchez, A. P. et al., "The selective therapeutic apheresis procedures," Journal of Clinical Apheresis, 28(1):20-29 (2013).
Sauna, Z. E. et al., "Silent polymorhisms speak: How they affect pharmacogenomics and the treatment of cancer," Cancer Res., 67(20):9609-9612 (2007).
Schmaldienst et al., "Treatment of systemic lupus erythematosus by immunoadsorption in a patient suffering from tuberculosis," Am. J. Kidney Dis., 39:415-418 (2002) [Abstract].
Schmidt, E. et al., "Immunoadsorption in dermatology," Arch. Dermatol. Res., 302:241-253 (2010).
Schmidt, E. et al., "Protein a immunoadsorption: a novel and effective adjuvant treatment of severe pemphigus," Br J Dermatol., 148(6):1222-1229 (2003).
Schmutz, J. et al., "The DNA sequence and comparative analysis of human chromosome 5," Nature, 431:268-274 (2004).
Seburn, K. L. et al., "An active dominant mutation of glycyl-tRNA synthetase causes neuropathy in a Charcot-Marie-Tooth 2D mouse model," Neuron, 51(6):715-726 (2006).
Sen, S. et al., "Developments in directed evolution for improving enzyme functions," Appl. Biochem. Biotechnol., 143:212-223 (2007).
Shiba, K., "Intron positions delineate the evolutionary path of a pervasively appended peptide in five human aminoacyl-tRNA synthetases," Journal of Molecular Evolution, 55:727-733 (2002).
Smith, D. F. et al., "Leukocyte phosphoinositide-3 kinase $\gamma$ is required for chemokine-induced, sustained adhesion under flow in vivo," Journal of Leukocyte Biology, 80(6):1491-1499 (2006).
Soejima, M. et al., "Role of Innate Immunity in a Murine Model of Histidyl-Transfer RNA Snythetase (Jo-1)-Mediated Myositis," Arthritis and Rheumatism, 63(2):479-487 (2011).
Staudt et al., "Immunohistological changes in dilated cardiomyopathy induced by immunoadsorption therapy and subsequent immunoglobulin substitution," Circulation, 103:2681-2686 (2001) [Abstract].
Staudt et al., "Potential role of autoantibodies belonging to the immunoglobulin G-3 subclass in cardiac dysfunction among patients with dilated cardiomyopathy," Circulation, 106:2448-2453 (2002) [Abstract].

(56) References Cited

OTHER PUBLICATIONS

Stone, K. D. et al., "Immunomodulatory therapy of eosinophil-associated gastrointestinal diseases," Clin. Exp. Allergy, 38(12):1858-1865 (2008).
Stummvoll, G. H., "Immunoadsorption (IAS) for systemic lupus erythematosus," Lupus, 20:115-119 (2011).
Stummvoll et al., "IgG immunoadsorption reduces systemic lupus erythematosus activity and proteinuria: a long term observational study," Ann. Rheum. Dis., 64:1015-1021 (2005) [Abstract].
Sultan, S. M. et al., "Re-classifiyng myositis," Rheumatology, 49:831-833 (2010).
Suzuki, K. et al., "Successful treatment of polymyositis by immunoadsorption in a patient with polymyositis-systemic sclerosis overlap," Japan J. Apheresis, 13(2):135-136 (1994).
Tarabishy, A. B. et al., "Retinal Vasculitis Associated with the Anti-Synthetase Syndrome," Ocular Immunology & Inflamation, 18(1):16-18 (2010).
Targoff, I. N., "Update on myositis-specific and myositis-associated autoantibodies," Current Opinion in Rheumatology, 12:475-481 (2000).
Toepfer et al., "Successful management of polyneuropathy associated with IgM gammopathy of undetermined significance with antibody-based immunoadsorption," Clin. Nephrol., 53:404-407 (2000) [Abstract].
Traves, S. L. et al., "Specific CXC but not CC chemokines cause elevated monocyte migration in COPD: a role for $CXCR_2$," Journal of Leukocyte Biology, 76(2):441-450 (2004).
Tsui, H. W. et al., "Transcriptional analyses of the gene region that encodes human histidyl-tRNA sysnthetase: identification of a novel bidirectional regulatory element," Gene, 131:201-208 (1993).
Tzioufas, A. G. et al., "Antisynthetase syndrome," Orphanet Encyclopedia, http://www.orpha.net/data/patho/GB/uk-antisynthetase.pdf, pp. 1-5 Nov. 2001.
Veronese, F. M. et al., "Preface: Introduction and overview of peptide and protein pegylation," Advanced Drug Delivery Reviews, 54:453-456 (2002).
Vestergaard, C. et al., "Expression of CCR2 on monocytes and macrophages in chronically inflamed skin in atopic dermatitis and psoriasis," Acta Derm. Venereol., 84:353-358 (2004).
Wakasugi, K. et al., "Two distinct cytokines released from a human aminoacyl-tRNA synthetase," Science, 284:147-151 (1999).
Wakasugi, K. et al., "A human aminoacyl-tRNA synthetase as a regulator of angiogenesis," PNAS USA, 99(1):173-177 (2002).
Wakasugi, K. et al., "Induction of angiogenesis by a frament of human tyrosyl-tRNA synthetase," The Journal of Biological Chemistry, 277(23):20124-20126 (2002).
Wallace, E. A. et al., "Diagnosis and management of inflammatory muscle disease," The Journal of Musculoskeletal Medicine, 27(12):1-7 (2010).
Whisstock, J. C. et al., "Prediction of protein function from protein sequence," Q. Rev. Biophysics., 36(3):307-340 (2003).
Wishart, M. J. et al., "A single mutation converts a novel phosphotyrosine binding domain into a dual-specificity phosphatase," J. Biol. Chem., 270(45):26782-26785 (1995).
Witkowski, A. et al., "Conversion of β-ketoacyl synthase to a Malonyl Decarboxylase by replacement of the active cysteine with glutamine," Biochemistry, 38:11643-11650 (1999).
WPI Database Accession No. 2002-090149 (2013).
WPI Database Accession No. 2002-501208 (2013).
WPI Database Accession No. 2002-501210 (2013).
WPI Database Accession No. 2002-692409 (2013).
WPI Database Accession No. 2002-714440 (2013).
Woolhouse, I. S. et al., "Endothelial interactions of neutrophils under flow in chronic obstructive pulmonary disease," Eur. Respir. J., 25:612-617 (2005).
Xie, W. et al., "Long-range structural effects of a Charcot-Marie-Tooth disease-causing mutation in human glycyl-tRNA synthetase," PNAS, 104(24):9976-9981 (2007).
Xu, Z. et al., "Internally deleted human tRNA synthetase suggest evolutionary pressure for repurposing," Structure, 20(9):1470-1477 (2012).
Yang, X-L et al., "Crystal structure of a human aminoacyl-tRNA synthetase cytokine," PNAS, 99(24):15369-15374 (2002).
Yang, X-L et al., "Relationship of two human tRNA synthetases used in cell signaling," Trends in Biochemical Sciences, 29(5):250-256 (2004).
Yang, X-L et al., "Gain-of-Function Mutational Activation of Human tRNA Synthetase Procytokine," Chemistry & Biology, 14(12):1323-1333 (2007).
Yousem, S. A. et al., "The pulmonary histopathologic manifestations of the anti-Jo-1 tRNA synthetase syndrome," Modern Pathology, 23:874-880 (2010).
Yu, Y. et al., "Crystal structure of human tryptophanyl-tRNA synthetase catalytic fragment," The Journal of Biological Chemistry, 279(9):8378-8388 (2004).
Zalipsky, S. et al., "Use of functionalized poly(ethylene glycol)s for modification of polypeptides," Polyethylene glycol chemistry: Biotechnical and Biomedical Applications, pp. 347-370, Plenum Press, New York (1992).
Zeitler et al., "Treatment of acquired hemophilia by the Bonn-Malmo Protocol: documentation of an in vivo immunomodulating concept," Blood, 105:2287-2293 (2005) [Abstract].
Zeitler et al., "Long-term effects of a multimodal approach including immunoadsorption for the treatment of myasthenic crisis," Artif. Organs, 30:597-605 (2006) [Abstract].
Zhang, L. et al., "Chemical activation of innate and specific immunity in contact dermatitis," J. Invest. Dermatol., 115:168-176 (2000).
Zhou, Q. et al., "Orthogonal use of a human tRNA synthetase active site to achieve multifunctionality," Nature Structural & Molecular Biology, 17(1):57-62 (2010).
Zillikens et al., "Treatment of severe pemphigus with protein A immunoadsorption, rituximab and intravenous immunoglobulins," Br. J. Dermatol., 158:382-388 (2008) [Abstract].
Zillikens, "Recommendations for the use of immunoapheresis in the treatment of autoimmune bullous diseases," J. Dtsch. Dermatol. Ges., 5:881-817 (2007) [Abstract].
Zwijnenburg, P. J. G. et al., B-1426, "Tyrosyl tRNA synthetase is a chemotactic factor in cerebrospinal fluid from patients with bacterial meningitis," Abstracts of the 42nd Interscience Conference on Antimicrobial Agents and Chemotherapy, San Diego, California, Sep. 27-30, 2002, Session 156(B), p. 55.
Chen et al., "Fusion protein linkers: Property, design and functionality," Adv. Drug Del. Rev., Oct. 15, 2013, vol. 65, No. 10, pp. 1357-1369.
Guo, H. H., "Protein tolerance to random amino acid change," PNAS, 101(25):9205-9210 (Jun. 22, 2004).
Matthews, B. W., "Structural and genetic analysis of protein stability," Annu. Rev. Biochem., 62:139-160 (1993).
Extended European Search Report for European Application No. 18194251.7, dated Jan. 8, 2019, 18 pages.
Friedman, A. W. et al., "Interstitial lung disease with autoantibodies against aminoacyl-tRNA synthetases in the absence of clinically apparent myositis," Semin. Arthritis Rheum. vol. 26, No. 1, Aug. 1, 1996, pp. 459-467.
Mertsching, E. et al., "Identification of a T cell immunomodulatory domain in histidyl-tRNA synthetase," Poster Presentation, aTyr Pharma, San Diego, CA, May 2, 2018, 1 page.
Mertsching, E. et al., "Identification of a T cell immunomodulatory domain in histidyl-tRNA synthetase," Journal of Immunology, vol. 200, No. 1, Supplement 1, 105th Annual Meeting of the American Association of Immunologists, Austin, TX, Abstract, May 2018, 1 page.
Ogilvie, K. et al., "ATYR1923 ameliorates dermal and pulmonary fibrosis in a murine model of sclerodermatous chronic graft vs. host disease," Poster presented at the Scleroderma Foundation National Patient Education Conference, Jul. 27-29, 2018, Philadelphia, PA, 1 page.
Paz, S. et al., "ATYR1923 reduces neutrophil infiltration in an acute lipopolysaccharide (LPS) lung injury model," Keystone Symposia 2019 Conference in Santa Fe, New Mexico, Feb. 24-28, 2019, 1 page.

(56) References Cited

OTHER PUBLICATIONS

Extended European Search Report for European Application No. 17169885.5, dated Oct. 6, 2017, 6 pages.
Supplementary European Search Report for European Application No. 15152652.2, dated Sep. 11, 2015.
Extended European Search Report for European Application No. 17189334.0, dated Jan. 23, 2018, 9 pages.
Belikov, V. G., "Dependency between the molecule structure of compounds and their effect on a body," Pharmaceutical Chemistry, In two parts, General Pharmaceutical Chemistry, Second Edition, Revised supplemented, Moscow, Vyshaya shkola, 1993.
Bergoin, C. et al., "The anti-synthetase syndrome," Rev. Mal. Respir. Jun. 2002; 19(3):371-374 (English Abstract).
Mahler, M. et al., "Idiopathic inflammatory myopathies and the anti-synthetase syndrome: A comprehensive review," Autoimmun. Rev. 2014; 13(0):367-371.
Diagnostic Automation / Cortez Diagnostics, Inc., "AccuDiag Jo-1 ELISA Kit," Cat# 2570-2, Sep. 14, 2014, XP055265960, Retrieved from the Internet: URL:http://www.rapidtest.com/pdf/Jo-1_2570-2(Sep. 14, 2015).pdf [retrieved on Apr. 15, 2016].
"D-Lactic Acid Production by Metabolically Engineered *Saccharomyces cereyisiae*," JBB, 101(2):172-177 (2006).
Fowler, S. B. et al., "Rational design of aggregation-resistant bioactive peptides: Reengineering human calcitonin," PNAS, 102(29):10105-10110 (Jul. 19, 2005).
Grant, G. A., "Synthetic Peptides for Production of Antibodies that Recognize Intact Proteins," Unit 9.2, Current Protocols in Immunology (2003) Supplement 55, 9.2.1-9.2.19.
GenBank Accession No. AK303778, *Home sapiens* cDNA FLJ58562 complete cds, EC6.1.1.21, Jul. 24, 2008, www.ncbi.nlm.nih.gov/nuccore/AK303778, 2 pages.
Hu, J. et al., "Matrix metalloproteinase inhibitors as therapy for inflammatory and vascular diseases," Nature Reviews, Drug Discovery, vol. 6, Jun. 2007, pp. 480-498.
Ito, H., "Anti-interleukin-6 therapy for Crohn's disease," Curr. Pharm. Des., 9(4):295-305 (2003) (Abstract).
Jackson, N. E. et al., "Alternate mRNA Splicing in Multiple Human Tryptase Genes Is Predicted to Regulate Tetramer Formation," J. Biol. Chem., vol. 283, No. 49, pp. 34178-34187 (Dec. 2008).
Japanese Abstract, Oct. 6, 2006, vol. 314, No. 5796, Science Japanese Edition, [retrieved on Dec. 4, 2015], Retrieved from the Internet, URL<http://www.sciencemag.jp/archive-2006-8/general/science/06/2006_10_6/sci_jsumm.htm>.
Jia, J. et al., "WHEP Domains Direct Noncanonical Function of Glutamyl-Prolyl tRNA Synthetase in Translational Control of Gene Expression," Molecular Cell, 29(6):679-690 (2008).
Jiten, S., Biochemical Dictionary, (1998), 3rd Ed., Second print, p. 696, "signal transduction".
Kajiura, S. et al., "Establishment and Characterization of Monoclonal and Polyclonal Antibodies Against Human Intestinal Fatty Acid-Binding Protein (I-FABP) using Synthetic Regional Peptides and Recombinant I-FABP," Journal of Immunoassay and Immunochemistry, 29(1):19-41 (2007).
Kim, T. et al., "Catalytic Peptide of Human Glutaminyl-tRNA Synthetase Is Essential for Its Assembly to the Aminoacyl-tRNA Synthetase Complex," Journal of Biological Chemistry, 275(28):21768-21772 (2000).
Ko, Y-G. et al., "Glutamine-dependent Antiapoptotic Interaction of Human Glutaminyl-tRNA Synthetase with Apoptosis Signal-regulating Kinase 1," Journal of Biological Chemistry, 276(8):6030-6036 (2001).
Almagro, J. C. et al., "Humanization of Antibodies," Frontiers in Bioscience, 13:1619-1633 (Jan. 2008).
De Genst, E. D. et al., "Antibody Repertoire Development in Camelids," Developmental and Comparative Immunology, 30:187-198 (2006).
Koh, Y. T. et al., "Role of Nucleic Acid-Sensing TLR's in Diverse Autoantibody Specifics and Anti-Nuclear Antibody-Producing B Cells," J Immunol., vol. 190(10):4982-4990, May 15, 2013.
Yoshinaga, K. et al., "Ig L-chain Shuffling for Affinity Maturation of Phage Library-derived Human Antihuman MCP-1 Antibody Blocking its Chemotactic Activity," J. Biochem., 143:593-601 (2008).
Kiely, P. D. W. et al., "Serum skeletal troponin I in inflammatory muscle disease: relation to creatine kinase, CKMB and cardiac troponin I," Letters to the Editor, Ann. Rheum. Dis., 2000;59:750-751.
Li, H. et al., "Tumor Necrosis Factor-related Weak Inducer of Apoptosis Augments Matrix Metalloproteinase 9 (MMP-9) Production in Skeletal Muscle through the Activation of Nuclear Factor-κB-inducing Kinase and p38 Mitogen-activated Protein Kinase: A potential role of MMP-9 in Myopathy," Journal of Biological Chemistry, 284(7):4439-4450 (Feb. 2009).
Mileti, L. M. et al., "Clinical Characteristics of Patients With Anti-Jo-1 Antibodies," Journal of Clinical Rheumatology, 15(5):254-255 (Aug. 2009).
Moore, B. A. et al., "Matrix Metalloproteinase-9 Inhibition Reduces Inflammation and Improves Motility in Murine Models of Postoperative Ileus," Gastroenterology, 141(4):1283-1292 (Jun. 2011).
Nameki, N. et al., Accession 1X59, "Chain A, Solution Structures of the WHEP-TRS Domain of Human Histidyl-TRNA Synthetase," May 15, 2015, 2 pages.
Ng, P. C. et al., "Predicting the effects of amino acid substitutions on protein function," Annu. Rev. Genomics Hum. Genet., 7:61-80 (2006).
Nishimoto, N. et al., "2-3). Anticytokine therapy in autoimmune diseases," Internal Medicine, 38(2):178-182 (Feb. 1999).
Ogilvie et al., "Resokine modulates immune cell infiltration into the lung and provides therapeutic activity in a bleomycin-induced lung fibrosis model," American Journal of Respiratory and Critical Care Medicine, vol. 195, p. A6428 (May 2017).
Ogilvie, K. et al., "Preclinical Characterization of ATYR1923 (iMod.Fc), an Immune-Modulatory Therapeutic with Potentially Broad Application in Interstitial Lung Diseases," (May 2018), Retrieved from the Internet Sep. 28, 2019: <https://wvvw.atyrpharma.com/wp-content/uploads/2019/01/Exh99.1-ATS-2018.pdf>, 1 page.
Pottle et al., "Management of acute antibody-mediated rejection after heart transplantation," Brit. J. Transplant., 2:10-15 (2007).
Roguin, L. P. et al., "Monoclonal Antibodies Inducing Conformational Changes on the Antigen Molecule," Scand. J. Immunol., vol. 58, pp. 387-394 (2003).
Rosenbaum, R. S. et al., "Structure of a B2-Adrenergic Receptor," vol. 318, No. 5854, Nov. 23, 2007, Science Japanese Edition, [retrieved on Dec. 4, 2015], Retrieved from the Internet, URL, <http://www.sciencemag.jp/archive-2006-8/general/science/07/2007_11_23/sci_jap.html>.
Rubtsov, A., et al., "TLR7 Drives Accumulation of ABC's and Autoantibody Production in Autoimmune-prone Mice," Immonol Res. Mar. 2013, vol. 55(0); 210-216, 12 pages.
Safdari, Y. et al., "Antibody humanization methods—a review and update," Biotechnology and Genetic Engineering Reviews, vol. 29, No. 2, pp. 175-186 (2013).
Scheper, G. C. et al., "Mitochondrial aspartyl-tRNA synthetase deficiency causes leukoencephalopathy with brain stem and spinal cord involvement and lactate elevation," Nat. Genet., vol. 39, No. 4, pp. 534-539 (Apr. 2007).
Schray, B. et al., "Glutaminyl-tRNA synthetase as a component of the high-molecular weight complex of human aminoacyl-tRNA synthetases. An immunological study," Biochimica et Biophysica Acta, 1087(2):226-234 (1990).
Simpson, J. A. et al., "Differential detection of skeletal troponin I isoforms in serum of a patient with rhabdomyolysis: Markers of muscle injury?", Clinical Chemistry, 48(7):1112-1114 (Jul. 2002).
Sorichter, S. et al., "Skeletal troponin I as a marker of exercise-induced muscle damage," Journal of Applied Physiology, 83(4):1076-1082 (Jan. 1997).
Targoff, I. N. et al., "Reaction of Anti-OJ Autoantibodies with Components of the Multi-enzyme Complex of Aminoacyl-tRNA Synthetases in Addition to Isoleucyl-tRNA Synthetases in Addition to Isoleucyl-tRNA Synthetase," Journal of Clinical Investigation, 91:2556-2564 (1993).

(56) References Cited

OTHER PUBLICATIONS

"Theoretical pl/Mw (average) for the user-entered sequence," ExPASy, Computepl/Mw tool, [retrieved on Jan. 27, 2016], [online], URL: <http://web.expasy.org/compute_pi/>.

Vassallo, J. D. et al., "Biomarkers of Drug-Induced Skeletal Muscle Injury in the Rat: Troponin I and Myoglobin," Toxicological Sciences, 111(2):402-412 (Jul. 2009).

Vennepureddy, A. et al., "Novel drugs and combination therapies for the treatment of metastatic melanoma," J. Clin. Med. Res. 8(2):63-75 (2016).

Gomard-Mennesson, E. et al., "Clinical significance of anti-histidyl-tRNA synthetase (Jo1) autoantibodies," Ann N Y Acad Sci. Aug. 2007;1109:414-420.

GenBank: NP_002100.2; "Histidine—tRNA ligase, cytoplasmic isoform 1 [*Homo sapiens*]," Publication Date: Nov. 20, 2011.

Stone, K. B. et al., "Anti-Jo-1 antibody levels correlate with disease activity in idiopathic inflammatory myopathy," Arthritis and Rheumatism, 56(9), 3125-3131 (2007).

Artificial Organs, 1983, vol. 12, No. 5, pp. 895-907.

Oka, K. et al., "Development of specific immunoadsorbent containing immobilized synthetic peptide of acetylcholine receptor for treatment of myasthenia gravis," Jpn. J. Artificial Organs, 1983, vol. 22, No. 1, pp. 194-197 (with English Abstract).

Oka, K. et al., "Study on the characteristics of adsorption in a specific immunoadsorbent containing immobilized synthetic peptide of acetylcholine receptor," Jpn J. Artificial Organs, 1995, vol. 24, No. 3, pp. 788-791 (with English Abstract).

Von Luettichau, I. et al., "Rantes chemokine expression in diseased and normal human tissues," Cytokine, vol. 8, No. 1, pp. 89-98 (Jan. 1996).

Han, J-H et al., "Macrophage inflammatory protein-1α is an osteoclastogenic factor in myeloma that is independent of receptor activator of nuclear factor κB ligand," Blood, vol. 97, No. 11 pp. 3349-3353 (Jun. 2001).

Hashimoto, T. et al., "Ability of myeloma cells to secrete macrophage inflammatory protein (MIP)-1α and MIP-1β correlates with lytic bone lesions in patients with multiple myeloma," British Journal of Haematology, vol. 125, No. 1, pp. 38-41 (Apr. 2004).

Doan, H. Q. et al., "Toll-like Receptor 4 Activation Increases Akt Phosphorylation in Colon Cancer Cells," Anticancer Research, vol. 29, No. 7, pp. 2473-2478 (Jul. 2009).

Eriani, G. et al., "Cytoplasmic aspartyl-tRNA synthetase from *Saccharomyces cerevisiae*. Study of its functional organisation by deletion analysis," European Journal of Biochemistry, 200(2):337-343 (1991).

Branden et al., "Introduction to Protein Structure," Garland Publishing Inc., New York, p. 247 (1991).

Extended European Search Report for European Application No. 17876227.4, dated Jun. 3, 2020, 9 pages.

International Search Report and Written Opinion for International Application No. PCT/US2017/064025, dated Jul. 9, 2018, 18 pages.

International Search Report and Written Opinion for International Application No. PCT/US2018/028417, dated Sep. 11, 2018, 14 pages.

International Search Report and Written Opinion for International Application No. PCT/US2019/026128, dated Aug. 12, 2019, 12 pages.

International Search Report and Written Opinion for International Application No. PCT/US2019/043755, dated Dec. 6, 2019, 14 pages.

Datson, N. A. et al., "Development of the first marmoset-specific DNA microarray (EUMAMA): a new genetic tool for large-scale expression profiling in a non-human primate," BMC Genomics, 8(190):1-9 (2007).

Park, S. G. et al., "Human lysyl-tRNA syntetase is secreted to trigger proinflammatory response," PNAS, 102(18):6356-6361 (2005).

Appleton, B. A. et al., "Structural studies of neuropilin/antibody complexes provide insights into semaphorin and VEGF binding," The EMBO Journal, 26(23):4902-4912 (Nov. 2007).

Zhu, J., et al., "Toll-Like Receptor Signaling Pathways—Therapeutic Opportunities," Hindawa Publishing Corporation, Mediators of Inflammation, vol. 2010, Article ID 781235, Mar. 2010, 7 pages.

| | |
|---|---|
| CCR5 | GATA3 |
| CD11B | IKZF2 |
| CD14 | ITGAL |
| CD18 | LTA |
| CD19 | MS4A1 |
| CD28 | PRF1 |
| CD3E | PTPRC |
| CD4 | IL12RB1 |
| CD56 | IL12RB2 |
| CD8a | IL2ra |
| CD8B | IL7r |
| EMR1 | KIT |
| FOXP3 | SDC1 |

A

B

| | |
|---|---|
| Atp2a1 | Ikbkb |
| Camk2g | Mapk1 |
| Capn3 | Mb |
| Cav3 | Myh2 |
| Cs | Neb |
| Dag1 | Pdk4 |
| Dysf | Rps6kb1 |
| Emd | Tnnc1 |
| Hk2 | Tnnt1 |

B

C

| | |
|---|---|
| Acta1 | Mbnl1 |
| Acvr2b | Mef2a |
| Adrb2 | Mef2c |
| Agrn | Mstn |
| Bcl2 | Musk |
| Bmp4 | Myf5 |
| Cast | Myf6 |
| Cav1 | Myod1 |
| Ctnnb1 | Myog |
| Dmd | Pax3 |
| Hdac5 | Ppp3ca |
| Igf1 | Rhoa |
| Igf2 | Tgfb1 |
| Igfbp3 | Utrn |
| Igfbp5 | |

H

HISTIDYL-TRNA SYNTHETASE-FC CONJUGATES

CROSS-REFERENCE TO RELATED APPLICATIONS

This application is a Continuation of U.S. application Ser. No. 16/577,992, filed Sep. 20, 2019, which is a Continuation of U.S. application Ser. No. 16/122,231, filed Sep. 5, 2018; which is a Continuation of U.S. application Ser. No. 15/415,369, filed Jan. 25, 2017, now U.S. Pat. No. 10,093,915, issued on Oct. 9, 2018; which is a Continuation of U.S. application Ser. No. 14/214,491, filed Mar. 14, 2014, now U.S. Pat. No. 9,587,235, issued on Mar. 7, 2017; which claims priority under 35 U.S.C. § 119(e) to U.S. Provisional Application No. 61/789,011, filed Mar. 15, 2013, each of which is hereby incorporated by reference in its entirety.

STATEMENT REGARDING SEQUENCE LISTING

The Sequence Listing associated with this application is provided in text format in lieu of a paper copy, and is hereby incorporated by reference into the specification. The name of the text file containing the Sequence Listing is ATYR_116_05 US_ST25.txt. The text file is about 400 KB, was created on Apr. 7, 2020, and is being submitted electronically via EFS-Web.

BACKGROUND

Technical Field

The present invention relates generally to conjugates, such as fusion polypeptides, of one or more histidyl-tRNA synthetase (HRS) polypeptide(s) and immunoglobulin Fc region(s), compositions comprising the same, and methods of using such polypeptides and compositions for treating or diagnosing a variety of conditions.

Description of the Related Art

Physiocrines are generally small, naturally-occurring protein domains found in the aminoacyl-tRNA synthetases (AARSs) gene family of higher organisms, which are not required for the well-established role of aminoacyl-tRNA synthetases in protein synthesis. Until the Physiocrine paradigm was discovered, aminoacyl-tRNA synthetases, a family of about 20 enzymes, were known only for their ubiquitous expression in all living cells, and their essential role in the process of protein synthesis. More recent scientific findings however now suggest that aminoacyl-tRNA synthetases possess additional roles beyond protein synthesis and in fact have evolved in multicellular organisms to play important homeostatic roles in tissue physiology and disease.

Evidence for the existence of the non-canonical function of AARSs includes well defined sequence comparisons that establish that during the evolution from simple unicellular organisms to more complex life forms, AARSs have evolved to be more structurally complex through the addition of appended domains, without losing the ability to facilitate protein synthesis.

Consistent with this hypothesis, a rich and diverse set of expanded functions for AARSs have been found in higher eukaryotes, and in particular for human tRNA synthetases. This data, which is based both on the direct analysis of individual domains, as well as the discovery of mutations in genes for tRNA synthetases that are causally linked to disease, but do not affect aminoacylation or protein synthesis activity, suggests that these newly appended domains, or Physiocrines, are central to the newly acquired non-canonical functions of AARSs.

Additionally, there is increasing recognition that specific tRNA synthetases such as histidyl-tRNA synthetase (HRS) can be released or secreted from living cells and can provide important locally acting signals with immunomodulatory, chemotactic, and angiogenic properties. Direct confirmation of the role of AARS as extracellular signaling molecules has been obtained through studies showing the secretion and extracellular release of specific tRNA synthetases, as well as the direct demonstration that the addition of fragments of the tRNA synthetases comprising the newly appended domains (Physiocrines), but not other fragments lacking these domains, are active in a range of extracellular signaling pathways. These Physiocrines such as HRS represent a new and previously untapped opportunity to develop new first in class therapeutic proteins to treat human disease.

To best exploit these and other activities in therapeutic or diagnostic settings, there is a need in the art for HRS polypeptides having improved pharmacokinetic properties. These improved therapeutic forms of the HRS polypeptides enable the development of more effective therapeutic regimens for the treatment of various diseases and disorders, and require significantly less frequent administration than the unmodified proteins.

BRIEF DESCRIPTION OF THE DRAWINGS

FIG. 5A shows the treatment dosing groups which included vehicle (n=11), 0.3 mpk HRS(1-506) (n=8), 1.0 mpk HRS(1-506) (n=8), 3.0 mpk HRS(1-506) (n=8); FIG. 5B shows the results of Troponin C measurements after 15 days of treatment with statins+/−HRS(1-506) at 0.3, 1.0, and 3.0 mg/Kg. The figure shows the positive effect of HRS(1-506) in reducing statin induced troponin C induction.

FIG. 10B shows the relative changes in gene expression of statin treated animals that were also treated with HRS(1-506) compared to animals treated with statin alone.

BRIEF SUMMARY OF THE INVENTION

Figure 1:
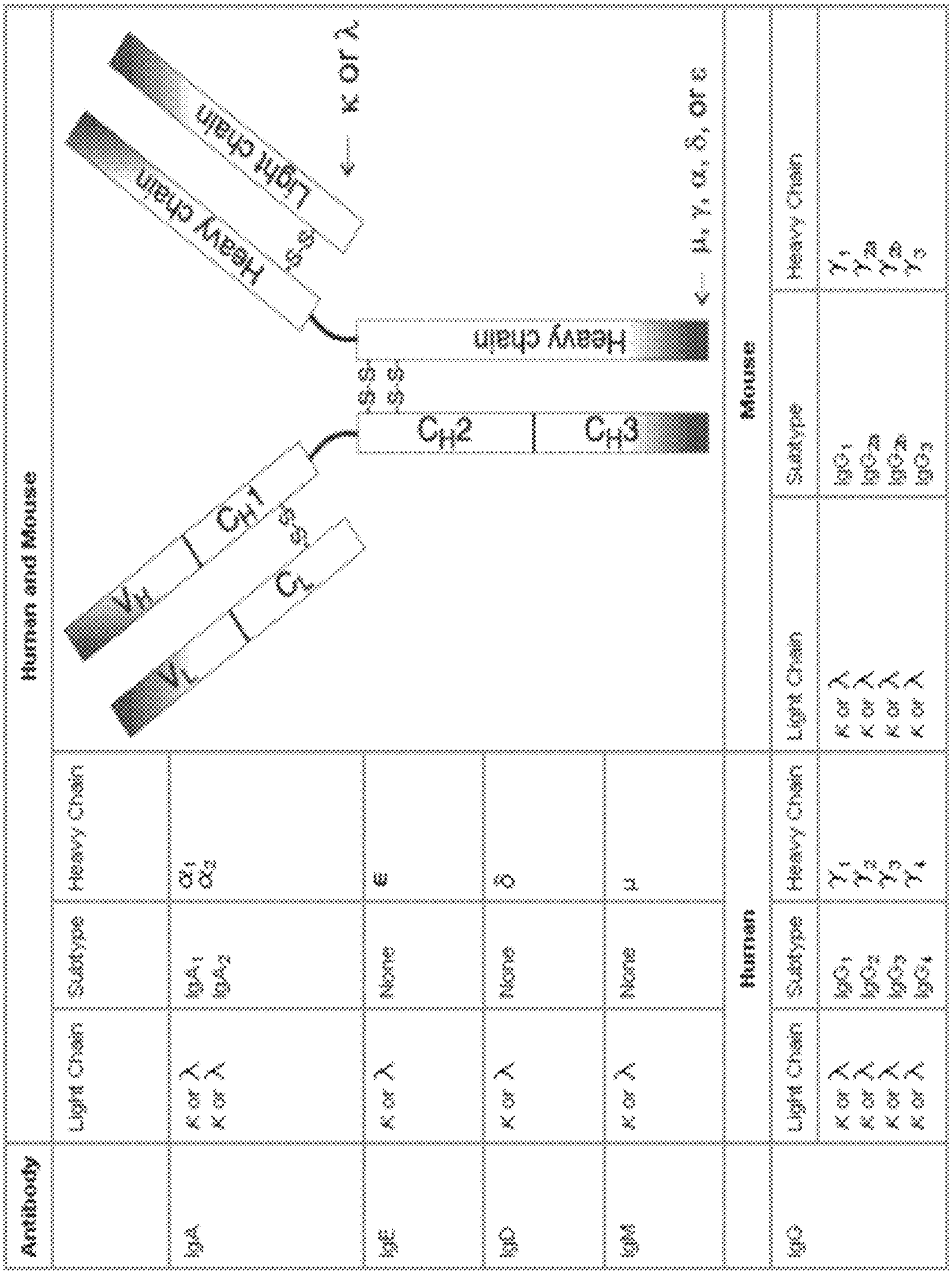
FIG. 1 illustrates the structural make-up of an exemplary immunoglobulin, and provides an overview of antibody classes and subclasses.

Embodiments of the present invention relate generally to histidyl-tRNA synthetase (HRS) polypeptide conjugates having one or more immunoglobulin Fc regions covalently attached thereto, pharmaceutical compositions comprising such molecules, methods of manufacture, and methods for their therapeutic use. Among other advantages, the HRS-Fc conjugates of the present invention can possess improved pharmacokinetic properties and/or improved therapeutically relevant biological activities, relative to corresponding, unmodified HRS polypeptides.

Certain embodiments therefore include HRS fusion polypeptides, comprising a HRS polypeptide that comprises an amino acid sequence at least 80% identical to any one of SEQ ID NOS:1-106, 170-181, or 185-191 or a sequence of any of Tables D1, D3-D6, or D8, and at least one Fc region fused to the C-terminus, the N-terminus, or both of the HRS polypeptide. In some embodiments, the HRS polypeptide comprises, consists, or consists essentially of an amino acid sequence at least 90% identical to any of SEQ ID NOS:1-106, 170-181, or 185-191 or a sequence of any of Tables D1, D3-D6, or D8. In particular embodiments, the HRS polypeptide comprises, consists, or consists essentially of an amino acid sequence of any one of SEQ ID NOS:1-106, 170-181, or 185-191 or a sequence of any of Tables D1, D3-D6, or D8.

In particular embodiments, the HRS polypeptide comprises amino acid residues 2-40, 2-45, 2-50, 2-55, 2-60, 2-66, or 1-506 of SEQ ID NO:1, or an amino acid sequence at least 90% identical to residues 2-40, 2-45, 2-50, 2-55, 2-60, 2-66, or 1-506 of SEQ ID NO: 1. In some embodiments, the HRS polypeptide is up to about 40-80 amino acids in length and comprises residues 2-45 of SEQ ID NO:1. In specific embodiments, the HRS polypeptide consists or consists essentially of amino acid residues 2-40, 2-45, 2-50, 2-55, 2-60, 2-66, or 1-506 of SEQ ID NO:1.

In some embodiments, at least one endogenous cysteine residue of the HRS polypeptide has been substituted with another amino acid or deleted. In certain embodiments, the at least one endogenous cysteine residue is selected from Cys174, Cys191, Cys224, Cys235, Cys507, and Cys509. In particular embodiments, the at least one endogenous cysteine residue is selected from Cys224, Cys235, Cys507, and Cys509. In specific embodiments, the endogenous cysteine residues are Cys507 and Cys509. In some embodiments, all endogenous surface exposed cysteine residues have been substituted with another amino acid or deleted.

In certain embodiments, the HRS polypeptide is tandemly repeated. In particular embodiments, the HRS polypeptide comprises a WHEP domain. In specific embodiments, the HRS polypeptide lacks a functional aminoacylation domain. In some embodiments, the HRS polypeptide consists essentially of a WHEP domain. In specific aspects, the WHEP domain of an HRS polypeptide or variant or fragment thereof has the consensus sequence in Table D5.

In some embodiments, the Fc region and the HRS polypeptide are separated by a peptide linker. In certain embodiments, the peptide linker is about 1-200 amino acids, 1-150 amino acids, 1-100 amino acids, 1-90 amino acids, 1-80 amino acids, 1-70 amino acids, 1-60 amino acids, 1-50 amino acids, 1-40 amino acids, 1-30 amino acids, 1-20 amino acids, 1-10 amino acids, or 1-5 amino acids in length. In particular embodiments, peptide linker is about 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 60, 70, 80, 90, or 100 amino acids in length. In certain embodiments, the peptide linker consists of Gly and/or Ser residues. In some embodiments, the peptide linker is a physiologically stable linker. In other embodiments, the peptide linker is a releasable linker, optionally an enzymatically-cleavable linker. In specific embodiments, the peptide linker comprises a sequence of any one of SEQ ID NOS:200-260, or other peptide linker described herein.

In some embodiments, the Fc region is fused to the C-terminus of the HRS polypeptide. In certain embodiments, the Fc region is fused to the N-terminus of the HRS polypeptide.

In certain embodiments, the Fc region comprises one or more of a hinge, $CH_2$, $CH_3$, and/or $CH_4$ domain from a mammalian IgA1, IgA2, IgD, IgE, IgG1, IgG2, IgG3, IgG4, and/or IgM. In some embodiments, the Fc region comprises IgG1 hinge, $CH_2$, and $CH_3$ domains. In some embodiments, the Fc region comprises IgG2 hinge, $CH_2$, and $CH_3$ domains. In some embodiments, the Fc region comprises IgG3 hinge, $CH_2$, and $CH_3$ domains. In particular embodiments, the HRS fusion polypeptide does not comprise the $CH_1$, $C_L$, $V_L$, and $V_H$ regions of an immunoglobulin.

In specific embodiments, the Fc region comprises any one of SEQ ID NOS:128-163 or 339-342, or a variant, or a fragment, or a combination thereof. In certain embodiments, the hinge domain is a modified IgG1 hinge domain that comprises SEQ ID NO:341.

In particular embodiments, the Fc region comprises an amino acid sequence at least 90% identical to

```
                                             (SEQ ID NO: 339)
MSDKTHTCPPCPAPELLGGPSVFLFPPKPKDTLMISRTPEVTCVVVDVSH

EDPEVKFNWYVDGVEVHNAKTKPREEQYNSTYRVVSVLTVLHQDWLNGKE

YKCKVSNKALPAPIEKTISKAKGQPREPQVYTLPPSREEMTKNQVSLTCL

VKGFYPSDIAVEWESNGQPENNYKTTPPVLDSDGSFFLYSKLTVDKSRWQ

QGNVFSCSVMHEALHNHYTQKSLSLSPGK
or

                                             (SEQ ID NO: 340)
SDKTHTCPPCPAPELLGGPSVFLFPPKPKDTLMISRTPEVTCVVVDVSHE

DPEVKFNWYVDGVEVHNAKTKPREEQYNSTYRVVSVLTVLHQDWLNGKEY

KCKVSNKALPAPIEKTISKAKGQPREPQVYTLPPSREEMTKNQVSLTCLV

KGFYPSDIAVEWESNGQPENNYKTTPPVLDSDGSFFLYSKLTVDKSRWQQ

GNVFSCSVMHEALHNHYTQKSLSLSPGK.
```

In certain embodiments, the HRS-Fc fusion polypeptide comprises an amino acid sequence at least 90% identical to Fc-HRS(2-60) (SEQ ID NO:337), or HRS(1-60)-Fc (SEQ ID NO:338), or Fc-HRS(2-40) (SEQ ID NO:381), or HRS (1-40)-Fc (SEQ ID NO:386), or Fc-HRS(2-45) (SEQ ID NO: 382), or HRS(1-45)-Fc (SEQ ID NO: 387), or Fc-HRS (2-50) (SEQ ID NO: 383), or HRS(1-50)-Fc (SEQ ID NO: 388), or Fc-HRS(2-55) (SEQ ID NO: 384), or HRS(1-55)-Fc (SEQ ID NO: 389), or Fc-HRS(2-66) (SEQ ID NO:385), or HRS(1-66)-Fc (SEQ ID NO:390), or Fc-HRS(2-60) HRS (2-60) (SEQ ID NO:396).

In certain instances, the HRS fusion polypeptide has altered pharmacokinetics relative to a corresponding HRS polypeptide. Examples of said altered pharmacokinetics include increased serum half-life, increased bioavailability, increased exposure, and/or decreased clearance. In certain instances, the exposure is increased by at least 100 fold. In some instances, the HRS fusion polypeptide has a half life of at least 30 hours in mice. In certain instances, the bioavailability is subcutaneous bioavailability that is increased by at least about 30%. In some instances, the HRS fusion polypeptide has altered immune effector activity relative to a corresponding HRS polypeptide. Examples of such immune effector activities include one or more of complement activation, complement-dependent cytotoxicity (CDC), antibody-dependent cell-mediated cytotoxicity (ADCC), or antibody-dependent cell-mediated phagocytosis (ADCP).

In certain embodiments, the Fc region comprises a variant Fc region, relative to a wild-type Fc region. In some embodiments, the variant Fc region comprises a sequence that is at least 90% identical to any one of SEQ ID NOS:128-163 or 341, or a combination of said sequences. In certain embodiments, the variant Fc region comprises a hybrid of one or more Fc regions from different species, different Ig classes, or different Ig subclasses. In particular embodiments, the variant Fc region comprises a hybrid of one or more hinge, $CH_2$, $CH_3$, and/or $CH_4$ domains of Fc regions from different species, different Ig classes, and/or different Ig subclasses.

In certain embodiments, the variant Fc region is a modified glycoform, relative to a corresponding, wild-type Fc region. In particular embodiments, the variant Fc region has altered pharmacokinetics relative to a corresponding, wild-type Fc region. Examples of such altered pharmacokinetics include serum half-life, bioavailability, and/or clearance. In some embodiments, the variant Fc region has altered effector activity relative to a corresponding, wild-type Fc region. Examples of such effector activities include one or more of complement activation, complement-dependent cytotoxicity (CDC), antibody-dependent cell-mediated cytotoxicity (ADCC), or antibody-dependent cell-mediated phagocytosis (ADCP).

In certain embodiments, the variant Fc region has altered binding to one or more Fcγ receptors, relative to a corresponding, wild-type Fc region. Exemplary Fcγ receptors are described herein and known in the art.

In certain embodiments, the variant Fc region has altered binding to one or more FcRn receptors, relative to a corresponding, wild-type Fc region. Exemplary FcRn receptors are described herein and known in the art.

In some embodiments, the variant Fc region has altered (e.g., increased) solubility, relative to a corresponding, wild-type Fc region, and the HRS-Fc fusion polypeptide has altered solubility, relative to a corresponding, unmodified HRS polypeptide.

In specific embodiments, the HRS-Fc fusion polypeptide is substantially in dimeric form in a physiological solution, or under other physiological conditions, such as in vivo conditions. In specific embodiments, the HRS-Fc fusion polypeptide has substantially the same secondary structure a corresponding unmodified or differently modified HRS polypeptide, as determined via UV circular dichroism analysis.

In some embodiments, the HRS-Fc fusion polypeptide has a plasma or sera pharmacokinetic AUC profile at least 5-fold greater than a corresponding, unmodified HRS polypeptide when administered to a mammal.

In certain embodiments, the HRS-Fc fusion polypeptide has substantially the same activity of a corresponding unmodified or differently modified HRS polypeptide in an assay of anti-inflammatory activity.

In certain embodiments, the HRS-Fc fusion polypeptide has greater than 2-fold the activity of a corresponding unmodified or differently modified HRS polypeptide in an assay of anti-inflammatory activity.

In certain embodiments, the HRS-Fc fusion polypeptide has a stability which is at least 30% greater than a corresponding unmodified or differently modified HRS polypeptide when compared under similar conditions at room temperature, for 7 days in PBS at pH 7.4.

Specific examples of HRS-Fc fusion polypeptides may comprise at least one of SEQ ID NO:107-110 or 337-338 or 349-350 or 381-390 or 396, or an amino acid sequence at least 80%, 90%, 95%, 98% identical to SEQ ID NO:107-110 or 337-338 or 349-350 or 381-390 or 396. SEQ ID NOS:107 and 338 are the amino acid sequences of exemplary C-terminal Fc fusion polypeptides to residues 1-60 of SEQ ID NO:1 (HRS(1-60)_Fc); SEQ ID NOS:108 and 337 are the amino acid sequences of exemplary N-terminal Fc fusion polypeptides to residues 1-60 of SEQ ID NO:1 (Fc_HRS (1-60)); SEQ ID NO:109 is the amino acid sequence of an exemplary C-terminal Fc fusion polypeptide to residues 1-506 of SEQ ID NO:1 (HRS(1-506)_Fc); and SEQ ID NO:110 is the amino acid sequence of an exemplary N-terminal Fc fusion polypeptide to residues 1-506 of SEQ ID NO:1 (Fc_HRS(1-506)).

In some embodiments, the HRS-Fc fusion polypeptide has an anti-inflammatory activity, for example, in a cell-based assay or upon administration to a subject.

Also included are compositions, for example, pharmaceutical or therapeutic compositions, comprising a HRS-Fc fusion polypeptide described herein and a pharmaceutically acceptable or pharmaceutical grade carrier or excipient. In some compositions, the polypeptide as is at least about 95% pure and less than about 5% aggregated. In some embodiments, the composition is formulated for delivery via oral, subcutaneous, intranasal, pulmonary or parental administration. In certain embodiments, the composition comprises a delivery vehicle selected from the group consisting of liposomes, micelles, emulsions, and cells.

In some embodiments, the composition is for use in a) treating an inflammatory or autoimmune disease, b) reducing muscle or lung inflammation optionally associated with an autoimmune or inflammatory disease, c) inducing tolerance to a histidyl-tRNA synthetase (HRS) autoantigen, d) eliminating a set or subset of T cells involved in an autoimmune response to a HRS autoantigen, e) reducing tissue inflammation in a subject, optionally muscle, lung, and/or skin tissue, f) treating a muscular dystrophy, g) treating rhabdomyolysis, muscle wasting, cachexia, muscle inflammation, or muscle injury, and/or h) treating a disease associated with an autoantibody.

Also included are dosing regimens which maintain an average steady-state concentration of an histidyl-tRNA synthetase (HRS)-Fc fusion polypeptide in a subject's plasma of between about 300 pM and about 1000 nM when using a dosing interval of 3 days or longer, comprising administering to the subject a therapeutic composition or HRS-Fc fusion polypeptide described herein.

Some embodiments include methods for maintaining histidyl-tRNA synthetase (HRS)-Fc fusion polypeptide levels above the minimum effective therapeutic level in a subject in need thereof, comprising administering to the subject a therapeutic composition or HRS-Fc fusion polypeptide described herein.

Also included are methods for treating an inflammatory or autoimmune disease or condition in a subject in need thereof, comprising administering to the subject a therapeutic composition or HRS-Fc fusion polypeptide described herein.

Some embodiments include methods of reducing muscle or lung inflammation associated with an autoimmune or inflammatory disease in a subject in need thereof, comprising administering to the subject a therapeutic composition or HRS-Fc fusion polypeptide described herein.

Certain embodiments include methods of inducing tolerance to a histidyl-tRNA synthetase (HRS) autoantigen in a subject in need thereof, comprising administering to the subject a therapeutic composition or HRS-Fc fusion polypeptide described herein.

Some embodiments include methods for eliminating a set or subset of T cells involved in an autoimmune response to a histidyl-tRNA synthetase (HRS) autoantigen in a subject in need thereof, comprising administering to the subject a therapeutic composition or HRS-Fc fusion polypeptide described herein.

Also included are methods of reducing tissue inflammation in a subject in need thereof, comprising administering to the subject a therapeutic composition or HRS-Fc fusion polypeptide described herein. In certain embodiments, the tissue is selected from muscle, gut, brain, lung, and skin.

Some embodiments include methods of treating a muscular dystrophy in a subject in need thereof, comprising administering to the subject a therapeutic composition or HRS-Fc fusion polypeptide described herein. In particular embodiments, the muscular dystrophy is selected from Duchenne muscular dystrophy, Becker muscular dystrophy, Emery-Dreifuss muscular dystrophy, Limb-girdle muscular dystrophy, facioscapulohumeral muscular dystrophy, myotonic dystrophy, oculopharyngeal muscular dystrophy, distal muscular dystrophy, and congenital muscular dystrophy.

Certain embodiments include methods of treating rhabdomyolysis, muscle wasting, cachexia, muscle inflammation, or muscle injury in a subject in need thereof, comprising administering to the subject a therapeutic composition or HRS-Fc fusion polypeptide described herein.

Some embodiments include methods of treating a disease associated with an autoantibody, comprising administering to a subject in need thereof a composition or AARS/HRS polypeptide described herein. In some embodiments, the disease is selected from the group consisting of inflammatory myopathies, including inflammatory myopathies, polymyositis, dermatomyositis and related disorders, polymyositis-scleroderma overlap, inclusion body myositis (IBM), anti-synthetase syndrome, interstitial lung disease, arthritis, and Reynaud's phenomenon. In some embodiments, the composition is administered to the subject prior to the appearance of disease symptoms. In some embodiments, the autoantibody is specific for histidyl-tRNA synthetase. In some embodiments, the HRS polypeptide comprises at least one epitope of the histidyl-tRNA synthetase recognized by the disease specific autoantibody. In some embodiments, the epitope is an immunodominant epitope recognized by antibodies in sera from the subject. In some embodiments, the HRS polypeptide blocks the binding of the autoantibody to native histidyl-tRNA synthetase. In some embodiments, the HRS polypeptide causes clonal deletion of auto-reactive T-cells. In some embodiments, the HRS polypeptide causes functional inactivation of the T cells involved in the autoimmune response. In some embodiments, administration of the HRS polypeptide results in reduced muscle or lung inflammation. In some embodiments, the HRS polypeptide induces tolerance to an auto-antigen.

In certain embodiments, the composition is formulated for delivery via oral, intranasal, pulmonary, intramuscular, or parental administration.

Also included are isolated polynucleotides, comprising a nucleotide sequence that encodes a HRS-Fc conjugate or fusion polypeptide described herein, including vectors that comprise such polynucleotides, and host cells that comprise said polynucleotides and/or vectors.

Some embodiments include methods for manufacturing a HRS-Fc fusion polypeptide described herein, comprising a) culturing a host cell (e.g., *E. coli* K-12 host cell) to express a HRS-Fc fusion polypeptide, wherein the host cell comprises a polynucleotide that encodes a HRS-Fc fusion polypeptide described herein, which is operably linked to a regulatory element; and b) isolating the HRS-Fc fusion polypeptide from the host cell. In specific embodiments, *E. coli* K-12 strain is selected from W3110 and UT5600.

DETAILED DESCRIPTION OF THE INVENTION

The practice of the present invention will employ, unless indicated specifically to the contrary, conventional methods of molecular biology and recombinant DNA techniques within the skill of the art, many of which are described below for the purpose of illustration. Such techniques are explained fully in the literature. See, e.g., Sambrook, et al., *Molecular Cloning: A Laboratory Manual* ($3^{rd}$ Edition, 2000); *DNA Cloning: A Practical Approach*, vol. I & II (D. Glover, ed.); *Oligonucleotide Synthesis* (N. Gait, ed., 1984); *Oligonucleotide Synthesis: Methods and Applications* (P. Herdewijn, ed., 2004); *Nucleic Acid Hybridization* (B. Hames & S. Higgins, eds., 1985); *Nucleic Acid Hybridization: Modern Applications* (Buzdin and Lukyanov, eds., 2009); *Transcription and Translation* (B. Hames & S. Higgins, eds., 1984); *Animal Cell Culture* (R. Freshney, ed., 1986); Freshney, R. I. (2005) *Culture of Animal Cells, a Manual of Basic Technique*, $5^{th}$ Ed. Hoboken N.J., John Wiley & Sons; B. Perbal, *A Practical Guide to Molecular Cloning* ($3^{rd}$ Edition 2010); Farrell, R., *RNA Methodologies: A Laboratory Guide for Isolation and Characterization* ($3^{rd}$ Edition 2005). *Poly(ethylene glycol), Chemistry and Biological Applications*, ACS, Washington, 1997; Veronese, F., and J. M. Harris, Eds., *Peptide and protein PEGylation, Advanced Drug Delivery Reviews,* 54(4) 453-609 (2002); Zalipsky, S., et al., "*Use of functionalized Poly(Ethylene Glycols) for modification of polypeptides*" in Polyethylene Glycol Chemistry: Biotechnical and Biomedical Applications.

All publications, patents and patent applications cited herein are hereby incorporated by reference in their entirety.

Definitions

Unless defined otherwise, all technical and scientific terms used herein have the same meaning as commonly understood by those of ordinary skill in the art to which the invention belongs. Although any methods and materials similar or equivalent to those described herein can be used in the practice or testing of the present invention, preferred methods and materials are described. For the purposes of the present invention, the following terms are defined below.

The articles "a" and "an" are used herein to refer to one or to more than one (i.e., to at least one) of the grammatical object of the article. By way of example, "an element" means one element or more than one element.

By "about" is meant a quantity, level, value, number, frequency, percentage, dimension, size, amount, weight or length that varies by as much as 30, 25, 20, 15, 10, 9, 8, 7, 6, 5, 4, 3, 2 or 1% to a reference quantity, level, value, number, frequency, percentage, dimension, size, amount, weight or length.

As used herein, the term "amino acid" is intended to mean both naturally occurring and non-naturally occurring amino acids as well as amino acid analogs and mimetics. Naturally occurring amino acids include the 20 (L)-amino acids utilized during protein biosynthesis as well as others such as 4-hydroxyproline, hydroxylysine, desmosine, isodesmosine, homocysteine, citrulline and ornithine, for example. Non-naturally occurring amino acids include, for example, (D)-amino acids, norleucine, norvaline, p-fluorophenylalanine, ethionine and the like, which are known to a person skilled in the art. Amino acid analogs include modified forms of naturally and non-naturally occurring amino acids. Such modifications can include, for example, substitution or replacement of chemical groups and moieties on the amino acid or by derivatization of the amino acid. Amino acid mimetics include, for example, organic structures which exhibit functionally similar properties such as charge and charge spacing characteristic of the reference amino acid. For example, an organic structure which mimics arginine (Arg or R) would have a positive charge moiety located in similar molecular space and having the same degree of mobility as the e-amino group of the side chain of the naturally occurring Arg amino acid. Mimetics also include constrained structures so as to maintain optimal spacing and charge interactions of the amino acid or of the amino acid functional groups. Those skilled in the art know or can determine what structures constitute functionally equivalent amino acid analogs and amino acid mimetics.

As used herein, a subject "at risk" of developing a disease or adverse reaction may or may not have detectable disease, or symptoms of disease, and may or may not have displayed detectable disease or symptoms of disease prior to the treatment methods described herein. "At risk" denotes that a subject has one or more risk factors, which are measurable parameters that correlate with development of a disease, as described herein and known in the art. A subject having one or more of these risk factors has a higher probability of developing disease, or an adverse reaction than a subject without one or more of these risk factor(s).

An "autoimmune disease" as used herein is a disease or disorder arising from and directed against an individual's own tissues. Examples of autoimmune diseases or disorders include, but are not limited to, inflammatory responses such as inflammatory skin diseases including psoriasis and dermatitis (e.g., atopic dermatitis); systemic scleroderma and sclerosis; responses associated with inflammatory bowel disease (such as Crohn's disease and ulcerative colitis); respiratory distress syndrome (including adult respiratory distress syndrome; ARDS); dermatitis; meningitis; encephalitis; uveitis; colitis; glomerulonephritis; allergic conditions such as eczema and asthma and other conditions involving infiltration of T cells and chronic inflammatory responses; atherosclerosis; leukocyte adhesion deficiency; rheumatoid arthritis; systemic lupus erythematosus (SLE); diabetes mellitus (e.g., Type I diabetes mellitus or insulin dependent diabetes mellitus); multiple sclerosis; Reynaud's syndrome; autoimmune thyroiditis; allergic encephalomyelitis; Sjorgen's syndrome; juvenile onset diabetes; and immune responses associated with acute and delayed hypersensitivity mediated by cytokines and T-lymphocytes typically found in tuberculosis, sarcoidosis, polymyositis, inflammatory myopathies, interstitial lung disease, granulomatosis and vasculitis; pernicious anemia (Addison's disease); diseases involving leukocyte diapedesis; central nervous system (CNS) inflammatory disorder; multiple organ injury syndrome; hemolytic anemia (including, but not limited to cryoglobinemia or Coombs positive anemia); myasthenia gravis; antigen-antibody complex mediated diseases; anti-glomerular basement membrane disease; antiphospholipid syndrome; allergic neuritis; Graves' disease; Lambert-Eaton myasthenic syndrome; pemphigoid bullous; pemphigus; autoimmune polyendocrinopathies; Reiter's disease; stiff-man syndrome; Behcet disease; giant cell arteritis; immune complex nephritis; IgA nephropathy; IgM polyneuropathies; immune thrombocytopenic purpura (ITP) or autoimmune thrombocytopenia, etc.

Throughout this specification, unless the context requires otherwise, the words "comprise," "comprises," and "comprising" will be understood to imply the inclusion of a stated step or element or group of steps or elements but not the exclusion of any other step or element or group of steps or elements. By "consisting of" is meant including, and limited to, whatever follows the phrase "consisting of" Thus, the phrase "consisting of" indicates that the listed elements are required or mandatory, and that no other elements may be present. By "consisting essentially of" is meant including any elements listed after the phrase, and limited to other elements that do not interfere with or contribute to the activity or action specified in the disclosure for the listed elements. Thus, the phrase "consisting essentially of" indicates that the listed elements are required or mandatory, but that other elements are optional and may or may not be present depending upon whether or not they materially affect the activity or action of the listed elements.

The term "clonal deletion" refers to the deletion (e.g., loss, or death) of auto-reactive T-cells. Clonal deletion can be achieved centrally in the thymus, or in the periphery, or both.

The term "conjugate" is intended to refer to the entity formed as a result of covalent attachment of a molecule, e.g., a biologically active molecule (e.g., HRS polypeptide), to an immunoglobulin Fc region. One example of a conjugate polypeptide is a "fusion protein" or "fusion polypeptide," that is, a polypeptide that is created through the joining of two or more coding sequences, which originally coded for separate polypeptides; translation of the joined coding sequences results in a single, fusion polypeptide, typically with functional properties derived from each of the separate polypeptides.

The recitation "endotoxin free" or "substantially endotoxin free" relates generally to compositions, solvents, and/or vessels that contain at most trace amounts (e.g., amounts having no clinically adverse physiological effects to a subject) of endotoxin, and preferably undetectable amounts of endotoxin. Endotoxins are toxins associated with certain bacteria, typically gram-negative bacteria, although endotoxins may be found in gram-positive bacteria, such as *Listeria monocytogenes*. The most prevalent endotoxins are lipopolysaccharides (LPS) or lipo-oligo-saccharides (LOS) found in the outer membrane of various Gram-negative bacteria, and which represent a central pathogenic feature in the ability of these bacteria to cause disease. Small amounts of endotoxin in humans may produce fever, a lowering of the blood pressure, and activation of inflammation and coagulation, among other adverse physiological effects.

Therefore, in pharmaceutical production, it is often desirable to remove most or all traces of endotoxin from drug products and/or drug containers, because even small amounts may cause adverse effects in humans. A depyrogenation oven may be used for this purpose, as temperatures in excess of 300° C. are typically required to break down most endotoxins. For instance, based on primary packaging material such as syringes or vials, the combination of a glass temperature of 250° C. and a holding time of 30 minutes is often sufficient to achieve a 3 log reduction in endotoxin levels. Other methods of removing endotoxins are contemplated, including, for example, chromatography and filtration methods, as described herein and known in the art. Also included are methods of producing HRS-Fc conjugates in and isolating them from eukaryotic cells such as mammalian cells to reduce, if not eliminate, the risk of endotoxins being present in a composition of the invention. Preferred are methods of producing HRS-Fc conjugates in and isolating them from serum free cells.

Endotoxins can be detected using routine techniques known in the art. For example, the Limulus Amoebocyte Lysate assay, which utilizes blood from the horseshoe crab, is a very sensitive assay for detecting presence of endotoxin. In this test, very low levels of LPS can cause detectable coagulation of the limulus lysate due a powerful enzymatic cascade that amplifies this reaction. Endotoxins can also be quantitated by enzyme-linked immunosorbent assay (ELISA). To be substantially endotoxin free, endotoxin levels may be less than about 0.001, 0.005, 0.01, 0.02, 0.03, 0.04, 0.05, 0.06, 0.08, 0.09, 0.1, 0.5, 1.0, 1.5, 2, 2.5, 3, 4, 5, 6, 7, 8, 9, or 10 EU/ml. Typically, 1 ng lipopolysaccharide (LPS) corresponds to about 1-10 EU.

As used herein, the terms "function" and "functional" and the like refer to a biological, enzymatic, or therapeutic function.

"Homology" refers to the percentage number of amino acids that are identical or constitute conservative substitutions. Homology may be determined using sequence comparison programs such as GAP (Deveraux et al., *Nucleic Acids Research.* 12, 387-395, 1984), which is incorporated herein by reference. In this way sequences of a similar or substantially different length to those cited herein could be compared by insertion of gaps into the alignment, such gaps being determined, for example, by the comparison algorithm used by GAP.

A "physiologically stable" linker refers to a linker that is substantially stable in water or under physiological conditions (e.g., in vivo, in vitro culture conditions, for example, in the presence of one or more proteases), that is to say, it does not undergo a degradation reaction (e.g., enzymatically degradable reaction) under physiological conditions to any appreciable extent over an extended period of time. Generally, a physiologically stable linker is one that exhibits a rate of degradation of less than about 0.5%, about 1%, about 2%, about 3%, about 4%, or about 5% per day under physiological conditions.

By "isolated" is meant material that is substantially or essentially free from components that normally accompany it in its native state. For example, an "isolated peptide" or an "isolated polypeptide" and the like, as used herein, includes the in vitro isolation and/or purification of a peptide or polypeptide molecule from its natural cellular environment, and from association with other components of the cell; i.e., it is not significantly associated with in vivo substances.

The term "half maximal effective concentration" or "$EC_{50}$" refers to the concentration of a HRS-Fc conjugate described herein at which it induces a response halfway between the baseline and maximum after some specified exposure time; the $EC_{50}$ of a graded dose response curve therefore represents the concentration of a compound at which 50% of its maximal effect is observed. In certain embodiments, the $EC_{50}$ of an agent provided herein is indicated in relation to a "non-canonical" activity, as noted above. $EC_{50}$ also represents the plasma concentration required for obtaining 50% of a maximum effect in vivo. Similarly, the "$EC_{90}$" refers to the concentration of an agent or composition at which 90% of its maximal effect is observed. The "$EC_{90}$" can be calculated from the "$EC_{50}$" and the Hill slope, or it can be determined from the data directly, using routine knowledge in the art. In some embodiments, the $EC_{50}$ of a HRS-Fc conjugate is less than about 0.01, 0.05, 0.1, 0.2, 0.3, 0.4, 0.5, 0.6, 0.7, 0.8, 0.9, 1, 2, 3, 4, 5, 6, 7, 8, 9, 10, 11, 12, 13, 14, 15, 16, 17, 18, 19, 20, 25, 30, 40, 50, 60, 70, 80, 90, or 100 nM. Preferably, biotherapeutic composition will have an $EC_{50}$ value of about 1 nM or less.

The "half-life" of a HRS-Fc conjugate can refer to the time it takes for the conjugate to lose half of its pharmacologic, physiologic, or other activity, relative to such activity at the time of administration into the serum or tissue of an organism, or relative to any other defined time-point. "Half-life" can also refer to the time it takes for the amount or concentration of a HRS-Fc conjugate to be reduced by half of a starting amount administered into the serum or tissue of an organism, relative to such amount or concentration at the time of administration into the serum or tissue of an organism, or relative to any other defined time-point. The half-life can be measured in serum and/or any one or more selected tissues.

The term "linkage," "linker," "linker moiety," or "L" is used herein to refer to a linker that can be used to separate a HRS polypeptides from another HRS polypeptide and/or from one or more Fc regions. The linker may be physiologically stable or may include a releasable linker such as an enzymatically degradable linker (e.g., proteolytically cleavable linkers). In certain aspects, the linker may be a peptide linker, for instance, as part of a HRS-Fc fusion protein. In some aspects, the linker may be a non-peptide linker.

The terms "modulating" and "altering" include "increasing," "enhancing" or "stimulating," as well as "decreasing" or "reducing," typically in a statistically significant or a physiologically significant amount or degree relative to a control. An "increased," "stimulated" or "enhanced" amount is typically a "statistically significant" amount, and may include an increase that is 1.1, 1.2, 2, 3, 4, 5, 6, 7, 8, 9, 10, 15, 20, 30 or more times (e.g., 500, 1000 times) (including all integers and decimal points in between and above 1, e.g., 1.5, 1.6, 1.7, 1.8, etc.) the amount produced by no composition (e.g., in the absence of any of the HRS-Fc conjugates of the invention) or a control composition, sample or test subject. A "decreased" or "reduced" amount is typically a "statistically significant" amount, and may include a 1%, 2%, 3%, 4%, 5%, 6%, 7%, 8%, 9%, 10%, 11%, 12%, 13%, 14%, 15%, 16%, 17%, 18%, 19%, 20%, 25%, 30%, 35%, 40%, 45%, 50%, 55%, 60%, 65%, 70%, 75%, 80%, 85%, 90%, 95%, or 100% decrease in the amount produced by no composition (the absence of an agent or compound) or a control composition, including all integers in between. As one non-limiting example, a control in comparing canonical and non-canonical activities could include the HRS-Fc conjugate of interest compared to a corresponding (sequence-wise), unmodified or differently modified HRS polypeptide. Other examples of comparisons and "statistically significant" amounts are described herein.

"Non-canonical" activity as used herein, refers generally to either i) a new, non-aminoacylation activity possessed by HRS polypeptide of the invention that is not possessed to any significant degree by the intact native full length parental protein, or ii) an activity that was possessed by the by the intact native full length parental protein, where the HRS polypeptide either exhibits a significantly higher (e.g., at least 20% greater) specific activity with respect to the non-canonical activity compared to the intact native full length parental protein, or exhibits the activity in a new context; for example by isolating the activity from other activities possessed by the intact native full length parental protein. In the case of HRS polypeptides, non-limiting examples of non-canonical activities include extracellular signaling including the modulation of cell proliferation, modulation of cell migration, modulation of cell differentiation (e.g., hematopoiesis, neurogenesis, myogenesis, osteogenesis, and adipogenesis), modulation of gene transcription, modulation of apoptosis or other forms of cell death, modulation of cell signaling, modulation of cellular uptake, or secretion, modulation of angiogenesis, modulation of cell binding, modulation of cellular metabolism, modulation of cytokine production or activity, modulation of cytokine receptor activity, modulation of inflammation, immunogenicity, and the like.

In certain embodiments, the "purity" of any given agent (e.g., HRS-Fc conjugate such as a fusion protein) in a composition may be specifically defined. For instance, certain compositions may comprise an agent that is at least 80, 85, 90, 91, 92, 93, 94, 95, 96, 97, 98, 99, or 100% pure, including all decimals in between, as measured, for example and by no means limiting, by high pressure liquid chromatography (HPLC), a well-known form of column chromatography used frequently in biochemistry and analytical chemistry to separate, identify, and quantify compounds.

Without wishing to be bound to any particular theory, an "enzymatically degradable linker" means a linker, e.g., amino acid sequence that is subject to degradation by one or more enzymes, e.g., peptidases or proteases.

The terms "polypeptide" and "protein" are used interchangeably herein to refer to a polymer of amino acid residues and to variants and synthetic analogues of the same. Thus, these terms apply to amino acid polymers in which one or more amino acid residues are synthetic non-naturally occurring amino acids, such as a chemical analogue of a corresponding naturally occurring amino acid, as well as to naturally-occurring amino acid polymers.

A "releasable linker" includes, but is not limited to, a physiologically cleavable linker and an enzymatically degradable linker. Thus, a "releasable linker" is a linker that may undergo either spontaneous hydrolysis, or cleavage by some other mechanism (e.g., enzyme-catalyzed, acid-catalyzed, base-catalyzed, and so forth) under physiological conditions. For example, a "releasable linker" can involve an elimination reaction that has a base abstraction of a proton, (e.g., an ionizable hydrogen atom, Hα), as the driving force. For purposes herein, a "releasable linker" is synonymous with a "degradable linker." In particular embodiments, a releasable linker has a half life at pH 7.4, 25° C., e.g., a physiological pH, human body temperature (e.g., in vivo), of about 30 minutes, about 1 hour, about 2 hour, about 3 hours, about 4 hours, about 5 hours, about 6 hours, about 12 hours, about 18 hours, about 24 hours, about 36 hours, about 48 hours, about 72 hours, or about 96 hours or more.

By "statistically significant," it is meant that the result was unlikely to have occurred by chance. Statistical significance can be determined by any method known in the art. Commonly used measures of significance include the p-value, which is the frequency or probability with which the observed event would occur, if the null hypothesis were true. If the obtained p-value is smaller than the significance level, then the null hypothesis is rejected. In simple cases, the significance level is defined at a p-value of 0.05 or less.

The term "solubility" refers to the property of a HRS-Fc conjugate polypeptide provided herein to dissolve in a liquid solvent and form a homogeneous solution. Solubility is typically expressed as a concentration, either by mass of solute per unit volume of solvent (g of solute per kg of solvent, g per dL (100 mL), mg/ml, etc.), molarity, molality, mole fraction or other similar descriptions of concentration. The maximum equilibrium amount of solute that can dissolve per amount of solvent is the solubility of that solute in that solvent under the specified conditions, including temperature, pressure, pH, and the nature of the solvent. In certain embodiments, solubility is measured at physiological pH, or other pH, for example, at pH 5.0, pH 6.0, pH 7.0, or pH 7.4. In certain embodiments, solubility is measured in water or a physiological buffer such as PBS or NaCl (with or without NaP). In specific embodiments, solubility is measured at relatively lower pH (e.g., pH 6.0) and relatively higher salt (e.g., 500 mM NaCl and 10 mM NaP). In certain embodiments, solubility is measured in a biological fluid (solvent) such as blood or serum. In certain embodiments, the temperature can be about room temperature (e.g., about 20, 21, 22, 23, 24, 25° C.) or about body temperature (37° C.). In certain embodiments, a HRS-Fc conjugate polypeptide has a solubility of at least about 0.1, 0.2, 0.3, 0.4, 0.5, 0.6, 0.7, 0.8, 0.9, 1, 2, 3, 4, 5, 6, 7, 8, 9, 10, 11, 12, 13, 14, 15, 16, 17, 18, 19, 20, 25, or 30 mg/ml at room temperature or at 37° C.

A "subject," as used herein, includes any animal that exhibits a symptom, or is at risk for exhibiting a symptom, which can be treated or diagnosed with a HRS-Fc conjugate polypeptide of the invention. Suitable subjects (patients) include laboratory animals (such as mouse, rat, rabbit, or guinea pig), farm animals, and domestic animals or pets (such as a cat or dog). Non-human primates and, preferably, human patients, are included.

"Substantially" or "essentially" means nearly totally or completely, for instance, 95%, 96%, 97%, 98%, 99% or greater of some given quantity.

"Treatment" or "treating," as used herein, includes any desirable effect on the symptoms or pathology of a disease or condition, and may include even minimal changes or improvements in one or more measurable markers of the disease or condition being treated. "Treatment" or "treating" does not necessarily indicate complete eradication or cure of the disease or condition, or associated symptoms thereof. The subject receiving this treatment is any subject in need thereof. Exemplary markers of clinical improvement will be apparent to persons skilled in the art.

Histidyl-tRNA Synthetase Derived Polypeptides

Embodiments of the present invention relate to histidyl-tRNA synthetase polypeptide ("HRS or HisRS polypeptides")-Fc conjugates, including HRS-Fc conjugates that comprise wild-type HRS sequences, naturally-occurring sequences, non-naturally occurring sequences, and/or variants and fragments thereof. Specific examples of HRS derived polypeptides include those with altered cysteine content. Histidyl-tRNA synthetases belong to the class II tRNA synthetase family, which has three highly conserved sequence motifs. Class I and II tRNA synthetases are widely recognized as being responsible for the specific attachment of an amino acid to its cognate tRNA in a two-step reaction: the amino acid (AA) is first activated by ATP to form AA-AMP and then transferred to the acceptor end of the tRNA. The full length histidyl-tRNA synthetases typically exist either as a cytosolic homodimer, or an alternatively spliced mitochondrial form.

More recently it has been established that some biological fragments, or alternatively spliced isoforms of eukaryotic histidyl-tRNA synthetases (Physiocrines, or HRS polypeptides), or in some contexts the intact synthetase, modulate certain cell-signaling pathways, or have anti-inflammatory properties. These activities, which are distinct from the classical role of tRNA synthetases in protein synthesis, are collectively referred to herein as “non-canonical activities.” These Physiocrines may be produced naturally by either alternative splicing or proteolysis, and can act in a cell autonomous fashion (i.e., within the host cell) or a non-cell autonomous fashion (i.e., outside the host cell) to regulate a variety of homeostatic mechanisms. For example, as provided in the present invention, HRS polypeptides such as the N-terminal fragment of histidyl-tRNA synthetase (e.g., HRS 1-48, HRS 1-60) are capable, inter alia, of exerting an anti-inflammatory signal by blocking the migration, activation, or differentiation of inflammatory cells (e.g., monocytes, macrophages, T cells, B cells) associated with the sites of active inflammation in vivo. In addition, certain mutations or deletions (e.g., HRS 1-506, HRS 1-60) relative to the full-length HRS polypeptide sequence confer increased activities and/or improved pharmacological properties. The sequences of certain exemplary HRS polypeptides are provided in Table D1.

TABLE D1

| Exemplary HRS polypeptides | | | |
|---|---|---|---|
| Name | Type/<br>species/<br>Residues | Amino acid and Nucleic Acid Sequences | SEQ ID NO: |
| | | N-terminal Physiocrines | |
| FL cytosolic wild type | Protein/<br>Human/ | MAERAALEELVKLQGERVRGLKQQKASAELIEEEVAKLLK<br>LKAQLGPDESKQKFVLKTPKGTRDYSPRQMAVREKVFDVII<br>RCFKRHGAEVIDTPVFELKETLMGKYGEDSKLIYDLKDQGG<br>ELLSLRYDLTVPFARYLAMNKLTNIKRYHIAKVYRRDNPAM<br>TRGRYREFYQCDFDIAGNFDPMIPDAECLKIMCEILSSLQIGD<br>FLVKVNDRRILDGMFAICGVSDSKFRTICSSVDKLDKVSWE<br>EVKNEMVGEKGLAPEVADRIGDYVQQHGGVSLVEQLLQDP<br>KLSQNKQALEGLGDLKLLFEYLTLFGIDDKISFDLSLARGLD<br>YYTGVIYEAVLLQTPAQAGEEPLGVGSVAAGGRYDGLVGM<br>FDPKGRKVPCVGLSIGVERIFSIVEQRLEALEEKIRTTETQVL<br>VASAQKKLLEERLKLVSELWDAGIKAELLYKKNPKLLNQL<br>QYCEEAGIPLVAIIGEQELKDGVIKLRSVTSREEVDVRREDL<br>VEEIKRRTGQPLCIC | 1 |
| FL mitochondrial wild type | Protein/<br>Human/ | MPLLGLLPRRAWASLLSQLLRPPCASCTGAVRCQSQVAEAV<br>LTSQLKAHQEKPNFIIKTPKGTRDLSPQHMVVREKILDLVISC<br>FKRHGAKGMDTPAFELKETLTEKYGEDSGLMYDLKDQGGE<br>LLSLRYDLTVPFARYLAMNKVKKMKRYHVGKVWRRESPTI<br>VQGRYREFCQCDFDIAGQFDPMIPDAECLKIMCEILSGLQLG<br>DFLIKVNDRRIVDGMFAVCGVPESKFRAICSSIDKLDKMAW<br>KDVRHEMVVKKGLAPEVADRIGDYVQCHGGVSLVEQMFQ<br>DPRLSQNKQALEGLGDLKLLFEYLTLFGIADKISFDLSLARG<br>LDYYTGVIYEAVLLQTPTQAGEEPLNVGSVAAGGRYDGLV<br>GMFDPKGHKVPCVGLSIGVERIFYIVEQRMKTKGEKVRTTE<br>TQVFVATPQKNFLQERLKLIAELWDSGIKAEMLYKNNPKLL<br>TQLHYCESTGIPLVVIIGEQELKEGVIKIRSVASREEVAIKREN<br>FVAEIQKRLSES | 2 |
| HisRS1$^{N1}$ | Protein/<br>Human/<br>1-141 | MAERAALEELVKLQGERVRGLKQQKASAELIEEEVAKLLK<br>LKAQLGPDESKQKFVLKTPKGTRDYSPRQMAVREKVFDVII<br>RCFKRHGAEVIDTPVFELKETLMGKYGEDSKLIYDLKDQGG<br>ELLSLRYDLTVPFARYLAM | 3 |
| HisRS1$^{N2}$ | Protein/<br>Human/<br>1-408 | MAERAALEELVKLQGERVRGLKQQKASAELIEEEVAKLLK<br>LKAQLGPDESKQKFVLKTPKGTRDYSPRQMAVREKVFDVII<br>RCFKRHGAEVIDTPVFELKETLMGKYGEDSKLIYDLKDQGG<br>ELLSLRYDLTVPFARYLAMNKLTNIKRYHIAKVYRRDNPAM<br>TRGRYREFYQCDFDIAGNFDPMIPDAECLKIMCEILSSLQIGD<br>FLVKVNDRRILDGMFAICGVSDSKFRTICSSVDKLDKVSWE<br>EVKNEMVGEKGLAPEVADRIGDYVQQHGGVSLVEQLLQDP<br>KLSQNKQALEGLGDLKLLFEYLTLFGIDDKISFDLSLARGLD<br>YYTGVIYEAVLLQTPAQAGEEPLGVGSVAAGGRYDGLVGM<br>FDPKGRKVPCVGLSIGVERIFSIVEQRLEALEEKIRTTE | 4 |
| HisRS1$^{N3}$ | Protein/<br>Human/<br>1-113 | MAERAALEELVKLQGERVRGLKQQKASAELIEEEVAKLLK<br>LKAQLGPDESKQKFVLKTPKGTRDYSPRQMAVREKVFDVII<br>RCFKRHGAEVIDTPVFELKETLMGKYGEDSKL | 5 |
| HisRS1$^{N4}$ | Protein/<br>Human/<br>1-60 | MAERAALEELVKLQGERVRGLKQQKASAELIEEEVAKLLK<br>LKAQLGPDESKQKFVLKTPK | 6 |
| HisRS1$^{N5}$ | Protein/<br>Human/<br>1-243 +<br>27 aa | MAERAALEELVKLQGERVRGLKQQKASAELIEEEVAKLLK<br>LKAQLGPDESKQKFVLKTPKGTRDYSPRQMAVREKVFDVII<br>RCFKRHGAEVIDTPVFELKETLMGKYGEDSKLIYDLKDQGG<br>ELLSLRYDLTVPFARYLAMNKLTNIKRYHIAKVYRRDNPAM<br>TRGRYREFYQCDFDIAGNFDPMIPDAECLKIMCEILSSLQIGD<br>FLVKVNDRRILDGMFAICGVSDSKFRTICSSVDKLDKVGYP<br>WWNSCSRILNYPKTSRPWRAWET | 7 |

TABLE D1-continued

| Exemplary HRS polypeptides | | | |
|---|---|---|---|
| C-terminal Physiocrines | | | |
| Name | Type/<br>species/<br>Residues | Amino acid and Nucleic Acid Sequences | SEQ ID<br>NO. |
| HisRS1$^{C1}$ | Protein/<br>Human/<br>405-509 | RTTETQVLVASAQKKLLEERLKLVSELWDAGIKAELLYKK<br>NPKLLNQLQYCEEAGIPLVAIIGEQELKDGVIKLRSVTSREE<br>VDVRREDLVEEIKRRTGQPLCIC | 8 |
| HisRS1$^{C2}$ | Protein/<br>Human/<br>1-60 + 175-<br>509 | MAERAALEELVKLQGERVRGLKQQKASAELIEEEVAKLLK<br>LKAQLGPDESKQKFVLKTPKDFDIAGNFDPMIPDAECLKIM<br>CEILSSLQIGDFLVKVNDRRILDGMFAICGVSDSKFRTICSSV<br>DKLDKVSWEEVKNEMVGEKGLAPEVADRIGDYVQQHGG<br>VSLVEQLLQDPKLSQNKQALEGLGDLKLLFEYLTLFGIDDK<br>ISFDLSLARGLDYYTGVIYEAVLLQTPAQAGEEPLGVGSVA<br>AGGRYDGLVGMFDPKGRKVPCVGLSIGVERIFSIVEQRLEA<br>LEEKIRTTETQVLVASAQKKLLEERLKLVSELWDAGIKAEL<br>LYKKNPKLLNQLQYCEEAGIPLVAIIGEQELKDGVIKLRSV<br>TSREEVDVRREDLVEEIKRRTGQPLCIC | 9 |
| HisRS1$^{C3}$ | Protein/<br>Human/<br>1-60 + 211-<br>509 | MAERAALEELVKLQGERVRGLKQQKASAELIEEEVAKLLK<br>LKAQLGPDESKQKFVLKTPKVNDRRILDGMFAICGVSDSK<br>FRTICSSVDKLDKVSWEEVKNEMVGEKGLAPEVADRIGDY<br>VQQHGGVSLVEQLLQDPKLSQNKQALEGLGDLKLLFEYLT<br>LFGIDDKISFDLSLARGLDYYTGVIYEAVLLQTPAQAGEEPL<br>GVGSVAAGGRYDGLVGMFDPKGRKVPCVGLSIGVERIFSI<br>VEQRLEALEEKIRTTETQVLVASAQKKLLEERLKLVSELW<br>DAGIKAELLYKKNPKLLNQLQYCEEAGIPLVAIIGEQELKD<br>GVIKLRSVTSREEVDVRREDLVEEIKRRTGQPLCIC | 10 |
| HisRS1$^{C4}$ | Protein/<br>Human/<br>1-100 +<br>211-509 | MAERAALEELVKLQGERVRGLKQQKASAELIEEEVAKLLK<br>LKAQLGPDESKQKFVLKTPKGTRDYSPRQMAVREKVFDVI<br>IRCFKRHGAEVIDTPVFELKVNDRRILDGMFAICGVSDSKF<br>RTICSSVDKLDKVSWEEVKNEMVGEKGLAPEVADRIGDYV<br>QQHGGVSLVEQLLQDPKLSQNKQALEGLGDLKLLFEYLTL<br>FGIDDKISFDLSLARGLDYYTGVIYEAVLLQTPAQAGEEPL<br>GVGSVAAGGRYDGLVGMFDPKGRKVPCVGLSIGVERIFSI<br>VEQRLEALEEKIRTTETQVLVASAQKKLLEERLKLVSELW<br>DAGIKAELLYKKNPKLLNQLQYCEEAGIPLVAIIGEQELKD<br>GVIKLRSVTSREEVDVRREDLVEEIKRRTGQPLCIC | 11 |
| HisRS1$^{C5}$ | Protein/<br>Human/<br>1-174 +<br>211-509 | MAERAALEELVKLQGERVRGLKQQKASAELIEEEVAKLLK<br>LKAQLGPDESKQKFVLKTPKGTRDYSPRQMAVREKVFDVI<br>IRCFKRHGAEVIDTPVFELKETLMGKYGEDSKLIYDLKDQG<br>GELLSLRYDLTVPFARYLAMNKLTNIKRYHIAKVYRRDNP<br>AMTRGRYREFYQCVNDRRILDGMFAICGVSDSKFRTICSSV<br>DKLDKVSWEEVKNEMVGEKGLAPEVADRIGDYVQQHGG<br>VSLVEQLLQDPKLSQNKQALEGLGDLKLLFEYLTLFGIDDK<br>ISFDLSLARGLDYYTGVIYEAVLLQTPAQAGEEPLGVGSVA<br>AGGRYDGLVGMFDPKGRKVPCVGLSIGVERIFSIVEQRLEA<br>LEEKIRTTETQVLVASAQKKLLEERLKLVSELWDAGIKAEL<br>LYKKNPKLLNQLQYCEEAGIPLVAIIGEQELKDGVIKLRSV<br>TSREEVDVRREDLVEEIKRRTGQPLCIC | 12 |
| HisRS1$^{C6}$ | Protein/<br>Human/<br>1-60 + 101-<br>509 | MAERAALEELVKLQGERVRGLKQQKASAELIEEEVAKLLK<br>LKAQLGPDESKQKFVLKTPKETLMGKYGEDSKLIYDLKDQ<br>GGELLSLRYDLTVPFARYLAMNKLTNIKRYHIAKVYRRDN<br>PAMTRGRYREFYQCDFDIAGNFDPMIPDAECLKIMCEILSS<br>LQIGDFLVKVNDRRILDGMFAICGVSDSKFRTICSSVDKLD<br>KVSWEEVKNEMVGEKGLAPEVADRIGDYVQQHGGVSLVE<br>QLLQDPKLSQNKQALEGLGDLKLLFEYLTLFGIDDKISFDL<br>SLARGLDYYTGVIYEAVLLQTPAQAGEEPLGVGSVAAGGR<br>YDGLVGMFDPKGRKVPCVGLSIGVERIFSIVEQRLEALEEKI<br>RTIETQVLVASAQKKLLEERLKLVSELWDAGIKAELLYKK<br>NPKLLNQLQYCEEAGIPLVAIIGEQELKDGVIKLRSVTSREE<br>VDVRREDLVEEIKRRTGQPLCIC | 13 |
| HisRS1$^{C7}$ | Protein/<br>Human/<br>1-100 +<br>175-509 | MAERAALEELVKLQGERVRGLKQQKASAELIEEEVAKLLK<br>LKAQLGPDESKQKFVLKTPKGTRDYSPRQMAVREKVFDVI<br>IRCFKRHGAEVIDTPVFELKDFDIAGNFDPMIPDAECLKIMC<br>EILSSLQIGDFLVKVNDRRILDGMFAICGVSDSKFRTICSSV<br>DKLDKVSWEEVKNEMVGEKGLAPEVADRIGDYVQQHGG<br>VSLVEQLLQDPKLSQNKQALEGLGDLKLLFEYLTLFGIDDK<br>ISFDLSLARGLDYYTGVIYEAVLLQTPAQAGEEPLGVGSVA<br>AGGRYDGLVGMFDPKGRKVPCVGLSIGVERIFSIVEQRLEA<br>LEEKIRTTETQVLVASAQKKLLEERLKLVSELWDAGIKAEL | 14 |

TABLE D1-continued

| Exemplary HRS polypeptides | | | |
|---|---|---|---|
| | | LYKKNPKLLNQLQYCEEAGIPLVAIIGEQELKDGVIKLRSV TSREEVDVRREDLVEEIKRRTGQPLCIC | |
| HisRS1$^{C8}$ | Protein/ Human/ 1-60 + 399-509 | MAERAALEELVKLQGERVRGLKQQKASAELIEEEVAKLLK LKAQLGPDESKQKFVLKTPKALEEKIRTIETQVLVASAQK KLLEERLKLVSELWDAGIKAELLYKKNPKLLNQLQYCEEA GIPLVAIIGEQELKDGVIKLRSVTSREEVDVRREDLVEEIKR RTGQPLCIC | 15 |
| HisRS1$^{C9}$ | Protein/ Human/ 1-100 + 399-509 | MAERAALEELVKLQGERVRGLKQQKASAELIEEEVAKLLK LKAQLGPDESKQKFVLKTPKGTRDYSPRQMAVREKVFDVI IRCFKRHGAEVIDTPVFELKALEEKIRTIETQVLVASAQKK LLEERLKLVSELWDAGIKAELLYKKNPKLLNQLQYCEEAG IPLVAIIGEQELKDGVIKLRSVTSREEVDVRREDLVEEIKRR TGQPLCIC | 16 |
| HisRS1$^{C10}$ | Protein/ Human/ 369-509 | MFDPKGRKVPCVGLSIGVERIFSIVEQRLEALEEKIRTTETQ VLVASAQKKLLEERLKLVSELWDAGIKAELLYKKNPKLLN QLQYCEEAGIPLVAIIGEQELKDGVIKLRSVTSREEVDVRRE DLVEEIKRRTGQPLCIC | 17 |
| Internal Physiocrines | | | |
| Name | Type/ species/ Residues | Amino acid and Nucleic Acid Sequences | ID SEQ NO. |
| HisRS1$^{I1}$ | Protein/ Human/ 191-333 | CLKIMCEILSSLQIGDFLVKVNDRRILDGMFAICGVSDSKFR TICSSVDKLDKVSWEEVKNEMVGEKGLAPEVADRIGDYV QQHGGVSLVEQLLQDPKLSQNKQALEGLGDLKLLFEYLTL FGIDDKISFDLSLARGLDYYTG | 18 |

A number of naturally occurring histidyl-tRNA synthetase single nucleotide polymorphisms (SNPs) and naturally occurring variants of the human gene have been sequenced, and are known in the art to be at least partially functionally interchangeable. Several such variants of histidyl-tRNA synthetase (i.e., representative histidyl-tRNA synthetase SNPs) are shown in Table D2.

TABLE D2

| Human Histidyl tRNA synthetase SNPs | | | |
|---|---|---|---|
| Gene Bank Accession Number | Nucleo-tide Change | Gene Bank Accession Number | Nucleotide Change |
| rs193103291 | A/G | rs186312047 | A/G |
| rs192923161 | C/T | rs186176857 | C/T |
| rs192784934 | A/G | rs186043734 | C/G |
| rs192164884 | A/G | rs185867584 | C/T |
| rs192090865 | A/C | rs185828130 | A/G |
| rs192015101 | A/T | rs185537686 | A/G |
| rs191999492 | A/G | rs185440931 | C/T |
| rs191852363 | C/T | rs185100584 | A/C |
| rs191532032 | A/T | rs185077558 | C/T |
| rs191391414 | C/T | rs184748736 | C/G |
| rs191385862 | A/G | rs184591417 | C/T |
| rs191205977 | A/G | rs184400035 | C/G |
| rs191104160 | A/G | rs184098206 | C/T |

TABLE D2-continued

| Human Histidyl tRNA synthetase SNPs | | | |
|---|---|---|---|
| Gene Bank Accession Number | Nucleo-tide Change | Gene Bank Accession Number | Nucleotide Change |
| rs190989313 | C/G | rs183982931 | C/T |
| rs190818970 | A/T | rs183942045 | A/G |
| rs190476138 | C/T | rs183854085 | A/G |
| rs190289555 | C/T | rs183430882 | G/T |
| rs190065567 | A/G | rs183419967 | A/C |
| rs189624055 | C/T | rs183366286 | A/G |
| rs189563577 | G/T | rs183084050 | C/T |
| rs189404434 | A/G | rs182948878 | C/T |
| rs189268935 | A/G | rs182813126 | A/G |
| rs189103453 | A/T | rs182498374 | A/G |
| rs188839103 | A/G | rs182161259 | A/T |
| rs188766717 | A/G | rs182119902 | C/T |
| rs188705391 | A/G | rs182106891 | C/T |
| rs188490030 | A/G | rs181930530 | A/G |
| rs188345926 | C/T | rs181819577 | A/G |
| rs188174426 | A/G | rs181706697 | C/T |
| rs187897435 | C/T | rs181400061 | G/T |
| rs187880261 | A/G | rs181240610 | G/T |

TABLE D2-continued

Human Histidyl tRNA synthetase SNPs

| Gene Bank Accession Number | Nucleo-tide Change | Gene Bank Accession Number | Nucleotide Change |
|---|---|---|---|
| rs187729939 | G/T | rs181150977 | A/C |
| rs187617985 | A/T | rs180848617 | A/G |
| rs187344319 | C/T | rs180765564 | A/G |
| rs187136933 | C/T | rs151330569 | C/G |
| rs186823043 | C/G | rs151258227 | C/T |
| rs186764765 | C/T | rs151174822 | C/T |
| rs186663247 | A/G | rs150874684 | C/T |
| rs186526524 | A/G | rs150589670 | A/G |
| rs150274370 | C/T | rs145059663 | C/T |
| rs150090766 | A/G | rs144588417 | C/T |
| rs149977222 | A/G | rs144457474 | A/G |
| rs149821411 | C/T | rs144322728 | C/T |
| rs149542384 | A/G | rs143897456 | -/C |
| rs149336018 | C/G | rs143569397 | G/T |
| rs149283940 | C/T | rs143476664 | C/T |
| rs149259830 | C/T | rs143473232 | C/G |
| rs149241235 | C/T | rs143436373 | G/T |
| rs149018062 | C/T | rs143166254 | A/G |
| rs148935291 | C/T | rs143011702 | C/G |
| rs148921342 | -/A | rs142994969 | A/G |
| rs148614030 | C/T | rs142880704 | A/G |
| rs148584540 | C/T | rs142630342 | A/G |
| rs148532075 | A/C | rs142522782 | -/AAAC |
| rs148516171 | C/T | rs142443502 | C/T |
| rs148394305 | -/AA | rs142305093 | C/T |
| rs148267541 | C/T | rs142289599 | A/G |
| rs148213958 | C/T | rs142088963 | A/C |
| rs147637634 | A/G | rs141765732 | A/C |
| rs147372931 | A/C/G | rs141386881 | A/T |
| rs147350096 | A/C | rs141291994 | A/G |
| rs147288996 | C/T | rs141285041 | C/T |
| rs147194882 | G/T | rs141220649 | C/T |
| rs147185134 | C/T | rs141147961 | -/C |
| rs147172925 | A/G | rs141123446 | -/A |
| rs147011612 | C/T | rs140516034 | A/G |
| rs147001782 | A/G | rs140169815 | C/T |
| rs146922029 | C/T | rs140005970 | G/T |

TABLE D2-continued

Human Histidyl tRNA synthetase SNPs

| Gene Bank Accession Number | Nucleo-tide Change | Gene Bank Accession Number | Nucleotide Change |
|---|---|---|---|
| rs146835587 | A/G | rs139699964 | C/T |
| rs146820726 | C/T | rs139555499 | A/G |
| rs146801682 | C/T | rs139447495 | C/T |
| rs146571500 | G/T | rs139364834 | -/A |
| rs146560255 | C/T | rs139362540 | A/G |
| rs146205151 | -/A | rs139300653 | -/A |
| rs146159952 | A/G | rs139251223 | A/G |
| rs145532449 | C/G | rs139145072 | A/G |
| rs145446993 | A/G | rs138612783 | A/G |
| rs145112012 | G/T | rs138582560 | A/G |
| rs138414368 | A/G | rs111863295 | C/T |
| rs138377835 | A/G | rs111519226 | C/G |
| rs138300828 | C/T | rs111314092 | C/T |
| rs138067637 | C/T | rs80074170 | A/T |
| rs138035024 | A/G | rs79408883 | A/C |
| rs137973748 | C/G | rs78741041 | G/T |
| rs137917558 | A/G | rs78677246 | A/T |
| rs117912126 | A/T | rs78299006 | A/G |
| rs117579809 | G/T | rs78085183 | A/T |
| rs116730458 | C/T | rs77844754 | C/T |
| rs116411189 | A/C | rs77585983 | A/T |
| rs116339664 | C/T | rs77576083 | A/G |
| rs116203404 | A/T | rs77154058 | G/T |
| rs115091892 | G/T | rs76999025 | A/G |
| rs114970855 | A/G | rs76496151 | C/T |
| rs114176478 | A/G | rs76471225 | G/T |
| rs113992989 | C/T | rs76085408 | G/T |
| rs113720830 | C/T | rs75409415 | A/G |
| rs113713558 | A/C | rs75397255 | C/G |
| rs113627177 | G/T | rs74336073 | A/G |
| rs113489608 | A/C | rs73791750 | C/T |
| rs113408729 | G/T | rs73791749 | A/T |
| rs113255561 | A/G | rs73791748 | C/T |
| rs113249111 | C/T | rs73791747 | A/T |
| rs113209109 | A/G | rs73273304 | C/T |
| rs113066628 | G/T | rs73271596 | C/T |
| rs112967222 | C/T | rs73271594 | C/T |

TABLE D2-continued

Human Histidyl tRNA synthetase SNPs

| Gene Bank Accession Number | Nucleo-tide Change | Gene Bank Accession Number | Nucleotide Change |
|---|---|---|---|
| rs112957918 | A/T | rs73271591 | A/G |
| rs112859141 | A/G | rs73271586 | A/T |
| rs112769834 | C/G | rs73271585 | A/G |
| rs112769758 | A/C | rs73271584 | A/G |
| rs112701444 | A/C | rs73271581 | C/T |
| rs112585944 | A/G | rs73271578 | A/T |
| rs112439761 | A/G | rs72800925 | G/T |
| rs112427345 | A/C | rs72800924 | C/T |
| rs112265354 | C/T | rs72800922 | A/T |
| rs112113896 | C/G | rs72432753 | -/A |
| rs112033118 | C/T | rs72427948 | -/A |
| rs112029988 | A/G | rs72388191 | -/A |
| rs72317985 | -/A | rs6873628 | C/T |
| rs71583608 | G/T | rs5871749 | -/C |
| rs67251579 | -/A | rs4334930 | A/T |
| rs67180750 | -/A | rs3887397 | A/G |
| rs63429961 | A/T | rs3776130 | A/C |
| rs61093427 | C/T | rs3776129 | C/T |
| rs61059042 | -/A | rs3776128 | A/G |
| rs60936249 | -/AA | rs3177856 | A/C |
| rs60916571 | -/A | rs2563307 | A/G |
| rs59925457 | C/T | rs2563306 | A/G |
| rs59702263 | -/A | rs2563305 | C/T |
| rs58302597 | C/T | rs2563304 | A/G |
| rs57408905 | A/T | rs2530242 | C/G |
| rs35790592 | A/C | rs2530241 | A/G |
| rs35609344 | -/A | rs2530240 | A/G |
| rs35559471 | -/A | rs2530239 | A/G |
| rs35217222 | -/C | rs2530235 | A/C |
| rs34903998 | -/A | rs2230361 | C/T |
| rs34790864 | C/G | rs2073512 | C/T |
| rs34732372 | C/T | rs1131046 | C/T |
| rs34291233 | -/C | rs1131045 | C/G |
| rs34246519 | -/T | rs1131044 | C/T |
| rs34176495 | -/C | rs1131043 | C/G |
| rs13359823 | A/G | rs1131042 | A/C |
| rs13180544 | A/C | rs1131041 | C/G |
| rs12653992 | A/C | rs1131040 | A/G |
| rs12652092 | A/G | rs1131039 | C/T |
| rs11954514 | A/C | rs1131038 | A/G |
| rs11745372 | C/T | rs1131037 | A/G |
| rs11548125 | A/G | rs1131036 | A/G |
| rs11548124 | C/G | rs1131035 | C/T |
| rs11344157 | -/C | rs1131034 | A/G |
| rs11336085 | -/A | rs1131033 | A/G |
| rs11318345 | -/A | rs1131032 | A/G |
| rs11309606 | -/A | rs1089305 | A/G |
| rs10713463 | -/A | rs1089304 | A/C |
| rs7706544 | C/T | rs1065342 | A/C |
| rs7701545 | A/T | rs1050252 | C/T |
| rs6880190 | C/T | rs1050251 | A/T |
| rs1050250 | A/G | rs145769024 | -/AAACAAAACAAAACA (SEQ ID NO: 164) |
| rs1050249 | C/T | rs10534452 | -/AAAAC |
| rs1050248 | A/C/T | rs10534451 | -/AAACAAAACA (SEQ ID NO: 165) |
| rs1050247 | C/T | rs59554063 | -/CAAAACAAAA (SEQ ID NO: 166) |
| rs1050246 | C/G | rs58606188 | -/CAAAACAAAACAAAA (SEQ ID NO:167) |
| rs1050245 | C/T | rs71835204 | (LARGEDELETION)/- |
| rs1050222 | C/T | rs71766955 | (LARGEDELETION)/- |
| rs813897 | A/G | rs144998196 | -/AAACAAAACA (SEQ ID NO: 168) |
| rs812381 | C/G | rs68038188 | -/ACAAAACAAA (SEQ ID NO: 169) |
| rs811382 | C/T | rs71980275 | -/AAAAC |
| rs801189 | C/T | rs71848069 | -/AAAC |
| rs801188 | A/C | rs60987104 | -/AAAC |
| rs801187 | A/T | rs801185 | C/T |
| rs801186 | A/G | rs702396 | C/G |

Additionally homologs and orthologs of the human gene exist in other species, as listed in Table D3, and it would thus be a routine matter to select a naturally occurring amino acid, or nucleotide variant present in a SNP, or other naturally occurring homolog in place of any of the human HRS polypeptide sequences listed in Tables D1, D4-D6, or D8.

TABLE D3

Homologs of Human Histidyl tRNA synthetase

| Type/species/<br>Residues | Amino acid Sequences | SEQ ID<br>NO: |
|---|---|---|
| *Mus musculus* | MADRAALEELVRLQGAHVRGLKEQKASAEQIEEEVTKLLKLKAQL<br>GQDEGKQKFVLKTPKGTRDYSPRQMAVREKVFDVIIRCFKRHGAEV<br>IDTPVFELKETLTGKYGEDSKLIYDLKDQGGELLSLRYDLTVPFARY<br>LAMNKLTNIKRYHIAKVYRRDNPAMTRGRYREFYQCDFDIAGQFDP<br>MIPDAECLKIMCEILSSLQIGNFLVKVNDRRILDGMFAVCGVPDSKFR<br>TICSSVDKLDKVSWEEVKNEMVGEKGLAPEVADRIGDYVQQHGGV<br>SLVEQLLQDPKLSQNKQAVEGLGDLKLLFEYLILFGIDDKISFDLSLA<br>RGLDYYTGVIYEAVLLQMPTQAGEEPLGVGSIAAGGRYDGLVGMF<br>DPKGRKVPCVGLSIGVERIFSIVEQRLEASEEKVRTTETQVLVASAQK<br>KLLEERLKLVSELWDAGIKAELLYKKNPKLLNQLQYWEEAGIPLVAI<br>IGEQELRDGVIKLRSVASREEVDVRREDLVEEIRRRTNQPLSTC | 19 |
| *Canis lupus*<br>*familiaris* | MAERAALEELVRLQGERVRGLKQQKASAEQIEEEVAKLLKLKAQLG<br>PDEGKQKFVLKTPKGTRDYSPRQMAVREKVFDVIISCFKRHGAEVID<br>TPVFELKETLTGKYGEDSKLIYDLKDQGGELLSLRYDLTVPFARYLA<br>MNKLTNIKRYHIAKVYRRDNPAMTRGRYREFYQCDFDIAGQFDPMI<br>PDAECLEIMCEILRSLQIGDFLVKVNDRRILDGMFAICGVPDSKFRTIC<br>SSVDKLDKVSWEEVKNEMVGEKGLAPEVADHIGDYVQQHGGISLV<br>EQLLQDPELSQNKQALEGLGDLKLLFEYLTLFGIADKISFDLSLARGL<br>DYYTGVIYEAVLLQTPVQAGEEPLGVGSVAAGGRYDGLVGMFDPK<br>GRKVPCVGLSIGVERIFSIVEQRLEATEEKVRTTETQVLVASAQKKLL<br>EERLKLVSELWNAGIKAELLYKKNPKLLNQLQYCEEAGIPLVAIIGE<br>QELKDGVIKLRSVASREEVDVPREDLVEEIKRRTSQPFCIC | 20 |
| *Bos taurus* | MADRAALEDLVRVQGERVRGLKQQKASAEQIEEEVAKLLKLKAQL<br>GPDEGKPKFVLKTPKGTRDYSPRQMAVREKVFDVIISCFKRHGAEVI<br>DTPVFELKETLTGKYGEDSKLIYDLKDQGGELLSLRYDLTVPFARYL<br>AMNKLTNIKRYHIAKVYRRDNPAMTRGRYREFYQCDFDIAGQFDP<br>MLPDAECLKIMCEILSSLQIGDFLVKVNDRRILDGMFAICGVPDSKFR<br>TICSSVDKLDKVSWEEVKNEMVGEKGLAPEVADRIGDYVQQHGGV<br>SLVEQLLQDPKLSQNKQALEGLGDLKLLFEYLTLFGIADKISFDLSLA<br>RGLDYYTGVIYEAVLLQPPARAGEEPLGVGSVAAGGRYDGLVGMF<br>DPKGRKVPCVGLSIGVERIFSIVEQRLEALEEKVRTTETQVLVASAQK<br>KLLEERLKLISELWDAGIKAELLYKKNPKLLNQLQYCEETGIPLVAII<br>GEQELKDGVIKLRSVASREEVDVRREDLVEEIKRRTSQPLCIC | 21 |
| *Rattus*<br>*norvegicus* | MADRAALEELVRLQGAHVRGLKEQKASAEQIEEEVTKLLKLKAQL<br>GHDEGKQKFVLKTPKGTRDYSPRQMAVREKVFDVIIRCFKRHGAEV<br>IDTPVFELKETLTGKYGEDSKLIYDLKDQGGELLSLRYDLTVPFARY<br>LAMNKLTNIKRYHIAKVYRRDNPAMTRGRYREFYQCDFDIAGQFDP<br>MIPDAECLKIMCEILSSLQIGNFQVKVNDRRILDGMFAVCGVPDSKF<br>RTICSSVDKLDKVSWEEVKNEMVGEKGLAPEVADRIGDYVQQHGG<br>VSLVEQLLQDPKLSQNKQAVEGLGDLKLLFEYLTLFGIDDKISFDLSL<br>ARGLDYYTGVIYEAVLLQMPTQAGEEPLGVGSIAAGGRYDGLVGM<br>FDPKGRKVPCVGLSIGVERIFSIVEQKLEASEEKVRTTETQVLVASAQ<br>KKLLEERLKLISELWDAGIKAELLYKKNPKLLNQLQYCEEAGIPLVAI<br>IGEQELKDGVIKLRSVTSREEVDVRREDLVEEIRRRTSQPLSM | 22 |
| *Gallus gallus* | MADEAAVRQQAEVVRRLKQDKAEPDEIAKEVAKLLEMKAHLGGD<br>EGKHKFVLKTPKGTRDYGPKQMAIRERVFSAIIACFKRHGAEVIDTP<br>VFELKETLTGKYGEDSKLIYDLKDQGGELLSLRYDLTVPFARYLAM<br>NKITNIKRYHIAKVYRRDNPAMTRGRYREFYQCDFDIAGQFDPMIPD<br>AECLKIVQEILSDLQLGDFLIKVNDRRILDGMFAVCGVPDSKFRTICS<br>SVDKLDKMPWEEVRNEMVGEKGLSPEAADRIGEYVQLHGGMDLIE<br>QLLQDPKLSQNKLVKEGLGDMKLLFEYLTLFGITGKISFDLSLARGL<br>DYYTGVIYEAVLLQQNDHGEESVSVGSVAGGGRYDGLVGMFDPKG<br>RKVPCVGISIGIERIFSILEQRVEASEEKIRTTETQVLVASAQKKLLEER<br>LKLISELWDAGIKAEVLYKKNPKLLNQLQYCEDTGIPLVAIVGEQEL<br>KDGVVKLRVVATGEEVNIRRESLVEEIRRRTNQL | 23 |
| *Danio rerio* | MAALGLVSMRLCAGLMGRRSAVRLHSLRVCSGMTISQIDEEVARLL<br>QLKAQLGGDEGKHVFVLKTAKGTRDYNPKQMAIREKVFNIIINCFK<br>RHGAETIDSPVFELKETLTGKYGEDSKLIYDLKDQGGELLSLRYDLT<br>VPFARYLANINKITNIKRYHIAKVYRRDNPAMTRGRYREFYQCDFDI<br>AGQYDAMIPDAECLKLVYEILSELDLGDFRIKVNDRRILDGMFAICG<br>VPDEKFRTICSTVDKLDKLAWEEVKKEMVNEKGLSEEVADRIRDYV<br>SMQGGKDLAERLLQDPKLSQSKQACAGITDMKLLFSYLELFQITDK<br>VVFDLSLARGLDYYTGVIYEAILTQANPAPASTPAEQNGAEDAGVSV<br>GSVAGGGRYDGLVGMFDPKAGKCPVWGSALALRGSSPSWSRRQSC<br>LQRRCAPLKLKCLWLQHRRTF | 24 |

Accordingly, in any of the methods therapeutic compositions and kits of the invention, the terms "HRS polypeptide" "HRS protein" or "HRS protein fragment" includes all naturally-occurring and synthetic forms of the histidyl-tRNA synthetase that possesses a non canonical activity, such as an anti-inflammatory activity and/or retains at least one epitope which specifically cross reacts with an autoantibody or auto reactive T-cell from a subject with a disease associated with autoantibodies to histidyl-tRNA synthetase. Such HRS polypeptides include the full length human protein, as well as the HRS peptides derived from the full length protein listed in Tables D1, D3-D6, or D8. In some embodiments, the term HRS polypeptide refers to a polypeptide sequence derived from human histidyl-tRNA synthetase (SEQ ID NO:1 in Table D1) of about 45 or 50 to about 250 amino acids in length. It will be appreciated that in any of HRS-Fc conjugates described herein the N-terminal acid of the HRS polypeptide (for example, the N-terminal Met) may be deleted from any of the sequences listed in Tables D1, D3-D6, or D8 when creating the fusion protein or conjugate.

In some embodiments, the HRS polypeptide is between about 20-509, 20-508, 20-507, 50-506, 20-505, 50-504, 20-503, 20-502, 20-501, 20-500, 20-400, 20-300, 20-250, 20-200, or 20-100 amino acids in length. For instance, in specific embodiments the polypeptide is between about 20-25, 20-35, 20-40, 20-45, 20-55, 20-60, 20-65, 20-70, 20-75, 20-80, 20-85, 20-90, 20-95, or 20-100 amino acids in length, or about 30-35, 30-40, 30-45, 30-55, 30-60, 30-65, 30-70, 30-75, 30-80, 30-85, 30-90, 30-95, or 30-100 amino acids in length, or about 40-45, 40-55, 40-60, 40-65, 40-70, 40-75, 40-80, 40-85, 40-90, 40-95, or 40-100 amino acids in length, or about 45-50, 45-55, 50-55, 50-60, 50-65, 50-70, 50-75, 50-80, 50-85, 50-90, 50-95, or 50-100 amino acids in length, or about 60-65, 60-70, 60-75, 60-80, 60-85, 60-90, 60-95, or 60-100 amino acids in length, or about 70-75, 70-80, 70-85, 70-90, 70-95, or 70-100 amino acids in length, or about 80-85, 80-90, 80-95, or 80-100 amino acids in length. In certain embodiments, the HRS polypeptide is about 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 150, 200, 250, 300, 350, 400, 450, 500, 501, 502, 503, 504, 505, 506, 507, 508, or 509 amino acids in length.

In some embodiments, the HRS polypeptide does not significantly compete for disease associated auto-antibody binding (e.g., Jo-1 antibody) to wild type histidyl-tRNA synthetase in a competitive ELISA up to a concentration of about 1 to $5\times10^{-7}$M, or higher. Accordingly, in some embodiments, the HRS polypeptide has a lower affinity to disease associated auto-antibody than wild type histidyl-tRNA synthetase (SEQ ID NO:1) as measured in a competitive ELISA. In some embodiments, the HRS polypeptide has an apparent affinity for the disease associated auto-antibody (e.g., Jo-1 antibody) which is at least about 10 fold less, or at least about 20 fold less, or at least about 50 fold less, or at least about 100 fold less than the affinity of the disease associated auto-antibody to wild type human (SEQ ID NO:1).

Thus all such homologues, orthologs, and naturally-occurring, or synthetic isoforms of histidyl-tRNA synthetase (e.g., any of the proteins listed in Tables D1, D3-D6, or D8) are included in any of the methods, HRS-Fc conjugates, kits and compositions of the invention, as long as they retain at least one epitope which specifically cross reacts with an auto-antibody or auto reactive T-cell from a subject with a disease associated with autoantibodies to histidyl tRNA synthetase, or possess a non canonical activity. The HRS polypeptides may be in their native form, i.e., as different variants as they appear in nature in different species which may be viewed as functionally equivalent variants of human histidyl-tRNA synthetase, or they may be functionally equivalent natural derivatives thereof, which may differ in their amino acid sequence, e.g., by truncation (e.g., from the N- or C-terminus or both) or other amino acid deletions, additions, insertions, substitutions, or post-translational modifications. Naturally-occurring chemical derivatives, including post-translational modifications and degradation products of any HRS polypeptide, are also specifically included in any of the methods and compositions of the invention including, e.g., pyroglutamyl, iso-aspartyl, proteolytic, phosphorylated, glycosylated, oxidatized, isomerized, and deaminated variants of a HRS polypeptide or HRS-Fc conjugate. HRS polypeptides and HRS-Fc conjugates can also be composed of naturally-occurring amino acids and/or non-naturally occurring amino acids, as described herein.

As noted above, embodiments of the present invention include all homologues, orthologs, and naturally-occurring isoforms of histidyl-tRNA synthetase (e.g., any of the proteins listed in or derivable from, or their corresponding nucleic acids listed in, the Tables or the Sequence Listing) and "variants" of these HRS reference polypeptides. The recitation polypeptide "variant" refers to polypeptides that are distinguished from a reference HRS polypeptide by the addition, deletion, and/or substitution of at least one amino acid residue, and which typically retain (e.g., mimic) or modulate (e.g., antagonize) one or more non-canonical activities of a reference HRS polypeptide. Variants also include polypeptides that have been modified by the addition, deletion, and/or substitution of at least one amino acid residue to have improved stability or other pharmaceutical properties.

In certain embodiments, a polypeptide variant is distinguished from a reference polypeptide by one or more substitutions, which may be conservative or non-conservative, as described herein and known in the art. In certain embodiments, the polypeptide variant comprises conservative substitutions and, in this regard, it is well understood in the art that some amino acids may be changed to others with broadly similar properties without changing the nature of the activity of the polypeptide. In some embodiments, the variant comprises one or more conserved residues, including one or more of Leu7, Gln14, Gly15, Val18, Arg19, Leu21, Lys22, Lys25, Ala26, Val35, Leu38, Leu39, Leu41, and Lys 42 (based on the numbering of SEQ ID NO:1).

Specific examples of HRS polypeptide variants useful in any of the methods and compositions of the invention include full-length HRS polypeptides, or truncations or splice variants thereof (e.g., any of the proteins listed in or derivable from the Tables or Sequence Listing) which i) retain detectable non canonical activity and/or retain at least one epitope which specifically cross reacts with an autoantibody or auto reactive T-cell from a subject with a disease associated with autoantibodies to histidyl-tRNA synthetase, and ii) have one or more additional amino acid insertions, substitutions, deletions, and/or truncations. In certain embodiments, a variant polypeptide includes an amino acid sequence having at least about 50%, 55%, 60%, 65%, 70%, 75%, 80%, 85%, 90%, 91%, 92%, 93%, 94%, 95%, 96%, 97%, 98% or more sequence identity or similarity to a corresponding sequence of a HRS reference polypeptide, as described herein, (e.g., any of the proteins listed in or derivable from the Tables or Sequence Listing) and substantially retains the non-canonical activity of that reference polypeptide. Also included are sequences differing from the reference HRS sequences by the addition, deletion, or substitution of 1, 2, 3, 4, 5, 6, 7, 8, 9, 10, 11, 12, 13, 14, 15, 16, 17, 18, 19, 20, 30, 40, 50, 60, 70, 80, 90, 100, 110, 120, 130, 140, 150 or more amino acids but which retain the properties of the reference HRS polypeptide. In certain embodiments, the amino acid additions or deletions occur at the C-terminal end and/or the N-terminal end of the HRS reference polypeptide. In certain embodiments, the amino acid additions include 1, 2, 3, 4, 5, 6, 7, 8, 9, 10, 11, 12, 13, 14, 15, 16, 17, 18, 19, 20, 30, 40, 50 or more wild-type residues (i.e., from the corresponding full-length HRS polypeptide) that are proximal to the C-terminal end and/or the N-terminal end of the HRS reference polypeptide.

In some embodiments, the HRS polypeptides comprise a polypeptide fragment of the full length histidyl tRNA synthetase of about 45 to 250 or about 50 to 250 amino acids, which comprises, consists, or consists essentially of the amino acids of the HRS polypeptide sequence set forth in one or more of SEQ ID NOS:1-106, 170-181, or 185-191. In some embodiments, the HRS polypeptide comprises, consists, or consists essentially of residues 1-141, 1-408, 1-113, or 1-60 of SEQ ID NO:1. In some aspects, the HRS polypeptide is a splice variant that comprises, consists, or consists essentially of residues 1-60+175-509, 1-60+211-509 or 1-60+101-509 of SEQ ID NO:1. In particular aspects, the HRS polypeptide comprises, consists, or consists essentially of residues 1-48 or 1-506 of SEQ ID NO:1.

In certain embodiments, a HRS polypeptide of the invention comprises, consists, or consists essentially of the minimal active fragment of a full-length HRS polypeptide capable of modulating an anti-inflammatory activity in vivo or having antibody or auto-reactive T-cell blocking activities. In one aspect, such a minimal active fragment comprises, consists, or consists essentially of the WHEP domain, (i.e., about amino acids 1-43 of SEQ ID NO:1). In some aspects, the minimal active fragment comprises, consists, or consists essentially of the aminoacylation domain, (i.e., about amino acids 54-398 of SEQ ID NO:1). In some aspects, the minimal active fragment comprises, consists, or consists essentially of the anticodon binding domain (i.e., about amino acids 406-501 of SEQ ID NO:1). Other exemplary active fragments are shown in Table D4 below.

TABLE D4

Exemplary HRS polypeptide fragments

| Name | Amino Acid Residue Range of SEQ ID NO: 1 | Amino acid sequence | SEQ ID NO: |
|---|---|---|---|
| HRS(1-500) | Protein/ Human/ 1-500 | MAERAALEELVKLQGERVRGLKQQKASAELIEEEVAKLLK LKAQLGPDESKQKFVLKTPKGTRDYSPRQMAVREKVFDVII RCFKRHGAEVIDTPVFELKETLMGKYGEDSKLIYDLKDQGG ELLSLRYDLTVPFARYLAMNKLTNIKRYHIAKVYRRDNPAM TRGRYREFYQCDFDIAGNFDPMIPDAECLKIMCEILSSLQIGD FLVKVNDRRILDGMFAICGVSDSKFRTICSSVDKLDKVSWE EVKNEMVGEKGLAPEVADRIGDYVQQHGGVSLVEQLLQDP KLSQNKQALEGLGDLKLLFEYLTLFGIDDKISFDLSLARGLD YYTGVIYEAVLLQTPAQAGEEPLGVGSVAAGGRYDGLVGM FDPKGRKVPCVGLSIGVERIFSIVEQRLEALEEKIRTTETQVL VASAQKKLLEERLKLVSELWDAGIKAELLYKKNPKLLNQL QYCEEAGIPLVAIIGEQELKDGVIKLRSVTSREEVDVRREDL VEEIKR | 170 |
| HRS(1-501) | Protein/ Human/ 1-501 | MAERAALEELVKLQGERVRGLKQQKASAELIEEEVAKLLK LKAQLGPDESKQKFVLKTPKGTRDYSPRQMAVREKVFDVII RCFKRHGAEVIDTPVFELKETLMGKYGEDSKLIYDLKDQGG ELLSLRYDLTVPFARYLAMNKLTNIKRYHIAKVYRRDNPAM TRGRYREFYQCDFDIAGNFDPMIPDAECLKIMCEILSSLQIGD FLVKVNDRRILDGMFAICGVSDSKFRTICSSVDKLDKVSWE EVKNEMVGEKGLAPEVADRIGDYVQQHGGVSLVEQLLQDP KLSQNKQALEGLGDLKLLFEYLTLFGIDDKISFDLSLARGLD YYTGVIYEAVLLQTPAQAGEEPLGVGSVAAGGRYDGLVGM FDPKGRKVPCVGLSIGVERIFSIVEQRLEALEEKIRTTETQVL VASAQKKLLEERLKLVSELWDAGIKAELLYKKNPKLLNQL QYCEEAGIPLVAIIGEQELKDGVIKLRSVTSREEVDVRREDL VEEIKRR | 171 |
| HRS(1-502) | Protein/ Human/ 1-502 | MAERAALEELVKLQGERVRGLKQQKASAELIEEEVAKLLK LKAQLGPDESKQKFVLKTPKGTRDYSPRQMAVREKVFDVII RCFKRHGAEVIDTPVFELKETLMGKYGEDSKLIYDLKDQGG ELLSLRYDLTVPFARYLAMNKLTNIKRYHIAKVYRRDNPAM TRGRYREFYQCDFDIAGNFDPMIPDAECLKIMCEILSSLQIGD FLVKVNDRRILDGMFAICGVSDSKFRTICSSVDKLDKVSWE EVKNEMVGEKGLAPEVADRIGDYVQQHGGVSLVEQLLQDP KLSQNKQALEGLGDLKLLFEYLTLFGIDDKISFDLSLARGLD YYTGVIYEAVLLQTPAQAGEEPLGVGSVAAGGRYDGLVGM FDPKGRKVPCVGLSIGVERIFSIVEQRLEALEEKIRTTETQVL VASAQKKLLEERLKLVSELWDAGIKAELLYKKNPKLLNQL QYCEEAGIPLVAIIGEQELKDGVIKLRSVTSREEVDVRREDL VEEIKRRT | 172 |

TABLE D4-continued

| Name | Amino Acid Residue Range of SEQ ID NO: 1 | Amino acid sequence | SEQ ID NO: |
|---|---|---|---|
| Exemplary HRS polypeptide fragments | | | |
| HRS(1-503) | Protein/ Human/ 1-503 | MAERAALEELVKLQGERVRGLKQQKASAELIEEEVAKLLK LKAQLGPDESKQKFVLKTPKGTRDYSPRQMAVREKVFDVII RCFKRHGAEVIDTPVFELKETLMGKYGEDSKLIYDLKDQGG ELLSLRYDLTVPFARYLAMNKLTNIKRYHIAKVYRRDNPAM TRGRYREFYQCDFDIAGNFDPMIPDAECLKIMCEILSSLQIGD FLVKVNDRRILDGMFAICGVSDSKFRTICSSVDKLDKVSWE EVKNEMVGEKGLAPEVADRIGDYVQQHGGVSLVEQLLQDP KLSQNKQALEGLGDLKLLFEYLTLFGIDDKISFDLSLARGLD YYTGVIYEAVLLQTPAQAGEEPLGVGSVAAGGRYDGLVGM FDPKGRKVPCVGLSIGVERIFSIVEQRLEALEEKIRTTETQVL VASAQKKLLEERLKLVSELWDAGIKAELLYKKNPKLLNQL QYCEEAGIPLVAIIGEQELKDGVIKLRSVTSREEVDVRREDL VEEIKRRTG | 173 |
| HRS(1-504) | Protein/ Human/ 1-504 | MAERAALEELVKLQGERVRGLKQQKASAELIEEEVAKLLK LKAQLGPDESKQKFVLKTPKGTRDYSPRQMAVREKVFDVII RCFKRHGAEVIDTPVFELKETLMGKYGEDSKLIYDLKDQGG ELLSLRYDLTVPFARYLAMNKLTNIKRYHIAKVYRRDNPAM TRGRYREFYQCDFDIAGNFDPMIPDAECLKIMCEILSSLQIGD FLVKVNDRRILDGMFAICGVSDSKFRTICSSVDKLDKVSWE EVKNEMVGEKGLAPEVADRIGDYVQQHGGVSLVEQLLQDP KLSQNKQALEGLGDLKLLFEYLTLFGIDDKISFDLSLARGLD YYTGVIYEAVLLQTPAQAGEEPLGVGSVAAGGRYDGLVGM FDPKGRKVPCVGLSIGVERIFSIVEQRLEALEEKIRTTETQVL VASAQKKLLEERLKLVSELWDAGIKAELLYKKNPKLLNQL QYCEEAGIPLVAIIGEQELKDGVIKLRSVTSREEVDVRREDL VEEIKRRTGQ | 174 |
| HRS(1-505) | Protein/ Human/ 1-505 | MAERAALEELVKLQGERVRGLKQQKASAELIEEEVAKLLK LKAQLGPDESKQKFVLKTPKGTRDYSPRQMAVREKVFDVII RCFKRHGAEVIDTPVFELKETLMGKYGEDSKLIYDLKDQGG ELLSLRYDLTVPFARYLAMNKLTNIKRYHIAKVYRRDNPAM TRGRYREFYQCDFDIAGNFDPMIPDAECLKIMCEILSSLQIGD FLVKVNDRRILDGMFAICGVSDSKFRTICSSVDKLDKVSWE EVKNEMVGEKGLAPEVADRIGDYVQQHGGVSLVEQLLQDP KLSQNKQALEGLGDLKLLFEYLTLFGIDDKISFDLSLARGLD YYTGVIYEAVLLQTPAQAGEEPLGVGSVAAGGRYDGLVGM FDPKGRKVPCVGLSIGVERIFSIVEQRLEALEEKIRTTETQVL VASAQKKLLEERLKLVSELWDAGIKAELLYKKNPKLLNQL QYCEEAGIPLVAIIGEQELKDGVIKLRSVTSREEVDVRREDL VEEIKRRTGQP | 175 |
| $HRS1^{N8}$ HRS(1-506) | Protein/ Human/ 1-506 | MAERAALEELVKLQGERVRGLKQQKASAELIEEEVAKLLK LKAQLGPDESKQKFVLKTPKGTRDYSPRQMAVREKVFDVII RCFKRHGAEVIDTPVFELKETLMGKYGEDSKLIYDLKDQGG ELLSLRYDLTVPFARYLAMNKLTNIKRYHIAKVYRRDNPAM TRGRYREFYQCDFDIAGNFDPMIPDAECLKIMCEILSSLQIGD FLVKVNDRRILDGMFAICGVSDSKFRTICSSVDKLDKVSWE EVKNEMVGEKGLAPEVADRIGDYVQQHGGVSLVEQLLQDP KLSQNKQALEGLGDLKLLFEYLTLFGIDDKISFDLSLARGLD YYTGVIYEAVLLQTPAQAGEEPLGVGSVAAGGRYDGLVGM FDPKGRKVPCVGLSIGVERIFSIVEQRLEALEEKIRTTETQVL VASAQKKLLEERLKLVSELWDAGIKAELLYKKNPKLLNQL QYCEEAGIPLVAIIGEQELKDGVIKLRSVTSREEVDVRREDL VEEIKRRTGQPL | 25 |
| HRS(1-507) | Protein/ Human/ 1-507 | MAERAALEELVKLQGERVRGLKQQKASAELIEEEVAKLLK LKAQLGPDESKQKFVLKTPKGTRDYSPRQMAVREKVFDVII RCFKRHGAEVIDTPVFELKETLMGKYGEDSKLIYDLKDQGG ELLSLRYDLTVPFARYLAMNKLTNIKRYHIAKVYRRDNPAM TRGRYREFYQCDFDIAGNFDPMIPDAECLKIMCEILSSLQIGD FLVKVNDRRILDGMFAICGVSDSKFRTICSSVDKLDKVSWE EVKNEMVGEKGLAPEVADRIGDYVQQHGGVSLVEQLLQDP KLSQNKQALEGLGDLKLLFEYLTLFGIDDKISFDLSLARGLD YYTGVIYEAVLLQTPAQAGEEPLGVGSVAAGGRYDGLVGM FDPKGRKVPCVGLSIGVERIFSIVEQRLEALEEKIRTTETQVL VASAQKKLLEERLKLVSELWDAGIKAELLYKKNPKLLNQL QYCEEAGIPLVAIIGEQELKDGVIKLRSVTSREEVDVRREDL VEEIKRRTGQPLC | 176 |

TABLE D4-continued

Exemplary HRS polypeptide fragments

| Name | Amino Acid Residue Range of SEQ ID NO: 1 | Amino acid sequence | SEQ ID NO: |
|---|---|---|---|
| HRS(1-508) | Protein/ Human/ 1-508 | MAERAALEELVKLQGERVRGLKQQKASAELIEEEVAKLLK LKAQLGPDESKQKFVLKTPKGTRDYSPRQMAVREKVFDVII RCFKRHGAEVIDTPVFELKETLMGKYGEDSKLIYDLKDQGG ELLSLRYDLTVPFARYLAMNKLTNIKRYHIAKVYRRDNPAM TRGRYREFYQCDFDIAGNFDPMIPDAECLKIMCEILSSLQIGD FLVKVNDRRILDGMFAICGVSDSKFRTICSSVDKLDKVSWE EVKNEMVGEKGLAPEVADRIGDYVQQHGGVSLVEQLLQDP KLSQNKQALEGLGDLKLLFEYLTLFGIDDKISFDLSLARGLD YYTGVIYEAVLLQTPAQAGEEPLGVGSVAAGGRYDGLVGM FDPKGRKVPCVGSIGVERIFSIVEQRLEALEEKIRTTETQVL VASAQKKLLEERLKLVSELWDAGIKAELLYKKNPKLLNQL QYCEEAGIPLVAIIGEQELKDGVIKLRSVTSREEVDVRREDL VEEIKRRTGQPLCI | 177 |
| HRS(1-509) | Protein/ Human/ 1-509 | MAERAALEELVKLQGERVRGLKQQKASAELIEEEVAKLLK LKAQLGPDESKQKFVLKTPKGTRDYSPRQMAVREKVFDVII RCFKRHGAEVIDTPVFELKETLMGKYGEDSKLIYDLKDQGG ELLSLRYDLTVPFARYLAMNKLTNIKRYHIAKVYRRDNPAM TRGRYREFYQCDFDIAGNFDPMIPDAECLKIMCEILSSLQIGD FLVKVNDRRILDGMFAICGVSDSKFRTICSSVDKLDKVSWE EVKNEMVGEKGLAPEVADRIGDYVQQHGGVSLVEQLLQDP KLSQNKQALEGLGDLKLLFEYLTLFGIDDKISFDLSLARGLD YYTGVIYEAVLLQTPAQAGEEPLGVGSVAAGGRYDGLVGM FDPKGRKVPCVGLSIGVERIFSIVEQRLEALEEKIRTTETQVL VASAQKKLLEERLKLVSELWDAGIKAELLYKKNPKLLNQL QYCEEAGIPLVAIIGEQELKDGVIKLRSVTSREEVDVRREDL VEEIKRRTGQPLCIC | 178 |
| HisRS1[N6] HRS(1-48) | Protein/ Human/ 1-48 | MAERAALEELVKLQGERVRGLKQQKASAELIEEEVAKLLK LKAQLGPD | 26 |

For some HRS polypeptides, about or at least about 20-40, 20-45, 20-50, 20-55, or 20-60, 20-65, or 20-67 contiguous or non-contiguous amino acids of the HRS polypeptide are from amino acids 1-67 of SEQ ID NO:1. In particular embodiments, about 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, or 67 contiguous or non-contiguous amino acids of the HRS polypeptide are from amino acids 1-67 of SEQ ID NO:1. The HRS polypeptide may comprise one or more of a WHEP domain, an aminoacylation domain, an anticodon binding domain, or any combination thereof. In particular embodiments, the HRS polypeptide lacks a functional aminoacylation domain. In some embodiments, the polypeptide consists essentially of the WHEP domain from human HRS. Without wishing to be bound by any one theory, the unique orientation, or conformation, of the WHEP domain in certain HRS polypeptides may contribute to the enhanced non canonical, and/or antibody blocking activities observed in these proteins.

Hence, in certain embodiments, the HRS polypeptide comprises, consists, or consists essentially of a human HRS WHEP domain sequence. In some embodiments, the human HRS WHEP domain sequence is defined by certain conserved residues. For example, in some aspects the HRS polypeptide comprises, consists, or consists essentially of the human HRS WHEP domain consensus sequence in Table D5 below.

In certain embodiments, the HRS polypeptide may comprise 1, 2, 3, 4, 5, 6, 7, 8, 9, 10, 11, 12, 13, 14, 15, 16, 17, 18, 19, 20, 21, 22, 23, 24, 25, 26, 27, 28, or all 29 amino acids of a flexible linker connecting the minimum domain to a heterologous protein (e.g., Fc domain), or splice variant.

The recitations "sequence identity" or, for example, comprising a "sequence 50% identical to," as used herein, refer to the extent that sequences are identical on a nucleotide-by-nucleotide basis or an amino acid-by-amino acid basis over a window of comparison. Thus, a "percentage of sequence identity" may be calculated by comparing two optimally aligned sequences over the window of comparison, determining the number of positions at which the identical nucleic acid base (e.g., A, T, C, G, I) or the identical amino acid residue (e.g., Ala, Pro, Ser, Thr, Gly, Val, Leu, Ile, Phe, Tyr, Trp, Lys, Arg, His, Asp, Glu, Asn, Gln, Cys and Met) occurs in both sequences to yield the number of matched positions, dividing the number of matched positions by the total number of positions in the window of comparison (i.e., the window size), and multiplying the result by 100 to yield the percentage of sequence identity.

Terms used to describe sequence relationships between two or more polypeptides include "reference sequence," "comparison window," "sequence identity," "percentage of sequence identity" and "substantial identity." A "reference sequence" is at least 12 but frequently 15 to 18 and often at least 25 monomer units, inclusive of nucleotides and amino acid residues, in length. Because two polypeptides may each comprise (1) a sequence (i.e., only a portion of the complete polypeptides sequence) that is similar between the two polypeptides, and (2) a sequence that is divergent between the two polypeptides, sequence comparisons between two (or more) polypeptides are typically performed by comparing sequences of the two polypeptides over a "comparison window" to identify and compare local regions of sequence similarity. A "comparison window" refers to a conceptual segment of at least 6 contiguous positions, usually about 50 to about 100, more usually about 100 to about 150 in which a sequence is compared to a reference sequence of the same number of contiguous positions after the two sequences are optimally aligned. The comparison window may comprise additions or deletions (i.e., gaps) of about 20% or less as compared to the reference sequence (which does not comprise additions or deletions) for optimal alignment of the two sequences. Optimal alignment of sequences for aligning a comparison window may be conducted by computerized implementations of algorithms (GAP, BESTFIT, FASTA, and TFASTA in the Wisconsin Genetics Software Package Release 7.0, Genetics Computer Group, 575 Science Drive Madison, Wis., USA) or by inspection and the best alignment (i.e., resulting in the highest percentage homology over the comparison window) generated by any of the various methods selected. Reference also may be made to the BLAST family of programs as for example disclosed by Altschul et al., 1997, *Nucl. Acids Res.* 25:3389. A detailed discussion of sequence analysis can be found in Unit 19.3 of Ausubel et al., "Current Protocols in Molecular Biology," John Wiley & Sons Inc, 1994-1998, Chapter 15.

Calculations of sequence similarity or sequence identity between sequences (the terms are used interchangeably herein) can be performed as follows. To determine the percent identity of two amino acid sequences, or of two nucleic acid sequences, the sequences can be aligned for optimal comparison purposes (e.g., gaps can be introduced in one or both of a first and a second amino acid or nucleic acid sequence for optimal alignment and non-homologous sequences can be disregarded for comparison purposes). In certain embodiments, the length of a reference sequence aligned for comparison purposes is at least 30%, preferably at least 40%, more preferably at least 50%, 60%, and even more preferably at least 70%, 80%, 90%, 100% of the length of the reference sequence. The amino acid residues or nucleotides at corresponding amino acid positions or nucleotide positions are then compared. When a position in the first sequence is occupied by the same amino acid residue or nucleotide as the corresponding position in the second sequence, then the molecules are identical at that position.

The percent identity between the two sequences is a function of the number of identical positions shared by the sequences, taking into account the number of gaps, and the length of each gap, which need to be introduced for optimal alignment of the two sequences.

The comparison of sequences and determination of percent identity between two sequences can be accomplished using a mathematical algorithm. In a preferred embodiment, the percent identity between two amino acid sequences is determined using the Needleman and Wunsch, (1970, *J. Mol. Biol.* 48: 444-453) algorithm which has been incorporated into the GAP program in the GCG software package, using either a Blossum 62 matrix or a PAM250 matrix, and a gap weight of 16, 14, 12, 10, 8, 6, or 4 and a length weight of 1, 2, 3, 4, 5, or 6. In yet another preferred embodiment, the percent identity between two nucleotide sequences is determined using the GAP program in the GCG software package, using a NWSgapdna.CMP matrix and a gap weight of 40, 50, 60, 70, or 80 and a length weight of 1, 2, 3, 4, 5, or 6. A particularly preferred set of parameters (and the one that should be used unless otherwise specified) are a Blossum 62 scoring matrix with a gap penalty of 12, a gap extend penalty of 4, and a frameshift gap penalty of 5. The percent identity between two amino acid or nucleotide sequences can also be determined using the algorithm of E. Meyers and W. Miller (1989, *Cabios,* 4: 11-17) which has been incorporated into the ALIGN program (version 2.0), using a PAM120 weight residue table, a gap length penalty of 12 and a gap penalty of 4.

The nucleic acid and protein sequences described herein can be used as a "query sequence" to perform a search against public databases, for example, to identify other family members or related sequences. Such searches can be performed using the NBLAST and XBLAST programs (version 2.0) of Altschul, et al., (1990, *J. Mol. Biol,* 215: 403-10). BLAST nucleotide searches can be performed with the NBLAST program, score=100, wordlength=12 to obtain nucleotide sequences homologous to nucleic acid molecules of the invention. BLAST protein searches can be performed with the XBLAST program, score=50, wordlength=3 to obtain amino acid sequences homologous to protein molecules of the invention. To obtain gapped alignments for comparison purposes, Gapped BLAST can be utilized as described in Altschul et al. (*Nucleic Acids Res.* 25:3389-3402, 1997). When utilizing BLAST and Gapped BLAST programs, the default parameters of the respective programs (e.g., XBLAST and NBLAST) can be used.

In certain embodiments, variant polypeptides differ from the corresponding HRS reference sequences by at least 1% but less than 20%, 15%, 10% or 5% of the residues. If this comparison requires alignment, the sequences should be aligned for maximum similarity. "Looped" out sequences from deletions or insertions, or mismatches, are considered differences. The differences are, suitably, differences or changes at a non-essential residue or a conservative substitution. In certain embodiments, the molecular weight of a variant HRS polypeptide differs from that of the HRS reference polypeptide by about 1%, 2%, 3%, 4%, 5%, 6%, 7%, 8%, 9%, 10%, 11%, 12%, 13%, 14%, 15%, 16%, 17%, 18%, 19%, 20%, or more.

Also included are biologically active "fragments" of the HRS reference polypeptides, i.e., biologically active fragments of the HRS protein fragments. Representative biologically active fragments generally participate in an interaction, e.g., an intramolecular or an inter-molecular interaction. An inter-molecular interaction can be a specific binding interaction or an enzymatic interaction. An intermolecular interaction can be between a HRS polypeptide and a cellular binding partner, such as a cellular receptor or other host molecule that participates in the non-canonical activity of the HRS polypeptide.

A biologically active fragment of an HRS reference polypeptide can be a polypeptide fragment which is, for example, 10, 11, 12, 13, 14, 15, 16, 17, 18, 19, 20, 21, 22, 23, 24, 25, 26, 27, 28, 29, 30, 35, 40, 45, 50, 55, 60, 65, 70, 75, 80, 85, 90, 95, 100, 110, 120, 130, 140, 150, 160, 170, 180, 190, 200, 220, 240, 260, 280, 300, 320, 321, 322, 323, 324, 325, 326, 327, 328, 329, 330, 331, 332, 333, 334, 335, 336, 337, 338, 339, 340, 341, 342, 343, 344, 345, 346, 347, 348, 349, 350, 351, 352, 353, 354, 355, 356, 357, 38, 359, 360, 361, 362, 363, 364, 365, 380, 400, 450, 500, 505, or more contiguous or non-contiguous amino acids, including all integers (e.g., 101, 102, 103) and ranges (e.g., 50-100, 50-150, 50-200) in between, of the amino acid sequences set forth in any one of the HRS reference polypeptides described herein. In certain embodiments, a biologically active fragment comprises a non-canonical activity-related sequence, domain, or motif. In certain embodiments, the C-terminal or N-terminal region of any HRS reference polypeptide may be truncated by about 1, 2, 3, 4, 5, 6, 7, 8, 9, 10, 11, 12, 13, 14, 15, 16, 17, 18, 19, 20, 25, 30, 35, 40, 45, 50, 60, 70, 80, 90, 100, 110, 120, 130, 140, 150, 160, 170, 180, 190, 200, 250, 300, 350, 400, 450, 500 or more amino acids, or by about 10-50, 20-50, 50-100, 100-150, 150-200, 200-250, 250-300, 300-350, 350-400, 400-450, 450-500 or more amino acids, including all integers and ranges in between (e.g., 101, 102, 103, 104, 105), so long as the truncated HRS polypeptide retains the non-canonical activity of the reference polypeptide. Certain exemplary truncated HRS polypeptides and a human HRS WHEP domain consensus sequence are shown in Table D5 below.

TABLE D5

| Exemplary truncated HRS polypeptides | | |
|---|---|---|
| HRS range | Sequence | SEQ ID NO: |
| C-terminal truncations | | |
| 1-80 | MAERAALEELVKLQGERVRGLKQQKASAELIEEEVAKLLK LKAQLGPDESKQKFVLKTPKGTRDYSPRQMAVREKVFDVI | 27 |
| 1-79 | MAERAALEELVKLQGERVRGLKQQKASAELIEEEVAKLLK LKAQLGPDESKQKFVLKTPKGTRDYSPRQMAVREKVFDV | 28 |
| 1-78 | MAERAALEELVKLQGERVRGLKQQKASAELIEEEVAKLLK LKAQLGPDESKQKFVLKTPKGTRDYSPRQMAVREKVFD | 29 |
| 1-77 | MAERAALEELVKLQGERVRGLKQQKASAELIEEEVAKLLK LKAQLGPDESKQKFVLKTPKGTRDYSPRQMAVREKVF | 30 |
| 1-76 | MAERAALEELVKLQGERVRGLKQQKASAELIEEEVAKLLK LKAQLGPDESKQKFVLKTPKGTRDYSPRQMAVREKV | 31 |
| 1-75 | MAERAALEELVKLQGERVRGLKQQKASAELIEEEVAKLLK LKAQLGPDESKQKFVLKTPKGTRDYSPRQMAVREK | 32 |
| 1-74 | MAERAALEELVKLQGERVRGLKQQKASAELIEEEVAKLLK LKAQLGPDESKQKFVLKTPKGTRDYSPRQMAVRE | 33 |
| 1-73 | MAERAALEELVKLQGERVRGLKQQKASAELIEEEVAKLLK LKAQLGPDESKQKFVLKTPKGTRDYSPRQMAVR | 34 |
| 1-72 | MAERAALEELVKLQGERVRGLKQQKASAELIEEEVAKLLK LKAQLGPDESKQKFVLKTPKGTRDYSPRQMAV | 35 |
| 1-71 | MAERAALEELVKLQGERVRGLKQQKASAELIEEEVAKLLK LKAQLGPDESKQKFVLKTPKGTRDYSPRQMA | 36 |
| 1-70 | MAERAALEELVKLQGERVRGLKQQKASAELIEEEVAKLLK LKAQLGPDESKQKFVLKTPKGTRDYSPRQM | 37 |
| 1-69 | MAERAALEELVKLQGERVRGLKQQKASAELIEEEVAKLLK LKAQLGPDESKQKFVLKTPKGTRDYSPRQ | 38 |
| 1-68 | MAERAALEELVKLQGERVRGLKQQKASAELIEEEVAKLLK LKAQLGPDESKQKFVLKTPKGTRDYSPR | 39 |
| 1-67 | MAERAALEELVKLQGERVRGLKQQKASAELIEEEVAKLLK LKAQLGPDESKQKFVLKTPKGTRDYSP | 40 |
| 1-66 | MAERAALEELVKLQGERVRGLKQQKASAELIEEEVAKLLK LKAQLGPDESKQKFVLKTPKGTRDYS | 41 |
| 1-65 | MAERAALEELVKLQGERVRGLKQQKASAELIEEEVAKLLK LKAQLGPDESKQKFVLKTPKGTRDY | 42 |
| 1-64 | MAERAALEELVKLQGERVRGLKQQKASAELIEEEVAKLLK LKAQLGPDESKQKFVLKTPKGTRD | 43 |
| 1-63 | MAERAALEELVKLQGERVRGLKQQKASAELIEEEVAKLLK LKAQLGPDESKQKFVLKTPKGTR | 44 |
| 1-62 | MAERAALEELVKLQGERVRGLKQQKASAELIEEEVAKLLK LKAQLGPDESKQKFVLKTPKGT | 45 |
| 1-61 | MAERAALEELVKLQGERVRGLKQQKASAELIEEEVAKLLK LKAQLGPDESKQKFVLKTPKG | 46 |
| 1-60 | MAERAALEELVKLQGERVRGLKQQKASAELIEEEVAKLLK LKAQLGPDESKQKFVLKTPK | 47 |
| 1-59 | MAERAALEELVKLQGERVRGLKQQKASAELIEEEVAKLLK LKAQLGPDESKQKFVLKTP | 48 |

TABLE D5-continued

| Exemplary truncated HRS polypeptides | | |
|---|---|---|
| 1-58 | MAERAALEELVKLQGERVRGLKQQKASAELIEEEVAKLLK LKAQLGPDESKQKFVLKT | 49 |
| 1-57 | MAERAALEELVKLQGERVRGLKQQKASAELIEEEVAKLLK LKAQLGPDESKQKFVLK | 50 |
| 1-56 | MAERAALEELVKLQGERVRGLKQQKASAELIEEEVAKLLK LKAQLGPDESKQKFVL | 51 |
| 1-55 | MAERAALEELVKLQGERVRGLKQQKASAELIEEEVAKLLK LKAQLGPDESKQKFV | 52 |
| 1-54 | MAERAALEELVKLQGERVRGLKQQKASAELIEEEVAKLLK LKAQLGPDESKQKF | 53 |
| 1-53 | MAERAALEELVKLQGERVRGLKQQKASAELIEEEVAKLLK LKAQLGPDESKQK | 54 |
| 1-52 | MAERAALEELVKLQGERVRGLKQQKASAELIEEEVAKLLK LKAQLGPDESKQ | 55 |
| 1-51 | MAERAALEELVKLQGERVRGLKQQKASAELIEEEVAKLLK LKAQLGPDESK | 56 |
| 1-50 | MAERAALEELVKLQGERVRGLKQQKASAELIEEEVAKLLK LKAQLGPDES | 57 |
| 1-49 | MAERAALEELVKLQGERVRGLKQQKASAELIEEEVAKLLK LKAQLGPDE | 58 |
| 1-48 | MAERAALEELVKLQGERVRGLKQQKASAELIEEEVAKLLKLKAQLGPD | 59 |
| 1-47 | MAERAALEELVKLQGERVRGLKQQKASAELIEEEVAKLLKLKAQLGP | 60 |
| 1-46 | MAERAALEELVKLQGERVRGLKQQKASAELIEEEVAKLLKLKAQLG | 61 |
| 1-45 | MAERAALEELVKLQGERVRGLKQQKASAELIEEEVAKLLKLKAQL | 62 |
| 1-44 | MAERAALEELVKLQGERVRGLKQQKASAELIEEEVAKLLKLKAQ | 63 |
| 1-43 | MAERAALEELVKLQGERVRGLKQQKASAELIEEEVAKLLK LKA | 64 |
| 1-42 | MAERAALEELVKLQGERVRGLKQQKASAELIEEEVAKLLK LK | 65 |
| 1-41 | MAERAALEELVKLQGERVRGLKQQKASAELIEEEVAKLLK L | 66 |
| 1-40 | MAERAALEELVKLQGERVRGLKQQKASAELIEEEVAKLLK | 67 |
| N-terminal truncations | | |
| 2-80 | AERAALEELVKLQGERVRGLKQQKASAELIEEEVAKLLK LKAQLGPDESKQKFVLKTPKGTRDYSPRQMAVREKVFDVI | 68 |
| 3-80 | ERAALEELVKLQGERVRGLKQQKASAELIEEEVAKLLK LKAQLGPDESKQKFVLKTPKGTRDYSPRQMAVREKVFDVI | 69 |
| 4-80 | RAALEELVKLQGERVRGLKQQKASAELIEEEVAKLLK LKAQLGPDESKQKFVLKTPKGTRDYSPRQMAVREKVFDVI | 70 |
| 5-80 | AALEELVKLQGERVRGLKQQKASAELIEEEVAKLLK LKAQLGPDESKQKFVLKTPKGTRDYSPRQMAVREKVFDVI | 71 |
| 6-80 | ALEELVKLQGERVRGLKQQKASAELIEEEVAKLLK LKAQLGPDESKQKFVLKTPKGTRDYSPRQMAVREKVFDVI | 72 |
| 7-80 | LEELVKLQGERVRGLKQQKASAELIEEEVAKLLK LKAQLGPDESKQKFVLKTPKGTRDYSPRQMAVREKVFDVI | 73 |
| 8-80 | EELVKLQGERVRGLKQQKASAELIEEEVAKLLK LKAQLGPDESKQKFVLKTPKGTRDYSPRQMAVREKVFDVI | 74 |
| 9-80 | ELVKLQGERVRGLKQQKASAELIEEEVAKLLK LKAQLGPDESKQKFVLKTPKGTRDYSPRQMAVREKVFDVI | 75 |

TABLE D5-continued

Exemplary truncated HRS polypeptides

| | | |
|---|---|---|
| 10-80 | LVKLQGERVRGLKQQKASAELIEEEVAKLLK LKAQLGPDESKQKFVLKTPKGTRDYSPRQMAVREKVFDVI | 76 |
| 11-80 | VKLQGERVRGLKQQKASAELIEEEVAKLLK LKAQLGPDESKQKFVLKTPKGTRDYSPRQMAVREKVFDVI | 77 |
| 12-80 | KLQGERVRGLKQQKASAELIEEEVAKLLK LKAQLGPDESKQKFVLKTPKGTRDYSPRQMAVREKVFDVI | 78 |
| 13-80 | LQGERVRGLKQQKASAELIEEEVAKLLK LKAQLGPDESKQKFVLKTPKGTRDYSPRQMAVREKVFDVI | 79 |
| 14-80 | QGERVRGLKQQKASAELIEEEVAKLLK LKAQLGPDESKQKFVLKTPKGTRDYSPRQMAVREKVFDVI | 80 |
| 15-80 | GERVRGLKQQKASAELIEEEVAKLLK LKAQLGPDESKQKFVLKTPKGTRDYSPRQMAVREKVFDVI | 81 |
| 16-80 | RVRGLKQQKASAELIEEEVAKLLK LKAQLGPDESKQKFVLKTPKGTRDYSPRQMAVREKVFDVI | 82 |
| 17-80 | VRGLKQQKASAELIEEEVAKLLK LKAQLGPDESKQKFVLKTPKGTRDYSPRQMAVREKVFDVI | 83 |
| 18-80 | RGLKQQKASAELIEEEVAKLLK LKAQLGPDESKQKFVLKTPKGTRDYSPRQMAVREKVFDVI | 84 |
| 19-80 | GLKQQKASAELIEEEVAKLLK LKAQLGPDESKQKFVLKTPKGTRDYSPRQMAVREKVFDVI | 85 |
| 20-80 | LKQQKASAELIEEEVAKLLK LKAQLGPDESKQKFVLKTPKGTRDYSPRQMAVREKVFDVI | 86 |
| 21-80 | KQQKASAELIEEEVAKLLK LKAQLGPDESKQKFVLKTPKGTRDYSPRQMAVREKVFDVI | 87 |
| 22-80 | QQKASAELIEEEVAKLLK LKAQLGPDESKQKFVLKTPKGTRDYSPRQMAVREKVFDVI | 88 |
| 23-80 | QKASAELIEEEVAKLLK LKAQLGPDESKQKFVLKTPKGTRDYSPRQMAVREKVFDVI | 89 |
| 24-80 | KASAELIEEEVAKLLK LKAQLGPDESKQKFVLKTPKGTRDYSPRQMAVREKVFDVI | 90 |
| 25-80 | ASAELIEEEVAKLLK LKAQLGPDESKQKFVLKTPKGTRDYSPRQMAVREKVFDVI | 91 |
| 26-80 | SAELIEEEVAKLLK LKAQLGPDESKQKFVLKTPKGTRDYSPRQMAVREKVFDVI | 92 |
| 27-80 | AELIEEEVAKLLK LKAQLGPDESKQKFVLKTPKGTRDYSPRQMAVREKVFDVI | 93 |
| 28-80 | ELIEEEVAKLLK LKAQLGPDESKQKFVLKTPKGTRDYSPRQMAVREKVFDVI | 94 |
| 29-80 | LIEEEVAKLLK LKAQLGPDESKQKFVLKTPKGTRDYSPRQMAVREKVFDVI | 95 |
| 30-80 | IEEEVAKLLK LKAQLGPDESKQKFVLKTPKGTRDYSPRQMAVREKVFDVI | 96 |
| 31-80 | EEEVAKLLK LKAQLGPDESKQKFVLKTPKGTRDYSPRQMAVREKVFDVI | 97 |
| 32-80 | EEVAKLLKLKAQLGPDESKQKFVLKTPKGTRDYSPRQMAVREKVFDVI | 98 |
| 33-80 | EVAKLLKLKAQLGPDESKQKFVLKTPKGTRDYSPRQMAVREKVFDVI | 99 |
| 34-80 | VAKLLKLKAQLGPDESKQKFVLKTPKGTRDYSPRQMAVREKVFDVI | 100 |
| 35-80 | AKLLKLKAQLGPDESKQKFVLKTPKGTRDYSPRQMAVREKVFDVI | 101 |
| 36-80 | KLLKLKAQLGPDESKQKFVLKTPKGTRDYSPRQMAVREKVFDVI | 102 |
| 37-80 | LLKLKAQLGPDESKQKFVLKTPKGTRDYSPRQMAVREKVFDVI | 103 |

TABLE D5-continued

| Exemplary truncated HRS polypeptides | | |
|---|---|---|
| 38-80 | LKLKAQLGPDESKQKFVLKTPKGTRDYSPRQMAVREKVFDVI | 104 |
| 39-80 | KLKAQLGPDESKQKFVLKTPKGTRDYSPRQMAVREKVFDVI | 105 |
| 40-80 | LKAQLGPDESKQKFVLKTPKGTRDYSPRQMAVREKVFDVI | 106 |
| HRS WHEP consensus | $X_A$-L-$X_B$-Q-G-X-X-V-R-X-L-K-X-X-K-A-$X_C$-V-X-X-L-L-X-L-K-$X_D$<br>Where<br>X is any amino acid<br>$X_A$ is 0-50 amino acids<br>$X_B$ is about 5-7 amino acids, preferably 6 amino acids<br>$X_C$ is about 7-9 amino acids, preferably 8 amino acids<br>$X_D$ is 0-50 amino acids | 322 |

It will be appreciated that in any of the HRS-Fc conjugates of the invention, the N-terminal acid of the HRS polypeptide (for example, the N-terminal Met) may additionally be deleted from any of the exemplary truncated HRS polypeptides or other HRS sequences described herein.

Typically, the biologically-active fragment has no less than about 1%, 10%, 25%, or 50% of an activity of the biologically-active (i.e., non-canonical activity) HRS reference polypeptide from which it is derived. Exemplary methods for measuring such non-canonical activities are described in the Examples.

In some embodiments, HRS proteins, variants, and biologically active fragments thereof, bind to one or more cellular binding partners with an affinity of at least about 0.01, 0.05, 0.1, 0.2, 0.3, 0.4, 0.5, 0.6, 0.7, 0.8, 0.9, 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 40, 50, 100, or 150 nM. In some embodiments, the binding affinity of a HRS protein fragment for a selected cellular binding partner, particularly a binding partner that participates in a non-canonical activity, can be stronger than that of the corresponding full length HRS polypeptide or a specific alternatively spliced HRS polypeptide variant, by at least about 1.5×, 2×, 2.5×, 3×, 3.5×, 4×, 4.5×, 5×, 6×, 7×, 8×, 9×, 10×, 15×, 20×, 25×, 30×, 40×, 50×, 60×, 70×, 80×, 90×, 100×, 200×, 300×, 400×, 500×, 600×, 700×, 800×, 900×, 1000× or more (including all integers in between).

As noted above, a HRS polypeptide may be altered in various ways including amino acid substitutions, deletions, truncations, and insertions. Methods for such manipulations are generally known in the art. For example, amino acid sequence variants of a HRS reference polypeptide can be prepared by mutations in the DNA. Methods for mutagenesis and nucleotide sequence alterations are well known in the art. See, for example, Kunkel (1985, *Proc. Natl. Acad. Sci. USA.* 82: 488-492), Kunkel et al., (1987, *Methods in Enzymol,* 154: 367-382), U.S. Pat. No. 4,873,192, Watson, J. D. et al., ("Molecular Biology of the Gene", Fourth Edition, Benjamin/Cummings, Menlo Park, Calif., 1987) and the references cited therein. Guidance as to appropriate amino acid substitutions that do not affect biological activity of the protein of interest may be found in the model of Dayhoff et al., (1978) Atlas of Protein Sequence and Structure (Natl. Biomed. Res. Found., Washington, D.C.).

Biologically active truncated and/or variant HRS polypeptides may contain conservative amino acid substitutions at various locations along their sequence, as compared to a reference HRS amino acid residue, and such additional substitutions may further enhance the activity or stability of the HRS polypeptides with altered cysteine content. A "conservative amino acid substitution" is one in which the amino acid residue is replaced with an amino acid residue having a similar side chain. Families of amino acid residues having similar side chains have been defined in the art, which can be generally sub-classified as follows:

Acidic: The residue has a negative charge due to loss of H ion at physiological pH and the residue is attracted by aqueous solution so as to seek the surface positions in the conformation of a peptide in which it is contained when the peptide is in aqueous medium at physiological pH. Amino acids having an acidic side chain include glutamic acid and aspartic acid.

Basic: The residue has a positive charge due to association with H ion at physiological pH or within one or two pH units thereof (e.g., histidine) and the residue is attracted by aqueous solution so as to seek the surface positions in the conformation of a peptide in which it is contained when the peptide is in aqueous medium at physiological pH. Amino acids having a basic side chain include arginine, lysine and histidine.

Charged: The residues are charged at physiological pH and, therefore, include amino acids having acidic or basic side chains (i.e., glutamic acid, aspartic acid, arginine, lysine and histidine).

Hydrophobic: The residues are not charged at physiological pH and the residue is repelled by aqueous solution so as to seek the inner positions in the conformation of a peptide in which it is contained when the peptide is in aqueous medium. Amino acids having a hydrophobic side chain include tyrosine, valine, isoleucine, leucine, methionine, phenylalanine and tryptophan.

Neutral/polar: The residues are not charged at physiological pH, but the residue is not sufficiently repelled by aqueous solutions so that it would seek inner positions in the conformation of a peptide in which it is contained when the peptide is in aqueous medium. Amino acids having a neutral/polar side chain include asparagine, glutamine, cysteine, histidine, serine and threonine.

This description also characterizes certain amino acids as "small" since their side chains are not sufficiently large, even if polar groups are lacking, to confer hydrophobicity. With the exception of proline, "small" amino acids are those with four carbons or less when at least one polar group is on the side chain and three carbons or less when not. Amino acids having a small side chain include glycine, serine, alanine and threonine. The gene-encoded secondary amino acid proline is a special case due to its known effects on the secondary conformation of peptide chains. The structure of proline differs from all the other naturally-occurring amino acids in that its side chain is bonded to the nitrogen of the α-amino group, as well as the α-carbon. Several amino acid similarity matrices are known in the art (see e.g., PAM120 matrix and PAM250 matrix as disclosed for example by Dayhoff et al., 1978, A model of evolutionary change in proteins). Matrices for determining distance relationships In M. O. Dayhoff, (ed.), Atlas of protein sequence and structure, Vol. 5, pp. 345-358, National Biomedical Research Foundation, Washington D.C.; and by Gonnet et al., (*Science,* 256: 14430-1445, 1992), however, include proline in the same group as glycine, serine, alanine and threonine. Accordingly, for the purposes of the present invention, proline is classified as a "small" amino acid.

The degree of attraction or repulsion required for classification as polar or nonpolar is arbitrary and, therefore, amino acids specifically contemplated by the invention have been classified as one or the other. Most amino acids not specifically named can be classified on the basis of known behavior.

Amino acid residues can be further sub-classified as cyclic or non-cyclic, and aromatic or non-aromatic, self-explanatory classifications with respect to the side-chain substituent groups of the residues, and as small or large. The residue is considered small if it contains a total of four carbon atoms or less, inclusive of the carboxyl carbon, provided an additional polar substituent is present; three or less if not. Small residues are, of course, always non-aromatic. Dependent on their structural properties, amino acid residues may fall in two or more classes. For the naturally-occurring protein amino acids, sub-classification according to this scheme is presented in Table A.

TABLE A

Amino acid sub-classification.

| Sub-classes | Amino acids |
|---|---|
| Acidic | Aspartic acid, Glutamic acid |
| Basic | Noncyclic: Arginine, Lysine; Cyclic: Histidine |
| Charged | Aspartic acid, Glutamic acid, Arginine, Lysine, Histidine |
| Small | Glycine, Serine, Alanine, Threonine, Proline |
| Polar/neutral | Asparagine, Histidine, Glutamine, Cysteine, Serine, Threonine |
| Polar/large | Asparagine, Glutamine |
| Hydrophobic | Tyrosine, Valine, Isoleucine, Leucine, Methionine, Phenylalanine, Tryptophan |
| Aromatic | Tryptophan, Tyrosine, Phenylalanine |
| Residues that influence chain orientation | Glycine and Proline |

Conservative amino acid substitution also includes groupings based on side chains. For example, a group of amino acids having aliphatic side chains is glycine, alanine, valine, leucine, and isoleucine; a group of amino acids having aliphatic-hydroxyl side chains is serine and threonine; a group of amino acids having amide-containing side chains is asparagine and glutamine; a group of amino acids having aromatic side chains is phenylalanine, tyrosine, and tryptophan; a group of amino acids having basic side chains is lysine, arginine, and histidine; and a group of amino acids having sulphur-containing side chains is cysteine and methionine. For example, it is reasonable to expect that replacement of a leucine with an isoleucine or valine, an aspartate with a glutamate, a threonine with a serine, or a similar replacement of an amino acid with a structurally related amino acid will not have a major effect on the properties of the resulting variant polypeptide. Whether an amino acid change results in a functional truncated and/or variant HRS polypeptide can readily be determined by assaying its non-canonical activity, as described herein. Conservative substitutions are shown in Table B under the heading of exemplary substitutions. Amino acid substitutions falling within the scope of the invention, are, in general, accomplished by selecting substitutions that do not differ significantly in their effect on maintaining (a) the structure of the peptide backbone in the area of the substitution, (b) the charge or hydrophobicity of the molecule at the target site, (c) the bulk of the side chain, or (d) the biological function. After the substitutions are introduced, the variants are screened for biological activity.

TABLE B

Exemplary Amino Acid Substitutions.

| Original Residue | Exemplary Substitutions | Preferred Substitutions |
|---|---|---|
| Ala | Val, Leu, Ile | Val |
| Arg | Lys, Gln, Asn | Lys |
| Asn | Gln, His, Lys, Arg | Gln |
| Asp | Glu | Glu |
| Cys | Ser, Ala, Leu, Val | Ser, Ala |
| Gln | Asn, His, Lys, | Asn |
| Glu | Asp, Lys | Asp |
| Gly | Pro | Pro |
| His | Asn, Gln, Lys, Arg | Arg |
| Ile | Leu, Val, Met, Ala, Phe, Norleu | Leu |
| Leu | Norleu, Ile, Val, Met, Ala, Phe | Ile |
| Lys | Arg, Gln, Asn | Arg |
| Met | Leu, Ile, Phe | Leu |
| Phe | Leu, Val, Ile, Ala | Leu |
| Pro | Gly | Gly |
| Ser | Thr | Thr |
| Thr | Ser | Ser |
| Trp | Tyr | Tyr |
| Tyr | Trp, Phe, Thr, Ser | Phe |
| Val | Ile, Leu, Met, Phe, Ala, Norleu | Leu |

Alternatively, similar amino acids for making conservative substitutions can be grouped into three categories based on the identity of the side chains. The first group includes glutamic acid, aspartic acid, arginine, lysine, histidine, which all have charged side chains; the second group includes glycine, serine, threonine, cysteine, tyrosine, glutamine, asparagine; and the third group includes leucine, isoleucine, valine, alanine, proline, phenylalanine, tryptophan, methionine, as described in Zubay, G., *Biochemistry*, third edition, Wm.C. Brown Publishers (1993).

The NMR structure of the human HRS WHEP domain has been determined (see Nameki et al., Accession 1X59_A). Further, the crystal structures of full-length human HRS and an internal catalytic domain deletion mutant of HRS (HRSACD) have also been determined (see Xu et al., *Structure.* 20:1470-7, 2012; and U.S. Application No. 61/674,639). In conjunction with the primary amino acid sequence of HRS, these detailed physical descriptions of the protein provide precise insights into the roles played by specific amino acids within the protein. Persons skilled in the art can thus use this information to identify structurally-conserved domains, linking regions, secondary structures such as alpha-helices, surface or solvent-exposed amino acids, non-exposed or internal regions, catalytic sites, and ligand-interacting surfaces, among other structural features. Such persons can then use that and other information to readily engineer HRS variants that retain or improve the non-canonical activity of interest, for instance, by conserving or altering the characteristics of the amino acid residues within or adjacent to these and other structural features, such as by conserving or altering the polarity, hydropathy index, charge, size, and/or positioning (i.e., inward, outward) of selected amino acid side chain(s) relative to wild-type residues (see, e.g., Zaiwara et al., *Mol Biotechnol.* 51:67-102, 2012; Perona and Hadd, *Biochemistry.* 51:8705-29, 2012; Morin et al., *Trends Biotechol.* 29:159-66, 2011; Collins et al., *Annu. Rev. Biophys.* 40:81-98, 2011; and U.S. Application No. 61/674,639).

Thus, a predicted non-essential amino acid residue in a truncated and/or variant HRS polypeptide is typically replaced with another amino acid residue from the same side chain family. Alternatively, mutations can be introduced randomly along all or part of a HRS coding sequence, such as by saturation mutagenesis, and the resultant mutants can be screened for an activity of the parent polypeptide to identify mutants which retain that activity. Following mutagenesis of the coding sequences, the encoded peptide can be expressed recombinantly and the activity of the peptide can be determined. A "non-essential" amino acid residue is a residue that can be altered from the reference sequence of an embodiment polypeptide without abolishing or substantially altering one or more of its non canonical activities. Suitably, the alteration does not substantially abolish one of these activities, for example, the activity is at least 20%, 40%, 60%, 70% or 80% 100%, 500%, 1000% or more of the reference HRS sequence. An "essential" amino acid residue is a residue that, when altered from the reference sequence of a HRS polypeptide, results in abolition of an activity of the parent molecule such that less than 20% of the reference activity is present. For example, such essential amino acid residues include those that are conserved in HRS polypeptides across different species, including those sequences that are conserved in the active binding site(s) or motif(s) of HRS polypeptides from various sources.

Assays to determine anti-inflammatory activity, including routine measurements of cytokine release from in vitro cell based, and animal studies are well established in the art (see, for example, Wittmann et al., *J Vis Exp.* (65):e4203. doi: 10.3791/4203, 2012; Feldman et al., *Mol Cell.* 47:585-95, 2012; Clutterbuck et al., *J Proteomics.* 74:704-15, 2011, Giddings and Maitra, *J Biomol Screen.* 15:1204-10, 2010; Wijnhoven et al., *Glycoconj J.* 25:177-85, 2008; and Frow et al., *Med Res Rev.* 24:276-98, 2004) and can be readily used to profile and optimize anti-inflammatory activity. An exemplary in vivo experimental system is also described in the accompanying Examples.

In some embodiments, HRS polypeptides may have one or more cysteine substitutions, where one or more naturally-occurring (non-cysteine) residues are substituted with cysteine (e.g., to alter stability, to facilitate thiol-based conjugation of an Fc fragment, to facilitate thiol-based attachment of PEG or other molecules). In some embodiments, cysteine substitutions are near the N-terminus and/or C-terminus of the HRS polypeptide (e.g., SEQ ID NOS:1-106, 170-181, or 185-191), or other surface exposed regions of a HRS polypeptide. Particular embodiments include where one or more of residues within 0, 1, 2, 3, 4, 5, 6, 7, 8, 9, 10, 11, 12, 13, 14, 15, 16, 17, 18, 19, 20, 21, 22, 23, 24, or 25 amino acids relative to the N-terminus and/or C-terminus of any one of SEQ ID NOS: 1-106, 170-181, or 185-191 are substituted with a cysteine residue. In some embodiments, cysteine residues may be added to the HRS polypeptide through the creation of N, or C-terminal fusion proteins. Such fusion proteins may be of any length, but will typically be about 1-5, or about 5-10, about 10 to 20, or about 20 to 30 amino acids in length. In some embodiments, fusion to the C-terminus is preferred.

Specific exemplary embodiments of such cysteine modified proteins are shown in Table D6, based on the HRS polypeptide HRS(1-60). This approach is directly applicable to the HRS polypeptides of Table D5, and other HRS polypeptides described herein.

TABLE D6

| Name | Protein Sequences | SEQ ID NO: |
|---|---|---|
| HRS(1-60)-M1MC- | MCAERAALEE LVKLQGERVR GLKQQKASAE LIEEEVAKLL KLKAQLGPDE SKQKFVLKTP K | 179 |
| HRS(1-60)-A26C- | MAERAALEEL VKLQGERVRG LKQQKCSAEL IEEEVAKLLK LKAQLGPDES KQKFVLKTPK | 180 |
| HRS(1-60)-C61 | MAERAALEEL VKLQGERVRG LKQQKASAEL IEEEVAKLLK LKAQLGPDES KQKFVLKTPK C | 181 |
| | DNA sequences | |
| HRS(1-60)-M1MC- | ATGTGTGCAGAAAGAGCCGCCCTGGAAGAGTTAGTTAAGTTGCAAGGT GAACGTGTCCGTGGTCTGAAGCAGCAGAAGGCTAGCGCGGAGCTGAT CGAAGAAGAGGTGGCCAAACTGCTGAAGCTGAAGGCGCAGCTGGGCC CGGACGAGAGCAAACAAAAGTTCGTCCTGAAAACCCCGAAA | 182 |
| HRS(1-60)-A26C- | ATGGCAGAACGTGCGGCATTGGAAGAATTGGTTAAACTGCAAGGTGA ACGTGTTCGTGGTCTGAAGCAGCAGAAGTGCAGCGCGGAGCTGATCGA AGAAGAGGTGGCCAAACTGCTGAAGCTGAAGGCGCAGCTGGGCCCGG ACGAGAGCAAACAAAAGTTCGTCCTGAAAACCCCGAAA | 183 |
| HRS(1-60)-C61 | ATGGCAGAACGTGCGGCATTGGAAGAATTGGTTAAACTGCAAGGTGA ACGTGTTCGTGGTCTGAAGCAGCAGAAGGCTAGCGCGGAGCTGATCGA AGAAGAGGTGGCCAAACTGCTGAAGCTGAAGGCGCAGCTGGGCCCGG ACGAGAGCAAACAAAAGTTCGTCCTGAAAACCCCGAAATGC | 184 |

In some embodiments, the HRS polypeptide can include mutants in which the endogenous or naturally-occurring cysteine residues have been mutated to alternative amino acids, or deleted. In some embodiments, the insertion or substitution of cysteine residue(s) into the HRS polypeptide may be combined with the elimination of other surface exposed reactive cysteine residues. Accordingly, in some embodiments, the HRS polypeptide may comprise one or more substitutions and/or deletions at Cys83, Cys174, Cys191, Cys196, Cys224, Cys235, Cys379, Cys455, Cys507, and/or Cys509 (as defined by SEQ ID NO:1), for instance, to remove naturally-occurring cysteine residues.

Specific embodiments include any one of SEQ ID NOS: 1-106, 170-181, or 185-191, or variants or fragments thereof, having at mutation or deletion of any one or more of Cys83, Cys174, Cys191, Cys196, Cys224, Cys235, Cys379, Cys455, or the deletion of Cys507 and Cys509, for instance, by the deletion of the C-terminal 3 amino acids (4507-509). Exemplary mutations at these positions include for example the mutation of cysteine to serine, alanine, leucine, valine or glycine. In certain embodiments, amino acid residues for specific cysteine substitutions can be selected from naturally-occurring substitutions that are found in HRS orthologs from other species and organisms. Exemplary substitutions of this type are presented in Table D7.

TABLE D7

| Naturally-occurring sequence variation at positions occupied by cysteine residues in human HRS | | | | | | | | | | | | |
|---|---|---|---|---|---|---|---|---|---|---|---|---|
| *H. sapiens* cysteine residue # | *P. troglodyte* | *M. mulatta* | *B. taurus* | *M. musculus* | *R. norvegicus* | *G. gallus* | *X. laevis* | *D. rerio* | *D. melanogaster* | *C. elegans* | *S. cerevisiae* | *E. coli* |
| 83 | C | C | C | C | C | C | C | C | V | T | L | V |
| 174 | C | C | C | C | C | C | C | C | C | C | C | L |
| 191 | C | C | C | C | C | C | C | C | C | V | C | A/L |
| 196 | C | C | C | C | C | Q | H | Y | S | M | V | L/A |
| 224 | C | C | C | C | C | C | C | C | C | S | A | A |
| 235 | C | C | C | C | C | C | C | C | C | C | S | E |
| 379 | C | C | C | C | C | C | C | V | C | C | C | A |
| 455 | C | C | C | C | C | C | C | — | C | C | A | A |
| 507 | C | R | C | S | S | — | — | — | — | S/Q | S/E | — |
| 509 | C | C | C | C | — | — | — | — | — | I | I/G | — |

In some embodiments, the naturally-occurring cysteines selected for mutagenesis are selected based on their surface exposure. Accordingly, in one aspect the cysteine residues selected for substitution are selected from Cys224, Cys235, Cys507 and Cys509. In some embodiments, the last three (C-terminal) residues of SEQ ID NO:1 are deleted so as to delete residues 507 to 509. In some embodiments, the cysteines are selected for mutation or deletion so as to eliminate an intramolecular cysteine pair, for example Cys174 and Cys191.

Specific additional examples of desired cysteine mutations/substitutions (indicated in bold underline) to reduce surface exposed cysteine residues include those listed below in Table D8.

TABLE D8

| HRS polypeptides with Substitutions to Remove Surface Exposed Cysteines | | |
|---|---|---|
| Name | Protein Sequence | SEQ ID NO: |
| HRS(1-506) C174A | MAERAALEELVKLQGERVRGLKQQKASAELIEEEVAKLLKLKAQLGPDESK<br>QKFVLKTPKGTRDYSPRQMAVREKVFDVIIRCFKRHGAEVIDTPVFELKETL<br>MGKYGEDSKLIYDLKDQGGELLSLRYDLTVPFARYLAMNKLTNIKRYHIAK<br>VYRRDNPAMTRGRYREFYQ**A**DFDIAGNFDPMIPDAECLKIMCEILSSLQIGD<br>FLVKVNDRRILDGMFAICGVSDSKFRTICSSVDKLDKVSWEEVKNEMVGEK<br>GLAPEVADRIGDYVQQHGGVSLVEQLLQDPKLSQNKQALEGLGDLKLLFEY<br>LTLFGIDDKISFDLSLARGLDYYTGVIYEAVLLQTPAQAGEEPLGVGSVAAG<br>GRYDGLVGMFDPKGRKVPCVGLSIGVERIFSIVEQRLEALEEKIRTTETQVLV<br>ASAQKKLLEERLKLVSELWDAGIKAELLYKKNPKLLNQLQYCEEAGIPLVAI<br>IGEQELKDGVIKLRSVTSREEVDVRREDLVEEIKRRTGQPL | 185 |
| HRS(1-506) C174V | MAERAALEELVKLQGERVRGLKQQKASAELIEEEVAKLLKLKAQLGPDESK<br>QKFVLKTPKGTRDYSPRQMAVREKVFDVIIRCFKRHGAEVIDTPVFELKETL<br>MGKYGEDSKLIYDLKDQGGELLSLRYDLTVPFARYLAMNKLTNIKRYHIAK<br>VYRRDNPAMTRGRYREFYQ**V**DFDIAGNFDPMIPDAECLKIMCEILSSLQIGD<br>FLVKVNDRRILDGMFAICGVSDSKFRTICSSVDKLDKVSWEEVKNEMVGEK<br>GLAPEVADRIGDYVQQHGGVSLVEQLLQDPKLSQNKQALEGLGDLKLLFEY<br>LTLFGIDDKISFDLSLARGLDYYTGVIYEAVLLQTPAQAGEEPLGVGSVAAG<br>GRYDGLVGMFDPKGRKVPCVGLSIGVERIFSIVEQRLEALEEKIRTTETQVLV<br>ASAQKKLLEERLKLVSELWDAGIKAELLYKKNPKLLNQLQYCEEAGIPLVAI<br>IGEQELKDGVIKLRSVTSREEVDVRREDLVEEIKRRTGQPL | 186 |
| HRS(1-506) C191A | MAERAALEELVKLQGERVRGLKQQKASAELIEEEVAKLLKLKAQLGPDESK<br>QKFVLKTPKGTRDYSPRQMAVREKVFDVIIRCFKRHGAEVIDTPVFELKETL<br>MGKYGEDSKLIYDLKDQGGELLSLRYDLTVPFARYLAMNKLTNIKRYHIAK<br>VYRRDNPAMTRGRYREFYQCDFDIAGNFDPMIPDAE**A**LKIMCEILSSLQIGD<br>FLVKVNDRRILDGMFAICGVSDSKFRTICSSVDKLDKVSWEEVKNEMVGEK<br>GLAPEVADRIGDYVQQHGGVSLVEQLLQDPKLSQNKQALEGLGDLKLLFEY<br>LTLFGIDDKISFDLSLARGLDYYTGVIYEAVLLQTPAQAGEEPLGVGSVAAG<br>GRYDGLVGMFDPKGRKVPCVGLSIGVERIFSIVEQRLEALEEKIRTTETQVLV<br>ASAQKKLLEERLKLVSELWDAGIKAELLYKKNPKLLNQLQYCEEAGIPLVAI<br>IGEQELKDGVIKLRSVTSREEVDVRREDLVEEIKRRTGQPL | 187 |
| HRS(1-506) C191S | MAERAALEELVKLQGERVRGLKQQKASAELIEEEVAKLLKLKAQLGPDESK<br>QKFVLKTPKGTRDYSPRQMAVREKVFDVIIRCFKRHGAEVIDTPVFELKETL<br>MGKYGEDSKLIYDLKDQGGELLSLRYDLTVPFARYLAMNKLTNIKRYHIAK<br>VYRRDNPAMTRGRYREFYQCDFDIAGNFDPMIPDAE**S**LKIMCEILSSLQIGDF<br>LVKVNDRRILDGMFAICGVSDSKFRTICSSVDKLDKVSWEEVKNEMVGEKG<br>LAPEVADRIGDYVQQHGGVSLVEQLLQDPKLSQNKQALEGLGDLKLLFEYL<br>TLFGIDDKISFDLSLARGLDYYTGVIYEAVLLQTPAQAGEEPLGVGSVAAGG<br>RYDGLVGMFDPKGRKVPCVGLSIGVERIFSIVEQRLEALEEKIRTTETQVLVA<br>SAQKKLLEERLKLVSELWDAGIKAELLYKKNPKLLNQLQYCEEAGIPLVAII<br>GEQELKDGVIKLRSVTSREEVDVRREDLVEEIKRRTGQPL | 188 |

TABLE D8-continued

| HRS polypeptides with Substitutions to Remove Surface Exposed Cysteines | | |
|---|---|---|
| HRS(1-506)<br>C191V | MAERAALEELVKLQGERVRGLKQQKASAELIEEEVAKLLKLKAQLGPDESK<br>QKFVLKTPKGTRDYSPRQMAVREKVFDVIIRCFKRHGAEVIDTPVFELKETL<br>MGKYGEDSKLIYDLKDQGGELLSLRYDLTVPFARYLAMNKLTNIKRYHIAK<br>VYRRDNPAMTRGRYREFYQCDFDIAGNFDPMIPDAEVLKIMCEILSSLQIGD<br>FLVKVNDRRILDGMFAICGVSDSKFRTICSSVDKLDKVSWEEVKNEMVGEK<br>GLAPEVADRIGDYVQQHGGVSLVEQLLQDPKLSQNKQALEGLGDLKLLFEY<br>LTLFGIDDKISFDLSLARGLDYYTGVIYEAVLLQTPAQAGEEPLGVGSVAAG<br>GRYDGLVGMFDPKGRKVPCVGLSIGVERIFSIVEQRLEALEEKIRTTETQVLV<br>ASAQKKLLEERLKLVSELWDAGIKAELLYKKNPKLLNQLQYCEEAGIPLVAI<br>IGEQELKDGVIKLRSVTSREEVDVRREDLVEEIKRRTGQPL | 189 |
| HRS(1-506)<br>C224S | MAERAALEELVKLQGERVRGLKQQKASAELIEEEVAKLLKLKAQLGPDESK<br>QKFVLKTPKGTRDYSPRQMAVREKVFDVIIRCFKRHGAEVIDTPVFELKETL<br>MGKYGEDSKLIYDLKDQGGELLSLRYDLTVPFARYLAMNKLTNIKRYHIAK<br>VYRRDNPAMTRGRYREFYQCDFDIAGNFDPMIPDAECLKIMCEILSSLQIGD<br>FLVKVNDRRILDGMFAISGVSDSKFRTICSSVDKLDKVSWEEVKNEMVGEK<br>GLAPEVADRIGDYVQQHGGVSLVEQLLQDPKLSQNKQALEGLGDLKLLFEY<br>LTLFGIDDKISFDLSLARGLDYYTGVIYEAVLLQTPAQAGEEPLGVGSVAAG<br>GRYDGLVGMFDPKGRKVPCVGLSIGVERIFSIVEQRLEALEEKIRTTETQVLV<br>ASAQKKLLEERLKLVSELWDAGIKAELLYKKNPKLLNQLQYCEEAGIPLVAI<br>IGEQELKDGVIKLRSVTSREEVDVRREDLVEEIKRRTGQPL | 190 |
| HRS(1-506)<br>C235S | MAERAALEELVKLQGERVRGLKQQKASAELIEEEVAKLLKLKAQLGPDESK<br>QKFVLKTPKGTRDYSPRQMAVREKVFDVIIRCFKRHGAEVIDTPVFELKETL<br>MGKYGEDSKLIYDLKDQGGELLSLRYDLTVPFARYLAMNKLTNIKRYHIAK<br>VYRRDNPAMTRGRYREFYQCDFDIAGNFDPMIPDAECLKIMCEILSSLQIGD<br>FLVKVNDRRILDGMFAICGVSDSKFRTISSSVDKLDKVSWEEVKNEMVGEK<br>GLAPEVADRIGDYVQQHGGVSLVEQLLQDPKLSQNKQALEGLGDLKLLFEY<br>LTLFGIDDKISFDLSLARGLDYYTGVIYEAVLLQTPAQAGEEPLGVGSVAAG<br>GRYDGLVGMFDPKGRKVPCVGLSIGVERIFSIVEQRLEALEEKIRTTETQVLV<br>ASAQKKLLEERLKLVSELWDAGIKAELLYKKNPKLLNQLQYCEEAGIPLVAI<br>IGEQELKDGVIKLRSVTSREEVDVRREDLVEEIKRRTGQPL | 191 |

| Name | DNA sequences | SEQ ID NO: |
|---|---|---|
| HRS(1-506)<br>C174A | ATGGCGGAACGTGCCGCACTGGAAGAATTGGTTAAATTACAGGGAGAAC<br>GCGTACGTGGTCTTAAACAACAAAAAGCCTCTGCGGAATTGATTGAAGA<br>AGAAGTTGCCAAATTACTGAAACTGAAAGCTCAACTTGGACCCGATGAA<br>AGTAAACAAAAATTTGTGTTGAAAACGCCCAAAGGAACCCGTGATTATA<br>GTCCACGTCAAATGGCCGTTCGTGAAAAAGTGTTCGACGTTATTATTCGC<br>TGTTTTAAACGTCACGGTGCTGAAGTAATCGATACCCCCGTATTTGAATT<br>GAAAGAGACTCTGATGGGCAAATATGGTGAAGATTCTAAACTGATTTAT<br>GATTTGAAAGACCAAGGAGGTGAACTGCTGAGCCTGCGCTACGACTTAA<br>CTGTGCCTTTTGCCCGTTACTTAGCCATGAATAAaTTaACCAACATCAAAC<br>GTTACCATATTGCAAAAGTATATCGCCGCGACAACCCTGCAATGACTCGT<br>GGACGCTATCGCGAATTCTATCAGGCTGATTTTGATATTGCCGGAAATTT<br>CGACCCGATGATCCCGGATGCCGAGTGTTTGAAAATTATGTGTGAAATTC<br>TGAGTTCGTTGCAGATCGGAGACTTTCTTGTAAAAGTTAATGACCGCCGT<br>ATTCTGGATGGTATGTTTGCTATTTGCGGTGTTTCTGATTCCAAATTCCGT<br>ACAATCTGCTCAAGCGTGGACAAATTGGATAAAGTGTCTTGGGAAGAAG<br>TAAAAAATGAAATGGTGGGAGAAAAAGGCCTGGCTCCAGAAGTAGCAG<br>ACCGTATTGGTGACTATGTTCAACAACATGGCGGTGTGTCCTTAGTCGAA<br>CAGTTATTACAGGATCCTAAACTGAGCCAAAATAAACAAGCACTTGAAG<br>GACTGGGAGATCTGAAATTACTCTTTGAATATCTGACCTTATTTGGGATT<br>GATGATAAAATTAGCTTTGATCTGAGCTTGGCCCGCGGTCTTGATTATTA<br>TACCGGCGTGATTTACGAAGCTGTTCTCTTGCAAACCCCAGCCCAGGCGG<br>GCGAAGAGCCTTTGGGAGTCGGCAGTGTGGCAGCCGGTGGTCGTTATGA<br>TGGTTTGGTAGGAATGTTTGACCCTAAAGGCCGTAAAGTACCATGTGTG<br>GGGCTTTCTATCGGTGTCGAACGTATCTTTTCTATTGTTGAACAACGTCTT<br>GAAGCTTTGGAGGAAAAGATCCGTACCACGGAAacCCAAGTCTTAGTTGC<br>aAGTGCCCAAAAAAAACTGTTAGAAGAACGCCTGAAACTCGTATCAGAA<br>CTTTGGGACGCCGGCATCAAGGCCGAACTGCTGTATAAAAAGAACCCGA<br>AATTGTTAAACCAACTCCAGTATTGTGAAGAAGCTGGGATCCCACTCGT<br>AGCTATTATTGGTGAGCAAGAATTAAAAGATGGCGTGATTAAACTGCGT<br>TCAGTAACAAGCCGTGAAGAGGTAGATGTACGTCGCGAAGACTTAGTGG<br>AAGAAATTAAACGCCGCACCGGTCAACCGTTA | 192 |
| HRS(1-506)<br>C174V | ATGGCGGAACGTGCCGCACTGGAAGAATTGGTTAAATTACAGGGAGAAC<br>GCGTACGTGGTCTTAAACAACAAAAAGCCTCTGCGGAATTGATTGAAGA<br>AGAAGTTGCCAAATTACTGAAACTGAAAGCTCAACTTGGACCCGATGAA<br>AGTAAACAAAAATTTGTGTTGAAAACGCCCAAAGGAACCCGTGATTATA<br>GTCCACGTCAAATGGCCGTTCGTGAAAAAGTGTTCGACGTTATTATTCGC<br>TGTTTTAAACGTCACGGTGCTGAAGTAATCGATACCCCCGTATTTGAATT<br>GAAAGAGACTCTGATGGGCAAATATGGTGAAGATTCTAAACTGATTTAT<br>GATTTGAAAGACCAAGGAGGTGAACTGCTGAGCCTGCGCTACGACTTAA | 193 |

TABLE D8-continued

HRS polypeptides with Substitutions to Remove Surface Exposed Cysteines

| | | |
|---|---|---|
| | CTGTGCCTTTTGCCCGTTACTTAGCCATGAATAAaTTaACCAACATCAAAC<br>GTTACCATATTGCAAAAGTATATCGCCGCGACAACCCTGCAATGACTCGT<br>GGACGCTATCGCGAATTCTATCAGGTTGATTTTGATATTGCCGGAAATTT<br>CGACCCGATGATCCCGGATGCCGAGTGTTTGAAAATTATGTGTGAAATTC<br>TGAGTTCGTTGCAGATCGGAGACTTTCTTGTAAAAGTTAATGACCGCCGT<br>ATTCTGGATGGTATGTTTGCTATTTGCGGTGTTTCTGATTCCAAATTCCGT<br>ACAATCTGCTCAAGCGTGGACAAATTGGATAAAGTGTCTTGGGAAGAAG<br>TAAAAAATGAAATGGTGGGAGAAAAAGGCCTGGCTCCAGAAGTAGCAG<br>ACCGTATTGGTGACTATGTTCAACAACATGGCGGTGTGTCCTTAGTCGAA<br>CAGTTATTACAGGATCCTAAACTGAGCCAAAATAAACAAGCACTTGAAG<br>GACTGGGAGATCTGAAATTACTCTTTGAATATCTGACCTTATTTGGGATT<br>GATGATAAAATTAGCTTTGATCTGAGCTTGGCCCGCGGTCTTGATTATTA<br>TACCGGCGTGATTTACGAAGCTGTTCTCTTGCAAACCCCAGCCCAGGCGG<br>GCGAAGAGCCTTTGGGAGTCGGCAGTGTGGCAGCCGGTGGTCGTTATGA<br>TGGTTTGGTAGGAATGTTTGACCCTAAAGGCCGTAAAGTACCATGTGTG<br>GGGCTTTCTATCGGTGTCGAACGTATCTTTTCTATTGTTGAACAACGTCTT<br>GAAGCTTTGGAGGAAAAGATCCGTACCACGGAAacCCAAGTCTTAGTTGC<br>aAGTGCCCAAAAAAAACTGTTAGAAGAACGCCTGAAACTCGTATCAGAA<br>CTTTGGGACGCCGGCATCAAGGCCGAACTGCTGTATAAAAAGAACCCGA<br>AATTGTTAAACCAACTCCAGTATTGTGAAGAAGCTGGGATCCCACTCGT<br>AGCTATTATTGGTGAGCAAGAATTAAAAGATGGCGTGATTAAACTGCGT<br>TCAGTAACAAGCCGTGAAGAGGTAGATGTACGTCGCGAAGACTTAGTGG<br>AAGAAATTAAACGCCGCACCGGTCAACCGTTA | |
| HRS(1-506)<br>C191A | ATGGCGGAACGTGCCGCACTGGAAGAATTGGTTAAATTACAGGGAGAAC<br>GCGTACGTGGTCTTAAACAACAAAAAGCCTCTGCGGAATTGATTGAAGA<br>AGAAGTTGCCAAATTACTGAAACTGAAAGCTCAACTTGGACCCGATGAA<br>AGTAAACAAAAATTTGTGTTGAAAACGCCCAAAGGAACCCGTGATTATA<br>GTCCACGTCAAATGGCCGTTCGTGAAAAAGTGTTCGACGTTATTATTCGC<br>TGTTTTAAACGTCACGGTGCTGAAGTAATCGATACCCCCGTATTTGAATT<br>GAAAGAGACTCTGATGGGCAAATATGGTGAAGATTCTAAACTGATTTAT<br>GATTTGAAAGACCAAGGAGGTGAACTGCTGAGCCTGCGCTACGACTTAA<br>CTGTGCCTTTTGCCCGTTACTTAGCCATGAATAAaTTaACCAACATCAAAC<br>GTTACCATATTGCAAAAGTATATCGCCGCGACAACCCTGCAATGACTCGT<br>GGACGCTATCGCGAATTCTATCAGTGTGATTTTGATATTGCCGGAAATTT<br>CGACCCGATGATCCCGGATGCCGAGGCTTTGAAAATTATGTGTGAAATT<br>CTGAGTTCGTTGCAGATCGGAGACTTTCTTGTAAAAGTTAATGACCGCCG<br>TATTCTGGATGGTATGTTTGCTATTTGCGGTGTTTCTGATTCCAAATTCCG<br>TACAATCTGCTCAAGCGTGGACAAATTGGATAAAGTGTCTTGGGAAGAA<br>GTAAAAAATGAAATGGTGGGAGAAAAAGGCCTGGCTCCAGAAGTAGCA<br>GACCGTATTGGTGACTATGTTCAACAACATGGCGGTGTGTCCTTAGTCGA<br>ACAGTTATTACAGGATCCTAAACTGAGCCAAAATAAACAAGCACTTGAA<br>GGACTGGGAGATCTGAAATTACTCTTTGAATATCTGACCTTATTTGGGAT<br>TGATGATAAAATTAGCTTTGATCTGAGCTTGGCCCGCGGTCTTGATTATT<br>ATACCGGCGTGATTTACGAAGCTGTTCTCTTGCAAACCCCAGCCCAGGCG<br>GGCGAAGAGCCTTTGGGAGTCGGCAGTGTGGCAGCCGGTGGTCGTTATG<br>ATGGTTTGGTAGGAATGTTTGACCCTAAAGGCCGTAAAGTACCATGTGT<br>GGGGCTTTCTATCGGTGTCGAACGTATCTTTTCTATTGTTGAACAACGTC<br>TTGAAGCTTTGGAGGAAAAGATCCGTACCACGGAAacCCAAGTCTTAGTT<br>GCaAGTGCCCAAAAAAAACTGTTAGAAGAACGCCTGAAACTCGTATCAG<br>AACTTTGGGACGCCGGCATCAAGGCCGAACTGCTGTATAAAAAGAACCC<br>GAAATTGTTAAACCAACTCCAGTATTGTGAAGAAGCTGGGATCCCACTC<br>GTAGCTATTATTGGTGAGCAAGAATTAAAAGATGGCGTGATTAAACTGC<br>GTTCAGTAACAAGCCGTGAAGAGGTAGATGTACGTCGCGAAGACTTAGT<br>GGAAGAAATTAAACGCCGCACCGGTCAACCGTTA | 194 |
| HRS(1-506)<br>C191S | ATGGCGGAACGTGCCGCACTGGAAGAATTGGTTAAATTACAGGGAGAAC<br>GCGTACGTGGTCTTAAACAACAAAAAGCCTCTGCGGAATTGATTGAAGA<br>AGAAGTTGCCAAATTACTGAAACTGAAAGCTCAACTTGGACCCGATGAA<br>AGTAAACAAAAATTTGTGTTGAAAACGCCCAAAGGAACCCGTGATTATA<br>GTCCACGTCAAATGGCCGTTCGTGAAAAAGTGTTCGACGTTATTATTCGC<br>TGTTTTAAACGTCACGGTGCTGAAGTAATCGATACCCCCGTATTTGAATT<br>GAAAGAGACTCTGATGGGCAAATATGGTGAAGATTCTAAACTGATTTAT<br>GATTTGAAAGACCAAGGAGGTGAACTGCTGAGCCTGCGCTACGACTTAA<br>CTGTGCCTTTTGCCCGTTACTTAGCCATGAATAAaTTaACCAACATCAAAC<br>GTTACCATATTGCAAAAGTATATCGCCGCGACAACCCTGCAATGACTCGT<br>GGACGCTATCGCGAATTCTATCAGTGTGATTTTGATATTGCCGGAAATTT<br>CGACCCGATGATCCCGGATGCCGAGAGTTTGAAAATTATGTGTGAAATT<br>CTGAGTTCGTTGCAGATCGGAGACTTTCTTGTAAAAGTTAATGACCGCCG<br>TATTCTGGATGGTATGTTTGCTATTTGCGGTGTTTCTGATTCCAAATTCCG<br>TACAATCTGCTCAAGCGTGGACAAATTGGATAAAGTGTCTTGGGAAGAA<br>GTAAAAAATGAAATGGTGGGAGAAAAAGGCCTGGCTCCAGAAGTAGCA<br>GACCGTATTGGTGACTATGTTCAACAACATGGCGGTGTGTCCTTAGTCGA<br>ACAGTTATTACAGGATCCTAAACTGAGCCAAAATAAACAAGCACTTGAA<br>GGACTGGGAGATCTGAAATTACTCTTTGAATATCTGACCTTATTTGGGAT<br>TGATGATAAAATTAGCTTTGATCTGAGCTTGGCCCGCGGTCTTGATTATT<br>ATACCGGCGTGATTTACGAAGCTGTTCTCTTGCAAACCCCAGCCCAGGCG<br>GGCGAAGAGCCTTTGGGAGTCGGCAGTGTGGCAGCCGGTGGTCGTTATG | 195 |

TABLE D8-continued

| HRS polypeptides with Substitutions to Remove Surface Exposed Cysteines | | |
|---|---|---|
| | ATGGTTTGGTAGGAATGTTTGACCCTAAAGGCCGTAAAGTACCATGTGT<br>GGGGCTTTCTATCGGTGTCGAACGTATCTTTTCTATTGTTGAACAACGTC<br>TTGAAGCTTTGGAGGAAAAGATCCGTACCACGGAAacCCAAGTCTTAGTT<br>GCaAGTGCCCAAAAAAAACTGTTAGAAGAACGCCTGAAACTCGTATCAG<br>AACTTTGGGACGCCGGCATCAAGGCCGAACTGCTGTATAAAAAGAACCC<br>GAAATTGTTAAACCAACTCCAGTATTGTGAAGAAGCTGGGATCCCACTC<br>GTAGCTATTATTGGTGAGCAAGAATTAAAAGATGGCGTGATTAAACTGC<br>GTTCAGTAACAAGCCGTGAAGAGGTAGATGTACGTCGCGAAGACTTAGT<br>GGAAGAAATTAAACGCCGCACCGGTCAACCGTTA | |
| HRS(1-506)<br>C191V | ATGGCGGAACGTGCCGCACTGGAAGAATTGGTTAAATTACAGGGAGAAC<br>GCGTACGTGGTCTTAAACAACAAAAAGCCTCTGCGGAATTGATTGAAGA<br>AGAAGTTGCCAAATTACTGAAACTGAAAGCTCAACTTGGACCCGATGAA<br>AGTAAACAAAAATTTGTGTTGAAAACGCCCAAAGGAACCCGTGATTATA<br>GTCCACGTCAAATGGCCGTTCGTGAAAAAGTGTTCGACGTTATTATTCGC<br>TGTTTTAAACGTCACGGTGCTGAAGTAATCGATACCCCCGTATTTGAATT<br>GAAAGAGACTCTGATGGGCAAATATGGTGAAGATTCTAAACTGATTTAT<br>GATTTGAAAGACCAAGGAGGTGAACTGCTGAGCCTGCGCTACGACTTAA<br>CTGTGCCTTTTGCCCGTTACTTAGCCATGAATAAaTTaACCAACATCAAAC<br>GTTACCATATTGCAAAAGTATATCGCCGCGACAACCCTGCAATGACTCGT<br>GGACGCTATCGCGAATTCTATCAGTGTGATTTTGATATTGCCGGAAATTT<br>CGACCCGATGATCCCGGATGCCGAGGTTTTGAAAATTATGTGTGAAATTC<br>TGAGTTCGTTGCAGATCGGAGACTTTCTTGTAAAAGTTAATGACCGCCGT<br>ATTCTGGATGGTATGTTTGCTATTTGCGGTGTTTCTGATTCCAAATTCCGT<br>ACAATCTGCTCAAGCGTGGACAAATTGGATAAAGTGTCTTGGGAAGAAG<br>TAAAAAATGAAATGGTGGGAGAAAAAGGCCTGGCTCCAGAAGTAGCAG<br>ACCGTATTGGTGACTATGTTCAACAACATGGCGGTGTGTCCTTAGTCGAA<br>CAGTTATTACAGGATCCTAAACTGAGCCAAAATAAACAAGCACTTGAAG<br>GACTGGGAGATCTGAAATTACTCTTTGAATATCTGACCTTATTTGGGATT<br>GATGATAAAATTAGCTTTGATCTGAGCTTGGCCCGCGGTCTTGATTATTA<br>TACCGGCGTGATTTACGAAGCTGTTCTCTTGCAAACCCCAGCCCAGGCGG<br>GCGAAGAGCCTTTGGGAGTCGGCAGTGTGGCAGCCGGTGGTCGTTATGA<br>TGGTTTGGTAGGAATGTTTGACCCTAAAGGCCGTAAAGTACCATGTGTG<br>GGGCTTTCTATCGGTGTCGAACGTATCTTTTCTATTGTTGAACAACGTCTT<br>GAAGCTTTGGAGGAAAAGATCCGTACCACGGAAacCCAAGTCTTAGTTGC<br>aAGTGCCCAAAAAAAACTGTTAGAAGAACGCCTGAAACTCGTATCAGAA<br>CTTTGGGACGCCGGCATCAAGGCCGAACTGCTGTATAAAAAGAACCCGA<br>AATTGTTAAACCAACTCCAGTATTGTGAAGAAGCTGGGATCCCACTCGT<br>AGCTATTATTGGTGAGCAAGAATTAAAAGATGGCGTGATTAAACTGCGT<br>TCAGTAACAAGCCGTGAAGAGGTAGATGTACGTCGCGAAGACTTAGTGG<br>AAGAAATTAAACGCCGCACCGGTCAACCGTTA | 196 |
| HRS(1-506)<br>C224S | ATGGCGGAACGTGCCGCACTGGAAGAATTGGTTAAATTACAGGGAGAAC<br>GCGTACGTGGTCTTAAACAACAAAAAGCCTCTGCGGAATTGATTGAAGA<br>AGAAGTTGCCAAATTACTGAAACTGAAAGCTCAACTTGGACCCGATGAA<br>AGTAAACAAAAATTTGTGTTGAAAACGCCCAAAGGAACCCGTGATTATA<br>GTCCACGTCAAATGGCCGTTCGTGAAAAAGTGTTCGACGTTATTATTCGC<br>TGTTTTAAACGTCACGGTGCTGAAGTAATCGATACCCCCGTATTTGAATT<br>GAAAGAGACTCTGATGGGCAAATATGGTGAAGATTCTAAACTGATTTAT<br>GATTTGAAAGACCAAGGAGGTGAACTGCTGAGCCTGCGCTACGACTTAA<br>CTGTGCCTTTTGCCCGTTACTTAGCCATGAATAAaTTaACCAACATCAAAC<br>GTTACCATATTGCAAAAGTATATCGCCGCGACAACCCTGCAATGACTCGT<br>GGACGCTATCGCGAATTCTATCAGTGTGATTTTGATATTGCCGGAAATTT<br>CGACCCGATGATCCCGGATGCCGAGTGTTTGAAAATTATGTGTGAAATTC<br>TGAGTTCGTTGCAGATCGGAGACTTTCTTGTAAAAGTTAATGACCGCCGT<br>ATTCTGGATGGTATGTTTGCTATTTCCGGTGTTTCTGATTCCAAATTCCGT<br>ACAATCTGCTCAAGCGTGGACAAATTGGATAAAGTGTCTTGGGAAGAAG<br>TAAAAAATGAAATGGTGGGAGAAAAAGGCCTGGCTCCAGAAGTAGCAG<br>ACCGTATTGGTGACTATGTTCAACAACATGGCGGTGTGTCCTTAGTCGAA<br>CAGTTATTACAGGATCCTAAACTGAGCCAAAATAAACAAGCACTTGAAG<br>GACTGGGAGATCTGAAATTACTCTTTGAATATCTGACCTTATTTGGGATT<br>GATGATAAAATTAGCTTTGATCTGAGCTTGGCCCGCGGTCTTGATTATTA<br>TACCGGCGTGATTTACGAAGCTGTTCTCTTGCAAACCCCAGCCCAGGCGG<br>GCGAAGAGCCTTTGGGAGTCGGCAGTGTGGCAGCCGGTGGTCGTTATGA<br>TGGTTTGGTAGGAATGTTTGACCCTAAAGGCCGTAAAGTACCATGTGTG<br>GGGCTTTCTATCGGTGTCGAACGTATCTTTTCTATTGTTGAACAACGTCTT<br>GAAGCTTTGGAGGAAAAGATCCGTACCACGGAAacCCAAGTCTTAGTTGC<br>aAGTGCCCAAAAAAAACTGTTAGAAGAACGCCTGAAACTCGTATCAGAA<br>CTTTGGGACGCCGGCATCAAGGCCGAACTGCTGTATAAAAAGAACCCGA<br>AATTGTTAAACCAACTCCAGTATTGTGAAGAAGCTGGGATCCCACTCGT<br>AGCTATTATTGGTGAGCAAGAATTAAAAGATGGCGTGATTAAACTGCGT<br>TCAGTAACAAGCCGTGAAGAGGTAGATGTACGTCGCGAAGACTTAGTGG<br>AAGAAATTAAACGCCGCACCGGTCAACCGTTA | 197 |
| HRS(1-506)<br>C235S | ATGGCGGAACGTGCCGCACTGGAAGAATTGGTTAAATTACAGGGAGAAC<br>GCGTACGTGGTCTTAAACAACAAAAAGCCTCTGCGGAATTGATTGAAGA<br>AGAAGTTGCCAAATTACTGAAACTGAAAGCTCAACTTGGACCCGATGAA<br>AGTAAACAAAAATTTGTGTTGAAAACGCCCAAAGGAACCCGTGATTATA | 198 |

TABLE D8-continued

| HRS polypeptides with Substitutions to Remove Surface Exposed Cysteines |
| --- |
| GTCCACGTCAAATGGCCGTTCGTGAAAAAGTGTTCGACGTTATTATTCGC<br>TGTTTTAAACGTCACGGTGCTGAAGTAATCGATACCCCCGTATTTGAATT<br>GAAAGAGACTCTGATGGGCAAATATGGTGAAGATTCTAAACTGATTTAT<br>GATTTGAAAGACCAAGGAGGTGAACTGCTGAGCCTGCGCTACGACTTAA<br>CTGTGCCTTTTGCCCGTTACTTAGCCATGAATAAaTTaACCAACATCAAAC<br>GTTACCATATTGCAAAAGTATATCGCCGCGACAACCCTGCAATGACTCGT<br>GGACGCTATCGCGAATTCTATCAGTGTGATTTTGATATTGCCGGAAATTT<br>CGACCCGATGATCCCGGATGCCGAGTGTTTGAAAATTATGTGTGAAATTC<br>TGAGTTCGTTGCAGATCGGAGACTTTCTTGTAAAAGTTAATGACCGCCGT<br>ATTCTGGATGGTATGTTTGCTATTTGCGGTGTTTCTGATTCCAAATTCCGT<br>ACAATCTCCTCAAGCGTGGACAAATTGGATAAAGTGTCTTGGGAAGAAG<br>TAAAAAATGAAATGGTGGGAGAAAAAGGCCTGGCTCCAGAAGTAGCAG<br>ACCGTATTGGTGACTATGTTCAACAACATGGCGGTGTGTCCTTAGTCGAA<br>CAGTTATTACAGGATCCTAAACTGAGCCAAAATAAACAAGCACTTGAAG<br>GACTGGGAGATCTGAAATTACTCTTTGAATATCTGACCTTATTTGGGATT<br>GATGATAAAATTAGCTTTGATCTGAGCTTGGCCCGCGGTCTTGATTATTA<br>TACCGGCGTGATTTACGAAGCTGTTCTCTTGCAAACCCCAGCCCAGGCGG<br>GCGAAGAGCCTTTGGGAGTCGGCAGTGTGGCAGCCGGTGGTCGTTATGA<br>TGGTTTGGTAGGAATGTTTGACCCTAAAGGCCGTAAAGTACCATGTGTG<br>GGGCTTTCTATCGGTGTCGAACGTATCTTTTCTATTGTTGAACAACGTCTT<br>GAAGCTTTGGAGGAAAAGATCCGTACCACGGAAacCCAAGTCTTAGTTGC<br>aAGTGCCCAAAAAAAACTGTTAGAAGAACGCCTGAAACTCGTATCAGAA<br>CTTTGGGACGCCGGCATCAAGGCCGAACTGCTGTATAAAAAGAACCCGA<br>AATTGTTAAACCAACTCCAGTATTGTGAAGAAGCTGGGATCCCACTCGT<br>AGCTATTATTGGTGAGCAAGAATTAAAAGATGGCGTGATTAAACTGCGT<br>TCAGTAACAAGCCGTGAAGAGGTAGATGTACGTCGCGAAGACTTAGTGG<br>AAGAAATTAAACGCCGCACCGGTCAACCGTTA |

In some embodiments, such cysteine substituted mutants are modified to engineer-in, insert, or otherwise introduce a new surface exposed cysteine residue at a defined surface exposed position, where the introduced residue does not substantially interfere with the non-canonical activity of the HRS polypeptide. Specific examples include for example the insertion (or re-insertion back) of additional cysteine residues at the N- or C-terminus of any of the reduced cysteine HRS polypeptides described above. In some embodiments, the insertion of such N- or C-terminal surface exposed cysteines involves the re-insertion of the last 1, last 2, or last 3 naturally occurring C-terminal amino acids of the full length human HRS to a reduced cysteine variant of a HRS polypeptide e.g., the re-insertion of all or part of the sequence CIC (Cys Ile Cys). Exemplary reduced cysteine mutants include for example any combination of mutations (or the deletion of) at residues Cys174, Cys191, Cys224, and Cys235, and or the deletion or substitution of Cys507 and Cys509 (based on the numbering of full length human HRS (SEQ ID NO:1) in any of the HRS polypeptides of SEQ ID NOS: 1-106, 170-181, or 185-191 or Tables D1, D3-D6 or D8.

For some types of site-specific conjugation or attachment to heterologous molecules such as Fc regions or PEG or other heterologous molecules, HRS polypeptides may have one or more glutamine substitutions, where one or more naturally-occurring (non-glutamine) residues are substituted with glutamine, for example, to facilitate transglutaminase-catalyzed attachment of the molecule(s) to the glutamine's amide group. In some embodiments, glutamine substitutions are introduced near the N-terminus and/or C-terminus of the HRS polypeptide (e.g., SEQ ID NOS:1-106, 170-181, or 185-191 or the HRS polypeptides of Tables D1, D3-D6 or D8). Particular embodiments include where one or more of residues within 0, 1, 2, 3, 4, 5, 6, 7, 8, 9, 10, 11, 12, 13, 14, 15, 16, 17, 18, 19, 20, 21, 22, 23, 24 or 25 amino acids relative to the N-terminus and/or C-terminus of any one of SEQ ID NOS:1-106, 170-181, or 185-191 are substituted with a glutamine residue. These and related HRS polypeptides can also include substitutions (e.g., conservative substitutions) to remove any naturally-occurring glutamine residues, if desired, and thereby regulate the degree of site-specific conjugation or attachment.

For certain types of site-specific conjugation or attachment to heterologous molecules such as Fc regions or PEG or other heterologous molecules, HRS polypeptides may have one or more lysine substitutions, where one or more naturally-occurring (non-lysine) residues are substituted with lysine, for example, to facilitate acylation or alkylation-based attachment of molecule(s) to the lysine's amino group. These methods also typically result in attachment of molecule(s) to the N-terminal residue. In some embodiments, lysine substations are near the N-terminus and/or C-terminus of the HRS polypeptide (e.g., SEQ ID NOS:1-106, 170-181, or 185-191 or the HRS polypeptides of Tables D1, D3-D6 or D8). Particular embodiments include where one or more of residues within 0, 1, 2, 3, 4, 5, 6, 7, 8, 9, 10, 11, 12, 13, 14, 15, 16, 17, 18, 19, 20, 21, 22, 23, 24 or 25 amino acids to the N-terminus and/or C-terminus of any one of SEQ ID NOS:1-106, 170-181, or 185-191 (or the HRS polypeptides of Tables D1, D3-D6 or D8) are substituted with a lysine residue. These and related HRS polypeptides can also include substitutions (e.g., conservative substitutions) to remove any naturally-occurring lysine residues, if desired, and thereby regulate the degree of site-specific conjugation or attachment.

Site-specific conjugation to HRS polypeptides may also be performed by substituting one or more solvent accessible surface amino acids of a HRS polypeptide. For example, suitable solvent accessible amino acids may be determined based on the predicted solvent accessibility using the SPIDDER server (http://sppider.cchmc.org/) using the published crystal structure of an exemplary HRS polypeptide (see Xu et al., *Structure.* 20:1470-7, 2012; and U.S. Application No. 61/674,639). Based on this analysis several amino acids on the surface may potentially be used as mutation sites to introduce functional groups suitable for conjugation or attachment. The surface accessibility score of amino acids based on the crystal structure can be calculated, where the higher scores represent better accessibility. In particular embodiments, higher scores (for example, >40) are preferred. Accordingly in some embodiments an amino acid position have a surface accessibility score of greater than 40 may used to introduce a cysteine, lysine, glutamine, or other non-naturally-occurring amino acid.

In particular embodiments, a solvent accessible surface amino acid is selected from the group consisting of: alanine, glycine, and serine, and can be substituted with naturally occurring amino acids including, but not limited to, cysteine, glutamine, or lysine, or a non-naturally occurring amino acid that is optimized for site specific conjugation or attachment.

In various embodiments, the present invention contemplates site-specific conjugation or attachment at any amino acid position in a HRS polypeptide by virtue of substituting a non-naturally-occurring amino acid comprising a functional group that will form a covalent bond with the functional group attached to a heterologous molecules such as an Fc region or PEG or other heterologous molecule. Non-natural amino acids can be inserted or substituted at, for example, one or more of residues within 0, 1, 2, 3, 4, 5, 6, 7, 8, 9, 10, 11, 12, 13, 14, 15, 16, 17, 18, 19, 20, 21, 22, 23, 24 or 25 amino acids relative to the N-terminus and/or C-terminus of any one of SEQ ID NOS:1-106, 170-181, or 185-191 (or the HRS polypeptides of Tables D1, D3-D6 or D8); at the N-terminus and/or C-terminus of any one of SEQ ID NOS:1-106, 170-181, or 185-191 (or the HRS polypeptides of Tables D1, D3-D6 or D8); or a solvent accessible surface amino acid residue as described herein.

In particular embodiments, non-naturally occurring amino acids include, without limitation, any amino acid, modified amino acid, or amino acid analogue other than selenocysteine and the following twenty genetically encoded alpha-amino acids: alanine, arginine, asparagine, aspartic acid, cysteine, glutamine, glutamic acid, glycine, histidine, isoleucine, leucine, lysine, methionine, phenylalanine, proline, serine, threonine, tryptophan, tyrosine, valine. The generic structure of an alpha-amino acid is illustrated by the following formula:

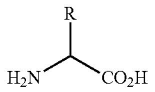

A non-natural amino acid is typically any structure having the foregoing formula wherein the R group is any substituent other than one used in the twenty natural amino acids. See, e.g., biochemistry texts such as Biochemistry by L. Stryer, 3rd ed. 1988, Freeman and Company, New York, for structures of the twenty natural amino acids. Note that the non-natural amino acids disclosed herein may be naturally occurring compounds other than the twenty alpha-amino acids above. Because the non-natural amino acids disclosed herein typically differ from the natural amino acids in side chain only, the non-natural amino acids form amide bonds with other amino acids, e.g., natural or non-natural, in the same manner in which they are formed in naturally occurring proteins. However, the non-natural amino acids have side chain groups that distinguish them from the natural amino acids. For example, R in foregoing formula optionally comprises an alkyl-, aryl-, aryl halide, vinyl halide, alkyl halide, acetyl, ketone, aziridine, nitrile, nitro, halide, acyl-, keto-, azido-, hydroxyl-, hydrazine, cyano-, halo-, hydrazide, alkenyl, alkynyl, ether, thio ether, epoxide, sulfone, boronic acid, boronate ester, borane, phenylboronic acid, thiol, seleno-, sulfonyl-, borate, boronate, phospho, phosphono, phosphine, heterocyclic-, pyridyl, naphthyl, benzophenone, a constrained ring such as a cyclooctyne, thio ester, enone, imine, aldehyde, ester, thioacid, hydroxylamine, amino, carboxylic acid, alpha-keto carboxylic acid, alpha or beta unsaturated acids and amides, glyoxyl amide, or organosilane group, or the like or any combination thereof.

Specific examples of unnatural amino acids include, but are not limited to, p-acetyl-L-phenylalanine, O-methyl-L-tyrosine, an L-3-(2-naphthyl)alanine, a 3-methyl-phenylalanine, an O-4-allyl-L-tyrosine, a 4-propyl-L-tyrosine, a tri-O-acetyl-GlcNAcβ-serine, β-O-GlcNAc-L-serine, a tri-O-acetyl-GalNAc-α-threonine, an α-GalNAc-L-threonine, an L-Dopa, a fluorinated phenylalanine, an isopropyl-L-phenylalanine, a p-azido-L-phenylalanine, a p-acyl-L-phenylalanine, a p-benzoyl-L-phenylalanine, an L-phosphoserine, a phosphonoserine, a phosphonotyrosine, a p-iodo-phenylalanine, a p-bromophenylalanine, a p-amino-L-phenylalanine, an isopropyl-L-phenylalanine, those listed below, or elsewhere herein, and the like.

Accordingly, one may select a non-naturally occurring amino acid comprising a functional group that forms a covalent bond with any preferred functional group of a desired molecule (e.g., Fc region, PEG). Non-natural amino acids, once selected, can either be purchased from vendors, or chemically synthesized. Any number of non-natural amino acids may be incorporated into the target molecule and may vary according to the number of desired molecules that are to be attached. The molecules may be attached to all or only some of the non-natural amino acids. Further, the same or different non-natural amino acids may be incorporated into a HRS polypeptide, depending on the desired outcome. In certain embodiments, about 1, 2, 3, 4, 5, 6, 7, 8, 9, 10 or more non-natural amino acids are incorporated into a HRS polypeptide any or all of which may be conjugated to a molecule comprising a desired functional group.

In certain aspects, the use of non-natural amino acids can be utilized to modify (e.g., increase) a selected non-canonical activity of a HRS polypeptide, or to alter the in vivo or in vitro half-life of the protein. Non-natural amino acids can also be used to facilitate (selective) chemical modifications (e.g., pegylation) of a HRS protein, as described elsewhere herein. For instance, certain non-natural amino acids allow selective attachment of polymers such as an Fc region or PEG to a given protein, and thereby improve their pharmacokinetic properties.

Specific examples of amino acid analogs and mimetics can be found described in, for example, Roberts and Vellaccio, The Peptides: Analysis, Synthesis, Biology, Eds. Gross and Meinhofer, Vol. 5, p. 341, Academic Press, Inc., New York, N.Y. (1983), the entire volume of which is incorporated herein by reference. Other examples include peralkylated amino acids, particularly permethylated amino acids. See, for example, Combinatorial Chemistry, Eds. Wilson and Czarnik, Ch. 11, p. 235, John Wiley & Sons Inc., New York, N.Y. (1997), the entire book of which is incorporated herein by reference. Yet other examples include amino acids whose amide portion (and, therefore, the amide backbone of the resulting peptide) has been replaced, for example, by a sugar ring, steroid, benzodiazepine or carbo cycle. See, for instance, Burger's Medicinal Chemistry and Drug Discovery, Ed. Manfred E. Wolff, Ch. 15, pp. 619-620, John Wiley & Sons Inc., New York, N.Y. (1995), the entire book of which is incorporated herein by reference. Methods for synthesizing peptides, polypeptides, peptidomimetics and proteins are well known in the art (see, for example, U.S. Pat. No. 5,420,109; M. Bodanzsky, Principles of Peptide Synthesis (1st ed. & 2d rev. ed.), Springer-Verlag, New York, N.Y. (1984 & 1993), see Chapter 7; Stewart and Young, Solid Phase Peptide Synthesis, (2d ed.), Pierce Chemical Co., Rockford, Ill. (1984), each of which is incorporated herein by reference). Accordingly, the HRS polypeptides of the present invention may be composed of naturally occurring and non-naturally occurring amino acids as well as amino acid analogs and mimetics.

Polynucleotides

Certain embodiments relate to polynucleotides that encode a HRS polypeptide or a HRS-Fc fusion protein. Also included are polynucleotides that encode any one or more of the Fc regions described herein, alone or in combination with a HRS coding sequence. Among other uses, these embodiments may be utilized to recombinantly produce a desired HRS, Fc region, or HRS-Fc polypeptide or variant thereof, or to express the HRS, Fc region, or HRS-Fc polypeptide in a selected cell or subject. It will be appreciated by those of ordinary skill in the art that, as a result of the degeneracy of the genetic code, there are many nucleotide sequences that encode a HRS polypeptide HRS-Fc fusion protein as described herein. Some of these polynucleotides may bear minimal homology to the nucleotide sequence of any native gene. Nonetheless, polynucleotides that vary due to differences in codon usage are specifically contemplated by the present invention, for example polynucleotides that are optimized for human, yeast or bacterial codon selection.

As will be recognized by the skilled artisan, polynucleotides may be single-stranded (coding or antisense) or double-stranded, and may be DNA (genomic, cDNA or synthetic) or RNA molecules. Additional coding or non-coding sequences may, but need not, be present within a polynucleotide of the present invention, and a polynucleotide may, but need not, be linked to other molecules and/or support materials.

Polynucleotides may comprise a native sequence (i.e., an endogenous sequence that encodes an HRS-Fc fusion polypeptide or a portion thereof) or may comprise a variant, or a biological functional equivalent of such a sequence. Polynucleotide variants may contain one or more substitutions, additions, deletions and/or insertions, as further described below, preferably such that the activity of the encoded polypeptide is not substantially diminished relative to the unmodified polypeptide.

In additional embodiments, the present invention provides isolated polynucleotides comprising various lengths of contiguous stretches of sequence identical to or complementary to a HRS polypeptide or HRS-Fc fusion protein, wherein the isolated polynucleotides encode a truncated HRS polypeptide as described herein Therefore, multiple polynucleotides can encode the HRS polypeptides, Fc regions, and fusion proteins of the invention. Moreover, the polynucleotide sequence can be manipulated for various reasons. Examples include but are not limited to the incorporation of preferred codons to enhance the expression of the polynucleotide in various organisms (see generally Nakamura et al., *Nuc. Acid. Res.* 28:292, 2000). In addition, silent mutations can be incorporated in order to introduce, or eliminate restriction sites, decrease the density of CpG dinucleotide motifs (see for example, Kameda et al., *Biochem. Biophys. Res. Commun.* 349:1269-1277, 2006) or reduce the ability of single stranded sequences to form stem-loop structures: (see, e.g., Zuker M., *Nucl. Acid Res.* 31:3406-3415, 2003). In addition, mammalian expression can be further optimized by including a Kozak consensus sequence (i.e., (a/g)cc(a/g)ccATGg) (SEQ ID NO:199) at the start codon. Kozak consensus sequences useful for this purpose are known in the art (Mantyh et al., *PNAS* 92: 2662-2666, 1995; Mantyh et al., *Prot. Exp. & Purif.* 6:124, 1995). Exemplary wild type and codon optimized versions of various HRS polypeptides are provided in Table D9 below.

TABLE D9

Codon Optimized DNA Sequences

| Name | Amino Acid Residue Range of SEQ ID NO: 1 | Nucleic acid sequence | SEQ ID NO: |
|---|---|---|---|
| Wild type (Full length HisRS) | 1-509 | ATGGCAGAGCGTGCGGCGCTGGAGGAGCTGGTGAAACTTCA<br>GGGAGAGCGCGTGCGAGGCCTCAAGCAGCAGAAGGCCAGCG<br>CCGAGCTGATCGAGGAGGAGGTGGCGAAACTCCTGAAACTG<br>AAGGCACAGCTGGGTCCTGATGAAAGCAAACAGAAATTTGTG<br>CTCAAAACCCCCAAGGGCACAAGAGACTATAGTCCCCGGCAG<br>ATGGCAGTTCGCGAGAAGGTGTTTGACGTAATCATCCGTTGC<br>TTCAAGCGCCACGGTGCAGAAGTCATTGATACACCTGTATTT<br>GAACTAAAGGAAACACTGATGGGAAAGTATGGGGAAGACTC<br>CAAGCTTATCTATGACCTGAAGGACCAGGGCGGGGAGCTCCT<br>GTCCCTTCGCTATGACCTCACTGTTCCTTTTGCTCGGTATTTGG<br>CAATGAATAAACTGACCAACATTAAACGCTACCACATAGCAA<br>AGGTATATCGGCGGGATAACCCAGCCATGACCCGTGGCCGAT<br>ACCGGGAATTCTACCAGTGTGATTTTGACATTGCTGGGAACTT<br>TGATCCCATGATCCCTGATGCAGAGTGCCTGAAGATCATGTG<br>CGAGATCCTGAGTTCACTTCAGATAGGCGACTTCCTGGTCAA<br>GGTAAACGATCGACGCATTCTAGATGGGATGTTTGCTATCTG<br>TGGTGTTTCTGACAGCAAGTTCCGTACCATCTGCTCCTCAGTA<br>GACAAGCTGGACAAGGTGTCCTGGGAAGAGGTGAAGAATGA<br>GATGGTGGGAGAGAAGGGCCTTGCACCTGAGGTGGCTGACC<br>GCATTGGGGACTATGTCCAGCAACATGGTGGGGTATCCCTGG<br>TGGAACAGCTGCTCCAGGATCCTAAACTATCCCAAAACAAGC<br>AGGCCTTGGAGGGCCTGGGAGACCTGAAGTTGCTCTTTGAGT<br>ACCTGACCCTATTTGGCATTGATGACAAAATCTCCTTTGACCT<br>GAGCCTTGCTCGAGGGCTGGATTACTACACTGGGGTGATCTA | 111 |

TABLE D9-continued

Codon Optimized DNA Sequences

| Name | Amino Acid Residue Range of SEQ ID NO: 1 | Nucleic acid sequence | SEQ ID NO: |
|---|---|---|---|
| | | TGAGGCAGTGCTGCTACAGACCCCAGCCCAGGCAGGGGAAG<br>AGCCCCTGGGTGTGGGCAGTGTGGCTGCTGGAGGACGCTATG<br>ATGGGCTAGTGGGCATGTTCGACCCCAAAGGGCGCAAGGTGC<br>CATGTGTGGGGCTCAGCATTGGGGTGGAGCGGATTTTCTCCA<br>TCGTGGAACAGAGACTAGAGGCTTTGGAGGAGAAGATACGG<br>ACCACGGAGACACAGGTGCTTGTGGCATCTGCACAGAAGAA<br>GCTGCTAGAGGAAAGACTAAAGCTTGTCTCAGAACTGTGGGA<br>TGCTGGGATCAAGGCTGAGCTGCTGTACAAGAAGAACCCAAA<br>GCTACTGAACCAGTTACAGTACTGTGAGGAGGCAGGCATCCC<br>ACTGGTGGCTATCATCGGCGAGCAGGAACTCAAGGATGGGGT<br>CATCAAGCTCCGTTCAGTGACGAGCAGGGAAGAGGTGGATGT<br>CCGAAGAGAAGACCTTGTGGAGGAAATCAAAAGGAGAACAG<br>GCCAGCCCCTCTGCATCTGC | |
| HisRS1$^{N1}$ | 1-141 | ATGGCAGAACGTGCCGCCCTGGAAGAGCTGGTAAAACTGCA<br>AGGCGAGCGTGTTCGTGGTCTGAAACAGCAGAAAGCAAGCG<br>CTGAACTGATCGAAGAAGAAGTGGCGAAACTGCTGAAACTG<br>AAAGCACAGCTGGGTCCTGATGAATCAAAACAAAAATTCGTC<br>CTGAAAACTCCGAAAGGAACCCGTGACTATTCTCCTCGTCAA<br>ATGGCCGTCCGTGAAAAAGTGTTCGACGTGATCATTCGCTGC<br>TTTAAACGCCATGGTGCCGAAGTGATTGATACCCCGGTGTTT<br>GAGCTGAAAGAGACACTGATGGGCAAATATGGTGAGGACAG<br>CAAACTGATTTATGACCTGAAAGATCAGGGTGGTGAACTGCT<br>GAGTCTGCGCTATGATCTGACAGTTCCGTTTGCCCGTTATCTG<br>GCAATG | 112 |
| HisRS1$^{N2}$ | 1-408 | ATGGCAGAACGTGCCGCCCTGGAAGAGCTGGTAAAACTGCA<br>AGGCGAGCGTGTTCGTGGTCTGAAACAGCAGAAAGCAAGCG<br>CTGAACTGATCGAAGAAGAAGTGGCGAAACTGCTGAAACTG<br>AAAGCACAGCTGGGTCCTGATGAATCAAAACAAAAATTCGTC<br>CTGAAAACTCCGAAAGGAACCCGTGACTATTCTCCTCGTCAA<br>ATGGCCGTCCGTGAAAAAGTGTTCGACGTGATCATTCGCTGC<br>TTTAAACGCCATGGTGCCGAAGTGATTGATACCCCGGTGTTT<br>GAGCTGAAAGAGACACTGATGGGCAAATATGGTGAGGACAG<br>CAAACTGATTTATGACCTGAAAGATCAGGGTGGTGAACTGCT<br>GAGTCTGCGCTATGATCTGACAGTTCCGTTTGCCCGTTATCTG<br>GCAATGAATAAACTGACCAACATTAAACGCTATCACATTGCT<br>AAAGTCTATCGCCGTGACAATCCTGCTATGACCCGTGGTCGTT<br>ATCGTGAGTTCTATCAGTGTGACTTCGATATTGCCGGCAACTT<br>TGATCCGATGATCCCGGATGCTGAATGCCTGAAAATCATGTG<br>TGAGATCCTGAGCAGTCTGCAGATTGGCGATTTCCTGGTGAA<br>AGTCAACGATCGCCGTATTCTGGATGGCATGTTCGCCATCTGT<br>GGTGTTAGCGACTCCAAATTCCGTACCATCTGTAGTAGTGTG<br>GACAAACTGGATAAAGTGAGCTGGGAGGAGGTGAAAAACGA<br>AATGGTGGGCGAGAAAGGTCTGGCTCCTGAAGTGGCTGACCG<br>TATTGGTGATTATGTCCAGCAGCACGGTGGAGTATCACTGGT<br>TGAGCAACTGCTGCAAGACCCTAAACTGAGTCAGAATAAACA<br>GGCCCTGGAGGGACTGGGAGATCTGAAACTGCTGTTCGAGTA<br>TCTGACCCTGTTCGGTATCGATGACAAAATCTCCTTTGACCTG<br>TCACTGGCTCGTGGACTGGACTATTATACCGGCGTGATCTATG<br>AAGCTGTACTGCTGCAAACTCCAGCACAAGCAGGTGAAGAGC<br>CTCTGGGTGTGGGTAGTGTAGCCGCTGGGGGACGTTATGATG<br>GACTGGTGGGGATGTTCGACCCTAAAGGCCGTAAAGTTCCGT<br>GTGTGGGTCTGAGTATCGGTGTTGAGCGTATCTTTTCCATCGT<br>CGAGCAACGTCTGGAAGCACTGGAGGAAAAAATCCGTACGA<br>CCGAA | 113 |
| HisRS1$^{N3}$ | 1-113 | ATGGCAGAACGTGCCGCCCTGGAAGAGCTGGTAAAACTGCA<br>AGGCGAGCGTGTTCGTGGTCTGAAACAGCAGAAAGCAAGCG<br>CTGAACTGATCGAAGAAGAAGTGGCGAAACTGCTGAAACTG<br>AAAGCACAGCTGGGTCCTGATGAATCAAAACAAAAATTCGTC<br>CTGAAAACTCCGAAAGGAACCCGTGACTATTCTCCTCGTCAA<br>ATGGCCGTCCGTGAAAAAGTGTTCGACGTGATCATTCGCTGC<br>TTTAAACGCCATGGTGCCGAAGTGATTGATACCCCGGTGTTT<br>GAGCTGAAAGAGACACTGATGGGCAAATATGGTGAGGACAG<br>CAAACTG | 114 |
| HisRS1$^{N4}$ | 1-60 | ATGGCAGAACGTGCCGCCCTGGAAGAGCTGGTAAAACTGCA<br>AGGCGAGCGTGTTCGTGGTCTGAAACAGCAGAAAGCAAGCG<br>CTGAACTGATCGAAGAAGAAGTGGCGAAACTGCTGAAACTG<br>AAAGCACAGCTGGGTCCTGATGAATCAAAACAAAAATTCGTC<br>CTGAAAACTCCGAAG | 115 |

TABLE D9-continued

| Name | Amino Acid Residue Range of SEQ ID NO: 1 | Nucleic acid sequence | SEQ ID NO: |
|---|---|---|---|
| Codon Optimized DNA Sequences | | | |
| $HisRS1^{N8}$ | 1-506 | ATGGCAGAGCGTGCGGCGCTGGAGGAGCTGGTGAAACTTCA<br>GGGAGAGCGCGTGCGAGGCCTCAAGCAGCAGAAGGCCAGCG<br>CCGAGCTGATCGAGGAGGAGGTGGCGAAACTCCTGAAACTG<br>AAGGCACAGCTGGGTCCTGATGAAAGCAAACAGAAATTTGTG<br>CTCAAAACCCCCAAGGGCACAAGAGACTATAGTCCCCGGCAG<br>ATGGCAGTTCGCGAGAAGGTGTTTGACGTAATCATCCGTTGC<br>TTCAAGCGCCACGGTGCAGAAGTCATTGATACACCTGTATTT<br>GAACTAAAGGAAACACTGATGGGAAAGTATGGGGAAGACTC<br>CAAGCTTATCTATGACCTGAAGGACCAGGGCGGGGAGCTCCT<br>GTCCCTTCGCTATGACCTCACTGTTCCTTTTGCTCGGTATTTGG<br>CAATGAATAAACTGACCAACATTAAACGCTACCACATAGCAA<br>AGGTATATCGGCGGGATAACCCAGCCATGACCCGTGGCCGAT<br>ACCGGGAATTCTACCAGTGTGATTTTGACATTGCTGGGAACTT<br>TGATCCCATGATCCCTGATGCAGAGTGCCTGAAGATCATGTG<br>CGAGATCCTGAGTTCACTTCAGATAGGCGACTTCCTGGTCAA<br>GGTAAACGATCGACGCATTCTAGATGGGATGTTTGCTATCTG<br>TGGTGTTTCTGACAGCAAGTTCCGTACCATCTGCTCCTCAGTA<br>GACAAGCTGGACAAGGTGTCCTGGGAAGAGGTGAAGAATGA<br>GATGGTGGGAGAGAAGGGCCTTGCACCTGAGGTGGCTGACC<br>GCATTGGGGACTATGTCCAGCAACATGGTGGGGTATCCCTGG<br>TGGAACAGCTGCTCCAGGATCCTAAACTATCCCAAAACAAGC<br>AGGCCTTGGAGGGCCTGGGAGACCTGAAGTTGCTCTTTGAGT<br>ACCTGACCCTATTTGGCATTGATGACAAAATCTCCTTTGACCT<br>GAGCCTTGCTCGAGGGCTGGATTACTACACTGGGGTGATCTA<br>TGAGGCAGTGCTGCTACAGACCCCAGCCCAGGCAGGGGAAG<br>AGCCCCTGGGTGTGGGCAGTGTGGCTGCTGGAGGACGCTATG<br>ATGGGCTAGTGGGCATGTTCGACCCCAAAGGGCGCAAGGTGC<br>CATGTGTGGGGCTCAGCATTGGGGTGGAGCGGATTTTCTCCA<br>TCGTGGAACAGAGACTAGAGGCTTTGGAGGAGAAGATACGG<br>ACCACGGAGACACAGGTGCTTGTGGCATCTGCACAGAAGAA<br>GCTGCTAGAGGAAAGACTAAAGCTTGTCTCAGAACTGTGGGA<br>TGCTGGGATCAAGGCTGAGCTGCTGTACAAGAAGAACCCAAA<br>GCTACTGAACCAGTTACAGTACTGTGAGGAGGCAGGCATCCC<br>ACTGGTGGCTATCATCGGCGAGCAGGAACTCAAGGATGGGGT<br>CATCAAGCTCCGTTCAGTGACGAGCAGGGAAGAGGTGGATGT<br>CCGAAGAGAAGACCTTGTGGAGGAAATCAAAAGGAGAACAG<br>GCCAGCCCCTC | 116 |
| $HisRS1^{N6}$ | 1-48 | ATGGCAGAACGTGCCGCCCTGGAAGAGCTGGTAAAACTGCA<br>AGGCGAGCGTGTTCGTGGTCTGAAACAGCAGAAAGCAAGCG<br>CTGAACTGATCGAAGAAGAAGTGGCGAAACTGCTGAAACTG<br>AAAGCACAGCTGGGTCCTGAT | 117 |
| $HisRS1^{I1}$ | 191-333 | TGCCTGAAAATCATGTGTGAGATCCTGAGTAGTCTGCAAATT<br>GGCGACTTTCTGGTCAAAGTGAACGATCGCCGTATTCTGGAT<br>GGCATGTTCGCCATCTGTGGTGTTAGCGACTCCAAATTCCGTA<br>CAATCTGTAGCAGCGTGGACAAACTGGATAAAGTGTCCTGGG<br>AAGAGGTGAAAAACGAAATGGTGGGTGAAAAAGGTCTGGCT<br>CCGGAGGTTGCTGACCGTATCGGTGATTATGTTCAGCAGCAC<br>GGCGGTGTTAGTCTGGTTGAACAACTGCTGCAAGACCCGAAA<br>CTGTCTCAGAACAAACAGGCCCTGGAAGGACTGGGAGATCTG<br>AAACTGCTGTTCGAGTATCTGACGCTGTTCGGCATTGATGAC<br>AAAATTTCTTTCGACCTGTCACTGGCACGTGGACTGGACTATT<br>ATACCGGT | 118 |
| $HisRS1^{C1}$ | 405-509 | CGTACCACCGAAACCCAAGTTCTGGTTGCCTCAGCTCAGAAA<br>AAACTGCTGGAAGAACGCCTGAAACTGGTTAGCGAACTGTGG<br>GATGCTGGCATTAAAGCCGAACTGCTGTATAAAAAAAACCCG<br>AAACTGCTGAATCAGCTGCAGTATTGTGAGGAAGCGGGTATT<br>CCTCTGGTGGCCATTATCGGAGAACAGGAACTGAAAGACGGC<br>GTTATTAAACTGCGTAGCGTGACCTCTCGTGAAGAAGTTGAC<br>GTTCGCCGTGAAGATCTGGTCGAGGAAATCAAACGTCGTACC<br>GGTCAACCTCTGTGTATTTGC | 119 |
| $HisRS1^{N5}$ | 1-243 + 27 aa | ATGGCAGAACGTGCCGCCCTGGAAGAGCTGGTAAAACTGCA<br>AGGCGAGCGTGTTCGTGGTCTGAAACAGCAGAAAGCAAGCG<br>CTGAACTGATCGAAGAAGAAGTGGCGAAACTGCTGAAACTG<br>AAAGCACAGCTGGGTCCTGATGAATCAAAACAAAAATTCGTC<br>CTGAAAACTCCGAAAGGAACCCGTGACTATTCTCCTCGTCAA<br>ATGGCCGTCCGTGAAAAAGTGTTCGACGTGATCATTCGCTGC<br>TTTAAACGCCATGGTGCCGAAGTGATTGATACCCCGGTGTTT | 120 |

TABLE D9-continued

Codon Optimized DNA Sequences

| Name | Amino Acid Residue Range of SEQ ID NO: 1 | Nucleic acid sequence | SEQ ID NO: |
|---|---|---|---|
| | | GAGCTGAAAGAGACACTGATGGGCAAATATGGTGAGGACAG<br>CAAACTGATCTATGACCTGAAAGACCAAGGCGGTGAACTGCT<br>GTCCCTGCGTTATGATCTGACTGTGCCGTTTGCCCGTTATCTG<br>GCCATGAATAAACTGACGAACATTAAACGCTATCACATTGCC<br>AAAGTGTATCGCCGTGACAATCCTGCTATGACTCGTGGACGT<br>TATCGTGAATTCTATCAGTGTGACTTCGATATTGCCGGCAACT<br>TCGACCCTATGATTCCGGATGCTGAATGCCTGAAAATCATGT<br>GTGAGATCCTGAGCAGCCTGCAAATTGGTGACTTCCTGGTGA<br>AAGTGAATGACCGTCGTATCCTGGATGGCATGTTTGCCATTTG<br>TGGTGTGAGCGATTCCAAATTCCGTACCATCTGTAGTAGTGTG<br>GACAAACTGGATAAAGTGGGCTATCCGTGGTGGAACTCTTGT<br>AGCCGTATTCTGAACTATCCTAAAACCAGCCGCCCGTGGCGT<br>GCTTGGGAAACT | |
| HisRS1[C2] | 1-60 + 175-509 | ATGGCAGAACGTGCCGCCCTGGAAGAGCTGGTAAAACTGCA<br>AGGCGAGCGTGTTCGTGGTCTGAAACAGCAGAAAGCAAGCG<br>CTGAACTGATCGAAGAAGAAGTGGCGAAACTGCTGAAACTG<br>AAAGCACAGCTGGGTCCTGATGAATCAAAACAAAAATTCGTC<br>CTGAAAACTCCGAAAGACTTCGATATTGCCGGGAATTTTGAC<br>CCTATGATCCCTGATGCCGAATGTCTGAAAATCATGTGTGAG<br>ATCCTGAGCAGTCTGCAGATTGGTGACTTCCTGGTGAAAGTG<br>AACGATCGCCGTATTCTGGATGGAATGTTTGCCATTTGTGGCG<br>TGTCTGACAGCAAATTTCGTACGATCTGTAGCAGCGTGGATA<br>AACTGGATAAAGTGAGCTGGGAGGAGGTGAAAAATGAGATG<br>GTGGGCGAAAAAGGTCTGGCACCTGAAGTGGCTGACCGTATC<br>GGTGATTATGTTCAGCAACATGGCGGTGTTTCTCTGGTCGAAC<br>AGCTGCTGCAAGACCCAAAACTGAGCCAGAACAAACAGGCA<br>CTGGAAGGACTGGGTGATCTGAAACTGCTGTTTGAGTATCTG<br>ACGCTGTTTGGCATCGATGACAAAATCTCGTTTGACCTGAGC<br>CTGGCACGTGGTCTGGATTATTATACCGGCGTGATCTATGAA<br>GCCGTCCTGCTGCAAACTCCAGCACAAGCAGGTGAAGAACCT<br>CTGGGTGTTGGTAGTGTAGCGGCAGGCGGACGTTATGATGGA<br>CTGGTGGGGATGTTTGATCCGAAAGGCCGTAAAGTTCCGTGT<br>GTCGGTCTGAGTATCGGGGTTGAGCGTATCTTTAGCATTGTGG<br>AGCAACGTCTGGAAGCTCTGGAGGAAAAAATCCGTACCACCG<br>AAACCCAAGTTCTGGTTGCCTCAGCTCAGAAAAAACTGCTGG<br>AAGAACGCCTGAAACTGGTTAGCGAACTGTGGGATGCTGGCA<br>TTAAAGCCGAACTGCTGTATAAAAAAAACCCGAAACTGCTGA<br>ATCAGCTGCAGTATTGTGAGGAAGCGGGTATTCCTCTGGTGG<br>CCATTATCGGAGAACAGGAACTGAAAGACGGCGTTATTAAAC<br>TGCGTAGCGTGACCTCTCGTGAAGAAGTTGACGTTCGCCGTG<br>AAGATCTGGTCGAGGAAATCAAACGTCGTACCGGTCAACCTC<br>TGTGTATTTGC | 121 |
| HisRS1[C3] | 1-60 + 211-509 | ATGGCAGAACGTGCCGCCCTGGAAGAGCTGGTAAAACTGCA<br>AGGCGAGCGTGTTCGTGGTCTGAAACAGCAGAAAGCAAGCG<br>CTGAACTGATCGAAGAAGAAGTGGCGAAACTGCTGAAACTG<br>AAAGCACAGCTGGGTCCTGATGAATCAAAACAAAAATTCGTC<br>CTGAAAACTCCGAAAGTGAATGATCGCCGTATCCTGGATGGC<br>ATGTTTGCCATTTGTGGTGTGAGCGACTCGAAATTCCGTACGA<br>TTTGCTCTAGCGTCGATAAACTGGACAAAGTGTCCTGGGAAG<br>AGGTGAAAAACGAGATGGTGGGTGAGAAAGGTCTGGCTCCT<br>GAAGTTGCCGACCGTATTGGTGATTATGTTCAGCAGCATGGC<br>GGTGTTTCACTGGTTGAACAACTGCTGCAAGACCCGAAACTG<br>TCTCAGAATAAACAGGCGCTGGAAGGACTGGGAGATCTGAA<br>ACTGCTGTTTGAGTATCTGACCCTGTTCGGCATTGATGACAAA<br>ATCAGCTTCGACCTGAGCCTGGCACGTGGTCTGGATTATTATA<br>CCGGCGTGATCTATGAAGCCGTTCTGCTGCAGACACCAGCAC<br>AAGCAGGCGAAGAACCTCTGGGTGTTGGTTCTGTGGCAGCCG<br>GTGGTCGTTATGATGGACTGGTAGGCATGTTCGATCCGAAAG<br>GCCGTAAAGTTCCGTGTGTGGGACTGAGTATCGGTGTTGAGC<br>GTATCTTTAGCATCGTGGAACAACGTCTGGAAGCGCTGGAGG<br>AGAAAATTCGTACCACCGAAACCCAAGTTCTGGTTGCCTCAG<br>CTCAGAAAAAACTGCTGGAAGAACGCCTGAAACTGGTTAGCG<br>AACTGTGGGATGCTGGCATTAAAGCCGAACTGCTGTATAAAA<br>AAAACCCGAAACTGCTGAATCAGCTGCAGTATTGTGAGGAAG<br>CGGGTATTCCTCTGGTGGCCATTATCGGAGAACAGGAACTGA<br>AAGACGGCGTTATTAAACTGCGTAGCGTGACCTCTCGTGAAG<br>AAGTTGACGTTCGCCGTGAAGATCTGGTCGAGGAAATCAAAC<br>GTCGTACCGGTCAACCTCTGTGTATTTGC | 122 |

TABLE D9-continued

| Codon Optimized DNA Sequences | | | |
|---|---|---|---|
| Name | Amino Acid Residue Range of SEQ ID NO: 1 | Nucleic acid sequence | SEQ ID NO: |
| HisRS1[C4] | 1-100 + 211-509 | ATGGCAGAACGTGCCGCCCTGGAAGAGCTGGTAAAACTGCA AGGCGAGCGTGTTCGTGGTCTGAAACAGCAGAAAGCAAGCG CTGAACTGATCGAAGAAGAAGTGGCGAAACTGCTGAAACTG AAAGCACAGCTGGGTCCTGATGAATCAAAACAAAAATTCGTC CTGAAAACTCCGAAAGGAACTCGTGATTATAGCCCTCGCCAG ATGGCTGTCCGTGAAAAAGTGTTCGATGTGATCATTCGCTGCT TCAAACGTCATGGTGCCGAAGTCATTGATACCCCGGTGTTCG AGCTGAAAGTGAACGATCGCCGTATTCTGGATGGCATGTTCG CCATTTGTGGTGTTAGCGATAGCAAATTCCGTACAATCTGCTC TAGCGTGGACAAACTGGACAAAGTGAGCTGGGAAGAGGTGA AAAACGAGATGGTGGGTGAGAAAGGCCTGGCTCCTGAAGTT GCCGACCGTATCGGAGATTATGTTCAGCAGCATGGCGGAGTT TCACTGGTTGAACAACTGCTGCAAGACCCGAAACTGTCTCAG AACAAACAGGCACTGGAAGGTCTGGGAGATCTGAAACTGCT GTTCGAGTATCTGACGCTGTTCGGTATTGACGACAAAATTTCC TTCGACCTGTCGCTGGCACGTGGTCTGGATTATTATACAGGCG TGATCTATGAGGCTGTACTGCTGCAGACACCAGCACAAGCAG GTGAAGAGCCTCTGGGTGTTGGTTCAGTTGCTGCCGGTGGAC GTTATGACGGACTGGTAGGGATGTTTGACCCAAAAGGCCGTA AAGTCCCGTGTGTAGGACTGTCTATTGGCGTTGAGCGTATCTT TAGCATCGTGGAGCAACGTCTGGAAGCTCTGGAGGAGAAAAT CCGTACCACCGAAACCCAAGTTCTGGTTGCCTCAGCTCAGAA AAAACTGCTGGAAGAACGCCTGAAACTGGTTAGCGAACTGTG GGATGCTGGCATTAAAGCCGAACTGCTGTATAAAAAAAACCC GAAACTGCTGAATCAGCTGCAGTATTGTGAGGAAGCGGGTAT TCCTCTGGTGGCCATTATCGGAGAACAGGAACTGAAAGACGG CGTTATTAAACTGCGTAGCGTGACCTCTCGTGAAGAAGTTGA CGTTCGCCGTGAAGATCTGGTCGAGGAAATCAAACGTCGTAC CGGTCAACCTCTGTGTATTTGC | 123 |
| HisRS1[C5] | 1-174 + 211-509 | ATGGCAGAACGTGCCGCCCTGGAAGAGCTGGTAAAACTGCA AGGCGAGCGTGTTCGTGGTCTGAAACAGCAGAAAGCAAGCG CTGAACTGATCGAAGAAGAAGTGGCGAAACTGCTGAAACTG AAAGCACAGCTGGGTCCTGATGAATCAAAACAAAAATTCGTC CTGAAAACTCCGAAAGGAACTCGTGATTATAGCCCTCGCCAG ATGGCTGTCCGTGAAAAAGTGTTCGATGTGATCATTCGCTGCT TCAAACGTCATGGTGCCGAAGTCATTGATACCCCGGTGTTCG AGCTGAAAGAAACCCTGATGGGCAAATATGGGGAAGATTCC AAACTGATCTATGACCTGAAAGACCAGGGAGGTGAACTGCTG TCTCTGCGCTATGACCTGACTGTTCCTTTTGCTCGCTATCTGG CCATGAATAAACTGACCAACATCAAACGCTATCATATCGCCA AAGTGTATCGCCGTGACAATCCAGCAATGACCCGTGGTCGTT ATCGTGAATTTTATCAGTGTGTGAACGATCGCCGTATTCTGGA CGGCATGTTCGCCATTTGTGGTGTGTCTGACTCCAAATTTCGT ACGATCTGCTCAAGCGTGGACAAACTGGACAAAGTGAGCTGG GAAGAGGTGAAAAACGAGATGGTGGGTGAGAAAGGCCTGGC TCCTGAAGTTGCCGACCGTATCGGAGATTATGTTCAGCAGCA TGGCGGAGTTTCACTGGTTGAACAACTGCTGCAAGACCCGAA ACTGTCACAGAACAAACAGGCACTGGAAGGTCTGGGGGATCT GAAACTGCTGTTCGAGTATCTGACGCTGTTCGGTATTGACGA CAAAATCAGCTTCGATCTGAGCCTGGCACGTGGTCTGGACTA TTATACCGGCGTGATTTATGAAGCCGTTCTGCTGCAGACTCCA GCACAAGCAGGTGAAGAGCCTCTGGGTGTTGGAAGTGTGGCA GCCGGTGGCCGTTATGATGGTCTGGTTGGCATGTTTGACCCG AAAGGCCGTAAAGTCCCGTGTGTAGGACTGTCTATCGGCGTG GAGCGTATTTTTAGCATCGTGGAACAACGCCTGGAAGCTCTG GAAGAGAAAATCCGTACCACCGAAACCCAAGTTCTGGTTGCC TCAGCTCAGAAAAAACTGCTGGAAGAACGCCTGAAACTGGTT AGCGAACTGTGGGATGCTGGCATTAAAGCCGAACTGCTGTAT AAAAAAAACCCGAAACTGCTGAATCAGCTGCAGTATTGTGAG GAAGCGGGTATTCCTCTGGTGGCCATTATCGGAGAACAGGAA CTGAAAGACGGCGTTATTAAACTGCGTAGCGTGACCTCTCGT GAAGAAGTTGACGTTCGCCGTGAAGATCTGGTCGAGGAAATC AAACGTCGTACCGGTCAACCTCTGTGTATTTGC | 124 |
| HisRS1[C6] | 1-60 + 101-509 | ATGGCAGAACGTGCCGCCCTGGAAGAGCTGGTAAAACTGCA AGGCGAGCGTGTTCGTGGTCTGAAACAGCAGAAAGCAAGCG CTGAACTGATCGAAGAAGAAGTGGCGAAACTGCTGAAACTG AAAGCACAGCTGGGTCCTGATGAATCAAAACAAAAATTCGTC CTGAAAACTCCGAAAGAAACCCTGATGGGCAAATATGGCGA AGATTCCAAACTGATCTATGACCTGAAAGACCAAGGCGGTGA | 125 |

TABLE D9-continued

| Codon Optimized DNA Sequences | | | |
|---|---|---|---|
| Name | Amino Acid Residue Range of SEQ ID NO: 1 | Nucleic acid sequence | SEQ ID NO: |
| | | ACTGCTGTCCCTGCGTTATGACCTGACTGTTCCGTTTGCTCGT<br>TATCTGGCCATGAATAAACTGACCAACATTAAACGCTATCAC<br>ATTGCCAAAGTGTATCGCCGTGACAATCCTGCTATGACTCGT<br>GGACGTTATCGTGAATTCTATCAGTGTGACTTCGATATTGCCG<br>GCAACTTCGACCCTATGATTCCGGATGCTGAATGCCTGAAAA<br>TCATGTGTGAGATCCTGAGCAGCCTGCAAATTGGTGACTTCCT<br>GGTGAAAGTGAATGACCGTCGTATCCTGGATGGCATGTTCGC<br>CATTTGTGGTGTTAGCGATTCCAAATTCCGTACCATCTGTAGT<br>AGTGTGGACAAACTGGATAAAGTGAGCTGGGAAGAGGTGAA<br>AAACGAAATGGTGGGCGAAAAAGGTCTGGCACCTGAGGTTG<br>CTGATCGTATCGGTGACTATGTCCAGCAGCATGGAGGTGTTT<br>CACTGGTTGAGCAACTGCTGCAAGATCCGAAACTGTCTCAGA<br>ACAAACAGGCCCTGGAAGGACTGGGTGATCTGAAACTGCTGT<br>TCGAGTATCTGACGCTGTTCGGTATTGATGACAAAATCTCGTT<br>CGACCTGTCTCTGGCTCGTGGACTGGATTATTATACGGGCGTA<br>ATCTATGAAGCTGTCCTGCTGCAGACACCAGCACAAGCAGGT<br>GAAGAGCCTCTGGGTGTTGGAAGTGTTGCTGCCGGTGGTCGC<br>TATGACGGACTGGTTGGCATGTTCGATCCGAAAGGCCGTAAA<br>GTTCCGTGTGTAGGACTGAGCATTGGCGTTGAGCGTATCTTTT<br>CCATCGTTGAGCAACGTCTGGAAGCACTGGAAGAGAAAATCC<br>GTACCACCGAAACCCAAGTTCTGGTTGCCTCAGCTCAGAAAA<br>AACTGCTGGAAGAACGCCTGAAACTGGTTAGCGAACTGTGGG<br>ATGCTGGCATTAAAGCCGAACTGCTGTATAAAAAAAACCCGA<br>AACTGCTGAATCAGCTGCAGTATTGTGAGGAAGCGGGTATTC<br>CTCTGGTGGCCATTATCGGAGAACAGGAACTGAAAGACGGCG<br>TTATTAAACTGCGTAGCGTGACCTCTCGTGAAGAAGTTGACG<br>TTCGCCGTGAAGATCTGGTCGAGGAAATCAAACGTCGTACCG<br>GTCAACCTCTGTGTATTTGC | |
| HisRS1$^{C7}$ | 1-100 + 175-509 | ATGGCAGAACGTGCCGCCCTGGAAGAGCTGGTAAAACTGCA<br>AGGCGAGCGTGTTCGTGGTCTGAAACAGCAGAAAGCAAGCG<br>CTGAACTGATCGAAGAAGAAGTGGCGAAACTGCTGAAACTG<br>AAAGCACAGCTGGGTCCTGATGAATCAAAACAAAAATTCGTC<br>CTGAAAACTCCGAAAGGAACTCGTGATTATAGCCCTCGCCAG<br>ATGGCTGTCCGTGAAAAAGTGTTCGATGTGATCATTCGCTGCT<br>TCAAACGTCATGGTGCCGAAGTCATTGATACCCCGGTGTTCG<br>AGCTGAAAGATTTCGATATTGCCGGCAACTTTGATCCGATGA<br>TTCCGGATGCTGAGTGTCTGAAAATCATGTGTGAGATCCTGA<br>GTAGTCTGCAGATTGGGGATTTCCTGGTGAAAGTGAACGATC<br>GCCGTATTCTGGACGGCATGTTTGCCATTTGTGGCGTTAGCGA<br>TAGCAAATTCCGTACGATCTGTAGCAGTGTGGACAAACTGGA<br>TAAAGTCTCTTGGGAAGAGGTCAAAAACGAGATGGTTGGTGA<br>GAAAGGCCTGGCTCCTGAAGTGGCTGACCGTATTGGTGATTA<br>TGTCCAGCAGCATGGTGGTGTTTCACTGGTTGAACAACTGCT<br>GCAAGACCCGAAACTGTCTCAGAACAAACAGGCACTGGAAG<br>GTCTGGGTGATCTGAAACTGCTGTTCGAGTATCTGACGCTGTT<br>CGGTATTGACGACAAAATTTCCTTCGACCTGTCACTGGCACGT<br>GGTCTGGATTATTATACAGGCGTAATCTATGAGGCTGTACTG<br>CTGCAAACTCCAGCACAAGCAGGTGAAGAACCTCTGGGAGTT<br>GGTAGTGTAGCGGCAGGGGGTCGTTATGATGGGCTGGTCGGG<br>ATGTTCGATCCAAAAGGCCGTAAAGTCCCGTGTGTTGGTCTG<br>TCTATTGGCGTTGAGCGTATCTTCTCCATCGTGGAGCAACGTC<br>TGGAAGCTCTGGAAGAAAAAATCCGTACCACCGAAACCCAA<br>GTTCTGGTTGCCTCAGCTCAGAAAAAACTGCTGGAAGAACGC<br>CTGAAACTGGTTAGCGAACTGTGGGATGCTGGCATTAAAGCC<br>GAACTGCTGTATAAAAAAAACCCGAAACTGCTGAATCAGCTG<br>CAGTATTGTGAGGAAGCGGGTATTCCTCTGGTGGCCATTATC<br>GGAGAACAGGAACTGAAAGACGGCGTTATTAAACTGCGTAG<br>CGTGACCTCTCGTGAAGAAGTTGACGTTCGCCGTGAAGATCT<br>GGTCGAGGAAATCAAACGTCGTACCGGTCAACCTCTGTGTAT<br>TTGC | 126 |
| HisRS1$^{C10}$ | 369-509 | ATGTTCGACCCAAAAGGCCGTAAAGTTCCGTGTGTAGGGCTG<br>TCTATCGGTGTTGAGCGTATCTTCTCCATCGTTGAGCAGCGTC<br>TGGAAGCACTGGAGGAAAAAATCCGTACGACCGAGACTCAA<br>GTCCTGGTTGCTAGTGCCCAGAAAAAACTGCTGGAAGAGCGC<br>CTGAAACTGGTTAGTGAGCTGTGGGATGCCGGTATTAAAGCC<br>GAACTGCTGTATAAAAAAAACCCGAAACTGCTGAATCAGCTG<br>CAGTATTGTGAAGAAGCGGGCATTCCGCTGGTAGCGATTATC<br>GGGGAACAAGAACTGAAAGATGGCGTGATCAAACTGCGTAG | 127 |

TABLE D9-continued

| Codon Optimized DNA Sequences | | | |
|---|---|---|---|
| Name | Amino Acid Residue Range of SEQ ID NO: 1 | Nucleic acid sequence | SEQ ID NO: |
| | | CGTTACAAGCCGTGAGGAAGTGGACGTCCGCCGTGAGGATCT GGTTGAAGAGATTAAACGCCGTACAGGTCAGCCTCTGTGTAT TTGC | |

Additional coding or non-coding sequences may, but need not, be present within a polynucleotide of the present invention, and a polynucleotide may, but need not, be linked to other molecules and/or support materials. Hence, the polynucleotides of the present invention, regardless of the length of the coding sequence itself, may be combined with other DNA or RNA sequences, such as promoters, polyadenylation signals, additional restriction enzyme sites, multiple cloning sites, other coding segments, and the like, such that their overall length may vary considerably.

It is therefore contemplated that a polynucleotide fragment of almost any length may be employed; with the total length preferably being limited by the ease of preparation and use in the intended recombinant DNA protocol. Included are polynucleotides of about 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 41, 43, 44, 45, 46, 47, 48, 49, 50, 60, 70, 80, 90, 100, 110, 120, 130, 140, 150, 160, 170, 180, 190, 200, 220, 240, 260, 270, 280, 300, 350, 400, 450, 500, 550, 600, 650, 700, 750, 800, 850, 900, 950, 1000, 1100, 1200, 1300, 1400, 1500, 1600, 1700, 1800, 1900, 2000, 2100, 2200, 2300, 2400, 2500, 2600, 2700, 2800, 2900, 3000 or more (including all integers in between) bases in length, including any portion or fragment (e.g., greater than about 6, 7, 8, 9, or 10 nucleotides in length) of a HRS reference polynucleotide (e.g., base number X-Y, in which X is about 1-3000 or more and Y is about 10-3000 or more), or its complement.

Embodiments of the present invention also include "variants" of the HRS reference polynucleotide sequences. Polynucleotide "variants" may contain one or more substitutions, additions, deletions and/or insertions in relation to a reference polynucleotide. Generally, variants of a HRS reference polynucleotide sequence may have at least about 30%, 40% 50%, 55%, 60%, 65%, 70%, generally at least about 75%, 80%, 85%, desirably about 90% to 95% or more, and more suitably about 98% or more sequence identity to that particular nucleotide sequence (Such as for example, SEQ ID NOS:111-127, 182-184, 192-198; see also the Examples) as determined by sequence alignment programs described elsewhere herein using default parameters. In certain embodiments, variants may differ from a reference sequence by about 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 41, 43, 44, 45, 46, 47, 48, 49, 50, 60, 70, 80, 90, 100 (including all integers in between) or more bases. In certain embodiments, such as when the polynucleotide variant encodes a HRS polypeptide having a non-canonical activity, the desired activity of the encoded HRS polypeptide is not substantially diminished relative to the unmodified polypeptide. The effect on the activity of the encoded polypeptide may generally be assessed as described herein. In some embodiments, the variants can alter the aggregation state of the HRS polypeptides, for example to provide for HRS polypeptides that exist in different embodiments primarily as a monomer, dimer or multimer.

Certain embodiments include polynucleotides that hybridize to a reference HRS polynucleotide sequence, (such as for example, SEQ ID NOS:111-127, 182-184, 192-198; see also the Examples) or to their complements, under stringency conditions described below. As used herein, the term "hybridizes under low stringency, medium stringency, high stringency, or very high stringency conditions" describes conditions for hybridization and washing. Guidance for performing hybridization reactions can be found in Ausubel et al., (1998, supra), Sections 6.3.1-6.3.6. Aqueous and non-aqueous methods are described in that reference and either can be used.

Reference herein to low stringency conditions include and encompass from at least about 1% v/v to at least about 15% v/v formamide and from at least about 1 M to at least about 2 M salt for hybridization at 42° C., and at least about 1 M to at least about 2 M salt for washing at 42° C. Low stringency conditions also may include 1% Bovine Serum Albumin (BSA), 1 mM EDTA, 0.5 M $NaHPO_4$ (pH 7.2), 7% SDS for hybridization at 65° C., and (i) 2×SSC, 0.1% SDS; or (ii) 0.5% BSA, 1 mM EDTA, 40 mM $NaHPO_4$ (pH 7.2), 5% SDS for washing at room temperature. One embodiment of low stringency conditions includes hybridization in 6× sodium chloride/sodium citrate (SSC) at about 45° C., followed by two washes in 0.2×SSC, 0.1% SDS at least at 50° C. (the temperature of the washes can be increased to 55° C. for low stringency conditions).

Medium stringency conditions include and encompass from at least about 16% v/v to at least about 30% v/v formamide and from at least about 0.5 M to at least about 0.9 M salt for hybridization at 42° C., and at least about 0.1 M to at least about 0.2 M salt for washing at 55° C. Medium stringency conditions also may include 1% Bovine Serum Albumin (BSA), 1 mM EDTA, 0.5 M $NaHPO_4$ (pH 7.2), 7% SDS for hybridization at 65° C., and (i) 2×SSC, 0.1% SDS; or (ii) 0.5% BSA, 1 mM EDTA, 40 mM $NaHPO_4$ (pH 7.2), 5% SDS for washing at 60-65° C. One embodiment of medium stringency conditions includes hybridizing in 6×SSC at about 45° C., followed by one or more washes in 0.2×SSC, 0.1% SDS at 60° C. High stringency conditions include and encompass from at least about 31% v/v to at least about 50% v/v formamide and from about 0.01 M to about 0.15 M salt for hybridization at 42° C., and about 0.01 M to about 0.02 M salt for washing at 55° C.

High stringency conditions also may include 1% BSA, 1 mM EDTA, 0.5 M $NaHPO_4$ (pH 7.2), 7% SDS for hybridization at 65° C., and (i) 0.2×SSC, 0.1% SDS; or (ii) 0.5% BSA, 1 mM EDTA, 40 mM $NaHPO_4$ (pH 7.2), 1% SDS for washing at a temperature in excess of 65° C. One embodiment of high stringency conditions includes hybridizing in 6×SSC at about 45° C., followed by one or more washes in 0.2×SSC, 0.1% SDS at 65° C. One embodiment of very high stringency conditions includes hybridizing in 0.5 M sodium phosphate, 7% SDS at 65° C., followed by one or more washes in 0.2×SSC, 1% SDS at 65° C.

Other stringency conditions are well known in the art and a skilled artisan will recognize that various factors can be manipulated to optimize the specificity of the hybridization. Optimization of the stringency of the final washes can serve to ensure a high degree of hybridization. For detailed examples, see Ausubel et al., supra at pages 2.10.1 to 2.10.16 and Sambrook et al. (1989, supra) at sections 1.101 to 1.104. While stringent washes are typically carried out at temperatures from about 42° C. to 68° C., one skilled in the art will appreciate that other temperatures may be suitable for stringent conditions. Maximum hybridization rate typically occurs at about 20° C. to 25° C. below the $T_m$ for formation of a DNA-DNA hybrid. It is well known in the art that the $T_m$ is the melting temperature, or temperature at which two complementary polynucleotide sequences dissociate. Methods for estimating $T_m$ are well known in the art (see Ausubel et al., supra at page 2.10.8).

In general, the $T_m$ of a perfectly matched duplex of DNA may be predicted as an approximation by the formula: $T_m$=81.5+16.6 ($log_{10}$+0.41 (% G+C)−0.63 (% formamide)−(600/length) wherein: M is the concentration of $Na^+$, preferably in the range of 0.01 molar to 0.4 molar; % G+C is the sum of guanosine and cytosine bases as a percentage of the total number of bases, within the range between 30% and 75% G+C; % formamide is the percent formamide concentration by volume; length is the number of base pairs in the DNA duplex. The $T_m$ of a duplex DNA decreases by approximately 1° C. with every increase of 1% in the number of randomly mismatched base pairs. Washing is generally carried out at $T_m$—15° C. for high stringency, or $T_m$—30° C. for moderate stringency.

In one example of a hybridization procedure, a membrane (e.g., a nitrocellulose membrane or a nylon membrane) containing immobilized DNA is hybridized overnight at 42° C. in a hybridization buffer (50% deionized formamide, 5×SSC, 5×Denhardt's solution (0.1% ficoll, 0.1% polyvinylpyrollidone and 0.1% bovine serum albumin), 0.1% SDS and 200 mg/mL denatured salmon sperm DNA) containing a labeled probe. The membrane is then subjected to two sequential medium stringency washes (i.e., 2×SSC, 0.1% SDS for 15 min at 45° C., followed by 2×SSC, 0.1% SDS for 15 min at 50° C.), followed by two sequential higher stringency washes (i.e., 0.2×SSC, 0.1% SDS for 12 min at 55° C. followed by 0.2×SSC and 0.1% SDS solution for 12 min at 65-68° C.

Production of HRS Polypeptides and HRS-Fc Conjugates

HRS-Fc conjugate polypeptides may be prepared by any suitable procedure known to those of skill in the art for example, by using standard solid-phase peptide synthesis (Merrifield, *J. Am. Chem. Soc.* 85:2149-2154 (1963)), or by recombinant technology using a genetically modified host. Protein synthesis may be performed using manual techniques or by automation. Automated synthesis may be achieved, for example, using Applied Biosystems 431A Peptide Synthesizer (Perkin Elmer). Alternatively, various fragments may be chemically synthesized separately and combined using chemical methods to produce the desired molecule.

HRS-Fc conjugates can also be produced by expressing a DNA or RNA sequence encoding the HRS polypeptide or HRS-Fc conjugates in question in a suitable host cell by well-known techniques. The polynucleotide sequence coding for the HRS-Fc conjugate or HRS polypeptide may be prepared synthetically by established standard methods, e.g., the phosphoamidite method described by Beaucage et al., *Tetrahedron Letters* 22:1859-1869, 1981; or the method described by Matthes et al., *EMBO Journal* 3:801-805, 1984. According to the phosphoramidite method, oligonucleotides are synthesized, e.g., in an automatic DNA synthesizer, purified, duplexed and ligated to form the synthetic DNA construct. Alternatively the DNA or RNA construct can be constructed using standard recombinant molecular biological techniques including restriction enzyme mediated cloning and PCR based gene amplification. In some embodiments for direct mRNA mediated expression the polynucleotide may be encapsulated in a nanoparticle or liposome to enable efficient delivery and uptake into the cell, and optionally include a modified cap or tail structure to enhance stability and translation.

The polynucleotide sequences may also be of mixed genomic, cDNA, RNA, and that of synthetic origin. For example, a genomic or cDNA sequence encoding a leader peptide may be joined to a genomic or cDNA sequence encoding the HRS polypeptide or HRS-Fc conjugate, after which the DNA or RNA sequence may be modified at a site by inserting synthetic oligonucleotides encoding the desired amino acid sequence for homologous recombination in accordance with well-known procedures or preferably generating the desired sequence by PCR using suitable oligonucleotides. In some embodiments a signal sequence can be included before the coding sequence. This sequence encodes a signal peptide N-terminal to the coding sequence which communicates to the host cell to direct the polypeptide to the cell surface or secrete the polypeptide into the media. Typically the signal peptide is clipped off by the host cell before the protein leaves the cell. Signal peptides can be found in variety of proteins in prokaryotes and eukaryotes.

A variety of expression vector/host systems are known and may be utilized to contain and express polynucleotide sequences. These include, but are not limited to, microorganisms such as bacteria transformed with recombinant bacteriophage, plasmid, or cosmid DNA expression vectors; yeast transformed with yeast expression vectors; insect cell systems infected with virus expression vectors (e.g., baculovirus); plant cell systems transformed with virus expression vectors (e.g., cauliflower mosaic virus, CaMV; tobacco mosaic virus, TMV) or with bacterial expression vectors (e.g., Ti or pBR322 plasmids); or animal cell systems, including mammalian cell and more specifically human cell systems transformed with viral, plasmid, episomal or integrating expression vectors.

The "control elements" or "regulatory sequences" present in an expression vector are non-translated regions of the vector—enhancers, promoters, 5' and 3' untranslated regions—which interact with host cellular proteins to carry out transcription and translation. Such elements may vary in their strength and specificity. Depending on the vector system and host utilized, any number of suitable transcription and translation elements, including constitutive and inducible promoters, may be used. For example, when cloning in bacterial systems, inducible promoters such as the hybrid lacZ promoter of the PBLUESCRIPT phagemid (Stratagene, La Jolla, Calif.) or PSPORT1 plasmid (Gibco BRL, Gaithersburg, Md.) and the like may be used. In mammalian cell systems, promoters from mammalian genes or from mammalian viruses are generally preferred. If it is necessary to generate a cell line that contains multiple copies of the sequence encoding a polypeptide, vectors based on SV40 or EBV may be advantageously used with an appropriate selectable marker.

Certain embodiments may employ E. cob-based expression systems (see, e.g., Structural Genomics Consortium et al., *Nature Methods.* 5:135-146, 2008). These and related embodiments may rely partially or totally on ligation-independent cloning (LIC) to produce a suitable expression vector. In specific embodiments, protein expression may be controlled by a T7 RNA polymerase (e.g., pET vector series), or modified pET vectors with alternate promoters, including for example the TAC promoter. These and related embodiments may utilize the expression host strain BL21 (DE3), a λDE3 lysogen of BL21 that supports T7-mediated expression and is deficient in lon and ompT proteases for improved target protein stability. Also included are expression host strains carrying plasmids encoding tRNAs rarely used in *E. coli*, such as ROSETTA™ (DE3) and Rosetta 2 (DE3) strains. In some embodiments other *E. coli* strains may be utilized, including other *E. coli* K-12 strains such as W3110 ($F^-$ lambda$^-$ IN(rrnD-rrnE)1 rph-1), and UT5600 (F, araC14, leuB6(Am), secA206(aziR), lacY1, proC14, tsx67, Δ(ompTfepC)266, entA403, glnX44(AS), $\lambda^-$, trpE38, rfbC1, rpsL109(strR), xylA5, mtl-1, thiE1), which can result in reduced levels of post-translational modifications during fermentation. Cell lysis and sample handling may also be improved using reagents sold under the trademarks BENZONASE® nuclease and BUGBUSTER® Protein Extraction Reagent. For cell culture, auto-inducing media can improve the efficiency of many expression systems, including high-throughput expression systems. Media of this type (e.g., OVERNIGHT EXPRESS™ Autoinduction System) gradually elicit protein expression through metabolic shift without the addition of artificial inducing agents such as IPTG.

Particular embodiments employ hexahistidine tags (such as those sold under the trademark HIS•TAG® fusions), followed by immobilized metal affinity chromatography (IMAC) purification, or related techniques. In certain aspects, however, clinical grade proteins can be isolated from *E. coli* inclusion bodies, without or without the use of affinity tags (see, e.g., Shimp et al., *Protein Expr Purif.* 50:58-67, 2006). As a further example, certain embodiments may employ a cold-shock induced *E. coli* high-yield production system, because over-expression of proteins in *Escherichia coli* at low temperature improves their solubility and stability (see, e.g., Qing et al., *Nature Biotechnology.* 22:877-882, 2004).

Also included are high-density bacterial fermentation systems. For example, high cell density cultivation of *Ralstonia eutropha* allows protein production at cell densities of over 150 g/L, and the expression of recombinant proteins at titers exceeding 10 g/L. In the yeast *Saccharomyces cerevisiae*, a number of vectors containing constitutive or inducible promoters such as alpha factor, alcohol oxidase, and PGH may be used. For reviews, see Ausubel et al. (supra) and Grant et al., Methods Enzymol. 153:516-544, 1987. Also included are *Pichia pandoris* expression systems (see, e.g., Li et al., *Nature Biotechnology.* 24, 210-215, 2006; and Hamilton et al., *Science,* 301:1244, 2003). Certain embodiments include yeast systems that are engineered to selectively glycosylate proteins, including yeast that have humanized N-glycosylation pathways, among others (see, e.g., Hamilton et al., *Science.* 313:1441-1443, 2006; Wildt et al., *Nature Reviews Microbiol.* 3:119-28, 2005; and Gerngross et al., *Nature-Biotechnology.* 22:1409-1414, 2004; U.S. Pat. Nos. 7,629,163; 7,326,681; and 7,029,872). Merely by way of example, recombinant yeast cultures can be grown in Fernbach Flasks or 15 L, 50 L, 100 L, and 200 L fermentors, among others.

In cases where plant expression vectors are used, the expression of sequences encoding polypeptides may be driven by any of a number of promoters. For example, viral promoters such as the 35S and 19S promoters of CaMV may be used alone or in combination with the omega leader sequence from TMV (Takamatsu, *EMBO J.* 6:307-311, 1987). Alternatively, plant promoters such as the small subunit of RUBISCO or heat shock promoters may be used (Coruzzi et al., *EMBO J.* 3:1671-1680, 1984; Broglie et al., *Science.* 224:838-843, 1984; and Winter et al., *Results Probl. Cell Differ.* 17:85-105, 1991). These constructs can be introduced into plant cells by direct DNA transformation or pathogen-mediated transfection. Such techniques are described in a number of generally available reviews (see, e.g., Hobbs in McGraw Hill, *Yearbook of Science and Technology*, pp. 191-196, 1992).

An insect system may also be used to express a polypeptide of interest. For example, in one such system, *Autographa californica* nuclear polyhedrosis virus (AcNPV) is used as a vector to express foreign genes in *Spodoptera frugiperda* cells or in *Trichoplusia* cells. The sequences encoding the polypeptide may be cloned into a non-essential region of the virus, such as the polyhedrin gene, and placed under control of the polyhedrin promoter. Successful insertion of the polypeptide-encoding sequence will render the polyhedrin gene inactive and produce recombinant virus lacking coat protein. The recombinant viruses may then be used to infect, for example, *S. frugiperda* cells or *Trichoplusia* cells in which the polypeptide of interest may be expressed (Engelhard et al., *PNAS USA.* 91:3224-3227, 1994). Also included are baculovirus expression systems, including those that utilize SF9, SF21, and *T. ni* cells (see, e.g., Murphy and Piwnica-Worms, *Curr Protoc Protein Sci.* Chapter 5:Unit5.4, 2001). Insect systems can provide post-translation modifications that are similar to mammalian systems.

In mammalian host cells, a number of expression systems are well known in the art and commercially available. Exemplary mammalian vector systems include for example, pCEP4, pREP4, and pREP7 from Invitrogen, the PerC6 system from Crucell, and Lentiviral based systems such as pLP1 from Invitrogen, and others. For example, in cases where an adenovirus is used as an expression vector, sequences encoding a polypeptide of interest may be ligated into an adenovirus transcription/translation complex consisting of the late promoter and tripartite leader sequence. Insertion in a non-essential E1 or E3 region of the viral genome may be used to obtain a viable virus which is capable of expressing the polypeptide in infected host cells (Logan & Shenk, *PNAS USA.* 81:3655-3659, 1984). In addition, transcription enhancers, such as the Rous sarcoma virus (RSV) enhancer, may be used to increase expression in mammalian host cells.

Examples of useful mammalian host cell lines include monkey kidney CV1 line transformed by SV40 (COS-7, ATCC CRL 1651); human embryonic kidney line (293 or 293 cells sub-cloned for growth in suspension culture, Graham et al., *J. Gen Vivol.* 36:59, 1977); baby hamster kidney cells (BHK, ATCC CCL 10); mouse sertoli cells (TM4*, Mather, Biol. Reprod.* 23:243-251, 1980); monkey kidney cells (CV1 ATCC CCL 70); African green monkey kidney cells (VERO-76, ATCC CRL-1587); human cervical carcinoma cells (HELA, ATCC CCL 2); canine kidney cells (MDCK, ATCC CCL 34); buffalo rat liver cells (BRL 3A, ATCC CRL 1442); human lung cells (W138, ATCC CCL 75); human liver cells (Hep G2, HB 8065); mouse mammary tumor (MMT 060562, ATCC CCL51); TR1 cells (Mather et al., *Annals N.Y. Acad. Sci.* 383:44-68, 1982); MRC 5 cells; FS4 cells; and a human hepatoma line (Hep G2). Other useful mammalian host cell lines include Chinese hamster ovary (CHO) cells, including DHFR-CHO cells (Urlaub et al., *PNAS USA.* 77:4216, 1980); and myeloma cell lines such as NSO and Sp2/0. For a review of certain mammalian host cell lines suitable for antibody production, see, e.g., Yazaki and Wu, *Methods in Molecular Biology*, Vol. 248 (B. K. C. Lo, ed., Humana Press, Totowa, N.J., 2003), pp. 255-268. Certain preferred mammalian cell expression systems include CHO and HEK293-cell based expression systems. Mammalian expression systems can utilize attached cell lines, for example, in T-flasks, roller bottles, or cell factories, or suspension cultures, for example, in 1 L and 5 L spinners, 5 L, 14 L, 40 L, 100 L and 200 L stir tank bioreactors, or 20/50 L and 100/200 L WAVE bioreactors, among others known in the art.

Also included are methods of cell-free protein expression. These and related embodiments typically utilize purified RNA polymerase, ribosomes, tRNA, and ribonucleotides. Such reagents can be produced, for example, by extraction from cells or from a cell-based expression system.

In addition, a host cell strain may be chosen for its ability to modulate the expression of the inserted sequences or to process the expressed protein in the desired fashion. Such modifications of the polypeptide include, but are not limited to, post-translational modifications such as acetylation, carboxylation, glycosylation, phosphorylation, lipidation, and acylation, or the insertion of non-naturally occurring amino acids (see generally U.S. Pat. Nos. 7,939,496; 7,816,320; 7,947,473; 7,883,866; 7,838,265; 7,829,310; 7,820,766; 7,820,766; 7,7737,226, 7,736,872; 7,638,299; 7,632,924; and 7,230,068). In some embodiments, such non-naturally occurring amino acids may be inserted at position Cys130. Post-translational processing which cleaves a "prepro" form of the protein may also be used to facilitate correct insertion, folding and/or function. Different host cells such as yeast, CHO, HeLa, MDCK, HEK293, and W138, in addition to bacterial cells, which have or even lack specific cellular machinery and characteristic mechanisms for such post-translational activities, may be chosen to ensure the correct modification and processing of the foreign protein.

The HRS polypeptides or HRS-Fc conjugates produced by a recombinant cell can be purified and characterized according to a variety of techniques known in the art. Exemplary systems for performing protein purification and analyzing protein purity include fast protein liquid chromatography (FPLC) (e.g., AKTA and Bio-Rad FPLC systems), high-pressure liquid chromatography (HPLC) (e.g., Beckman and Waters HPLC). Exemplary chemistries for purification include ion exchange chromatography (e.g., Q, S), size exclusion chromatography, salt gradients, affinity purification (e.g., Ni, Co, FLAG, maltose, glutathione, protein A/G), gel filtration, reverse-phase, ceramic HYPERD® ion exchange chromatography, and hydrophobic interaction columns (HIC), among others known in the art. Several exemplary methods are also disclosed in the Examples sections.

HRS-Fc Conjugates

As noted above, embodiments of the present invention relate to HRS-Fc conjugates, which comprise at least one Fc region that is covalently attached to one or more HRS polypeptides. Examples of HRS-Fc conjugates include fusion proteins and various forms of chemically cross-linked proteins. A wide variety of Fc region sequences may be employed in the HRS-Fc conjugates of the present invention, including wild-type sequences from any number of species, as well as variants, fragments, hybrids, and chemically modified forms thereof. The HRS-Fc polypeptides may also (optionally) comprise one or more linkers, which typically separate the Fc region(s) from the HRS polypeptide(s), including peptide linkers and chemical linkers, as described herein and known in the art. It will be appreciated that in any of these HRS-Fc conjugates the native N or C terminal amino acid of the HRS polypeptides, or native N or C-amino acid in the Fc domain, may be deleted and/or replaced with non native amino acid(s), for example, to facilitate expression and or cloning or to serve as a linker sequence between the two proteins.

HRS-Fc conjugate polypeptides can provide a variety of advantages relative to un-conjugated or unmodified HRS polypeptides, e.g., corresponding HRS polypeptides of the same or similar sequence having no Fc region(s) attached thereto. Merely by way of illustration, the covalent attachment of one or more Fc regions can alter (e.g., increase, decrease) the HRS polypeptide's solubility, half-life (e.g., in serum, in a selected tissue, in a test tube under storage conditions, for example, at room temperature or under refrigeration), dimerization or multimerization properties, biological activity or activities, for instance, by providing Fc-region-associated effector functions (e.g., activation of the classical complement cascade, interaction with immune effector cells via the Fc receptor (FcR), compartmentalization of immunoglobulins), cellular uptake, intracellular transport, tissue distribution, and/or bioavailability, relative to an unmodified HRS polypeptide having the same or similar sequence. In certain aspects, Fc regions can confer effector functions relating to complement-dependent cytotoxicity (CDC), antibody-dependent cell-mediated cytotoxicity (ADCC), and/or antibody-dependent cell-mediated phagocytocis (ADCP), which are believed to play a role in clearing specific target cells such as tumor cells and infected cells.

Certain embodiments employ HRS-Fc fusion proteins. "Fusion proteins" are defined elsewhere herein and well known in the art, as are methods of making fusion proteins (see, e.g., U.S. Pat. Nos. 5,116,964; 5,428,130; 5,455,165; 5,514,582; 6,406,697; 6,291,212; and 6,300,099 for general disclosure and methods related to Fc fusion proteins). In a HRS-Fc fusion protein, the Fc region can be fused to the N-terminus of the HRS polypeptide, the C-terminus, or both. In some embodiments, one or more Fc regions can be fused internally relative to HRS sequences, for instance, by placing an Fc region between a first HRS sequence (e.g., domain) and a second HRS sequence (e.g., domain), where the first HRS sequence is fused to the N-terminus of the Fc region and the second HRS sequence is fused to the C-terminus of the Fc region. In specific embodiments, the first and second HRS sequences are identical. In other embodiments, the first and second HRS sequences are different (e.g., they include different functional domains of the HRS polypeptide). Certain HRS-Fc fusion proteins can also include additional heterologous protein sequences, that is, non-Fc region and non-HRS polypeptide sequences.

The term "HRS-Fc" can indicate, but does not necessarily indicate, the N-terminal or C-terminal attachment of the Fc region to the HRS polypeptide. For instance, in certain instances the term "Fc-HRS" indicates fusion of the Fc region to the N-terminus of the HRS polypeptide, and the term "HRS-Fc" indicates fusion of the Fc region to the C-terminus of the HRS polypeptide. However, either term can be used more generally to refer to any fusion protein or conjugate of an Fc region and a HRS polypeptide.

In some embodiments the HRS-Fc fusion proteins may comprise tandemly repeated copies of the HRS polypeptide coupled to a single Fc domain, optionally separated by linker peptides. Exemplary tandemly repeated HRS-Fc fusion proteins are provided in Table D10. The preparation and sequences for specific tandemly repeated HRS-Fc conjugates are illustrated in the Examples.

TABLE D10

| Exemplary Tandem HRS-Fc conjugates |
| --- |
| HRS polypeptide-L-HRS-polypeptide-L-Fc |
| HRS-polypeptide-L-HRS -polypeptide-L-HRS-polypeptide-L-Fc |
| HRS-polypeptide-L-HRS-polypeptide-L-HRS-polypeptide-L-HRS-polypeptide -L-Fc |
| Fc-L-HRS-polypeptide -L-HRS-polypeptide |
| Fc-L-HRS-polypeptide -L-HRS-L-HRS-polypeptide |
| Fc-L-HRS-polypeptide -L-HRS-L-HRS-L-HRS-polypeptide |

Where:
"Fc" is an Fc domain as described herein.
"HRS-polypeptide" is any of the truncated HRS polypeptides described in Table D5.
"L" is an optional peptide linker.

Certain embodiments relate to HRS-Fc conjugates, where, for instance, one or more Fc regions are chemically conjugated or cross-linked to the HRS polypeptide(s). In these and related aspects, the Fc region can be conjugated to the HRS polypeptide at the N-terminal region (e.g., within the first 10, 20, 30, 40, 50, 60, 70, 80, 90, 100 or so amino acids), the internal region (between the N-terminal and C-terminal regions), and/or the C-terminal region (e.g., within the last 10, 20, 30, 40, 50, 60, 70, 80, 90, 100 or so amino acids). Polypeptides can be conjugated or cross-linked to other polypeptides according to a variety of routine techniques in the art. For instance, certain techniques employ the carboxyl-reactive carbodiimide crosslinker EDC (or EDAC), which covalently attaches via D, E, and C-terminal carboxyl groups. Other techniques employ activated EDC, which covalently attaches via K and N-terminal amino groups). Still other techniques employ m-maleimidobenzoyl-N-hydoxysuccinimide ester (MBS) or Sulfo-MBS, which covalently attach via the thiol group of a cysteine residue (see also U.S. Application No. 2007/0092940 for cysteine engineered Ig regions that can be used for thiol conjugation). Such cross-linked proteins can also comprise linkers, including cleavable or otherwise releasable linkers (e.g., enzymatically cleavable linkers, hydrolysable linkers), and non-cleavable linkers (i.e., physiologically-stable linkers). Certain embodiments may employ non-peptide polymers (e.g., PEG polymers; HRS-N-PEG-N-Fc conjugate) as a cross-linker between the Fc region(s) and the HRS polypeptide(s), as described, for example, in U.S. Application No. 2006/0269553. See also US Application No. 2007/0269369 for exemplary descriptions of Fc region conjugation sites.

In certain embodiments, discussed in greater detail below, variant or otherwise modified Fc regions can be employed, including those having altered properties or biological activities relative to wild-type Fc region(s). Examples of modified Fc regions include those having mutated sequences, for instance, by substitution, insertion, deletion, or truncation of one or more amino acids relative to a wild-type sequence, hybrid Fc polypeptides composed of domains from different immunoglobulin classes/subclasses, Fc polypeptides having altered glycosylation/sialylation patterns, and Fc polypeptides that are modified or derivatized, for example, by biotinylation (see, e.g., US Application No. 2010/0209424), phosphorylation, sulfation, etc., or any combination of the foregoing. Such modifications can be employed to alter (e.g., increase, decrease) the binding properties of the Fc region to one or more particular FcRs (e.g., FcγRI, FcγRIIa, FcγRIIb, FcγRIIc, FcγRIIIa, FcγRIIIb, FcRn), its pharmacokinetic properties (e.g., stability or half-life, bioavailability, tissue distribution, volume of distribution, concentration, elimination rate constant, elimination rate, area under the curve (AUC), clearance, $C_{max}$, $t_{max}$, $C_{min}$, fluctuation), its immunogenicity, its complement fixation or activation, and/or the CDC/ADCC/ADCP-related activities of the Fc region, among other properties described herein, relative to a corresponding wild-type Fc sequence.

The "Fc region" of a HRS-Fc conjugate provided herein is usually derived from the heavy chain of an immunoglobulin (Ig) molecule. A typical Ig molecule is composed of two heavy chains and two light chains. The heavy chains can be divided into at least three functional regions: the Fd region, the Fc region (fragment crystallizable region), and the hinge region (see FIG. 1), the latter being found only in IgG, IgA, and IgD immunoglobulins. The Fd region comprises the variable ($V_H$) and constant ($CH_1$) domains of the heavy chains, and together with the variable ($V_L$) and constant ($C_L$) domains of the light chains forms the antigen-binding fragment or Fab region.

The Fc region of IgG, IgA, and IgD immunoglobulins comprises the heavy chain constant domains 2 and 3, designated respectively as $CH_2$ and $CH_3$ regions; and the Fc region of IgE and IgM immunoglobulins comprises the heavy chain constant domains 2, 3, and 4, designated respectively as $CH_2$, $CH_3$, and $CH_4$ regions. The Fc region is mainly responsible for the immunoglobulin effector functions, which include, for example, complement fixation and binding to cognate Fc receptors of effector cells.

The hinge region (found in IgG, IgA, and IgD) acts as a flexible spacer that allows the Fab portion to move freely in space relative to the Fc region. In contrast to the constant regions, the hinge regions are structurally diverse, varying in both sequence and length among immunoglobulin classes and subclasses. The hinge region may also contain one or more glycosylation site(s), which include a number of structurally distinct types of sites for carbohydrate attachment. For example, IgA1 contains five glycosylation sites within a 17 amino acid segment of the hinge region, conferring significant resistance of the hinge region polypeptide to intestinal proteases. Residues in the hinge proximal region of the $CH_2$ domain can also influence the specificity of the interaction between an immunoglobulin and its respective Fc receptor(s) (see, e.g., Shin et al., Intern. Rev. Immunol. 10:177-186, 1993).

The term "Fc region" or "Fc fragment" or "Fc" as used herein, thus refers to a protein that contains one or more of a $CH_2$ region, a $CH_3$ region, and/or a $CH_4$ region from one or more selected immunoglobulin(s), including fragments and variants and combinations thereof. An "Fc region" may also include one or more hinge region(s) of the heavy chain constant region of an immunoglobulin. In certain embodiments, the Fc region does not contain one or more of the $CH_1$, $C_L$, $V_L$, and/or $V_H$ regions of an immunoglobulin.

Figure 2:
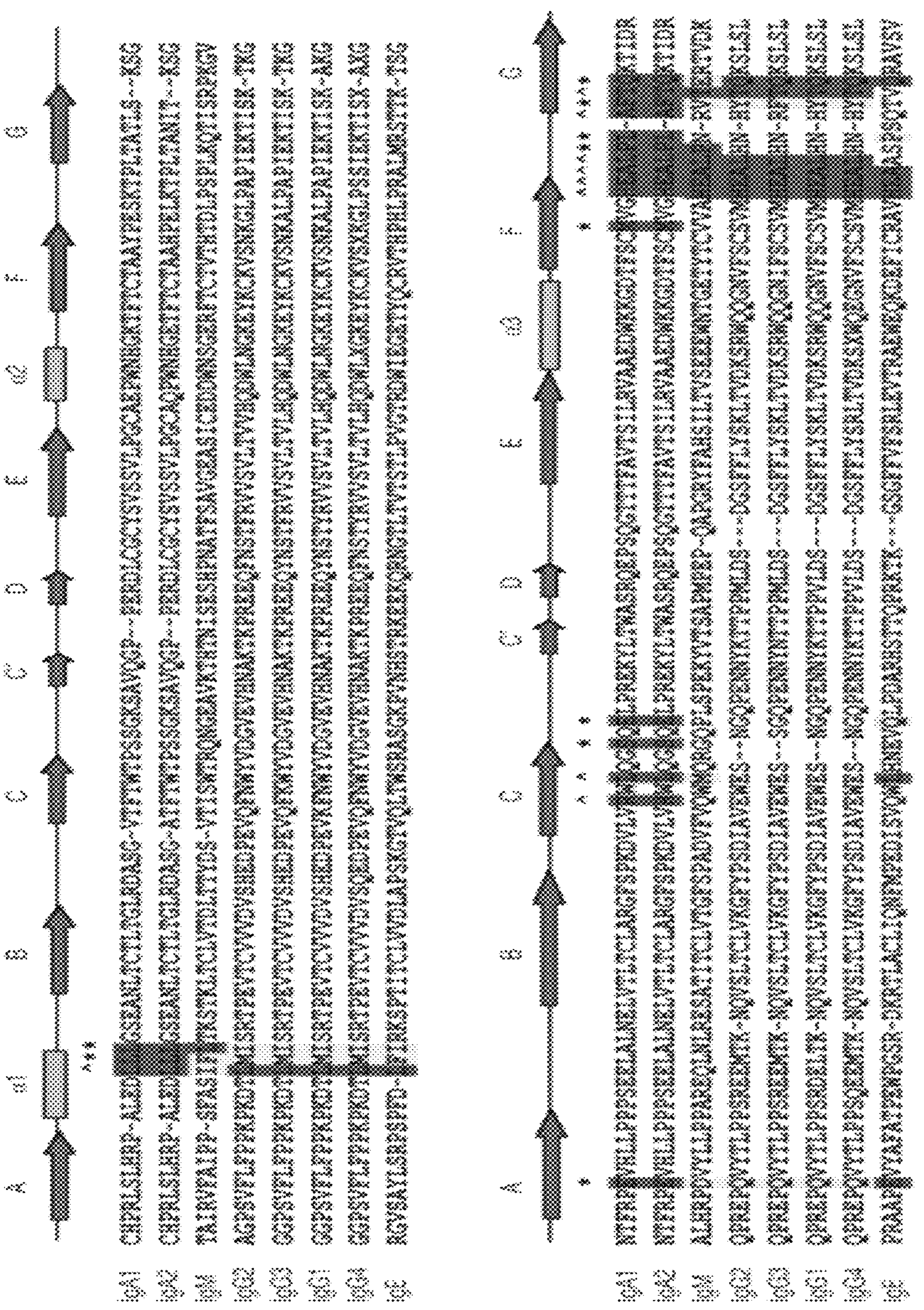
FIG. 2 shows an alignment of Fc regions from human IgA1 (SEQ ID NO:156), IgA2 (SEQ ID NO:157), IgM (SEQ ID NO:158), IgG1 (SEQ ID NO:159), IgG2 (SEQ ID NO:160), IgG3 (SEQ ID NO:161), IgG4 (SEQ ID NO:162), and IgE (SEQ ID NO:163). The secondary structure of Fcα is shown above the sequences. Carets (^) and asterisks (*) show residues that contribute respectively to 0-4% and 5-12% of the binding surface.

The Fc region can be derived from the $CH_2$ region, $CH_3$ region, $CH_4$ region, and/or hinge region(s) of any one or more immunoglobulin classes, including but not limited to IgA, IgD, IgE, IgG, IgM, including subclasses and combinations thereof. In some embodiments, the Fc region is derived from an IgA immunoglobulin, including subclasses IgA1 and/or IgA2. In certain embodiments, the Fc region is derived from an IgD immunoglobulin. In particular embodiments, the Fc region is derived from an IgE immunoglobulin. In some embodiments, the Fc region is derived from an IgG immunoglobulin, including subclasses IgG1, IgG2, IgG2, IgG3, and/or IgG4. In certain embodiments, the Fc region is derived from an IgM immunoglobulin. FIG. 2 shows an alignment of Fc regions from human IgA1 (SEQ ID NO:156), IgA2 (SEQ ID NO:157), IgM (SEQ ID NO:158), IgG1 (SEQ ID NO:159), IgG2 (SEQ ID NO:160), IgG3 (SEQ ID NO:161), IgG4(SEQ ID NO:162), and IgE (SEQ ID NO:163).

Certain Fc regions demonstrate specific binding for one or more Fc-receptors (FcRs). Examples of classes of Fc receptors include Fcγ receptors (FcγR), Fcα receptors (FcαR), Fcε receptors (FcεR), and the neonatal Fc receptor (FcRn). For instance, certain Fc regions have increased binding to (or affinity for) one or more FcγRs, relative to FcαRs, FcγRs, and/or FcRn. In some embodiments, Fc regions have increased binding to FcαRs, relative to one or more FcγRs, FcγRs, and/or FcRn. In other embodiments, Fc regions have increased binding to FcγRs (e.g., FcαRI), relative to one or more FcγRs, FcαRs, and/or FcRn. In particular embodiments, Fc regions have increased binding to FcRn, relative to one or more FcγRs, FcαRs, and/or FcγRs. In certain embodiments, the binding (or affinity) of an Fc region to one or more selected FcR(s) is increased relative to its binding to (or affinity for) one or more different FcR(s), typically by about 1.5×, 2×, 2.5×, 3×, 3.5×, 4×, 4.5×, 5×, 6×, 7×, 8×, 9×, 10×, 15×, 20×, 25×, 30×, 40×, 50×, 60×, 70×, 80×, 90×, 100×, 200×, 300×, 400×, 500×, 600×, 700×, 800×, 900×, 1000× or more (including all integers in between).

Examples of FcγRs include FcγRI, FcγRIIa, FcγRIIb, FcγRIIc, FcγRIIIa, and FcγRIIIb. FcγRI (CD64) is expressed on macrophages and dendritic cells and plays a role in phagocytosis, respiratory burst, cytokine stimulation, and dendritic cell endocytic transport. Expression of FcγRI is upregulated by both GM-CSF and γ-interferon (γ-IFN) and downregulated by interleukin-4 (IL-4). FcγRIIa is expressed on polymorphonuclear leukocytes (PMN), macrophages, dendritic cells, and mast cells. FcγRIIa plays a role in phagocytosis, respiratory burst, and cytokine stimulation. Expression of FcγRIIa is upregulated by GM-CSF and γ-IFN, and decreased by IL-4. FcγIIb is expressed on B cells, PMN, macrophages, and mast cells. FcγIIb inhibits immunoreceptor tyrosine-based activation motif (ITAM) mediated responses, and is thus an inhibitory receptor. Expression of FcγRIIc is upregulated by intravenous immunoglobulin (IVIG) and IL-4 and decreased by γ-IFN. FcγRIIc is expressed on NK cells. FcγRIIIa is expressed on natural killer (NK) cells, macrophages, mast cells, and platelets. This receptor participates in phagocytosis, respiratory burst, cytokine stimulation, platelet aggregation and degranulation, and NK-mediated ADCC. Expression of FcγRIII is upregulated by C5a, TGF-β, and γ-IFN and downregulated by IL-4. Fc γ RIIIb is a GPI-linked receptor expressed on PMN.

Certain Fc regions have increased binding to FcγRI, relative to FcγRIIa, FcγRIIb, FcγRIIc, FcγRIIIa, and/or FcγRIIIb. Some embodiments have increased binding to FcγRIIa, relative to FcγRI, FcγRIIb, FcγRIIc, FcγRIIIa, and/or FcγRIIIb. Particular Fc regions have increased binding to FcγRIIb, relative to FcγRI, FcγRIIa, FcγRIIc, FcγRIIIa, and/or FcγRIIIb. Certain Fc regions have increased binding to FcγRIIc, relative to FcγRI, FcγRIIa, FcγRIIb, FcγRIIIa, and/or FcγRIIIb. Some Fc regions have increased binding to FcγRIIIa, relative to FcγRI, FcγRIIa, FcγRIIb, FcγRIIc, and/or FcγRIIIb. Specific Fc regions have increased binding to FcγRIIIb, relative to FcγRI, FcγRIIa, FcγRIIb, FcγRIIc, and/or FcγRIIIa.

FcαRs include FcαRI (CD89). FcαRI is found on the surface of neutrophils, eosinophils, monocytes, certain macrophages (e.g., Kupffer cells), and certain dendritic cells. FcαRI is composed of two extracellular Ig-like domains, is a member of both the immunoglobulin superfamily and the multi-chain immune recognition receptor (MIRR) family, and signals by associating with two FcRγ signaling chains.

FcαRs include FcεRI and FcεRII. The high-affinity receptor FcεRI is a member of the immunoglobulin superfamily, is expressed on epidermal Langerhans cells, eosinophils, mast cells and basophils, and plays a major role in controlling allergic responses. FcεRI is also expressed on antigen-presenting cells, and regulates the production pro-inflammatory cytokines. The low-affinity receptor FcεRII (CD23) is a C-type lectin that can function as a membrane-bound or soluble receptor. FcεRII regulates B cell growth and differentiation, and blocks IgE-binding of eosinophils, monocytes, and basophils. Certain Fc regions have increased binding to FcεRI, relative to FcεRII. Other Fc regions have increased binding to FcεRII, relative to FcεRI.

Table F1 below summarizes the characteristics of certain FcRs.

TABLE F1

Exemplary Fc-Receptors

| Receptor | Primary Antibody Ligand | Ligand Affinity | Cell Distribution | Exemplary Effects Following Binding to Fc Ligand |
|---|---|---|---|---|
| FcγRI (CD64) | IgG1 and IgG3 | High (Kd~$10^{-9}$ M) | Macrophages<br>Neutrophils<br>Eosinophils<br>Dendritic cells | Phagocytosis<br>Cell activation<br>Activation of respiratory burst<br>Induction of microbe killing |
| FcγRIIa (CD32) | IgG | Low (Kd > $10^{-7}$ M) | Macrophages<br>Neutrophils<br>Eosinophils<br>Platelets<br>Langerhans cells | Phagocytosis<br>Degranulation (eosinophils) |
| FcγRIIb1 (CD32) | IgG | Low (Kd > $10^{-7}$ M) | B Cells<br>Mast cells | No phagocytosis<br>Inhibition of cell activity |
| FcγRIIb2 (CD32) | IgG | Low (Kd > $10^{-7}$ M) | Macrophages<br>Neutrophils<br>Eosinophils | Phagocytosis<br>Inhibition of cell activity |
| FcγRIIIa (CD16a) | IgG | Low (Kd > $10^{-6}$ M) | NK cells<br>Macrophages (certain tissues) | Induction of antibody-dependent cell-mediated cytotoxicity (ADCC)<br>Induction of cytokine release by macrophages |

TABLE F1-continued

Exemplary Fc-Receptors

| Receptor | Primary Antibody Ligand | Ligand Affinity | Cell Distribution | Exemplary Effects Following Binding to Fc Ligand |
|---|---|---|---|---|
| FcγRIIIb (CD16b) | IgG | Low (Kd > $10^{-6}$ M) | Eosinophils<br>Macrophages<br>Neutrophils<br>Mast cells<br>Follicular dendritic cells | Induction of microbe killing |
| FcεRI | IgE | High (Kd~$10^{-10}$ M) | Mast cells<br>Eosinophils<br>Basophils<br>Langerhans cells | Degranulation |
| FcεRII (CD23) | IgE | Low (Kd > $10^{-7}$ M) | B cells<br>Eosinophils<br>Langerhans cells | Possible adhesion molecule |
| FcαRI (CD89) | IgA | Low (Kd > $10^{-6}$ M) | Monocytes<br>Macrophages<br>Neutrophils<br>Eosinophils | Phagocytosis<br>Induction of microbe killing |
| Fcα/μR | IgA and IgM | High for IgM, Moderate for IgA | B cells<br>Mesangial cells<br>Macrophages | Endocytosis<br>Induction of microbe killing |
| FcRn | IgG | | Monocytes<br>Macrophages<br>Dendrite cells<br>Epithelial cells<br>Endothelial cells<br>Hepatocytes | Transfers IgG from a mother to fetus through the placenta<br>Transfers IgG from a mother to infant in milk<br>Protects IgG from degradation |

Fc regions can be derived from the immunoglobulin molecules of any animal, including vertebrates such as mammals such cows, goats, swine, dogs, mice, rabbits, hamsters, rats, guinea pigs, non-human primates, and humans. The amino acid sequences of $CH_2$, $CH_3$, $CH_4$, and hinge regions from exemplary, wild-type human IgA1, IgA2, IgD, IgE, IgG1, IgG2, IgG3, IgG4, and IgM immunoglobulins are shown below (SEQ ID NOS:128-154).

SEQ ID NO: 128 is the amino acid sequence of a human IgA1 hinge region (VPSTPPTPSPSTPPTPSPS).

SEQ ID NO: 129 is the amino acid sequence of a human IgA1 CH2 region (CCHPRLSLHRPALEDLLLGSEANLTCTLTGLRDASGVTFTWTPSSGKSAVQGPPERDLCGCYSV SSVLPGCAEPWNHGKTFTCTAAYPESKTPLTATLSKS).

SEQ ID NO: 130 is the amino acid sequence of a human IgA1 CH3 region (GNTFRPEVHLLPPPSEELALNELVTLTCLARGFSPKDVLVRWLQGSQELPREKYLTWASRQEPS QGTTTFAVTSILRVAAEDWKKGDTFSCMVGHEALPLAFTQKTIDRLAGKPTHVNVSVVMAEVD GTCY).

SEQ ID NO: 131 is the amino acid sequence of a human IgA2 hinge region (VPPPPP).

SEQ ID NO: 132 is the amino acid sequence of a human IgA2 CH2 region (CCHPRLSLHRPALEDLLLGSEANLTCTLTGLRDASGATFTWTPSSGKSAVQGPPERDLCGCYSV SSVLPGCAQPWNHGETFTCTAAHPELKTPLTANITKS).

SEQ ID NO: 133 is the amino acid sequence of a human IgA2 CH3 region (GNTFRPEVHLLPPPSEELALNELVTLTCLARGFSPKDVLVRWLQGSQELPREKYLTWASRQEPS QGTTTFAVTSILRVAAEDWKKGDTFSCMVGHEALPLAFTQKTIDRLAGKPTHVNVSVVMAEVD GTCY).

SEQ ID NO: 134 is the amino acid sequence of a human IgD hinge region (ESPKAQASSVPTAQPQAEGSLAKATTAPATTRNTGRGGEEKKKEKEKEEQEERETKTP).

SEQ ID NO: 135 is the amino acid sequence of a human IgD CH2 region (ECPSHTQPLGVYLLTPAVQDLWLRDKATFTCFVVGSDLKDAHLTWEVAGKVPTGGVEEGLLER HSNGSQSQHSRLTLPRSLWNAGTSVTCTLNHPSLPPQRLMALREP).

SEQ ID NO: 136 is the amino acid sequence of a human IgD CH3 region (AAQAPVKLSLNLLASSDPPEAASWLLCEVSGFSPPNILLMWLEDQREVNTSGFAPARPPPQPRST TFWAWSVLRVPAPPSPQPATYTCVVSHEDSRTLLNASRSLEVSYVTDHGPMK).

SEQ ID NO: 137 is the amino acid sequence of a human IgE CH2 region (VCSRDFTPPTVKILQSSCDGGGHFPPTIQLLCLVSGYTPGTINITWLEDGQVMDVDLSTASTTQE GELASTQSELTLSQKHWLSDRTYTCQVTYQGHTFEDSTKKCA).

-continued

SEQ ID NO: 138 is the amino acid sequence of a human IgE CH3 region (DSNPRGVSAYLSRPSPFDLFIRKSPTITCLVVDLAPSKGTVNLTWSRASGKPVNHSTRKEEKQRN GTLTVTSTLPVGTRDWIEGETYQCRVTHPHLPRALMRSTTKTS).

SEQ ID NO: 139 is the amino acid sequence of a human IgE CH4 region (GPRAAPEVYAFATPEWPGSRDKRTLACLIQNFMPEDISVQWLHNEVQLPDARHSTTQPRKTKGS GFFVFSRLEVIRAEWEQKDEFICRAVHEAASPSQTVQRAVSVNPGK).

SEQ ID NO: 140 is the amino acid sequence of a human IgG1 hinge region (EPKSCDKTHTCPPCP).

SEQ ID NO: 341 is the amino acid sequence of a modified human IgG1 hinge region derived sequence (SDKTHTCPPCP).

SEQ ID NO: 141 is the amino acid sequence of a human IgG1 CH2 region (APELLGGPSVFLFPPKPKDTLMISRTPEVTCVVVDVSHEDPEVKFNWYVDGVEVHNAKTKPREE QYNSTYRVVSVLTVLHQDWLNGKEYKCKVSNKALPAPIEKTISKAK).

SEQ ID NO: 142 is the amino acid sequence of a human IgG1 CH3 region (GQPREPQVYTLPPSRDELTKNQVSLTCLVKGFYPSDIAVEWESNGQPENNYKTTPPVLDSDGSFF LYSKLTVDKSRWQQGNVFSCSVMHEALHNHYTQKSLSLSPGK).

SEQ ID NO: 342 is the amino acid sequence of a human IgG1 heavy chain sequence (MSDKTHTCPPCPAPELLGGPSVFLFPPKPKDTLMISRTPEVTCVVVDVSHEDPEVKFNWYVDGV EVHNAKTKPREEQYNSTYRVVSVLTVLHQDWLNGKEYKCKVSNKALPAPIEKTISKAKGQPREP QVYTLPPSREEMTKNQVSLTCLVKGFYPSDIAVEWESNGQPENNYKTTPPVLDSDGSFFLYSKLT VDKSRWQQGNVFSCSVMHEALHNHYTQKSLSLSPGK). It will be appreciated that the Met residue in this human IgG1 heavy chain sequence can be deleted, for instance, upon N-terminal fusion to a HRS polypeptide (see SEQ ID NO: 340).

SEQ ID NO: 143 is the amino acid sequence of a human IgG2 hinge region (ERKCCVECPPCP).

SEQ ID NO: 144 is the amino acid sequence of a human IgG2 CH2 region (APPVAGPSVFLFPPKPKDTLMISRTPEVTCVVVDVSHEDPEVQFNWYVDGVEVHNAKTKPREE QFNSTFRVVSVLTVVHQDWLNGKEYKCKVSNKGLPAPIEKTISKTK).

SEQ ID NO: 145 is the amino acid sequence of a human IgG2 CH3 region (GQPREPQVYTLPPSREEMTKNQVSLTCLVKGFYPSDIAVEWESNGQPENNYKTTPPMLDSDGSF FLYSKLTVDKSRWQQGNVFSCSVMHEALHNHYTQKSLSLSPGK).

SEQ ID NO: 146 is the amino acid sequence of a human IgG3 hinge region (ELKTPLGDTTHTCPRCPEPKSCDTPPPCPRCPEPKSCDTPPPCPRCPEPKSCDTPPPCPRCP).

SEQ ID NO: 147 is the amino acid sequence of a human IgG3 CH2 region (APELLGGPSVFLFPPKPKDTLMISRTPEVTCVVVDVSHEDPEVQFKWYVDGVEVHNAKTKPREE QYNSTFRVVSVLTVLHQDWLNGKEYKCKVSNKALPAPIEKTISKTK).

SEQ ID NO: 148 is the amino acid sequence of a human IgG3 CH3 region (GQPREPQVYTLPPSREEMTKNQVSLTCLVKGFYPSDIAVEWESSGQPENNYNTTPPMLDSDGSF FLYSKLTVDKSRWQQGNIFSCSVMHEALHNRFTQKSLSLSPGK).

SEQ ID NO: 149 is the amino acid sequence of a human IgG4 hinge region (ESKYGPPCPSCP).

SEQ ID NO: 150 is the amino acid sequence of a human IgG4 CH2 region (APEFLGGPSVFLFPPKPKDTLMISRTPEVTCVVVDVSQEDPEVQFNWYVDGVEVHNAKTKPREE QFNSTYRVVSVLTVLHQDWLNGKEYKCKVSNKGLPSSIEKTISKAK).

SEQ ID NO: 151 is the amino acid sequence of a human IgG4 CH3 region (GQPREPQVYTLPPSQEEMTKNQVSLTCLVKGFYPSDIAVEWESNGQPENNYKTTPPVLDSDGSF FLYSRLTVDKSRWQEGNVFSCSVMHEALHNHYTQKSLSLSLGK).

SEQ ID NO: 152 is the amino acid sequence of a human IgM CH2 region (VIAELPPKVSVFVPPRDGFFGNPRKSKLICQATGFSPRQIQVSWLREGKQVGSGVTTDQVQAEA KESGPTTYKVTSTLTIKESDWLGQSMFTCRVDHRGLTFQQNASSMCVP).

SEQ ID NO: 153 is the amino acid sequence of a human IgM CH3 region (DQDTAIRVFAIPPSFASIFLTKSTKLTCLVTDLTTYDSVTISWTRQNGEAVKTHTNISESHPNATFS AVGEASICEDDWNSGERFTCTVTHTDLPSPLKQTISRPK).

SEQ ID NO: 154 is the amino acid sequence of a human IgM CH4 region (GVALHRPDVYLLPPAREQLNLRESATITCLVTGFSPADVFVQWMQRGQPLSPEKYVTSAPMPEP QAPGRYFAHSILTVSEEEWNTGETYTCVVAHEALPNRVTERTVDKSTGKPTLYNVSLVMSDTAG TCY).

A HRS-Fc conjugate of the present invention can thus comprise, consist of, or consist essentially of one or more of the human Fc region amino acid sequences of SEQ ID NOS:128-163 or 339-342, including variants, fragments, homologs, orthologs, paralogs, and combinations thereof. Certain illustrative embodiments comprise an Fc region that ranges in size from about 20-50, 20-100, 20-150, 20-200, 20-250, 20-300, 20-400, 50-100, 50-150, 50-200, 50-250, 50-300, 50-400, 100-150, 100-200, 100-250, 100-300, 100-350, 100-400, 200-250, 200-300, 200-350, or 200-400 amino acids in length, and optionally comprises, consists of, or consists essentially of any one or more of SEQ ID NOS:128-154 or 341-342. Certain embodiments comprise an Fc region of up to about 50, 60, 70, 80, 90, 100, 110, 120, 130, 140, 150, 160, 170, 180, 190, 200, 210, 220, 230, 240, 250, 300, 350, 400 or more amino acids, which optionally comprises, consists of, or consists essentially of any one or more of SEQ ID NOS: 128-154 or 339-342.

Certain Fc regions comprise, consist of, or consist essentially of human IgA1 sequences set forth in SEQ ID NOS: 128-130 or 156, in any order reading from N-terminus to C-terminus, including combinations thereof (e.g., SEQ ID NOS:128 and 129 and 130, SEQ ID NOS:128 and 129; SEQ ID NOS:128 and 130; SEQ ID NOS:129 and 130), and variants and fragments thereof. Certain Fc regions comprise, consist of, or consist essentially of human the IgA1 sequence set forth in SEQ ID NOS:128. Certain Fc regions comprise, consist of, or consist essentially of the human IgA1 sequence set forth in SEQ ID NOS:129. Certain Fc regions comprise, consist of, or consist essentially of the human IgA1 sequence set forth in SEQ ID NOS:130.

Some Fc regions comprise, consist of, or consist essentially of human IgA2 sequences set forth in SEQ ID NOS: 131-133 or 157, in any order reading from N-terminus to C-terminus, including combinations thereof (e.g., SEQ ID NOS:131 and 132 and 133, SEQ ID NOS:131 and 132; SEQ ID NOS:131 and 133; SEQ ID NOS:132 and 133), and variants and fragments thereof. Certain Fc regions comprise, consist of, or consist essentially of human the IgA2 sequence set forth in SEQ ID NOS:131. Certain Fc regions comprise, consist of, or consist essentially of the human IgA2 sequence set forth in SEQ ID NOS:132. Certain Fc regions comprise, consist of, or consist essentially of the human IgA2 sequence set forth in SEQ ID NOS:133.

Certain Fc regions comprise, consist of, or consist essentially of human IgD sequences set forth in SEQ ID NOS: 134-136, in any order reading from N-terminus to C-terminus, including combinations thereof (e.g., SEQ ID NOS:134 and 135 and 136, SEQ ID NOS:134 and 135; SEQ ID NOS:134 and 136; SEQ ID NOS:135 and 136), and variants and fragments of these sequences and combinations. Certain Fc regions comprise, consist of, or consist essentially of human the IgD sequence set forth in SEQ ID NOS:134. Certain Fc regions comprise, consist of, or consist essentially of the human IgD sequence set forth in SEQ ID NOS:135. Certain Fc regions comprise, consist of, or consist essentially of the human IgD sequence set forth in SEQ ID NOS:136.

Certain Fc regions comprise, consist of, or consist essentially of human IgE sequences set forth in SEQ ID NOS: 137-139 or 163, in any order reading from N-terminus to C-terminus, including combinations thereof (e.g., SEQ ID NOS:137 and 138 and 139, SEQ ID NOS:137 and 138; SEQ ID NOS:137 and 139; SEQ ID NOS:138 and 139), and variants and fragments of these sequences and combinations. Certain Fc regions comprise, consist of, or consist essentially of human the IgE sequence set forth in SEQ ID NOS:137. Certain Fc regions comprise, consist of, or consist essentially of the human IgE sequence set forth in SEQ ID NOS:138. Certain Fc regions comprise, consist of, or consist essentially of the human IgE sequence set forth in SEQ ID NOS:139.

Certain Fc regions comprise, consist of, or consist essentially of human IgG1 sequences set forth in SEQ ID NOS: 140-142 or 159 or 339-342, in any order reading from N-terminus to C-terminus, including combinations thereof (e.g., SEQ ID NOS:140 and 141 and 142, SEQ ID NOS:140 and 141; SEQ ID NOS:140 and 142; SEQ ID NOS:141 and 142), and variants and fragments of these sequences and combinations. Certain Fc regions comprise, consist of, or consist essentially of human the IgG1 sequence set forth in SEQ ID NOS:140. Certain Fc regions comprise, consist of, or consist essentially of the human IgG1 sequence set forth in SEQ ID NOS:141. Certain Fc regions comprise, consist of, or consist essentially of the human IgG1 sequence set forth in SEQ ID NOS:142. Certain Fc regions comprise, consist of, or consist essentially of the human IgG1 sequence set forth in SEQ ID NOS:339. Certain Fc regions comprise, consist of, or consist essentially of the human IgG1 sequence set forth in SEQ ID NOS:340. Certain Fc regions comprise, consist of, or consist essentially of the human IgG1 sequence set forth in SEQ ID NOS:341. Certain Fc regions comprise, consist of, or consist essentially of the human IgG1 sequence set forth in SEQ ID NOS:342.

Certain Fc regions comprise, consist of, or consist essentially of human IgG2 sequences set forth in SEQ ID NOS: 143-145 or 160, in any order reading from N-terminus to C-terminus, including combinations thereof (e.g., SEQ ID NOS:143 and 144 and 145, SEQ ID NOS:143 and 144; SEQ ID NOS:143 and 145; SEQ ID NOS:144 and 145), and variants and fragments of these sequences and combinations. Certain Fc regions comprise, consist of, or consist essentially of human the IgG2 sequence set forth in SEQ ID NOS:143. Certain Fc regions comprise, consist of, or consist essentially of the human IgG2 sequence set forth in SEQ ID NOS:144. Certain Fc regions comprise, consist of, or consist essentially of the human IgG2 sequence set forth in SEQ ID NOS:145.

Certain Fc regions comprise, consist of, or consist essentially of human IgG3 sequences set forth in SEQ ID NOS: 146-148 or 161, in any order reading from N-terminus to C-terminus, including combinations thereof (e.g., SEQ ID NOS:146 and 147 and 148, SEQ ID NOS:146 and 147; SEQ ID NOS:146 and 148; SEQ ID NOS:147 and 148), and variants and fragments of these sequences and combinations. Certain Fc regions comprise, consist of, or consist essentially of human the IgG3 sequence set forth in SEQ ID NOS:146. Certain Fc regions comprise, consist of, or consist essentially of the human IgG3 sequence set forth in SEQ ID NOS:147. Certain Fc regions comprise, consist of, or consist essentially of the human IgG3 sequence set forth in SEQ ID NOS:148.

Certain Fc regions comprise, consist of, or consist essentially of human IgG4 sequences set forth in SEQ ID NOS: 149-151 or 162, in any order reading from N-terminus to C-terminus, including combinations thereof (e.g., SEQ ID NOS:149 and 150 and 151, SEQ ID NOS:149 and 150; SEQ ID NOS:149 and 151; SEQ ID NOS:150 and 151), and variants and fragments of these sequences and combinations. Certain Fc regions comprise, consist of, or consist essentially of human the IgG4 sequence set forth in SEQ ID NOS:149. Certain Fc regions comprise, consist of, or consist essentially of the human IgG4 sequence set forth in SEQ ID NOS:150. Certain Fc regions comprise, consist of, or consist essentially of the human IgG4 sequence set forth in SEQ ID NOS:151.

Certain Fc regions comprise, consist of, or consist essentially of human IgM sequences set forth in SEQ ID NOS: 152-154 or 158, in any order reading from N-terminus to C-terminus, including combinations thereof (e.g., SEQ ID NOS:152 and 153 and 154, SEQ ID NOS:152 and 153; SEQ ID NOS:152 and 154; SEQ ID NOS:153 and 154), and variants and fragments of these sequences and combinations. Certain Fc regions comprise, consist of, or consist essentially of human the IgM sequence set forth in SEQ ID NOS:152. Certain Fc regions comprise, consist of, or consist essentially of the human IgM sequence set forth in SEQ ID NOS:153. Certain Fc regions comprise, consist of, or consist essentially of the human IgM sequence set forth in SEQ ID NOS:154.

As noted above, certain embodiments employ variants, fragments, hybrids, and/or otherwise modified forms an Fc region described herein and known in the art (e.g., the human Ig sequences of SEQ ID NOS:128-163).

Included are variants having one or more amino acid substitutions, insertions, deletions, and/or truncations relative to a reference sequence, such as any one or more of the reference sequences set forth in SEQ ID NOS:128-163. In certain embodiments, a variant Fc region includes an amino acid sequence having at least about 50%, 55%, 60%, 65%, 70%, 75%, 80%, 85%, 90%, 91%, 92%, 93%, 94%, 95%, 96%, 97%, 98% or more sequence identity or similarity or homology to any one or more of SEQ ID NOS:128-163. Also included are Fc regions differing from one or more of SEQ ID NOS:128-163 by the addition, deletion, insertion, or substitution of 1, 2, 3, 4, 5, 6, 7, 8, 9, 10, 11, 12, 13, 14, 15, 16, 17, 18, 19, 20, 30, 40, 50, 60, 70, 80, 90, 100, 110, 120, 130, 140, 150 or more amino acids. In certain embodiments, the amino acid additions or deletions occur at the C-terminal end and/or the N-terminal end of the Fc reference sequence.

In particular embodiments, a variant Fc region comprises an amino acid sequence that can be optimally aligned with any one or more of SEQ ID NOS:128-163 to generate a BLAST bit scores or sequence similarity scores of at least about 50, 60, 70, 80, 90, 100, 100, 110, 120, 130, 140, 150, 160, 170, 180, 190, 200, 210, 220, 230, 240, 250, 260, 270, 280, 290, 300, 310, 320, 330, 340, 350, 360, 370, 380, 390, 400, 410, 420, 430, 440, 450, 460, 470, 480, 490, 500, 510, 520, 530, 540, 550, 560, 570, 580, 590, 600, 610, 620, 630, 640, 650, 660, 670, 680, 690, 700, 710, 720, 730, 740, 750, 760, 770, 780, 790, 800, 810, 820, 830, 840, 850, 860, 870, 880, 890, 900, 910, 920, 930, 940, 950, 960, 970, 980, 990, 1000, or more, including all integers and ranges in between, wherein the BLAST alignment used the BLOSUM62 matrix, a gap existence penalty of 11, and a gap extension penalty of 1.

Also included are hybrid Fc regions, for example, Fc regions that comprise a combination of Fc domains (e.g., hinge, $CH_2$, $CH_3$, $CH_4$) from immunoglobulins of different species, different Ig classes, and/or different Ig subclasses. General examples include hybrid Fc regions that comprise, consist of, or consist essentially of the following combination of $CH_2$/$CH_3$ domains: IgA1/IgA1, IgA1/IgA2, IgA1/IgD, IgA1/IgE, IgA1/IgG1, IgA1/IgG2, IgA1/IgG3, IgA1/IgG4, IgA1/IgM, IgA2/IgA1, IgA2/IgA2, IgA2/IgD, IgA2/IgE, IgA2/IgG1, IgA2/IgG2, IgA2/IgG3, IgA2/IgG4, IgA2/IgM, IgD/IgA1, IgD/IgA2, IgD/IgD, IgD/IgE, IgD/IgG1, IgD/IgG2, IgD/IgG3, IgD/IgG4, IgD/IgM, IgE/IgA1, IgE/IgA2, IgE/IgD, IgE/IgE, IgE/IgG2, IgE/IgG3, IgE/IgG4, IgE/IgM, IgG1/IgA1, IgG1/IgA2, IgG1/IgD, IgG1/IgE, IgG1/IgG2, IgG1/IgG3, IgG1/IgG4, IgG1/IgM, IgG2/IgA1, IgG2/IgA2, IgG2/IgD, IgG2/IgE, IgG2/IgG1, IgG2/IgG2, IgG2/IgG3, IgG2/IgG4, IgG2/IgM, IgG3/IgA1, IgG3/IgA2, IgG3/IgD, IgG3/IgE, IgG3/IgG1, IgG3/IgG2, IgG3/IgG3, IgG3/IgG4, IgG3/IgM, IgG4/IgA1, IgG4/IgA2, IgG4/IgD, IgG4/IgE, IgG4/IgG1, IgG4/IgG2, IgG4/IgG3, IgG4/IgG4, IgG4/IgM, IgM/IgA1, IgM/IgA2, IgM/IgD, IgM/IgE, IgM/IgG1, IgM/IgG2, IgM/IgG3, IgM/IgG4, IgM/IgM (or fragments or variants thereof), and optionally include a hinge from one or more of IgA1, IgA2, IgD, IgG1, IgG2, IgG3, or IgG4, and/or a $CH_4$ domain from IgE and/or IgM. In specific embodiments, the hinge, $CH_2$, $CH_3$, and $CH_4$ domains are from human Ig.

Additional examples include hybrid Fc regions that comprise, consist of, or consist essentially of the following combination of $CH_2$/$CH_4$ domains: IgA1/IgE, IgA2/IgE, IgD/IgE, IgE/IgE, IgG1/IgE, IgG2/IgE, IgG3/IgE, IgG4/IgE, IgM/IgE, IgA1/IgM, IgA2/IgM, IgD/IgM, IgE/IgM, IgG2/IgM, IgG3/IgM, IgG4/IgM, IgM/IgM (or fragments or variants thereof), and optionally include a hinge from one or more of IgA1, IgA2, IgD, IgG1, IgG2, IgG3, IgG4, and/or a $CH_3$ domain from one or more of IgA1, IgA2, IgD, IgE, IgG1, IgG2, IgG3, IgG4, or IgM. In specific embodiments, the hinge, $CH_2$, $CH_3$, and $CH_4$ domains are from human Ig.

Certain examples include hybrid Fc regions that comprise, consist of, or consist essentially of the following combination of $CH_3$/$CH_4$ domains: IgA1/IgE, IgA2/IgE, IgD/IgE, IgE/IgE, IgG1/IgE, IgG2/IgE, IgG3/IgE, IgG4/IgE, IgM/IgE, IgA1/IgM, IgA2/IgM, IgD/IgM, IgE/IgM, IgG1/IgM, IgG2/IgM, IgG3/IgM, IgG4/IgM, IgM/IgM (or fragments or variants thereof), and optionally include a hinge from one or more of IgA1, IgA2, IgD, IgG1, IgG2, IgG3, IgG4, and/or a $CH_2$ domain from one or more of IgA1, IgA2, IgD, IgE, IgG1, IgG2, IgG3, IgG4, or IgM. In specific embodiments, the hinge, $CH_2$, $CH_3$, and $CH_4$ domains are from human Ig.

Particular examples include hybrid Fc regions that comprise, consist of, or consist essentially of the following combination of hinge/$CH_2$ domains: IgA1/IgA1, IgA1/IgA2, IgA1/IgD, IgA1/IgE, IgA1/IgG1, IgA1/IgG2, IgA1/IgG3, IgA1/IgG4, IgA1/IgM, IgA2/IgA1, IgA2/IgA2, IgA2/IgD, IgA2/IgE, IgA2/IgG1, IgA2/IgG2, IgA2/IgG3, IgA2/IgG4, IgA2/IgM, IgD/IgA1, IgD/IgA2, IgD/IgD, IgD/IgE, IgD/IgG1, IgD/IgG2, IgD/IgG3, IgD/IgG4, IgD/IgM, IgG1/IgA1, IgG1/IgA2, IgG1/IgD, IgG1/IgE, IgG1/IgG1, IgG1/IgG2, IgG1/IgG3, IgG1/IgG4, IgG1/IgM, IgG2/IgA1, IgG2/IgA2, IgG2/IgD, IgG2/IgE, IgG2/IgG1, IgG2/IgG2, IgG2/IgG3, IgG2/IgG4, IgG2/IgM, IgG3/IgA1, IgG3/IgA2, IgG3/IgD, IgG3/IgE, IgG3/IgG1, IgG3/IgG2, IgG3/IgG3, IgG3/IgG4, IgG3/IgM, IgG4/IgA1, IgG4/IgA2, IgG4/IgD, IgG4/IgE, IgG4/IgG1, IgG4/IgG2, IgG4/IgG3, IgG4/IgG4, IgG4/IgM (or fragments or variants thereof), and optionally include a $CH_3$ domain from one or more of IgA1, IgA2, IgD, IgE, IgG1, IgG2, IgG3, IgG4, or IgM, and/or a $CH_4$ domain from IgE and/or IgM. In specific embodiments, the hinge, $CH_2$, $CH_3$, and $CH_4$ domains are from human Ig.

Certain examples include hybrid Fc regions that comprise, consist of, or consist essentially of the following combination of hinge/$CH_3$ domains: IgA1/IgA1, IgA1/IgA2, IgA1/IgD, IgA1/IgE, IgA1/IgG1, IgA1/IgG2, IgA1/IgG3, IgA1/IgG4, IgA1/IgM, IgA2/IgA1, IgA2/IgA2, IgA2/IgD, IgA2/IgE, IgA2/IgG1, IgA2/IgG2, IgA2/IgG3, IgA2/IgG4, IgA2/IgM, IgD/IgA1, IgD/IgA2, IgD/IgD, IgD/IgE, IgD/IgG1, IgD/IgG2, IgD/IgG3, IgD/IgG4, IgD/IgM, IgG1/IgA1, IgG1/IgA2, IgG1/IgD, IgG1/IgE, IgG1/IgG1, IgG1/IgG2, IgG1/IgG3, IgG1/IgG4, IgG1/IgM, IgG2/IgA1, IgG2/IgA2, IgG2/IgD, IgG2/IgE, IgG2/IgG1, IgG2/IgG2, IgG2/IgG3, IgG2/IgG4, IgG2/IgM, IgG3/IgA1, IgG3/IgA2, IgG3/IgD, IgG3/IgE, IgG3/IgG1, IgG3/IgG2, IgG3/IgG3, IgG3/IgG4, IgG3/IgM, IgG4/IgA1, IgG4/IgA2, IgG4/IgD, IgG4/IgE, IgG4/IgG1, IgG4/IgG2, IgG4/IgG3, IgG4/IgG4, IgG4/IgM (or fragments or variants thereof), and optionally include a $CH_2$ domain from one or more of IgA1, IgA2, IgD, IgE, IgG1, IgG2, IgG3, IgG4, or IgM, and/or a $CH_4$ domain from IgE and/or IgM. In specific embodiments, the hinge, $CH_2$, $CH_3$, and $CH_4$ domains are from human Ig.

Some examples include hybrid Fc regions that comprise, consist of, or consist essentially of the following combination of hinge/$CH_4$ domains: IgA1/IgE, IgA1/IgM, IgA2/IgE, IgA2/IgM, IgD/IgE, IgD/IgM, IgG1/IgE, IgG1/IgM, IgG2/IgE, IgG2/IgM, IgG3/IgE, IgG3/IgM, IgG4/IgE, IgG4/IgM (or fragments or variants thereof), and optionally include a $CH_2$ domain from one or more of IgA1, IgA2, IgD, IgE, IgG1, IgG2, IgG3, IgG4, or IgM, and/or a $CH_3$ domain from one or more of IgA1, IgA2, IgD, IgE, IgG1, IgG2, IgG3, IgG4, or IgM.

Specific examples of hybrid Fc regions can be found, for example, in WO 2008/147143, which are derived from combinations of IgG subclasses or combinations of human IgD and IgG.

Also included are derivatized or otherwise modified Fc regions. In certain aspects, the Fc region may be modified by phosphorylation, sulfation, acrylation, glycosylation, methylation, farnesylation, acetylation, amidation, and the like, for instance, relative to a wild-type or naturally-occurring Fc region. In certain embodiments, the Fc region may comprise wild-type or native glycosylation patterns, or alternatively, it may comprise increased glycosylation relative to a native form, decreased glycosylation relative to a native form, or it may be entirely deglycosylated. As one example of a modified Fc glycoform, decreased glycosylation of an Fc region reduces binding to the C1q region of the first complement component C1, a decrease in ADCC-related activity, and/or a decrease in CDC-related activity. Certain embodiments thus employ a deglycosylated or aglycosylated Fc region. See, e.g., WO 2005/047337 for the production of exemplary aglycosylated Fc regions. Another example of an Fc region glycoform can be generated by substituting the Q295 position with a cysteine residue (see, e.g., U.S. Application No. 2010/0080794), according to the Kabat et al. numbering system. Certain embodiments may include Fc regions where about 80-100% of the glycoprotein in Fc region comprises a mature core carbohydrate structure that lacks fructose (see, e.g., U.S. Application No. 2010/0255013). Some embodiments may include Fc regions that are optimized by substitution or deletion to reduce the level of fucosylation, for instance, to increase affinity for FcγRI, FcγRIa, or FcγRIIIa, and/or to improve phagocytosis by FcγRIIa-expressing cells (see U.S. Application Nos. 2010/0249382 and 2007/0148170).

As another example of a modified Fc glycoform, an Fc region may comprise oligomannose-type N-glycans, and optionally have one or more of the following: increased ADCC activity, increased binding affinity for FcγRIIIA (and certain other FcRs), similar or increased binding specificity for the target of the HRS polypeptide, similar or higher binding affinity for the target of the HRS polypeptide, and/or similar or lower binding affinity for mannose receptor, relative to a corresponding Fc region or HRS-Fc conjugate that contains complex-type N-glycans (see, e.g., U.S. Application No. 2007/0092521 and U.S. Pat. No. 7,700,321). As another example, enhanced affinity of Fc regions for FcγRs has been achieved using engineered glycoforms generated by expression of antibodies in engineered or variant cell lines (see, e.g., Umana et al., *Nat Biotechnol.* 17:176-180, 1999; Davies et al., *Biotechnol Bioeng.* 74:288-294, 2001; Shields et al., *J Biol Chem.* 277:26733-26740, 2002; Shinkawa et al., 2003, *J Biol Chem.* 278:3466-3473, 2003; and U.S. Application No. 2007/0111281). Certain Fc region glycoforms comprise an increased proportion of N-glycoside bond type complex sugar chains, which do not have the 1-position of fucose bound to the 6-position of N-acetylglucosamine at the reducing end of the sugar chain (see, e.g., U.S. Application No. 2010/0092997). Particular embodiments may include IgG Fc region that is glycosylated with at least one galactose moiety connected to a respective terminal sialic acid moiety by an α-2,6 linkage, optionally where the Fc region has a higher anti-inflammatory activity relative to a corresponding, wild-type Fc region (see U.S. Application No. 2008/0206246). Certain of these and related altered glycosylation approaches have generated substantial enhancements of the capacity of Fc regions to selectively bind FcRs such as FcγRIII, to mediate ADCC, and to alter other properties of Fc regions, as described herein.

Certain variant, fragment, hybrid, or otherwise modified Fc regions may have altered binding to one or more FcRs, relative to a corresponding, wild-type Fc sequence (e.g., same species, same Ig class, same Ig subclass). For instance, such Fc regions may have increased binding to one or more of Fcγ receptors, Fcα receptors, Fcεreceptors, and/or the neonatal Fc receptor, relative to a corresponding, wild-type Fc sequence. In other embodiments, variant, fragment, hybrid, or modified Fc regions may have decreased binding to one or more of Fcγ receptors, Fcα receptors, Fcεreceptors, and/or the neonatal Fc receptor, relative to a corresponding, wild-type Fc sequence. Specific FcRs are described elsewhere herein.

Specific examples of Fc variants having altered (e.g., increased, decreased) FcR binding can be found, for example, in U.S. Pat. Nos. 5,624,821 and 7,425,619; U.S. Application Nos. 2009/0017023, 2009/0010921, and 2010/0203046; and WO 2000/42072 and WO 2004/016750. Certain examples include human Fc regions having a one or more substitutions at position 298, 333, and/or 334, for example, S298A, E333A, and/or K334A (based on the numbering of the EU index of Kabat et al.), which have been shown to increase binding to the activating receptor FcγRIIIa and reduce binding to the inhibitory receptor FcγRIIb. These mutations can be combined to obtain double and triple mutation variants that have further improvements in binding to FcRs. Certain embodiments include a S298A/E333A/K334A triple mutant, which has increased binding to FcγRIIIa, decreased binding to FcγRIIb, and increased ADCC (see, e.g., Shields et al., *J Biol Chem.* 276:6591-6604, 2001; and Presta et al., *Biochem Soc Trans.* 30:487-490, 2002). See also engineered Fc glycoforms that have increased binding to FcRs, as disclosed in Umana et al., supra; and U.S. Pat. No. 7,662,925. Some embodiments include Fc regions that comprise one or more substitutions selected from 434S, 252Y/428L, 252Y/434S, and 428L/4345 (see U.S. Application Nos. 2009/0163699 and 20060173170), based on the EU index of Kabat et al.

Certain variant, fragment, hybrid, or modified Fc regions may have altered effector functions, relative to a corresponding, wild-type Fc sequence. For example, such Fc regions may have increased complement fixation or activation, increased C1q binding affinity, increased CDC-related activity, increased ADCC-related activity, and/or increased ADCP-related activity, relative to a corresponding, wild-type Fc sequence. In other embodiments, such Fc regions may have decreased complement fixation or activation, decreased C1q binding affinity, decreased CDC-related activity, decreased ADCC-related activity, and/or decreased ADCP-related activity, relative to a corresponding, wild-type Fc sequence. As merely one illustrative example, an Fc region may comprise a deletion or substitution in a complement-binding site, such as a C1q-binding site, and/or a deletion or substitution in an ADCC site. Examples of such deletions/substitutions are described, for example, in U.S. Pat. No. 7,030,226. Many Fc effector functions, such as ADCC, can be assayed according to routine techniques in the art. (see, e.g., Zuckerman et al., *CRC Crit Rev Microbiol.* 7:1-26, 1978). Useful effector cells for such assays includes, but are not limited to, natural killer (NK) cells, macrophages, and other peripheral blood mononuclear cells (PBMC). Alternatively, or additionally, certain Fc effector functions may be assessed in vivo, for example, by employing an animal model described in Clynes et al. PNAS. 95:652-656, 1998.

Certain variant hybrid, or modified Fc regions may have altered stability or half-life relative to a corresponding, wild-type Fc sequence. In certain embodiments, such Fc regions may have increased half-life relative to a corresponding, wild-type Fc sequence. In other embodiments, variant hybrid, or modified Fc regions may have decreased half-life relative to a corresponding, wild-type Fc sequence. Half-life can be measured in vitro (e.g., under physiological conditions) or in vivo, according to routine techniques in the art, such as radiolabeling, ELISA, or other methods. In vivo measurements of stability or half-life can be measured in one or more bodily fluids, including blood, serum, plasma, urine, or cerebrospinal fluid, or a given tissue, such as the liver, kidneys, muscle, central nervous system tissues, bone, etc. As one example, modifications to an Fc region that alter its ability to bind the FcRn can alter its half-life in vivo. Assays for measuring the in vivo pharmacokinetic properties (e.g., in vivo mean elimination half-life) and non-limiting examples of Fc modifications that alter its binding to the FcRn are described, for example, in U.S. Pat. Nos. 7,217,797 and 7,732,570; and U.S. Application Nos. US 2010/0143254 and 2010/0143254.

Additional non-limiting examples of modifications to alter stability or half-life include substitutions/deletions at one or more of amino acid residues selected from 251-256, 285-290, and 308-314 in the $CH_2$ domain, and 385-389 and 428-436 in the $CH_3$ domain, according to the numbering system of Kabat et al. See U.S. Application No. 2003/0190311. Specific examples include substitution with leucine at position 251, substitution with tyrosine, tryptophan or phenylalanine at position 252, substitution with threonine or serine at position 254, substitution with arginine at position 255, substitution with glutamine, arginine, serine, threonine, or glutamate at position 256, substitution with threonine at position 308, substitution with proline at position 309, substitution with serine at position 311, substitution with aspartate at position 312, substitution with leucine at position 314, substitution with arginine, aspartate or serine at position 385, substitution with threonine or proline at position 386, substitution with arginine or proline at position 387, substitution with proline, asparagine or serine at position 389, substitution with methionine or threonine at position 428, substitution with tyrosine or phenylalanine at position 434, substitution with histidine, arginine, lysine or serine at position 433, and/or substitution with histidine, tyrosine, arginine or threonine at position 436, including any combination thereof. Such modifications optionally increase affinity of the Fc region for the FcRn and thereby increase half-life, relative to a corresponding, wild-type Fc region.

Certain variant hybrid, or modified Fc regions may have altered solubility relative to a corresponding, wild-type Fc sequence. In certain embodiments, such Fc regions may have increased solubility relative to a corresponding, wild-type Fc sequence. In other embodiments, variant hybrid, or modified Fc regions may have decreased solubility relative to a corresponding, wild-type Fc sequence. Solubility can be measured, for example, in vitro (e.g., under physiological conditions) according to routine techniques in the art. Exemplary solubility measurements are described elsewhere herein.

Additional examples of variants include IgG Fc regions having conservative or non-conservative substitutions (as described elsewhere herein) at one or more of positions 250, 314, or 428 of the heavy chain, or in any combination thereof, such as at positions 250 and 428, or at positions 250 and 314, or at positions 314 and 428, or at positions 250, 314, and 428 (see, e.g., U.S. Application No. 2011/0183412). In specific embodiments, the residue at position 250 is substituted with glutamic acid or glutamine, and/or the residue at position 428 is substituted with leucine or phenylalanine. As another illustrative example of an IgG Fc variant, any one or more of the amino acid residues at positions 214 to 238, 297 to 299, 318 to 322, and/or 327 to 331 may be used as a suitable target for modification (e.g., conservative or non-conservative substitution, deletion). In particular embodiments, the IgG Fc variant $CH_2$ domain contains amino acid substitutions at positions 228, 234, 235, and/or 331 (e.g., human IgG4 with Ser228Pro and Leu235Ala mutations) to attenuate the effector functions of the Fc region (see U.S. Pat. No. 7,030,226). Here, the numbering of the residues in the heavy chain is that of the EU index (see Kabat et al., "Sequences of Proteins of Immunological Interest," $5^{th}$ Ed., National Institutes of Health, Bethesda, Md. (1991)). Certain of these and related embodiments have altered (e.g., increased, decreased) FcRn binding and/or serum half-life, optionally without reduced effector functions such as ADCC or CDC-related activities.

Additional examples include variant Fc regions that comprise one or more amino acid substitutions at positions 279, 341, 343 or 373 of a wild-type Fc region, or any combination thereof (see, e.g., U.S. Application No. 2007/0224188). The wild-type amino acid residues at these positions for human IgG are valine (279), glycine (341), proline (343) and tyrosine (373). The substation(s) can be conservative or non-conservative, or can include non-naturally occurring amino acids or mimetics, as described herein. Alone or in combination with these substitutions, certain embodiments may also employ a variant Fc region that comprises at least 1, 2, 3, 4, 5, 6, 7, 8, 9, 10 or more amino acid substitutions selected from the following: 235G, 235R, 236F, 236R, 236Y, 237K, 237N, 237R, 238E, 238G, 238H, 238I, 238L, 238V, 238W, 238Y, 244L, 245R, 247A, 247D, 247E, 247F, 247M, 247N, 247Q, 247R, 247S, 247T, 247W, 247Y, 248F, 248P, 248Q, 248W, 249L, 249M, 249N, 249P, 249Y, 251H, 251I, 251W, 254D, 254E, 254F, 254G, 254H, 254I, 254K, 254L, 254M, 254N, 254P, 254Q, 254R, 254V, 254W, 254Y, 255K, 255N, 256H, 256I, 256K, 256L, 256V, 256W, 256Y, 257A, 257I, 257M, 257N, 257S, 258D, 260S, 262L, 264S, 265K, 265S, 267H, 267I, 267K, 268K, 269N, 269Q, 271T, 272H, 272K, 272L, 272R, 279A, 279D, 279F, 279G, 279H, 279I, 279K, 279L, 279M, 279N, 279Q, 279R, 279S, 279T, 279W, 279Y, 280T, 283F, 283G, 283H, 283I, 283K, 283L, 283M, 283P, 283R, 283T, 283W, 283Y, 285N, 286F, 288N, 288P, 292E, 292F, 292G, 292I, 292L, 293S, 293V, 301W, 304E, 307E, 307M, 312P, 315F, 315K, 315L, 315P, 315R, 316F, 316K, 317P, 317T, 318N, 318P, 318T, 332F, 332G, 332L, 332M, 332S, 332V, 332W, 339D, 339E, 339F, 339G, 339H, 339I, 339K, 339L, 339M, 339N, 339Q, 339R, 339S, 339W, 339Y, 341D, 341E, 341F, 341H, 341I, 341K, 341L, 341M, 341N, 341P, 341Q, 341R, 341S, 341T, 341V, 341W, 341Y, 343A, 343D, 343E, 343F, 343G, 343H, 343I, 343K, 343L, 343M, 343N, 343Q, 343R, 343S, 343T, 343V, 343W, 343Y, 373D, 373E, 373F, 373G, 373H, 373I, 373K, 373L, 373M, 373N, 373Q, 373R, 373S, 373T, 373V, 373W, 375R, 376E, 376F, 376G, 376H, 376I, 376L, 376M, 376N, 376P, 376Q, 376R, 376S, 376T, 376V, 376W, 376Y, 377G, 377K, 377P, 378N, 379N, 379Q, 379S, 379T, 380D, 380N, 380S, 380T, 382D, 382F, 382H, 382I, 382K, 382L, 382M, 382N, 382P, 382Q, 382R, 382S, 382T, 382V, 382W, 382Y, 385E, 385P, 386K, 423N, 424H, 424M, 424V, 426D, 426L, 427N, 429A, 429F, 429M, 430A, 430D, 430F, 430G, 430H, 430I, 430K, 430L, 430M, 430N, 430P, 430Q, 430R, 430S, 430T, 430V, 430W, 430Y, 431H, 431K, 431P, 432R, 432S, 438G, 438K, 438L, 438T, 438W, 439E, 439H, 439Q, 440D, 440E, 440F, 440G, 440H, 440I, 440K, 440L, 440M, 440Q, 440T, 440V or 442K. As above, the numbering of the residues in the heavy chain is that of the EU index (see Kabat et al., supra). Such variant Fc regions typically confer an altered effector function or altered serum half-life upon HRS polypeptide to which the variant Fc region is operably attached. Preferably the altered effector function is an increase in ADCC, a decrease in ADCC, an increase in CDC, a decrease in CDC, an increase in C1q binding affinity, a decrease in C1q binding affinity, an increase in FcR (preferably FcRn) binding affinity or a decrease in FcR (preferably FcRn) binding affinity as compared to a corresponding Fc region that lacks such amino acid substitution(s).

Additional examples include variant Fc regions that comprise an amino acid substitution at one or more of position(s) 221, 222, 224, 227, 228, 230, 231, 223, 233, 234, 235, 236, 237, 238, 239, 240, 241, 243, 244, 245, 246, 247, 249, 250, 258, 262, 263, 264, 265, 266, 267, 268, 269, 270, 271, 272, 273, 274, 275, 276, 278, 280, 281, 283, 285, 286, 288, 290, 291, 293, 294, 295, 296, 297, 298, 299, 300, 302, 313, 317, 318, 320, 322, 323, 324, 325, 326, 327, 328, 329, 330, 331, 332, 333, 334, 335 336 and/or 428 (see, e.g., U.S. Pat. No. 7,662,925). In specific embodiments, the variant Fc region comprises at least one amino acid substitution selected from the group consisting of: P230A, E233D, L234E, L234Y, L234I, L235D, L235S, L235Y, L235I, S239D, S239E, S239N, S239Q, S239T, V240I, V240M, F243L, V264I, V264T, V264Y, V266I, E272Y, K274T, K274E, K274R, K274L, K274Y, F275W, N276L, Y278T, V302I, E318R, S324D, S324I, S324V, N325T, K326I, K326T, L328M, L328I, L328Q, L328D, L328V, L328T, A330Y, A330L, A330I, I332D, I332E, I332N, I332Q, T335D, T335R, and T335Y. In other specific embodiments, the variant Fc region comprises at least one amino acid substitution selected from the group consisting of: V264I, F243L/V264I, L328M, I332E, L328M/I332E, V264I/I332E, S298A/I332E, S239E/I332E, S239Q/I332E, S239E, A330Y, I332D, L328I/I332E, L328Q/I332E, V264T, V240I, V266I, S239D, S239D/I332D, S239D/I332E, S239D/I332N, S239D/I332Q, S239E/I332D, S239E/I332N, S239E/I332Q, S239N/I332D, S239N/I332E, S239Q/I332D, A330Y/I332E, V264I/A330Y/I332E, A330L/I332E, V264I/A330L/I332E, L234E, L234Y, L234I, L235D, L235S, L235Y, L235I, S239T, V240M, V264Y, A330I, N325T, L328D/I332E, L328V/I332E, L328T/I332E, L328I/I332E, S239EN264I/I332E, S239QN264I/I332E, S239EN264I/A330Y/I332E, S239D/A330Y/I332E, S239N/A330Y/I332E, S239D/A330L/I332E, S239N/A330L/I332E, V264I/S298A/I332E, S239D/S298A/I332E, S239N/S298A/I332E, S239DN264I/I332E, S239DN264I/S298A/I332E, S239DN264I/A330L/I332E, S239D/I332E/A330I, P230A, P230A/E233D/I332E, E272Y, K274T, K274E, K274R, K274L, K274Y, F275W, N276L, Y278T, V302I, E318R, S324D, S324I, S324V, K326I, K326T, T335D, T335R, T335Y, V240I/V266I, S239D/A330Y/I332E/L234I, S239D/A330Y/I332E/L235D, S239D/A330Y/I332EN240I, S239D/A330Y/I332EN264T, S239D/A330Y/I332E/K326E, and S239D/A330Y/I332E/K326T, In more specific embodiments, the variant Fc region comprises a series of substitutions selected from the group consisting of: N297D/I332E, F241Y/F243Y/V262T/V264T/N297D/I332E, S239D/N297D/I332E, S239E/N297D/I332E, S239D/D265Y/N297D/I332E, S239D/D265H/N297D/I332E, V264E/N297D/I332E, Y296N/N297D/I332E, N297D/A330Y/I332E, S239D/D265V/N297D/I332E, S239D/D265I/N297D/I332E, and N297D/S298A/A330Y/I332E. In specific embodiments, the variant Fc region comprises an amino acid substitution at position 332 (using the numbering of the EU index, Kabat et al., supra). Examples of substitutions include 332A, 332D, 332E, 332F, 332G, 332H, 332K, 332L, 332M, 332N, 332P, 332Q, 332R, 332S, 332T, 332V, 332W and 332Y. The numbering of the residues in the Fc region is that of the EU index of Kabat et al. Among other properties described herein, such variant Fc regions may have increased affinity for an FcγR, increased stability, and/or increased solubility, relative to a corresponding, wild-type Fc region.

Further examples include variant Fc regions that comprise one or more of the following amino acid substitutions: 224N/Y, 225A, 228L, 230S, 239P, 240A, 241L, 243S/L/G/H/I, 244L, 246E, 247L/A, 252T, 254T/P, 258K, 261Y, 265V, 266A, 267G/N, 268N, 269K/G, 273A, 276D, 278H, 279M, 280N, 283G, 285R, 288R, 289A, 290E, 291L, 292Q, 297D, 299A, 300H, 301C, 304G, 305A, 306I/F, 311R, 312N, 315D/K/S, 320R, 322E, 323A, 324T, 325S, 326E/R, 332T, 333D/G, 335I, 338R, 339T, 340Q, 341E, 342R, 344Q, 347R, 351S, 352A, 354A, 355W, 356G, 358T, 361D/Y, 362L, 364C, 365Q/P, 370R, 372L, 377V, 378T, 383N, 389S, 390D, 391C, 393A, 394A, 399G, 404S, 408G, 409R, 411I, 412A, 414M, 421S, 422I, 426F/P, 428T, 430K, 431S, 432P, 433P, 438L, 439E/R, 440G, 441F, 442T, 445R, 446A, 447E, optionally where the variant has altered recognition of an Fc ligand and/or altered effector function compared with a parent Fc polypeptide, and wherein the numbering of the residues is that of the EU index as in Kabat et al. Specific examples of these and related embodiments include variant Fc regions that comprise or consist of the following sets of substitutions: (1) N276D, R292Q, V305A, I377V, T394A, V412A and K439E; (2) P244L, K246E, D399G and K409R; (3) 5304G, K320R, S324T, K326E and M358T; (4) F243S, P247L, D265V, V266A, S383N and T411I; (5) H224N, F243L, T393A and H433P; (6) V240A, S267G, G341E and E356G; (7) M252T, P291L, P352A, R355W, N390D, 5408G, S426F and A431S; (8) P228L, T289A, L365Q, N389S and 5440G; (9) F241L, V273A, K340Q and L441F; (10) F241L, T299A, I332T and M428T; (11) E269K, Y300H, Q342R, V422I and G446A; (12) T225A, R301c, 5304G, D312N, N315D, L351S and N421S; (13) S254T, L306I, K326R and Q362L; (14) H224Y, P230S, V323A, E333D, K338R and S364C; (15) T335I, K414M and P445R; (16) T335I and K414M; (17) P247A, E258K, D280N, K288R, N297D, T299A, K322E, Q342R, S354A and L365P; (18) H268N, V279M, A339T, N361D and S426P; (19) C261Y, K290E, L306F, Q311R, E333G and Q438L; (20) E283G, N315K, E333G, R344Q, L365P and S442T; (21) Q347R, N361Y and K439R; (22) S239P, S254P, S267N, H285R, N3155, F372L, A378T, N390D, Y391C, F404S, E430K, L432P and K447E; and (23) E269G, Y278H, N325S and K370R, wherein the numbering of the residues is that of the EU index as in Kabat et al. (see, e.g., U.S. Application No. 2010/0184959).

Another specific example of an Fc variant comprises the sequence of SEQ ID NO:155, wherein Xaa at position 1 is Ala or absent; Xaa at position 16 is Pro or Glu; Xaa at position 17 is Phe, Val, or Ala; Xaa at position 18 is Leu, Glu, or Ala; Xaa at position 80 is Asn or Ala; and/or Xaa at position 230 is Lys or is absent (see, e.g., U.S. Application No. 2007/0253966). Certain of these Fc regions, and related HRS-Fc conjugates, have increased half-life, reduced effector activity, and/or are significantly less immunogenic than wild-type Fc sequences.

Variant Fc regions can also have one or more mutated hinge regions, as described, for example, in U.S. Application No. 2003/0118592. For instance, one or more cysteines in a hinge region can be deleted or substituted with a different amino acid. The mutated hinge region can comprise no cysteine residues, or it can comprise 1, 2, or 3 fewer cysteine residues than a corresponding, wild-type hinge region. In some embodiments, an Fc region having a mutated hinge region of this type exhibits a reduced ability to dimerize, relative to a wild-type Ig hinge region.

As noted above, HRS-Fc conjugates such as HRS-Fc fusion proteins typically have altered (e.g., improved, increased, decreased) pharmacokinetic properties relative to corresponding HRS polypeptides. Examples of pharmacokinetic properties include stability or half-life, bioavailability (the fraction of a drug that is absorbed), tissue distribution, volume of distribution (apparent volume in which a drug is distributed immediately after it has been injected intravenously and equilibrated between plasma and the surrounding tissues), concentration (initial or steady-state concentration of drug in plasma), elimination rate constant (rate at which drugs are removed from the body), elimination rate (rate of infusion required to balance elimination), area under the curve (AUC or exposure; integral of the concentration-time curve, after a single dose or in steady state), clearance (volume of plasma cleared of the drug per unit time), $C_{max}$ (peak plasma concentration of a drug after oral administration), $t_{max}$ (time to reach $C_{max}$), $C_{min}$ (lowest concentration that a drug reaches before the next dose is administered), and fluctuation (peak trough fluctuation within one dosing interval at steady state). In some aspects, these improved properties are achieved without significantly altering the secondary structure and/or reducing the non-canonical biological activity of the HRS polypeptide. Indeed, some HRS-Fc conjugates have increased non-canonical biological activity.

Hence, in some embodiments, the HRS-Fc conjugate or HRS-Fc fusion polypeptide has a plasma or sera pharmacokinetic AUC profile at least 2, 3, 4, 5, 6, 7, 8, 9, 10, 11, 12, 13, 14, 15, 16, 17, 18, 19, 20, 50, 100, 200, 300, 400, or 500-fold greater than a corresponding unmodified or differently modified HRS polypeptide when administered to a mammal under the same or comparable conditions. In certain embodiments, the HRS-Fc conjugate or HRS-Fc fusion polypeptide has a stability (e.g., as measured by half-life) which is at least 10%, 20%, 30%, 40%, 50%, 60%, 70%, 80%, 90%, 100%, 200%, 300%, 400%, or 500% greater than a corresponding unmodified or differently modified HRS polypeptide when compared under similar conditions at room temperature, for example, in PBS at pH 7.4 for about 1, 2, 3, 4, 5, 6, 7, 8, 9, 10, 11, 12, 13, 14 days, or 1, 2, 3, 4 weeks or so.

In particular embodiments, a HRS-Fc conjugate or HRS-Fc fusion polypeptide has a biological half life at pH 7.4, 25° C., e.g., a physiological pH, human body temperature (e.g., in vivo, in serum, in a given tissue, in a given species such as rat, mouse, monkey, or human), of about or at least about 30 minutes, about 1 hour, about 2 hour, about 3 hours, about 4 hours, about 5 hours, about 6 hours, about 12 hours, about 18 hours, about 20 hours, about 24 hours, about 30 hours, about 36 hours, about 40 hours, about 48 hours, about 50 hours, about 60 hours, about 70 hours, about 72 hours, about 80 hours, about 84 hours, about 90 hours, about 96 hours, about 120 hours, or about 144 hours or more or any intervening half-life.

In certain embodiments, the HRS-Fc conjugate or HRS-Fc fusion polypeptide has greater bioavailability after subcutaneous (SC) administration compared to a corresponding unmodified HRS-polypeptide. In certain embodiments, the HRS-Fc conjugate or HRS-Fc fusion polypeptide has at least about 20%, at least about 30%, at least about 40%, at least about 50%, at least about 60%, at least about 70%, at least about 80%, at least about 90%, or at least about 100%, or more bioavailability compared to the corresponding unmodified HRS polypeptide.

In certain embodiments, the HRS-Fc fusion polypeptide has substantially the same secondary structure as a corresponding unmodified or differently modified HRS polypeptide, as determined via UV circular dichroism analysis. In certain embodiments, the HRS-Fc fusion polypeptide has substantially the same activity of a corresponding unmodified or differently modified HRS polypeptide in an assay of anti-inflammatory activity. In other embodiments, the HRS-Fc fusion polypeptide has greater than 2, 3, 4, 5, 6, 7, 8, 9, 10, 11, 12, 13, 14, 15, 16, 17, 18, 19, or 20-fold the activity of a corresponding unmodified or differently modified HRS polypeptide in an assay of anti-inflammatory activity.

Peptide Linkers

In certain embodiments, a peptide linker sequence may be employed to separate the HRS polypeptide(s) and the Fc region(s) by a distance sufficient to ensure that each polypeptide folds into its desired secondary and tertiary structures. Such a peptide linker sequence can be incorporated into the fusion protein using standard techniques well known in the art.

Certain peptide linker sequences may be chosen based on the following exemplary factors: (1) their ability to adopt a flexible extended conformation; (2) their inability to adopt a secondary structure that could interact with functional epitopes on the first and second polypeptides; (3) their physiological stability; and (4) the lack of hydrophobic or charged residues that might react with the polypeptide functional epitopes, or other features. See, e.g., George and Heringa, *J Protein Eng.* 15:871-879, 2002.

The linker sequence may generally be from 1 to about 200 amino acids in length. Particular linkers can have an overall amino acid length of about 1-200 amino acids, 1-150 amino acids, 1-100 amino acids, 1-90 amino acids, 1-80 amino acids, 1-70 amino acids, 1-60 amino acids, 1-50 amino acids, 1-40 amino acids, 1-30 amino acids, 1-20 amino acids, 1-10 amino acids, 1-5 amino acids, 1-4 amino acids, 1-3 amino acids, or about 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 60, 70, 80, 90, 100 or more amino acids.

A peptide linker may employ any one or more naturally-occurring amino acids, non-naturally occurring amino acid(s), amino acid analogs, and/or amino acid mimetics as described elsewhere herein and known in the art. Certain amino acid sequences which may be usefully employed as linkers include those disclosed in Maratea et al., *Gene* 40:39-46, 1985; Murphy et al., *PNAS USA.* 83:8258-8262, 1986; U.S. Pat. Nos. 4,935,233 and 4,751,180. Particular peptide linker sequences contain Gly, Ser, and/or Asn residues. Other near neutral amino acids, such as Thr and Ala may also be employed in the peptide linker sequence, if desired.

Certain exemplary linkers include Gly, Ser and/or Asn-containing linkers, as follows: $[G]_x$, $[S]_x$, $[GS]_x$, $[GGS]_x$, $[GSS]_x$, $[GSGS]_x$ (SEQ ID NO:200), $[GGSG]_x$ (SEQ ID NO:201), $[GGGS]_x$ (SEQ ID NO:202), $[GGGGS]_x$ (SEQ ID NO:203), $[GN]_x$, $[GGN]_x$, $[GNN]_x$, $[GNGN]_x$ (SEQ ID NO: 204), $[GGNG]_x$ (SEQ ID NO:205), $[GGGN]_x$ (SEQ ID NO:206), $[GGGGN]_x$ (SEQ ID NO:207) linkers, where x is 1, 2, 3, 4, 5, 6, 7, 8, 9, 10, 11, 12, 13, 14, 15, 16, 17, 18, 19, or 20 or more. Other combinations of these and related amino acids will be apparent to persons skilled in the art.

Additional examples of linker peptides include, but are not limited to the following amino acid sequences: Gly-Gly-Gly-Gly-Ser-Gly-Gly-Gly-Gly-Ser-Gly-Gly-Gly-Gly-Ser-(SEQ ID NO:208); Gly-Ser-Gly-Gly-Gly-Gly-Ser-Gly-Gly-Gly-Gly-Ser-Gly-Gly-Gly-Gly-Ser-Gly-Gly-Gly-Gly-Ser-(SEQ ID NO:209); Gly-Gly-Gly-Gly-Ser-Gly-Gly-Gly-Gly-Ser-Gly-Gly-Gly-Gly-Ser-Gly-Gly-Gly-Gly-Ser-Gly-Gly-Gly-Gly-Ser-Gly-Gly-Gly-Gly-Ser-(SEQ ID NO:210); Asp-Ala-Ala-Ala-Lys-Glu-Ala-Ala-Ala-Lys-Asp-Ala-Ala-Ala-Arg-Glu-Ala-Ala-Ala-Arg-Asp-Ala-Ala-Ala-Lys-(SEQ ID NO:211); and Asn-Val-Asp-His-Lys-Pro-Ser-Asn-Thr-Lys-Val-Asp-Lys-Arg-(SEQ ID NO:212).

Further non-limiting examples of linker peptides include DGGGS (SEQ ID NO:213); TGEKP (SEQ ID NO:214) (see, e.g., Liu et al., *PNAS.* 94:5525-5530, 1997); GGRR (SEQ ID NO:215) (Pomerantz et al. 1995); $(GGGGS)_n$ (SEQ ID NO:203) (Kim et al., *PNAS.* 93:1156-1160, 1996); EGKSSGSGSESKVD (SEQ ID NO:216) (Chaudhary et al., *PNAS.* 87:1066-1070, 1990); KESGSVSSEQLAQFRSLD (SEQ ID NO:217) (Bird et al., *Science.* 242:423-426, 1988), GGRRGGGS (SEQ ID NO:218); LRQRDGERP (SEQ ID NO:219); LRQKDGGGSERP (SEQ ID NO:220); LRQKd $(GGGS)_2$ ERP (SEQ ID NO:221). In specific embodiments, the linker sequence comprises a Gly3 linker sequence, which includes three glycine residues. In particular embodiments, flexible linkers can be rationally designed using a computer program capable of modeling both DNA-binding sites and the peptides themselves (Desjarlais & Berg, *PNAS.* 90:2256-2260, 1993; and *PNAS.* 91:11099-11103, 1994) or by phage display methods.

The peptide linkers may be physiologically stable or may include a releasable linker such as a physiologically degradable or enzymatically cleavable linker (e.g., proteolytically cleavable linker). In certain embodiments, one or more releasable linkers can result in a shorter half-life and more rapid clearance of the conjugate. These and related embodiments can be used, for example, to enhance the solubility and blood circulation lifetime of HRS polypeptides in the bloodstream, while also delivering a HRS polypeptide into the bloodstream that, subsequent to linker degradation, is substantially free of the Fc region(s). These aspects are especially useful in those cases where HRS polypeptides, when permanently conjugated to an Fc region, demonstrate reduced activity. By using the linkers as provided herein, such HRS polypeptides can maintain their therapeutic activity when in conjugated form. As another example, a large and relatively inert HRS-Fc conjugate polypeptide may be administered, which is then degraded in vivo (via the degradable linker) to generate a bioactive HRS polypeptide possessing a portion of the Fc region or lacking the Fc region entirely. In these and other ways, the properties of the HRS-Fc conjugate polypeptide can be more effectively tailored to balance the bioactivity and circulating half-life of the HRS polypeptide over time.

In particular embodiments, the linker peptide comprises an autocatalytic or self-cleaving peptide cleavage site. In a particular embodiment, self-cleaving peptides include those polypeptide sequences obtained from potyvirus and cardiovirus 2A peptides, FMDV (foot-and-mouth disease virus), equine rhinitis A virus, Thosea asigna virus and porcine teschovirus. In certain embodiments, the self-cleaving polypeptide site comprises a 2A or 2A-like site, sequence or domain (Donnelly et al., *J. Gen. Virol.* 82:1027-1041, 2001). Exemplary 2A sites include the following sequences: LLNFDLLKLAGDVESNPGP (SEQ ID NO:222); TLNFDLLKLAGDVESNPGP (SEQ ID NO: 223); LLKLAGDVESNPGP (SEQ ID NO:224); NFDLLKLAGDVESNPGP (SEQ ID NO:225); QLLNFDLLKLAGDVESNPGP (SEQ ID NO:226); APVKQTLNFDLLKLAGDVESNPGP (SEQ ID NO:227); VTELLYRMKRAETYCPRPLLAIHPTEARHKQKIVA-PVKQT (SEQ ID NO:228); LNFDLLKLAGDVESNPGP (SEQ ID NO:229); LLAIHPTEARHKQKIVAPVK-QTLNFDLLKLAGDVESNPGP (SEQ ID NO:230); and EARHKQKIVAPVKQTLNFDLLKLAGDVESNPGP (SEQ ID NO:231). In one embodiment, the autocatalytic peptide cleavage site comprises a translational 2A signal sequence, such as, e.g., the 2A region of the aphthovirus foot-and-mouth disease virus (FMDV) polyprotein, which is an18 amino acid sequence. Additional examples of 2A-like sequences that may be used include insect virus polyproteins, the NS34 protein of type C rotaviruses, and repeated sequences in *Trypanosoma* spp., as described, for example, in Donnelly et al., *Journal of General Virology.* 82:1027-1041, 2001.

Suitable protease cleavages sites and self-cleaving peptides are known to the skilled person (see, e.g., Ryan et al., *J. Gener. Virol.* 78:699-722, 1997; and Scymczak et al., *Nature Biotech.* 5:589-594, 2004). Exemplary protease cleavage sites include, but are not limited to the cleavage sites of potyvirus NIa proteases (e.g., tobacco etch virus protease), potyvirus HC proteases, potyvirus P1 (P35) proteases, byovirus NIa proteases, byovirus RNA-2-encoded proteases, aphthovirus L proteases, enterovirus 2A proteases, rhinovirus 2A proteases, picorna 3C proteases, comovirus 24K proteases, nepovirus 24K proteases, RTSV (rice tungro spherical virus) 3C-like protease, PYVF (parsnip yellow fleck virus) 3C-like protease, heparin, thrombin, factor Xa and enterokinase. Due to its high cleavage stringency, TEV (tobacco etch virus) protease cleavage sites are included in some embodiments, e.g., EXXYXQ(G/S) (SEQ ID NO:232), for example, ENLYFQG (SEQ ID NO:233) and ENLYFQS (SEQ ID NO:234), wherein X represents any amino acid (cleavage by TEV occurs between Q and G or Q and S).

Further examples of enzymatically degradable linkers suitable for use in particular embodiments of the present invention include, but are not limited to: an amino acid sequence cleaved by a serine protease such as thrombin, chymotrypsin, trypsin, elastase, kallikrein, or substilisin. Illustrative examples of thrombin-cleavable amino acid sequences include, but are not limited to: -Gly-Arg-Gly-Asp-(SEQ ID NO:235), -Gly-Gly-Arg-, -Gly-Arg-Gly-Asp-Asn-Pro-(SEQ ID NO: 236), -Gly-Arg-Gly-Asp-Ser-(SEQ ID NO:237), -Gly-Arg-Gly-Asp-Ser-Pro-Lys-(SEQ ID NO: 238), -Gly-Pro-Arg-, -Val-Pro-Arg-, and -Phe-Val-Arg-. Illustrative examples of elastase-cleavable amino acid sequences include, but are not limited to: -Ala-Ala-Ala-, -Ala-Ala-Pro-Val-(SEQ ID NO:239), -Ala-Ala-Pro-Leu-(SEQ ID NO:240), -Ala-Ala-Pro-Phe-(SEQ ID NO:241), -Ala-Ala-Pro-Ala-(SEQ ID NO:242), and -Ala-Tyr-Leu-Val-(SEQ ID NO:243).

Enzymatically degradable linkers also include amino acid sequences that can be cleaved by a matrix metalloproteinase such as collagenase, stromelysin, and gelatinase. Illustrative examples of matrix metalloproteinase-cleavable amino acid sequences include, but are not limited to: -Gly-Pro-Y-Gly-Pro-Z-(SEQ ID NO:244), -Gly-Pro-, Leu-Gly-Pro-Z-(SEQ ID NO:245), -Gly-Pro-Ile-Gly-Pro-Z-(SEQ ID NO:246), and -Ala-Pro-Gly-Leu-Z-(SEQ ID NO:247), where Y and Z are amino acids. Illustrative examples of collagenase-cleavable amino acid sequences include, but are not limited to: -Pro-Leu-Gly-Pro-D-Arg-Z-(SEQ ID NO:248), -Pro-Leu-Gly-Leu-Leu-Gly-Z-(SEQ ID NO:249), -Pro-Gln-Gly-Ile-Ala-Gly-Trp-(SEQ ID NO:250), -Pro-Leu-Gly-Cys(Me)-His-(SEQ ID NO:251), -Pro-Leu-Gly-Leu-Tyr-Ala-(SEQ ID NO:252), -Pro-Leu-Ala-Leu-Trp-Ala-Arg-(SEQ ID NO:253), and -Pro-Leu-Ala-Tyr-Trp-Ala-Arg-(SEQ ID NO:254), where Z is an amino acid. An illustrative example of a stromelysin-cleavable amino acid sequence is -Pro-Tyr-Ala-Tyr-Tyr-Met-Arg-(SEQ ID NO:255); and an example of a gelatinase-cleavable amino acid sequence is -Pro-Leu-Gly-Met-Tyr-Ser-Arg-(SEQ ID NO:256).

Enzymatically degradable linkers suitable for use in particular embodiments of the present invention also include amino acid sequences that can be cleaved by an angiotensin converting enzyme, such as, for example, -Asp-Lys-Pro-, -Gly-Asp-Lys-Pro-(SEQ ID NO:257), and -Gly-Ser-Asp-Lys-Pro-(SEQ ID NO:258).

Enzymatically degradable linkers suitable for use in particular embodiments of the present invention also include amino acid sequences that can be degraded by cathepsin B, such as, for example, Val-Cit, Ala-Leu-Ala-Leu-(SEQ ID NO:259), Gly-Phe-Leu-Gly-(SEQ ID NO:260) and Phe-Lys.

In particular embodiments, a releasable linker has a half life at pH 7.4, 25° C., e.g., a physiological pH, human body temperature (e.g., in vivo, in serum, in a given tissue), of about 30 minutes, about 1 hour, about 2 hour, about 3 hours, about 4 hours, about 5 hours, about 6 hours, about 12 hours, about 18 hours, about 24 hours, about 36 hours, about 48 hours, about 72 hours, or about 96 hours or more or any intervening half-life. One having skill in the art would appreciate that the half life of a HRS-Fc conjugate polypeptide can be finely tailored by using a particular releasable linker.

In certain embodiments, however, any one or more of the peptide linkers are optional. For instance, linker sequences may not required when the first and second polypeptides have non-essential N-terminal and/or C-terminal amino acid regions that can be used to separate the functional domains and prevent steric interference.

Methods for Use

Embodiments of the present invention relate to the discovery that Fc region-histidyl-tRNA synthetase (HRS-Fc) conjugate polypeptides, and fragments and variants thereof, offer improved methods of modulating inflammatory responses in a variety of useful ways, both in vitro and in vivo. The compositions of the invention may thus be useful as immunomodulators for treating a broad range of pro-inflammatory, inflammatory, and/or autoimmune indications, including inflammatory responses, chronic inflammation, acute inflammation, and immune diseases, by modulating the cells that mediate, either directly or indirectly, such inflammatory and/or autoimmune diseases, conditions and disorders. The utility of the compositions of the invention as immunomodulators can be monitored using any of a number of known and available techniques in the art including, for example, migration assays (e.g., using leukocytes or lymphocytes), cytokine production assays, or cell viability or cell differentiation assays (e.g., using B-cells, T-cells, monocytes or NK cells).

"Inflammation" refers generally to the biological response of tissues to harmful stimuli, such as pathogens, damaged cells (e.g., wounds), and irritants. The term "inflammatory response" refers to the specific mechanisms by which inflammation is achieved and regulated, including, merely by way of illustration, immune cell activation or migration, migration, autoimmunity and autoimmune disease, cytokine production, vasodilation, including kinin release, fibrinolysis, and coagulation, among others described herein and known in the art. Ideally, inflammation is a protective attempt by the body to both remove the injurious stimuli and initiate the healing process for the affected tissue or tissues. In the absence of inflammation, wounds and infections would never heal, creating a situation in which progressive destruction of the tissue would threaten survival. On the other hand, excessive or chronic inflammation may associate with a variety of diseases, such as hay fever, atherosclerosis, and rheumatoid arthritis, among others described herein and known in the art.

Clinical signs of chronic inflammation are dependent upon duration of the illness, inflammatory lesions, cause and anatomical area affected, (see, e.g., Kumar et al., Robbins Basic Pathology-8 ft Ed., 2009 Elsevier, London; Miller, L M, Pathology Lecture Notes, Atlantic Veterinary College, Charlottetown, PEI, Canada). Chronic inflammation is associated with a variety of pathological conditions or diseases, including, for example, allergies, Alzheimer's disease, anemia, aortic valve stenosis, arthritis such as rheumatoid arthritis and osteoarthritis, cancer, congestive heart failure, fibromyalgia, fibrosis, heart attack, kidney failure, lupus, pancreatitis, stroke, surgical complications, inflammatory lung disease, inflammatory bowel diseases including Crohn's disease (CD) and ulcerative colitis (UC), atherosclerosis, neurological disorders, diabetes, metabolic disorders, obesity, and psoriasis, among others described herein and known in the art. Many other chronic diseases may also include an inflammatory component, and thus may be treated with the HRS-Fc conjugates of the invention including, for example, muscular dystrophies and rhabdomyolysis. Hence, HRS-Fc conjugates may be used to treat or manage chronic inflammation, modulate any of one or more of the individual chronic inflammatory responses, or treat any one or more diseases or conditions associated with chronic inflammation.

Certain specific inflammatory responses include cytokine production and activity, and related pathways. For instance, certain exemplary embodiments relate to modulating cell-signaling through nuclear factor-kB (NF-kB), such as by increasing the downstream activities of this transcription factor. In certain instances, increases in NF-kB activity can lead to increases in cytokine signaling or activity, such as pro-inflammatory cytokines (e.g., TNF-alpha or beta), and anti-inflammatory cytokines (e.g., IL-10).

Criteria for assessing the signs and symptoms of inflammatory and other conditions, including for purposes of making differential diagnosis and also for monitoring treatments such as determining whether a therapeutically effective dose has been administered in the course of treatment, e.g., by determining improvement according to accepted clinical criteria, will be apparent to those skilled in the art and are exemplified by the teachings of e.g., Berkow et al., eds., The Merck Manual, 16th edition, Merck and Co., Rahway, N.J., 1992; Goodman et al., eds., Goodman and Gilman's The Pharmacological Basis of Therapeutics, 10th edition, Pergamon Press, Inc., Elmsford, N.Y., (2001); Avery's Drug Treatment: Principles and Practice of Clinical Pharmacology and Therapeutics, 3rd edition, ADIS Press, Ltd., Williams and Wilkins, Baltimore, Md. (1987); Ebadi, Pharmacology, Little, Brown and Co., Boston, (1985); Osolci al., eds., Remington's Pharmaceutical Sciences, 18th edition, Mack Publishing Co., Easton, Pa. (1990); Katzung, Basic and Clinical Pharmacology, Appleton and Lange, Norwalk, Conn. (1992).

Also included are methods of modulating an immune response, such as an innate or adaptive immune response via the use of any of the HRS-Fc conjugates described herein. As used herein, the term "immune response" includes a measurable or observable reaction to an antigen, vaccine composition, or immunomodulatory molecule mediated by one or more cells of the immune system. An immune response typically begins with an antigen or immunomodulatory molecule binding to an immune system cell. A reaction to an antigen or immunomodulatory molecule may be mediated by many cell types, including a cell that initially binds to an antigen or immunomodulatory molecule and cells that participate in mediating an innate, humoral, cell-mediated immune response.

Also included are methods of treating immune diseases. Illustrative immune system diseases, disorders or conditions that may be treated according to the present invention include, but are not limited to, primary immunodeficiencies, immune-mediated thrombocytopenia, Kawasaki syndrome, bone marrow transplant (for example, recent bone marrow transplant in adults or children), chronic B cell lymphocytic leukemia, HIV infection (for example, adult or pediatric HIV infection), chronic inflammatory demyelinating polyneuropathy, post-transfusion purpura, and the like.

Additionally, further diseases, disorders and conditions which may be treated with any of the HRS-Fc conjugates described herein include Guillain-Barre syndrome, anemia (for example, anemia associated with parvovirus B19, patients with stable multiple myeloma who are at high risk for infection (for example, recurrent infection), autoimmune hemolytic anemia (for example, warm-type autoimmune hemolytic anemia), thrombocytopenia (for example, neonatal thrombocytopenia), and immune-mediated neutropenia), transplantation (for example, cytomegalovirus (CMV)-negative recipients of CMV-positive organs), hypogammaglobulinemia (for example, hypogammaglobulinemic neonates with risk factor for infection or morbidity), epilepsy (for example, intractable epilepsy), systemic vasculitic syndromes, myasthenia gravis (for example, decompensation in myasthenia gravis), dermatomyositis, and polymyositis.

Further autoimmune diseases, disorders and conditions which may be treated with any of the HRS-Fc conjugates described herein include but are not limited to, autoimmune hemolytic anemia, autoimmune neonatal thrombocytopenia, idiopathic thrombocytopenia purpura, autoimmunocytopenia, hemolytic anemia, antiphospholipid syndrome, dermatitis, allergic encephalomyelitis, myocarditis, relapsing polychondritis, rheumatic heart disease, glomerulonephritis (for example, IgA nephropathy), multiple sclerosis, neuritis, uveitis ophthalmia, polyendochnopathies, purpura (for example, Henloch-Scoenlein purpura), Reiter's disease, stiff-man syndrome, autoimmune pulmonary inflammation, Guillain-Barre Syndrome, insulin dependent diabetes mellitus, and autoimmune inflammatory eye disease.

Additional autoimmune diseases, disorders or conditions which may be treated with any of the HRS-Fc conjugates described herein include, but are not limited to, autoimmune thyroiditis; hypothyroidism, including Hashimoto's thyroiditis and thyroiditis characterized, for example, by cell-mediated and humoral thyroid cytotoxicity; SLE (which is often characterized, for example, by circulating and locally generated immune complexes); Goodpasture's syndrome (which is often characterized, for example, by anti-basement membrane antibodies); pemphigus (which is often characterized, for example, by epidermal acantholytic antibodies); receptor autoimmunities such as, for example, Graves' disease (which is often characterized, for example, by antibodies to a thyroid stimulating hormone receptor; myasthenia gravis, which is often characterized, for example, by acetylcholine receptor antibodies); insulin resistance (which is often characterized, for example, by insulin receptor antibodies); autoimmune hemolytic anemia (which is often characterized, for example, by phagocytosis of antibody-sensitized red blood cells); and autoimmune thrombocytopenic purpura (which is often characterized, for example, by phagocytosis of antibody-sensitized platelets).

Further autoimmune diseases, disorders or conditions which may be treated with any of the HRS-Fc conjugates described herein include, but are not limited to, rheumatoid arthritis (which is often characterized, for example, by immune complexes in joints); scleroderma with anti-collagen antibodies (which is often characterized, for example, by nucleolar and other nuclear antibodies); mixed connective tissue disease, (which is often characterized, for example, by antibodies to extractable nuclear antigens, for example, ribonucleoprotein); polymyositis/dermatomyositis (which is often characterized, for example, by nonhistone anti-nuclear antibodies); pernicious anemia (which is often characterized, for example, by antiparietal cell, antimicrosome, and anti-intrinsic factor antibodies); idiopathic Addison's disease (which is often characterized, for example, by humoral and cell-mediated adrenal cytotoxicity); infertility (which is often characterized, for example, by antispennatozoal antibodies); glomerulonephritis (which is often characterized, for example, by glomerular basement membrane antibodies or immune complexes); by primary glomerulonephritis, by IgA nephropathy; bullous pemphigoid (which is often characterized, for example, by IgG and complement in the basement membrane); Sjogren's syndrome (which is often characterized, for example, by multiple tissue antibodies and/or the specific nonhistone anti-nuclear antibody (SS-B)); diabetes mellitus (which is often characterized, for example, by cell-mediated and humoral islet cell antibodies); and adrenergic drug resistance, including adrenergic drug resistance with asthma or cystic fibrosis (which is often characterized, for example, by beta-adrenergic receptor antibodies).

Still further autoimmune diseases, disorders or conditions which may be treated with any of the HRS-Fc conjugates described herein include, but are not limited to chronic active hepatitis (which is often characterized, for example by smooth muscle antibodies); primary biliary cirrhosis (which is often characterized, for example, by anti-mitochondrial antibodies); other endocrine gland failure (which is characterized, for example, by specific tissue antibodies in some cases); vitiligo (which is often characterized, for example, by anti-melanocyte antibodies); vasculitis (which is often characterized, for example, by immunoglobulin and complement in vessel walls and/or low serum complement); post-myocardial infarction conditions (which are often characterized, for example, by anti-myocardial antibodies); cardiotomy syndrome (which is often characterized, for example, by anti-myocardial antibodies); urticaria (which is often characterized, for example, by IgG and IgM antibodies to IgE); atopic dermatitis (which is often characterized, for example, by IgG and IgM antibodies to IgE); asthma (which is often characterized, for example, by IgG and IgM antibodies to IgE); inflammatory myopathies; and other inflammatory, granulomatous, degenerative, and atrophic disorders.

Additional diseases and disorders which may be treated with any of the HRS-Fc conjugates described herein include those that result from or associate with an imbalance of Th17 or other Th cell subtypes. Examples include psoriasis, psoriatic arthritis, atopic dermatitis (eczema), Balo concentric sclerosis, Schilder's diffuse sclerosis, Marburg MS, IBD, Crohn's, ulcerative colitis, collagenous colitis, lymphocytic colitis, ischaemic colitis, diversion colitis, Behçet's disease, indeterminate colitis, asthma, autoimmune myocarditis, endometriosis, Adult onset Still's disorder (AOSD), Henoch-Schonlein purpura (HSP), Vogt-Koyanagi-Harada (VKH), periodontal disease, organ transplantation failure, graft versus host disease, and Devic's disease (neuromyelitis optica).

In some aspects, the present invention includes a method of reducing muscle or lung inflammation associated with an autoimmune disease comprising administering to a subject in need thereof a composition comprising any of the HRS-Fc conjugates described herein. Exemplary muscular inflammatory diseases and disorders include muscular dystrophies, exercise-induced muscle inflammation, inflammation associated with muscle injury or surgery, rhabdomyolysis, and related diseases and disorders as described herein.

Also included are methods of treating a disease associated with an autoantibody comprising administering to a subject in need thereof a therapeutic composition comprising any of the HRS-Fc conjugates described herein, wherein the HRS polypeptide comprises at least one epitope specifically recognized by the autoantibody.

Certain embodiments include methods of inducing tolerance to a histidyl-tRNA synthetase (HisRS) antigen, said method comprising administering to a subject a composition comprising any of the HRS-Fc conjugates described herein, wherein the HRS polypeptide comprises at least one epitope specifically recognized by the autoantibody, and wherein administration of the composition causes tolerization to the autoantigen.

Also included are methods for eliminating a set or subset of T cells involved in an autoimmune response to a histidyl tRNA synthetase (HisRS) autoantigen, the method comprising administering to a subject a composition comprising any of the HRS-Fc conjugates described herein, wherein the HRS polypeptide comprises at least one epitope specifically recognized by the autoantibody, or auto-reactive T cell, and wherein administration of the composition causes clonal deletion of auto-reactive T-cells.

In another embodiment, the present invention includes a method for inducing anergy in T cells involved in an autoimmune response to a histidyl tRNA synthetase (HRS) autoantigen, the method comprising administering to a subject a composition comprising any of the HRS-Fc conjugates described herein, wherein the HRS polypeptide comprises at least one epitope specifically recognized by the autoantibody, or T cell, and wherein administration of the composition causes functional inactivation of the T cells involved in the autoimmune response.

In another embodiment, the present invention includes a replacement therapy for treating a disease associated with an insufficiency of histidyl tRNA synthetase comprising administering to a subject in need thereof a therapeutic composition comprising any of the HRS-Fc conjugates described herein, wherein the HRS polypeptide functionally compensates for the histidyl tRNA synthetase insufficiency.

In one aspect of this replacement therapy, the histidyl tRNA synthetase insufficiency is caused by the presence of anti-Jo-1 antibodies. In one aspect of this replacement therapy, the histidyl tRNA synthetase insufficiency is caused by mutations in an endogenous histidyl tRNA synthetase which modulate the activity, expression or cellular distribution of the endogenous histidyl tRNA synthetase. In one aspect the histidyl tRNA synthetase insufficiency is associated with Perrault syndrome or Usher syndrome.

In any of these methods, the term "tolerance" refers to the sustained reduction or absence of an immune response to a specific antigen in a mammal, particularly a human. Tolerance is distinct from generalized immunosuppression, in which all, or all of a specific class of immune cells, such as B cell mediated immune responses, of an immune responses are diminished, or eliminated. The development of tolerance may be routinely monitored by the absence, or a decrease, in the concentration of antibodies to HRS polypeptides in the serum of the host subject after administration, in single or successive doses of the treating HRS-Fc conjugate. The development of tolerance will typically be sufficient to decrease the symptoms of the autoimmune disease in the patient, for example a patient may be sufficiently improved so as to maintain normal activities in the absence, or in the presence of reduced amounts, of general immunosuppressants, e.g. corticosteroids.

In any of these methods, and compositions tolerance will typically be sustained, meaning that it will have a duration of about one month, about two months, about three months, about 4 months, about 5 months, or about 6 months or longer. Tolerance may result in selective B-cell anergy, or T-cell anergy or both.

In any of these methods, treatments and therapeutic compositions, the term "a disease associated with autoantibodies specific for histidyl tRNA synthetase" refers to any disease or disorder in which antibodies to histidyl tRNA synthetase are detected, or detectable, irrespective of whether other autoantibodies are also detected, or thought to play a role in disease progression or cause. Methods for detecting antibodies in patient samples may be carried out by any standard procedure including for example, by RIA, ELISA, by immunoprecipitation, by staining of tissues or cells (including transfected cells), antigen microarrays, mass spec analysis, specific neutralization assays or one of a number of other methods known in the art for identifying desired antigen specificity. In some aspects, antibody specificity can be further characterized by determining the ability of the antibodies to selectively bind to different splice variants and truncated or proteolytic forms of histidyl tRNA synthetase. A relatively well known human auto-antibody to histidyl tRNA synthetase includes for example antibodies to Jo-1.

In some embodiments of any of the claimed methods, and compositions, the HRS polypeptide or HRS-Fc conjugate comprises an epitope from histidyl tRNA synthetase which specifically cross reacts with a disease associated auto-antibody to histidyl-tRNA synthetase. In some embodiments of any of the claimed methods, and compositions, the HRS polypeptide or HRS-Fc conjugate comprises an epitope from histidyl tRNA synthetase which specifically cross reacts with a disease associated auto-reactive T cell to histidyl-tRNA synthetase. In some embodiments of any of the claimed methods, and compositions, the HRS polypeptide or HRS-Fc conjugate comprises an epitope which specifically cross reacts with a disease associated auto-antibody to either another tRNA synthetase, or to a non tRNA synthetase auto antibody.

In some embodiments of any of the claimed methods the HRS polypeptide or HRS-Fc conjugate comprises an immunodominant epitope which is specifically recognized by the majority of antibodies from the sera of a patient with a disease associated with auto antibodies to histidyl-tRNA synthetase. In some embodiments of any of the claimed methods the HRS polypeptide or HRS-Fc conjugate comprises an immunodominant epitope which is specifically recognized by the majority of autoreactive T cells from the sera of a patient with a disease associated with auto antibodies to histidyl-tRNA synthetase.

In some embodiments, the epitope is comprised within the WHEP domain of the HRS polypeptide (approximately amino acids 1-43 of SEQ ID NO:1); the aminoacylation domain (approximately amino acids 54-398 of SEQ ID NO:1); or the anticodon binding domain (approximately amino acids 406-501 of SEQ ID NO:1) or any combination thereof.

In some embodiments, the HRS polypeptide does not comprise an epitope which specifically cross reacts with a disease associated auto-antibody to histidyl-tRNA synthetase. In some embodiments, the HRS polypeptide does not significantly compete for disease associated auto-antibody binding to histidyl-tRNA synthetase in a competitive ELISA up to a concentration of about $1\times10^{-7}$M. In some embodiments, the HRS polypeptide does not significantly compete for disease associated auto-antibody binding to histidyl-tRNA synthetase in a competitive ELISA up to a concentration of about $5\times10^{-7}$M. In some embodiments, the HRS polypeptide does not significantly compete for disease associated auto-antibody binding to histidyl-tRNA synthetase in a competitive ELISA up to a concentration of about $1\times10^{-6}$ M.

Accordingly in some embodiments, the HRS polypeptide has a lower affinity to a disease associated auto-antibody than wild type histidyl-tRNA synthetase (SEQ ID NO:1) as measured in a competitive ELISA. In some embodiments, the HRS polypeptide has an apparent affinity for the disease associated auto-antibody which is at least about 10 fold less, or at least about 20 fold less, or at least about 50 fold less, or at least about 100 fold less than the affinity of the disease associated auto-antibody to wild type human (SEQ ID NO:1). In one aspect, the auto-antibody to histidyl-tRNA synthetase is directed to the Jo-1 antigen.

Examples of diseases associated with autoantibodies specific for histidyl-tRNA synthetase (as well as diseases associated with an insufficiency of histidyl-tRNA synthetase) include without limitation, autoimmune diseases, inflammatory diseases, and inflammatory myopathies, including idiopathic inflammatory myopathies, polymyositis, statin induced myopathies, dermatomyositis, interstitial lung disease (and other pulmonary fibrotic conditions) and related disorders, such as polymyositis-scleroderma overlap and inclusion body myositis (IBM) and conditions such as those found in anti-synthetase syndromes, including for example, interstitial lung disease, arthritis, esophageal dysmotility, cardiovascular disease and other vascular manifestations such as Reynaud's phenomenon; other examples of diseases associated with an insufficiency of histidyl-tRNA synthetase include genetic disorders that result in an insufficiency of active histidyl-tRNA synthetase including Usher syndrome and Perrault syndrome.

Polymyositis affects skeletal muscles (involved with making movement) on both sides of the body. It is rarely seen in persons under age 18; most cases are in people between the ages of 31 and 60. In addition to symptoms listed above, progressive muscle weakness leads to difficulty swallowing, speaking, rising from a sitting position, climbing stairs, lifting objects, or reaching overhead. People with polymyositis may also experience arthritis, shortness of breath, and heart arrhythmias. Polymyositis is often associated with antibodies to synthetases, including HisRS, resulting in immune cell invasion into the damaged muscle cells. HRS-Fc conjugates may thus be used to reduce immune cell activation and invasion, and to treat polymyositis.

Dermatomyositis is characterized by a skin rash that precedes or accompanies progressive muscle weakness. The rash looks patchy, with purple or red discolorations, and characteristically develops on the eyelids and on muscles used to extend or straighten joints, including knuckles, elbows, knees, and toes. Red rashes may also occur on the face, neck, shoulders, upper chest, back, and other locations, and there may be swelling in the affected areas. The rash sometimes occurs without obvious muscle involvement. Adults with dermatomyositis may experience weight loss or a low-grade fever, have inflamed lungs, and be sensitive to light. Adult dermatomyositis, unlike polymyositis, may accompany tumors of the breast, lung, female genitalia, or bowel. Children and adults with dermatomyositis may develop calcium deposits, which appear as hard bumps under the skin or in the muscle (called calcinosis). Calcinosis most often occurs 1-3 years after disease onset but may occur many years later. These deposits are seen more often in childhood dermatomyositis than in dermatomyositis that begins in adults. Dermatomyositis may be associated with collagen-vascular or autoimmune diseases.

In some cases of polymyositis and dermatomyositis, distal muscles (away from the trunk of the body, such as those in the forearms and around the ankles and wrists) may be affected as the disease progresses. Polymyositis and dermatomyositis may be associated with collagen-vascular or autoimmune diseases resulting in immune cell invasion into the damaged muscle cells. HRS-Fc conjugates may thus be used to reduce immune cell activation and invasion, and to treat dermatomyositis.

Inclusion body myositis (IBM) is characterized by progressive muscle weakness and wasting. The onset of muscle weakness is generally gradual (over months or years) and affects both proximal and distal muscles. Muscle weakness may affect only one side of the body. Small holes called vacuoles are sometimes seen in the cells of affected muscle fibers. Falling and tripping are usually the first noticeable symptoms of IBM. For some individuals the disorder begins with weakness in the wrists and fingers that causes difficulty with pinching, buttoning, and gripping objects. There may be weakness of the wrist and finger muscles and atrophy (thinning or loss of muscle bulk) of the forearm muscles and quadricep muscles in the legs. Difficulty swallowing occurs in approximately half of IBM cases. Symptoms of the disease usually begin after the age of 50, although the disease can occur earlier. Unlike polymyositis and dermatomyositis, IBM occurs more frequently in men than in women. As with other muscular dystrophies, IBM also results in progressive immune cell invasion into the damaged muscle cells. HRS-Fc conjugates may thus be used to reduce immune cell activation and invasion, and to treat IBM.

Juvenile myositis has some similarities to adult dermatomyositis and polymyositis. It typically affects children ages 2 to 15 years, with symptoms that include proximal muscle weakness and inflammation, edema (an abnormal collection of fluids within body tissues that causes swelling), muscle pain, fatigue, skin rashes, abdominal pain, fever, and contractures (chronic shortening of muscles or tendons around joints, caused by inflammation in the muscle tendons, which prevents the joints from moving freely). Children with juvenile myositis may also have difficulty swallowing and breathing, and the heart may be affected. Approximately 20 to 30 percent of children with juvenile dermatomyositis develop calcinosis. Affected children may not show higher than normal levels of the muscle enzyme creatine kinase in their blood but have higher than normal levels of other muscle enzymes. Juvenile myositis also results in progressive immune cell invasion into the damaged muscle cells. HRS-Fc conjugates may thus be used to reduce immune cell activation and invasion, and to treat juvenile myositis.

Statin Induced Myopathies are associated with the long term use of statins which act via the inhibition of 3-hydroxy-3-methylglutaryl coenzyme A reductase (HMGCR). Generally well-tolerated, these medications have been described as inducers of myotoxicity. More recently, there have been reports of patients in whom statin myopathies persist even after drug cessation, which are hypothesized to have an autoimmune cause. The benefits of statins are undisputed in reducing the risk of coronary heart disease and the progression of coronary atherosclerosis. Nevertheless, associated complications can be life-threatening. More than 38 million people in the U.S. are currently estimated to be taking statins and up to 7% (>2.6 million) of these are predicted to develop muscle symptoms with up to 0.5% (>190,000) of these potentially going on to develop life-threatening myopathies.

All the statins can cause muscle problems and the risk increases along with increases in their lipophilicity, cholesterol-lowering potency, and dosage. Cerivastatin in particular has been implicated as having a higher risk and it has been withdrawn from the US market. Of the remaining statins, atorvastatin and simvastatin have higher myotoxicity rates. Other nonstatin lipid-lowering agents such as niacin and fibrates also carry risks of muscle problems, particularly when combined with statins. While it is not possible to predict what patients will have statin-induced muscle problems, prior muscle problems may be a risk factor and should be considered when initiating statin treatment. A family history of myopathy is relevant if a patient might be a carrier of a genetic myopathy because it could be unmasked by the added stress of statin treatment. Other risk factors may include age over 80 years, low body weight, female sex, hypothyroidism, certain genetic defects and Asian descent, as well as concomitant use of certain medications, including calcium channel blockers, macrolide antibiotics, omeprazole, amiodarone, azole antifungals, histamine H2 receptor antagonists, nefazodone, cyclosporin, HIV protease inhibitors, warfarin, and grapefruit juice.

The most common muscle symptom caused by statins is muscle pain or myalgia and it occurs in about 7% of statin users. The myalgia can be anywhere from mild to severe and is often worsened by muscle activity. If the symptom is tolerable and the indication for statin treatment strong, for example, in a patient with hypercholesterolemia and a recent myocardial infarction, continued statin treatment may be appropriate.

Baseline creatine kinase (CK) levels are not uniformly recommended before initiation of statin treatment by the organizations guiding statin treatment, but CK levels can provide very useful information if muscle symptoms later develop. Muscle weakness can also occur, and it is often fatigable in quality and combined with pain and elevated CK. Like most myopathies, the weakness is most pronounced proximally. Rare episodes of rhabdomyolysis have also occurred with statin therapy; these are far less frequent but can possibly be fatal. The changes that can be seen on muscle histology that are most typical of a statin myopathy are cytochrome oxidase negative fibers, increased lipid content, and ragged red fibers. Autoimmune necrotizing myopathy is a rare form of statin myopathy. In these patients, discontinuation of the statin drug does not translate into recovery even after several months off the drug. Patients have a predominantly proximal, often painless weakness.

Diagnosis is based on the individual's medical history, results of a physical exam and tests of muscle strength, and blood samples that show elevated levels of various muscle enzymes and autoantibodies. Diagnostic tools include electromyography to record the electrical activity that controls muscles during contraction and at rest, ultrasound to look for muscle inflammation, and magnetic resonance imaging to reveal abnormal muscle and evaluate muscle disease. A muscle biopsy can be examined by microscopy for signs of chronic inflammation, muscle fiber death, vascular deformities, or the changes specific to the diagnosis of IBM. HRS-Fc conjugates may thus be used to reduce immune cell activation and invasion into damaged muscle, and to treat statin induced myopathies and rhabdomyolysis.

Interstitial lung disease (ILD) is a broad category of lung diseases that includes more than 130 disorders characterized by scarring (i.e., "fibrosis") and/or inflammation of the lungs. ILD accounts for 15 percent of the cases seen by pulmonologists. Interstitial lung disease (ILD) can develop from a variety of sources, ranging from other diseases to environmental factors. Some of the known causes of ILD include: connective tissue or autoimmune disease, including for example, scleroderma/progressive systemic sclerosis, lupus (systemic lupus erythematosus), rheumatoid arthritis and polymyositis/dermatomyositis; and occupational and environmental exposures, including for example, exposure to dust and certain gases, poisons, chemotherapy and radiation therapy.

In ILD, the tissue in the lungs becomes inflamed and/or scarred. The interstitium of the lung includes the area in and around the small blood vessels and alveoli (air sacs) where the exchange of oxygen and carbon dioxide takes place. Inflammation and scarring of the interstitium disrupts this tissue and leads to a decrease in the ability of the lungs to extract oxygen from the air. HRS-Fc conjugates may thus be used to reduce immune cell activation and invasion into damaged lung, and to treat ILD.

The progression of ILD varies from disease to disease and from person to person. Because interstitial lung disease disrupts the transfer of oxygen and carbon dioxide in the lungs, its symptoms typically manifest as problems with breathing. The two most common symptoms of ILD are shortness of breath with exercise and a non-productive cough.

Usher Syndrome is the most common condition that affects both hearing and vision. The major symptoms of Usher syndrome are hearing loss and retinitis pigmentosa (RP). RP causes night-blindness and a loss of peripheral vision (side vision) through the progressive degeneration of the retina. As RP progresses, the field of vision narrows until only central vision remains. Many people with Usher syndrome also have severe balance problems. Approximately 3 to 6 percent of all children who are deaf and another 3 to 6 percent of children who are hard-of-hearing have Usher syndrome. In developed countries such as the United States, about four babies in every 100,000 births have Usher syndrome. Usher syndrome is inherited as an autosomal recessive trait. Several genetic loci have been associated with Usher syndrome including histidyl t-RNA synthetase (Puffenberger et al., (2012) *PLoS ONE* 7(1) e28936 doi: 10.1371/journal.pone.0028936).

There are three clinical types of Usher syndrome: type 1, type 2, and type 3. In the United States, types 1 and 2 are the most common types. Together, they account for approximately 90 to 95 percent of all cases of children who have Usher syndrome.

Children with type 1 Usher syndrome are profoundly deaf at birth and have severe balance problems. Because of the balance problems associated with type 1 Usher syndrome, children with this disorder are slow to sit without support and typically don't walk independently before they are 18 months old. These children usually begin to develop vision problems in early childhood, almost always by the time they reach age 10. Vision problems most often begin with difficulty seeing at night, but tend to progress rapidly until the person is completely blind.

Children with type 2 Usher syndrome are born with moderate to severe hearing loss and normal balance. Although the severity of hearing loss varies, most of these children can benefit from hearing aids and can communicate orally. The vision problems in type 2 Usher syndrome tend to progress more slowly than those in type 1, with the onset of RP often not apparent until the teens.

Children with type 3 Usher syndrome have normal hearing at birth. Although most children with the disorder have normal to near-normal balance, some may develop balance problems later on. Hearing and sight worsen over time, but the rate at which they decline can vary from person to person, even within the same family. A person with type 3 Usher syndrome may develop hearing loss by the teens, and he or she will usually require hearing aids by mid- to late adulthood. Night blindness usually begins sometime during puberty. Blind spots appear by the late teens to early adulthood, and, by mid-adulthood, the person is usually legally blind.

Perrault syndrome (PS) is characterized by the association of ovarian dysgenesis in females with sensorineural hearing impairment, and in some subjects, neurologic abnormalities, including progressive cerebellar ataxia and intellectual deficit. The exact prevalence for Perrault syndrome is unknown, and is probably underdiagnosed, particularly in males where hypogonadism is not a feature and the syndrome remains undetected. Mean age at diagnosis is 22 years following presentation with delayed puberty in females with sensorineural deafness. Hearing defects were noted in all but one of the reported cases (mean age at diagnosis of 8 years). The hearing loss is always sensorineural and bilateral but the severity is variable (mild to profound), even in affected patients from the same family. Ovarian dysgenesis has been reported in all female cases but no gonad defects are detected in males. Amenorrhea is generally primary but secondary amenorrhea has also been reported. Delayed growth (height below the third percentile) was reported in half the documented cases. The exact frequency of the neurological abnormalities is unknown, but nine females and two males (16-37 years old) lacking neurological abnormalities have been reported. Neurological signs are progressive and generally appear later in life, however, walking delay or early frequent falls have been noted in young PS patients. Common neurological signs are ataxia, dyspraxia, limited extraocular movements, and polyneuropathy. Some cases with scoliosis have also been reported. Transmission of PS is autosomal recessive and mutations in mitochondrial histidyl tRNA synthetase have recently been identified to cause the ovarian dysgenesis and sensorineural hearing loss associated with Perrault syndrome. (Pierce et al., *PNAS USA*. 108(16) 6543-6548, 2011).

Muscular dystrophy refers to a group of inherited disorders in which strength and muscle bulk gradually decline. All of the muscular dystrophies are marked by muscle weakness that is driven by a primary genetic defect in one or more muscle specific genes. Additionally muscular dystrophies, typically have a variable inflammatory component that drives muscular inflammation and ultimately enhances the degeneration of muscular tissues. Accordingly HRS-Fc conjugates may be used to reduce immune cell activation and invasion into damaged muscle, and to treat muscular dystrophies. At least nine types of muscular dystrophies are generally recognized. In some aspects, the muscular dystrophy is selected from Duchenne muscular dystrophy, Becker muscular dystrophy, Emery-Dreifuss muscular dystrophy, Limb-girdle muscular dystrophy, facioscapulohumeral muscular dystrophy, myotonic dystrophy, oculopharyngeal muscular dystrophy, distal muscular dystrophy and congenital muscular dystrophy.

Duchenne muscular dystrophy (DMD): DMD affects young boys, causing progressive muscle weakness, usually beginning in the legs. It is the most severe form of muscular dystrophy. DMD occurs in about 1 in 3,500 male births, and affects approximately 8,000 boys and young men in the United States. A milder form occurs in very few female carriers.

DMD is caused by mutations in the gene encoding dystrophin, a subsarcolemmal protein functioning within the dystrophin-associated glycoprotein complex (DGC) which prevent the production of functional protein. The amount of dystrophin correlates with the severity of the disease (i.e., the less dystrophin present, the more severe the phenotype). The DGC complex connects the intracellular cytoskeleton to the extracellular matrix. The DGC is concentrated at the Z-lines of the sarcomere and confers the transmission of force across the muscle fibre. Disruption of this link results in membrane instability, which eventually leads to sarcolemmal ruptures. Influx of extracellular calcium alters molecular processes like muscle contraction and activates proteolytic activity. Affected muscle fibres become necrotic or apoptotic, and release mitogenic chemoattractants, which initiate inflammatory processes. Cycles of degeneration and regeneration eventually lead to irreversible muscle wasting and replacement by fibrotic and adipose tissue.

A boy with Duchenne muscular dystrophy usually begins to show symptoms as a pre-schooler. The legs are affected first, making walking difficult and causing balance problems. Most patients walk three to six months later than expected and have difficulty running Contractures (permanent muscle tightening) usually begin by age five or six, most severely in the calf muscles. Frequent falls and broken bones are common beginning at this age. Climbing stairs and rising unaided may become impossible by age nine or ten, and most boys use a wheelchair for mobility by the age of 12. Weakening of the trunk muscles around this age often leads to scoliosis (a side-to-side spine curvature) and kyphosis (a front-to back curvature).

One of the most serious weakness of DMD is weakness of the diaphragm, the sheet of muscles at the top of the abdomen that perform the main work of breathing and coughing. Diaphragm weakness leads to reduced energy and stamina, and increased lung infection because of the inability to cough effectively. Young men with DMD can live into their twenties and beyond, provided they have mechanical ventilation assistance and good respiratory hygiene.

In some embodiments, a subject having DMD is characterized by one or more of the following: a positive Gower's sign, reflecting impairment of the lower extremity muscles; high levels of creatine kinase (CPK-MM) in the blood; genetic errors in the Xp21 gene; or reduced levels of absence of dystrophin, for instance, as measured by muscle biopsy.

HRS-Fc conjugates may be used in the treatment of DMD, either alone or in combination with other therapies, such as antisense oligonucleotides (e.g., exon-skipping therapies such as Eteplirsen), corticosteroids, beta2-agonists, physical therapy, respiratory support, stem cell therapies, and gene replacement therapies. In some embodiments, administration of HRS-Fc conjugates leads to statistically significant improvements in the 6-minute walk test.

Becker muscular dystrophy (BMD): BMD affects older boys and young men, following a milder course than DMD. BMD occurs in about 1 in 30,000 male births. Becker muscular dystrophy is a less severe variant of Duchenne muscular dystrophy and is caused by the production of a truncated, but partially functional form of dystrophin.

The symptoms of BMD usually appear in late childhood to early adulthood. Though the progression of symptoms may parallel that of DMD, the symptoms are usually milder and the course more variable. Scoliosis may occur, but is usually milder and progresses more slowly. Heart muscle disease (cardiomyopathy), occurs more commonly in BMD. Problems may include irregular heartbeats (arrhythmias) and congestive heart failure. Symptoms may include fatigue, shortness of breath, chest pain, and dizziness. Respiratory weakness also occurs, and may lead to the need for mechanical ventilation. HRS-Fc conjugates may be used in the treatment of BMD, either alone or in combination with other therapies.

Emery-Dreifuss muscular dystrophy (EDMD): EDMD affects young boys, causing contractures and weakness in the calves, weakness in the shoulders and upper arms, and problems in the way electrical impulses travel through the heart to make it beat (heart conduction defects). There are three subtypes of Emery-Dreifuss Muscular Dystrophy, distinguishable by their pattern of inheritance: X-Linked, autosomal dominant and autosomal recessive. The X-linked form is the most common. Each type varies in prevalence and symptoms. The disease is caused by mutations in the LMNA gene, or more commonly, the EMD gene. Both genes encode for protein components of the nuclear envelope.

EDMD usually begins in early childhood, often with contractures preceding muscle weakness. Weakness affects the shoulder and upper arm originally, along with the calf muscles, leading to foot-drop. Most men with EDMD survive into middle age, although a defect in the heart's rhythm (heart block) may be fatal if not treated with a pacemaker. HRS-Fc conjugates may be used in the treatment of EDMD, either alone or in combination with other therapies.

Limb-girdle muscular dystrophy (LGMD): LGMD begins in late childhood to early adulthood and affects both men and women, causing weakness in the muscles around the hips and shoulders. It is the most variable of the muscular dystrophies, and there are several different forms of the disease now recognized. Many people with suspected LGMD have probably been misdiagnosed in the past, and therefore the prevalence of the disease is difficult to estimate. The number of people affected in the United States may be in the low thousands.

While there are at least a half-dozen genes that cause the various types of LGMD, two major clinical forms of LGMD are usually recognized. A severe childhood form is similar in appearance to DMD, but is inherited as an autosomal recessive trait.

Limb Girdle Muscular Dystrophy type 2B (LGMD2B) is caused by the loss of function mutations in the dysferlin gene. Dysferlin is primarily expressed in skeletal and cardiac muscle, but also in monocytes, macrophages, and other tissues where it is localized to cytoplasmic vesicles and the cell membrane. Dysferlin appears to be involved in membrane fusion and trafficking, as well as repair processes. LGMD2B is a late onset (teens/young adults) muscle disease that is characterized by progressive symmetrical muscle weakness, and notably aggressive immune/inflammatory pathology. Muscle biopsies typically show marked inflammatory cell infiltration, consisting primarily of macrophages/macrophage activation markers (HLA-DR, HLA-ABC, CD86), $CD8^+$ cytotoxic T cells, and $CD4^+$ T cells, together with muscle fiber degeneration/regeneration. Accordingly, HRS-Fc conjugates may be used to reduce immune cell activation and invasion into damaged muscle, and to treat Limb Girdle Muscular Dystrophy.

Symptoms of adult-onset LGMD usually appear in a person's teens or twenties, and are marked by progressive weakness and wasting of the muscles closest to the trunk. Contractures may occur, and the ability to walk is usually lost about 20 years after onset. Some people with LGMD develop respiratory weakness that requires use of a ventilator. Lifespan may be somewhat shortened. (Autosomal dominant forms usually occur later in life and progress relatively slowly.)

Facioscapulohumeral muscular dystrophy (FSH): FSH, also known as Landouzy-Dejerine disease, begins in late childhood to early adulthood and affects both men and women, causing weakness in the muscles of the face, shoulders, and upper arms. The hips and legs may also be affected. FSH occurs in about 1 out of every 20,000 people, and affects approximately 13,000 people in the United States.

FSH varies in its severity and age of onset, even among members of the same family. Symptoms most commonly begin in the teens or early twenties, though infant or childhood onset is possible. Symptoms tend to be more severe in those with earlier onset. The disease is named for the regions of the body most severely affected by the disease: muscles of the face (facio-), shoulders (scapulo-), and upper arms (humeral). Hips and legs may be affected as well. Children with FSH often develop partial or complete deafness.

Two defects are needed for FSHD, the first is the deletion of D4Z4 repeats and the second is a "toxic gain of function" of the DUX4 gene. The first symptom noticed is often difficulty lifting objects above the shoulders. The weakness may be greater on one side than the other. Shoulder weakness also causes the shoulder blades to jut backward, called scapular winging. FSHD is associated with inflammatory invasion is specific muscle groups, and accordingly HRS-Fc conjugates may thus be used to reduce immune cell activation and invasion into damaged muscles, and to treat FSHD.

Myotonic dystrophy: Myotonic dystrophy, also known as Steinert's disease, affects both men and women, causing generalized weakness first seen in the face, feet, and hands. It is accompanied by the inability to relax the affected muscles (myotonia). Symptoms may begin from birth through adulthood. Myotonic muscular dystrophy type 1 (DM1) is the most common form of muscular dystrophy, affecting more than 30,000 people in the United States. It results from the expansion of a short (CTG) repeat in the DNA sequence of the DMPK (myotonic dystrophy protein kinase) gene. Myotonic muscular dystrophy type 2 (DM2) is much rarer and is a result of the expansion of the CCTG repeat in the ZNF9 (zinc finger protein 9) gene.

Symptoms of myotonic dystrophy include facial weakness and a slack jaw, drooping eyelids (ptosis), and muscle wasting in the forearms and calves. A person with this dystrophy has difficulty relaxing his grasp, especially if the object is cold. Myotonic dystrophy affects heart muscle, causing arrhythmias and heart block, and the muscles of the digestive system, leading to motility disorders and constipation. Other body systems are affected as well: Myotonic dystrophy may cause cataracts, retinal degeneration, low IQ, frontal balding, skin disorders, testicular atrophy, sleep apnea, and insulin resistance. An increased need or desire for sleep is common, as is diminished motivation. Severe disability affects most people with this type of dystrophy within 20 years of onset, although most do not require a wheelchair even late in life. HRS-Fc conjugates can thus be used to treat myotonic dystrophy, for instance, by reducing inflammation associated with muscle tissue, including skeletal muscle (e.g., quadricep muscles) and/or heart tissue, among other tissues.

Oculopharyngeal muscular dystrophy (OPMD): OPMD affects adults of both sexes, causing weakness in the eye muscles and throat. It is most common among French Canadian families in Quebec, and in Spanish-American families in the southwestern United States.

OPMD usually begins in a person's thirties or forties, with weakness in the muscles controlling the eyes and throat. Symptoms include drooping eyelids, difficulty swallowing (dysphagia), and weakness progresses to other muscles of the face, neck, and occasionally the upper limbs. Swallowing difficulty may cause aspiration, or the introduction of food or saliva into the airways. Pneumonia may follow. HRS-Fc conjugates can thus be used to treat OPMD, for instance, by reducing inflammation associated with muscle tissue.

Distal muscular dystrophy (DD): DD begins in middle age or later, causing weakness in the muscles of the feet and hands. It is most common in Sweden, and rare in other parts of the world. DD usually begins in the twenties or thirties, with weakness in the hands, forearms, and lower legs. Difficulty with fine movements such as typing or fastening buttons may be the first symptoms. Symptoms progress slowly, and the disease usually does not affect life span. HRS-Fc conjugates can thus be used to treat DD, by reducing inflammation associated with muscle tissue inflammation.

Congenital muscular dystrophy (CMD): CMD is present from birth, results in generalized weakness, and usually progresses slowly. A subtype, called Fukuyama CMD, also involves mental retardation. Both are rare; Fukuyama CMD is more common in Japan.

CMD is marked by severe muscle weakness from birth, with infants displaying "floppiness" and very little voluntary movement. Nonetheless, a child with CMD may learn to walk, either with or without some assistive device, and live into young adulthood or beyond. In contrast, children with Fukuyama CMD are rarely able to walk, and have severe mental retardation. Most children with this type of CMD die in childhood. As with the other muscular dystrophies, HRS-Fc conjugates can thus be used to treat CMD, for example, by reducing inflammation associated with muscle tissue inflammation.

Cachexia: Cachexia (or wasting syndrome) is typically characterized by loss of weight, muscle atrophy, fatigue, weakness, and significant loss of appetite in someone who is not actively trying to lose weight. The formal definition of cachexia is the loss of body mass that cannot be reversed nutritionally. Even if the affected patient consumes more calories, lean body mass is lost, indicating the existence of a primary pathology.

Cachexia is experienced by patients with cancer, AIDS, chronic obstructive lung disease, multiple sclerosis, congestive heart failure, tuberculosis, familial amyloid polyneuropathy, mercury poisoning (acrodynia), and hormonal deficiency, among other disease.

Cachexia can also be a sign of various underlying disorders, including cancer, metabolic acidosis (i.e., decreased protein synthesis and increased protein catabolism), certain infectious diseases (e.g., tuberculosis, AIDS), chronic pancreatitis, autoimmune disorders, or addiction to amphetamines. Cachexia physically weakens patients to a state of immobility stemming from loss of appetite, asthenia, and anemia, and response to standard treatment is usually poor.

About 50% of all cancer patients suffer from cachexia. Those with upper gastrointestinal and pancreatic cancers have the highest frequency of developing a cachexic symptom. In addition to increasing morbidity and mortality, aggravating the side effects of chemotherapy, and reducing quality of life, cachexia is considered the immediate cause of death of a large proportion of cancer patients, ranging from 22% to 40% of the patients. Symptoms of cancer cachexia include progressive weight loss and depletion of host reserves of adipose tissue and skeletal muscle. Traditional treatment approaches include the use of appetite stimulants, 5-$HT_3$ antagonists, nutrient supplementation, and COX-2 inhibitors.

Although the pathogenesis of cachexia is poorly understood, multiple biologic pathways are expected to be involved, including pro-inflammatory cytokines such as TNF-α, neuroendocrine hormones, IGF-1, and tumor-specific factors such as proteolysis-inducing factor.

HRS-Fc conjugates may thus be used to treat cachexia and any of its related, underlying, or secondary disorders or complications. HRS-Fc conjugates can be used alone or in combination with other therapies, such as dietary supplementation with a combination of high protein, leucine and fish oil, antioxidants, progestogen (megestrol acetate, medroxyprogesterone acetate), and anticyclooxygenase-2 drugs, appetite stimulants, and 5-$HT_3$ antagonists, among others.

Rhabdomyolysis: Rhabdomyolysis is the breakdown of muscle fibers in skeletal muscle tissue. The breakdown products are released into the bloodstream, and certain some of these products, such as myoglobin, are harmful to the kidneys and may lead to kidney failure.

Symptoms include muscle pain, vomiting, confusion, coma, or abnormal heart rate and rhythm and their severity usually depends on the extent of muscle damage and whether kidney failure develops. Damage to the kidneys may cause decreased or absent urine production, usually about 12 to 24 hours after the initial muscle damage. Swelling of the damaged muscle can cause compartment syndrome, or compression of surrounding tissues, such as nerves and blood vessels, in the same fascial compartment, and lead to blood loss and damage to (e.g., loss of function) the affected body parts. Symptoms of this complication include pain or reduced sensation in the affected limb. Other complications include disseminated intravascular coagulation (DIC), a severe disruption in blood clotting that may lead to uncontrollable bleeding.

The initial muscle damage may be caused, for instance, by physical factors (e.g. crush injury, strenuous exercise), altered blood supply (e.g., arterial thrombosis, embolism), altered metabolism (e.g., hyperglycemic hyperosmolar state, hyper- and hyponatremia, hypokalemia, hypocalcemia, hypophosphatemia, ketoacidosis, hypothyroidism), altered body temperature (hyperthermia, hypothermia), medications and toxins (e.g., statins, anti-psychotic medications, neuromuscular blocking agents, diuretics, heavy metals, hemlock, insect or snake venoms), drug abuse (e.g., alcohol, amphetamine, cocaine, heroin, ketamine, LDS, MDMA), infections (e.g., Coxsackie virus, influenza A virus, influenza B virus, Epstein-Barr virus, primary HIV infection, *Plasmodium falciparum*, herpes viruses, *Legionella pneumophila, salmonella*), and autoimmune muscle damage (e.g., polymyositis, dermatomyositis). Also, certain hereditary conditions increase the risk of rhabdomyolysis, including glycolysis and glycogenolysis defects (e.g., McArdle's disease, phosphofructokinase deficiency, glycogen storage diseases VIII, IX, X and XI), lipid metabolism defects (e.g., carnitine palmitoyltransferase I and II deficiency, deficiency of subtypes of acyl CoA dehydrogenase (e.g., LCAD, SCAD, MCAD, VLCAD, 3-hydroxyacyl-coenzyme A dehydrogenase deficiency), thiolase deficiency), mitochondrial myopathies (e.g., deficiency of succinate dehydrogenase, cytochrome c oxidase and coenzyme Q10), and others such as glucose-6-phosphate dehydrogenase deficiency, myoadenylate deaminase deficiency, and muscular dystrophies.

Rhabdomyolysis is usually diagnosed with blood tests and urinalysis, and can be indicated by abnormally raised or increasing creatinine and urea levels, falling urine output, or reddish-brown discoloration of the urine. The primary treatments include intravenous fluids, dialysis, and hemofiltration.

HRS-Fc conjugates may thus be used to treat rhabdomyolysis and any of its related, secondary, or underlying disorders or complications. HRS-Fc conjugates can be used alone or in combination with other therapies, including those meant to treat shock and preserve kidney function. Exemplary therapies include administration of intravenous fluids, usually isotonic saline (0.9% weight per volume sodium chloride solution) and renal replacement therapies (RRT) such as hemodialysis, continuous hemofiltration and peritoneal dialysis.

More generally, the HRS-Fc conjugates described herein can reduce an inflammatory response, such as by reducing the activation, differentiation, migration, or infiltration of immune cells into selected tissues, increasing the production of anti-inflammatory cytokines, or reducing the production or activity of pro-inflammatory cytokines, among other mechanisms. Moreover, certain of the present methods, by blocking the binding, action, or production of anti-histidyl-tRNA synthetase antibodies or auto-reactive T cells, have utility to treat a broad range of auto-immune and inflammatory diseases and disorders associated with anti-histidyl-tRNA synthetase antibodies, other auto-antibodies, as well as other causes of histidyl-tRNA synthetase insufficiency.

Pharmaceutical Formulations, Administration, and Kits

Embodiments of the present invention include compositions comprising HRS-Fc conjugate polypeptides formulated in pharmaceutically-acceptable or physiologically-acceptable solutions for administration to a cell, subject, or an animal, either alone, or in combination with one or more other modalities of therapy. It will also be understood that, if desired, the compositions of the invention may be administered in combination with other agents as well, for example, other proteins or polypeptides or various pharmaceutically-active agents. There is virtually no limit to other components that may also be included in the compositions, provided that the additional agents do not adversely affect the modulatory or other effects desired to be achieved.

For pharmaceutical production, HRS-Fc conjugate therapeutic compositions will typically be substantially endotoxin free. Endotoxins are toxins associated with certain bacteria, typically gram-negative bacteria, although endotoxins may be found in gram-positive bacteria, such as *Listeria monocytogenes*. The most prevalent endotoxins are lipopolysaccharides (LPS) or lipo-oligo-saccharides (LOS) found in the outer membrane of various Gram-negative bacteria, and which represent a central pathogenic feature in the ability of these bacteria to cause disease. Small amounts of endotoxin in humans may produce fever, a lowering of the blood pressure, and activation of inflammation and coagulation, among other adverse physiological effects.

Endotoxins can be detected using routine techniques known in the art. For example, the Limulus Amoebocyte Lysate assay, which utilizes blood from the horseshoe crab, is a very sensitive assay for detecting presence of endotoxin. In this test, very low levels of LPS can cause detectable coagulation of the limulus lysate due a powerful enzymatic cascade that amplifies this reaction. Endotoxins can also be quantitated by enzyme-linked immunosorbent assay (ELISA).

To be substantially endotoxin free, endotoxin levels may be less than about 0.001, 0.005, 0.01, 0.02, 0.03, 0.04, 0.05, 0.06, 0.08, 0.09, 0.1, 0.5, 1.0, 1.5, 2, 2.5, 3, 4, 5, 6, 7, 8, 9, or 10 EU/mg of protein. Typically, 1 ng lipopolysaccharide (LPS) corresponds to about 1-10 EU.

In certain embodiments, as noted herein, the HRS-Fc conjugate compositions have an endotoxin content of less than about 10 EU/mg of HRS-Fc conjugate, or less than about 5 EU/mg of HRS-Fc conjugate, less than about 3 EU/mg of HRS-Fc conjugate, or less than about 1 EU/mg of HRS-Fc conjugate or less than about 0.1 EU/mg of HRS-Fc conjugate, or less than about 0.01 EU/mg of HRS-Fc conjugate. In certain embodiments, as noted above, the HRS-Fc conjugate pharmaceutical compositions are about 95% endotoxin free, preferably about 99% endotoxin free, and more preferably about 99.99% endotoxin free on wt/wt protein basis.

Pharmaceutical compositions comprising a therapeutic dose of a HRS-Fc conjugate polypeptide include all homologues, orthologs, and naturally-occurring isoforms of histidyl-tRNA synthetase.

In some embodiments such pharmaceutical compositions may comprise a histidine buffer, which may be present in any of the pharmaceutical compositions within the range of about 1 mM to about 100 mM. In some embodiments, the histidine buffer may be present at a concentration of about 1 mM, about 2 mM, about 3 mM, about 4 mM, about 5 mM, about 6 mM, about 7 mM, about 8 mM, about 9 mM, about 10 mM, about 11 mM, about 12 mM, about 13 mM, about 14 mM, about 15 mM, about 16 mM, about 17 mM, about 18 mM, about 19 mM, about 20 mM, about 25 mM, about 30 mM, about 40 mM, about 50 mM, about 60 mM, about 70 mM, about 80 mM, about 90 mM, or about 100 mM, including all integers and ranges in between said concentrations.

In one aspect such compositions may comprises HRS-Fc conjugate polypeptides that are substantially monodisperse, meaning that the HRS-Fc conjugate compositions exist primarily (i.e., at least about 90%, or greater) in one apparent molecular weight form when assessed for example, by size exclusion chromatography, dynamic light scattering, or analytical ultracentrifugation.

In another aspect, such compositions have a purity (on a protein basis) of at least about 90%, or in some aspects at least about 95% purity, or in some embodiments, at least 98% purity. Purity may be determined via any routine analytical method as known in the art.

In another aspect, such compositions have a high molecular weight aggregate content of less than about 10%, compared to the total amount of protein present, or in some embodiments such compositions have a high molecular weight aggregate content of less than about 5%, or in some aspects such compositions have a high molecular weight aggregate content of less than about 3%, or in some embodiments a high molecular weight aggregate content of less than about 1%. High molecular weight aggregate content may be determined via a variety of analytical techniques including for example, by size exclusion chromatography, dynamic light scattering, or analytical ultracentrifugation.

Pharmaceutical compositions may include pharmaceutically acceptable salts of a HRS-Fc conjugate polypeptide. For a review on suitable salts, see *Handbook of Pharmaceutical Salts: Properties, Selection, and Use* by Stahl and Wermuth (Wiley-VCH, 2002). Suitable base salts are formed from bases which form non-toxic salts. Representative examples include the aluminum, arginine, benzathine, calcium, choline, diethylamine, diolamine, glycine, lysine, magnesium, meglumine, olamine, potassium, sodium, tromethamine, and zinc salts. Hemisalts of acids and bases may also be formed, e.g., hemisulphate and hemicalcium salts. Compositions to be used in the invention suitable for parenteral administration may comprise sterile aqueous solutions and/or suspensions of the pharmaceutically active ingredients preferably made isotonic with the blood of the recipient, generally using sodium chloride, glycerin, glucose, mannitol, sorbitol, and the like. Organic acids suitable for forming pharmaceutically acceptable acid addition salts include, by way of example and not limitation, acetic acid, trifluoroacetic acid, propionic acid, hexanoic acid, cyclopentanepropionic acid, glycolic acid, oxalic acid, pyruvic acid, lactic acid, malonic acid, succinic acid, malic acid, maleic acid, fumaric acid, tartaric acid, citric acid, palmitic acid, benzoic acid, 3-(4-hydroxybenzoyl) benzoic acid, cinnamic acid, mandelic acid, alkylsulfonic acids (e.g., methanesulfonic acid, ethanesulfonic acid, 1,2-ethane-disulfonic acid, 2-hydroxyethanesulfonic acid), arylsulfonic acids (e.g., benzenesulfonic acid, 4-chlorobenzenesulfonic acid, 2-naphthalenesulfonic acid, 4-toluenesulfonic acid, camphorsulfonic acid), 4-methylbicyclo(2.2.2)-oct-2-ene-1-carboxylic acid, glucoheptonic acid, 3-phenylpropionic acid, trimethylacetic acid, tertiary butylacetic acid, lauryl sulfuric acid, gluconic acid, glutamic acid, hydroxynaphthoic acid, salicylic acid, stearic acid, muconic acid, and the like.

In particular embodiments, the carrier may include water. In some embodiments, the carrier may be an aqueous solution of saline, for example, water containing physiological concentrations of sodium, potassium, calcium, magnesium, and chloride at a physiological pH. In some embodiments, the carrier may be water and the formulation may further include NaCl. In some embodiments, the formulation may be isotonic. In some embodiments, the formulation may be hypotonic. In other embodiments, the formulation may be hypertonic. In some embodiments, the formulation may be isomostic. In some embodiments, the formulation is substantially free of polymers (e.g., gel-forming polymers, polymeric viscosity-enhancing agents). In some embodiments, the formulation is substantially free of viscosity-increasing agents (e.g., carboxymethylcellulose, polyanionic polymers). In some embodiments, the formulation is substantially free of gel-forming polymers. In some embodiments, the viscosity of the formulation is about the same as the viscosity of a saline solution containing the same concentration of a HRS-Fc conjugate (or a pharmaceutically acceptable salt thereof).

In the pharmaceutical compositions of the invention, formulation of pharmaceutically-acceptable excipients and carrier solutions is well-known to those of skill in the art, as is the development of suitable dosing and treatment regimens for using the particular compositions described herein in a variety of treatment regimens, including e.g., oral, parenteral, intravenous, intranasal, and intramuscular administration and formulation.

In certain embodiments, the HRS-Fc conjugate polypeptide have a solubility that is desirable for the particular mode of administration, such intravenous administration. Examples of desirable solubility's include at least about 1 mg/ml, at least about 10 mg/ml, at least about 25 mg/ml, and at least about 50 mg/ml.

In certain applications, the pharmaceutical compositions disclosed herein may be delivered via oral administration to a subject. As such, these compositions may be formulated with an inert diluent or with an edible carrier, or they may be enclosed in hard- or soft-shell gelatin capsule, or they may be compressed into tablets, or they may be incorporated directly with the food of the diet.

Pharmaceutical compositions suitable for the delivery of HRS-Fc conjugates and methods for their preparation will be readily apparent to those skilled in the art. Such compositions and methods for their preparation may be found, for example, in Remington's Pharmaceutical Sciences, 19th Edition (Mack Publishing Company, 1995).

Administration of a therapeutic dose of a HRS-Fc conjugate may be by any suitable method known in the medicinal arts, including for example, oral, intranasal, parenteral administration include intravitreal, subconjuctival, subtenon, retrobulbar, suprachoroidal intravenous, intra-arterial, intraperitoneal, intrathecal, intraventricular, intraurethral, intrasternal, intracranial, intramuscular, intrasynovial, intraocular, topical and subcutaneous. Suitable devices for parenteral administration include needle (including microneedle) injectors, needle-free injectors, and infusion techniques.

Parenteral formulations are typically aqueous solutions which may contain excipients such as salts, carbohydrates, and buffering agents (preferably to a pH of from 3 to 9), but, for some applications, they may be more suitably formulated as a sterile non-aqueous solution or as a dried form to be used in conjunction with a suitable vehicle such as sterile, pyrogen-free water. The preparation of parenteral formulations under sterile conditions, for instance, by lyophilization, may readily be accomplished using standard pharmaceutical techniques well-known to those skilled in the art.

Formulations for parenteral administration may be formulated to be immediate and/or sustained release. Sustained release compositions include delayed, modified, pulsed, controlled, targeted and programmed release. Thus a HRS-Fc conjugate may be formulated as a suspension or as a solid, semi-solid, or thixotropic liquid for administration as an implanted depot providing sustained release of HRS-Fc conjugates. Examples of such formulations include without limitation, drug-coated stents and semi-solids and suspensions comprising drug-loaded poly(DL-lactic-co-glycolic) acid (PGLA), poly(DL-lactide-co-glycolide) (PLG) or poly (lactide) (PLA) lamellar vesicles or microparticles, hydrogels (Hoffman AS: *Ann. N.Y. Acad. Sci.* 944: 62-73 (2001)), poly-amino acid nanoparticles systems, such as the Medusa system developed by Flamel Technologies Inc., non aqueous gel systems such as Atrigel developed by Atrix, Inc., and SABER (Sucrose Acetate Isobutyrate Extended Release) developed by Durect Corporation, and lipid-based systems such as DepoFoam developed by SkyePharma.

Solutions of the active compounds as free base or pharmacologically acceptable salts may be prepared in water suitably mixed with a surfactant, such as hydroxypropylcellulose. Dispersions may also be prepared in glycerol, liquid polyethylene glycols, and mixtures thereof and in oils. Under ordinary conditions of storage and use, these preparations contain a preservative to prevent the growth of microorganisms.

The pharmaceutical forms suitable for injectable use include sterile aqueous solutions or dispersions and sterile powders for the extemporaneous preparation of sterile injectable solutions or dispersions (U.S. Pat. No. 5,466,468, incorporated by reference in its entirety). In all cases the form should be sterile and should be fluid to the extent that easy syringability exists. It should be stable under the conditions of manufacture and storage and should be preserved against the contaminating action of microorganisms, such as bacteria and fungi. The carrier can be a solvent or dispersion medium containing, for example, water, ethanol, polyol (e.g., glycerol, propylene glycol, liquid polyethylene glycol, and the like), suitable mixtures thereof, and/or vegetable oils. Proper fluidity may be maintained, for example, by the use of a coating, such as lecithin, by the maintenance of the required particle size in the case of dispersion and by the use of surfactants. The prevention of the action of microorganisms can be facilitated by various antibacterial and antifungal agents, for example, parabens, chlorobutanol, phenol, sorbic acid, thimerosal, and the like. In many cases, it will be preferable to include isotonic agents, for example, sugars or sodium chloride. Prolonged absorption of the injectable compositions can be brought about by the use in the compositions of agents delaying absorption, for example, aluminum monostearate and gelatin.

For parenteral administration in an aqueous solution, for example, the solution should be suitably buffered if necessary and the liquid diluent first rendered isotonic with sufficient saline or glucose. These particular aqueous solutions are especially suitable for intravenous, intramuscular, subcutaneous and intraperitoneal administration. In this connection, a sterile aqueous medium that can be employed will be known to those of skill in the art in light of the present disclosure. For example, one dosage may be dissolved in 1 ml of isotonic NaCl solution and either added to 1000 ml of hypodermoclysis fluid or injected at the proposed site of infusion (see, e.g., *Remington's Pharmaceutical Sciences,* 15th Edition, pp. 1035-1038 and 1570-1580). Some variation in dosage will necessarily occur depending on the condition of the subject being treated. The person responsible for administration will, in any event, determine the appropriate dose for the individual subject. Moreover, for human administration, preparations should meet sterility, pyrogenicity, and the general safety and purity standards as required by FDA Office of Biologics standards.

Sterile injectable solutions can be prepared by incorporating the active compounds in the required amount in the appropriate solvent with the various other ingredients enumerated above, as required, followed by filtered sterilization. Generally, dispersions are prepared by incorporating the various sterilized active ingredients into a sterile vehicle which contains the basic dispersion medium and the required other ingredients from those enumerated above. In the case of sterile powders for the preparation of sterile injectable solutions, the preferred methods of preparation are vacuum-drying and freeze-drying techniques which yield a powder of the active ingredient plus any additional desired ingredient from a previously sterile-filtered solution thereof.

The compositions disclosed herein may be formulated in a neutral or salt form. Pharmaceutically-acceptable salts, include the acid addition salts (formed with the free amino groups of the protein) and which are formed with inorganic acids such as, for example, hydrochloric or phosphoric acids, or such organic acids as acetic, oxalic, tartaric, mandelic, and the like. Salts formed with the free carboxyl groups can also be derived from inorganic bases such as, for example, sodium, potassium, ammonium, calcium, or ferric hydroxides, and such organic bases as isopropylamine, trimethylamine, histidine, procaine and the like. Upon formulation, solutions will be administered in a manner compatible with the dosage formulation and in such amount as is therapeutically effective. The formulations are easily administered in a variety of dosage forms such as injectable solutions, drug-release capsules, and the like.

As used herein, "carrier" includes any and all solvents, dispersion media, vehicles, coatings, diluents, antibacterial and antifungal agents, isotonic and absorption delaying agents, buffers, carrier solutions, suspensions, colloids, and the like. The use of such media and agents for pharmaceutical active substances is well known in the art. Except insofar as any conventional media or agent is incompatible with the active ingredient, its use in the therapeutic compositions is contemplated. Supplementary active ingredients can also be incorporated into the compositions.

The phrase "pharmaceutically-acceptable" refers to molecular entities and compositions that do not produce an allergic or similar untoward reaction when administered to a human. The preparation of an aqueous composition that contains a protein as an active ingredient is well understood in the art. Typically, such compositions are prepared as injectables, either as liquid solutions or suspensions; solid forms suitable for solution in, or suspension in, liquid prior to injection can also be prepared. The preparation can also be emulsified.

HRS-Fc conjugate polypeptides for use in the present invention may also be administered topically, (intra)dermally, or transdermally to the skin, mucosa, or surface of the eye, either alone or in combination with one or more antihistamines, one or more antibiotics, one or more antifungal agents, one or more beta blockers, one or more anti-inflammatory agents, one or more antineoplastic agents, one or more immunosuppressive agents, one or more antiviral agents, one or more antioxidant agents, or other active agents. Formulations for topical and ocular administration may be formulated to be immediate and/or modified release. Modified release formulations include delayed, sustained, pulsed, controlled, targeted and programmed release.

Typical formulations for this purpose include gels, hydrogels, lotions, solutions, eye drops, creams, ointments, dusting powders, dressings, foams, films, skin patches, wafers, implants, sponges, fibers, bandages, and microemulsions. Liposomes may also be used. Typical carriers include alcohol, water, mineral oil, liquid petrolatum, white petrolatum, glycerin, polyethylene glycol, and propylene glycol. Penetration enhancers may be incorporated—see, e.g., Finnin and Morgan: *J. Pharm. Sci.* 88(10): 955-958, (1999). Other means of topical administration include delivery by electroporation, iontophoresis, phonophoresis, sonophoresis, and microneedle or needle-free injection (e.g., the systems sold under the trademarks POWDERJECT™, BIOJECT™).

Examples of antihistamines include, but are not limited to, loradatine, hydroxyzine, diphenhydramine, chlorpheniramine, brompheniramine, cyproheptadine, terfenadine, clemastine, triprolidine, carbinoxamine, diphenylpyraline, phenindamine, azatadine, tripelennamine, dexchlorpheniramine, dexbrompheniramine, methdilazine, and trimprazine doxylamine, pheniramine, pyrilamine, chiorcyclizine, thonzylamine, and derivatives thereof.

Examples of antibiotics include, but are not limited to, aminoglycosides (e.g., amikacin, apramycin, arbekacin, bambermycins, butirosin, dibekacin, dihydrostreptomycin, fortimicin(s), gentamicin, isepamicin, kanamycin, micronomicin, neomycin, neomycin undecylenate, netilmicin, paromomycin, ribostamycin, sisomicin, spectinomycin, streptomycin, tobramycin, trospectomycin), amphenicols (e.g., azidamfenicol, chloramphenicol, florfenicol, thiamphenicol), ansamycins (e.g., rifamide, rifampin, rifamycin sv, rifapentine, rifaximin), lactams (e.g., carbacephems (e.g., loracarbef), carbapenems (e.g., biapenem, imipenem, meropenem, panipenem), cephalosporins (e.g., cefaclor, cefadroxil, cefamandole, cefatrizine, cefazedone, cefazolin, cefcapene pivoxil, cefclidin, cefdinir, cefditoren, cefepime, cefetamet, cefixime, cefinenoxime, cefodizime, cefonicid, cefoperazone, ceforanide, cefotaxime, cefotiam, cefozopran, cefpimizole, cefpiramide, cefpirome, cefpodoxime proxetil, cefprozil, cefroxadine, cefsulodin, ceftazidime, cefteram, ceftezole, ceftibuten, ceftizoxime, ceftriaxone, cefuroxime, cefuzonam, cephacetrile sodium, cephalexin, cephaloglycin, cephaloridine, cephalosporin, cephalothin, cephapirin sodium, cephradine, pivcefalexin), cephamycins (e.g., cefbuperazone, cefinetazole, cefininox, cefotetan, cefoxitin), monobactams (e.g., aztreonam, carumonam, tigemonam), oxacephems, flomoxef, moxalactam), penicillins (e.g., amdinocillin, amdinocillin pivoxil, amoxicillin, ampicillin, apalcillin, aspoxicillin, azidocillin, azlocillin, bacampicillin, benzylpenicillinic acid, benzylpenicillin sodium, carbenicillin, carindacillin, clometocillin, cloxacillin, cyclacillin, dicloxacillin, epicillin, fenbenicillin, floxacillin, hetacillin, lenampicillin, metampicillin, methicillin sodium, mezlocillin, nafcillin sodium, oxacillin, penamecillin, penethamate hydriodide, penicillin g benethamine, penicillin g benzathine, penicillin g benzhydrylamine, penicillin g calcium, penicillin g hydrabamine, penicillin g potassium, penicillin g procaine, penicillin n, penicillin o, penicillin v, penicillin v benzathine, penicillin v hydrabamine, penimepicycline, phenethicillin potassium, piperacillin, pivampicillin, propicillin, quinacillin, sulbenicillin, sultamicillin, talampicillin, temocillin, ticarcillin), other (e.g., ritipenem), lincosamides (e.g., clindamycin, lincomycin), macrolides (e.g., azithromycin, carbomycin, clarithromycin, dirithromycin, erythromycin, erythromycin acistrate, erythromycin estolate, erythromycin glucoheptonate, erythromycin lactobionate, erythromycin propionate, erythromycin stearate, josamycin, leucomycins, midecamycins, miokamycin, oleandomycin, primycin, rokitamycin, rosaramicin, roxithromycin, spiramycin, troleandomycin), polypeptides (e.g., amphomycin, bacitracin, capreomycin, colistin, enduracidin, enviomycin, fusafungine, gramicidin s, gramicidin(s), mikamycin, polymyxin, pristinamycin, ristocetin, teicoplanin, thiostrepton, tuberactinomycin, tyrocidine, tyrothricin, vancomycin, viomycin, virginiamycin, zinc bacitracin), tetracyclines (e.g., apicycline, chlortetracycline, clomocycline, demeclocycline, doxycycline, guamecycline, lymecycline, meclocycline, methacycline, minocycline, oxytetracycline, penimepicycline, pipacycline, rolitetracycline, sancycline, tetracycline), and others (e.g., cycloserine, mupirocin, tuberin). 2,4-Diaminopyrimidines (e.g., brodimoprim, tetroxoprim, trimethoprim), nitrofurans (e.g., furaltadone, furazolium chloride, nifuradene, nifuratel, nifurfoline, nifurpirinol, nifurprazine, nifurtoinol, nitrofurantoin), quinolones and analogs (e.g., cinoxacin, ciprofloxacin, clinafloxacin, difloxacin, enoxacin, fleroxacin, flumequine, grepafloxacin, lomefloxacin, miloxacin, nadifloxacin, nalidixic acid, norfloxacin, ofloxacin, oxolinic acid, pazufloxacin, pefloxacin, pipemidic acid, piromidic acid, rosoxacin, rufloxacin, sparfloxacin, temafloxacin, tosufloxacin, trovafloxacin), sulfonamides (e.g., acetyl sulfamethoxypyrazine, benzylsulfamide, chloramine-b, chloramine-t, dichloramine t, $n^2$-formylsulfisomidine, mafenide, 4'-(methylsulfamoyl)sulfanilanilide, noprylsulfamide, phthalylsulfacetamide, phthalylsulfathiazole, salazosulfadimidine, succinylsulfathiazole, sulfabenzamide, sulfacetamide, sulfachlorpyridazine, sulfachrysoidine, sulfacytine, sulfadiazine, sulfadicramide, sulfadimethoxine, sulfadoxine, sulfaethidole, sulfaguanidine, sulfaguanol, sulfalene, sulfaloxic acid, sulfamerazine, sulfameter, sulfamethazine, sulfamethizole, sulfamethomidine, sulfamethoxazole, sulfamethoxypyridazine, sulfametrole, sulfamidochrysoidine, sulfamoxole, sulfanilamide, 4-sulfanilamidosalicylic acid, $n^4$-sulfanilylsulfanilamide, sulfanilylurea, n-sulfanilyl-3,4-xylamide, sulfanitran, sulfaperine, sulfaphenazole, sulfaproxyline, sulfapyrazine, sulfapyridine, sulfasomizole, sulfasymazine, sulfathiazole, sulfathiourea, sulfatolamide, sulfisomidine, sulfisoxazole) sulfones (e.g., acedapsone, acediasulfone, acetosulfone sodium, dapsone, diathymosulfone, glucosulfone sodium, solasulfone, succisulfone, sulfanilic acid, p-sulfanilylbenzylamine, sulfoxone sodium, thiazolsulfone), and others (e.g., clofoctol, hexedine, methenamine, methenamine anhydromethylene-citrate, methenamine hippurate, methenamine mandelate, methenamine sulfosalicylate, nitroxoline, taurolidine, xibornol).

Examples of antifungal agents include, but are not limited to Polyenes (e.g., amphotericin b, candicidin, dermostatin, filipin, fungichromin, hachimycin, hamycin, lucensomycin, mepartricin, natamycin, nystatin, pecilocin, perimycin), others (e.g., azaserine, griseofulvin, oligomycins, neomycin undecylenate, pyrrolnitrin, siccanin, tubercidin, viridin), Allylamines (e.g., butenafine, naftifine, terbinafine), imidazoles (e.g., bifonazole, butoconazole, chlordantoin, chlormidazole, cloconazole, clotrimazole, econazole, enilconazole, fenticonazole, flutrimazole, isoconazole, ketoconazole, lanoconazole, miconazole, omoconazole, oxiconazole nitrate, sertaconazole, sulconazole, tioconazole), thiocarbamates (e.g., tolciclate, tolindate, tolnaftate), triazoles (e.g., fluconazole, itraconazole, saperconazole, terconazole) others (e.g., acrisorcin, amorolfine, biphenamine, bromosalicylchloranilide, buclosamide, calcium propionate, chlorphenesin, ciclopirox, cloxyquin, coparaffinate, diamthazole dihydrochloride, exalamide, flucytosine, halethazole, hexetidine, loflucarban, nifuratel, potassium iodide, propionic acid, pyrithione, salicylanilide, sodium propionate, sulbentine, tenonitrozole, triacetin, ujothion, undecylenic acid, zinc propionate).

Examples of beta blockers include but are not limited to acebutolol, atenolol, labetalol, metoprolol, propranolol, timolol, and derivatives thereof.

Examples of antineoplastic agents include, but are not limited to antibiotics and analogs (e.g., aclacinomycins, actinomycin $f_1$, anthramycin, azaserine, bleomycins, cactinomycin, carubicin, carzinophilin, chromomycins, dactinomycin, daunorubicin, 6-diazo-5-oxo-L-norleucine, doxorubicin, epirubicin, idarubicin, menogaril, mitomycins, mycophenolic acid, nogalamycin, olivomycines, peplomycin, pirarubicin, plicamycin, porfiromycin, puromycin, streptonigrin, streptozocin, tubercidin, zinostatin, zorubicin), antimetabolites (e.g. folic acid analogs (e.g., denopterin, edatrexate, methotrexate, piritrexim, pteropterin, Tomudex®, trimetrexate), purine analogs (e.g., cladribine, fludarabine, 6-mercaptopurine, thiamiprine, thioguanine), pyrimidine analogs (e.g., ancitabine, azacitidine, 6-azauridine, carmofur, cytarabine, doxifluridine, emitefur, enocitabine, floxuridine, fluorouracil, gemcitabine, tagafur).

Examples of anti-inflammatory agents include but are not limited to steroidal anti-inflammatory agents and non-steroidal anti-inflammatory agents. Exemplary steroidal anti-inflammatory agents include acetoxypregnenolone, alclometasone, algestone, amcinonide, beclomethasone, betamethasone, budesonide, chloroprednisone, clobetasol, clobetasone, clocortolone, cloprednol, corticosterone, cortisone, cortivazol, deflazacort, desonide, desoximetasone, dexamethasone, diflorasone, diflucortolone, difluprednate, enoxolone, fluazacort, flucloronide, flumethasone, flunisolide, fluocinolone acetonide, fluocinonide, fluocortin butyl, fluocortolone, fluorometholone, fluperolone acetate, fluprednidene acetate, fluprednisolone, flurandrenolide, fluticasone propionate, formocortal, halcinonide, halobetasol propionate, halometasone, halopredone acetate, hydrocortamate, hydrocortisone, loteprednol etabonate, mazipredone, medrysone, meprednisone, methylprednisolone, mometasone furoate, paramethasone, prednicarbate, prednisolone, prednisolone 25-diethylamino-acetate, prednisolone sodium phosphate, prednisone, prednival, prednylidene, rimexolone, tixocortol, triamcinolone, triamcinolone acetonide, triamcinolone benetonide, and triamcinolone hexacetonide.

Exemplary non-steroidal anti-inflammatory agents include aminoarylcarboxylic acid derivatives (e.g., enfenamic acid, etofenamate, flufenamic acid, isonixin, meclofenamic acid, mefenamic acid, niflumic acid, talniflumate, terofenamate, tolfenamic acid), arylacetic acid derivatives (e.g., aceclofenac, acemetacin, alclofenac, amfenac, amtolmetin guacil, bromfenac, bufexamac, cinmetacin, clopirac, diclofenac sodium, etodolac, felbinac, fenclozic acid, fentiazac, glucametacin, ibufenac, indomethacin, isofezolac, isoxepac, lonazolac, metiazinic acid, mofezolac, oxametacine, pirazolac, proglumetacin, sulindac, tiaramide, tolmetin, tropesin, zomepirac), arylbutyric acid derivatives (e.g., bumadizon, butibufen, fenbufen, xenbucin), arylcarboxylic acids (e.g., clidanac, ketorolac, tinoridine), arylpropionic acid derivatives (e.g., alminoprofen, benoxaprofen, bermoprofen, bucloxic acid, carprofen, fenoprofen, flunoxaprofen, flurbiprofen, ibuprofen, ibuproxam, indoprofen, ketoprofen, loxoprofen, naproxen, oxaprozin, piketoprolen, pirprofen, pranoprofen, protizinic acid, suprofen, tiaprofenic acid, ximoprofen, zaltoprofen), pyrazoles (e.g., difenamizole, epirizole), pyrazolones (e.g., apazone, benzpiperylon, feprazone, mofebutazone, morazone, oxyphenbutazone, phenylbutazone, pipebuzone, propyphenazone, ramifenazone, suxibuzone, thiazolinobutazone), salicylic acid derivatives (e.g., acetaminosalol, aspirin, benorylate, bromosaligenin, calcium acetylsalicylate, diflunisal, etersalate, fendosal, gentisic acid, glycol salicylate, imidazole salicylate, lysine acetylsalicylate, mesalamine, morpholine salicylate, 1-naphthyl salicylate, olsalazine, parsalmide, phenyl acetylsalicylate, phenyl salicylate, salacetamide, salicylamide o-acetic acid, salicylsulfuric acid, salsalate, sulfasalazine), thiazinecarboxamides (e.g., ampiroxicam, droxicam, isoxicam, lornoxicam, piroxicam, tenoxicam), ε-acetamidocaproic acid, s-adenosylmethionine, 3-amino-4-hydroxybutyric acid, amixetrine, bendazac, benzydamine, bucolome, difenpiramide, ditazol, emorfazone, fepradinol, guaiazulene, nabumetone, nimesulide, oxaceprol, paranyline, perisoxal, proquazone, superoxide dismutase, tenidap, and zileuton.

Examples of antiviral agents include interferon gamma, zidovudine, amantadine hydrochloride, ribavirin, acyclovir, valciclovir, dideoxycytidine, phosphonoformic acid, ganciclovir, and derivatives thereof Examples of antioxidant agents include ascorbate, alpha-tocopherol, mannitol, reduced glutathione, various carotenoids, cysteine, uric acid, taurine, tyrosine, superoxide dismutase, lutein, zeaxanthin, cryotpxanthin, astazanthin, lycopene, N-acetyl-cysteine, carnosine, gamma-glutamylcysteine, quercitin, lactoferrin, dihydrolipoic acid, citrate, *Ginkgo Biloba* extract, tea catechins, bilberry extract, vitamins E or esters of vitamin E, retinyl palmitate, and derivatives thereof. Other therapeutic agents include squalamine, carbonic anhydrase inhibitors, alpha-2 adrenergic receptor agonists, antiparasitics, antifungals, and derivatives thereof.

The exact dose of each component administered will, of course, differ depending on the specific components prescribed, on the subject being treated, on the severity of the disease, for example, severity of the inflammatory reaction, on the manner of administration and on the judgment of the prescribing physician. Thus, because of patient-to-patient variability, the dosages given above are a guideline and the physician may adjust doses of the compounds to achieve the treatment that the physician considers appropriate.

As will be understood by the skilled artisan, for HRS-Fc conjugate formulations where the carrier includes a gel-forming polymer, in certain formulations the inclusion of salt(s), in particular saline solution, is contraindicated as inclusion of salt may either cause the solution to gel prior to topical administration, as with certain in situ gel-forming polymers (e.g., gellan gel), or the inclusion of salts may inhibit the gelling properties of the gel-forming polymer. The skilled artisan will be able to select appropriate combinations based on the desired properties of the formulation and characteristics of gel-forming polymers known in the art.

Suitable aqueous saline solutions will be understood by those of skill in the art and may include, for example, solutions at a pH of from about pH 4.5 to about pH 8.0. In further variations of aqueous solutions (where water is included in the carrier), the pH of the formulation is between any of about 6 and about 8.0; between about 6 and about 7.5; between about 6 and about 7.0; between about 6.2 and about 8; between about 6.2 and about 7.5; between about 7 and about 8; between about 6.2 and about 7.2; between about 5.0 and about 8.0; between about 5 and about 7.5; between about 5.5 and about 8.0; between about 6.1 and about 7.7; between about 6.2 and about 7.6; between about 7.3 and about 7.4; about 6.0; about 7.1; about 6.2; about 7.3; about 6.4; about 6.5; about 6.6; about 6.7; about 6.8; about 6.9; about 7.0; about 7.1; about 7.2; about 7.3; about 7.4; about 7.5; about 7.6; or about 8.0. In some variations, the HRS-Fc conjugate formulation has a pH of about 6.0 to about 7.0. In some variations, the formulation has a pH of about 7.4. In particular variations, the formulation has a pH of about 6.2 to about 7.5.

In certain embodiments the concentration of the salt (e.g., NaCl) will be, for example, from about 0% to about 0.9% (w/v). For example, the concentration of salt may be from about 0.01 to about 0.9%, from about 0.02% to about 0.9%, from about 0.03% to about 9%, from about 0.05% to about 0.9% from about 0.07% to about 0.9%, from about 0.09% to about 0.9%, from about 0.1% to about 0.9% from about 0.2% to about 0.9%, from about 0.3% to about 0.9%, from about 0.4% to about 0.9% from about 0.5% to about 0.9%, from about 0.6% to about 0.9%, from about 0.7% to about 0.9%, from about 0.8% to about 0.9%, about 0.9%, about 0%, about 0.05%, about 0.01%, about 0.09%, about 0.1%, about 0.2%, about 0.3%, about 0.4%, about 0.5%, about 0.6%, about 0.7%, or about 0.8%. In certain embodiments, the aqueous saline solution will be isotonic (e.g., NaCl concentration of about 0.9% NaCl (w/v)). In certain embodiments, the aqueous solution will contain a NaCl concentration of about 0.5%, about 0.7%, about 0.8%, about 0.85, or about 0.75%. As will be appreciated the skilled artisan, depending on the concentrations of other components, for example where the HRS-Fc conjugates are present as salts of, the concentration of NaCl or other salt needed to achieve an formulation suitable for administration may vary.

In some embodiments, where the formulation is substantially free of viscosity-increasing agents, the formulation may be substantially free of viscosity-increasing agents such as, but not limited to polyanionic polymers, water soluble cellulose derivatives (e.g., hypromellose (also known as HPMC, hydroxypropylmethyl cellulose, and hydroxypropylcellulose), hydroxyethylcellulose, carboxmethylcellulose, etc.), polyvinyl alcohol, polyvinyl pyrrolidone, chondroitin sulfate, hyaluronic acid, soluble starches, etc. In some variations, the formulation does not incorporate a hydrogel or other retention agent (e.g., such as those disclosed in U.S. Pat. Pub. No. 2005/0255144 (incorporated by reference herein in its entirety)), e.g., where the hydrogel may include hydrogels incorporating homopolymers; copolymers (e.g., tetrapolymers of hydroxymethylmethacrylate, ethylene glycol, dimethylmethacrylate, and methacrylic acid), copolymers of trimethylene carbonate and polyglycolicacid, polyglactin 910, glyconate, poly-p-dioxanone, polyglycolic acid, polyglycolic acid felt, poly-4-hydroxybutyrate, a combination of poly(L-lactide) and poly(L-lactide-co-glycolide), glycol methacrylate, poly-DL-lactide, or Primacryl); composites of oxidized regenerated cellulose, polypropylene, and polydioxanone or a composite of polypropylene and poligelcaprone; etc. In some variations, the formulations do not include one or more of polyvinyl alcohol, hydroxypropyl methylcellulose, polyethylene glycol 400 castor oil emulsion, carboxymethylcellulose sodium, propylene glycol, hydroxypropyl guar, carboxymethylcelluose sodium, white petrolatum, mineral oil, dextran 70, glycerin, hypromellose, flaxseed oil, fish oils, omega 3 and omega 6 fatty acids, lutein, or primrose oil. In some variations, the formulations do not include one or more of the carriers described in U.S. Pat. No. 4,888,354 (incorporated by reference herein in its entirety), e.g., such as one or more of oleic acid, ethanol, isopropanol, glycerol monooleate, glycerol diooleate, methyl laurate, propylene glycol, propanol or dimethyl sulfoxide. In some variations, the formulations are substantially free of glycerol diooleate and isopropanol.

In particular embodiments, the gel-forming polymer may be, for example, a polysaccharide. In certain embodiments, the polysaccharide is gellan gum. Gellan gum refers to a heteropolysaccharide elaborated by the bacterium *Pseudomonas elodea*, though the name "gellan gum" is more commonly used in the field. Gellan gum, in particular the formulation GELRITE® is described in detail in U.S. Pat. No. 4,861,760 (hereby incorporated by reference in its entirety), in particular in its use in formulation of timolol. GELRITE®, a low acetyl clarified grade of gellan gum, is commercially available from Merck & Co (Rahway, N.J.) and gellan gum can be commercially obtained from, among others CPKelco (Atlanta, Ga.). The preparation of polysaccharides such as gellan gum is described in, for example, U.S. Pat. Nos. 4,326,053 and 4,326,052, which are hereby incorporated by reference in their entirety.

In certain embodiments, the gel-forming polymer is present at a concentration of from about 0.03% to about 2% (w/v). In some embodiments, the gel-forming polymer is present at a concentration from about 0.03% to about 1.75%; from about 0.03% to about 1.5%, from about 0.03% to about 1.25%, from about 0.03% to about 1%, from about 0.03% to about 0.9%, from about 0.03% to about 0.8%, from about 0.03% to about 0.7%, from about 0.03% to about 0.6%, from about 0.03% to about 0.5%, from about 0.05% to about 2%, from about 0.05% to about 1.75%; from about 0.05% to about 1.5%, from about 0.05% to about 1.25%, from about 0.05% to about 1%, from about 0.05% to about 0.9%, from about 0.05% to about 0.8%, from about 0.05% to about 0.7%, from about 0.05% to about 0.6%, from about 0.05% to about 0.5%, from about 0.1% to about 2%, from about 0.1% to about 1.75%; from about 0.1% to about 1.5%, from about 0.1% to about 1.25%, from about 0.1% to about 1%, from about 0.1% to about 0.9%, from about 0.1% to about 0.8%, from about 0.1% to about 0.7%, from about 0.1% to about 0.6%, from about 0.1% to about 0.5%, from about 0.2% to about 2%, from about 0.2% to about 1.75%; from about 0.2% to about 1.5%, from about 0.2% to about 1.25%, from about 0.2% to about 1%, from about 0.2% to about 0.9%, from about 0.2% to about 0.8%, from about 0.2% to about 0.7%, from about 0.2% to, about 0.6%, from about 0.2% to about 0.5%, or from about 0.5% to about 1.5%. In some embodiments, the concentration of gel-forming polymer is about 0.1%, about 0.2%, about 0.4%, about 0.6%, about 0.8%, about 1%.

In particular embodiments, the gel-forming polymer is gellan gum at a concentration of from about 0.05% to about 2% (w/v), from about 0.1% to about 2% (w/v), from about 0.1% to about 1% (w/v), from about 0.05% to about 1% (w/v) or from about 0.1% to about 0.6% (w/v). In some embodiments, the concentration of gellan gum is about 0.1%, about 0.2%, about 0.4%, about 0.6%, about 0.8%, about 1%.

In some embodiments of the formulations, the formulation may include additional components such as one or more preservatives, one or more surfactants, or one or more pharmaceutical agents. In particular embodiments, the formulation may include additional components such as one or more preservatives, one or more surfactants, one or more tonicity agents, one or more buffering agents, one or more chelating agents, one or more viscosity-increasing agents, one or more salts, or one or more pharmaceutical agents. In certain of these embodiments, the formulation may include (in addition to a HRS-Fc conjugate (or a pharmaceutically acceptable salt thereof) and carrier): one or more preservatives, one or more buffering agents (e.g., one, two, three, etc.), one or more chelating agents, and one or more salts. In some embodiments, the formulation may include (in addition to a HRS-Fc conjugate (or a pharmaceutically acceptable salt thereof) and carrier): one or more preservatives, one or more tonicity agents, one or more buffering agents, one or more chelating agents, and one or more viscosity-increasing agents.

In some embodiments, the viscosity of the formulation is about the same as the viscosity of a saline solution containing the same concentration of a HRS-Fc conjugate (or a pharmaceutically acceptable salt thereof). In some embodiments, the formulation is substantially free of gel-forming polymers. In certain embodiments, where the carrier is water, the formulation may additionally include one or more chelating agents (e.g., EDTA disodium (EDTA), one or more preservatives (e.g., benzalkonium chloride, benzethonium chloride, chlorhexidine, chlorobutanol, methylparaben, phenylethyl alcohol, propylparaben, thimerosal, phenylmercuric nitrate, phenylmercuric borate, phenylmercuric acetate, or combinations of two or more of the foregoing), salt (e.g., NaCl) and one or more buffering agents (e.g., one or more phosphate buffers (e.g., dibasic sodium phosphate, monobasic sodium phosphate, combinations thereof, etc.), citrate buffers, maleate buffers, borate buffers, and combination of two or more of the foregoing.).

In particular embodiments, the chelating agent is EDTA disodium, the preservative is benzalkonium chloride, the salt is NaCl, and the buffering agents are dibasic sodium phosphate and monobasic sodium phosphate. In certain of these embodiments, the formulation is substantially free of polymer. In some embodiments, the formulation is substantially free of substantially viscosity-increasing agent(s) (e.g., carboxymethylcellulose, polyanionic polymers, etc.). In some embodiments, the viscosity of the formulation is about the same as the viscosity of a saline solution containing the same concentration of a HRS-Fc conjugate (or a pharmaceutically acceptable salt thereof). In some of these embodiments, the concentration of a HRS-Fc conjugate (or a pharmaceutically acceptable salt thereof) if from about 0.02% to about 3%, from about 0.02% to about 2%, from about 0.02% to about 1% (w/v). In certain embodiments, the concentration of a HRS-Fc conjugate (or a pharmaceutically acceptable salt thereof), is about 0.01%, about 0.02%, about 0.03%, about 0.05%, about 0.07%, about 0.1%, about 0.3%, about 0.4%, about 0.5%, about 0.6%, about 0.8% or about 1% (w/v).

In certain embodiments, where the carrier includes water, a viscosity-increasing agent may also be included in the formulation. The skilled artisan will be familiar with viscosity-increasing agents that are suitable (e.g., water-soluble cellulose derivatives (e.g., hypromellose (also known as HPMC, hydroxypropylmethyl cellulose, and hydroxypropylcellulose), hydroxyethylcellulose, carboxmethylcellulose, etc.), polyvinyl alcohol, polyvinyl pyrrolidone, chondroitin sulfate, hyaluronic acid, and soluble starches. It is intended that when viscosity-increasing agents are used, they are not included in high enough concentrations such that the formulation would form a gel prior to or after administration (e.g., wherein the concentration of the viscosity-increasing agent is not sufficient to induce gel formation).

While exact concentrations of viscosity-increasing agents will depend upon the selection and concentration of other components in the formulation as well as the particular viscosity-increasing agent(s) selected, in general, viscosity-increasing agents may be present in a concentration such that the viscosity of the resulting solution is less than about 1000 centipoise. In certain embodiments, the viscosity of the formulation is less than about 900, less than about 800, less than about 700, less than about 600, less than about 500, less than about 400, less than about 300, less than about 200, less than about 150, less than about 100, less than about 50 centipoise. In some embodiments, the viscosity of the formulation is about 200, about 150, about 100, about 50 centipoise. In particular embodiments, the viscosity is less than about 200 centipoise. In others, less than about 120 centipoise or less than about 100 centipoise. In some embodiments, the viscosity is about 100 centipoise. In others about 50 centipoise. In still other embodiments the viscosity is about 200 centipoise. Methods for measuring viscosity are well known to the skilled artisan. For example, as described in United States Pharmacopoeia 29 (Chapter 911) Viscosity, page 2785 (which is herein incorporated by reference in its entirety). As is well known to the skilled artisan, formulations commonly considered "gels" will have viscosity significantly greater than 1000 centipoise, for example, greater than about 2000 centipoise, greater than about 5000 centipoise.

In some embodiments, including (but not limited to) where the use of salts is contraindicated as described above, the formulation may further include one or more tonicity agents. As used herein, the term "tonicity agent" and its cognates refers to agents that adjust the tonicity of the formulation, but are not salts (e.g., not NaCl), which, as will be appreciated by the skill artisan in view of the teaching provided herein, are contraindicated for some formulations due to the presence of certain of the gel-forming polymers or viscosity-increasing agents. These agents may be used to prepare formulations that are isotonic or near isotonic (e.g., somewhat hyper- or hypo-isotonic; e.g., within about ±20%, about ±15%, about ±10%, about ±5% of being isotonic). Tonicity agent(s) may also be used in formulations where the use of salts is not contraindicated.

Tonicity agents that may be used to adjust the tonicity of formulation the formulations described herein and are known to the skilled artisan and can be selected based on the teaching provided herein. For example, tonicity agents include polyols (e.g., sugar alcohols (e.g., mannitol, etc.), trihydroxy alcohols (e.g., glycerin, etc.), propylene glycol or polyethylene glycol, etc.), or combinations of two or more polyols. Likewise, the concentration of the tonicity agent(s) will depend upon the identity and concentrations of the other components in the formulation and can be readily determined by the skilled artisan in view of the teaching provided herein.

In certain embodiments, the tonicity agent is glycerin or mannitol. In some embodiments, the tonicity agent is glycerin. In other embodiments it is, mannitol. In still others a combination of mannitol and glycerin may be used. Exemplary concentrations of tonicity agents include, for example from about 0.001 to about 3%. In some embodiments, the concentration of the tonicity agent (e.g., mannitol or glycerin) is, for example, about 0.001% to about 2.7%, about 0.001% to about 2.5%, about 0.001% to about 2%, about 0.001% to about 1.5%, about 0.001% to about 1%, about 0.01% to about 3%, about 0.01% to about 2.7%, about 0.01% to about 2.5%, about 0.01% to about 2%, about 0.01% to about 1.5%, about 0.01% to about 1%, about 0.1% to about 3%, about 0.1% to about 2.7%, about 0.1% to about 2.5%, about 0.1% to about 2%, about 0.1% to about 1.5%, about 0.1% to about 1%, about 0.01% about 1% to about 3%; about 1% to about 2.5%; about 1% to about 2%; about 1% to about 1.8%; about 1% to about 1.5%; or about 0.001%, about 0.01%, about 0.05%, about 0.08%, about 0.1%, about 0.2%, about 0.5%, about 0.8%, about 1%, about 1.5%, about 1.8%, about 2%, about 2.2%, about 2.5%, about 2.8%, or about 3% (w/v). In certain embodiments, the tonicity agent is mannitol. In some of these embodiments, the carrier includes a gel-forming agent (e.g., gellan gum).

In some embodiments, the tonicity agent is mannitol. In certain of these embodiments, the carrier includes a viscosity-increasing agent (e.g., water soluble cellulose derivatives (e.g., hypromellose), polyvinyl alcohol, polyvinyl pyrrolidone, chondroitin sulfate, hyaluronic acid, or soluble starches).

In some embodiments, the formulation may additionally include a preservative (e.g., benzalkonium chloride, benzethonium chloride, chlorhexidine, chlorobutanol, methylparaben, Phenylethyl alcohol, propylparaben, thimerosal, phenylmercuric nitrate, phenylmercuric borate, or phenylmercuric acetate, peroxides), or a combination of two or more of the foregoing preservatives. In certain embodiments, the preservative is benzalkonium chloride.

As will be appreciated by the skilled artisan, preservatives may be present in concentrations of from about 0.001% to about 0.7% (w/v). In particular embodiments, the preservative(s) may be present in a concentration of from about 0.001% to about 0.5% (w/v); from about 0.001% to about 0.05% (w/v), from about 0.001% to about 0.02% (w/v), from about 0.001% to about 0.015% (w/v), from about 0.001% to about 0.005% (w/v), from about 0.01% to about 0.02%, from about 0.002% to about 0.01%, from about 0.015% to about 0.05%, less than about <0.5%, from about 0.005% to about 0.01%, from about 0.001% to about 0.15%, from about 0.002% to about 0.004%, from about 0.001% to about 0.002%. In some embodiments the concentration of the preservative may be, for example, about 0.001%, about 0.005%, about 0.01%, about 0.02%, about 0.03%, about 0.05%, about 0.1%, about 0.2%, about 0.5%, or about 0.7% (w/v). Typical concentrations (w/v) for various commonly used preservatives are listed in Table C below.

TABLE C

| Preservative | Approximate Concentration Range (w/v) |
|---|---|
| Benzalkonium chloride | 0.01-0.02% |
| Benzethonium chloride | 0.01-0.02% |
| Chlorhexidine | 0.002-0.01% |
| Chlorobutanol | <0.5% |
| Methylparaben | 0.015-0.05% |
| Phenylethyl alcohol | <0.5% |
| Propylparaben | 0.005-0.01% |
| Thimerosal | 0.001-0.15% |
| Phenylmercuric nitrate | 0.002-0.004% |
| Phenylmercuric borate | 0.002-0.004 |
| Phenylmercuric acetate | 0.001-0.002 |

In certain embodiments, the formulation may additionally include a surfactant, or combinations of two or more surfactants. In particular embodiments, the formulation is substantially free of surfactant. As used herein, the term "substantially free" is intended to refer to levels of a particular component that are undetectable using routine detection methods and protocols known to the skilled artisan. For example, HPLC (including chiral HPLC, chiral HPLC/MS, LC/MS/MS etc.), thin layer chromatography, mass spectrometry, polarimetry measurements, gas-chromatography-mass spectrometry, or others.

In particular embodiments, the formulation may further include a chelating agent (e.g., EDTA disodium (EDTA) (e.g., EDTA disodium (dihydrate), etc.) citrates, etc.). In some embodiments, a combination of chelating agents may be present. As will be appreciated by those of skill in the field, chelating agents can be used to hinder degradation of the formulation components and thereby increase the shelf life of formulations. As will be appreciated by the skilled artisan, use of EDTA in combination with gellan gum formulation may be contraindicated as the EDTA can cause gel formation prior to administration of the gellan gum formulation.

Typical concentrations for chelating agents are from about 0.005% to 0.1% (w/v). For example, from about 0.005% to about 0.09%, from about 0.005% to about 0.08%, from about 0.005% to about 07%, from about 0.005%, to about 0.06%, from about 0.005% to about 0.05%, from about 0.005 to about 0.04%, from about 0.005% to about 0.03%, from about 0.01% to about 0.1%, from about 0.01% to about 0.09%, from about 0.01% to about 0.08%, from about 0.01% to about 0.07%, from about 0.01% to about 0.06%, from about 0.01% to about 0.05%, from about 0.01% to about 0.04%, etc. In certain embodiments, the concentration of chelating agent(s) is about 0.005%, about 0.01%, about 0.02%, about 0.03%, about 0.05%, about 0.06%, about 0.07%, about 0.08%, about 0.09%, or about 0.1%.

In particular embodiments, the chelating agent is EDTA disodium. In certain embodiments, the chelating agent is EDTA disodium (dihydrate). In some of these embodiments, the EDTA disodium dihydrate is present at a concentration of about 0.01% (w/v).

In some embodiments, the formulation may additionally include one or more buffering agents (e.g., phosphate buffer(s) (e.g., sodium phosphate buffers (e.g., dibasic sodium phosphate, monobasic sodium phosphate, etc.), citrate buffers, maleate buffers, borate buffers, etc.). As will be appreciated by the skilled artisan, the one or more buffering agent(s) should be selected in combination with the other components of a given formulation to achieve a pH suitable for use (e.g., pH of about 4.5 to about 8).

In certain embodiments, the buffering agent is a phosphate buffer or combination of two or more phosphate buffers. In certain embodiments, the buffering agents are dibasic sodium phosphate and monobasic sodium phosphate.

Typical concentrations for buffering agent(s) for example, phosphate buffering agent(s) may be from about 0.005 molar to 0.1 molar. In some embodiments, the buffering agent(s) may be at a concentration of about 0.01 to about 0.1, from about 0.01 to about 0.08, from about 0.01 to about 0.05, from about 0.01 to about 0.04, from about 0.02 to about 0.1, from about 0.02 to about 0.08, from about 0.02 to about 0.06, from about 0.02 to about 0.05, from about 0.02 to about 0.04 molar, etc. In particular embodiments, there are two buffering agents. Exemplary buffering agents include a combination of dibasic sodium phosphate (e.g., dibasic sodium phosphate.$7H_2O$) and monobasic sodium phosphate (e.g., monobasic sodium phosphate anhydrous). In some embodiments, the concentration of the buffering agent(s) is about 0.005 molar, about 0.01 molar, about 0.02 molar, about 0.03 molar, about 0.04 molar, about 0.05 molar, about 0.06 molar, about 0.07 molar, or about 0.1 molar.

An additional aspect of the invention includes use of the formulations as described herein in the manufacture of a medicament. Particularly, the manufacture of a medicament for use in the treatment and/or prevention of conditions as described herein. Further, the formulations, variously described herein, are also intended for use in the manufacture of a medicament for use in treatment and/or prevention of the conditions and, in accordance with the methods, described herein, unless otherwise noted.

Methods of formulation are well known in the art and are disclosed, for example, in Remington: The Science and Practice of Pharmacy, Mack Publishing Company, Easton, Pa., 19th Edition (1995). The compositions and agents provided herein may be administered according to the methods of the present invention in any therapeutically effective dosing regimen. The dosage amount and frequency are selected to create an effective level of the agent without harmful effects. The effective amount of a compound of the present invention will depend on the route of administration, the type of warm-blooded animal being treated, and the physical characteristics of the specific warm-blooded animal under consideration. These factors and their relationship to determining this amount are well known to skilled practitioners in the medical arts. This amount and the method of administration can be tailored to achieve optimal efficacy but will depend on such factors as weight, diet, concurrent medication and other factors which those skilled in the medical arts will recognize.

In certain embodiments, the pharmaceutical compositions may be delivered by intranasal sprays, inhalation, and/or other aerosol delivery vehicles. Methods for delivering genes, polynucleotides, and peptide compositions directly to the lungs via nasal aerosol sprays have been described e.g., in U.S. Pat. Nos. 5,756,353 and 5,804,212 (each specifically incorporated herein by reference in its entirety). Likewise, the delivery of drugs using intranasal microparticle resins (Takenaga et al., 1998) and lysophosphatidyl-glycerol compounds (U.S. Pat. No. 5,725,871, specifically incorporated herein by reference in its entirety) are also well-known in the pharmaceutical arts. Likewise, transmucosal drug delivery in the form of a polytetrafluoroetheylene support matrix is described in U.S. Pat. No. 5,780,045 (specifically incorporated herein by reference in its entirety).

In certain embodiments, the delivery may occur by use of liposomes, nanocapsules, microparticles, microspheres, lipid particles, vesicles, and the like, for the introduction of the compositions of the present invention into suitable host cells. In particular, the compositions of the present invention may be formulated for delivery either encapsulated in a lipid particle, a liposome, a vesicle, a nanosphere, a nanoparticle or the like. The formulation and use of such delivery vehicles can be carried out using known and conventional techniques.

In certain embodiments, the agents provided herein may be attached to a pharmaceutically acceptable solid substrate, including biocompatible and biodegradable substrates such as polymers and matrices. Examples of such solid substrates include, without limitation, polyesters, hydrogels (for example, poly(2-hydroxyethyl-methacrylate), or poly(vinylalcohol)), polylactides (U.S. Pat. No. 3,773,919), copolymers of L-glutamic acid and γ-ethyl-L-glutamate, non-degradable ethylene-vinyl acetate, degradable lactic acid-glycolic acid copolymers such as poly(lactic-co-glycolic acid) (PLGA) and the LUPRON DEPOT™ (injectable microspheres composed of lactic acid-glycolic acid copolymer and leuprolide acetate), poly-D-(−)-3-hydroxybutyric acid, collagen, metal, hydroxyapatite, bioglass, aluminate, bioceramic materials, and purified proteins.

In one particular embodiment, the solid substrate comprises Atrigel™ (QLT, Inc., Vancouver, B.C.). The Atrigel® drug delivery system consists of biodegradable polymers dissolved in biocompatible carriers. Pharmaceuticals may be blended into this liquid delivery system at the time of manufacturing or, depending upon the product, may be added later by the physician at the time of use. When the liquid product is injected into the subcutaneous space through a small gauge needle or placed into accessible tissue sites through a cannula, water in the tissue fluids causes the polymer to precipitate and trap the drug in a solid implant. The drug encapsulated within the implant is then released in a controlled manner as the polymer matrix biodegrades with time.

In particular embodiments, the amount of a HRS-Fc conjugate composition administered will generally range from a dosage of from about 0.1 to about 100 mg/kg, and typically from about 0.1 to 10 or 20 mg/kg where administered orally, subcutaneously, or intravenously. In particular embodiments, a dosage is about 1 mg/kg, about 3 mg/kg, about 5 mg/kg, about 7.5 mg/kg, or about 10 mg/kg. In certain embodiments, a composition is administered in a single dosage of 0.1 to 10 mg/kg or 0.5 to 5 mg/kg. In some embodiments, a composition is administered in a dosage of 0.1 to 50 mg/kg, 0.5 to 20 mg/kg, or 5 to 20 mg/kg.

For humans, the daily dosage used may range from, about 0.1 mg/kg to 0.5 mg/kg, about 1 mg/kg to 5 mg/kg, about 5 mg/kg to 10 mg/kg, about 10 mg/kg to 20 mg/kg, about 20 mg/kg to 30 mg/kg, about 30 mg/kg to 50 mg/kg, and about 50 mg/kg to 100 mg/kg/24 hours.

For HRS-Fc conjugates with longer half lives, the human dosage used may range, for example, from about 0.1 mg/kg/week to 0.5 mg/kg/week, about 1 mg/kg/week to 5 mg/kg/week, about 5 mg/kg/week to 10 mg/kg/week, about 10 mg/kg/week to 20 mg/kg/week, about 20 mg/kg/week to 30 mg/kg/week, about 30 mg/kg/week to 50 mg/kg/week, or about 50 mg/kg/week to 100 mg/kg/week.

HRS-Fc conjugates with still longer half lives may be dosed in humans about 0.1 mg/kg/month to 0.5 mg/kg/month, about 1 mg/kg/month to 5 mg/kg/month, about 5 mg/kg/month to 10 mg/kg/month, about 10 mg/kg/month to 20 mg/kg/month, about 20 mg/kg/month to 30 mg/kg/month, about 30 mg/kg/month to 50 mg/kg/month, or about 50 mg/kg/month to 100 mg/kg/month.

In various embodiments, the dosage is about 50-2500 mg per day, 100-2500 mg/day, 300-1800 mg/day, or 500-1800 mg/day, or 500-2500 mg per week, 1000-2500 mg/week, 300-1800 mg/week, or 500-1800 mg/week, or 500-2500 mg per month, 1000-2500 mg/month, 300-1800 mg/month, or 500-1800 mg/month. In some embodiments, the dosage is between about 100 to 600 mg/day, 100 to 600 mg/week, or 100 to 600 mg/month. In some embodiments, the dosage is between about 300 and 1200 mg/day, 300 and 1200 mg/week, or 300 and 1200 mg/month. In particular embodiments, the composition or agent is administered at a dosage of 100 mg/week, 2.4 mg/week 300 mg/week, 600 mg/week, 1000 mg/week, 1200 mg/week or 1800 mg/week, in one or more doses per week or per month (i.e., where the combined doses achieve the desired weekly or monthly dosage). In some embodiments, a dosage is 100 mg bid, 150 mg bid, 240 mg bid, 300 mg bid, 500 mg bid, or 600 mg bid. In various embodiments, the composition or agent is administered in single or repeat dosing. The initial dosage and subsequent dosages may be the same or different.

In some embodiments, total daily dose may be about 0.001 mg, about 0.005 mg, about 0.01 mg, about 0.05 mg, about 0.1 mg, 0.5 mg, 1 mg, about 2 mg, about 3 mg, about 4 mg, about 5 mg, about 6 mg, about 7 mg, about 8 mg, about 9 mg, about 10 mg, about 20 mg, about 30 mg, about 40 mg, about 50 mg, about 60 mg, about 70 mg, about 80 mg, about 90 mg or about 100 mg/24 hours.

In some embodiments, total weekly dose may be about 0.001 mg, about 0.005 mg, about 0.01 mg, about 0.05 mg, about 0.1 mg, 0.5 mg, 1 mg, about 2 mg, about 3 mg, about 4 mg, about 5 mg, about 6 mg, about 7 mg, about 8 mg, about 9 mg, about 10 mg, about 20 mg, about 30 mg, about 40 mg, about 50 mg, about 60 mg, about 70 mg, about 80 mg, about 90 mg or about 100 mg/week.

In some embodiments, total monthly dose may be about 0.001 mg, about 0.005 mg, about 0.01 mg, about 0.05 mg, about 0.1 mg, 0.5 mg, 1 mg, about 2 mg, about 3 mg, about 4 mg, about 5 mg, about 6 mg, about 7 mg, about 8 mg, about 9 mg, about 10 mg, about 20 mg, about 30 mg, about 40 mg, about 50 mg, about 60 mg, about 70 mg, about 80 mg, about 90 mg or about 100 mg/month.

For repeated administrations over several days or longer, depending on the condition, the treatment is sustained until a desired suppression of disease symptoms occurs. The progress of these and other therapies (e.g., ex vivo therapies)

can be readily monitored by conventional methods and assays and based on criteria known to the physician or other persons of skill in the art.

It will be further appreciated that for sustained delivery devices and compositions the total dose of HRS contained in such delivery system will be correspondingly larger depending upon the release profile of the sustained release system. Thus, a sustained release composition or device that is intended to deliver HRS-Fc conjugates over a period of 5 days will typically comprise at least about 5 to 10 times the daily dose of HRS-Fc conjugate; a sustained release composition or device that is intended to deliver a HRS-Fc conjugate over a period of 365 days will typically comprise at least about 400 to 800 times the daily dose of the HRS-Fc conjugate (depending upon the stability and bioavailability of the HRS-Fc conjugate when administered using the sustained release system).

In certain embodiments, a composition or agent is administered intravenously, e.g., by infusion over a period of time of about, e.g., 10 minutes to 90 minutes. In other related embodiments, a composition or agent is administered by continuous infusion, e.g., at a dosage of between about 0.1 to about 10 mg/kg/hr over a time period. While the time period can vary, in certain embodiments the time period may be between about 10 minutes to about 24 hours or between about 10 minutes to about three days.

In particular embodiments, an effective amount or therapeutically effective amount is an amount sufficient to maintain a concentration of the HRS-Fc conjugate in the blood plasma of a subject above about 300 pM, above about 1 nM, above about 10 nM, above about 100 nM, or above about 1000 nM.

In certain embodiments, an IV or SC dosage is an amount sufficient to achieve a blood plasma concentration ($C_{max}$) of between about 1,000 nM to about 5,000 nM or between about 200 nM to about 1,000 nM, or about 20 nM to about 200 nM.

In particular embodiments, a HRS-Fc conjugate is administered in an amount and frequency sufficient to achieve in the mammal a blood plasma concentration having a mean trough concentration of between about 300 pM and about 1 nM and/or a steady state concentration of between about 300 pM and about 1 nM. In some embodiments, the $C_{min}$ of the HRS-Fc conjugate in the blood plasma of the mammal is maintained above about 1 nM and/or a steady state concentration of between about 1 nM and about 10 nM. In certain embodiments, the $C_{min}$ of the HRS-Fc conjugate in the blood plasma of the mammal is maintained above about 10 nM and/or a steady state concentration of between about 10 nM and about 100 nM. In certain embodiments, the $C_{min}$ of the HRS-Fc conjugate in the blood plasma of the mammal is maintained above about 100 nM and/or a steady state concentration of between about 100 nM and about 1000 nM.

In particular embodiments of the present invention, an effective amount of the HRS-Fc conjugate, or the blood plasma concentration of the HRS-Fc conjugate, is achieved or maintained, with a single administration, e.g., for at least 15 minutes, at least 30 minutes, at least 45 minutes, at least 60 minutes, at least 90 minutes, at least 2 hours, at least 3 hours, at least 4 hours, at least 8 hours, at least 12 hours, at least 24 hours, at least 48 hours, at least 3 days, at least 4 days, at least 5 days, at least 6 days, at least one week, at least 2 weeks, at least one month, at least 2 months, at least 3 months, at least 4 months, or at least 6 months.

In particular embodiments, the effective dosage achieves the blood plasma levels or mean trough concentration of a composition or agent described herein. These may be readily determined using routine procedures.

Embodiments of the present invention, in other aspects, provide kits comprising one or more containers filled with one or more of the HRS-Fc conjugates, polypeptides, polynucleotides, antibodies, multiunit complexes, compositions thereof, etc., of the invention, as described herein. The kits can include written instructions on how to use such compositions (e.g., to modulate cellular signaling, angiogenesis, cancer, inflammatory conditions, diagnosis etc.).

The kits herein may also include a one or more additional therapeutic agents or other components suitable or desired for the indication being treated, or for the desired diagnostic application. An additional therapeutic agent may be contained in a second container, if desired. Examples of additional therapeutic agents include, but are not limited to anti-neoplastic agents, anti-inflammatory agents, antibacterial agents, antiviral agents, angiogenic agents, etc.

The kits herein can also include one or more syringes or other components necessary or desired to facilitate an intended mode of delivery (e.g., stents, implantable depots, etc.).

Certain embodiments of the present invention now will be illustrated by the following Examples. The present invention may, however, be embodied in many different forms and should not be construed as limited to the embodiments set forth herein; rather, these embodiments are provided so that this disclosure will be thorough and complete, and will fully convey the scope of the invention to those skilled in the art.

EXAMPLES

Example 1

Production of His Tagged Resokine (HRS Comprising Amino Acids 1-60)

Codon optimization and gene synthesis. DNA encoding Resokine (HRS(1-60)) was codon-optimized for *E. coli* expression using the algorithm developed by DNA2.0 (Menlo Park, Calif.).

The codon-optimized DNA sequence is as follows:

```
                                     (SEQ ID NO: 261)
ATGGCAGAACGTGCGGCATTGGAAGAATTGGTTAAACTGCAAGGTGAACG

TGTTCGTGGTCTGAAGCAGCAGAAGGCTAGCGCGGAGCTGATCGAAGAAG

AGGTGGCCAAACTGCTGAAGCTGAAGGCGCAGCTGGGCCCGGACGAGAGC

AAACAAAAGTTCGTCCTGAAAACCCCGAAACACCACCATCACCATCAC
```

The translated protein sequence is as follows:

```
                                     (SEQ ID NO: 262)
MAERAALEELVKLQGERVRGLKQQKASAELIEEEVAKLLKLKAQLGPDES
KQKFVLKTPKHHHHHH
```

Additionally, engineered versions of this construct were prepared with cysteine residues inserted close to the N-terminus (comprising additional N-terminal Met and Cys residues), C-terminus (comprising an additional C-terminal cysteine at position 61), and in the linker domain joining the 2 alpha helical sections of the molecule (comprising the mutation Ala 26→Cys). The codon optimized DNA sequences, and corresponding amino acid sequences for these constructs are listed below.

H-N4: 1-H (codon-HRS(1-60)-M1MC-6×His):

```
                                      (SEQ ID NO: 263)
ATGTGTGCAGAAAGAGCCGCCCTGGAAGAGTTAGTTAAGTTGCAAGGTGA

ACGTGTCCGTGGTCTGAAGCAGCAGAAGGCTAGCGCGGAGCTGATCGAAG

AAGAGGTGGCCAAACTGCTGAAGCTGAAGGCGCAGCTGGGCCCGGACGAG

AGCAAACAAAAGTTCGTCCTGAAAACCCCGAAACACCACCATCACCATCA

C
```

The translated protein sequence is as follows:

```
                                      (SEQ ID NO: 264)
MCAERAALEELVKLQGERVRGLKQQKASAELIEEEVAKLLKLKAQLGPD
ESKQKFVLKTPKHHHHHH
```

```
H-N4:2-H (codon-HRS(1-60)-A26C-6xHis):
                                      (SEQ ID NO: 265)
ATGGCAGAACGTGCGGCATTGGAAGAATTGGTTAAACTGCAAGGTGAAC

GTGTTCGTGGTCTGAAGCAGCAGAAGTGCAGCGCGGAGCTGATCGAAGA

AGAGGTGGCCAAACTGCTGAAGCTGAAGGCGCAGCTGGGCCCGGACGAG

AGCAAACAAAAGTTCGTCCTGAAAACCCCGAAACACCACCATCACCATC

AC
```

The translated protein sequence is as follows:

```
                                      (SEQ ID NO: 266)
MAERAALEELVKLQGERVRGLKQQKCSAELIEEEVAKLLKLKAQLGPDES
KQKFVLKTPKHHHHHH
```

```
H-N4:3-H (codon-HRS(1-60)-C61-6xHis):
                                      (SEQ ID NO: 267)
ATGGCAGAACGTGCGGCATTGGAAGAATTGGTTAAACTGCAAGGTGAACG

TGTTCGTGGTCTGAAGCAGCAGAAGGCTAGCGCGGAGCTGATCGAAGAAG

AGGTGGCCAAACTGCTGAAGCTGAAGGCGCAGCTGGGCCCGGACGAGAGC

AAACAAAAGTTCGTCCTGAAAACCCCGAAATGCCACCACCATCACCATCA

C
```

The translated protein sequence is as follows:

```
                                      (SEQ ID NO: 268)
MAERAALEELVKLQGERVRGLKQQKASAELIEEEVAKLLKLKAQLGPDES
KQKFVLKTPKCHHHHHH
```

The corresponding genes were synthesized (DNA 2.0) with a C-terminal 6×His tag and subcloned into the pJexpress411 expression vector where the T7 promoter was used to drive the transcription and kanamycin resistance was used for antibiotic selection.

Expression Strain.

BL21(DE3) competent cells (Novagen, cat. no. 69450) were transformed with the relevant codon-optimized expression construct, as described. Briefly, the plasmid (1 μL) was added into 50 μL of the competent cells. The reaction was mixed and incubated on ice for 30 minutes. The reaction was heat-shocked for at 42° C. for 30 seconds followed by a cold-shock on ice for 2 minutes. Then the SOC medium (500 μL) was added and the tube was incubated at 37° C., 250 rpm for 1 hour. Finally, an aliquot of the culture (50 μL) was spread on the Kanamycin plate (Teknova S9641) and incubated at 37° C. overnight. A single colony was picked and used for expression scale-up.

Medium.

M9YE medium was prepared by mixing 200 mL sterile M9 minimal salt 5× (BD248510), 778 mL of 30 g/L yeast extract in sterile purified water (BD212750), 20 mL sterilized 20% glucose (Sigma G7021) and 2 mL sterile 1.0 M $MgSO_4$ (Sigma M7506). The feeding solution contains 5% yeast extract, 50% glucose, trace elements and 2 g/L magnesium sulfate. Kanamycin sulfate (Invitrogen 15160) was added to a final concentration of 100 μg/mL in both M9YE and feeding solution.

Fed-Batch Fermentation.

A 4 L fermentor (Sartorius Biostat B plus) with MFCS/DA software was used for the fed-batch fermentation. The agitation was set at 1000 rpm. The pH value was controlled at 7.0 automatically by the addition of 30% ammonium hydroxide (Sigma 221228) and 30% phosphoric acid (Sigma P5811). The air was provided at a flow rate of 4 L/min with an oil-free diaphragm air compressor (Cole-Parmer). The air was passed through a 0.2 μm Midisart 2000 filter (Sartorius 17805). The pure oxygen (West Air) was supplied automatically to control the dissolved oxygen level at 70%. The temperature was controlled at 30° C. with a Neslab RTE7 circulator (Thermo Scientific). The foaming was controlled by addition of the antifoam 204 (Sigma A8311). The initial volume of M9YE medium in the fermentor was 3L. The fermentor was inoculated with 150 mL of the seed culture grown overnight at 30° C. and 250 rpm. When the glucose was depleted in the vessel, the concentrated feeding solution was introduced into the vessel by a peristaltic pump set at 0.9 mL/min. When the optical density of the cells at 600 nm reached about 30, the culture was induced with 0.5 mM IPTG (Fisher Scientific BP1755). The culture was run overnight (about 18-hour fed-batch phase) and harvested by centrifugation at 6,000×g for 1 hour. The cell pellet was stored at −20° C. until purification. The expression of Resokine was confirmed on the SDS-PAGE.

Purification of Proteins.

Resokine and the Cys variants thereof were purified from *E. coli* cell paste through cell lysis and clarification; immobilized metal affinity chromatography, and cation exchange chromatography. Frozen cells weighing 10 g and containing Resokine or Cys variants were thawed and resuspended in 1× NiNTA buffer (50 mM Tris, 0.3 M NaCl 25 mM imidazole pH 8) at a 4:1 ml/g paste ratio along with 5 mM beta-mercaptoethanol (Sigma Cat #M7154-25ML) and 1 protease inhibitor cocktail tablet (Roche Cat #05 056 489 001). After all cells were resuspended, cells were lysed on ice in a Microfluidizer M-110Y, 2 passes at 15000 psi on ice to release soluble Resokine or Cys variants. NiNTA buffer was added after the second pass to flush remaining lysate through the Microfluidizer (100-120 ml final volume after lysis). Lysate was centrifuged for 15000×g @ 4 C for 30 min. Supernatant was filtered 0.45/0.2 um with an Acropak 200 (Pall Cat #12094). Filtered supernatant is clarified lysate.

Immobilized Metal Affinity Chromatography (IMAC) Purification.

Clarified lysate from 10 g cell paste was loaded onto a gravity-flow column containing 3 ml NiNTA resin (Qiagen #30210) and pre-equilibrated in NiNTA buffer. Resin was washed with 50 column volumes (CV) of 0.1% Triton X-114 in 1× NiNTA buffer to remove endotoxin, then 30 CV 1× NiNTA buffer, followed by elution with 5 CV NiNTA elution buffer (50 mM Tris, 0.3 M NaCl, 0.3 M imidazole pH 8 @ 4 C.

Cation Exchange (CEX) Chromatography Purification.

CEX load was prepared by diluting NiNTA eluent 1/20× in CEX A buffer (10 mM sodium phosphate pH 7.0, 2 mM DTT), then loaded onto SP Sepharose High Performance column equilibrated in CEX A. Protein was eluted with a linear gradient of 0-100% B over 20 CV, where A=10 mM sodium phosphate pH 7.0, 2 mM DTT and B=10 mM sodium phosphate, 1 M sodium chloride 2 mM DTT pH 7.0, monitoring absorbance at 214 nm. Fractions were pooled corresponding to the main peak in the elution gradient by absorbance at 214 nm. CEX pool was buffer exchanged into 1×PBS pH 7.4 (Gibco #10010) using Amicon Ultra-15 3 kD MWCO ultracentrifugal devices.

Example 2

Production of His Tagged Full-Length Histidyl-tRNA Synthetase (Hrs)

Codon Optimization and Gene Synthesis.

The full length HisRS gene was codon-optimized for *E. coli* expression and subcloned into pET21a vector where the T7 promoter was used to drive the transcription. In addition, a 5-amino acid linker and 6×His tag were attached to the C-terminus.

The DNA sequence is as follows:

```
                                          (SEQ ID NO: 269)
ATGGCGGAACGTGCCGCACTGGAAGAATTGGTTAAATTACAGGGAGAACG

CGTACGTGGTCTTAAACAACAAAAAGCCTCTGCGGAATTGATTGAAGAAG

AAGTTGCCAAATTACTGAAACTGAAAGCTCAACTTGGACCCGATGAAAGT

AAACAAAAATTTGTGTTGAAAACGCCCAAAGGAACCCGTGATTATAGTCC

ACGTCAAATGGCCGTTCGTGAAAAAGTGTTCGACGTTATTATTCGCTGTT

TTAAACGTCACGGTGCTGAAGTAATCGATACCCCCGTATTTGAATTGAAA

GAGACTCTGATGGGCAAATATGGTGAAGATTCTAAACTGATTTATGATTT

GAAAGACCAAGGAGGTGAACTGCTGAGCCTGCGCTACGACTTAACTGTGC

CTTTTGCCCGTTACTTAGCCATGAATAAaTTaACCAACATCAAACGTTAC

CATATTGCAAAAGTATATCGCCGCGACAACCCTGCAATGACTCGTGGACG

CTATCGCGAATTCTATCAGTGTGATTTTGATATTGCCGGAAATTTCGACC

CGATGATCCCGGATGCCGAGTGTTTGAAAATTATGTGTGAAATTCTGAGT

TCGTTGCAGATCGGAGACTTTCTTGTAAAAGTTAATGACCGCCGTATTCT

GGATGGTATGTTTGCTATTTGCGGTGTTTCTGATTCCAAATTCCGTACAA

TCTGCTCAAGCGTGGACAAATTGGATAAAGTGTCTTGGGAAGAAGTAAAA

AATGAAATGGTGGGAGAAAAAGGCCTGGCTCCAGAAGTAGCAGACCGTAT

TGGTGACTATGTTCAACAACATGGCGGTGTGTCCTTAGTCGAACAGTTAT

TACAGGATCCTAAACTGAGCCAAAATAAACAAGCACTTGAAGGACTGGGA

GATCTGAAATTACTCTTTGAATATCTGACCTTATTTGGGATTGATGATAA

AATTAGCTTTGATCTGAGCTTGGCCCGCGGTCTTGATTATTATACCGGCG

TGATTTACGAAGCTGTTCTCTTGCAAACCCCAGCCCAGGCGGGCGAAGAG

CCTTTGGGAGTCGGCAGTGTGGCAGCCGGTGGTCGTTATGATGGTTTGGT

AGGAATGTTTGACCCTAAAGGCCGTAAAGTACCATGTGTGGGGCTTTCTA
```

-continued

```
TCGGTGTCGAACGTATCTTTTCTATTGTTGAACAACGTCTTGAAGCTTTG

GAGGAAAAGATCCGTACCACGGAAacCCAAGTCTTAGTTGCaAGTGCCCA

AAAAAAACTGTTAGAAGAACGCCTGAAACTCGTATCAGAACTTTGGGACG

CCGGCATCAAGGCCGAACTGCTGTATAAAAAGAACCCGAAATTGTTAAAC

CAACTCCAGTATTGTGAAGAAGCTGGGATCCCACTCGTAGCTATTATTGG

TGAGCAAGAATTAAAAGATGGCGTGATTAAACTGCGTTCAGTAACAAGCC

GTGAAGAGGTAGATGTACGTCGCGAAGACTTAGTGGAAGAAATTAAACGC

CGCACCGGTCAACCGTTATGTATTTGCGCGGCCGCACTCGAGCACCACCA

CCACCACCACTGA
```

The sequence of the translated protein is as follows:

```
                                          (SEQ ID NO: 270)
MAERAALEELVKLQGERVRGLKQQKASAELIEEEVAKLLKLKAQLGPDE

SKQKFVLKTPKGTRDYSPRQMAVREKVFDVIIRCFKRHGAEVIDTPVFE

LKETLMGKYGEDSKLIYDLKDQGGELLSLRYDLTVPFARYLAMNKLTNI

KRYHIAKVYRRDNPAMTRGRYREFYQCDFDIAGNFDPMIPDAECLKIMC

EILSSLQIGDFLVKVNDRRILDGMFAICGVSDSKFRTICSSVDKLDKVS

WEEVKNEMVGEKGLAPEVADRIGDYVQQHGGVSLVEQLLQDPKLSQNKQ

ALEGLGDLKLLFEYLTLFGIDDKISFDLSLARGLDYYTGVIYEAVLLQT

PAQAGEEPLGVGSVAAGGRYDGLVGMFDPKGRKVPCVGLSIGVERIFSI

VEQRLEALEEKIRTTETQVLVASAQKKLLEERLKLVSELWDAGIKAELL

YKKNPKLLNQLQYCEEAGIPLVAIIGEQELKDGVIKLRSVTSREEVDVR

REDLVEEIKRRTGQPLCICAAALEHHHHHH
```

Expression Strain.

The BL21(DE3) competent cells (Novagen, cat. no. 69450) were transformed with the codon-optimized expression construct. Briefly, the plasmid (1 μL) was added into 50 μL of the competent cells. The reaction was mixed and incubated on ice for 30 minutes. The reaction was heat-shocked for at 42° C. for 30 seconds followed by a cold-shock on ice for 2 minutes. Then the SOC medium (500 μL) was added and the tube was incubated at 37° C., 250 rpm for 1 hour. Finally, an aliquot of the culture (50 μL) was spread on the Ampicillin plate (Teknova S9641) and incubated at 37° C. overnight. Single colony was picked and used for expression scale-up.

Medium.

The M9YE medium was prepared by mixing 200 mL sterile M9 minimal salt 5× (BD248510), 778 mL of 30 g/L yeast extract in sterile purified water (BD212750), 20 mL sterilized 20% glucose (Sigma G7021) and 2 mL sterile 1.0 M $MgSO_4$ (Sigma M7506). The feeding solution contains 5% yeast extract, 50% glucose, trace elements and 2 g/L magnesium sulfate. Ampicillin was added to a final concentration of 100 μg/mL in both M9YE and feeding solution.

Fed-Batch Fermentation.

A 4 L fermentor (Sartorius Biostat B plus) with MFCS/DA software was used for the fed-batch fermentation. The agitation was set at 1000 rpm. The pH value was controlled at 7.0 automatically by the addition of 30% ammonium hydroxide (Sigma 221228) and 30% phosphoric acid (Sigma P5811). The air was provided at a flow rate of 4 L/min with an oil-free diaphragm air compressor (Cole-Parmer). The air was passed through a 0.2 μm Midisart 2000 filter (Sartorius 17805). The pure oxygen (West Air) was supplied automatically to control the dissolved oxygen level at 70%. The temperature was controlled at 30° C. with a Neslab RTE7 circulator (Thermo Scientific). The foaming was controlled by addition of the antifoam 204 (Sigma A8311). The initial volume of M9YE medium in the fermentor was 3L. The fermentor was inoculated with 150 mL of the seed culture grown overnight at 30° C. and 250 rpm. When the glucose was depleted in the vessel, the concentrated feeding solution was introduced into the vessel by a peristaltic pump set at 0.9 mL/min. When the optical density of the cells at 600 nm reached about 30, the culture was induced with 0.5 mM IPTG (Fisher Scientific BP1755). The culture was run overnight (about 18-hour fed-batch phase) and harvested by centrifugation at 6,000×g for 1 hour. The cell pellet was stored at −20° C. until purification. The expression of HisRS was confirmed on the SDS-PAGE.

Purification of HisRS.

Frozen cell paste (40 g) were resuspended in 160 mL (i.e. 4 mL/g cell paste) of Lysis Buffer (20 mM Tris, 400 mM NaCl, 20 mM Imidazole, 14 mM β-ME, pH 8.0 at 4° C.). Complete EDTA-FREE protease inhibitor tablets (Roche) were added to the suspension at a ratio of 1 tablet/50 mL. The suspension was passed through a microfluidizer (Microfluidics) twice at 15,000 psi with cooling by ice. The lysate was centrifuged at 35,000×g for 45 min at 4° C. The supernatant was filtered through 0.22 μm Acropak 200 capsule filters (Pall).

The clarified lysate was bound to the Ni-NTA resin (Qiagen), pre-equilibrated with Ni-NTA Binding Buffer (20 mM Tris, 400 mM NaCl, 20 mM Imidazole, 5 mM β-ME, pH 8.0 at 4° C.). The column was washed with 500 column volumes of Ni-NTA Binding Buffer+0.1% Triton X-114 followed by 50 column volumes of the Ni-NTA Binding Buffer. The bound protein, HisRS, was eluted with 5 column volumes of Ni-NTA Elution Buffer (20 mM Tris, 400 mM NaCl, 500 mM Imidazole, 5 mM β-ME, pH 8.0 at 4° C.).

The Ni-NTA eluate was further purified by an anion exchange column. Specifically, the Ni-NTA eluate was dialyzed against Q Binding Buffer (20 mM Tris, 50 mM NaCl, 1 mM DTT, pH 7.4) and loaded onto a 5 mL Q-sepharose column, pre-equilibrated with the Q Binding Buffer. The desired product was eluted off the column with a linear gradient of 0-1 M NaCl in the Q Binding Buffer over 10 column volumes. The purified HisRS was concentrated and buffer exchanged into PBS (Invitrogen product #10010)+1 mM DTT, and filtered through a 0.22 μm sterile filter.

Example 3

Active Site Titration of the Cysteine Residues in Full Length Hars

To determine the location and identity of the surface exposed cysteine residues in full length HARS, purified recombinant protein was incubated with iodoacetamide under native and denatured conditions to alkylate any surface exposed cysteine residues. Samples were then analyzed by limiting proteolysis followed by LC-mass analysis to determine the location and identity of the modified cysteine residues.

To perform the alkylation studies, full length, polyhistidine tagged HARS (6.65 mg/ml in PBS, 10% glycerol, 2 mM DTT, pH7.4, (Example 2) was first fully reduced by incubation with 10 mM DTT for 45 minutes at room temperature. Incubations with iodoacetamide were conducted with an iodoacetamide concentration at either 30 mM ("Low") or a 100 mM ("High") for 30 minutes in the dark, and were conducted on native and denatured samples of HARS to confirm that the reaction was successful. Denatured HARS was prepared by pre-incubation of the protein with 4M guanidine for 45 min at 50 C. After incubation with iodoacetamide, samples were dialyzed in PBS pH 7.4 at 4 C using 10 KDa molecular weight cutoff dialysis membrane, and with at least 3 buffer exchanges, and then used for mass spectroscopy analysis as described below.

In brief, samples were prepared by diluting the proteins into 0.1% formic acid to a final concentration of 1 m/ml and 5 μg samples of the proteins were injected and analyzed by reverse phase HPLC followed by mass spectrum analysis using an Agilent TOF mass spectrometer. Samples were first separated on a C3 HPLC column (Agilent ZORBAX 300SB-C3, 5 μm, 2.1×150 mm column) using a linear gradient of (mobile phase B of 2-60%) over 18 min (mobile phase A: 0.1% formic acid; mobile phase B: 0.1% formic acid in acetonitrile). Mass spectrometry analysis of the samples was in profile mode. Data was acquired and analyzed by MassHunter (Agilent). Measured molecular weight was calculated by MassHunter Bioconfirm Agilent).

The results (data not shown) demonstrated that under native conditions only 3 or 4 cysteine residues are readily modified, whereas by comparison when the protein is first denatured to disrupt its native conformation all 10 cysteines were readily denatured.

To identify the identity of the modified cysteine residues, samples before and after incubation with iodoacetamide were subjected to denaturation in 4 M Guanidine HCl at 3TC for 30 min followed by proteolytic cleavage with LysC using a by a 10:1 ratio (w/w) at room temperature for 20h. Protein digests were analyzed by LC/MS/MS using Dionex HPLC and Thermo LTQ XL mass spectrometer. Samples were first separated on C18 HPLC column (Agilent ZORBAX 300SB-C18, 5 μm, 2.1×150 mm) using a gradient of mobile phase B (mobile phase A: 0.1% formic acid; mobile phase B: 0.1% formic acid in acetonitrile). The gradient start off with 1-3% B in 10 min and then to 40% B in 76 min. Separated protein digests were analyzed either by full MS in profile mode or by a full MS scan were analyzed by tandem MS/MS scan on the top three identified ions. Data was acquired and analyzed by Xcalibur (Thermo). Peptide sequencing was based on the MS/MS spectra of each peptide, in which b- and γ-ion peaks match their theoretical ions. Identification of the peptides and mapping of the modification sites are based on the molecular weight and confirmed by peptide sequencing using MS/MS spectra, and are listed in Table E1.

TABLE E1

LC-MS Peptide mapping results after limiting trypsin digestion

| Cys residue | From-To | Sequence | RT (min) | MH+ |
|---|---|---|---|---|
| Cys83 | 76-85 | VFDVIIR<u>C</u>FK (SEQ ID NO: 271) | 56.24 | 1239.68 |
| Cys174; Cys191 | 155-193 | VYRRDNPAMTRGRYREFYQ<u>C</u>DFDIAGNFDPMIPDAE<u>C</u>LK (SEQ ID NO: 272) | 61.27 | 4673.14 |

TABLE E1-continued

| LC-MS Peptide mapping results after limiting trypsin digestion | | | | |
|---|---|---|---|---|
| Cys residue | From-To | Sequence | RT (min) | MH+ |
| Cys196 | 194-210 | IMCEILSSLQIGDFLVK (SEQ ID NO: 273) | 73.14 | 1909.01 |
| Cys224 | 211-230 | VNDRRILDGMFAICGVSDSK (SEQ ID NO: 274) | 58.53 | 2196.08 |
| Cys235 | 231-240 | FRTICSSVDK (SEQ ID NO: 275) | 22.8 | 1155.57 |
| Cys235 | 231-243 | FRTICSSVDKLDK (SEQ ID NO: 276) | 28.77 | 1511.79 |
| Cys379 | 377-403 | VPCVGLSIGVERIFSIVEQRLEALEEK (SEQ ID NO: 277) | 81.00 | 3013.63 |
| Cys445 | 448-472 | LLNQLQYCEEAGIPLVAIIGEQELK (SEQ ID NO: 278) | 72.46 | 2784.48 |
| Cys505; Cys509 | 500-509 | RRTGQPLCIC (SEQ ID NO: 279) | 27.17 | 1146.57 |

The results revealed (data not shown) that Cys235, Cys507 and Cys509 are readily modified by iodoacetamide treatment and are thus likely to be surface-exposed residues that are readily amenable to chemical modification.

Example 4

Creation of Modified Hrs Polypeptides with Altered Cysteine Content

To determine whether any of the 10 naturally-occurring cysteine residues in full length HRS could be mutated to alternative naturally occurring amino acid residues, or deleted, primers were designed to selectively mutate each cysteine residue. To accomplish this, primers based on the following may be used (see Table E2).

TABLE E2

| Mutation | Oligo sequence | SEQ ID NO: |
|---|---|---|
| C83 | 5'-GTTTGACGTAATCATCCGTTGCTTCAAGCGCCACGGTGCAG-3' (Forward) | 280 |
| C83 | 5'-CTG CAC CGT GGC GCT TGA AGC AAC GGA TGA TTA CGT CAA AC-3' (Reverse) | 281 |
| C174 | 5'-GCCGATACCGGGAATTCTACCAGTGTGATTTTGACATTGCTGGG-3' (Forward) | 282 |
| C174 | 5'-CCC AGC AAT GTC AAA ATC ACA CTG GTA GAA TTC CCG GTA TCG GC-3' (Reverse) | 283 |
| C191 | 5'-CCATGATCCCTGATGCAGAGTGCCTGAAGATCATGTGCGAG-3' (Forward) | 284 |
| C191 | 5'-CTC GCA CAT GAT CTT CAG GCA CTC TGC ATC AGG GAT CAT GG-3' (Reverse) | 285 |
| C196 | 5'-GCAGAGTGCCTGAAGATCATGTGCGAGATCCTGAGTTCACTTC-3' (Forward) | 286 |
| C196 | 5'-GAA GTG AAC TCA GGA TCT CGC ACA TGA TCT TCA GGC ACT CTG C-3' (Reverse) | 287 |

TABLE E2-continued

| Mutation | Oligo sequence | SEQ ID NO: |
|---|---|---|
| C224 | 5'-CTAGATGGGATGTTTGCTATCTGTGGTGTTTCTGACAGCAAGTTC-3' (Forward) | 288 |
| C224 | 5'-GAA CTT GCT GTC AGA AAC ACC ACA GAT AGC AAA CAT CCC ATC TAG-3' (Reverse) | 289 |
| C235 | 5'-CAGCAAGTTCCGTACCATCTGCTCCTCAGTAGACAAGCTGG-3' (Forward) | 290 |
| C235 | 5'-CCA GCT TGT CTA CTG AGG AGC AGA TGG TAC GGA ACT TGC TG-3' | 291 |
| C379 | 5'-GGGCGCAAGGTGCCATGTGTGGGGCTCAGCATTGGGG-3' (Forward) | 292 |
| C379 | 5'-CCC CAA TGC TGA GCC CCA CAC ATG GCA CCT TGC GCC C-3' (Reverse) | 293 |
| C455 | 5'-CTGAACCAGTTACAGTACTGTGAGGAGGCAGGCATCCC-3' (Forward) | 294 |
| C455 | 5'-GGG ATG CCT GCC TCC TCA CAG TAC TGT AAC TGG TTC AG-3' (Reverse) | 295 |
| C507 | 5'-GAGAACAGGCCAGCCCCTCTGCATCTGCTAGAACCCAGC-3' (Forward) | 296 |
| C507 | 5'-GCT GGG TTC TAG CAG ATG CAG AGG GGC TGG CCT GTT CTC-3' (Reverse) | 297 |
| C509 | 5'-CCAGCCCCTCTGCATCTGCTAGAACCCAGCTTTCTTG-3' (Forward) | 298 |
| C509 | 5'-CAA GAA AGC TGG GTT CTA GCA GAT GCA GAG GGG CTG G-3' (Reverse) | 299 |
| Last 3 codon removal | 5' GAACAGGCCAGCCCCTCTAGAACCCAGCTTTCTTG 3' (Forward) | 300 |
| Last 3 codon removal | 5'-CAA GAA AGC TGG GTT CTA GAG GGG CTG GCC TGT TC-3' (Reverse) | 301 |

To confirm the active site titration data, the crystal structure of full length HRS was analyzed using the program Getarea1.1 to assess the relative location of the 10 cysteine residues. The results (data not shown) suggest that in addition to C235, C507 and C509, the cysteines at positions C174, C191 and C224 of SEQ ID NO:1, are at least partially exposed to the surface and could likely be modified via standard reagents. Additionally, analysis of the crystal structure of HRS suggests that C174 and C191 are capable of making an internal disulfide bond, while C507 and C509 are capable of making interchain disulfide bonds within the HRS dimer, both potentially contributing to microheterogeneity that could be beneficially eliminated.

Figure 3:
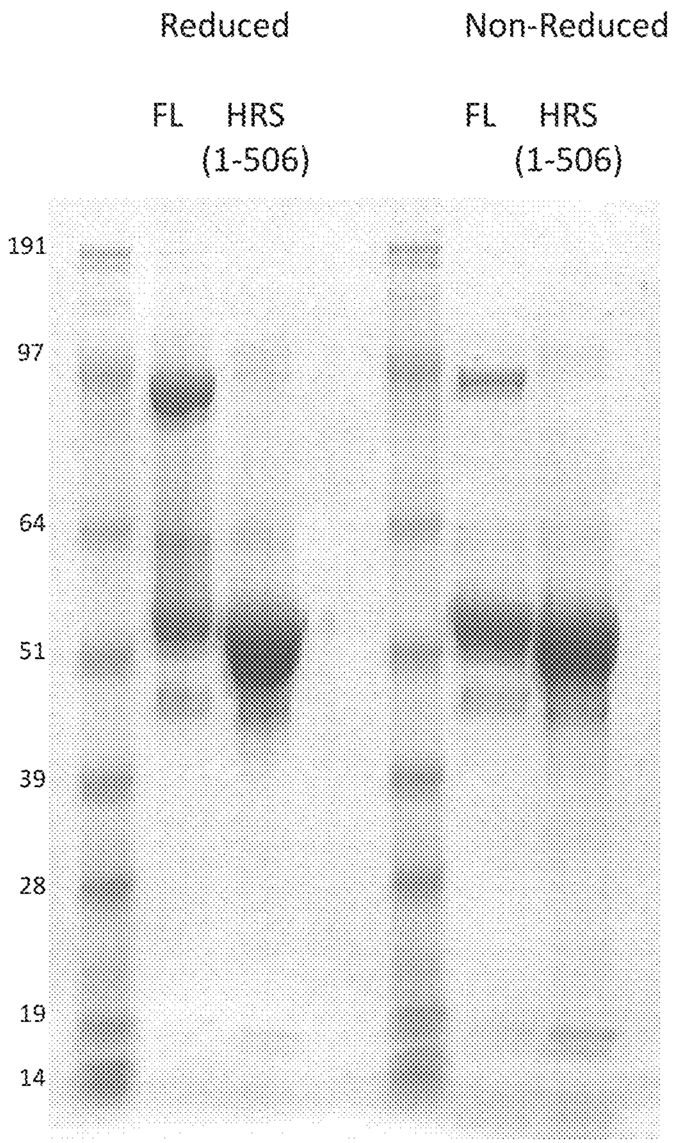
FIG. 3 shows the results of SDS-PAGE analysis under reducing and non reducing conditions of full length HRS and HRS(1-506). The results show that HRS(1-506) dramatically reduces the formation of disulfide mediated interchain bond formation compared to the full length protein. Samples (10 μg) were loaded on a 4-12% Bis-Tris gel, using a MOPS-SDS running buffer.

To directly assess the significance of the two C-terminal cysteine residues in contributing to interchain disulfide bond formation, His-tagged versions of the full length and the C-terminally deleted versions of HRS (HRS(1-506)) were compared by SDS PAGE analysis before and after reduction. The results, shown in FIG. 3, demonstrate that full length HRS is a 50:50 mixture of non-covalent and SS-linked dimer, while HRS(1-506) dramatically reduces the SS-linked dimer. Comparison of the two proteins by competitive ELISA, as described below, revealed that both proteins had comparable IC50 values with respect to Jo-1 antibody binding (data not shown). The dramatically reduced interchain disulfide bond formation associated with HRS(1-506) suggests that this variant is a suitable starting point for the development of improved next generation product forms.

To determine whether any of the remaining four partially exposed cysteine residues in full length HRS could be mutated to alternative naturally occurring amino acid residues, primers were designed to selectively mutate C174, C191, C224 and C235 residues. To accomplish this, the following primers were used as listed in Table E3:

TABLE E3

| Mutation | Oligo sequence | SEQ ID NO: |
|---|---|---|
| C1 | CCCGGATGCCGAGGCTTTGAAAATTATGTG (Forward) | 302 |
| C191A | CAC ATA ATT TTC AAA GCC TCG GCA TCC GGG (Reverse) | 303 |

TABLE E3-continued

| Mutation | Oligo sequence | SEQ ID NO: |
|---|---|---|
| C191S | GATCCCGGATGCCGAGAGTTTGAAAATTATGTGTG (Forward) | 304 |
| C191S | CAC ACA TAA TTT TCA AAC TCT CGG CAT CCG GGA TC (Reverse) | 305 |
| C191V | GATCCCGGATGCCGAGGTTTTGAAAATTATGTGTG (Forward) | 306 |
| C191V | CAC ACA TAA TTT TCA AAA CCT CGG CAT CCG GGA TC (Reverse) | 307 |
| C174A | CGCGAATTCTATCAGGCTGATTTTGATATTGCCGG (Forward) | 308 |
| C174A | CCG GCA ATA TCA AAA TCA GCC TGA TAG AAT TCG CG (Reverse) | 309 |
| C174V | CGCGAATTCTATCAGGTTGATTTTGATATTGCCG (Forward) | 310 |
| C174V | CGG CAA TAT CAA AAT CAA CCT GAT AGA ATT CGC G (Reverse) | 311 |
| C224S | GGTATGTTTGCTATTTCCGGTGTTTCTGATTCC (Forward) | 312 |
| C224S | GGA ATC AGA AAC ACC GGA AAT AGC AAA CAT ACC (Reverse) | 313 |
| C235S | CCAAATTCCGTACAATCTCCTCAAGCGTGGACAAATTGG (Forward) | 314 |
| C235S | CCA ATT TGT CCA CGC TTG AGG AGA TTG TAC GGA ATT TGG (Reverse) | 315 |
| C191A | CCCGGATGCCGAGGCTTTGAAAATTATGTG (Forward) | 316 |
| C191A | CAC ATA ATT TTC AAA GCC TCG GCA TCC GGG (Reverse) | 317 |

Mutations were introduced by mutagenesis using the QuikChange Lightning Site-Directed Mutagenesis Kit (Agilent, cat. no. 210518) following the manufacturer's instructions. After mutagenesis, the sample were treated with Dpn I enzyme at 37° C. and transformed into XL10 gold competent cells using routine procedures. Multiple colonies are grown in terrific broth overnight at 37° C. and the resulting plasmids are purified with QIAprep Spin Miniprep Kit (Qiagen cat. no. 27106). The plasmids are sequenced to confirm the identity of the amino acid substitution of each clone. The representative clones were transformed into NovaBlue competent cells (Novagen cat. no. 70181) and grown in 250 ml M9YE medium at 37° C. overnight. A maxiprep was performed using the HiSpeed Plasmid Maxi Kit (Qiagen cat. no. 12663) to create a plasmid stock of mutant for further analysis. The concentration and purity were determined by measuring A260, A280 and A230. The purified plasmids were stored at −20° C. before transfection into *E. coli* or mammalian cells following standard protocols.

To assess the impact of the mutation of the mutation of each residue, representative clones were transformed into *E. coli*, or mammalian cells, and the production yields, endotoxin contents, stability and relative activity in an ELISA assay to determine Jo-1 antibody binding as described below.

Protein Production.

BL21(DE3) competent cells (Novagen, cat. no. 69450) or W3110 cells (ATTC) were transformed with the codon-optimized expression constructs encoding the reduced cysteine constructs as described above. The expression system, fermentation media, fermentation conditions and purification steps used to produce recombinant protein were essentially the same as those described in Example 4 below, after adjusting for the production scale, and amount of cell paste used. Table E4 below shows the purification yields, and endotoxin levels for the proteins made.

TABLE E4

Purification yields and endotoxin levels of reduced cysteine variants

| Name | Yield (mg/g cell paste) | Endotoxin (EU/mg) |
|---|---|---|
| HRS(1-506) | +++ | 0.32 |
| HRS(1-506)C174V | ++ | 0.71 |
| HRS(1-506)C174A | ++ | 0.30 |
| HRS(1-506)C191A | ++ | 0.46 |
| HRS(1-506)C191V | +++ | 0.33 |
| HRS(1-506)C1191S | +++ | 0.32 |
| HRS(1-506)C224S | ++ | 0.54 |
| HRS(1-506)C235S | +++ | 0.60 |

+++ greater than 7 mg protein/g cell paste;
++ greater than 5 mg/g cell paste
+ less than 5 mg/g cell paste.

The results show that all of the reduced variants were relatively well expressed, and were successfully purified with low endotoxin levels. In particular the reduced cysteine variants based on the mutation of Cys191, and Cys235 displayed favorable expression levels; though all clones exhibited reasonable levels of expression, and low endotoxin levels.

To assess the impact of the cysteine mutations on the charge heterogeneity of the purified proteins, samples of each clone were analyzed by isoelectric focusing. Samples (10 μg) were loaded onto an isolectric focusing gel (pH 3-10) using a Life Technologies Novex pH 3-10 IEF gel 1.0 mm (Cat No. P/N EC6645BOX), Novex IEF Marker 3-10 (Cat No. P/N 391201), Novex pH 3-10IEF buffer kit (Cat. No. P/N LC5317), run with 1× cathode buffer (upper chamber) and 1× anode buffer (lower chamber) at 100V for 1 hour, 200V for 1 hour, and 500V for 30 minutes. Gels were fixed with 12% TCA with 3.5% sulfosalicylic acid for 30 minutes and stained with Expedeon InstantBlue (Cat No. P/N ISB1L). The data, (results not shown) demonstrate that the mutation of the cysteine at position 174 significantly reduced isoelectric point heterogeneity, consistent with the possibility that this cysteine residue undergoes an intramolecular disulfide bond formation with cysteine 191.

To assess the impact of the cysteine modifications on the thermal stability, aggregation propensity, structure, and tRNA synthetase activity of the resultant proteins, the proteins were assessed by differential scanning fluorimetry, size exclusion HPLC (SE-HPLC), competitive ELISA and active site titration. The results are shown in Table E5 below.

Differential scanning fluorimetry was performed on protein samples by monitoring fluorescence as a function of the fluorescence intensity of a lipophilic dye during thermal denaturation. Studies were carried on samples after they were diluted to 0.5 mg/mL into 1004 final volume of PBS pH 7.0 (150 mM NaCl, 20 mM phosphate) and mixed with a thermal shift dye solution, which was prepared by diluting the stock solution (Applied Biosystems/Life Technologies, P/N 4461146) 20-fold in ultrapure distilled water (Gibco, P/N 10977). Five μL of the diluted dye was added to 100 μL of sample. The mixture was plated into a 384 well clear optical reaction plate (Applied Biosystems/Life Technologies P/N 4309849) at 20 μL each well and 4 well replicates per sample. The plate was read by the ViiA 7 Real Time PCR Instrument (Applied Biosystems/Life Technologies, P/N 4453552). The thermal denaturation protocol commenced with a rate of change of 1.6° C./s, until a temperature of 25° C. was attained, at which point the instrument held this temperature for 2 minutes, before further increasing the temperature to 99° C., at a rate of 0.5° C./s at which point this temperature was held for a further 2 minutes.

Size exclusion HPLC analysis was completed on the purified protein samples using a TSKgel Super SW3000, 4.6 mm ID×30 cm, 4 am particle size, 250 Å column (Tosoh, 18675) using a mobile phase of 200 mM NaPhosphate, 150 mM NaCl pH 7.0, at a flow rate of 0.3 ml/min, with an Agilent 1260 HPLC system equipped with a vacuum degasser, binary/quaternary pump, thermostatted autosampler, thermostatted column compartment, diode array detector (DAD), and Chemstation chromatography software). Undiluted samples (40 μg) of each protein were injected after brief centrifugation. System suitability sample (bovine serum albumin, BSA, Thermo Scientific, P/N: 23209) and internal control (wild type HRS) were used to bracket samples to ensure the validity of the test.

Competitive ELISAs were performed in 96-well plates (Immulon 4HBX) which had been coated with a 50 μL solution of full length his-tagged HARS, adjusted to a concentration of 2 μg/mL with PBS. Plates were sealed and incubated overnight at 4° C. Prior to use, plates were washed five times with PBST and subsequently blocked with 100 al 1% BSA in PBS for one hour at room temperature. While the ELISA plates were blocking, the reduced cysteine competition molecules (over a concentration range of $1\times10^{-6}$ M to $1\times10^{-13}$ M) were incubated with α-Jo-1 antibodies (GenWay GWB-FB7A3D or Immunovision HJO-0100) at 1:10,000 dilution in 1% BSA PBS in a separate incubation plate (Costar 3357 96-well) for one hour at 4° C. After blocking was finished, the ELISA plates were washed three times with PBST and 50 μL of solution containing antibody and competitor was added to the ELISA plate and the samples incubated at room temperature for 1.5 hours. Following initial binding incubation, plates were washed five times with PBST. Next, 50 μL of detection antibody (AbD Serotec Goat Anti-human IgG F(ab')2:HRP 0500-0099) was added a 1:5,000 dilution and incubated for one hour at room temperature. Following secondary binding incubation, plates were washed with five times PBST and 50 μL TMB substrate (Thermo Scientific Pierce TMB Substrate PI-34021) was added. Reactions proceeded for 8 minutes at which point 50 μL of 2M sulfuric acid stop solution was added. Colorimetric quantification was performed using a SpectraMax plate reader at 450 nM.

To determine the number of catalytic active sites in each HARS506 cysteine variant the active site titration assay (as described in Fersht et al., (1975) Biochemistry) was employed. Briefly, assays were performed at room temperature with 5 μM HARS, 10 mM MgCl2, 50 μM ATP, 20 mM L-histidine, 2 ug/mL inorganic pyrophosphatase, 1.65 μM [γ-32P]ATP in standard buffer (100 mM HEPES pH 7.5, 20 mM KCl). Reactions were initiated with enzyme in low profile PCR plates and time points were quenched in 96-well PVDF multiScreen filter plates Millipore containing HClO4/charcoal slurry (1:4 7% HClO4:10% charcoal slurry) at 30s, 1 min, 2 min, 4 min, 6 min and 10 min. After mixing up and down by pipetting and samples were spun into a collection plate with Supermix scintillant, and counted in a Microbetae plate reader.

TABLE E5

Effect of cysteine modification on thermal stability, aggregation and activity of HARS

| Name | Tm | % Low molecular weight aggregates | IC50 by ELISA Assay | Active site titration |
|---|---|---|---|---|
| HRS(1-506) | 49.0 | 2.0 | 0.15 | 63.3 |
| HRS(1-506)C174V | 47.8 | 7.8 | 0.39 | 55.5 |
| HRS(1-506)C174A | 49.2 | 3.0 | 0.19 | 59.8 |
| HRS(1-506)C191A | 44.7 | 5.1 | 0.14 | 66.2 |
| HRS(1-506)C191V | 47.8 | 1.8 | 0.16 | 60.8 |
| HRS(1-506)C191S | 45.8 | 2.3 | 0.16 | 63.2 |
| HRS(1-506)C224S | 48.9 | 4.9 | 0.14 | 60.5 |
| HRS(1-506)C235S | 48.8 | 3.1 | 0.14 | 64.6 |

The results from these studies confirm that all of the cysteine mutants are active, with little or no loss in activity, stability, or conformation as measured by active site titration, ELISA binding and Tm determinations for thermal denaturation. Active site titration of tRNA synthetase activity reveals that all of the reduced cysteine mutants are active, and thus suitable for use in any of the compositions, methods and kits of the invention. In general the Cys191 substitutions displayed overall lower thermostability, while the Cys174 mutants exhibited significantly less heterogeneity as determined by isoelectric focusing.

Example 5

Creation of Modified (Tag Free) Hrs Polypeptides with a C-Terminal Truncation ($HisRS^{N8}$) or (HRS(1-506)

To delete the last three amino acids and the linker between wild type HisRS and the His-tag, primers were designed for use with QuikChange Lightning Site-Directed Mutagenesis Kit (Agilent, cat no 210519). To accomplish this, the following primers are used as listed in Table E6.

TABLE E6

| Mutation | Oligo sequence | SEQ ID NO: |
|---|---|---|
| Delete CICAAALE | 5'-CGCCGCACCGGTCAACCGTTACACCACCACCACCACCACTG-3' (Forward) | 318 |
| Delete CICAAALE | 5'-CAG TGG TGG TGG TGG TGG TGT AAC GGT TGA CCG GTG CGG CG-3' (Reverse) | 319 |

The deletion was made per the QuikChange Lightning Site-Directed Mutagenesis Kit manufacturer's instructions. After mutagenesis, the sample was treated with Dpn I enzyme at 37° C. and transformed into XL10 gold competent cells using routine procedures. Multiple colonies were grown in luria-bertani broth overnight at 37° C. and the resulting plasmids were purified with QIAprep Spin Miniprep Kit (Qiagen cat. no. 27106). The plasmids were sequenced to confirm the identity of the amino acid substitution of each clone. To delete the His tag, primers were designed for use with QuikChange Lightning Site-Directed Mutagenesis Kit (Agilent, cat no 210519). To accomplish this, the following primers were used as listed in Table E7.

TABLE E7

| Mutation | Oligo sequence | SEQ ID NO: |
|---|---|---|
| Delete His-tag Forward | 5'-CGC CGC ACC GGT CAA CCG TTA TGA GAT CCG GCT GCT AAC-3' | 320 |
| Delete His-tag Reverse | 5'-GTT AGC AGC CGG ATC TCA TAA CGG TTG ACC GGT GCG GCG-3' | 321 |

The deletion was made per the QuikChange Lightning Site-Directed Mutagenesis Kit manufacturer's instructions, as described above.

Protein Production.

BL21(DE3) competent cells (Novagen, cat. no. 69450) or W3110 cells (ATTC) were transformed with the codon-optimized expression construct encoding HisRS' (HRS(1-506)) as described in Example 2. The expression system, fermentation media, and fermentation conditions used to produce recombinant proteins were essentially the same as those described in Example 2.

Purification of Tag-Free HisRS$^{N8}$ (HisRS(1-506)).

Frozen cell paste (400 g) was resuspended in 4-volumes (1600 mL) of Lysis Buffer (50 mM Tris, 50 mM NaCl, 5 mM $MgCl_2$, 2 mM L-Cysteine, pH7.4). Complete EDTA-FREE protease inhibitor tablets (Roche, Cat #05 056 489 001) were added to the suspension at a ratio of 1 tablet/50 mL. The suspension was passed through a microfluidizer (Microfluidics) twice at 18,000 psi with cooling by ice. The lysate was centrifuged at 15,000×g for 45 min at 4° C. The supernatant was filtered through 2-3 AcroPak 1500 capsules (0.8/0.2 μm, Pall, PN12675).

The clarified lysate was loaded onto a 382 ml Q HP column (5×19.5 cm) pre-equilibrated with Q Buffer A (50 mM Tris, 50 mM NaCl, pH 7.4). The product was eluted with a linear gradient of 0-30% Q Buffer B (50 mM Tris, 1 M NaCl, pH 7.4) over 10 column volumes (CV). Fractions were collected at ½ CV/fraction and analyzed by SDS-PAGE. Pooling was based on gel analysis.

A 3.5 M ammonium sulfate solution was added to the Q HP pool above to a final concentration of 1.2 M. The mixture was filter through an AcroPak 200 (0.2 um) and loaded onto a 481 ml Phenyl HP column (5×24.5 cm) pre-equilibrated with 20 mM Tris, 1.2 M ammonium sulfate, pH 7.0. The product was eluted with a linear gradient of 1.2-0 M ammonium sulfate in 20 mM Tris/pH 7.0 over 10 CV. Fractions (½ CV/fraction) containing the product based on SDS-PAGE analysis were pooled.

The Phenyl Pool from above was concentrated to 0.5 L via a TFF system, consisting of a Pellicon Mini cassette holder (Millipore Cat #XX42PMINI), a Masterflex I/P pump, and 2×0.1 $m^2$ cassette (30 kD MWCO, Novasep Cat #PP030M01L). The concentrated solution was then buffer exchanged with 6 diavolumes (3 L) of CHT Buffer A (10 mM sodium phosphate, 150 mM NaCl, pH 7.0). The retentate was filtered through a 0.2 μm Millex GP-50 filter (Millipore part #SLGP 05010) before proceeding to the next step.

The above solution was loaded onto a 380 ml ceramic hydroxyapatite (CHT) column (5×19.4 cm) pre-equilibrated with CHT Buffer A. The column was washed with Buffer A and followed by 6% Buffer B (500 mM sodium phosphate, 150 mM NaCl, pH 7.0). The product was eluted with a linear gradient of 6-56% Buffer B over 10 CV. Fractions (½ CV/fraction) containing the product based on SDS-PAGE analysis were pooled.

Using the same TFF system, the CHT Pool was concentrated to ~0.2 L, buffer exchanged with 6 diavolumes of the current formulation buffer (20 mM sodium phosphate, 150 mM NaCl, pH 7.0), and concentrated to a target concentration of ~10 mg/ml. The product solution was filtered through a 0.2 μm Millex GP-50 filter (Millipore part #SLGP 05010), and stored in −80° C. freezer.

Example 6

Evaluation of HRS(1-60) (Resokine) as an Anti-Inflammatory Agent

To evaluate the potential anti-inflammatory property of HRS derived polypeptides, an N-terminal, naturally occurring splice variant comprising amino acids 1-60 of HRS ("Resokine") was tested in a TNBS induced model of colitis. Studies were performed in male BDF-1 mice, with 12 mice/group; Budesonide was added at 5 mg/kg orally.

Figure 4:
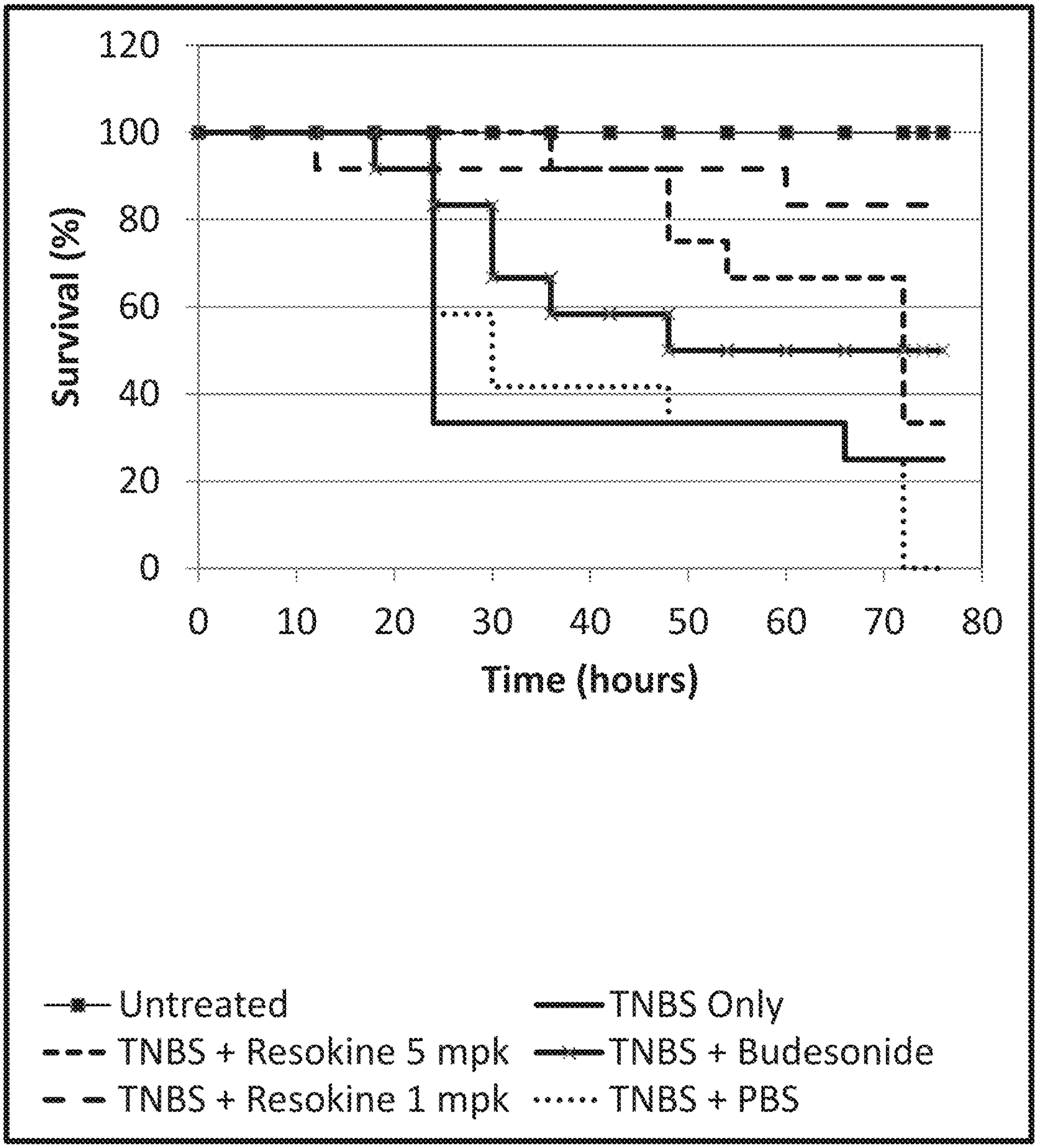
FIG. 4 shows the anti-inflammatory properties of an exemplary HRS-derived polypeptide in a TNBS-induced mouse model of colitis. Studies were performed on male BDF-1 mice, with 12 mice/group. TNBS and budesonide were added at 5 mg/kg to the water. HRS(1-60) (Resokine, (HisRS$^{N4}$)) was administered daily by IV injection, starting 3 days prior to TNBS treatment, at a concentration of 1 or 5 mg/kg. This figure shows the percent (%) survival of treated and untreated mice over about 80 hours.

In this study Resokine was administered daily by IV injection, starting 3 days prior to TNBS treatment, at a concentration of 1 or 5 mg/Kg. The data shown in FIG. 4 demonstrates that treatment with Resokine at either concentration resulted in a significant increase in survival. Accordingly Resokine appears to have potent anti-inflammatory effects, consistent with the hypothesis that HRS polypeptides are involved in the local control of inflammatory processes.

Example 7

Evaluation of Hrs Polypeptides for the Treatment of Statin-Induced Myositis and Rhabdomyolysis Statins are HMG CoA Reductase inhibitors which inhibit the synthesis of mevalonate, the rate limiting step in cholesterol synthesis. Statin therapy has proved beneficial in lowering cholesterol levels in patients. However, side-effects and complications of statin therapy include muscle weakness, myositis and rhabdomyolysis. Muscle myopathy is a complication with several statins on the market and patients are often removed from their statin-therapy if they exhibit any of these symptoms. Like many other myopathies, muscular dystrophies and inflammatory disorders of muscle, disease progression in statin induced myopathy appears to occur as the result of an initial chemical, genetic or physical injury, which becomes increasingly inflamed as a result of immune cell invasion into the damaged muscle cells.

Accordingly statin induced myopathy represents a broadly applicable model system to study drug induced myositis, which is directly applicable to other myopathies and muscular dystrophies, all of which all share a common inflammatory component which mediates disease progression by promoting immune cell invasion of the damaged muscle tissue.

The purpose of this study was to evaluate the efficacy of HRS(1-506) in reversing the effects of statin-induced muscular myositis, as indicated by altered circulating enzyme levels, and changes in gene expression of muscle function and inflammatory markers in response to treatment with HRS(1-506).

To achieve this, rats were dosed daily with 1 mg/kg Cerivastatin and then switched to an every other day (qod) dosing with Cerivastatin. The goal of this dosing regimen was to maintain a sustained disease state in the animals, but not to have such severe disease that rat survival is greatly impacted. The efficacy of a dose range of HRS(1-506) was then evaluated in rats after statin-dosing had already initiated measurable changes in circulating markers of myositis.

Protocol and Methods.

In this study, 10 week old female Sprague-Dawley rats were treated with 1 mg/kg Cerivastatin ((Sigma, Cat No. SML0005) in 0.5% methylcellulose, starting on day 1 via oral gavage. After 7 days of daily administration, rats were switched to an every other day dosing strategy (qod) on days 9, 11 and 13. HRS(1-506) and vehicle administration were initiated on day 6 through intravenous injection and rats were dosed daily to day 14 (shown schematically in FIG. 5A). All rats were taken down on day 15, 24 hours after the final test article dosing and 48 hours after the last statin administration. HRS(1-506) was administered at 3 doses (0.3, 1.0 and 3.0 mg/kg) in 20 mM $NaPO_4$, 0.15M NaCl, pH 7.0 daily.

To address the primary objective of this study, the following study measurements and endpoints were performed: rat survival, weight, circulating serum CK levels at days 12 and 15, H&E staining on day 15 hamstring samples, Troponin-I ELISA, CBC on day 15 blood, qPCR on hamstring samples and serum endogenous HARS levels.

qPCR methods.

Mouse hamstring was excised from the animals and stored at −80° C. until analysis. Tissue was prepped in groups of 10 hamstrings using Qiagen's RNeasy Fibrous Tissue Midi Kit (Catalog #75742). Once RNA was eluted from the Qiagen column, it was run on an Agilent's Bioanalyzer 2100 to test RNA integrity and NanoDrop to determine RNA concentration and purity. RNA was then stored at −80° C.

Reverse transcription (RT) of RNA to cDNA was performed in a 96 well PCR plate format in Eppendorf's Mastercycler PCR machine with the following program: 37° C. for 60 minutes, 95° C. for 5 minutes. The edge wells of the 96 well plate were not used and filled with 50 mcL water to prevent evaporation of inside wells. 20 mcL RNA and 30 mcL of reverse transcription master mix (Ambion's TaqMan PreAmp Cells to CT Kit catalog #4387299) was used per sample RT. Once RT was completed, next step was to pre-amplify genes of interest in the sample cDNA. Primers of genes of interest (DELTAgene primers designed by Fluidigm) were combined to a final concentration of 200 nM. Using these primers, genes of interest were pre-amplified in each sample. Pre-amplification was performed in 10 mcL reactions (2.5 mcL cDNA, 7.5 mcL Pre-Amp master-mix) in 384-well format using an Applied Biosystems ViiA7 PCR machine with the following program: 95° C. for 10 minutes, 14 cycles of 95° C. for 15 seconds and 60° C. for 4 minutes. After pre-amplification step, exonuclease (New England BioLabs catalog #M0293L) was added to remove unincorporated primers from each sample. This exonuclease reaction was also completed in the ViiA7 PCR machine with the following program: 37° C. for 30 minutes, 80° C. for 15 minutes. After exonuclease, the RT sample was further diluted 1:5 (7 mcL exonuclease sample+18 mcL low EDTA buffer).

The chip used to run qPCR on Fluidigm's Biomark system was a 96.96 Dynamic Array IFC for Gene Expression. The chip was first primed with the IFC controller HX as per manufacturer's recommendations before sample and assays were loaded. To prepare assays to be loaded on a chip, 4.4 mcL assay master mix (Fluidigm's 2× Assay Loading Reagent catalog #8500736 and low EDTA TE) to 3.6 mcL 20 mcM forward and reverse primers for each gene of interest were prepared in a 96 well plate. To prepare samples, 4.5 mcL sample master mix (Ambion's 2× TaqMan Gene Expression Master Mix, Fluidigm's 20×DNA Binding Dye Sample Loading Reagent catalog number 100-0388, and Biotium's 20× EvaGreen catalog #31000) was added to 3 mcL diluted pre-amplified/exonuclease sample in a 96 well plate. Once the chip had been primed, 5 mcL sample or assay prepared above were loaded onto the chip. The chip was them returned to the IFC controller for the samples to be loaded into the chip. After the chip had finished loading, qPCR could then be run on the Biomark using preset program for 96.96 Dynamic Array for Gene Expression with a melt curve to determine primer specificity. Relative gene expression was determined by the delta delta Ct method.

Quantification of Extracellular HARS.

A 96 well based ELISA was developed in-house using 2 mouse anti-HARS monoclonal antibodies M03 (Sigma #SAB1403905, and Abnova #H00003035-M03) and M01 (Abgent #AT2317a) in a sandwich format to detect HARS in rat serum. Assays were run in 96 well Costar plates (Costar 96-well plate #3369) using a seven point standard curve which was generated ranging from 75 to 0.1 ng/ml using a stock solution of HRS(1-506); (7.5 mg/ml in 20 mM NaPO4, 0.15 M NaCl pH 7.0, using 1×PBST (0.05% Tween-20) as a diluent). The M01 mouse monoclonal, clone 1C8 (Abgent #AT2317a) was biotinylated in house and used as the detection antibody, and the M03 mouse monoclonal antibody (Sigma #SAB1403905, lot #11238, 0.5 mg/mL and Abnova #H00003035-M03, lot #11238, 0.5 mg/mL) was used as a capture antibody. Casein (Thermo Scientific #37528) was used as a blocking agent, and 1x PBST (0.05% Tween-20) was used as a wash buffer. Antibody binding was quantified using Streptavidin-HRP (Invitrogen cat #434323, Lot#816755A) using TMB Substrate (Thermo #34021) and with 2M sulfuric acid as the stop solution.

ELISA assays were run by coating plates overnight with 0.6 to 2 μg/ml M03 antibody in 1×PBS, which were then blocked by incubation with casein for one hour 1 hour, and washed 3× with PBST. Plates were then incubated with standards and samples for 1 hour, washed 3×PBST, and then incubated with 500 ng/ml biotinylated-M01 diluted in PBST, 1 hour, washed 3×PBST, incubated with 200 ng/ml streptavidin-HRP for 1 hour, washed 3× with PBST, and then the TMB substrate added for 4 minutes. Reactions were stopped with stop solution and absorbance read at 450 nm.

The results were quantified based on the standard curve based on the average raw absorbance values without background subtraction. Prism was used for standard curve fitting. Model: Log(agonist) vs. response fit [4-parameter logistic regression] Percent recovery was calculated for each individual concentration point (not averaged) by:

$$\frac{(\text{measured} - \text{actual}) \times 100\%}{(\text{actual})}$$

Other Readouts.

Rats were weighed daily. Serum samples were taken on days 1, 8, 12 (via tail vein) and day 15 (terminal) to be used for circulating enzyme analysis (Idexx) and serum skeletal muscle Troponin-I measurements, were measured using a commercial ELISA kit. Urinalysis was performed on days 3, 5, 8, 10, 12 and 15 prior to dosing on that day. CBC analysis was run on blood isolated on day 15 prior to euthanizing rats. On day 15, the rats were euthanized and a portion of the hamstring muscle and lung (not inflated) was placed in 10% NBF for paraffin embedding and H&E staining of sections (Premier Laboratory). Another portion of hamstring muscle and lung was placed at −80C to use for RNA extraction and profiling. Liver, kidney and heart were also isolated on day 15 and placed in zinc-formalin for paraffin embedding (TSRI Histology) for long-term tissue storage.

Results.

There was 100% survival in this study, and all rats survived to the scheduled takedown on day 15. Statin-dosed rats had lower average weights than control rats not dosed with statin. On day 15, the statin+vehicle group had the lowest average rat weight of all the groups, whereas the Statin+3 mg/kg HRS(1-506)-dosed group had the highest weight average of all the statin-treated animals (data not shown). CBC analysis showed overall similar patterns of changes between different animal treatment groups (data not shown).

Figures 5A, 5B:
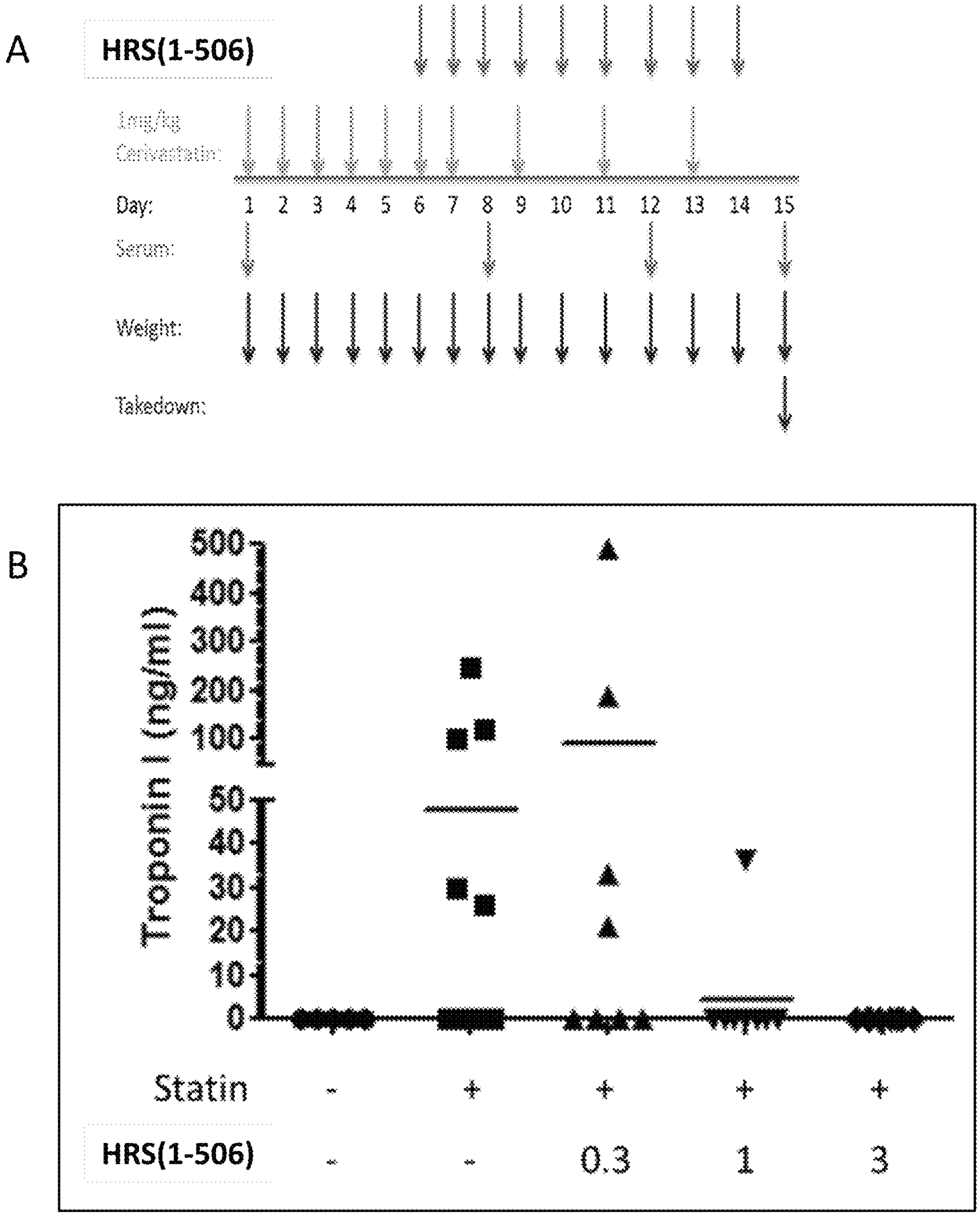
FIGS. 5A-5B show the dosing regimen used to evaluate the therapeutic utility of HRS(1-506) in the statin myopathy model.
Figures 6A, 6B:
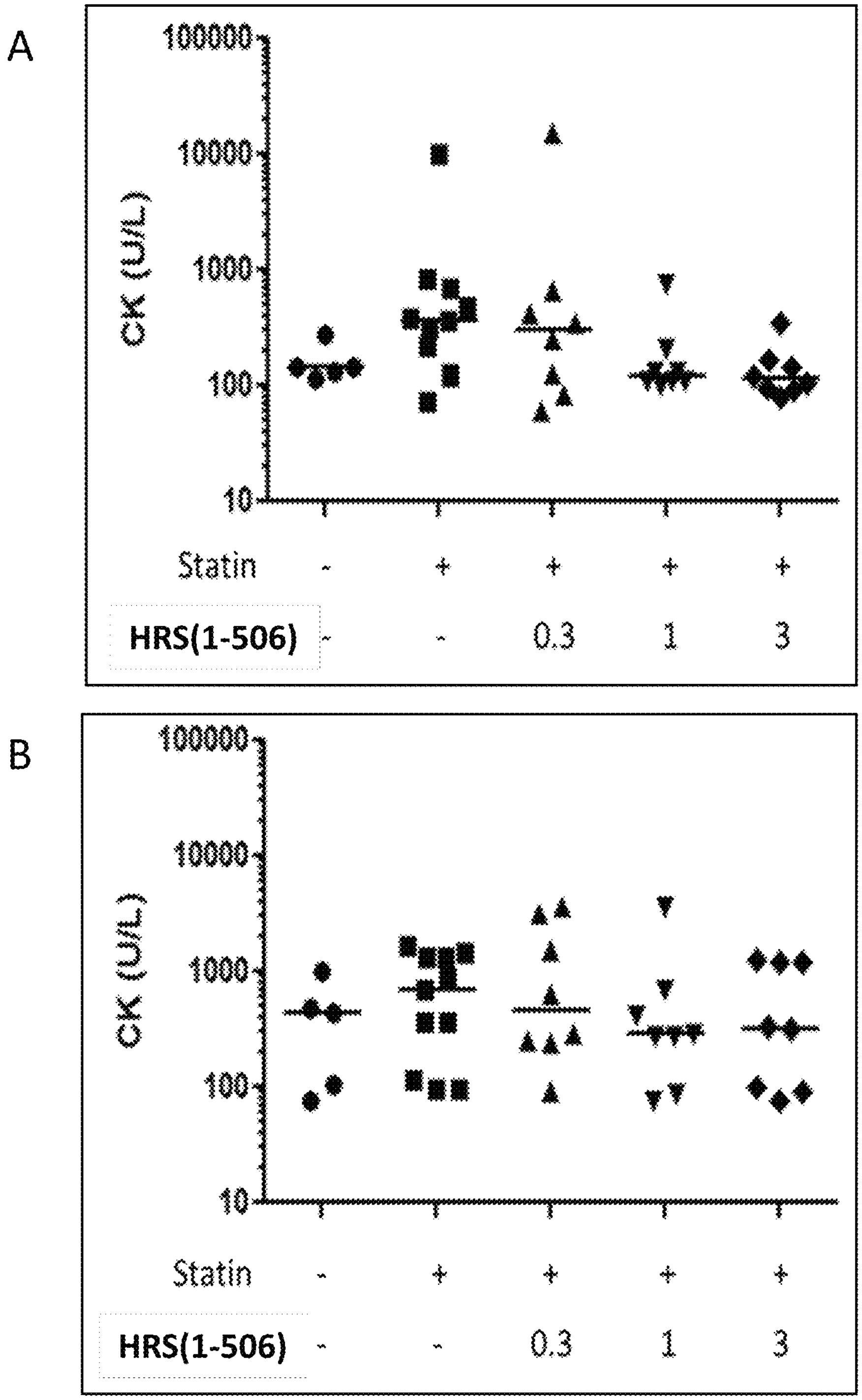
FIG. 6A shows the results of CK measurements after 12 days of treatment with statins+/−HRS(1-506) at 0.3, 1.0, and 3.0 mg/Kg.
FIG. 6B shows the same data after 15 days of treatment. The figure shows the positive effect of HRS(1-506) in reducing statin induced CK levels.
Figure 7:
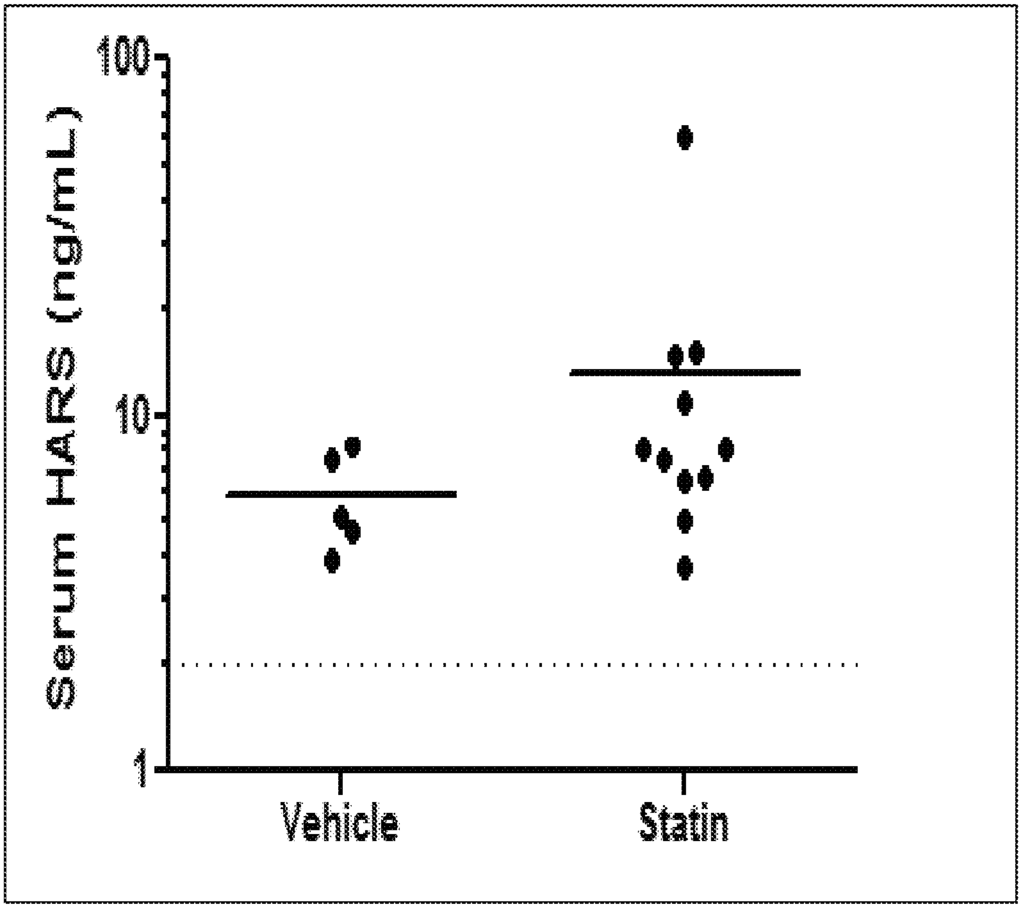
FIG. 7 shows the levels of circulating HARS after 15 days of treatment with statins compared to the vehicle control. The figure shows that stains induce the release of extracellular HARS.
Figure 8:
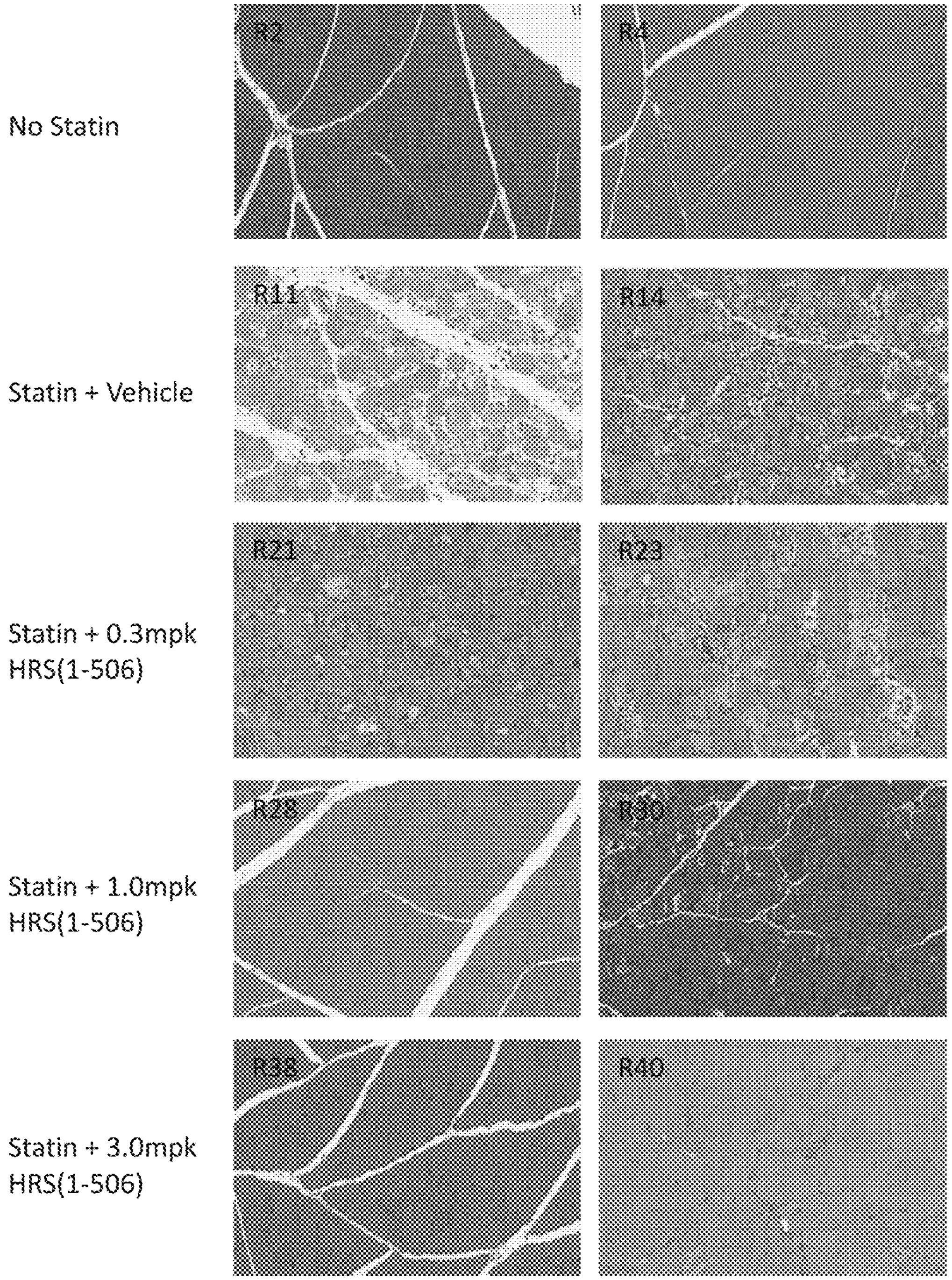
FIG. 8 shows representative H&E images of hamstring sections at 10× magnification after 15 days of treatment with statins+/−HRS(1-506) at 0.3, 1.0, and 3.0 mg/Kg.

A small increase in serum CK was observed in statin treated rats over untreated controls on days 12 and 15. On day 12, rats dosed with 1 mg/kg and 3 mg/kg HRS(1-506) had smaller, tighter CK averages compared to Statin+Vehicle treated animals (FIGS. 6A-B), consistent with a positive impact of HRS(1-506) treatment on statin induced myositis, also consistent with a positive effect of HRS(1-506) on muscle function, muscle troponin C levels were also reduced in HRS(1-506) treated animals (FIG. 5B). Moreover endogenous serum HRS levels were elevated in statin-treated rats compared to rats not receiving statin (FIG. 7), suggesting that the release of HRS may play a role as an endogenous regulator of muscle inflammation. H&E staining on hamstrings demonstrated reduced muscle degeneration/necrosis and inflammation scores in statin-treated rats dosed with 1 mg/kg and 3 mg/kg HRS(1-506) compared to vehicle-dosed and 0.3 mg/kg HRS(1-506)-dosed rats (FIG. 8).

Figure 9:
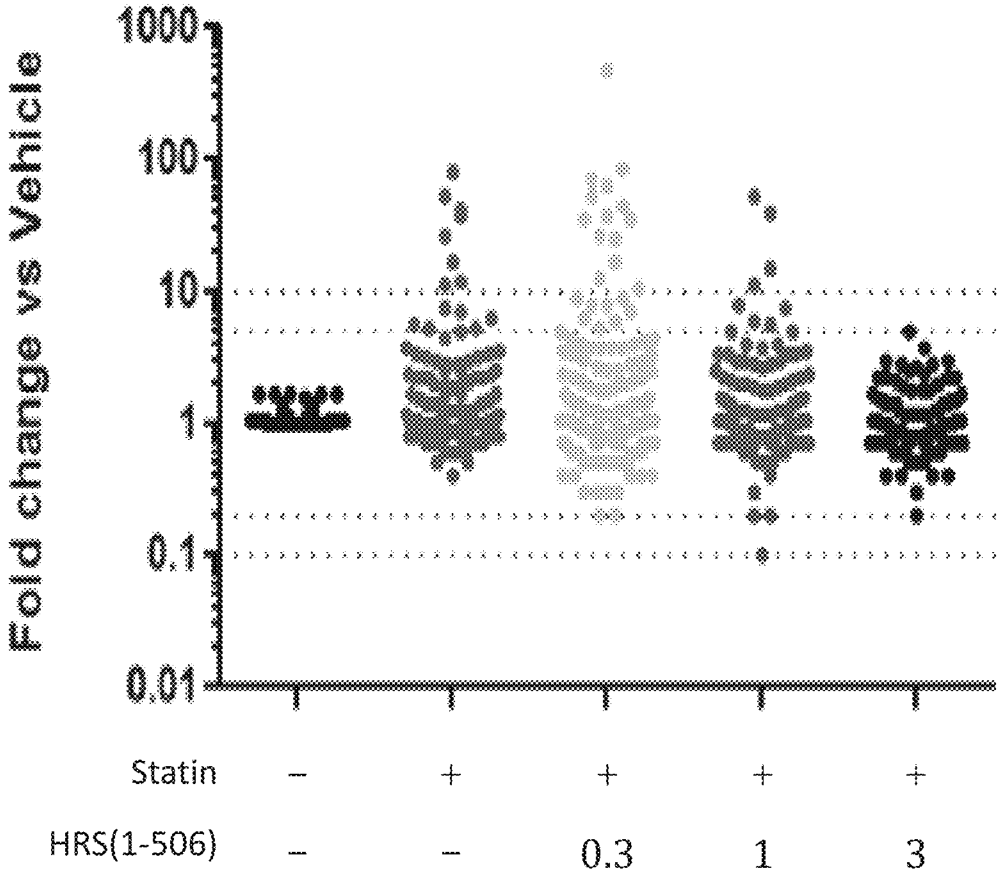
FIG. 9 shows the results of gene expression profiling of statin treated rat hamstrings. The data depicts changes in the expression of 137 genes selected to track markers of muscle, and immune cell function, inflammation, metabolic status, tissue recovery, muscle growth and atrophy. Gene expression values were normalized to reference genes and represented as fold change vs. the vehicle treated group.
Figures 10A, 10B:
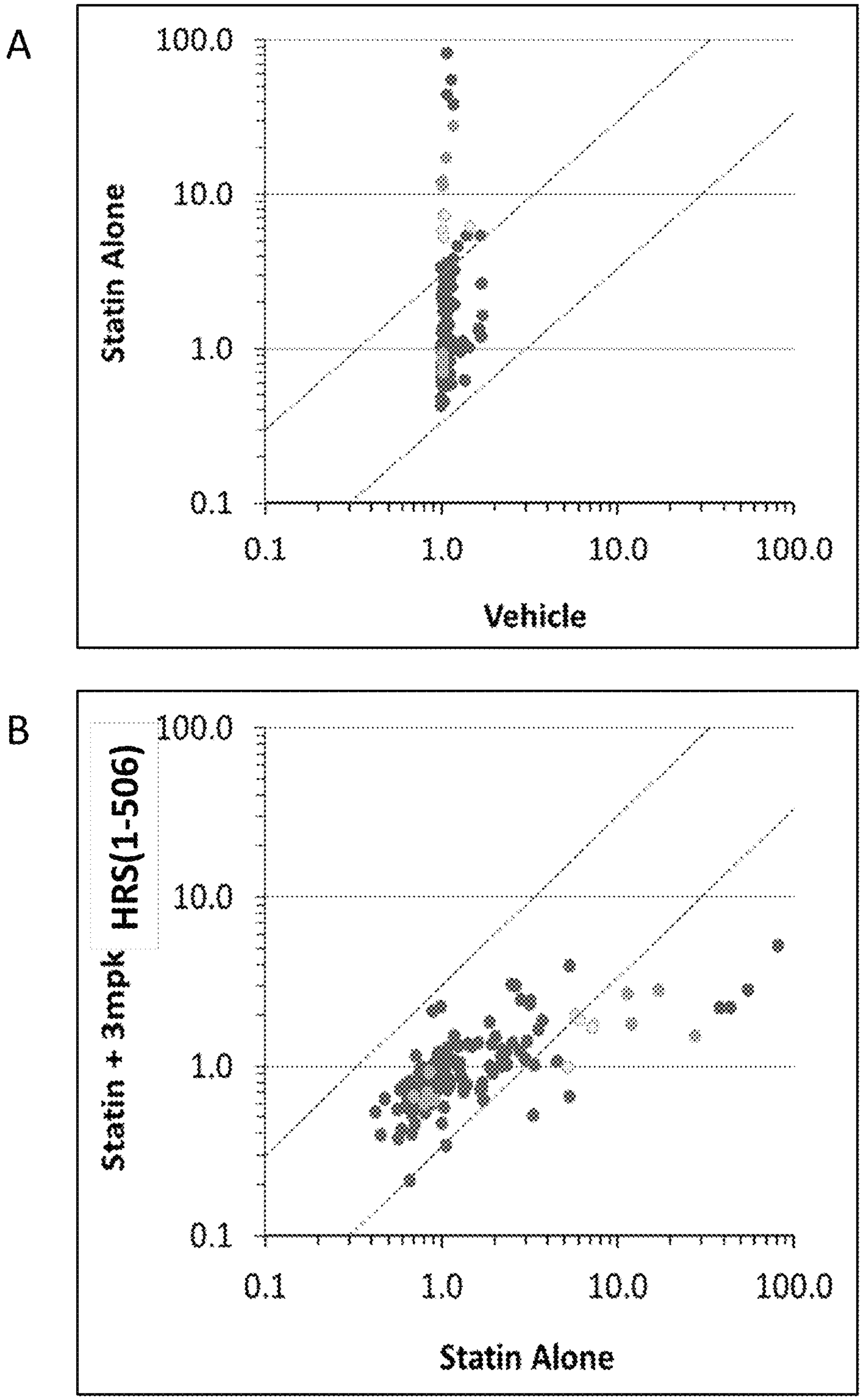
FIGS. 10A-10B show the results of gene expression profiling of statin treated rat hamstrings. The data in FIG. 10A depicts changes in the expression of 137 genes (as in FIG. 7) to compare the relative changes in gene expression of statin treated animals compared to vehicle treated animals.

To further investigate the mechanistic basis for the effects of HRS on statin induced myopathy, changes in gene expression in the hamstrings from treated animals was examined after the completion of the study. RNA profiling was performed on hamstring muscles isolated from the rats on day 15 as described above. The results from these studies demonstrated that all 13 genes that were elevated by more than 5 fold in response to statin treatment were reduced by treatment with HRS(1-506) (see Table E8; and FIGS. 9-10)

TABLE E8

| Gene regulated by more than 25 fold | Gene regulated by more than 10 fold | Gene regulated by more than 4 fold | No Change |
|---|---|---|---|
| CD8a | MCP1 | CD11a | HARS |
| MMP9 | CD8b | CD11b | HARS2 |
| IL6 | CCR5 | CD45 | DARS |
| IL10 | CD18 | SDC1 | GARS |
| | | IFNg | QARS |

Figure 11:
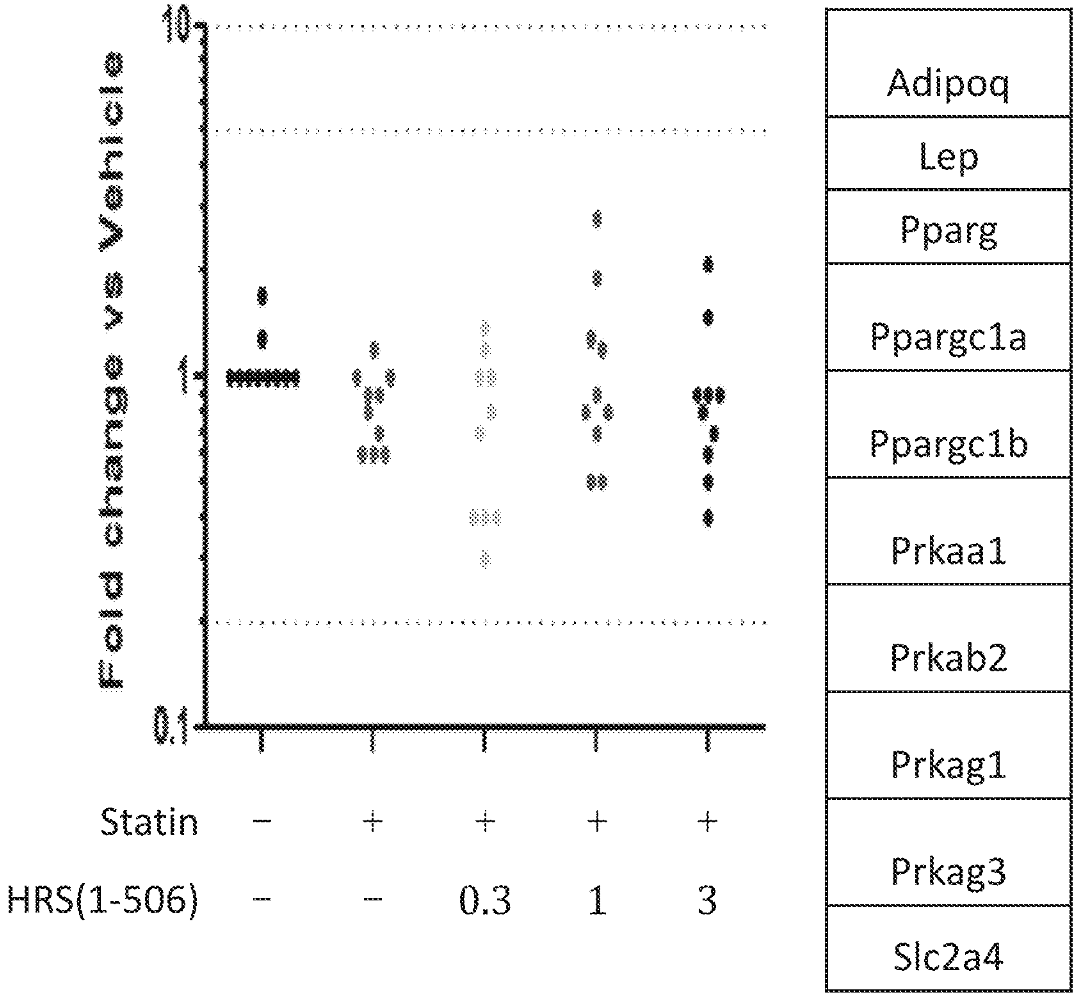
FIG. 11 shows the results of gene expression profiling of statin treated rat hamstrings of 10 diabetes/metabolic syndrome related genes after 15 days of treatment with statins+/−HRS(1-506) at 0.3, 1.0, and 3.0 mg/Kg.
Figure 12:
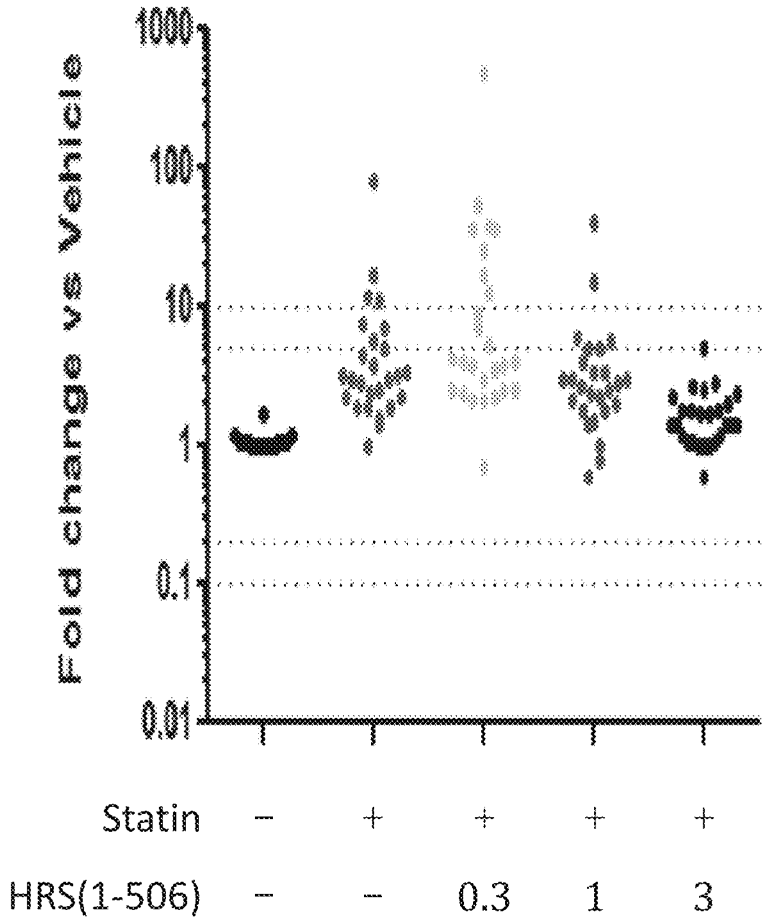
FIG. 12 shows the results of gene expression profiling of statin treated rat hamstrings of 26 immune cell marker genes after 15 days of treatment with statins+/−HRS(1-506) at 0.3, 1.0, and 3.0 mg/Kg.
Figures 13A, 13B:
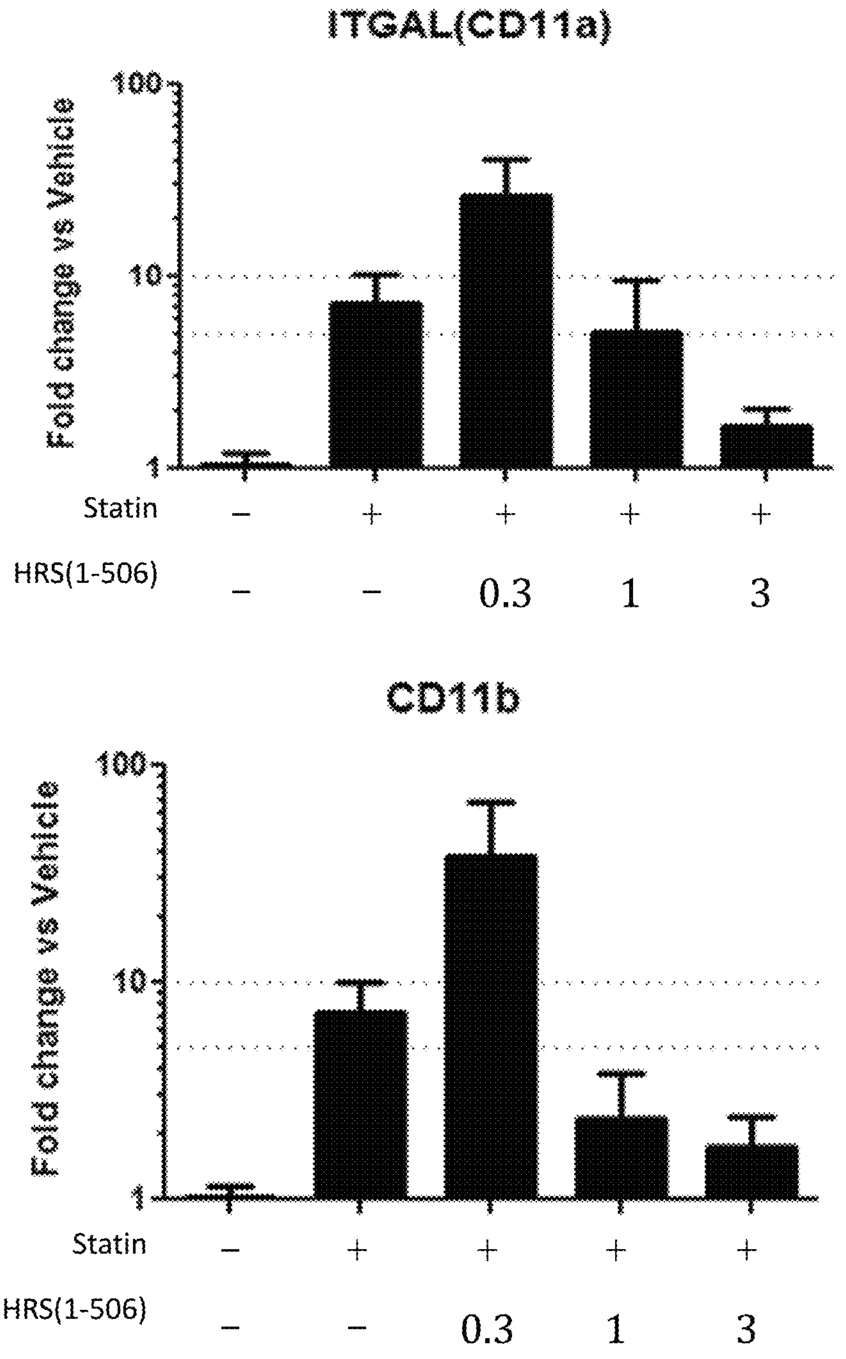
FIGS. 13A-13B and FIGS. 13C-13D show the results of gene expression profiling of the CD11a, CD11b, CD8a, and CD8b genes in statin treated rat hamstrings after 15 days of treatment with statins+/−HRS(1-506) at 0.3, 1.0, and 3.0 mg/Kg.
Figures 13C, 13D:
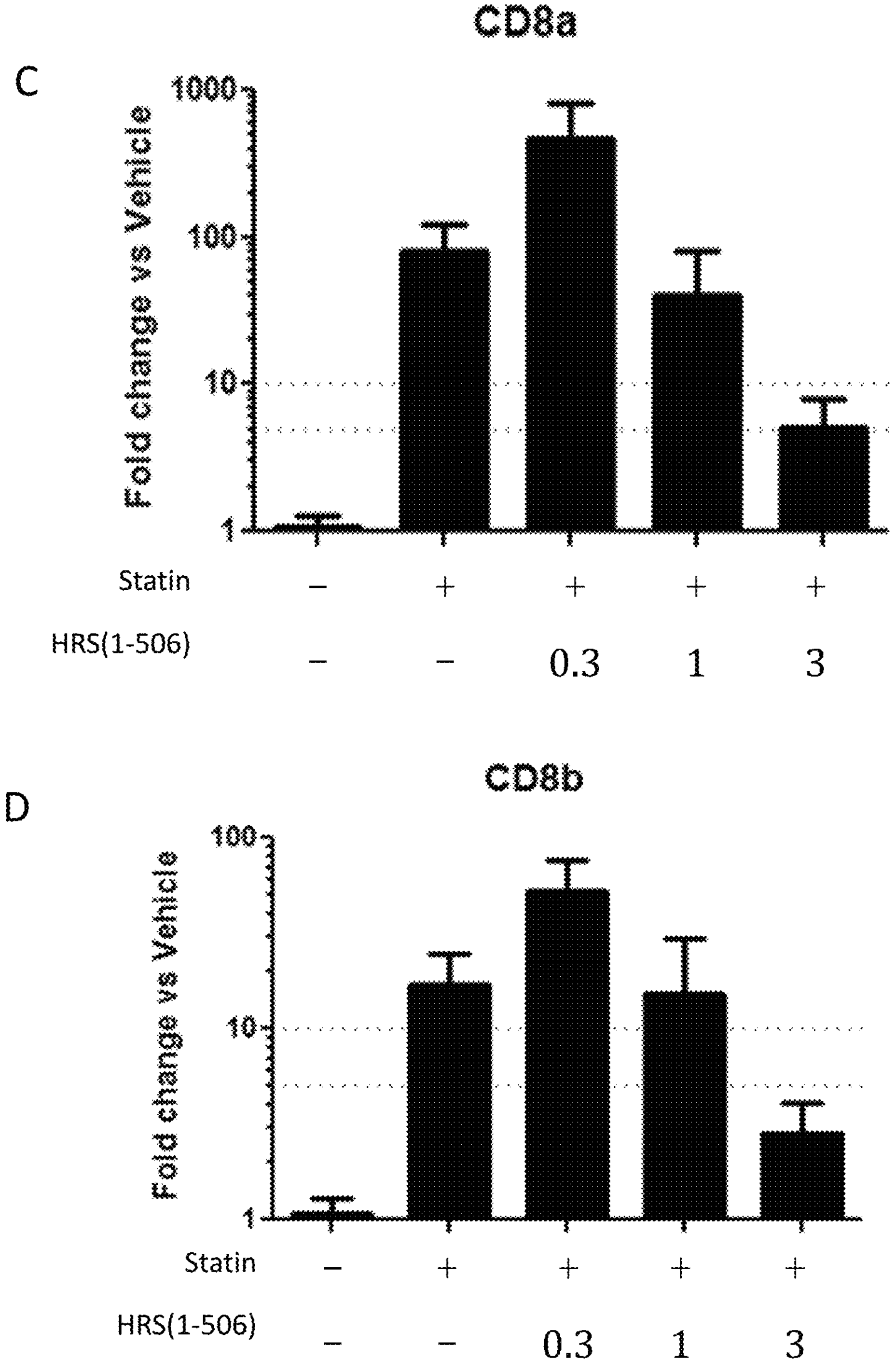
Figures 14A, 14B:
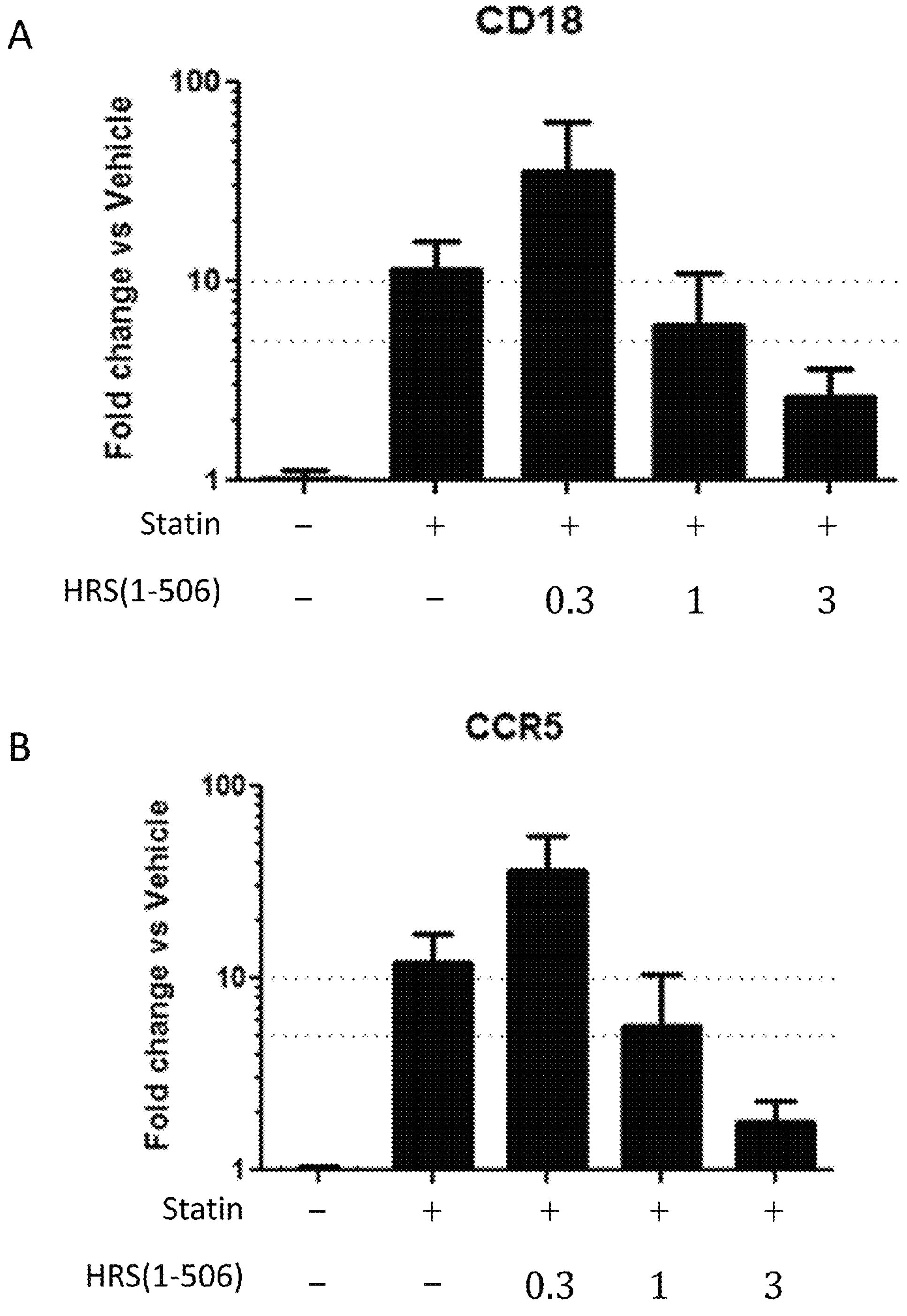
FIGS. 14A-14B and FIG. 14C show the results of gene expression profiling of the CD18, CCR5 and CD45R genes in statin treated rat hamstrings after 15 days of treatment with statins+/−HRS(1-506) at 0.3, 1.0, and 3.0 mg/Kg.
Figure 14C:
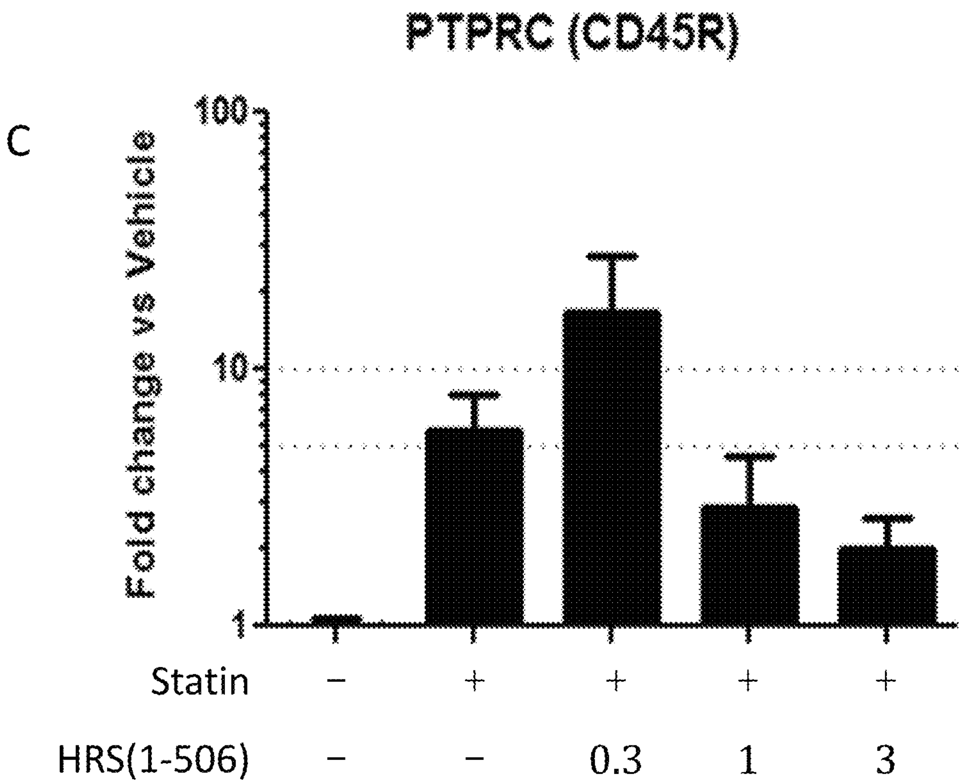
Figure 15:
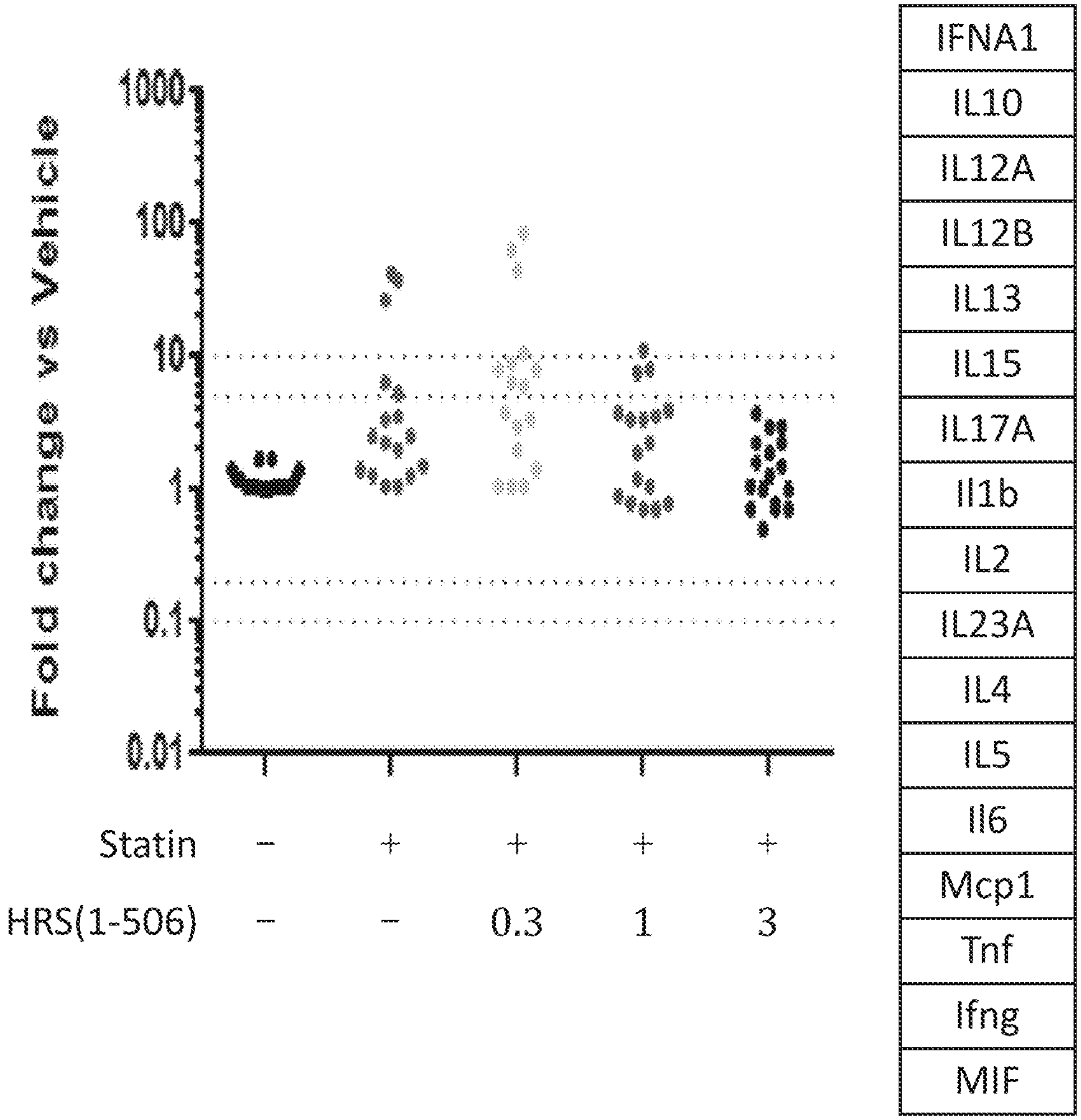
FIG. 15 shows the results of gene expression profiling of 17 inflammatory marker genes in statin treated rat hamstrings after 15 days of treatment with statins+/−HRS(1-506) at 0.3, 1.0, and 3.0 mg/Kg.
Figures 16A, 16B:
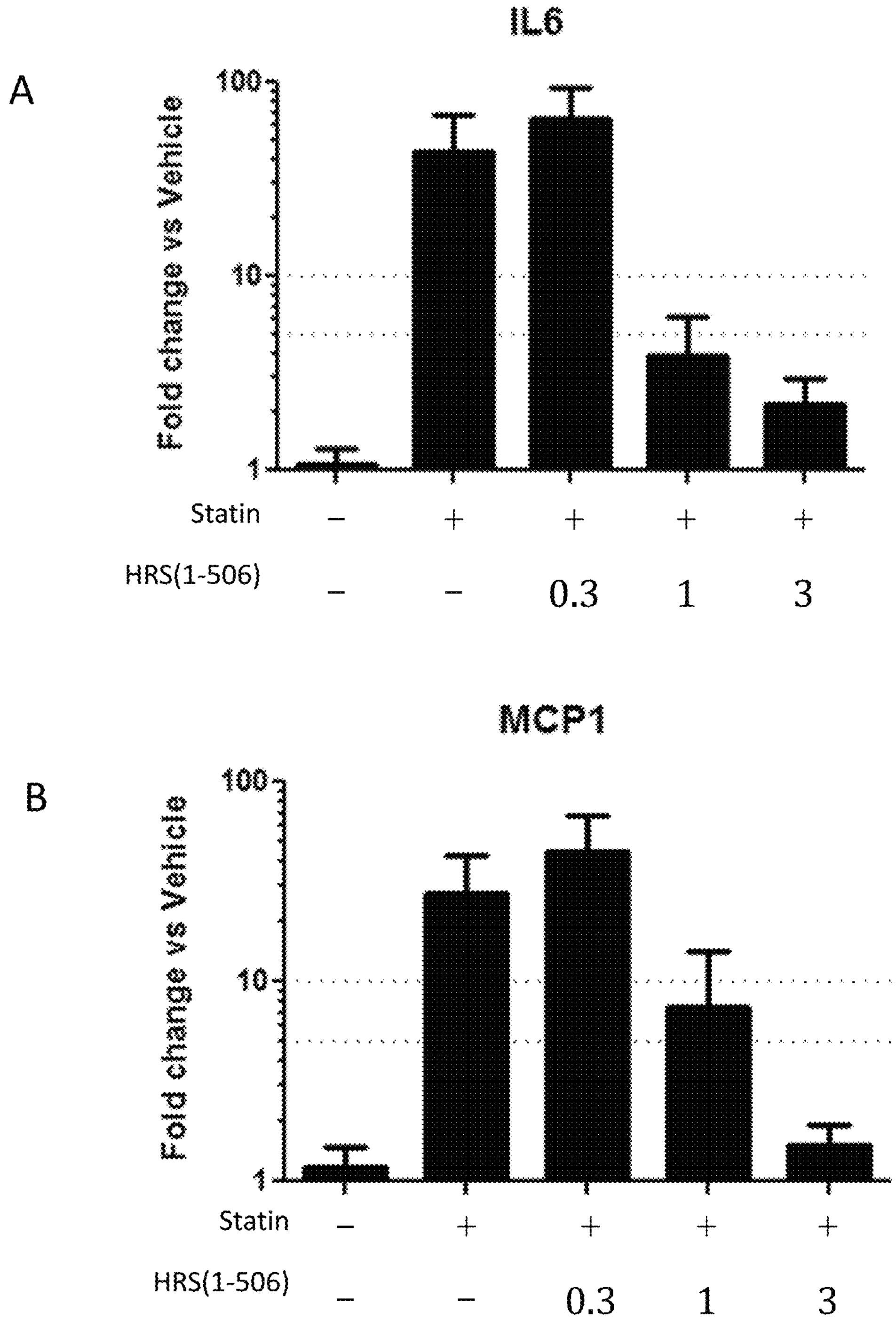
FIGS. 16A-16B and FIGS. 16C-16D show the results of gene expression profiling of the inflammatory cytokines IL-6, MCP1, IL-10, and interferon-gamma (IFN-γ) in statin treated rat hamstrings after 15 days of treatment with statins+/−HRS(1-506) at 0.3, 1.0, and 3.0 mg/Kg.
Figures 16C, 16D:
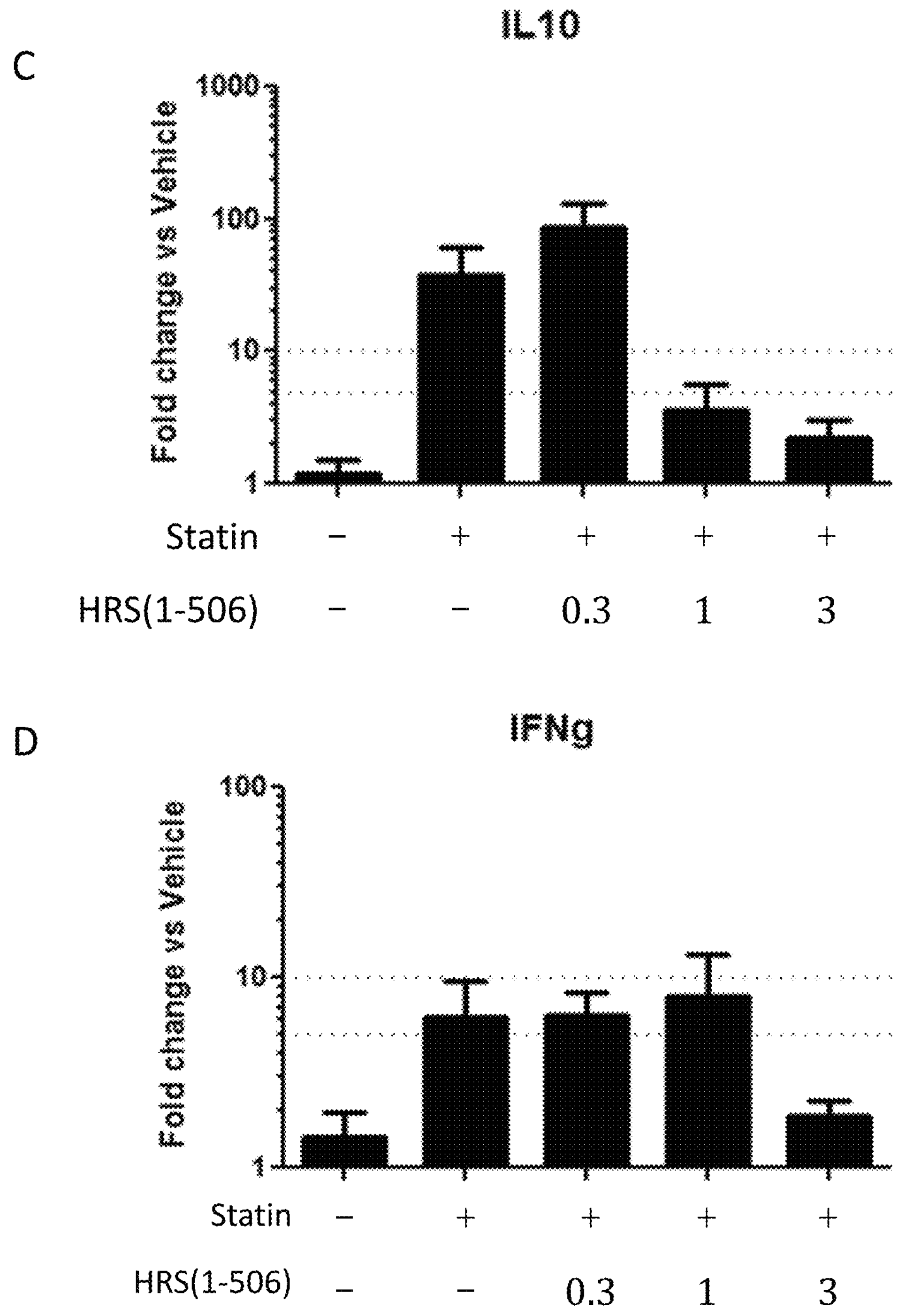
Figure 17:
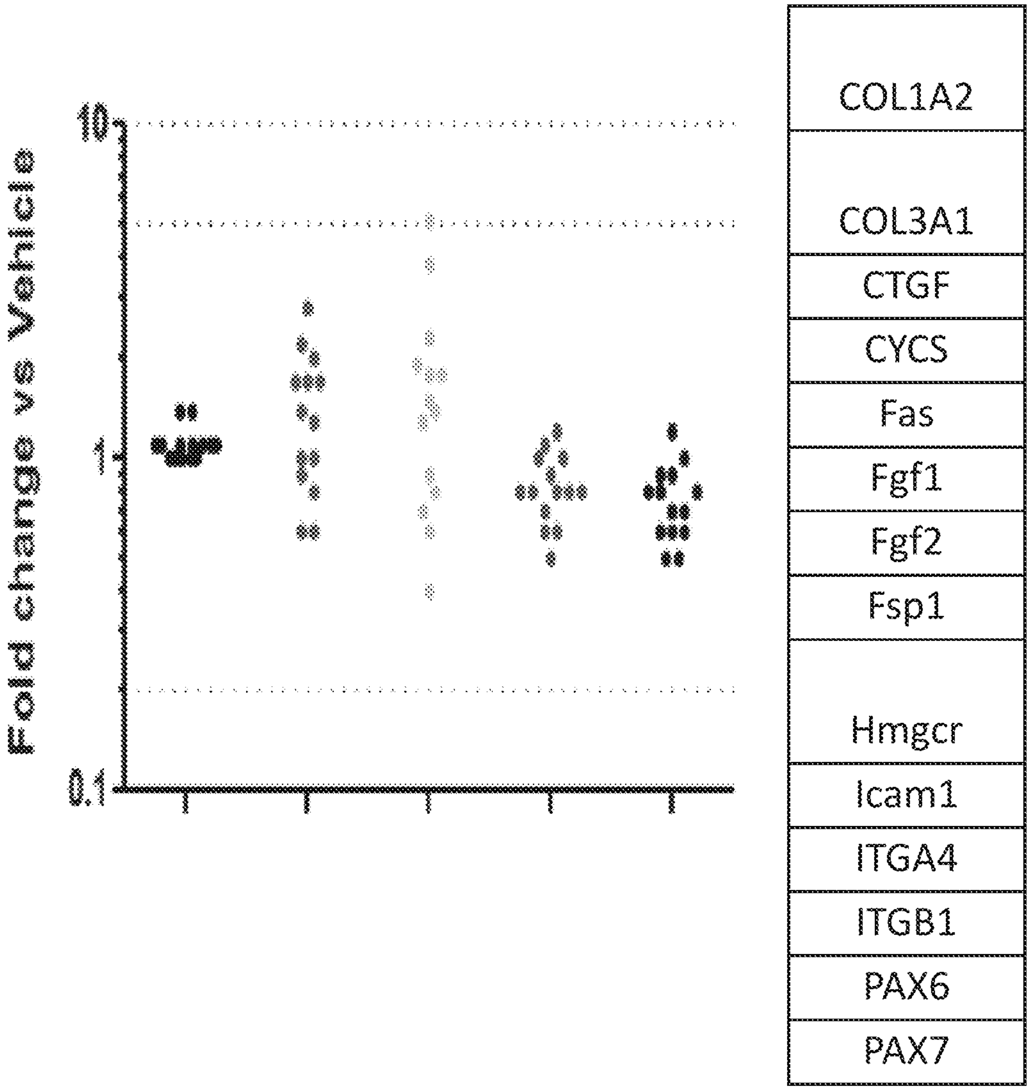
FIG. 17 shows the results of gene expression profiling of statin treated rat hamstrings of 14 adhesion, development, and fibrosis related genes after 15 days of treatment with statins+/−HRS(1-506) at 0.3, 1.0, and 3.0 mg/Kg.
Figure 18:
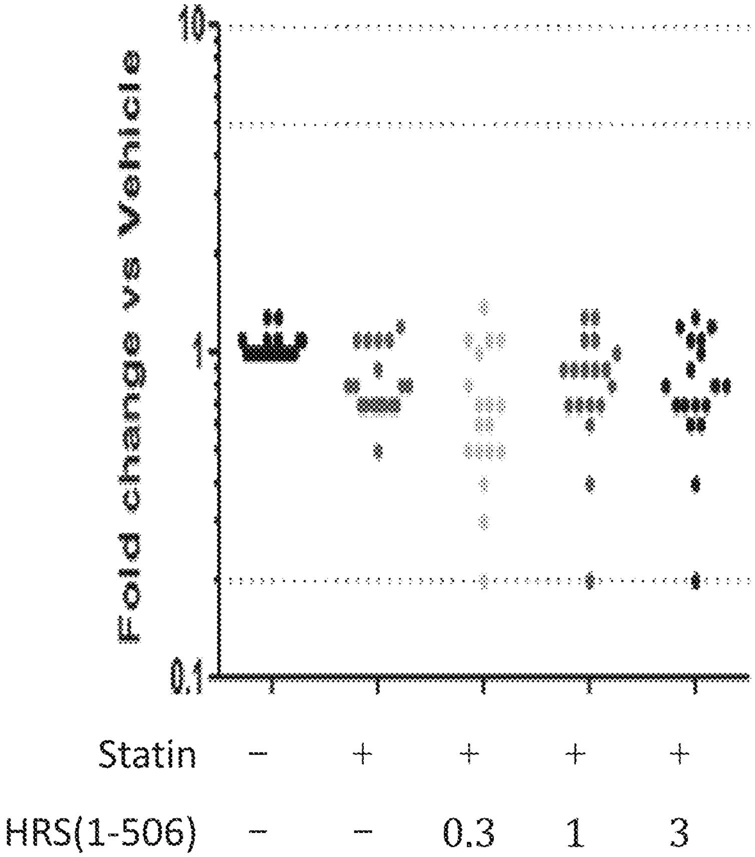
FIG. 18 shows the results of gene expression profiling of statin treated rat hamstrings of 14 muscle wasting/atrophy related genes after 15 days of treatment with statins+/−HRS (1-506) at 0.3, 1.0, and 3.0 mg/Kg.
Figure 19A:
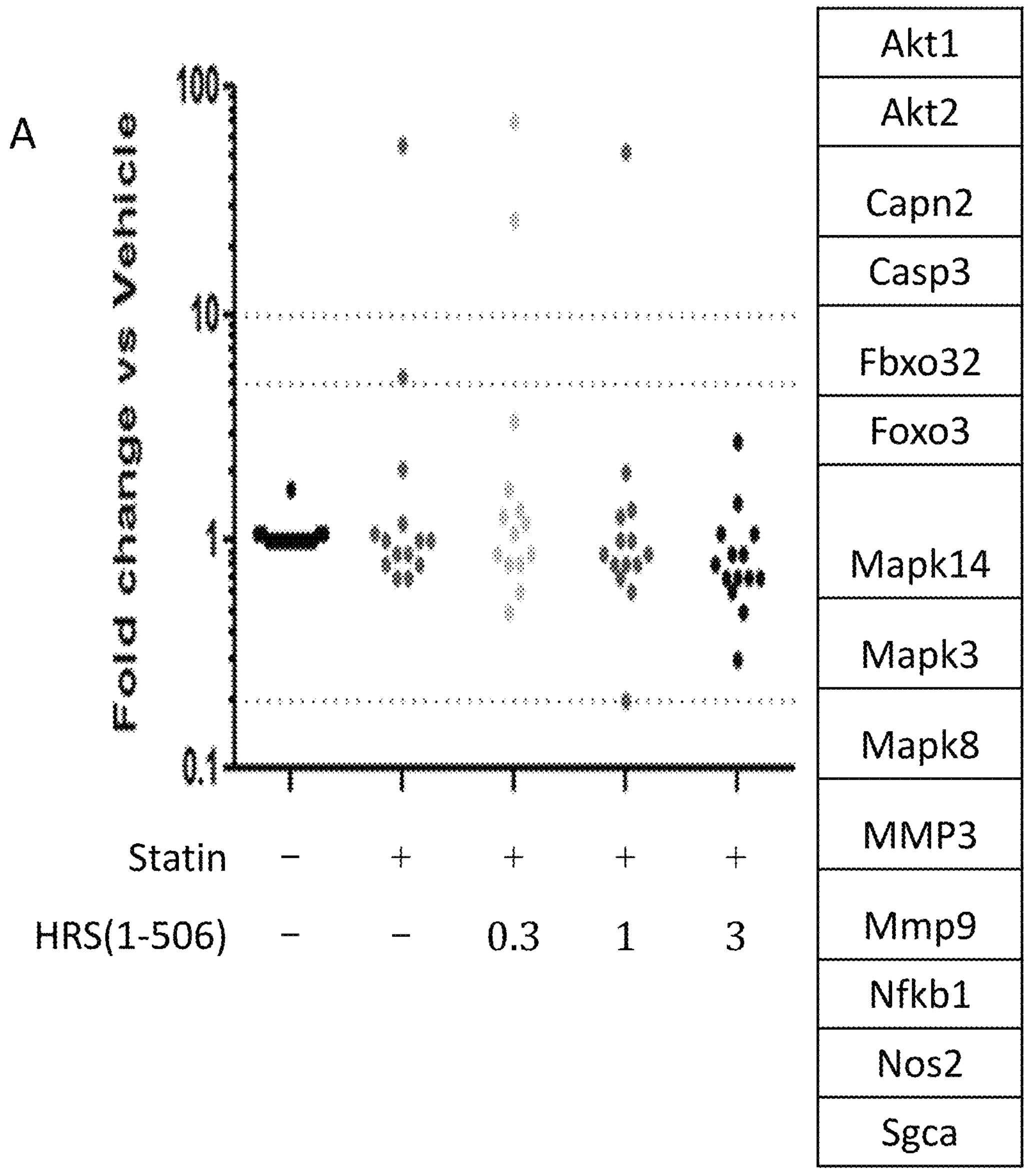
FIG. 19A shows the results of gene expression profiling of statin treated rat hamstrings of 14 muscle wasting/atrophy related genes after 15 days of treatment with statins+/−HRS (1-506) at 0.3, 1.0, and 3.0 mg/Kg.
Figure 19B:
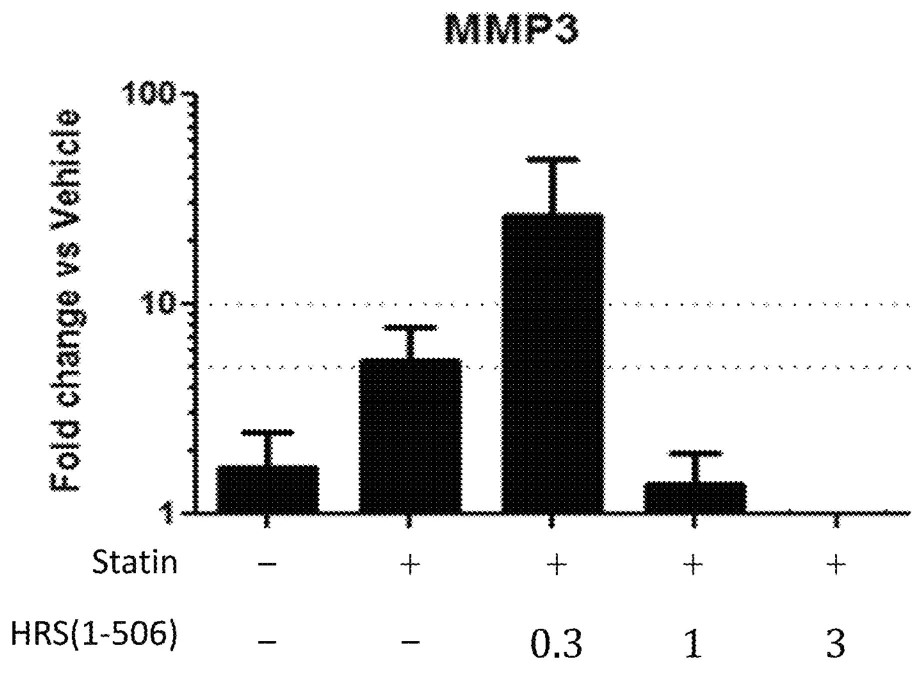
FIG. 19B shows specific changes in MMP-3.
Figure 19C:
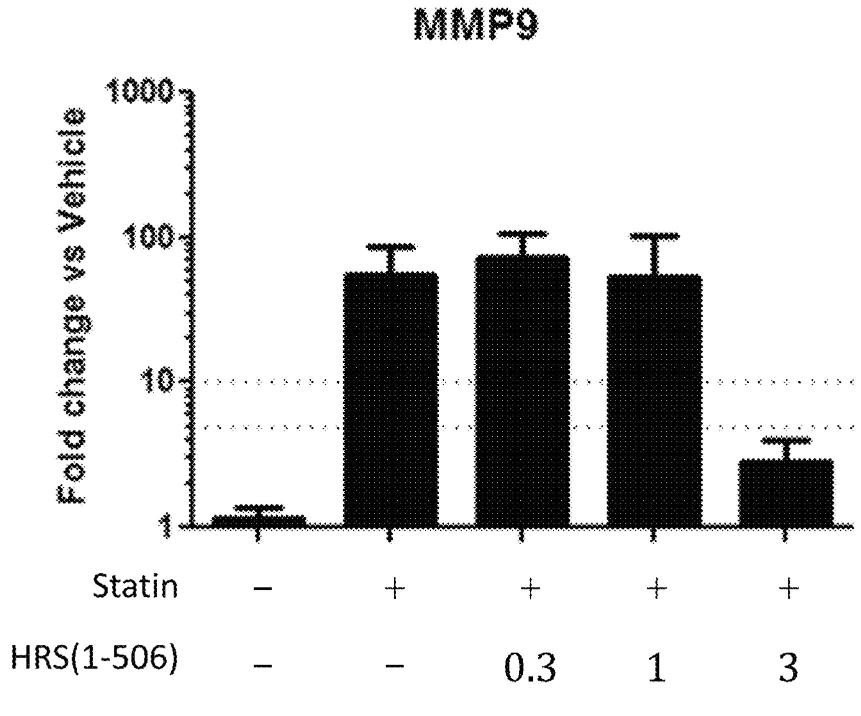
FIG. 19C shows specific changes in MMP-9 gene expression under the same conditions.
Figure 20:
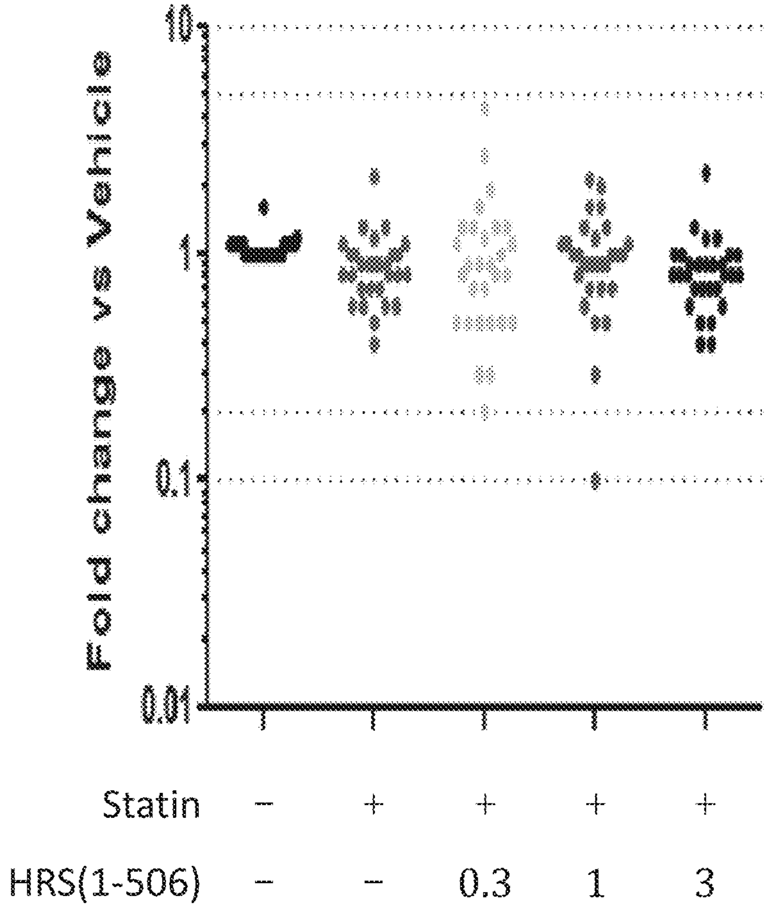
FIG. 20 shows the results of gene expression profiling of statin treated rat hamstrings of 29 myogenesis related genes after 15 days of treatment with Statins+/−HRS(1-506) at 0.3, 1.0, and 3.0 mg/Kg.

Transcriptional profiling of statin treated rat hamstrings: revealed that 10 diabetes/metabolic syndrome related genes (FIG. 11) and several housekeeping genes (data not shown) were not significantly impacted by HRS treatment. By contrast, transcriptional profiling of statin treated rat hamstrings of 26 immune cell marker genes revealed significant changes in a larger number of genes (see FIGS. 12-14), including the dose dependent inhibition of ITGAL(CD11a), CD11b, CD8a, CD8b, CD18, CCR5, PTPPC and (CD45R) expression. Additionally HRS(1-506) was effective in reducing the expression of a number of inflammatory marker genes including IL6, MCP1, IL10 and IFN gamma (see FIGS. 15-16). Transcriptional changes were also observed in 14 adhesion, development, and fibrosis related genes (see FIGS. 17-18), the muscle contractility gene Neb (data not shown), and in genes associated with muscular wasting, atrophy, and myogenesis (see FIGS. 19-20).

Conclusions.

Decreased CK, serum Troponin-I and muscle cell degeneration/necrosis and muscle inflammation were all observed in animals receiving higher doses of HRS(1-506), either at 1.0 mg/kg or 3.0 mg/kg in contrast to animals receiving either Vehicle or low dose 0.3 mg/kg HRS(1-506). RNA profiling data supported these results by demonstrating reduced CD8a, IL-6, MCP-1 and MMP-9 expression in hamstrings of statin-treated rats dosed with higher doses of HRS(1-506). Up-regulation of these genes is most likely due to increased immune cell infiltrate into damaged muscle tissue. Based on the identity of the expressed genes, the infiltrating immune cells are likely to be made up of one of more of the following cell types, T cells, dendritic cell, NK cells, and macrophage/monocytes. All of these cell types have been associated with muscle inflammation, and the ability of the HRS polypeptides, including HRS(1-506) to mediate a dramatic inhibition of this immune cell influx suggests that HRS polypeptides such as HRS(1-506) represent potent immunoregulators, which are capable of acting as potent immunomodulators in a broad range of inflammatory and autoimmune diseases and disorders.

Example 8

Preparation of HRS-Fc Polypeptides

N-terminal and C-terminal Fc-histidyl tRNA synthetase (HRS-Fc) fusion proteins were prepared, purified, and analyzed as follows.

Plasmid Construction.

The human IgG1 Fc domain was amplified by polymerase chain reaction (PCR) before inserting into the C-term or N-term of the HRS polypeptide HRS(1-60) via sequential PCR reactions using the primers below, and the resulting amplified DNA fragments inserted into C-term or N-term of HRS(1-60) located in the pET28 expression vector (Novagen 69864). It will be appreciated that the creation of the N-terminal Fc fusion protein results in the deletion/replacement of the N-terminal methionine in HRS(1-60) with the C-terminal amino acid of the Fc domain, and vice versa where appropriate.

The following primers were used to create the N-terminally fused HRS(1-60) Fc fusion protein (Fc-HRS(2-60)) (Table E9):

TABLE E9

| Primer Sequences | | |
|---|---|---|
| Primer Name | Sequence | SEQ ID NO: |
| FcNSV9-F | TAATTTTGTTTAACTTTAAGAAGGAGATATACATATGTCTGACAAAACTC ACACATGCCC | 323 |
| FcNSV9tail | AGCCTCTCCCTGTCTCCGGGTAAAGCAGAGCGTGCGGCGCTGG | 324 |
| FcNSV9-R | CCAGCGCCGCACGCTCTGCTTTACCCGGAGACAGGGAGAGGCT | 325 |
| FcNSV9-F2 | TTTTGTTTAACTTTAAGAAGGAGATATACATATGTCTGACAAAACTCACA CATGCCC | 326 |
| FcNSV9tail2 | CTCTCCCTGTCTCCGGGTAAAGCAGAGCGTGCGGCGC | 327 |
| FcNSV9-R2 | GCGCCGCACGCTCTGCTTTACCCGGAGACAGGGAGAG | 328 |

The following primers were used to create the C-terminally fused HRS(1-60) Fc fusion protein (HRS(1-60)-Fc) (Table E10).

TABLE E10

| Primer Sequences | | |
|---|---|---|
| Primer Name | Sequence | SEQ ID NO: |
| FcCSV9-F | CAAACAGAAATTTGTGCTCAAAACCCCCAAGTCT**GACAAAACTCACAC ATGCCCACCG** | 329 |
| FcC5V9tail | **AGCCTCTCCCTGTCTCCGGGTAAA**TGAGATCCGGCTGCTAACAAAGCC C | 330 |
| FcCSV9-R | GGGCTTTGTTAGCAGCCGGATCTCATTTACCCGGAGACAGGGAGAGGCT | 331 |
| FcCSV9-F2 | CAGAAATTTGTGCTCAAAACCCCCAAGTCT**GACAAAACTCACACATGC CC** | 332 |
| FcCSV9tail2 | **CTCTCCCTGTCTCCGGGTAAA**TGAGATCCGGCTGCTAACAAAG | 333 |
| FcCSV9-R2 | CTTTGTTAGCAGCCGGATCTCATTTACCCGGAGACAGGGAGAG | 334 |

The PCR reactions were performed using recommended thermal cycling parameters, and the PCR-amplified fragments were verified on by gel electrophoresis. Sequences were confirmed by performing alignments with the theoretical sequences using EMBOSS Pairwise Alignment Algorithms. The cloned DNA and protein sequences of Fc-HRS (2-60) and HRS(1-60)-Fc are shown below.

DNA sequence of Fc-HRS(2-60) (N-terminal Fc fusion):

(SEQ ID NO: 335)

ATGTCTGACAAAACTCACACATGCCCACCGTGCCCAGCACCTGAACTCCT

GGGGGGACCGTCAGTCTTCCTCTTCCCCCCAAAACCCAAGGACACCCTCA

TGATCTCCCGGACCCCTGAGGTCACATGCGTGGTGGTGGACGTGAGCCAC

GAAGACCCTGAGGTCAAGTTCAACTGGTACGTGGACGGCGTGGAGGTGCA

TAATGCCAAGACAAAGCCGCGGGAGGAGCAGTACAACAGCACGTACCGTG

TGGTCAGCGTCCTCACCGTCCTGCACCAGGACTGGCTGAATGGCAAGGAG

TACAAGTGCAAGGTCTCCAACAAAGCCCTCCCAGCCCCCATCGAGAAAAC

CATCTCCAAAGCCAAAGGGCAGCCCCGAGAACCACAGGTGTACACCCTGC

CCCCATCCCGGGAGGAGATGACCAAGAACCAGGTCAGCCTGACCTGCCTG

GTCAAAGGCTTCTATCCCAGCGACATCGCCGTGGAGTGGGAGAGCAATGG

GCAGCCGGAGAACAACTACAAGACCACGCCTCCCGTGCTGGACTCCGACG

GCTCCTTCTTCCTCTACAGCAAGCTCACCGTGGACAAGAGCAGGTGGCAG

CAGGGGAACGTCTTCTCATGCTCCGTGATGCACGAGGCTCTGCACAACCA

CTACACGCAGAAGAGCCTCTCCCTGTCTCCGGGTAAAGCAGAGCGTGCGG

CGCTGGAGGAGCTGGTGAAACTTCAGGGAGAGCGCGTGCGAGGCCTCAAG

CAGCAGAAGGCCAGCGCCGAGCTGATCGAGGAGGAGGTGGCGAAACTCCT

GAAACTGAAGGCACAGCTGGGTCCTGATGAAAGCAAACAGAAATTTGTGC

TCAAAACCCCCAAG TGA

DNA sequence of HRS(1-60)-Fc (C-terminal Fc fusion).

(SEQ ID NO: 336)

ATGGCAGAGCGTGCGGCGCTGGAGGAGCTGGTGAAACTTCAGGGAGAGCG

CGTGCGAGGCCTCAAGCAGCAGAAGGCCAGCGCCGAGCTGATCGAGGAGG

AGGTGGCGAAACTCCTGAAACTGAAGGCACAGCTGGGTCCTGATGAAGCA

AACAGAAATTTGTGCTCAAAACCCCCAAGTCTGACAAAACTCACACATGC

CCACCGTGCCCAGCACCTGAACTCCTGGGGGGACCGTCAGTCTTCCTCTT

CCCCCCAAAACCCAAGGACACCCTCATGATCTCCCGGACCCCTGAGGTCA

CATGCGTGGTGGTGGACGTGAGCCACGAAGACCCTGAGGTCAAGTTCAAC

TGGTACGTGGACGGCGTGGAGGTGCATAATGCCAAGACAAAGCCGCGGGA

GGAGCAGTACAACAGCACGTACCGTGTGGTCAGCGTCCTCACCGTCCTGC

ACCAGGACTGGCTGAATGGCAAGGAGTACAAGTGCAAGGTCTCCAACAAA

GCCCTCCCAGCCCCCATCGAGAAAACCATCTCCAAAGCCAAAGGGCAGCC

CCGAGAACCACAGGTGTACACCCTGCCCCCATCCCGGGAGGAGATGACCA

AGAACCAGGTCAGCCTGACCTGCCTGGTCAAAGGCTTCTATCCCAGCGAC

ATCGCCGTGGAGTGGGAGAGCAATGGGCAGCCGGAGAACAACTACAAGAC

CACGCCTCCCGTGCTGGACTCCGACGGCTCCTTCTTCCTCTACAGCAAGC

-continued

TCACCGTGGACAAGAGCAGGTGGCAGCAGGGGAACGTCTTCTCATGCTCC

GTGATGCACGAGGCTCTGCACAACCACTACACGCAGAAGAGC CTC TCC

CTG TCT CCG GGTAAATGA

Protein sequence of Fc-HRS(2-60) (N-terminal Fc fusion)

(SEQ ID NO: 337)

MSDKTHTCPPCPAPELLGGPSVFLFPPKPKDTLMISRTPEVTCVVVDVSH

EDPEVKFNWYVDGVEVHNAKTKPREEQYNSTYRVVSVLTVLHQDWLNGKE

YKCKVSNKALPAPIEKTISKAKGQPREPQVYTLPPSREEMTKNQVSLTCL

VKGFYPSDIAVEWESNGQPENNYKTTPPVLDSDGSFFLYSKLTVDKSRWQ

QGNVFSCSVMHEALHNHYTQKSLSLSPGKAERAALEELVKLQGERVRGLK

QQKASAELIEEEVAKLLKLKAQLGPDESKQKFVLKTPK

Protein sequence of HRS(1-60)-Fc (C-terminal Fc fusion)

(SEQ ID NO: 338)

MAERAALEELVKLQGERVRGLKQQKASAELIEEEVAKLLKLKAQLGPDES

KQKFVLKTPKSDKTHTCPPCPAPELLGGPSVFLFPPKPKDTLMISRTPEV

TCVVVDVSHEDPEVKFNWYVDGVEVHNAKTKPREEQYNSTYRVVSVLTVL

HQDWLNGKEYKCKVSNKALPAPIEKTISKAKGQPREPQVYTLPPSREEMT

KNQVSLTCLVKGFYPSDIAVEWESNGQPENNYKTTPPVLDSDGSFFLYSK

LTVDKSRWQQGNVFSCSVMHEALHNHYTQKSLSLSPGK

Additional N-terminal and C-terminal Fc-histidyl tRNA synthetase (HRS-Fc) DNA constructs were prepared as follows.

Plasmid Construction.

HRS (2-60) with an N-terminal Fc or HRS (1-60) with a C-terminal Fc (Example 8) were subcloned into a modified pET24b vector (EMD, Gibbstown, N.J.) containing a TAC promoter instead of T7 ("pET24b_TAC"). The Fc-HRS (2-60) and HRS (1-60)-Fc were amplified by polymerase chain reaction (PCR) using the primers below which contain a 5' NdeI site and a 3' XhoI site, and the resulting amplified DNA was subcloned into pET24b_TAC using the NdeI and XhoI restriction sites.

The following primers were used to amplify the Fc-HRS (2-60) (N-terminal Fc fusion) (Table E11):

TABLE E11

| Primer Sequences | | |
|---|---|---|
| Primer Name | Sequence | SEQ ID NO: |
| 1921-NdeI-FWD | GATATACATATGTCTGACAAAACTCACACATGCC | 343 |
| 1921-XhoI-REV | GATCCTCGAGTCACTTGGGGGTTTTG | 344 |

The following primers were used to amplify the HRS (1-60)-Fc (C-terminal Fc fusion) (Table E12).

TABLE E12

| Primer Sequences | | |
|---|---|---|
| Primer Name | Sequence | SEQ ID NO: |
| 1922-NdeI-FWD | GATATACATATGGCAGAGCGTGCGG | 345 |
| 1922-XhoI-REV | GATCCTCGAGTCATTTACCCGGAGAC | 346 |

The PCR reactions were performed using recommended thermal cycling parameters, and the PCR-amplified fragments were verified by gel electrophoresis. Sequences were confirmed by performing alignments with the theoretical sequences using DNASTAR Lasergene SeqMan Pro. The cloned DNA and protein sequences of Fc-HRS(2-60) and HRS(1-60)-Fc are shown below.

DNA sequence of Fc-HRS(2-60) (N-terminal Fc fusion):

(SEQ ID NO: 347)

ATGTCTGACAAAACTCACACATGCCCACCGTGCCCAGCACCTGAACTCCT

GGGGGGACCGTCAGTCTTCCTCTTCCCCCCAAAACCCAAGGACACCCTCA

TGATCTCCCGGACCCCTGAGGTCACATGCGTGGTGGTGGACGTGAGCCAC

GAAGACCCTGAGGTCAAGTTCAACTGGTACGTGGACGGCGTGGAGGTGCA

TAATGCCAAGACAAAGCCGCGGGAGGAGCAGTACAACAGCACGTACCGTG

TGGTCAGCGTCCTCACCGTCCTGCACCAGGACTGGCTGAATGGCAAGGAG

TACAAGTGCAAGGTCTCCAACAAAGCCCTCCCAGCCCCCATCGAGAAAAC

CATCTCCAAAGCCAAAGGGCAGCCCCGAGAACCACAGGTGTACACCCTGC

CCCCATCCCGGGAGGAGATGACCAAGAACCAGGTCAGCCTGACCTGCCTG

GTCAAAGGCTTCTATCCCAGCGACATCGCCGTGGAGTGGGAGAGCAATGG

GCAGCCGGAGAACAACTACAAGACCACGCCTCCCGTGCTGGACTCCGACG

GCTCCTTCTTCCTCTACAGCAAGCTCACCGTGGACAAGAGCAGGTGGCAG

CAGGGGAACGTCTTCTCATGCTCCGTGATGCACGAGGCTCTGCACAACCA

CTACACGCAGAAGAGCCTCTCCCTGTCTCCGGGTAAAGCAGAGCGTGCGG

CGCTGGAGGAGCTGGTGAAACTTCAGGGAGAGCGCGTGCGAGGCCTCAAG

CAGCAGAAGGCCAGCGCCGAGCTGATCGAGGAGGAGGTGGCGAAACTCCT

GAAACTGAAGGCACAGCTGGGTCCTGATGAAAGCAAACAGAAATTTGTGC

TCAAAACCCCCAAG tga

DNA sequence of HRS(1-60)-Fc (C-terminal Fc fusion):

(SEQ ID NO: 348)

ATGGCAGAGCGTGCGGCGCTGGAGGAGCTGGTGAAACTTCAGGGAGAGCG

CGTGCGAGGCCTCAAGCAGCAGAAGGCCAGCGCCGAGCTGATCGAGGAGG

AGGTGGCGAAACTCCTGAAACTGAAGGCACAGCTGGGTCCTGATGAAAGC

AAACAGAAATTTGTGCTCAAAACCCCCAAGTCTGACAAAACTCACACATG

CCCACCGTGCCCAGCACCTGAACTCCTGGGGGGACCGTCAGTCTTCCTCT

TCCCCCCAAAACCCAAGGACACCCTCATGATCTCCCGGACCCCTGAGGTC

ACATGCGTGGTGGTGGACGTGAGCCACGAAGACCCTGAGGTCAAGTTCAA

-continued

CTGGTACGTGGACGGCGTGGAGGTGCATAATGCCAAGACAAAGCCGCGGG

AGGAGCAGTACAACAGCACGTACCGTGTGGTCAGCGTCCTCACCGTCCTG

CACCAGGACTGGCTGAATGGCAAGGAGTACAAGTGCAAGGTCTCCAACAA

AGCCCTCCCAGCCCCCATCGAGAAAACCATCTCCAAAGCCAAAGGGCAGC

CCCGAGAACCACAGGTGTACACCCTGCCCCCATCCCGGGAGGAGATGACC

AAGAACCAGGTCAGCCTGACCTGCCTGGTCAAAGGCTTCTATCCCAGCGA

CATCGCCGTGGAGTGGGAGAGCAATGGGCAGCCGGAGAACAACTACAAGA

CCACGCCTCCCGTGCTGGACTCCGACGGCTCCTTCTTCCTCTACAGCAAG

CTCACCGTGGACAAGAGCAGGTGGCAGCAGGGGAACGTCTTCTCATGCTC

CGTGATGCACGAGGCTCTGCACAACCACTACACGCAGAAGAGCCTCTCCC

TGTCTCCGGGTAAA tga

Protein sequence of Fc-HRS(2-60) (N-terminal Fc fusion):

(SEQ ID NO: 349)

MSDKTHTCPPCPAPELLGGPSVFLFPPKPKDTLMISRTPEVTCVVVDVSH

EDPEVKFNWYVDGVEVHNAKTKPREEQYNSTYRVVSVLTVLHQDWLNGKE

YKCKVSNKALPAPIEKTISKAKGQPREPQVYTLPPSREEMTKNQVSLTCL

VKGFYPSDIAVEWESNGQPENNYKTTPPVLDSDGSFFLYSKLTVDKSRWQ

QGNVFSCSVMHEALHNHYTQKSLSLSPGKAERAALEELVKLQGERVRGLK

QQKASAELIEEEVAKLLKLKAQLGPDESKQKFVLKTPK.

Protein sequence of HRS(1-60)-Fc (C-terminal Fc fusion):

(SEQ ID NO: 350)

MAERAALEELVKLQGERVRGLKQQKASAELIEEEVAKLLKLKAQLGPDES

KQKFVLKTPKSDKTHTCPPCPAPELLGGPSVFLFPPKPKDTLMISRTPEV

TCVVVDVSHEDPEVKFNWYVDGVEVHNAKTKPREEQYNSTYRVVSVLTVL

HQDWLNGKEYKCKVSNKALPAPIEKTISKAKGQPREPQVYTLPPSREEMT

KNQVSLTCLVKGFYPSDIAVEWESNGQPENNYKTTPPVLDSDGSFFLYSK

LTVDKSRWQQGNVFSCSVMHEALHNHYTQKSLSLSPGK

Additional N-terminal and C-terminal Fc-histidyl tRNA synthetase (HRS-Fc) DNA constructs were prepared as follows.

Plasmid Construction.

HRS (2-40), (2-45), (2-50), (2-55), (2-66) with an N-terminal Fc or HRS (1-40), (1-45), (1-50), (1-55), (1-66) with a C-terminal Fc were generated using Quikchange Mutagenesis (Agilent, Santa Clara, Calif.). Previously generated pET24b_TAC constructs containing Fc-HRS(2-60) and HRS(1-60)-Fc in combination with the primers listed below, were used in the Quikchange reaction to generate the HRS-Fc constructs.

The following primers were used to amplify the Fc-HRS (2-40), (2-45), (2-50), (2-55), (2-66) polypeptides (N-terminal Fc fusion) (Table E13):

TABLE E13

| Primer Sequences | | |
|---|---|---|
| Primer Name | Sequence | SEQ ID NO: |
| Fc-H-aa2-40 FWD | 5'-GGT GGC GAA ACT CCT GAA ATG ACT CGA GGA TCC GGC TGC-3' | 351 |
| Fc-H-aa2-40 REV | 5'-GCA GCC GGA TCC TCG AGT CAT TTC AGG AGT TTC GCC ACC-3' | 352 |
| Fc-H-aa2-45 FWD | 5'-CTG AAG GCA CAG CTG TGA CTC GAG GAT CCG GCT GC-3' | 353 |
| Fc-H-aa2-45 REV | 5'-GCA GCC GGA TCC TCG AGT CAC AGC TGT GCC TTC AG-3' | 354 |
| Fc-H-aa2-50 FWD | 5'-GGG TCC TGA TGA AAG CTG ACT CGA GGA TCC GGC TGC-3' | 355 |
| Fc-H-aa2-50 REV | 5'-GCA GCC GGA TCC TCG AGT CAG CTT TCA TCA GGA CCC-3' | 356 |
| Fc-H-aa2-55 FWD | 5'-GCA AAC AGA AAT TTG TGT GAC TCG AGG ATC CGG CTG C-3' | 357 |
| Fc-H-aa2-55 REV | 5'-GCA GCC GGA TCC TCG AGT CAC ACA AAT TTC TGT TTG C-3' | 358 |
| Fc-H-add-aa61-66 FWD | 5'-GCT CAA AAC CCC CAA GGG AAC CCG TGA TTA TAG TTG ACT CGA GGA TCC GG-3' | 359 |
| Fc-H-add-aa61-66 REV | 5'-CCG GAT CCT CGA GTC AAC TAT AAT CAC GGG TTC CCT TGG GGG TTT TGA GC-3' | 360 |

The following primers were used to amplify the HRS (1-40), (1-45), (1-50), (1-55), (1-66) -Fc (C-terminal Fc fusion): (Table E14).

TABLE E14

| Primer Sequences | | |
|---|---|---|
| Primer Name | Sequence | SEQ ID NO: |
| H-aa1-40-Fc FWD | 5'-GGT GGC GAA ACT CCT GAA ATC TGA CAA AAC TCA CAC ATG C-3' | 361 |
| H-aa1-40-Fc REV | 5'-GCA TGT GTG AGT TTT GTC AGA TTT CAG GAG TTT CGC CAC C-3' | 362 |
| H-aa1-45-Fc FWD | 5'-CTG AAA CTG AAG GCA CAG CTG TCT GAC AAA ACT CAC ACA TGC-3' | 363 |
| H-aa1-45-Fc REV | 5'-GCA TGT GTG AGT TTT GTC AGA CAG CTG TGC CTT CAG TTT CAG-3' | 364 |
| H-aa1-50-Fc FWD | 5'-GCT GGG TCC TGA TGA AAG CTC TGA CAA AAC TCA CAC ATG C-3' | 365 |
| H-aa1-50-Fc REV | 5'-GCA TGT GTG AGT TTT GTC AGA GCT TTC ATC AGG ACC CAG C-3' | 366 |
| H-aa1-55-Fc FWD | 5'-GAA AGC AAA CAG AAA TTT GTG TCT GAC AAA ACT CAC ACA TGC-3' | 367 |
| H-aa1-55-Fc REV | 5'-GCA TGT GTG AGT TTT GTC AGA CAC AAA TTT CTG TTT GCT TTC-3' | 368 |
| H-add-aa61-66-Fc FWD | 5'-GCT CAA AAC CCC CAA GGG AAC CCG TGA TTA TAG TTC TGA CAA AAC TCA C-3' | 369 |
| H-add-aa61-66-Fc REV | 5'-GTG AGT TTT GTC AGA ACT ATA ATC ACG GGT TCC CTT GGG GGT TTT GAG C-3' | 370 |

The PCR reactions were performed using manufacturer recommended thermal cycling parameters. Sequences were confirmed by performing alignments with the theoretical sequences using DNASTAR Lasergene SeqMan Pro. The cloned DNA and protein sequences of the HRS-Fc constructs are shown below.

DNA sequence of Fc-HRS(2-40) (N-terminal Fc fusion):

(SEQ ID NO: 371)

ATGTCTGACAAAACTCACACATGCCCACCGTGCCCAGCACCTGAACTCCT
GGGGGGACCGTCAGTCTTCCTCTTCCCCCCAAAACCCAAGGACACCCTCA
TGATCTCCCGGACCCCTGAGGTCACATGCGTGGTGGTGGACGTGAGCCAC
GAAGACCCTGAGGTCAAGTTCAACTGGTACGTGGACGGCGTGGAGGTGCA
TAATGCCAAGACAAAGCCGCGGGAGGAGCAGTACAACAGCACGTACCGTG
TGGTCAGCGTCCTCACCGTCCTGCACCAGGACTGGCTGAATGGCAAGGAG
TACAAGTGCAAGGTCTCCAACAAAGCCCTCCCAGCCCCCATCGAGAAAAC
CATCTCCAAAGCCAAAGGGCAGCCCCGAGAACCACAGGTGTACACCCTGC
CCCCATCCCGGGAGGAGATGACCAAGAACCAGGTCAGCCTGACCTGCCTG
GTCAAAGGCTTCTATCCCAGCGACATCGCCGTGGAGTGGGAGAGCAATGG
GCAGCCGGAGAACAACTACAAGACCACGCCTCCCGTGCTGGACTCCGACG
GCTCCTTCTTCCTCTACAGCAAGCTCACCGTGGACAAGAGCAGGTGGCAG
CAGGGGAACGTCTTCTCATGCTCCGTGATGCACGAGGCTCTGCACAACCA
CTACACGCAGAAGAGCCTCTCCCTGTCTCCGGGTAAAGCAGAGCGTGCGG
CGCTGGAGGAGCTGGTGAAACTTCAGGGAGAGCGCGTGCGAGGCCTCAAG
CAGCAGAAGGCCAGCGCCGAGCTGATCGAGGAGGAGGTGGCGAAACTCCT
GAAATGA

DNA sequence of Fc-HRS(2-45) (N-terminal Fc fusion):

(SEQ ID NO: 372)

ATGTCTGACAAAACTCACACATGCCCACCGTGCCCAGCACCTGAACTCCT
GGGGGGACCGTCAGTCTTCCTCTTCCCCCCAAAACCCAAGGACACCCTCA
TGATCTCCCGGACCCCTGAGGTCACATGCGTGGTGGTGGACGTGAGCCAC
GAAGACCCTGAGGTCAAGTTCAACTGGTACGTGGACGGCGTGGAGGTGCA
TAATGCCAAGACAAAGCCGCGGGAGGAGCAGTACAACAGCACGTACCGTG
TGGTCAGCGTCCTCACCGTCCTGCACCAGGACTGGCTGAATGGCAAGGAG
TACAAGTGCAAGGTCTCCAACAAAGCCCTCCCAGCCCCCATCGAGAAAAC
CATCTCCAAAGCCAAAGGGCAGCCCCGAGAACCACAGGTGTACACCCTGC
CCCCATCCCGGGAGGAGATGACCAAGAACCAGGTCAGCCTGACCTGCCTG
GTCAAAGGCTTCTATCCCAGCGACATCGCCGTGGAGTGGGAGAGCAATGG
GCAGCCGGAGAACAACTACAAGACCACGCCTCCCGTGCTGGACTCCGACG
GCTCCTTCTTCCTCTACAGCAAGCTCACCGTGGACAAGAGCAGGTGGCAG
CAGGGGAACGTCTTCTCATGCTCCGTGATGCACGAGGCTCTGCACAACCA
CTACACGCAGAAGAGCCTCTCCCTGTCTCCGGGTAAAGCAGAGCGTGCGG
CGCTGGAGGAGCTGGTGAAACTTCAGGGAGAGCGCGTGCGAGGCCTCAAG
CAGCAGAAGGCCAGCGCCGAGCTGATCGAGGAGGAGGTGGCGAAACTCCT
GAAACTGAAGGCACAGCTGTGA

-continued

DNA sequence of Fc-HRS(2-50) (N-terminal Fc fusion):

(SEQ ID NO: 373)

ATGTCTGACAAAACTCACACATGCCCACCGTGCCCAGCACCTGAACTCCT
GGGGGGACCGTCAGTCTTCCTCTTCCCCCCAAAACCCAAGGACACCCTCA
TGATCTCCCGGACCCCTGAGGTCACATGCGTGGTGGTGGACGTGAGCCAC
GAAGACCCTGAGGTCAAGTTCAACTGGTACGTGGACGGCGTGGAGGTGCA
TAATGCCAAGACAAAGCCGCGGGAGGAGCAGTACAACAGCACGTACCGTG
TGGTCAGCGTCCTCACCGTCCTGCACCAGGACTGGCTGAATGGCAAGGAG
TACAAGTGCAAGGTCTCCAACAAAGCCCTCCCAGCCCCCATCGAGAAAAC
CATCTCCAAAGCCAAAGGGCAGCCCCGAGAACCACAGGTGTACACCCTGC
CCCCATCCCGGGAGGAGATGACCAAGAACCAGGTCAGCCTGACCTGCCTG
GTCAAAGGCTTCTATCCCAGCGACATCGCCGTGGAGTGGGAGAGCAATGG
GCAGCCGGAGAACAACTACAAGACCACGCCTCCCGTGCTGGACTCCGACG
GCTCCTTCTTCCTCTACAGCAAGCTCACCGTGGACAAGAGCAGGTGGCAG
CAGGGGAACGTCTTCTCATGCTCCGTGATGCACGAGGCTCTGCACAACCA
CTACACGCAGAAGAGCCTCTCCCTGTCTCCGGGTAAAGCAGAGCGTGCGG
CGCTGGAGGAGCTGGTGAAACTTCAGGGAGAGCGCGTGCGAGGCCTCAAG
CAGCAGAAGGCCAGCGCCGAGCTGATCGAGGAGGAGGTGGCGAAACTCCT
GAAACTGAAGGCACAGCTGGGTCCTGATGAAAGCTGA

DNA sequence of Fc-HRS(2-55) (N-terminal Fc fusion):

(SEQ ID NO: 374)

ATGTCTGACAAAACTCACACATGCCCACCGTGCCCAGCACCTGAACTCCT
GGGGGGACCGTCAGTCTTCCTCTTCCCCCCAAAACCCAAGGACACCCTCA
TGATCTCCCGGACCCCTGAGGTCACATGCGTGGTGGTGGACGTGAGCCAC
GAAGACCCTGAGGTCAAGTTCAACTGGTACGTGGACGGCGTGGAGGTGCA
TAATGCCAAGACAAAGCCGCGGGAGGAGCAGTACAACAGCACGTACCGTG
TGGTCAGCGTCCTCACCGTCCTGCACCAGGACTGGCTGAATGGCAAGGAG
TACAAGTGCAAGGTCTCCAACAAAGCCCTCCCAGCCCCCATCGAGAAAAC
CATCTCCAAAGCCAAAGGGCAGCCCCGAGAACCACAGGTGTACACCCTGC
CCCCATCCCGGGAGGAGATGACCAAGAACCAGGTCAGCCTGACCTGCCTG
GTCAAAGGCTTCTATCCCAGCGACATCGCCGTGGAGTGGGAGAGCAATGG
GCAGCCGGAGAACAACTACAAGACCACGCCTCCCGTGCTGGACTCCGACG
GCTCCTTCTTCCTCTACAGCAAGCTCACCGTGGACAAGAGCAGGTGGCAG
CAGGGGAACGTCTTCTCATGCTCCGTGATGCACGAGGCTCTGCACAACCA
CTACACGCAGAAGAGCCTCTCCCTGTCTCCGGGTAAAGCAGAGCGTGCGG
CGCTGGAGGAGCTGGTGAAACTTCAGGGAGAGCGCGTGCGAGGCCTCAAG
CAGCAGAAGGCCAGCGCCGAGCTGATCGAGGAGGAGGTGGCGAAACTCCT
GAAACTGAAGGCACAGCTGGGTCCTGATGAAAGCAAACAGAAATTTGTGT
GA

-continued

DNA sequence of Fc-HRS(2-66) (N-terminal Fc fusion):

(SEQ ID NO: 375)

ATGTCTGACAAAACTCACACATGCCCACCGTGCCCAGCACCTGAACTCCT
GGGGGGACCGTCAGTCTTCCTCTTCCCCCCAAAACCCAAGGACACCCTCA
TGATCTCCCGGACCCCTGAGGTCACATGCGTGGTGGTGGACGTGAGCCAC
GAAGACCCTGAGGTCAAGTTCAACTGGTACGTGGACGGCGTGGAGGTGCA
TAATGCCAAGACAAAGCCGCGGGAGGAGCAGTACAACAGCACGTACCGTG
TGGTCAGCGTCCTCACCGTCCTGCACCAGGACTGGCTGAATGGCAAGGAG
TACAAGTGCAAGGTCTCCAACAAAGCCCTCCCAGCCCCCATCGAGAAAAC
CATCTCCAAAGCCAAAGGGCAGCCCCGAGAACCACAGGTGTACACCCTGC
CCCCATCCCGGGAGGAGATGACCAAGAACCAGGTCAGCCTGACCTGCCTG
GTCAAAGGCTTCTATCCCAGCGACATCGCCGTGGAGTGGGAGAGCAATGG
GCAGCCGGAGAACAACTACAAGACCACGCCTCCCGTGCTGGACTCCGACG
GCTCCTTCTTCCTCTACAGCAAGCTCACCGTGGACAAGAGCAGGTGGCAG
CAGGGGAACGTCTTCTCATGCTCCGTGATGCACGAGGCTCTGCACAACCA
CTACACGCAGAAGAGCCTCTCCCTGTCTCCGGGTAAAGCAGAGCGTGCGG
CGCTGGAGGAGCTGGTGAAACTTCAGGGAGAGCGCGTGCGAGGCCTCAAG
CAGCAGAAGGCCAGCGCCGAGCTGATCGAGGAGGAGGTGGCGAAACTCCT
GAAACTGAAGGCACAGCTGGGTCCTGATGAAAGCAAACAGAAATTTGTGC
TCAAAACCCCCAAGGGAACCCGTGATTATAGTTGA

DNA sequence of HRS(1-40)-Fc (C-terminal Fc fusion):

(SEQ ID NO: 376)

ATGGCAGAGCGTGCGGCGCTGGAGGAGCTGGTGAAACTTCAGGGAGAGCG
CGTGCGAGGCCTCAAGCAGCAGAAGGCCAGCGCCGAGCTGATCGAGGAGG
AGGTGGCGAAACTCCTGAAATCTGACAAAACTCACACATGCCCACCGTGC
CCAGCACCTGAACTCCTGGGGGGACCGTCAGTCTTCCTCTTCCCCCCAAA
ACCCAAGGACACCCTCATGATCTCCCGGACCCCTGAGGTCACATGCGTGG
TGGTGGACGTGAGCCACGAAGACCCTGAGGTCAAGTTCAACTGGTACGTG
GACGGCGTGGAGGTGCATAATGCCAAGACAAAGCCGCGGGAGGAGCAGTA
CAACAGCACGTACCGTGTGGTCAGCGTCCTCACCGTCCTGCACCAGGACT
GGCTGAATGGCAAGGAGTACAAGTGCAAGGTCTCCAACAAAGCCCTCCCA
GCCCCCATCGAGAAAACCATCTCCAAAGCCAAAGGGCAGCCCCGAGAACC
ACAGGTGTACACCCTGCCCCCATCCCGGGAGGAGATGACCAAGAACCAGG
TCAGCCTGACCTGCCTGGTCAAAGGCTTCTATCCCAGCGACATCGCCGTG
GAGTGGGAGAGCAATGGGCAGCCGGAGAACAACTACAAGACCACGCCTCC
CGTGCTGGACTCCGACGGCTCCTTCTTCCTCTACAGCAAGCTCACCGTGG
ACAAGAGCAGGTGGCAGCAGGGGAACGTCTTCTCATGCTCCGTGATGCAC
GAGGCTCTGCACAACCACTACACGCAGAAGAGCCTCTCCCTGTCTCCGGG
TAAATGA

DNA sequence of HRS(1-45)-Fc (C-terminal Fc fusion):

(SEQ ID NO: 377)

ATGGCAGAGCGTGCGGCGCTGGAGGAGCTGGTGAAACTTCAGGGAGAGCG
CGTGCGAGGCCTCAAGCAGCAGAAGGCCAGCGCCGAGCTGATCGAGGAGG
AGGTGGCGAAACTCCTGAAACTGAAGGCACAGCTGTCTGACAAAACTCAC
ACATGCCCACCGTGCCCAGCACCTGAACTCCTGGGGGGACCGTCAGTCTT
CCTCTTCCCCCCAAAACCCAAGGACACCCTCATGATCTCCCGGACCCCTG
AGGTCACATGCGTGGTGGTGGACGTGAGCCACGAAGACCCTGAGGTCAAG
TTCAACTGGTACGTGGACGGCGTGGAGGTGCATAATGCCAAGACAAAGCC
GCGGGAGGAGCAGTACAACAGCACGTACCGTGTGGTCAGCGTCCTCACCG
TCCTGCACCAGGACTGGCTGAATGGCAAGGAGTACAAGTGCAAGGTCTCC
AACAAAGCCCTCCCAGCCCCCATCGAGAAAACCATCTCCAAAGCCAAAGG
GCAGCCCCGAGAACCACAGGTGTACACCCTGCCCCCATCCCGGGAGGAGA
TGACCAAGAACCAGGTCAGCCTGACCTGCCTGGTCAAAGGCTTCTATCCC
AGCGACATCGCCGTGGAGTGGGAGAGCAATGGGCAGCCGGAGAACAACTA
CAAGACCACGCCTCCCGTGCTGGACTCCGACGGCTCCTTCTTCCTCTACA
GCAAGCTCACCGTGGACAAGAGCAGGTGGCAGCAGGGGAACGTCTTCTCA
TGCTCCGTGATGCACGAGGCTCTGCACAACCACTACACGCAGAAGAGCCT
CTCCCTGTCTCCGGGTAAATGA

DNA sequence of HRS(1-50)-Fc (C-terminal Fc fusion):

(SEQ ID NO: 378)

ATGGCAGAGCGTGCGGCGCTGGAGGAGCTGGTGAAACTTCAGGGAGAGCG
CGTGCGAGGCCTCAAGCAGCAGAAGGCCAGCGCCGAGCTGATCGAGGAGG
AGGTGGCGAAACTCCTGAAACTGAAGGCACAGCTGGGTCCTGATGAAAGC
TCTGACAAAACTCACACATGCCCACCGTGCCCAGCACCTGAACTCCTGGG
GGGACCGTCAGTCTTCCTCTTCCCCCCAAAACCCAAGGACACCCTCATGA
TCTCCCGGACCCCTGAGGTCACATGCGTGGTGGTGGACGTGAGCCACGAA
GACCCTGAGGTCAAGTTCAACTGGTACGTGGACGGCGTGGAGGTGCATAA
TGCCAAGACAAAGCCGCGGGAGGAGCAGTACAACAGCACGTACCGTGTGG
TCAGCGTCCTCACCGTCCTGCACCAGGACTGGCTGAATGGCAAGGAGTAC
AAGTGCAAGGTCTCCAACAAAGCCCTCCCAGCCCCCATCGAGAAAACCAT
CTCCAAAGCCAAAGGGCAGCCCCGAGAACCACAGGTGTACACCCTGCCCC
CATCCCGGGAGGAGATGACCAAGAACCAGGTCAGCCTGACCTGCCTGGTC
AAAGGCTTCTATCCCAGCGACATCGCCGTGGAGTGGGAGAGCAATGGGCA
GCCGGAGAACAACTACAAGACCACGCCTCCCGTGCTGGACTCCGACGGCT
CCTTCTTCCTCTACAGCAAGCTCACCGTGGACAAGAGCAGGTGGCAGCAG
GGGAACGTCTTCTCATGCTCCGTGATGCACGAGGCTCTGCACAACCACTA
CACGCAGAAGAGCCTCTCCCTGTCTCCGGGTAAATGA

-continued

DNA sequence of HRS(1-55)-Fc (C-terminal Fc fusion):

(SEQ ID NO: 379)

ATGGCAGAGCGTGCGGCGCTGGAGGAGCTGGTGAAACTTCAGGGAGAGCG

CGTGCGAGGCCTCAAGCAGCAGAAGGCCAGCGCCGAGCTGATCGAGGAGG

AGGTGGCGAAACTCCTGAAACTGAAGGCACAGCTGGGTCCTGATGAAAGC

AAACAGAAATTTGTGTCTGACAAAACTCACACATGCCCACCGTGCCCAGC

ACCTGAACTCCTGGGGGGACCGTCAGTCTTCCTCTTCCCCCCAAAACCCA

AGGACACCCTCATGATCTCCCGGACCCCTGAGGTCACATGCGTGGTGGTG

GACGTGAGCCACGAAGACCCTGAGGTCAAGTTCAACTGGTACGTGGACGG

CGTGGAGGTGCATAATGCCAAGACAAAGCCGCGGGAGGAGCAGTACAACA

GCACGTACCGTGTGGTCAGCGTCCTCACCGTCCTGCACCAGGACTGGCTG

AATGGCAAGGAGTACAAGTGCAAGGTCTCCAACAAAGCCCTCCCAGCCCC

CATCGAGAAAACCATCTCCAAAGCCAAAGGGCAGCCCCGAGAACCACAGG

TGTACACCCTGCCCCCATCCCGGGAGGAGATGACCAAGAACCAGGTCAGC

CTGACCTGCCTGGTCAAAGGCTTCTATCCCAGCGACATCGCCGTGGAGTG

GGAGAGCAATGGGCAGCCGGAGAACAACTACAAGACCACGCCTCCCGTGC

TGGACTCCGACGGCTCCTTCTTCCTCTACAGCAAGCTCACCGTGGACAAG

AGCAGGTGGCAGCAGGGGAACGTCTTCTCATGCTCCGTGATGCACGAGGC

TCTGCACAACCACTACACGCAGAAGAGCCTCTCCCTGTCTCCGGGTAAAT

GA

DNA sequence of HRS(1-66)-Fc (C-terminal Fc fusion):

(SEQ ID NO: 380)

ATGGCAGAGCGTGCGGCGCTGGAGGAGCTGGTGAAACTTCAGGGAGAGCG

CGTGCGAGGCCTCAAGCAGCAGAAGGCCAGCGCCGAGCTGATCGAGGAGG

AGGTGGCGAAACTCCTGAAACTGAAGGCACAGCTGGGTCCTGATGAAAGC

AAACAGAAATTTGTGCTCAAAACCCCCAAGGGAACCCGTGATTATAGTTC

TGACAAAACTCACACATGCCCACCGTGCCCAGCACCTGAACTCCTGGGGG

GACCGTCAGTCTTCCTCTTCCCCCCAAAACCCAAGGACACCCTCATGATC

TCCCGGACCCCTGAGGTCACATGCGTGGTGGTGGACGTGAGCCACGAAGA

CCCTGAGGTCAAGTTCAACTGGTACGTGGACGGCGTGGAGGTGCATAATG

CCAAGACAAAGCCGCGGGAGGAGCAGTACAACAGCACGTACCGTGTGGTC

AGCGTCCTCACCGTCCTGCACCAGGACTGGCTGAATGGCAAGGAGTACAA

GTGCAAGGTCTCCAACAAAGCCCTCCCAGCCCCCATCGAGAAAACCATCT

CCAAAGCCAAAGGGCAGCCCCGAGAACCACAGGTGTACACCCTGCCCCCA

TCCCGGGAGGAGATGACCAAGAACCAGGTCAGCCTGACCTGCCTGGTCAA

AGGCTTCTATCCCAGCGACATCGCCGTGGAGTGGGAGAGCAATGGGCAGC

CGGAGAACAACTACAAGACCACGCCTCCCGTGCTGGACTCCGACGGCTCC

TTCTTCCTCTACAGCAAGCTCACCGTGGACAAGAGCAGGTGGCAGCAGGG

GAACGTCTTCTCATGCTCCGTGATGCACGAGGCTCTGCACAACCACTACA

CGCAGAAGAGCCTCTCCCTGTCTCCGGGTAAATGA

-continued

Protein sequence of Fc-HRS(2-40) (N-terminal Fc fusion):

(SEQ ID NO: 381)

MSDKTHTCPPCPAPELLGGPSVFLFPPKPKDTLMISRTPEVTCVVVDVSH

EDPEVKFNWYVDGVEVHNAKTKPREEQYNSTYRVVSVLTVLHQDWLNGKE

YKCKVSNKALPAPIEKTISKAKGQPREPQVYTLPPSREEMTKNQVSLTCL

VKGFYPSDIAVEWESNGQPENNYKTTPPVLDSDGSFFLYSKLTVDKSRWQ

QGNVFSCSVMHEALHNHYTQKSLSLSPGKAERAALEELVKLQGERVRGLK

QQKASAELIEEEVAKLLK

Protein sequence of Fc-HRS(2-45) (N-terminal Fc fusion):

(SEQ ID NO: 382)

MSDKTHTCPPCPAPELLGGPSVFLFPPKPKDTLMISRTPEVTCVVVDVSH

EDPEVKFNWYVDGVEVHNAKTKPREEQYNSTYRVVSVLTVLHQDWLNGKE

YKCKVSNKALPAPIEKTISKAKGQPREPQVYTLPPSREEMTKNQVSLTCL

VKGFYPSDIAVEWESNGQPENNYKTTPPVLDSDGSFFLYSKLTVDKSRWQ

QGNVFSCSVMHEALHNHYTQKSLSLSPGKAERAALEELVKLQGERVRGLK

QQKASAELIEEEVAKLLKLKAQL

Protein sequence of Fc-HRS(2-50) (N-terminal Fc fusion):

(SEQ ID NO: 383)

MSDKTHTCPPCPAPELLGGPSVFLFPPKPKDTLMISRTPEVTCVVVDVSH

EDPEVKFNWYVDGVEVHNAKTKPREEQYNSTYRVVSVLTVLHQDWLNGKE

YKCKVSNKALPAPIEKTISKAKGQPREPQVYTLPPSREEMTKNQVSLTCL

VKGFYPSDIAVEWESNGQPENNYKTTPPVLDSDGSFFLYSKLTVDKSRWQ

QGNVFSCSVMHEALHNHYTQKSLSLSPGKAERAALEELVKLQGERVRGLK

QQKASAELIEEEVAKLLKLKAQLGPDES

Protein sequence of Fc-HRS(2-55) (N-terminal Fc fusion):

(SEQ ID NO: 384)

MSDKTHTCPPCPAPELLGGPSVFLFPPKPKDTLMISRTPEVTCVVVDVSH

EDPEVKFNWYVDGVEVHNAKTKPREEQYNSTYRVVSVLTVLHQDWLNGKE

YKCKVSNKALPAPIEKTISKAKGQPREPQVYTLPPSREEMTKNQVSLTCL

VKGFYPSDIAVEWESNGQPENNYKTTPPVLDSDGSFFLYSKLTVDKSRWQ

QGNVFSCSVMHEALHNHYTQKSLSLSPGKAERAALEELVKLQGERVRGLK

QQKASAELIEEEVAKLLKLKAQLGPDESKQKFV

Protein sequence of Fc-HRS(2-66) (N-terminal Fc fusion):

(SEQ ID NO: 385)

MSDKTHTCPPCPAPELLGGPSVFLFPPKPKDTLMISRTPEVTCVVVDVSH

EDPEVKFNWYVDGVEVHNAKTKPREEQYNSTYRVVSVLTVLHQDWLNGKE

YKCKVSNKALPAPIEKTISKAKGQPREPQVYTLPPSREEMTKNQVSLTCL

VKGFYPSDIAVEWESNGQPENNYKTTPPVLDSDGSFFLYSKLTVDKSRWQ

QGNVFSCSVMHEALHNHYTQKSLSLSPGKAERAALEELVKLQGERVRGLK

QQKASAELIEEEVAKLLKLKAQLGPDESKQKFVLKTPKGTRDYS

-continued

Protein sequence of HRS(1-40)-Fc (C-terminal Fc fusion):

(SEQ ID NO: 386)

MAERAALEELVKLQGERVRGLKQQKASAELIEEEVAKLLKSDKTHTCPPC

PAPELLGGPSVFLFPPKPKDTLMISRTPEVTCVVVDVSHEDPEVKFNWYV

DGVEVHNAKTKPREEQYNSTYRVVSVLTVLHQDWLNGKEYKCKVSNKALP

APIEKTISKAKGQPREPQVYTLPPSREEMTKNQVSLTCLVKGFYPSDIAV

EWESNGQPENNYKTTPPVLDSDGSFFLYSKLTVDKSRWQQGNVFSCSVMH

EALHNHYTQKSLSLSPGK

Protein sequence of HRS(1-45)-Fc (C-terminal Fc fusion):

(SEQ ID NO: 387)

MAERAALEELVKLQGERVRGLKQQKASAELIEEEVAKLLKLKAQLSDKTH

TCPPCPAPELLGGPSVFLFPPKPKDTLMISRTPEVTCVVVDVSHEDPEVK

FNWYVDGVEVHNAKTKPREEQYNSTYRVVSVLTVLHQDWLNGKEYKCKVS

NKALPAPIEKTISKAKGQPREPQVYTLPPSREEMTKNQVSLTCLVKGFYP

SDIAVEWESNGQPENNYKTTPPVLDSDGSFFLYSKLTVDKSRWQQGNVFS

CSVMHEALHNHYTQKSLSLSPGK

Protein sequence of HRS(1-50)-Fc (C-terminal Fc fusion):

(SEQ ID NO: 388)

MAERAALEELVKLQGERVRGLKQQKASAELIEEEVAKLLKLKAQLGPDES

SDKTHTCPPCPAPELLGGPSVFLFPPKPKDTLMISRTPEVTCVVVDVSHE

DPEVKFNWYVDGVEVHNAKTKPREEQYNSTYRVVSVLTVLHQDWLNGKEY

KCKVSNKALPAPIEKTISKAKGQPREPQVYTLPPSREEMTKNQVSLTCLV

KGFYPSDIAVEWESNGQPENNYKTTPPVLDSDGSFFLYSKLTVDKSRWQQ

GNVFSCSVMHEALHNHYTQKSLSLSPGK

Protein sequence of HRS(1-55)-Fc (C-terminal Fc fusion):

(SEQ ID NO: 389)

MAERAALEELVKLQGERVRGLKQQKASAELIEEEVAKLLKLKAQLGPDES

KQKFVSDKTHTCPPCPAPELLGGPSVFLFPPKPKDTLMISRTPEVTCVVV

-continued

DVSHEDPEVKFNWYVDGVEVHNAKTKPREEQYNSTYRVVSVLTVLHQDWL

NGKEYKCKVSNKALPAPIEKTISKAKGQPREPQVYTLPPSREEMTKNQVS

LTCLVKGFYPSDIAVEWESNGQPENNYKTTPPVLDSDGSFFLYSKLTVDK

SRWQQGNVFSCSVMHEALHNHYTQKSLSLSPGK

Protein sequence of HRS(1-66)-Fc (C-terminal Fc fusion):

(SEQ ID NO: 390)

MAERAALEELVKLQGERVRGLKQQKASAELIEEEVAKLLKLKAQLGPDES

KQKFVLKTPKGTRDYSSDKTHTCPPCPAPELLGGPSVFLFPPKPKDTLMI

SRTPEVTCVVVDVSHEDPEVKFNWYVDGVEVHNAKTKPREEQYNSTYRVV

SVLTVLHQDWLNGKEYKCKVSNKALPAPIEKTISKAKGQPREPQVYTLPP

SREEMTKNQVSLTCLVKGFYPSDIAVEWESNGQPENNYKTTPPVLDSDGS

FFLYSKLTVDKSRWQQGNVFSCSVMHEALHNHYTQKSLSLSPGK

N-terminal Fc-histidyl tRNA synthetase (HRS-Fc) tandem fusion DNA construct was prepared as follows.

Plasmid Construction.

HRS (2-60)_HRS (2-60) with an N-terminal Fc was generated using pET24b_TAC_Fc-HRS (2-60) construct. The HRS (2-60) gene was PCR amplified with the primers listed below, which contain a 5' and 3' XhoI site. The PCR reactions were performed using recommended thermal cycling parameters. pET24b_TAC_Fc-HRS (2-60) construct was digested with XhoI, dephosphorylated, and gel purified. The PCR generated fragment was also digested with XhoI and gel purified. The gel purified HRS (2-60) was subcloned into the XhoI site of pET24b_TAC_Fc-HRS (2-60). To generate the final construct, QuikChange mutagenesis was used to remove the stop codon and XhoI site between the tandem HRS (2-60) fragments using the primers listed below. Sequences were confirmed by performing alignments with the theoretical sequences using DNASTAR Lasergene SeqMan Pro.

The following primers were used to amplify the Fc-HRS (2-60) (Table E15):

TABLE E15

Primer Sequences

| Primer Name | Sequence | SEQ ID NO: |
|---|---|---|
| XhoI-H-aa2-60 FWD | 5'-TAT TCT CGA GGC AGA GCG TGC GGC-3' | 391 |
| H-aa2-60-stop-XhoI REV | 5'-GCGCCTCGAGTCACTTGGGGGTTTTG-3' | 392 |
| delete stop-XhoI concatemer FWD | 5'-GTG CTC AAA ACC CCC AAG GCA GAG CGT GCG GCG CTG G-3 | 393 |
| delete stop-XhoI concatemer REV | 5'-CCA GCG CCG CAC GCT CTG CCT TGG GGG TTT TGA GCA C-3' | 394 |

DNA sequence of Fc-HRS(2-60) HRS(2-60) (N-terminal Fc fusion):

(SEQ ID NO: 395)

```
ATGTCTGACAAAACTCACACATGCCCACCGTGCCCAGCACCTGAACTCCT
GGGGGGACCGTCAGTCTTCCTCTTCCCCCCAAAACCCAAGGACACCCTCA
TGATCTCCCGGACCCCTGAGGTCACATGCGTGGTGGTGGACGTGAGCCAC
GAAGACCCTGAGGTCAAGTTCAACTGGTACGTGGACGGCGTGGAGGTGCA
TAATGCCAAGACAAAGCCGCGGGAGGAGCAGTACAACAGCACGTACCGTG
TGGTCAGCGTCCTCACCGTCCTGCACCAGGACTGGCTGAATGGCAAGGAG
TACAAGTGCAAGGTCTCCAACAAAGCCCTCCCAGCCCCCATCGAGAAAAC
CATCTCCAAAGCCAAAGGGCAGCCCCGAGAACCACAGGTGTACACCCTGC
CCCCATCCCGGGAGGAGATGACCAAGAACCAGGTCAGCCTGACCTGCCTG
GTCAAAGGCTTCTATCCCAGCGACATCGCCGTGGAGTGGGAGAGCAATGG
GCAGCCGGAGAACAACTACAAGACCACGCCTCCCGTGCTGGACTCCGACG
GCTCCTTCTTCCTCTACAGCAAGCTCACCGTGGACAAGAGCAGGTGGCAG
CAGGGGAACGTCTTCTCATGCTCCGTGATGCACGAGGCTCTGCACAACCA
CTACACGCAGAAGAGCCTCTCCCTGTCTCCGGGTAAAGCAGAGCGTGCGG
CGCTGGAGGAGCTGGTGAAACTTCAGGGAGAGCGCGTGCGAGGCCTCAAG
CAGCAGAAGGCCAGCGCCGAGCTGATCGAGGAGGAGGTGGCGAAACTCCT
GAAACTGAAGGCACAGCTGGGTCCTGATGAAAGCAAACAGAAATTTGTGC
TCAAAACCCCCAAGGCAGAGCGTGCGGCGCTGGAGGAGCTGGTGAAACTT
CAGGGAGAGCGCGTGCGAGGCCTCAAGCAGCAGAAGGCCAGCGCCGAGCT
GATCGAGGAGGAGGTGGCGAAACTCCTGAAACTGAAGGCACAGCTGGGTC
CTGATGAAAGCAAACAGAAATTTGTGCTCAAAACCCCCAAG
TGA
```

Protein sequence of Fc-HRS(2-60) HRS(2-60) (N-terminal Fc fusion):

(SEQ ID NO: 396)

```
MSDKTHTCPPCPAPELLGGPSVFLFPPKPKDTLMISRTPEVTCVVVDVSH
EDPEVKFNWYVDGVEVHNAKTKPREEQYNSTYRVVSVLTVLHQDWLNGKE
YKCKVSNKALPAPIEKTISKAKGQPREPQVYTLPPSREEMTKNQVSLTCL
VKGFYPSDIAVEWESNGQPENNYKTTPPVLDSDGSFFLYSKLTVDKSRWQ
QGNVFSCSVMHEALHNHYTQKSLSLSPGKAERAALEELVKLQGERVRGLK
QQKASAELIEEEVAKLLKLKAQLGPDESKQKFVLKTPKAERAALEELVKL
QGERVRGLKQQKASAELIEEEVAKLLKLKAQLGPDESKQKFVLKTPK
```

Preparation and purification of HRS(1-60)-Fc and Fc-HRS(2-60) fusion proteins. *E. coli* strain. The *E. coli* BL21-CodonPlus® (DE3) RIPL Competent Cells (Agilent 230280) transformed with the pET expression constructs described above were used for initial production of Fc fusion proteins.

Media. M9YE medium was prepared by mixing sterile 5× M9 minimal salt (BD 248510), yeast extract solution in sterile purified water (BD 212750), sterilized 20% glucose (Sigma G7021), and sterile 1.0 M MgSO4 (Sigma M7506). For the feeding solution, the yeast extract solution (5%), glucose solution (50%), and 10 ml concentrated trace element solution (containing $Fe^{3+}$, $Mn^{2+}$, boric acid, $Mo^{6+}$, $Co^{2+}$, $Cu^{2+}$, $Zn^{2+}$ and EDTA), as well 10 ml magnesium sulfate solution, were autoclaved separately. The components were mixed just prior to the fed-batch phase. Kanamycin sulfate was added to a final concentration of 100 μg/ml in the culture medium.

Fed-batch fermentation. A 0.5 L Multifors fermentors (HT-Infors) with Iris software was used for the fed-batch fermentation process. The agitation was set at 1000 rpm. The pH value was controlled at 7.0 automatically by the addition of 30% ammonium hydroxide (Sigma 221228) and 30% phosphoric acid (Sigma P5811). Air was provided at a flow rate of 0.5 L/min with an oil-free diaphragm air compressor (Cole-Parmer) and passed through a 0.2 μm filter. The dissolved oxygen level was controlled at 70% by providing pure oxygen (West Air). The temperature was controlled at 30° C. with a Neslab RTE7 circulator (Thermo Scientific). Foaming was controlled by addition of the antifoam 204 (Sigma A8311).

The initial volume of M9YE medium in the fermentor was 0.3 L. The fermentor was inoculated with 15 ml of the seed culture grown overnight at 30° C. and 250 rpm. When the carbon source was depleted in the vessel, the concentrated feeding solution was introduced into the vessel by a peristaltic pump at 0.12 ml/min. When the optical density of the cells at 600 nm reached exponential phase, the culture was induced with 0.5 mM IPTG (Fisher Scientific BP1755). The culture was grown overnight (about 17-hour induction) and the final $OD_{600}$ reached about 120. The cells were harvested by centrifugation at 8,000 g for 30 min. The supernatant was decanted and the pellet was stored at −20° C. until purification.

Additional HRS-Fc fusion proteins were prepared using a modified pET24b vector (EMD, Gibbstown, N.J.) containing a TAC promoter instead of T7 ("pET24b_TAC") and transformed into UT5600 competent cells. UT5600 competent cells were prepared from bacterial stock obtained from the Coli Genetic Stock Center (CGSC, Yale). UT5600 is a K12 derivative strain of *E. coli* and is designated as genotype: F, araC14, leuB6(Am), secA206(aziR), lacY1, proC14, tsx-67, A(ompT-fepC)266, entA403, glnX44(AS), trpE38, rpsL109(strR), xylA5, mtl-1, thiE1.

Expression vectors comprising these constructs were transformed into UT5600 cells using standard procedures, and glycerol stocks prepared.

Fermentation Medium.

UT5600_M9_YE medium was prepared by mixing, for the batch media: 16 grams/L Yeast Extract (Difco 212750), 8 g/L Glycerol (Sigma G2025), 11.28 g/L M9 Salts (Difco 248510) and 100 μl/L Antifoam 204 (Sigma AG6426) to Deionized water and sterilized via autoclave. Post autoclave additions were 0.64 ml/L Trace Metals Solution, 2.3 ml/L 100× Magnesium Sulfate and 45.83 g/L L-Leucine. Feed Media was prepared by mixing 250 g/L Yeast Extract, 225 g/L Glycerol and 100 μl/L Antifoam 204 to deionized water and sterilized via autoclave. Post-sterilization additions were 10 ml/L Trace Metals Solution, 2.3 ml/L 100× Magnesium Sulfate, 45.83 ml/L L-Leucine.

Fed-Batch Fermentation.

A 0.5 L fermentor (Infors) with MFCS/DA software was used for the fed-batch fermentation. The agitation was set to cascade at 500-1200 rpm. The pH value was controlled at 7.0±0.1 automatically by the addition of 30% ammonium hydroxide (Sigma 221228) and 30% phosphoric acid (Sigma P5811). The air was provided at a flow rate of 0.5 L/min with an oil-free diaphragm air compressor (Cole-Parmer). The air was passed through a 0.2 μm Midisart 2000 filter (Sartorius 17805). The pure oxygen (West Air) was supplied automatically to control the dissolved oxygen level at 30%. The temperature was controlled at 30° C. with a Neslab RTE7 circulator (Thermo Scientific). The foaming was controlled by addition of the antifoam 204 (Sigma A8311) as needed. The initial volume of UT5600_M9_YE medium in the fermentor was 0.24 L. The fermentor was inoculated with ≈10 OD Units (approximately 1-2 ml of seed at OD 5-10) of the seed culture grown for 6 hours at 37° C. and 250 rpm. When the batch glycerol was depleted in the vessel (~4 hours), the concentrated feeding solution was introduced into the vessel by a peristaltic pump set on an exponential feeding program. When the optical density of the cells at 600 nm reached ~150, the culture was induced with 0.5 mM IPTG (Fisher Scientific BP1755). The culture was incubated 4 hours post induction and harvested by centrifugation at 10,000×g for 30 minutes. Approximate final cell pellet yield was 150-200 grams per liter wet cell weight (WCW). The cell pellet was stored at −80° C. until purification. The expression of target protein was confirmed via SDS-PAGE and western blot to Goat anti-Human IgG, HRP conjugated antibody (Thermo p/n 31413).

Purification of FC Fusion Proteins.

Frozen cell pellets were resuspended in 4 volumes (i.e., 4 mL/g cell pellet) of Lysis Buffer (50 mM Tris, 500 mM NaCl, 14 mM β-ME, pH 7.5). Complete EDTA-FREE protease inhibitor tablets (Roche) were added to the suspension at a ratio of 1 tablet/50 mL. The suspension was passed through a microfluidizer (Microfluidics) twice at 14,000 psi with cooling by ice. The lysate was centrifuged at ≥10, 000×g for 45 min at 4° C. The supernatant was filtered through 0.45+0.22 μm Sartobran capsule filters (Sartorius).

The clarified lysate was bound to the MabSelect resin (GE Healthcare), pre-equilibrated with Binding Buffer (50 mM Tris, 500 mM NaCl, pH 7.5) at a ratio of 1 ml resin per 10 g cell paste. The column was washed with 500 column volumes of Binding Buffer+0.1% Triton X-114 followed by 100 column volumes of the Binding Buffer. The bound protein, fusion proteins were eluted with 3.75 column volumes of Elution Buffer (0.1 M glycine, 0.5 M Arginine, pH 3.0) to a collection tube containing 1.25 column volumes of Neutralization Buffer (1 M Tris, pH 8.0).

Optionally, for further removal of high molecular weight species the material was concentrated in Amicon 30 kDa ultracentrifugal concentrating devices (Millipore) and loaded onto a HiLoad Superdex 200 pg 16/600 size-exclusion chromatography column (GE Healthcare). The material was eluted in 1.1 column volumes of 1×PBS pH 7.4 (Gibco #10010), and fractions corresponding to the main peak based on the process chromatogram absorbance at 280 nm were pooled.

If size-exclusion chromatography was not performed, the purified Fc fusion proteins were buffer exchanged into a buffer containing PBS, at pH 7.4. The dialyzed protein was passed through a Q membrane filter (Sartobind-Q from Sartorius or Mustang-Q from Pall) or a Q-Sepharose column (GE Healthcare) for further endotoxin removal, and filtered through a 0.22 μm sterile filter.

Scaleable Purification Process for FC Fusion Proteins.

The purification process using MabSelect followed by size-exclusion chromatography was used to purify multiple Fc fusion proteins using a robust process effective with minimal purification development. However, the use of detergent wash during Protein A (MabSelect) and a size-exclusion chromatography step limits the ability to scale up purification. A purification process for scale-up was also developed for Fc fusion proteins using lysate flocculation, Protein A chromatography, cation exchange (CEX), and ceramic hydroxyapatite (CHT) chromatography.

Resuspension, and lysis were performed as described above, with the omission of protease inhibitor tables and β-ME from the Lysis Buffer. After lysis, the lysate was flocculated with addition of polyethyleneimine, Mw 1300 (Sigma Aldrich) to 0.04% (v/v) and incubated for 30 min @ 4° C. Centrifugation and clarification were performed as described above. Protein A chromatography was performed on clarified lysate using MabSelect resin in a packed chromatography column at a load ratio of 1 ml resin per 4 g cell paste, with a wash step of 5 column volumes in 50 mM Tris, 500 mM NaCl pH 7.5, followed by elution in 3 column volumes of 0.1 M glycine pH 3.0 and neutralization in 0.3 column volumes of 1 M Tris pH 8.0. Following Protein A, CEX load was prepared by 5× dilution of post-Protein A eluent in CEX Equilibration buffer (20 mM sodium phosphate, pH 6.0), loaded onto a SP Sepharose High Performance column, washed with 5 column volumes of Equilibration buffer, and eluted over a linear sodium chloride gradient from 0 to 300 mM NaCl over 10 column volumes. CEX fractions were pooled based on SDS-PAGE analysis of elution peak fractions. Ceramic hydroxyapatite was performed on CEX pool by loading onto a CHT Type I 40 μm column (Bio-Rad) equilibrated in CHT Equilibration Buffer (5 mM sodium phosphate, 150 mM sodium chloride, 1 μM calcium chloride pH 6.5), washed with 5 columns of equilibration buffer and eluted over a linear sodium chloride gradient from 150 mM to 1.5 M sodium chloride over 10 column volumes and a 1.5 M NaCl hold for up to 20 column volumes to complete the elution. Following CHT, protein was buffer exchanged into 1×PBS pH 7.4 using Amicon 30 kDa centrifugal concentrating devices (Millipore).

The fusion protein concentration was determined by Bradford protein assay (Thermo Scientific) or by UV absorbance at 280 nm. The fusion protein concentration was determined by Bradford protein assay (Thermo Scientific). The endotoxin level was below 4 EU/mg as determined by EndoSafe PTS LAL assay (Charles River).

Analysis of HRS-Fc Fusion Proteins.

Figure 21:
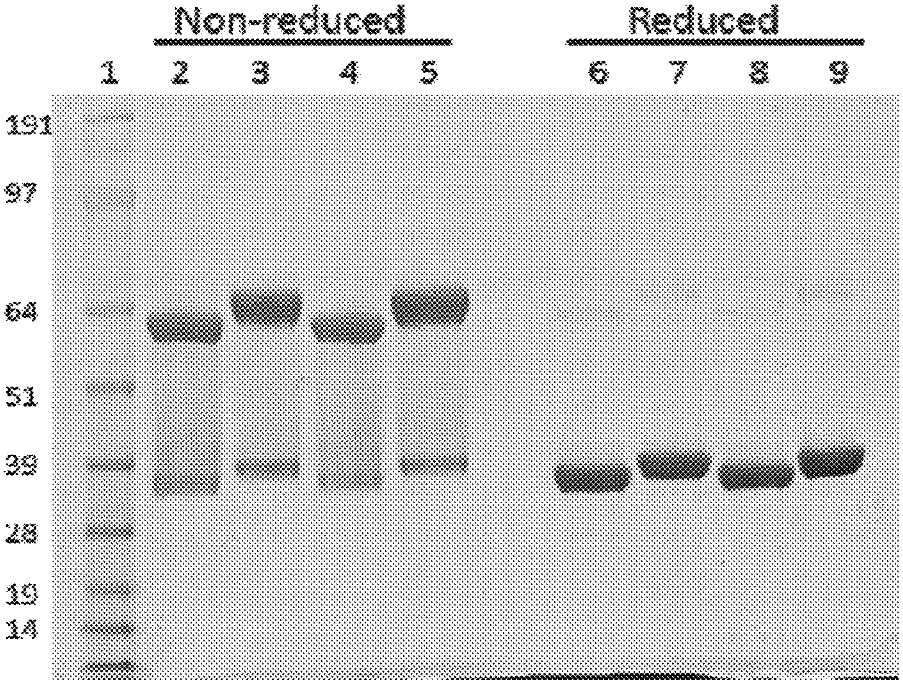
FIG. 21 shows the results of SDS-PAGE analysis of purified Fc fusion proteins. Lane 1: See Blue Plus2 protein ladder (Life Technologies). Lane 2 and 6: Fc-HRS(2-60) lot #472. Lane 3 and 7: HRS(1-60)-Fc lot #473. Lane 4 and 8: Fc-HRS(2-60) lot #480. Lane 5 and 9: HRS(1-60)-Fc lot #482. Lanes 2-5 were run under non-reduced conditions, and lanes 6-9 reduced conditions.

The purified HRS-Fc fusion proteins were analyzed by SDS-PAGE as shown in FIG. 21. Samples of 10 μg protein load were run on NuPAGE 4-12% Bis-Tris gels, 150 V for 60 minutes in MOPS-SDS buffer, and stained with Instant Blue. Reduced samples had 25 mM DTT, and were heated at 95° C. for 10 minutes in 1×LDS buffer prior to loading.

Figure 22:
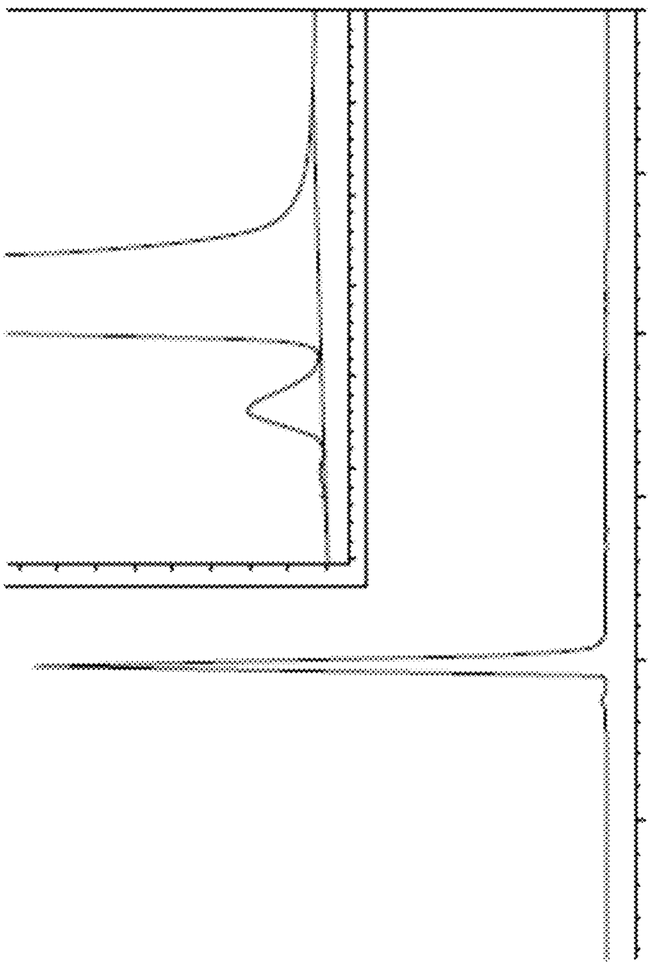
FIG. 22 shows an analytical size-exclusion HPLC analysis of representative purified Fc-HRS(2-60) fusion after Protein A, cation exchange, and hydroxyapatite chromatography (overlay of duplicate injections). Purity is 99.2% main peak, and 0.8% high molecular weight (HMW) species.

The purified HRS-Fc fusion proteins were also analyzed by a size-exclusion chromatography (SEC) method. The samples were loaded to aTSK-Gel Super SW3000 column (TOSOH, 4.6 mm ID×30 cm, 4 μm) on an Agilent 1260 HPLC system. A 30 minute isocratic run was carried out at 0.3 ml/min with a mobile phase containing 0.1 M NaCl, 0.2M Na phosphate and 5% 2-propanol at pH7. UV detection was performed at 280 nm. The chromatogram is shown in FIG. 22.

Approximately 83% of the protein is in the desired dimer form. after Protein A and prior to size-exclusion chromatography purification, with the remaining quantity present as high molecular weight species. After size-exclusion chromatography, the proportion of dimer increases to 95 to 99%. Using the Protein A, cation exchange, and hydroxyapatite purification process the proportion of dimer is greater than 99%. Most of the dimer protein contains the inter-chain disulfide bond in the Fc hinge region, while some non-covalent dimer also exists.

Analysis of the intact mass spectral data obtained using LC/ESI-MS demonstrates that the molecular size of the FC fusion proteins under non-reducing conditions is consistent with the expected molecular mass of approximately 64,520 daltons (data not shown). The CD spectra of the Fc fusion proteins in the far and near UV regions reveals that the structure of the fusion proteins is consistent with the expected domain structures. Additionally the deconvoluted differential scanning calorimetry data obtained from the HRS-Fc fusion proteins demonstrates that the Fc fusion proteins are folded with two major thermal transitions characteristic of the CH1 and CH2 domains of the Fc component (data not shown), consistent with predicted structures.

To assess the pharmacokinetic characteristics of the HRS-Fc fusion protein constructs compared to the unmodified HRS proteins, proteins were administered to normal C57BL/6 mice via a single intravenous or subcutaneous bolus at a dose of 8 mg/kg. Blood was serially sampled with sampling times distributed across nine animals per product form. For each time point, sera from three independent mice were drawn. Test article concentrations were measured by ELISA and pharmacokinetic parameters were derived using non-compartmental analysis on Phoenix software.

Figure 23A:
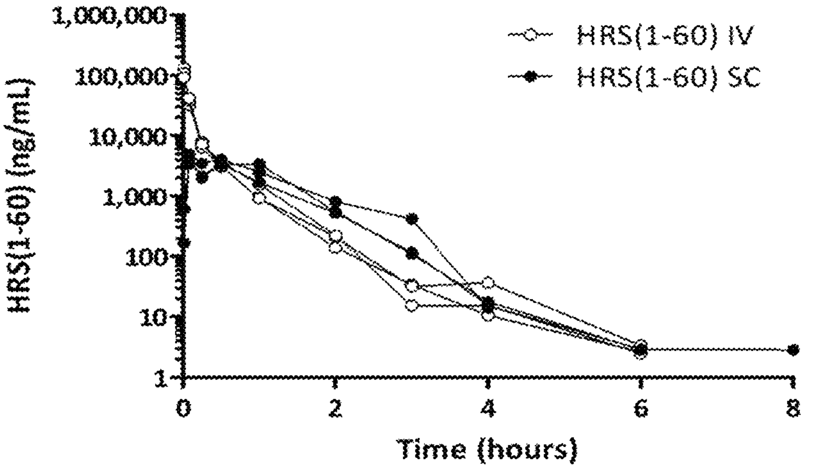
FIG. 23A shows the time versus concentration of HRS (1-60) following either intravenous or subcutaneous injection to mice.
Figure 23B:
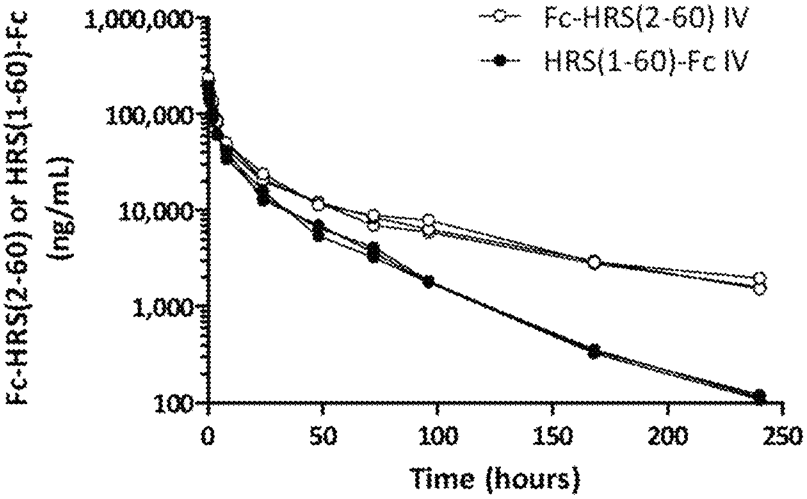
FIG. 23B shows the time versus concentration of Fc-HRS(2-60) and HRS(1-60)-Fc following intravenous injection to mice.
Figure 23C:
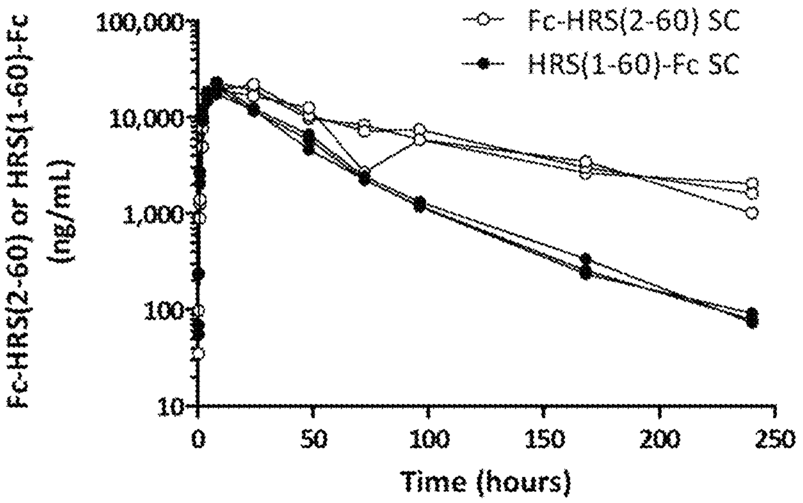
FIG. 23C shows the time versus concentration of Fc-HRS(2-60) and HRS(1-60)-Fc following subcutaneous injection to mice.

The results, shown in FIGS. 23A, 23B, and 23C demonstrate that the creation of the Fc fusion proteins resulted in significantly enhanced half life, exposure and SC bioavailability

TABLE E16

Pharmacokinetic analysis of HRS-Fc fusion proteins

| Product Form | Route | $V_d$[1] (ml/kg) | CL[2] (ml/hr/kg) | Half-life (hr) | Bioavailability[3] (%) | AUC[4] (hr*nM) | Fold increase in exposure[5] |
|---|---|---|---|---|---|---|---|
| HRS(1-60) | IV | 119 | 574 | 0.5 | — | 1,835 | — |
| Fc-HRS(2-60) | IV | 176 | 2.8 | 72 | — | 89,916 | 209 |
| HRS(1-60)-Fc | IV | 127 | 5.1 | 33 | — | 49,364 | 115 |
| HRS(1-60) | SC | 1,457 | 1,541 | 0.7 | 37 | 683 | |
| Fc-HRS(2-60) | SC | 452 | 4.4 | 71 | 63 | 56,307 | 352 |
| HRS(1-60)-Fc | SC | 537 | 10.2 | 37 | 50 | 24,623 | 154 |

[1]Volume of distribution at steady state for IV administration or terminal phase for SC administration
[2]Clearance for IV administration or clearance as a function of bioavailability for SC administration
[3]Compared to same product form administered IV
[4]Area under the curve from time of dose predicted to infinity
[5]Fold increase in molar exposure compared to unmodified protein delivered the same route The pharmacokinetic analysis shown in Table E16 demonstrates that HRS-Fc fusion constructs exhibit significantly improved systemic exposure, clearance and half-life compared to the unmodified proteins. Creation of the Fc fusion proteins also improved the subcutaneous bioavailability of the proteins compared to the unmodified proteins. In particular Fc-HRS(1-60) increased exposure compared to the unmodified protein by 200 to 300 fold depending on the route of administration, additionally SC bioavailability and half life were both significantly enhanced.

Example 9

Testing of Fc Fusion Proteins in TNBS Induced Colitis

The large intestine is lined by an epithelial mucosa that is invaginated into flask-like structures, crypts. Unlike the small intestine there are no villi in this region, with the top of the crypts opening onto a flat table region. The cells of the crypt are generated by stem cells located at the crypt base, whose daughter cells divide rapidly and differentiate into the predominant colonocytes and mucin producing goblet cells (a smaller number of endocrine cells and M cells are also produced). The size of the crypt and the number of goblet cells per crypt increase along the large intestine from caecum to rectum, presumably to aid the passage of faeces and provide sufficient mucosal and stem cell protection as water is absorbed from the faeces.

Normally, the rate of cell production in the intestinal crypt is precisely matched to the rate of cell loss—a very sensitive homeostatic mechanism operates. Disruption of the mucosal barrier allows bacterial entry into the body, with resultant disease implications. Conversely, hyperplasia can generate polyps and ultimately tumours. Disruption of the intestinal barrier can be caused by exposure to non-cell type specific (often proliferation specific) cytotoxic agents—typically anti-cancer therapies. However, perturbation of epithelial cell turnover is also a common feature of inflammatory diseases.

Current rodent models of inflammatory bowel disease (IBD) include for example models generated by triggering an autoimmune disease by manipulation of the T-cell population, irritating the mucosal lining of the intestine by the accumulation of particulate material in the large bowel (such as with DSS, dextran sulphate sodium), or chemical disruption of the epithelium (such as with Trinitrobenzene sulfonate, TNBS).

In any of these models disease severity may be assessed by a variety of subjective assessments of the observed pathological grades, as well as more objective and quantitative measures of the damage, to provide more meaningful insights into the underlying biology. It is possible to broaden the analysis by using computer assisted length/area measurements to map the changes in the mucosa/submucosa and obtain more quantitative measures of the damage, and hence therapeutic efficacy. While each of these models as different pros and cons, the TNBS colitis model is an established model of various aspects of inflammatory bowel disease in humans, which has been successfully used to validate and optimize the efficacy of human therapeutics.

TNBS Mouse Model.

In this model of colitis, colonic irritation is induced by intracolonic administration of TNBS in ethanol. This provokes an acute colitis that has a TH1-type cytokine profile, which is characterised by the expression of genes coding for TNF-α, IFN-γ and IL-12 amongst others (Fichtner-Feigl et al. J. Clin. Invest. 2005. 115: 3057-3071). The colitis can be severe and localised to the area of the colon into which the TNBS is introduced. The inflammatory response results in localised swelling, inflammatory cell infiltration, and epithelial loss.

In this study, the efficacy of the unmodified HRS polypeptide, (HRS(1-60), was compared to the Fc fusion proteins Fc-HRS(2-60) and HRS(1-60)-Fc to assess their efficacy in ameliorating TNBS-induced acute colitis in mice. Three different dosing regimens, employing either i.v. or s.c. administration of test item, were evaluated. Budesonide (p.o.) was used as a reference item for the study.

Animals and Caging:

A total of 100 BDF-1 (*H. Pylori*-free, murine norovirus-free) male mice (Harlan Laboratories, UK) were used in the study. Animals were 8-10 weeks old on supply and used at 10-12 weeks of age. All mice were held in individually ventilated cages (IVCs) in an SPF (Specific Pathogen Free) barrier unit. The animals were identified by numbered cages and by ear punches.

Diet and Animal Welfare: The animals were fed Rat and Mouse Expanded diet from B & K.

Water was supplied in HYDROPAC™ water pouches (filtered RO water; Hydropac/lab products, Delaware, USA). Both feed and water were available ad libitum. There was a constant room temperature of 21±2° C. and a mean relative humidity of 55±10%. The day-night cycle was constant, with light and dark phases of 12 hours each (07:00 hr/19:00 hr switch). Animal health was monitored daily and cages were cleaned at regular intervals. All procedures were certified according to the UK Animal (Scientific Procedures) Act 1986.

Groups, Dosages, Administration and Formulations:

A total of 100 mice were randomised into ten study groups (Table E17). All the mice in any one cage received the same treatment and were ear punched for identification purposes. Daily body weight measurements were used to calculate the volume of test item or vehicle administered to the applicable groups.

TABLE E17

| Study groups | | | | | |
|---|---|---|---|---|---|
| Treatment | Dose of test item | Volume and route of adminis-tration | Fre-quency of dosing | Dura-tion of dosing | Mouse codes |
| Vehicle (PBS) only | — | 5 ml/kg, i.v. | q.d. | day 0 to day 3 | 1-6 |
| TNBS/vehicle (PBS) | — | 5 ml/kg, i.v. | q.d. | day 0 to day 3 | 7-18 |
| TNBS + budesonide | — | 5 ml/kg, i.v. | q.d. | day 0 to day 3 | 19-28 |
| TNBS + HRS(1-60) | 1 mg/kg | 5 ml/kg, i.v. | q.d. | day 0 to day 3 | 29-40 |
| TNBS + Fc-HRS(2-60) | 5 mg/kg | 5 ml/kg, i.v. | q.d. | day 0 to day 3 | 41-50 |
| TNBS + Fc-HRS(2-60) | 5 mg/kg | 5 ml/kg, i.v. | once only | day 0 | 51-60 |
| TNBS + Fc-HRS(2-60) | 15 mg/kg | 5 ml/kg, s.c. | q.d. | day 0 to day 3 | 61-70 |
| TNBS + HRS(1-60)-Fc | 5 mg/kg | 5 ml/kg, i.v. | q.d. | day 0 to day 3 | 71-80 |
| TNBS + HRS(1-60)-Fc | 5 mg/kg | 5 ml/kg, i.v. | once only | day 0 | 81-90 |
| TNBS + HRS(1-60)-Fc | 15 mg/kg | 5 ml/kg, s.c | q.d. | day 0 to day 3 | 91-100 |

Preparation and Administration of TNBS and Test Items.

TNBS: TNBS (Sigma; lot #SLBD6811V) was prepared as a 15 mg/ml solution in saline/50% ethanol. A single dose of 200 µl (3 mg TNBS) was instilled into the colon, using a plastic catheter, placed 4 cm proximal to the anal verge, at 11:00 hr on study day 0. Animals were maintained in an inverted position for 1 minute after introduction of TNBS into the colon, in order to minimise leakage of the compound.

HRS(1-60):

The test item was received as four vials of frozen stock solution (0.033 ml volume in each) at 17.1 mg/ml, which was stored at −80° C. until use. On each day of test item administration, a single aliquot was taken and thawed on wet ice. After thawing, the contents of the vial were mixed by pipetting them up and down ten times. Subsequently, the test item was diluted with cold vehicle (sterile, ×1 PBS, pH 7.4) to give a solution at 0.2 mg/ml; the solution was mixed by pipetting up and down ten times. This solution was administered daily (from study day 0 until study day 3) by intravenous injection, at 5 ml/kg, in order to give a dose of 1 mg/kg.

Fc-HRS(2-60):

The test item was received as four vials of frozen stock solution (one vial of 2.51 ml and three vials of 2.01 ml) at 4.7 mg/ml, which was stored at −80° C. until use. On each day of test item administration, a single aliquot was taken and thawed on wet ice. After thawing, the contents of the vial were mixed by pipetting them up and down ten times. Subsequently, the test item was diluted with cold vehicle (sterile, ×1 PBS, pH 7.4) to gives solutions at 3 mg/ml and 1 mg/ml; the solutions were mixed by pipetting up and down ten times. Fc-HRS(2-60) was administered according to 3 different regimens: i) the 1 mg/ml solution was administered daily (from study day 0 until study day 3) by intravenous injection, at 5 ml/kg, in order to give a dose of 5 mg/kg; ii) the 1 mg/ml solution was administered daily, once only on study day 0, by intravenous injection, at 5 ml/kg, in order to give a dose of 5 mg/kg; iii) the 3 mg/ml solution was administered daily (from study day 0 until study day 3) by subcutaneous injection, at 5 ml/kg, in order to give a dose of 15 mg/kg.

HRS(1-60)-Fc:

The test item was received as four vials of frozen stock solution (one vial of 2.37 ml and three vials of 1.89 ml) at 4.99 mg/ml, which was stored at −80° C. until use. On each day of test item administration, a single aliquot was taken and thawed on wet ice. After thawing, the contents of the vial were mixed by pipetting them up and down ten times. Subsequently, the test item was diluted with cold vehicle (sterile, ×1 PBS, pH 7.4) to gives solutions at 3 mg/ml and 1 mg/ml; the solutions were mixed by pipetting up and down ten times. HRS(1-60)-Fc was administered according to 3 different regimens: i) the 1 mg/ml solution was administered daily (from study day 0 until study day 3) by intravenous injection, at 5 ml/kg, in order to give a dose of 5 mg/kg; ii) the 1 mg/ml solution was administered daily, once only on study day 0, by intravenous injection, at 5 ml/kg, in order to give a dose of 5 mg/kg; iii) the 3 mg/ml solution was administered daily (from study day 0 until study day 3) by subcutaneous injection, at 5 ml/kg, in order to give a dose of 15 mg/kg.

Budesonide:

Budesonide was obtained from Tocris (Tocris 1101, lot #1A/128902) and was stored in the dark at ambient temperature until use. On each day of administration, budesonide was formulated as a 1 mg/ml solution in peanut oil (Sigma). Budesonide was administered daily (from study day 0 until study day 3) by oral gavage, at 5 ml/kg, in order to give a dose of 5 mg/kg.

Clinical Examinations and Analgesia.

Any animal demonstrating more than 15% weight loss was considered unwell and treatment may have been with-held. Any animal was culled if the weight loss was greater than 20%. Animal well-being was monitored daily. Once daily from day −1 until the end of the study, all mice were weighed and assessed for stool consistency, and the presence of overt blood in the stool or around the anus according to the criteria in Table E18.

TABLE E18

Scoring criteria for in-life disease parameters.

| Score | Weight Loss (% day 0 weight) | Stool observation | Overt blood (in stool/ around anus) |
|---|---|---|---|
| 0 | <1% | Normal | None |
| 1 | ≥1% <5% | Soft; empty colon/rectum at necropsy; No observation in a 30 minute period | Slight |
| 2 | ≥5% <10% | Unformed | Moderate |
| 3 | ≥10% <15% | Watery/gel-like | Severe |
| 4 | ≥15% | | |

Use of Analgesia:

Analgesia was not used in this study, at the direction of the Sponsor, as it may have interfered with test item action.

Harvesting and Preparation of Tissue for Histological Examination:

Upon sacrifice, mice were anaesthetised with 4% isofluorane, with 2 L/min 02 and 2 L/min N20. When fully anaesthetised, blood was withdrawn by direct cardiac puncture and death confirmed by cervical dislocation.

Preparation of Whole Blood and Plasma Samples.

Blood was collected by cardiac puncture from all mice into 1.5 ml microcentrifuge tubes. Blood samples were immediately placed on ice and left to clot for 60 minutes. Samples were then centrifuged at 3000 g for 7 minutes, at 4° C. Immediately after centrifugation, the serum was transferred by sterile pipette into pre-labelled vials and immediately frozen on dry ice.

Preparation of Intestinal Samples.

The large intestine was removed and flushed with PBS and its length and wet weight were recorded, prior to cutting into proximal, mid and distal regions and fixation in Carnoy's solution. In addition, a small sample of colon was snap-frozen in liquid nitrogen. Fixed tissue was dehydrated through a series of alcohols and xylene and embedded in paraffin, using a Leica TP1020 tissue processor and an EG1140H work station. Sections (5 μm thick) were cut using a Leica RM2125RTF microtome, and air-dried on to microscope slides, overnight at 37° C. Subsequently, slides were dewaxed in xylene and rehydrated through graded alcohols to PBS. All sections were then stained with haematoxylin and eosin (H&E), and mounted.

Histological Analysis:

Histological sections were assessed in a blinded fashion. Sections were observed microscopically, and assigned a subjective severity score ranging between 0 and 5, according to the criteria outlined in Table E19. Up to twelve transverse cross-sections from the mid and distal large bowel were assessed.

TABLE E19

Epistem's standard severity scoring system.

| Severity Score | Description |
|---|---|
| 0 | Crypts appeared normal. |
| 1 | Crypts present but damaged (abnormal pathology). No ulceration. |

TABLE E19-continued

Epistem's standard severity scoring system.

| Severity Score | Description |
|---|---|
| 2 | Some crypts depleted and some ulceration/inflammation. 20-70% of crypts depleted and increased ulceration/inflammation. |
| 4 | >70% crypts depleted with substantial ulceration/inflammation. |
| 5 | No crypts remaining. Totally ulcerated/inflamed. |

Statistical Analysis:

Where mentioned, statistical comparisons of group data were performed using ANOVA, in combination with post hoc tests, using Graph Pad Prism.

qPCR Analysis:

Mouse colon was excised from the animals and stored at −80° C. until analysis. RNA was prepped from colons using Qiagen's RNeasy Mini Kit (Catalog #74106). Once RNA was eluted from the Qiagen column, it was run on an Agilent Bioanalyzer 2100 to test RNA integrity and NanoDrop to determine RNA concentration and purity. RNA was then stored at −80° C.

Reverse transcription (RT) of RNA to cDNA was performed in a 96 well PCR plate format in Eppendorf's Mastercycler PCR machine with the following program: 37° C. for 60 minutes, 95° C. for 5 minutes. The edge wells of the 96 well plate were not used and filled with 50 mcL water to prevent evaporation of inside wells. 100 ng of RNA in 25 mcL of reverse transcription master mix (Life Technologies #4387406) was used per sample RT. Once RT was completed, the next step was to pre-amplify genes of interest in the sample cDNA. Primers of genes of interest (DELTAgene primers designed by Fluidigm) were combined to a final concentration of 200 nM. Using these primers, genes of interest were pre-amplified in each sample. Pre-amplification was performed in 10 mcL reactions (2.5 mcL cDNA, 7.5 mcL Pre-Amp mastermix) in 384-well format using an Applied Biosystems ViiA7 PCR machine with the following program: 95° C. for 10 minutes, 14 cycles of 95° C. for 15 seconds and 60° C. for 4 minutes. After pre-amplification step, exonuclease (New England BioLabs catalog #M0293L) was added to remove unincorporated primers from each sample. This exonuclease reaction was also completed in the ViiA7 PCR machine with the following program: 37° C. for 30 minutes, 80° C. for 15 minutes. After exonuclease, the RT sample was further diluted 1:5 (7 mcL exonuclease sample+18 mcL low EDTA buffer).

The chip used to run qPCR on Fluidigm's Biomark system was a 96.96 Dynamic Array IFC for Gene Expression. The chip was first primed with the IFC controller HX as per manufacturer's recommendations before sample and assays were loaded. To prepare assays to be loaded on a chip, 4.4 mcL assay master mix (Fluidigm's 2× Assay Loading Reagent catalog #8500736 and low EDTA TE) to 3.6 mcL 20 mcM forward and reverse primers for each gene of interest were prepared in a 96 well plate. To prepare samples, 4.5 mcL sample master mix (Ambion's 2× TaqMan Gene Expression Master Mix, Fluidigm's 20×DNA Binding Dye Sample Loading Reagent catalog number 100-0388, and Biotium's 20× EvaGreen catalog #31000) was added to 3 mcL diluted pre-amplified/exonuclease sample in a 96 well plate. Once the chip had been primed, 5 mcL sample or assay prepared above were loaded onto the chip. The chip was them returned to the IFC controller for the samples to be loaded into the chip. After the chip had finished loading, qPCR could then be run on the Biomark using preset program for 96.96 Dynamic Array for Gene Expression with a melt curve to determine primer specificity. Relative gene expression was determined by the delta delta Ct method using multiple housekeeping genes.

Results:

In-Life Parameters—

All TNBS-recipient groups demonstrated an acute decrease in mean body weight, of between 8-10% of starting body weight over the first 24 hours following administration of the colitic agent; subsequently, there was a slower decrease in mean body weight, with all groups showing a significant decline in mean body weight to between 80-90% of starting weight by the end of the study (p≤0.0158). The body weight of vehicle-only treated mice showed a minimal change over the period of the study, with a final mean body weight of 99.6±1.7% of starting body weight, by study day 4 (mean±standard deviation). The TNBS/vehicle group had the lowest mean final body weight, at 79.8±1.8%. Final mean body weights for some groups (i.e. TNBS/Fc-HRS(2-60)-s.c. group and TNBS/budesonide group) were artificially high, due to the higher incidence of early morbidity in these groups. Of the groups that demonstrated the least early morbidity, the TNBS/Fc-HRS(2-60)-QD -i.v. group had the highest mean final body weight of 85.6±7.1%, although this was not significantly different from the TNBS/vehicle group (p>0.05) (data not shown).

The majority of TNBS-recipient mice demonstrated diarrhoea at some stage during the study, although observations of mucosal bleeding were less common. There were reductions in the incidence of diarrhoea in response to some test item treatments. The TNBS/vehicle group had a cumulative (normalised) diarrhoea score of 31 by the end of the study on day 4; with the TNBS/Fc-HRS(2-60)-QD-i.v. and TNBS/HRS(1-60)-Fc-QD-i.v. groups having the lowest scores of 26 (data not shown).

Figure 24A:
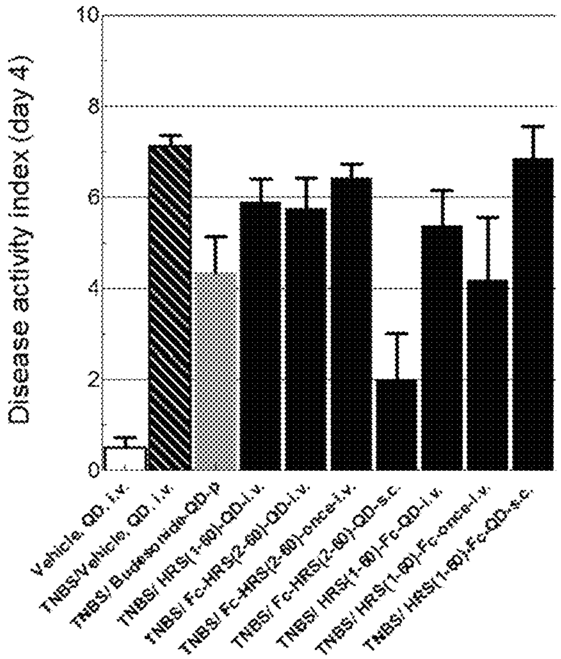
FIG. 24A shows disease activity index (DAI) scores at termination in mice treated with different HRS-Fc fusion proteins. Bars represent the mean DAI (±SEM) for each treatment group. The DAI incorporates information on bleeding and diarrhea together with a score for weight loss.

The clinical condition of the mice can be best obtained by combining information on bleeding and diarrhoea together with a score for weight loss, in order to give a disease activity index (DAI) score. This can be most accurately determined on the day that a mouse is euthanised, as missing stool consistency observation data can be supplemented with observations of stool in the rectum. For mice surviving on day 4, there was a significant increase in the mean DAI scores for all the TNBS-recipient groups, in comparison to the untreated control group (at p≤0.0062), except for the TNBS/Fc-HRS(2-60)-s.c. group, although in this group only three mice remained in the study at the scheduled end point. The mean DAI for surviving mice on day 4 in the TNBS/vehicle group was 7.13±0.64; in comparison, the TNBS/budesonide and TNBS/HRS(1-60)-Fc-once-i.v. groups had significantly lower mean DAIs, at 4.33±1.97 and 4.20±3.03, respectively (p≤0.0304). Inclusion of all mice, surviving to at least 07:00 hr on day 1, in the calculation of DAI gave similar results, although the effect observed in the TNBS/budesonide and TNBS/HRS(1-60)-Fc -once-i.v. groups was no longer significant (p>0.05) (see FIG. 24A).

Post Mortem Observations—

Figure 24B:
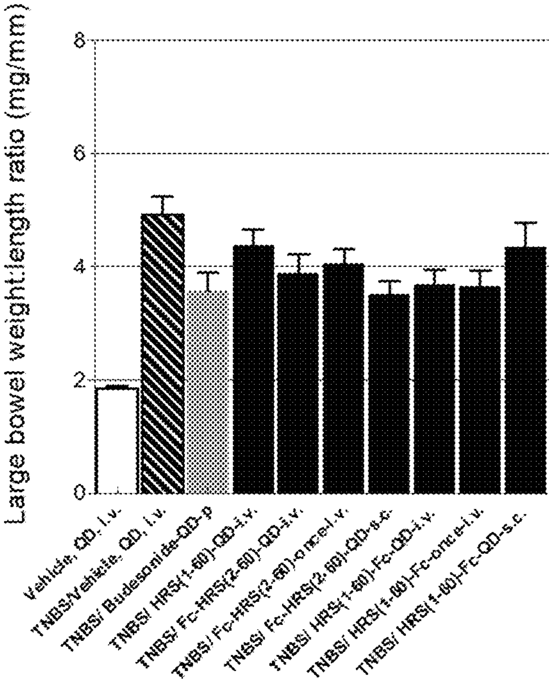
FIG. 24B shows colon weight: length ratio at termination in mice treated with compounds. Bars represent the mean ratio (±SEM) for each treatment group.

For the vehicle-only mice, mean large bowel weight and length were 200.4±21.7 mg and 108.3±7.8 mm, respectively; the mean large bowel weight:length ratio was 1.85±0.12 (mg/mm). All TNBS-treated groups demonstrated a significant increase in large bowel weight relative to the untreated control mice (p≤0.0215), with the TNBS/vehicle group having a mean large bowel weight of 368.4±70.1 mg. The TNBS/budesonide group had the lowest mean large bowel weight of all the TNBS-recipient groups, at 298.0±62.0 mg. TNBS administration was associated also with a significant reduction in large bowel length in all TNBS-recipient groups (p≤0.0285), with the TNBS/vehicle group having a mean large bowel length of 75.6±9.3 mm; in comparison, the TNBS/HRS(1-60)-Fc-QD-i.v. group demonstrated a significant amelioration of large bowel shortening, with a mean large bowel length of 94.9±11.8 mm (p=0.0019). The changes in large bowel weight and length resulted in a significant increase in large bowel weight: length ratio for all TNBS-recipient groups (p≤0.0116). The TNBS/vehicle group had the highest mean large bowel weight:length ratio of all groups, at 4.92±0.99 (mg/mm). The TNBS/budesonide group, TNBS/Fc-HRS(2-60)-s.c. group, TNBS/HRS(1-60)-Fc -QD-i.v. group and the TNBS/HRS(1-60)-Fc -once-i.v. group all demonstrated a significant reduction in large bowel weight:length ratio, relative to the TNBS/vehicle control group, although the mean ratio for the TNBS/HRS(1-60)-Fc -QD-i.v. group was group was skewed by the number of mice that were euthanised early in the study. The mean large bowel weight:length ratios for the TNBS/budesonide and TNBS/HRS(1-60)-Fc -QD-i.v. groups were 3.57±1.01 and 3.56±0.80, respectively (p=0.0143 and p=0.0456) (see FIG. 24B).

Histopathology—

Histopathological changes associated with TNBS-induced colitis were assessed according to Epistem's standard histological scoring procedure. All TNBS-recipient groups demonstrated a significant increase in histopathology score (p≤0.0036). The T cell/vehicle group had a mean histopathology score of 2.32±0.65, with the TNBS/HRS(1-60)-Fc -s.c. group having the highest mean histopathology score at 2.41±0.68. Other treatment groups had lower mean histopathology scores than the TNBS/vehicle group, with the TNBS/budesonide and TNBS/Fc-HRS(2-60)-QD-i.v. groups having the lowest scores of 1.66±1.08 and 1.68±1.03, respectively, although these reductions were not statistically significant. On a regional basis, the effect of these treatments was more apparent in the distal third of the large bowel, although still not of statistical significance.

Morbidity—

Only one group, TNBS/HRS(1-60)-Fc -QD-i.v. demonstrated survival of all (eligible) mice (mouse 75 excluded due to large bowel perforation during TNBS administration and mouse 78 excluded due to lack of disease induction). Survival in other groups ranged from 80% (TNBS/Fc-HRS(2-60)-QD-i.v. group) to 33.3% (TNBS/Fc-HRS(2-60)-s.c. group); survival in the TNBS/budesonide group was 60%. Mice were euthanised when they presented with poor condition (withdrawn/failure to demonstrate normal behaviour); despite six-hourly checks, two mice (40 and 50) were found dead at 19:00 hr on study day 3 (data not shown).

qPCR Results.

Figure 25:
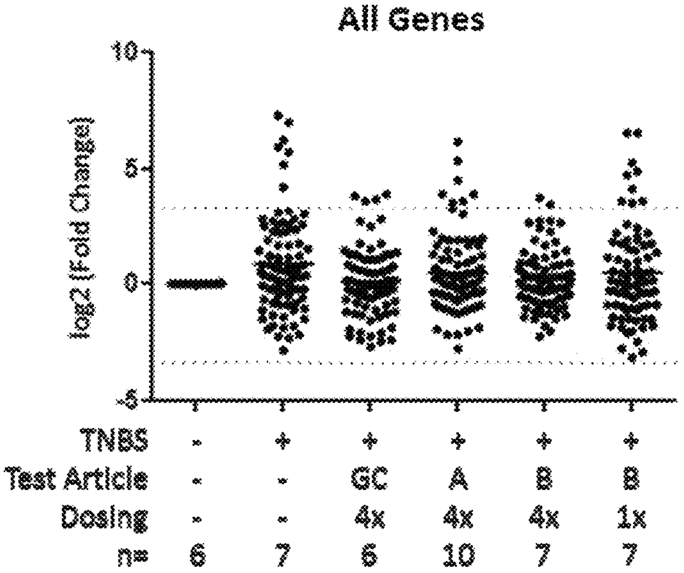
FIG. 25 shows an overview of transcriptional changes in TNBS study. Relative transcriptional changes in TNBS treated animals (group 2), animals treated with TNBS and budesonide (group 3), TNBS and test article A (HRS(1-60); group 4), and TNBS and test article B (Fc-HRS(2-60); groups 5 and 6) are shown following normalization to naïve animals (group 1). Each dot in the scatter plot represents a gene measured. 7 genes in group 2 were up-regulated more than 10-fold (IL6, IL1b, MCP-1, MMP3, MMP9, CD11b, and IL10).
Figures 26A, 26B, 26C:
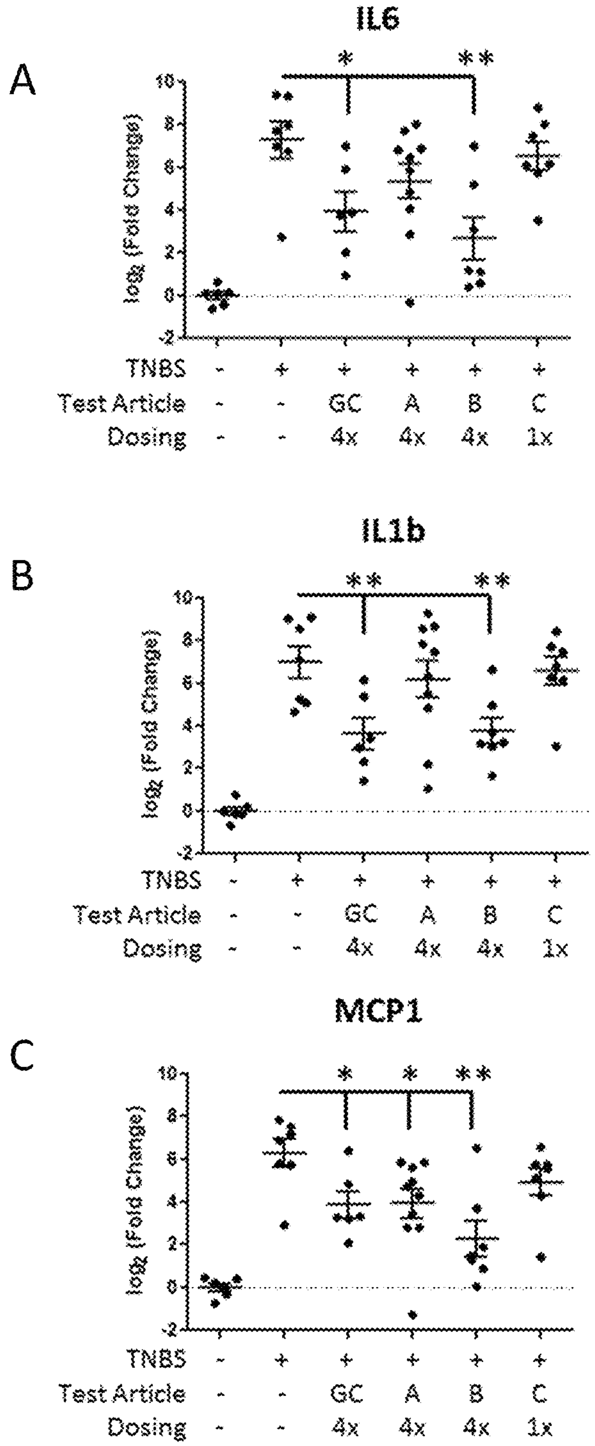
FIGS. 26A-26C and FIGS. 26D-26F and FIG. 26H show the immune and inflammatory related genes up regulated by TNBS. Relative transcriptional changes of individual genes in TNBS treated animals (group 2), animals treated with TNBS and budesonide (group3), TNBS and test article A (HRS(1-60); group 4), and TNBS and test article B (Fc-HRS(2-60); groups 5 and 6) are shown following normalization to naïve animals (group 1). Each dot in the scatter plot represents the abundance of the gene of interest in each animal within the group. Significance was calculated using a student's t-test where *=p-value <0.05 and **=p-value <0.01.
Figures 26D, 26E, 26F:
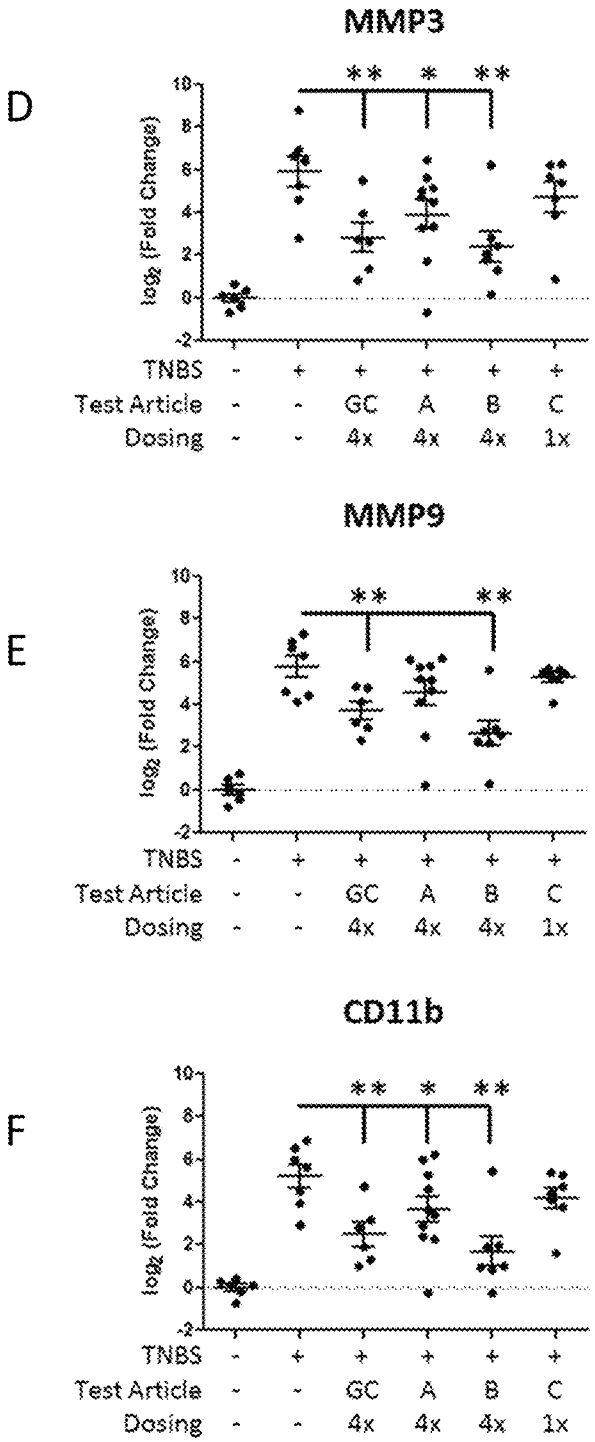
Figure 26H:
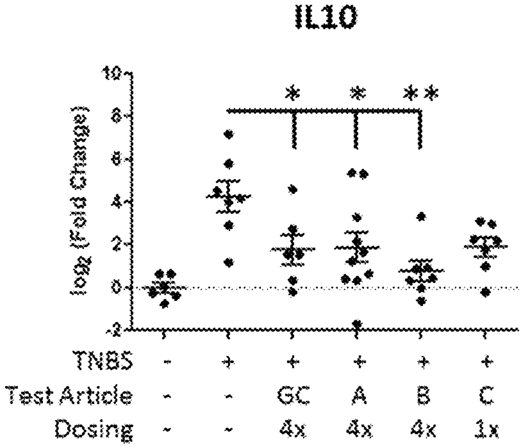

To further investigate the mechanistic basis for the effects of HRS(1-60) and Fc-HRS(2-60) on TNBS induced colitis, changes in gene expression in the colons from animals was examined after the completion of the study. RNA profiling was performed on colons isolated from the mice on day as described above. The results from these studies demonstrated that seven genes were elevated by more than 10 fold in response to TNBS treatment were significantly reduced by treatment with Fc-HRS(2-60) (see Table E20; and FIG. 25).

TABLE E20

| Genes regulated by more than 10 fold |
|---|
| IL6 |
| IL1b |
| MCP1 |
| MMP3 |
| MMP9 |
| CD11B |
| IL10 |

Transcriptional profiling of TNBS treated mouse colons revealed many genes, including several housekeeping genes (data not shown) were not significantly impacted by Fc-HRS (2-60) treatment. By contrast, transcriptional profiling of TNBS treated mouse colons revealed significant reduction of TNBS regulated immune and inflammatory related genes by Fc-HRS(2-60). This result was fortified by the finding that HRS(1-60) also significantly reduces TNBS induced levels of MCP1, MMP3, CD11b, and IL10 (see FIGS. 26A-26H).

Conclusion:

Intracolonic administration of TNBS to BDF-1 mice resulted in the development of colitis characterised by acute weight loss, with a moderate increase in the incidence of diarrhoea and mucosal bleeding. Post mortem examination demonstrated significant change in the large bowel weight: length ratio and ulcerative lesions in the large bowel, with stenosis and accompanying stool accumulation within the bowel. Treatment with budesonide was associated with improvements in both in-life and post mortem disease parameters, and although having the lowest mean histopathology score of all TNBS-recipient groups, the reduction in this disease parameter did not achieve significance. Treatment with Fc-HRS(2-60)-QD-i.v. had a similar effect to budesonide in reducing histopathology score and was associated with superior survival. The TNBS/HRS(1-60)-Fc -QD-i.v. group showed the highest level of survival and significant improvement in large bowel weight:length ratio, although it was less effective than either budesonide or Fc-HRS(2-60) in reducing the histopathology score. With regard to histopathology score, all three of these test items appeared to have their greatest effect on the distal third of the large bowel. Improvements in disease parameters were observed for the TNBS/Fc-HRS(2-60)-s.c. group, and the TNBS/HRS(1-60)-Fc -once-i.v. group (e.g. body weight and large bowel weight:length ratio). Additionally, transcriptional profiling of TNBS treated mouse colons revealed significant reduction of TNBS regulated immune and inflammatory related genes by Fc-HRS(2-60). This result was fortified by the finding that HRS(1-60) also significantly reduces TNBS induced levels of MCP1, MMP3, CD11b, and IL10, demonstrating the HRS-Fc fusion proteins were active in immunomodulating gene expression in this system.

Overall, the data suggest that Fc-HRS(2-60) and HRS(1-60)-Fc have significant potential in the treatment of intestinal inflammation, and other inflammatory conditions.

Example 10

Impact of Hrs-Fc Fusion Proteins on T Cell Populations

To evaluate the potential impact of HRS-Fc conjugates on T cell populations in vivo, Fc-HRS(2-60) was tested in a TNBS induced model of colitis, similar to that described above. Studies were performed in male BDF-1 mice. Briefly, male BDF-1 mice (Jackson Laboratories), were acclimated for a minimum of 1 week prior to experimentation, were fasted beginning 16 hours prior to TNBS administration and 13 hours prior to dosing. Fc-HRS(2-60) was administered at a single dose, 0.5 mg/Kg, IV at the same time as commencing TNBS treatment. Splenocytes from three animals per group were analyzed for immune populations. To choose the animals for analysis, the mice that had the most severe and the least severe disease scores were excluded (based on clinical observations, stool consistency and body weight). From the remaining animals, three animals from each treatment group were picked based on representing the mean of their respective group.

Procedures.

Spleens were harvested from BDF-1 mice and placed directly into 10 ml cold Cell Staining Buffer (Biolegend, catalog #420201, lot #B166478) on ice. Spleens were mechanically disassociated between two frosted autoclaved slides in a tissue culture dish. The cell suspension was filtered through a 70 μm filter and cells were pelleted by centrifugation at 300 g for 5 minutes, 4° C. Cells were washed once in 10 ml Cell Staining Buffer and counted using the Nexcelom Cellometer Auto 2000 Cell Viability Counter. Splenocytes were reconstituted at $5\times10^5$ cells/ml in Cell Staining Buffer and were immediately stained with antibodies for flow cytometry.

A total of $1\times10^6$ cells were stained for T regulatory markers (CD4, CD25 and FOXP3) using the One Step Staining Mouse Treg Flow Kit (Biolegend catalog #13680, lot numbers #B177852, B177853, B174309, B176365) according to manufacturer's instructions.

For phenotyping of immune cells, a total of $1\times10^6$ cells were stained with fluorescently-labeled antibodies against CD3ε (catalog #100334, lot #162956), CD4 (catalog #100529, lot #B152907) and CD8 (catalog #100714, lot #B165226) (antibodies were purchased from Biolegend). Cells were stained with antibodies diluted at manufacturer's recommended concentrations in Cell Staining Buffer and incubated for 30 minutes at 4° C. Cells were thoroughly washed with Cell Staining Buffer and fixed using Stabilizing Fixative Buffer (BD Biosciences catalog #338036, lot #2291614).

Flow cytometry was performed at the VA Flow Cytometry Research Core facility (VA San Diego, La Jolla, Calif.). The samples were analyzed on a 3 laser BD Canto instrument (488 Argon, 633 HeNe, 405 Violet). Raw FACS files were analyzed using FlowJo software (Tree Star).

Results.

Extracellularly-stained splenocytes were gated on a live lymphocyte population and $CD3^+$ cells to determine a total T cell percentage. To generate population percentages of $CD4^+$ and $CD8^+$, cells were gated into $CD3^+CD4^+$ T cells and $CD3^+CD8^+$ T double-positive cells from the live lymphocyte gate. T regulatory cells (Treg) were gated on a live lymphocyte gate and then on $CD4^+$ cells. Treg cells were determined based on expression of CD25 and FoxP3. In these data (see FIGS. 27A-27D), each dot represents one animal, the line represents the mean.

Figures 27A, 27B, 27C, 27D:
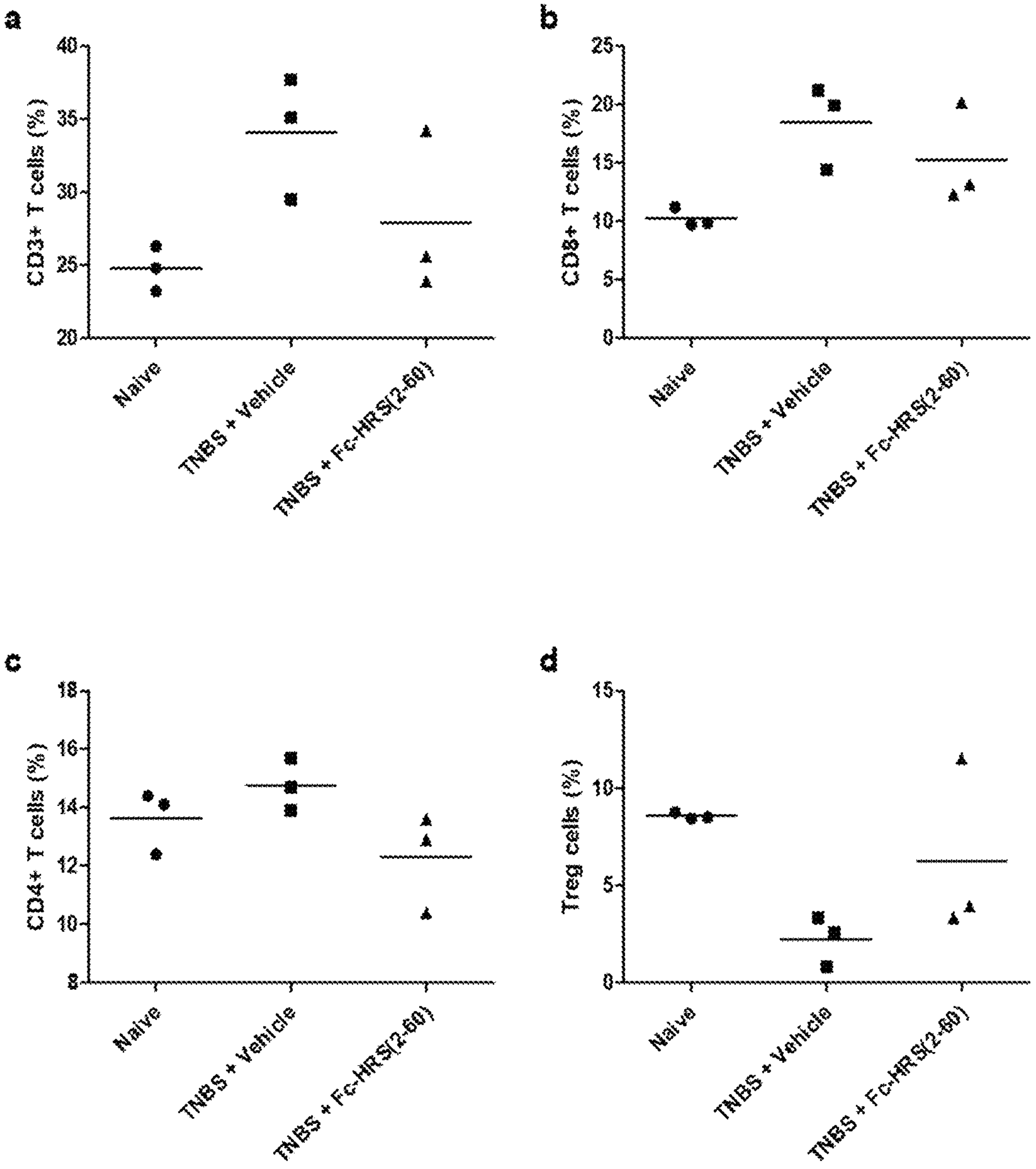
FIGS. 27A-27D shows the relative percentages of different T cell populations in the spleens of naïve mice or mice treated intracolonically with TNBS to induce experimental colitis, treated with TNBS±0.5 mg/kg Fc-HRS(2-60). Shown are the percentage of live lymphocytes stained for (27A) CD3, (27B) CD8, (27C) CD4, and (27D) CD25 and FoxP3. Treg cells were additionally gated on $CD4^+$ cells.

In TNBS-treated mice, there was an increase in $CD3^+$ T cells (FIG. 27A), compared to naïve animals. By contrast, two out of the three Fc-HRS(2-60) treated mice showed a reduction in $CD3^+$ T cells compared to the TNBS treated animals. To determine which $CD3^+$ populations were accounting for this change, $CD8^+$, $CD4^+$ and Treg cells populations were further investigated. FIG. 27B and FIG. 27C show that $CD8^+$ T and $CD4^+$ cells were elevated in TNBS-treated animals and treatment with Fc-HRS(2-60)

reduced levels in both cases. Furthermore, Treg cells were depleted in TNBS-treated animals, compared to naïve animals, but were elevated compared to the TNBS treated animals in the Fc-HRS(2-60) treated group (FIG. 27D). Moreover, one mouse treated with Fc-HRS(2-60) showed Treg levels similar to naïve animals. Together, these results suggest that TNBS alters T cell populations in the spleen to a more inflammatory phenotype through increased $CD8^+$ T cells and decreased Treg cells and that treatment with Fc-HRS(2-60) restores these populations towards homeostatic levels.

These and other changes can be made to the embodiments in light of the above-detailed description. In general, in the following claims, the terms used should not be construed to limit the claims to the specific embodiments disclosed in the specification and the claims, but should be construed to include all possible embodiments along with the full scope of equivalents to which such claims are entitled. Accordingly, the claims are not limited by the disclosure.

The invention claimed is:

1. A method of reducing a lung inflammatory response in a subject in need thereof, comprising administering to the subject a composition comprising a histidyl-tRNA synthetase (HRS) fusion polypeptide having at least one Fc region (HRS-Fc fusion polypeptide), wherein the HRS-Fc fusion polypeptide has an amino acid sequence that is at least 95% identical to SEQ ID NO:337, wherein the HRS-Fc fusion polypeptide is at least about 95% pure and less than about 5% aggregated, and wherein the composition is substantially endotoxin-free.

2. The method of claim 1, wherein the HRS-Fc fusion polypeptide reduces immune cell activation and invasion into damaged lung.

3. The method of claim 1, wherein the HRS-Fc fusion polypeptide increases production of anti-inflammatory cytokines, reduces production or activity of pro-inflammatory cytokines, or both.

4. The method of claim 1, wherein the HRS fusion polypeptide comprises an amino acid sequence at least 97% identical to SEQ ID NO: 337.

5. The method of claim 4, wherein the HRS fusion polypeptide comprises an amino acid sequence at least 98% identical to SEQ ID NO: 337.

6. The method of claim 1, wherein the Fc region and the HRS polypeptide are separated by a peptide linker.

7. The method of claim 1, wherein the HRS-Fc fusion polypeptide is substantially in dimeric form in a physiological solution.

8. The method of claim 1, wherein the HRS-Fc fusion polypeptide has substantially the same secondary structure as a corresponding unmodified HRS polypeptide, as determined via UV circular dichroism analysis.

9. The method of claim 1, wherein the HRS-Fc fusion polypeptide has a plasma or sera pharmacokinetic AUC profile at least 5-fold greater than a corresponding, unmodified HRS polypeptide.

10. The method of claim 1, comprising intravenously administering the composition to the subject.

11. The method of any one of claims 1-10, wherein the subject has problems with breathing.

12. The method of claim 1, wherein the problems with breathing comprise shortness of breath, a non-productive cough, or both.

* * * * *

UNITED STATES PATENT AND TRADEMARK OFFICE

CERTIFICATE OF CORRECTION

PATENT NO. : 11,072,787 B2
APPLICATION NO. : 16/842200
DATED : July 27, 2021
INVENTOR(S) : Chi-Fang Wu et al.

It is certified that error appears in the above-identified patent and that said Letters Patent is hereby corrected as shown below:

In the Claims

At Column 506, Claim number 12, Line number 49:
"12. The method of claim 1, wherein the problems with"
Should read:
-- 12. The method of claim 11, wherein the problems with --

Signed and Sealed this
First Day of March, 2022

Drew Hirshfeld
*Performing the Functions and Duties of the*
*Under Secretary of Commerce for Intellectual Property and*
*Director of the United States Patent and Trademark Office*

SEQUENCE LISTING

```
<160> NUMBER OF SEQ ID NOS: 396

<210> SEQ ID NO 1
<211> LENGTH: 509
<212> TYPE: PRT
<213> ORGANISM: Homo sapiens

<400> SEQUENCE: 1

Met Ala Glu Arg Ala Ala Leu Glu Glu Leu Val Lys Leu Gln Gly Glu
1               5                   10                  15

Arg Val Arg Gly Leu Lys Gln Gln Lys Ala Ser Ala Glu Leu Ile Glu
            20                  25                  30

Glu Glu Val Ala Lys Leu Leu Lys Leu Lys Ala Gln Leu Gly Pro Asp
        35                  40                  45

Glu Ser Lys Gln Lys Phe Val Leu Lys Thr Pro Lys Gly Thr Arg Asp
    50                  55                  60

Tyr Ser Pro Arg Gln Met Ala Val Arg Glu Lys Val Phe Asp Val Ile
65                  70                  75                  80

Ile Arg Cys Phe Lys Arg His Gly Ala Glu Val Ile Asp Thr Pro Val
                85                  90                  95

Phe Glu Leu Lys Glu Thr Leu Met Gly Lys Tyr Gly Glu Asp Ser Lys
            100                 105                 110

Leu Ile Tyr Asp Leu Lys Asp Gln Gly Gly Glu Leu Leu Ser Leu Arg
        115                 120                 125

Tyr Asp Leu Thr Val Pro Phe Ala Arg Tyr Leu Ala Met Asn Lys Leu
    130                 135                 140

Thr Asn Ile Lys Arg Tyr His Ile Ala Lys Val Tyr Arg Arg Asp Asn
145                 150                 155                 160

Pro Ala Met Thr Arg Gly Arg Tyr Arg Glu Phe Tyr Gln Cys Asp Phe
                165                 170                 175

Asp Ile Ala Gly Asn Phe Asp Pro Met Ile Pro Asp Ala Glu Cys Leu
            180                 185                 190

Lys Ile Met Cys Glu Ile Leu Ser Ser Leu Gln Ile Gly Asp Phe Leu
        195                 200                 205

Val Lys Val Asn Asp Arg Arg Ile Leu Asp Gly Met Phe Ala Ile Cys
    210                 215                 220

Gly Val Ser Asp Ser Lys Phe Arg Thr Ile Cys Ser Ser Val Asp Lys
225                 230                 235                 240

Leu Asp Lys Val Ser Trp Glu Glu Val Lys Asn Glu Met Val Gly Glu
                245                 250                 255

Lys Gly Leu Ala Pro Glu Val Ala Asp Arg Ile Gly Asp Tyr Val Gln
            260                 265                 270

Gln His Gly Gly Val Ser Leu Val Glu Gln Leu Leu Gln Asp Pro Lys
        275                 280                 285
```

-continued

Leu Ser Gln Asn Lys Gln Ala Leu Glu Gly Leu Gly Asp Leu Lys Leu
    290                 295                 300

Leu Phe Glu Tyr Leu Thr Leu Phe Gly Ile Asp Asp Lys Ile Ser Phe
305                 310                 315                 320

Asp Leu Ser Leu Ala Arg Gly Leu Asp Tyr Tyr Thr Gly Val Ile Tyr
                325                 330                 335

Glu Ala Val Leu Leu Gln Thr Pro Ala Gln Ala Gly Glu Glu Pro Leu
            340                 345                 350

Gly Val Gly Ser Val Ala Ala Gly Gly Arg Tyr Asp Gly Leu Val Gly
        355                 360                 365

Met Phe Asp Pro Lys Gly Arg Lys Val Pro Cys Val Gly Leu Ser Ile
    370                 375                 380

Gly Val Glu Arg Ile Phe Ser Ile Val Glu Gln Arg Leu Glu Ala Leu
385                 390                 395                 400

Glu Glu Lys Ile Arg Thr Thr Glu Thr Gln Val Leu Val Ala Ser Ala
                405                 410                 415

Gln Lys Lys Leu Leu Glu Glu Arg Leu Lys Leu Val Ser Glu Leu Trp
            420                 425                 430

Asp Ala Gly Ile Lys Ala Glu Leu Leu Tyr Lys Lys Asn Pro Lys Leu
        435                 440                 445

Leu Asn Gln Leu Gln Tyr Cys Glu Glu Ala Gly Ile Pro Leu Val Ala
    450                 455                 460

Ile Ile Gly Glu Gln Glu Leu Lys Asp Gly Val Ile Lys Leu Arg Ser
465                 470                 475                 480

Val Thr Ser Arg Glu Glu Val Asp Val Arg Arg Glu Asp Leu Val Glu
                485                 490                 495

Glu Ile Lys Arg Arg Thr Gly Gln Pro Leu Cys Ile Cys
            500                 505

<210> SEQ ID NO 2
<211> LENGTH: 506
<212> TYPE: PRT
<213> ORGANISM: Homo sapiens

<400> SEQUENCE: 2

Met Pro Leu Leu Gly Leu Leu Pro Arg Arg Ala Trp Ala Ser Leu Leu
1               5                   10                  15

Ser Gln Leu Leu Arg Pro Pro Cys Ala Ser Cys Thr Gly Ala Val Arg
            20                  25                  30

Cys Gln Ser Gln Val Ala Glu Ala Val Leu Thr Ser Gln Leu Lys Ala
        35                  40                  45

His Gln Glu Lys Pro Asn Phe Ile Ile Lys Thr Pro Lys Gly Thr Arg
    50                  55                  60

Asp Leu Ser Pro Gln His Met Val Val Arg Glu Lys Ile Leu Asp Leu
65                  70                  75                  80

Val Ile Ser Cys Phe Lys Arg His Gly Ala Lys Gly Met Asp Thr Pro
                85                  90                  95

Ala Phe Glu Leu Lys Glu Thr Leu Thr Glu Lys Tyr Gly Glu Asp Ser
            100                 105                 110

Gly Leu Met Tyr Asp Leu Lys Asp Gln Gly Gly Glu Leu Leu Ser Leu
        115                 120                 125

Arg Tyr Asp Leu Thr Val Pro Phe Ala Arg Tyr Leu Ala Met Asn Lys
    130                 135                 140

Val Lys Lys Met Lys Arg Tyr His Val Gly Lys Val Trp Arg Arg Glu
145                 150                 155                 160

-continued

Ser Pro Thr Ile Val Gln Gly Arg Tyr Arg Glu Phe Cys Gln Cys Asp
165 170 175

Phe Asp Ile Ala Gly Gln Phe Asp Pro Met Ile Pro Asp Ala Glu Cys
180 185 190

Leu Lys Ile Met Cys Glu Ile Leu Ser Gly Leu Gln Leu Gly Asp Phe
195 200 205

Leu Ile Lys Val Asn Asp Arg Arg Ile Val Asp Gly Met Phe Ala Val
210 215 220

Cys Gly Val Pro Glu Ser Lys Phe Arg Ala Ile Cys Ser Ser Ile Asp
225 230 235 240

Lys Leu Asp Lys Met Ala Trp Lys Asp Val Arg His Glu Met Val Val
245 250 255

Lys Lys Gly Leu Ala Pro Glu Val Ala Asp Arg Ile Gly Asp Tyr Val
260 265 270

Gln Cys His Gly Gly Val Ser Leu Val Glu Gln Met Phe Gln Asp Pro
275 280 285

Arg Leu Ser Gln Asn Lys Gln Ala Leu Glu Gly Leu Gly Asp Leu Lys
290 295 300

Leu Leu Phe Glu Tyr Leu Thr Leu Phe Gly Ile Ala Asp Lys Ile Ser
305 310 315 320

Phe Asp Leu Ser Leu Ala Arg Gly Leu Asp Tyr Tyr Thr Gly Val Ile
325 330 335

Tyr Glu Ala Val Leu Leu Gln Thr Pro Thr Gln Ala Gly Glu Glu Pro
340 345 350

Leu Asn Val Gly Ser Val Ala Ala Gly Gly Arg Tyr Asp Gly Leu Val
355 360 365

Gly Met Phe Asp Pro Lys Gly His Lys Val Pro Cys Val Gly Leu Ser
370 375 380

Ile Gly Val Glu Arg Ile Phe Tyr Ile Val Glu Gln Arg Met Lys Thr
385 390 395 400

Lys Gly Glu Lys Val Arg Thr Thr Glu Thr Gln Val Phe Val Ala Thr
405 410 415

Pro Gln Lys Asn Phe Leu Gln Glu Arg Leu Lys Leu Ile Ala Glu Leu
420 425 430

Trp Asp Ser Gly Ile Lys Ala Glu Met Leu Tyr Lys Asn Asn Pro Lys
435 440 445

Leu Leu Thr Gln Leu His Tyr Cys Glu Ser Thr Gly Ile Pro Leu Val
450 455 460

Val Ile Ile Gly Glu Gln Glu Leu Lys Glu Gly Val Ile Lys Ile Arg
465 470 475 480

Ser Val Ala Ser Arg Glu Glu Val Ala Ile Lys Arg Glu Asn Phe Val
485 490 495

Ala Glu Ile Gln Lys Arg Leu Ser Glu Ser
500 505

<210> SEQ ID NO 3
<211> LENGTH: 141
<212> TYPE: PRT
<213> ORGANISM: Homo sapiens

<400> SEQUENCE: 3

Met Ala Glu Arg Ala Ala Leu Glu Glu Leu Val Lys Leu Gln Gly Glu
1 5 10 15

Arg Val Arg Gly Leu Lys Gln Gln Lys Ala Ser Ala Glu Leu Ile Glu

```
            20                  25                  30

Glu Glu Val Ala Lys Leu Leu Lys Leu Lys Ala Gln Leu Gly Pro Asp
        35                  40                  45

Glu Ser Lys Gln Lys Phe Val Leu Lys Thr Pro Lys Gly Thr Arg Asp
    50                  55                  60

Tyr Ser Pro Arg Gln Met Ala Val Arg Glu Lys Val Phe Asp Val Ile
65                  70                  75                  80

Ile Arg Cys Phe Lys Arg His Gly Ala Glu Val Ile Asp Thr Pro Val
                85                  90                  95

Phe Glu Leu Lys Glu Thr Leu Met Gly Lys Tyr Gly Glu Asp Ser Lys
            100                 105                 110

Leu Ile Tyr Asp Leu Lys Asp Gln Gly Gly Glu Leu Leu Ser Leu Arg
        115                 120                 125

Tyr Asp Leu Thr Val Pro Phe Ala Arg Tyr Leu Ala Met
    130                 135                 140


<210> SEQ ID NO 4
<211> LENGTH: 408
<212> TYPE: PRT
<213> ORGANISM: Homo sapiens

<400> SEQUENCE: 4

Met Ala Glu Arg Ala Ala Leu Glu Glu Leu Val Lys Leu Gln Gly Glu
1               5                   10                  15

Arg Val Arg Gly Leu Lys Gln Gln Lys Ala Ser Ala Glu Leu Ile Glu
            20                  25                  30

Glu Glu Val Ala Lys Leu Leu Lys Leu Lys Ala Gln Leu Gly Pro Asp
        35                  40                  45

Glu Ser Lys Gln Lys Phe Val Leu Lys Thr Pro Lys Gly Thr Arg Asp
    50                  55                  60

Tyr Ser Pro Arg Gln Met Ala Val Arg Glu Lys Val Phe Asp Val Ile
65                  70                  75                  80

Ile Arg Cys Phe Lys Arg His Gly Ala Glu Val Ile Asp Thr Pro Val
                85                  90                  95

Phe Glu Leu Lys Glu Thr Leu Met Gly Lys Tyr Gly Glu Asp Ser Lys
            100                 105                 110

Leu Ile Tyr Asp Leu Lys Asp Gln Gly Gly Glu Leu Leu Ser Leu Arg
        115                 120                 125

Tyr Asp Leu Thr Val Pro Phe Ala Arg Tyr Leu Ala Met Asn Lys Leu
    130                 135                 140

Thr Asn Ile Lys Arg Tyr His Ile Ala Lys Val Tyr Arg Arg Asp Asn
145                 150                 155                 160

Pro Ala Met Thr Arg Gly Arg Tyr Arg Glu Phe Tyr Gln Cys Asp Phe
                165                 170                 175

Asp Ile Ala Gly Asn Phe Asp Pro Met Ile Pro Asp Ala Glu Cys Leu
            180                 185                 190

Lys Ile Met Cys Glu Ile Leu Ser Ser Leu Gln Ile Gly Asp Phe Leu
        195                 200                 205

Val Lys Val Asn Asp Arg Arg Ile Leu Asp Gly Met Phe Ala Ile Cys
    210                 215                 220

Gly Val Ser Asp Ser Lys Phe Arg Thr Ile Cys Ser Ser Val Asp Lys
225                 230                 235                 240

Leu Asp Lys Val Ser Trp Glu Glu Val Lys Asn Glu Met Val Gly Glu
                245                 250                 255
```

```
Lys Gly Leu Ala Pro Glu Val Ala Asp Arg Ile Gly Asp Tyr Val Gln
            260                 265                 270

Gln His Gly Gly Val Ser Leu Val Glu Gln Leu Leu Gln Asp Pro Lys
        275                 280                 285

Leu Ser Gln Asn Lys Gln Ala Leu Glu Gly Leu Gly Asp Leu Lys Leu
    290                 295                 300

Leu Phe Glu Tyr Leu Thr Leu Phe Gly Ile Asp Asp Lys Ile Ser Phe
305                 310                 315                 320

Asp Leu Ser Leu Ala Arg Gly Leu Asp Tyr Tyr Thr Gly Val Ile Tyr
                325                 330                 335

Glu Ala Val Leu Leu Gln Thr Pro Ala Gln Ala Gly Glu Glu Pro Leu
            340                 345                 350

Gly Val Gly Ser Val Ala Ala Gly Gly Arg Tyr Asp Gly Leu Val Gly
        355                 360                 365

Met Phe Asp Pro Lys Gly Arg Lys Val Pro Cys Val Gly Leu Ser Ile
    370                 375                 380

Gly Val Glu Arg Ile Phe Ser Ile Val Glu Gln Arg Leu Glu Ala Leu
385                 390                 395                 400

Glu Glu Lys Ile Arg Thr Thr Glu
                405


<210> SEQ ID NO 5
<211> LENGTH: 113
<212> TYPE: PRT
<213> ORGANISM: Homo sapiens

<400> SEQUENCE: 5

Met Ala Glu Arg Ala Ala Leu Glu Glu Leu Val Lys Leu Gln Gly Glu
1               5                   10                  15

Arg Val Arg Gly Leu Lys Gln Gln Lys Ala Ser Ala Glu Leu Ile Glu
            20                  25                  30

Glu Glu Val Ala Lys Leu Leu Lys Leu Lys Ala Gln Leu Gly Pro Asp
        35                  40                  45

Glu Ser Lys Gln Lys Phe Val Leu Lys Thr Pro Lys Gly Thr Arg Asp
    50                  55                  60

Tyr Ser Pro Arg Gln Met Ala Val Arg Glu Lys Val Phe Asp Val Ile
65                  70                  75                  80

Ile Arg Cys Phe Lys Arg His Gly Ala Glu Val Ile Asp Thr Pro Val
                85                  90                  95

Phe Glu Leu Lys Glu Thr Leu Met Gly Lys Tyr Gly Glu Asp Ser Lys
            100                 105                 110

Leu


<210> SEQ ID NO 6
<211> LENGTH: 60
<212> TYPE: PRT
<213> ORGANISM: Homo sapiens

<400> SEQUENCE: 6

Met Ala Glu Arg Ala Ala Leu Glu Glu Leu Val Lys Leu Gln Gly Glu
1               5                   10                  15

Arg Val Arg Gly Leu Lys Gln Gln Lys Ala Ser Ala Glu Leu Ile Glu
            20                  25                  30

Glu Glu Val Ala Lys Leu Leu Lys Leu Lys Ala Gln Leu Gly Pro Asp
        35                  40                  45

Glu Ser Lys Gln Lys Phe Val Leu Lys Thr Pro Lys
```

50 55 60

<210> SEQ ID NO 7
<211> LENGTH: 270
<212> TYPE: PRT
<213> ORGANISM: Homo sapiens

<400> SEQUENCE: 7

Met Ala Glu Arg Ala Ala Leu Glu Glu Leu Val Lys Leu Gln Gly Glu
1 5 10 15

Arg Val Arg Gly Leu Lys Gln Gln Lys Ala Ser Ala Glu Leu Ile Glu
20 25 30

Glu Glu Val Ala Lys Leu Leu Lys Leu Lys Ala Gln Leu Gly Pro Asp
35 40 45

Glu Ser Lys Gln Lys Phe Val Leu Lys Thr Pro Lys Gly Thr Arg Asp
50 55 60

Tyr Ser Pro Arg Gln Met Ala Val Arg Glu Lys Val Phe Asp Val Ile
65 70 75 80

Ile Arg Cys Phe Lys Arg His Gly Ala Glu Val Ile Asp Thr Pro Val
85 90 95

Phe Glu Leu Lys Glu Thr Leu Met Gly Lys Tyr Gly Glu Asp Ser Lys
100 105 110

Leu Ile Tyr Asp Leu Lys Asp Gln Gly Gly Glu Leu Leu Ser Leu Arg
115 120 125

Tyr Asp Leu Thr Val Pro Phe Ala Arg Tyr Leu Ala Met Asn Lys Leu
130 135 140

Thr Asn Ile Lys Arg Tyr His Ile Ala Lys Val Tyr Arg Arg Asp Asn
145 150 155 160

Pro Ala Met Thr Arg Gly Arg Tyr Arg Glu Phe Tyr Gln Cys Asp Phe
165 170 175

Asp Ile Ala Gly Asn Phe Asp Pro Met Ile Pro Asp Ala Glu Cys Leu
180 185 190

Lys Ile Met Cys Glu Ile Leu Ser Ser Leu Gln Ile Gly Asp Phe Leu
195 200 205

Val Lys Val Asn Asp Arg Arg Ile Leu Asp Gly Met Phe Ala Ile Cys
210 215 220

Gly Val Ser Asp Ser Lys Phe Arg Thr Ile Cys Ser Ser Val Asp Lys
225 230 235 240

Leu Asp Lys Val Gly Tyr Pro Trp Trp Asn Ser Cys Ser Arg Ile Leu
245 250 255

Asn Tyr Pro Lys Thr Ser Arg Pro Trp Arg Ala Trp Glu Thr
260 265 270

<210> SEQ ID NO 8
<211> LENGTH: 105
<212> TYPE: PRT
<213> ORGANISM: Homo sapiens

<400> SEQUENCE: 8

Arg Thr Thr Glu Thr Gln Val Leu Val Ala Ser Ala Gln Lys Lys Leu
1 5 10 15

Leu Glu Glu Arg Leu Lys Leu Val Ser Glu Leu Trp Asp Ala Gly Ile
20 25 30

Lys Ala Glu Leu Leu Tyr Lys Lys Asn Pro Lys Leu Leu Asn Gln Leu
35 40 45

Gln Tyr Cys Glu Glu Ala Gly Ile Pro Leu Val Ala Ile Ile Gly Glu

-continued

```
    50                  55                  60

Gln Glu Leu Lys Asp Gly Val Ile Lys Leu Arg Ser Val Thr Ser Arg
65                  70                  75                  80

Glu Glu Val Asp Val Arg Arg Glu Asp Leu Val Glu Glu Ile Lys Arg
                85                  90                  95

Arg Thr Gly Gln Pro Leu Cys Ile Cys
            100                 105


<210> SEQ ID NO 9
<211> LENGTH: 395
<212> TYPE: PRT
<213> ORGANISM: Homo sapiens

<400> SEQUENCE: 9

Met Ala Glu Arg Ala Ala Leu Glu Glu Leu Val Lys Leu Gln Gly Glu
1               5                   10                  15

Arg Val Arg Gly Leu Lys Gln Gln Lys Ala Ser Ala Glu Leu Ile Glu
            20                  25                  30

Glu Glu Val Ala Lys Leu Leu Lys Leu Lys Ala Gln Leu Gly Pro Asp
        35                  40                  45

Glu Ser Lys Gln Lys Phe Val Leu Lys Thr Pro Lys Asp Phe Asp Ile
    50                  55                  60

Ala Gly Asn Phe Asp Pro Met Ile Pro Asp Ala Glu Cys Leu Lys Ile
65                  70                  75                  80

Met Cys Glu Ile Leu Ser Ser Leu Gln Ile Gly Asp Phe Leu Val Lys
                85                  90                  95

Val Asn Asp Arg Arg Ile Leu Asp Gly Met Phe Ala Ile Cys Gly Val
            100                 105                 110

Ser Asp Ser Lys Phe Arg Thr Ile Cys Ser Ser Val Asp Lys Leu Asp
        115                 120                 125

Lys Val Ser Trp Glu Glu Val Lys Asn Glu Met Val Gly Glu Lys Gly
    130                 135                 140

Leu Ala Pro Glu Val Ala Asp Arg Ile Gly Asp Tyr Val Gln Gln His
145                 150                 155                 160

Gly Gly Val Ser Leu Val Glu Gln Leu Leu Gln Asp Pro Lys Leu Ser
                165                 170                 175

Gln Asn Lys Gln Ala Leu Glu Gly Leu Gly Asp Leu Lys Leu Leu Phe
            180                 185                 190

Glu Tyr Leu Thr Leu Phe Gly Ile Asp Asp Lys Ile Ser Phe Asp Leu
        195                 200                 205

Ser Leu Ala Arg Gly Leu Asp Tyr Tyr Thr Gly Val Ile Tyr Glu Ala
    210                 215                 220

Val Leu Leu Gln Thr Pro Ala Gln Ala Gly Glu Glu Pro Leu Gly Val
225                 230                 235                 240

Gly Ser Val Ala Ala Gly Gly Arg Tyr Asp Gly Leu Val Gly Met Phe
                245                 250                 255

Asp Pro Lys Gly Arg Lys Val Pro Cys Val Gly Leu Ser Ile Gly Val
            260                 265                 270

Glu Arg Ile Phe Ser Ile Val Glu Gln Arg Leu Glu Ala Leu Glu Glu
        275                 280                 285

Lys Ile Arg Thr Thr Glu Thr Gln Val Leu Val Ala Ser Ala Gln Lys
    290                 295                 300

Lys Leu Leu Glu Glu Arg Leu Lys Leu Val Ser Glu Leu Trp Asp Ala
305                 310                 315                 320
```

-continued

```
Gly Ile Lys Ala Glu Leu Leu Tyr Lys Lys Asn Pro Lys Leu Leu Asn
                325                 330                 335

Gln Leu Gln Tyr Cys Glu Glu Ala Gly Ile Pro Leu Val Ala Ile Ile
            340                 345                 350

Gly Glu Gln Glu Leu Lys Asp Gly Val Ile Lys Leu Arg Ser Val Thr
        355                 360                 365

Ser Arg Glu Glu Val Asp Val Arg Arg Glu Asp Leu Val Glu Glu Ile
    370                 375                 380

Lys Arg Arg Thr Gly Gln Pro Leu Cys Ile Cys
385                 390                 395


<210> SEQ ID NO 10
<211> LENGTH: 359
<212> TYPE: PRT
<213> ORGANISM: Homo sapiens

<400> SEQUENCE: 10

Met Ala Glu Arg Ala Ala Leu Glu Glu Leu Val Lys Leu Gln Gly Glu
1               5                   10                  15

Arg Val Arg Gly Leu Lys Gln Gln Lys Ala Ser Ala Glu Leu Ile Glu
            20                  25                  30

Glu Glu Val Ala Lys Leu Leu Lys Leu Lys Ala Gln Leu Gly Pro Asp
        35                  40                  45

Glu Ser Lys Gln Lys Phe Val Leu Lys Thr Pro Lys Val Asn Asp Arg
    50                  55                  60

Arg Ile Leu Asp Gly Met Phe Ala Ile Cys Gly Val Ser Asp Ser Lys
65                  70                  75                  80

Phe Arg Thr Ile Cys Ser Ser Val Asp Lys Leu Asp Lys Val Ser Trp
                85                  90                  95

Glu Glu Val Lys Asn Glu Met Val Gly Glu Lys Gly Leu Ala Pro Glu
            100                 105                 110

Val Ala Asp Arg Ile Gly Asp Tyr Val Gln Gln His Gly Gly Val Ser
        115                 120                 125

Leu Val Glu Gln Leu Leu Gln Asp Pro Lys Leu Ser Gln Asn Lys Gln
    130                 135                 140

Ala Leu Glu Gly Leu Gly Asp Leu Lys Leu Leu Phe Glu Tyr Leu Thr
145                 150                 155                 160

Leu Phe Gly Ile Asp Asp Lys Ile Ser Phe Asp Leu Ser Leu Ala Arg
                165                 170                 175

Gly Leu Asp Tyr Tyr Thr Gly Val Ile Tyr Glu Ala Val Leu Leu Gln
            180                 185                 190

Thr Pro Ala Gln Ala Gly Glu Glu Pro Leu Gly Val Gly Ser Val Ala
        195                 200                 205

Ala Gly Gly Arg Tyr Asp Gly Leu Val Gly Met Phe Asp Pro Lys Gly
    210                 215                 220

Arg Lys Val Pro Cys Val Gly Leu Ser Ile Gly Val Glu Arg Ile Phe
225                 230                 235                 240

Ser Ile Val Glu Gln Arg Leu Glu Ala Leu Glu Glu Lys Ile Arg Thr
                245                 250                 255

Thr Glu Thr Gln Val Leu Val Ala Ser Ala Gln Lys Lys Leu Leu Glu
            260                 265                 270

Glu Arg Leu Lys Leu Val Ser Glu Leu Trp Asp Ala Gly Ile Lys Ala
        275                 280                 285

Glu Leu Leu Tyr Lys Lys Asn Pro Lys Leu Leu Asn Gln Leu Gln Tyr
    290                 295                 300
```

Cys Glu Glu Ala Gly Ile Pro Leu Val Ala Ile Ile Gly Glu Gln Glu
305 310 315 320

Leu Lys Asp Gly Val Ile Lys Leu Arg Ser Val Thr Ser Arg Glu Glu
325 330 335

Val Asp Val Arg Arg Glu Asp Leu Val Glu Glu Ile Lys Arg Arg Thr
340 345 350

Gly Gln Pro Leu Cys Ile Cys
355

<210> SEQ ID NO 11
<211> LENGTH: 399
<212> TYPE: PRT
<213> ORGANISM: Homo sapiens

<400> SEQUENCE: 11

Met Ala Glu Arg Ala Ala Leu Glu Glu Leu Val Lys Leu Gln Gly Glu
1 5 10 15

Arg Val Arg Gly Leu Lys Gln Gln Lys Ala Ser Ala Glu Leu Ile Glu
20 25 30

Glu Glu Val Ala Lys Leu Leu Lys Leu Lys Ala Gln Leu Gly Pro Asp
35 40 45

Glu Ser Lys Gln Lys Phe Val Leu Lys Thr Pro Lys Gly Thr Arg Asp
50 55 60

Tyr Ser Pro Arg Gln Met Ala Val Arg Glu Lys Val Phe Asp Val Ile
65 70 75 80

Ile Arg Cys Phe Lys Arg His Gly Ala Glu Val Ile Asp Thr Pro Val
85 90 95

Phe Glu Leu Lys Val Asn Asp Arg Arg Ile Leu Asp Gly Met Phe Ala
100 105 110

Ile Cys Gly Val Ser Asp Ser Lys Phe Arg Thr Ile Cys Ser Ser Val
115 120 125

Asp Lys Leu Asp Lys Val Ser Trp Glu Glu Val Lys Asn Glu Met Val
130 135 140

Gly Glu Lys Gly Leu Ala Pro Glu Val Ala Asp Arg Ile Gly Asp Tyr
145 150 155 160

Val Gln Gln His Gly Gly Val Ser Leu Val Glu Gln Leu Leu Gln Asp
165 170 175

Pro Lys Leu Ser Gln Asn Lys Gln Ala Leu Glu Gly Leu Gly Asp Leu
180 185 190

Lys Leu Leu Phe Glu Tyr Leu Thr Leu Phe Gly Ile Asp Asp Lys Ile
195 200 205

Ser Phe Asp Leu Ser Leu Ala Arg Gly Leu Asp Tyr Tyr Thr Gly Val
210 215 220

Ile Tyr Glu Ala Val Leu Leu Gln Thr Pro Ala Gln Ala Gly Glu Glu
225 230 235 240

Pro Leu Gly Val Gly Ser Val Ala Ala Gly Gly Arg Tyr Asp Gly Leu
245 250 255

Val Gly Met Phe Asp Pro Lys Gly Arg Lys Val Pro Cys Val Gly Leu
260 265 270

Ser Ile Gly Val Glu Arg Ile Phe Ser Ile Val Glu Gln Arg Leu Glu
275 280 285

Ala Leu Glu Glu Lys Ile Arg Thr Thr Glu Thr Gln Val Leu Val Ala
290 295 300

Ser Ala Gln Lys Lys Leu Leu Glu Glu Arg Leu Lys Leu Val Ser Glu

```
305                 310                 315                 320

Leu Trp Asp Ala Gly Ile Lys Ala Glu Leu Leu Tyr Lys Lys Asn Pro
                325                 330                 335

Lys Leu Leu Asn Gln Leu Gln Tyr Cys Glu Glu Ala Gly Ile Pro Leu
            340                 345                 350

Val Ala Ile Ile Gly Glu Gln Glu Leu Lys Asp Gly Val Ile Lys Leu
        355                 360                 365

Arg Ser Val Thr Ser Arg Glu Glu Val Asp Val Arg Arg Glu Asp Leu
    370                 375                 380

Val Glu Glu Ile Lys Arg Arg Thr Gly Gln Pro Leu Cys Ile Cys
385                 390                 395


<210> SEQ ID NO 12
<211> LENGTH: 473
<212> TYPE: PRT
<213> ORGANISM: Homo sapiens

<400> SEQUENCE: 12

Met Ala Glu Arg Ala Ala Leu Glu Glu Leu Val Lys Leu Gln Gly Glu
1               5                   10                  15

Arg Val Arg Gly Leu Lys Gln Gln Lys Ala Ser Ala Glu Leu Ile Glu
            20                  25                  30

Glu Glu Val Ala Lys Leu Leu Lys Leu Lys Ala Gln Leu Gly Pro Asp
        35                  40                  45

Glu Ser Lys Gln Lys Phe Val Leu Lys Thr Pro Lys Gly Thr Arg Asp
    50                  55                  60

Tyr Ser Pro Arg Gln Met Ala Val Arg Glu Lys Val Phe Asp Val Ile
65                  70                  75                  80

Ile Arg Cys Phe Lys Arg His Gly Ala Glu Val Ile Asp Thr Pro Val
                85                  90                  95

Phe Glu Leu Lys Glu Thr Leu Met Gly Lys Tyr Gly Glu Asp Ser Lys
            100                 105                 110

Leu Ile Tyr Asp Leu Lys Asp Gln Gly Gly Glu Leu Leu Ser Leu Arg
        115                 120                 125

Tyr Asp Leu Thr Val Pro Phe Ala Arg Tyr Leu Ala Met Asn Lys Leu
    130                 135                 140

Thr Asn Ile Lys Arg Tyr His Ile Ala Lys Val Tyr Arg Arg Asp Asn
145                 150                 155                 160

Pro Ala Met Thr Arg Gly Arg Tyr Arg Glu Phe Tyr Gln Cys Val Asn
                165                 170                 175

Asp Arg Arg Ile Leu Asp Gly Met Phe Ala Ile Cys Gly Val Ser Asp
            180                 185                 190

Ser Lys Phe Arg Thr Ile Cys Ser Ser Val Asp Lys Leu Asp Lys Val
        195                 200                 205

Ser Trp Glu Glu Val Lys Asn Glu Met Val Gly Glu Lys Gly Leu Ala
    210                 215                 220

Pro Glu Val Ala Asp Arg Ile Gly Asp Tyr Val Gln Gln His Gly Gly
225                 230                 235                 240

Val Ser Leu Val Glu Gln Leu Leu Gln Asp Pro Lys Leu Ser Gln Asn
                245                 250                 255

Lys Gln Ala Leu Glu Gly Leu Gly Asp Leu Lys Leu Leu Phe Glu Tyr
            260                 265                 270

Leu Thr Leu Phe Gly Ile Asp Asp Lys Ile Ser Phe Asp Leu Ser Leu
        275                 280                 285
```

Ala Arg Gly Leu Asp Tyr Tyr Thr Gly Val Ile Tyr Glu Ala Val Leu
290 295 300

Leu Gln Thr Pro Ala Gln Ala Gly Glu Glu Pro Leu Gly Val Gly Ser
305 310 315 320

Val Ala Ala Gly Gly Arg Tyr Asp Gly Leu Val Gly Met Phe Asp Pro
325 330 335

Lys Gly Arg Lys Val Pro Cys Val Gly Leu Ser Ile Gly Val Glu Arg
340 345 350

Ile Phe Ser Ile Val Glu Gln Arg Leu Glu Ala Leu Glu Glu Lys Ile
355 360 365

Arg Thr Thr Glu Thr Gln Val Leu Val Ala Ser Ala Gln Lys Lys Leu
370 375 380

Leu Glu Glu Arg Leu Lys Leu Val Ser Glu Leu Trp Asp Ala Gly Ile
385 390 395 400

Lys Ala Glu Leu Leu Tyr Lys Lys Asn Pro Lys Leu Leu Asn Gln Leu
405 410 415

Gln Tyr Cys Glu Glu Ala Gly Ile Pro Leu Val Ala Ile Ile Gly Glu
420 425 430

Gln Glu Leu Lys Asp Gly Val Ile Lys Leu Arg Ser Val Thr Ser Arg
435 440 445

Glu Glu Val Asp Val Arg Arg Glu Asp Leu Val Glu Glu Ile Lys Arg
450 455 460

Arg Thr Gly Gln Pro Leu Cys Ile Cys
465 470

<210> SEQ ID NO 13
<211> LENGTH: 469
<212> TYPE: PRT
<213> ORGANISM: Homo sapiens

<400> SEQUENCE: 13

Met Ala Glu Arg Ala Ala Leu Glu Glu Leu Val Lys Leu Gln Gly Glu
1 5 10 15

Arg Val Arg Gly Leu Lys Gln Gln Lys Ala Ser Ala Glu Leu Ile Glu
20 25 30

Glu Glu Val Ala Lys Leu Leu Lys Leu Lys Ala Gln Leu Gly Pro Asp
35 40 45

Glu Ser Lys Gln Lys Phe Val Leu Lys Thr Pro Lys Glu Thr Leu Met
50 55 60

Gly Lys Tyr Gly Glu Asp Ser Lys Leu Ile Tyr Asp Leu Lys Asp Gln
65 70 75 80

Gly Gly Glu Leu Leu Ser Leu Arg Tyr Asp Leu Thr Val Pro Phe Ala
85 90 95

Arg Tyr Leu Ala Met Asn Lys Leu Thr Asn Ile Lys Arg Tyr His Ile
100 105 110

Ala Lys Val Tyr Arg Arg Asp Asn Pro Ala Met Thr Arg Gly Arg Tyr
115 120 125

Arg Glu Phe Tyr Gln Cys Asp Phe Asp Ile Ala Gly Asn Phe Asp Pro
130 135 140

Met Ile Pro Asp Ala Glu Cys Leu Lys Ile Met Cys Glu Ile Leu Ser
145 150 155 160

Ser Leu Gln Ile Gly Asp Phe Leu Val Lys Val Asn Asp Arg Arg Ile
165 170 175

Leu Asp Gly Met Phe Ala Ile Cys Gly Val Ser Asp Ser Lys Phe Arg
180 185 190

```
Thr Ile Cys Ser Ser Val Asp Lys Leu Asp Lys Val Ser Trp Glu Glu
        195                 200                 205

Val Lys Asn Glu Met Val Gly Glu Lys Gly Leu Ala Pro Glu Val Ala
    210                 215                 220

Asp Arg Ile Gly Asp Tyr Val Gln Gln His Gly Gly Val Ser Leu Val
225                 230                 235                 240

Glu Gln Leu Leu Gln Asp Pro Lys Leu Ser Gln Asn Lys Gln Ala Leu
                245                 250                 255

Glu Gly Leu Gly Asp Leu Lys Leu Leu Phe Glu Tyr Leu Thr Leu Phe
            260                 265                 270

Gly Ile Asp Asp Lys Ile Ser Phe Asp Leu Ser Leu Ala Arg Gly Leu
        275                 280                 285

Asp Tyr Tyr Thr Gly Val Ile Tyr Glu Ala Val Leu Leu Gln Thr Pro
    290                 295                 300

Ala Gln Ala Gly Glu Glu Pro Leu Gly Val Gly Ser Val Ala Ala Gly
305                 310                 315                 320

Gly Arg Tyr Asp Gly Leu Val Gly Met Phe Asp Pro Lys Gly Arg Lys
                325                 330                 335

Val Pro Cys Val Gly Leu Ser Ile Gly Val Glu Arg Ile Phe Ser Ile
            340                 345                 350

Val Glu Gln Arg Leu Glu Ala Leu Glu Glu Lys Ile Arg Thr Thr Glu
        355                 360                 365

Thr Gln Val Leu Val Ala Ser Ala Gln Lys Lys Leu Leu Glu Glu Arg
    370                 375                 380

Leu Lys Leu Val Ser Glu Leu Trp Asp Ala Gly Ile Lys Ala Glu Leu
385                 390                 395                 400

Leu Tyr Lys Lys Asn Pro Lys Leu Leu Asn Gln Leu Gln Tyr Cys Glu
                405                 410                 415

Glu Ala Gly Ile Pro Leu Val Ala Ile Ile Gly Glu Gln Glu Leu Lys
            420                 425                 430

Asp Gly Val Ile Lys Leu Arg Ser Val Thr Ser Arg Glu Glu Val Asp
        435                 440                 445

Val Arg Arg Glu Asp Leu Val Glu Glu Ile Lys Arg Arg Thr Gly Gln
    450                 455                 460

Pro Leu Cys Ile Cys
465


<210> SEQ ID NO 14
<211> LENGTH: 435
<212> TYPE: PRT
<213> ORGANISM: Homo sapiens

<400> SEQUENCE: 14

Met Ala Glu Arg Ala Ala Leu Glu Glu Leu Val Lys Leu Gln Gly Glu
1               5                   10                  15

Arg Val Arg Gly Leu Lys Gln Gln Lys Ala Ser Ala Glu Leu Ile Glu
            20                  25                  30

Glu Glu Val Ala Lys Leu Leu Lys Leu Lys Ala Gln Leu Gly Pro Asp
        35                  40                  45

Glu Ser Lys Gln Lys Phe Val Leu Lys Thr Pro Lys Gly Thr Arg Asp
    50                  55                  60

Tyr Ser Pro Arg Gln Met Ala Val Arg Glu Lys Val Phe Asp Val Ile
65                  70                  75                  80

Ile Arg Cys Phe Lys Arg His Gly Ala Glu Val Ile Asp Thr Pro Val
```

-continued

```
                85                  90                  95

Phe Glu Leu Lys Asp Phe Asp Ile Ala Gly Asn Phe Asp Pro Met Ile
            100                 105                 110

Pro Asp Ala Glu Cys Leu Lys Ile Met Cys Glu Ile Leu Ser Ser Leu
        115                 120                 125

Gln Ile Gly Asp Phe Leu Val Lys Val Asn Asp Arg Arg Ile Leu Asp
    130                 135                 140

Gly Met Phe Ala Ile Cys Gly Val Ser Asp Ser Lys Phe Arg Thr Ile
145                 150                 155                 160

Cys Ser Ser Val Asp Lys Leu Asp Lys Val Ser Trp Glu Glu Val Lys
                165                 170                 175

Asn Glu Met Val Gly Glu Lys Gly Leu Ala Pro Glu Val Ala Asp Arg
            180                 185                 190

Ile Gly Asp Tyr Val Gln Gln His Gly Gly Val Ser Leu Val Glu Gln
        195                 200                 205

Leu Leu Gln Asp Pro Lys Leu Ser Gln Asn Lys Gln Ala Leu Glu Gly
    210                 215                 220

Leu Gly Asp Leu Lys Leu Leu Phe Glu Tyr Leu Thr Leu Phe Gly Ile
225                 230                 235                 240

Asp Asp Lys Ile Ser Phe Asp Leu Ser Leu Ala Arg Gly Leu Asp Tyr
                245                 250                 255

Tyr Thr Gly Val Ile Tyr Glu Ala Val Leu Leu Gln Thr Pro Ala Gln
            260                 265                 270

Ala Gly Glu Glu Pro Leu Gly Val Gly Ser Val Ala Ala Gly Gly Arg
        275                 280                 285

Tyr Asp Gly Leu Val Gly Met Phe Asp Pro Lys Gly Arg Lys Val Pro
    290                 295                 300

Cys Val Gly Leu Ser Ile Gly Val Glu Arg Ile Phe Ser Ile Val Glu
305                 310                 315                 320

Gln Arg Leu Glu Ala Leu Glu Glu Lys Ile Arg Thr Thr Glu Thr Gln
                325                 330                 335

Val Leu Val Ala Ser Ala Gln Lys Lys Leu Leu Glu Glu Arg Leu Lys
            340                 345                 350

Leu Val Ser Glu Leu Trp Asp Ala Gly Ile Lys Ala Glu Leu Leu Tyr
        355                 360                 365

Lys Lys Asn Pro Lys Leu Leu Asn Gln Leu Gln Tyr Cys Glu Glu Ala
    370                 375                 380

Gly Ile Pro Leu Val Ala Ile Ile Gly Glu Gln Glu Leu Lys Asp Gly
385                 390                 395                 400

Val Ile Lys Leu Arg Ser Val Thr Ser Arg Glu Glu Val Asp Val Arg
                405                 410                 415

Arg Glu Asp Leu Val Glu Glu Ile Lys Arg Arg Thr Gly Gln Pro Leu
            420                 425                 430

Cys Ile Cys
        435


<210> SEQ ID NO 15
<211> LENGTH: 171
<212> TYPE: PRT
<213> ORGANISM: Homo sapiens

<400> SEQUENCE: 15

Met Ala Glu Arg Ala Ala Leu Glu Glu Leu Val Lys Leu Gln Gly Glu
1               5                   10                  15
```

-continued

```
Arg Val Arg Gly Leu Lys Gln Gln Lys Ala Ser Ala Glu Leu Ile Glu
            20                  25                  30

Glu Glu Val Ala Lys Leu Leu Lys Leu Lys Ala Gln Leu Gly Pro Asp
        35                  40                  45

Glu Ser Lys Gln Lys Phe Val Leu Lys Thr Pro Lys Ala Leu Glu Glu
    50                  55                  60

Lys Ile Arg Thr Thr Glu Thr Gln Val Leu Val Ala Ser Ala Gln Lys
65                  70                  75                  80

Lys Leu Leu Glu Glu Arg Leu Lys Leu Val Ser Glu Leu Trp Asp Ala
                85                  90                  95

Gly Ile Lys Ala Glu Leu Leu Tyr Lys Lys Asn Pro Lys Leu Leu Asn
            100                 105                 110

Gln Leu Gln Tyr Cys Glu Glu Ala Gly Ile Pro Leu Val Ala Ile Ile
        115                 120                 125

Gly Glu Gln Glu Leu Lys Asp Gly Val Ile Lys Leu Arg Ser Val Thr
    130                 135                 140

Ser Arg Glu Glu Val Asp Val Arg Arg Glu Asp Leu Val Glu Glu Ile
145                 150                 155                 160

Lys Arg Arg Thr Gly Gln Pro Leu Cys Ile Cys
                165                 170


<210> SEQ ID NO 16
<211> LENGTH: 211
<212> TYPE: PRT
<213> ORGANISM: Homo sapiens

<400> SEQUENCE: 16

Met Ala Glu Arg Ala Ala Leu Glu Glu Leu Val Lys Leu Gln Gly Glu
1               5                   10                  15

Arg Val Arg Gly Leu Lys Gln Gln Lys Ala Ser Ala Glu Leu Ile Glu
            20                  25                  30

Glu Glu Val Ala Lys Leu Leu Lys Leu Lys Ala Gln Leu Gly Pro Asp
        35                  40                  45

Glu Ser Lys Gln Lys Phe Val Leu Lys Thr Pro Lys Gly Thr Arg Asp
    50                  55                  60

Tyr Ser Pro Arg Gln Met Ala Val Arg Glu Lys Val Phe Asp Val Ile
65                  70                  75                  80

Ile Arg Cys Phe Lys Arg His Gly Ala Glu Val Ile Asp Thr Pro Val
                85                  90                  95

Phe Glu Leu Lys Ala Leu Glu Glu Lys Ile Arg Thr Thr Glu Thr Gln
            100                 105                 110

Val Leu Val Ala Ser Ala Gln Lys Lys Leu Leu Glu Glu Arg Leu Lys
        115                 120                 125

Leu Val Ser Glu Leu Trp Asp Ala Gly Ile Lys Ala Glu Leu Leu Tyr
    130                 135                 140

Lys Lys Asn Pro Lys Leu Leu Asn Gln Leu Gln Tyr Cys Glu Glu Ala
145                 150                 155                 160

Gly Ile Pro Leu Val Ala Ile Ile Gly Glu Gln Glu Leu Lys Asp Gly
                165                 170                 175

Val Ile Lys Leu Arg Ser Val Thr Ser Arg Glu Glu Val Asp Val Arg
            180                 185                 190

Arg Glu Asp Leu Val Glu Glu Ile Lys Arg Arg Thr Gly Gln Pro Leu
        195                 200                 205

Cys Ile Cys
    210
```

<210> SEQ ID NO 17
<211> LENGTH: 141
<212> TYPE: PRT
<213> ORGANISM: Homo sapiens

<400> SEQUENCE: 17

```
Met Phe Asp Pro Lys Gly Arg Lys Val Pro Cys Val Gly Leu Ser Ile
1               5                   10                  15

Gly Val Glu Arg Ile Phe Ser Ile Val Glu Gln Arg Leu Glu Ala Leu
            20                  25                  30

Glu Glu Lys Ile Arg Thr Thr Glu Thr Gln Val Leu Val Ala Ser Ala
        35                  40                  45

Gln Lys Lys Leu Leu Glu Glu Arg Leu Lys Leu Val Ser Glu Leu Trp
    50                  55                  60

Asp Ala Gly Ile Lys Ala Glu Leu Leu Tyr Lys Lys Asn Pro Lys Leu
65                  70                  75                  80

Leu Asn Gln Leu Gln Tyr Cys Glu Glu Ala Gly Ile Pro Leu Val Ala
                85                  90                  95

Ile Ile Gly Glu Gln Glu Leu Lys Asp Gly Val Ile Lys Leu Arg Ser
            100                 105                 110

Val Thr Ser Arg Glu Glu Val Asp Val Arg Arg Glu Asp Leu Val Glu
        115                 120                 125

Glu Ile Lys Arg Arg Thr Gly Gln Pro Leu Cys Ile Cys
    130                 135                 140
```

<210> SEQ ID NO 18
<211> LENGTH: 143
<212> TYPE: PRT
<213> ORGANISM: Homo sapiens

<400> SEQUENCE: 18

```
Cys Leu Lys Ile Met Cys Glu Ile Leu Ser Ser Leu Gln Ile Gly Asp
1               5                   10                  15

Phe Leu Val Lys Val Asn Asp Arg Arg Ile Leu Asp Gly Met Phe Ala
            20                  25                  30

Ile Cys Gly Val Ser Asp Ser Lys Phe Arg Thr Ile Cys Ser Ser Val
        35                  40                  45

Asp Lys Leu Asp Lys Val Ser Trp Glu Glu Val Lys Asn Glu Met Val
    50                  55                  60

Gly Glu Lys Gly Leu Ala Pro Glu Val Ala Asp Arg Ile Gly Asp Tyr
65                  70                  75                  80

Val Gln Gln His Gly Gly Val Ser Leu Val Glu Gln Leu Leu Gln Asp
                85                  90                  95

Pro Lys Leu Ser Gln Asn Lys Gln Ala Leu Glu Gly Leu Gly Asp Leu
            100                 105                 110

Lys Leu Leu Phe Glu Tyr Leu Thr Leu Phe Gly Ile Asp Asp Lys Ile
        115                 120                 125

Ser Phe Asp Leu Ser Leu Ala Arg Gly Leu Asp Tyr Tyr Thr Gly
    130                 135                 140
```

<210> SEQ ID NO 19
<211> LENGTH: 509
<212> TYPE: PRT
<213> ORGANISM: Mus musuculus

<400> SEQUENCE: 19

-continued

```
Met Ala Asp Arg Ala Ala Leu Glu Glu Leu Val Arg Leu Gln Gly Ala
1               5                   10                  15

His Val Arg Gly Leu Lys Glu Gln Lys Ala Ser Ala Glu Gln Ile Glu
            20                  25                  30

Glu Glu Val Thr Lys Leu Leu Lys Leu Lys Ala Gln Leu Gly Gln Asp
        35                  40                  45

Glu Gly Lys Gln Lys Phe Val Leu Lys Thr Pro Lys Gly Thr Arg Asp
    50                  55                  60

Tyr Ser Pro Arg Gln Met Ala Val Arg Glu Lys Val Phe Asp Val Ile
65                  70                  75                  80

Ile Arg Cys Phe Lys Arg His Gly Ala Glu Val Ile Asp Thr Pro Val
                85                  90                  95

Phe Glu Leu Lys Glu Thr Leu Thr Gly Lys Tyr Gly Glu Asp Ser Lys
            100                 105                 110

Leu Ile Tyr Asp Leu Lys Asp Gln Gly Gly Glu Leu Leu Ser Leu Arg
        115                 120                 125

Tyr Asp Leu Thr Val Pro Phe Ala Arg Tyr Leu Ala Met Asn Lys Leu
    130                 135                 140

Thr Asn Ile Lys Arg Tyr His Ile Ala Lys Val Tyr Arg Arg Asp Asn
145                 150                 155                 160

Pro Ala Met Thr Arg Gly Arg Tyr Arg Glu Phe Tyr Gln Cys Asp Phe
                165                 170                 175

Asp Ile Ala Gly Gln Phe Asp Pro Met Ile Pro Asp Ala Glu Cys Leu
            180                 185                 190

Lys Ile Met Cys Glu Ile Leu Ser Ser Leu Gln Ile Gly Asn Phe Leu
        195                 200                 205

Val Lys Val Asn Asp Arg Arg Ile Leu Asp Gly Met Phe Ala Val Cys
    210                 215                 220

Gly Val Pro Asp Ser Lys Phe Arg Thr Ile Cys Ser Ser Val Asp Lys
225                 230                 235                 240

Leu Asp Lys Val Ser Trp Glu Glu Val Lys Asn Glu Met Val Gly Glu
                245                 250                 255

Lys Gly Leu Ala Pro Glu Val Ala Asp Arg Ile Gly Asp Tyr Val Gln
            260                 265                 270

Gln His Gly Gly Val Ser Leu Val Glu Gln Leu Leu Gln Asp Pro Lys
        275                 280                 285

Leu Ser Gln Asn Lys Gln Ala Val Glu Gly Leu Gly Asp Leu Lys Leu
    290                 295                 300

Leu Phe Glu Tyr Leu Ile Leu Phe Gly Ile Asp Asp Lys Ile Ser Phe
305                 310                 315                 320

Asp Leu Ser Leu Ala Arg Gly Leu Asp Tyr Tyr Thr Gly Val Ile Tyr
                325                 330                 335

Glu Ala Val Leu Leu Gln Met Pro Thr Gln Ala Gly Glu Glu Pro Leu
            340                 345                 350

Gly Val Gly Ser Ile Ala Ala Gly Gly Arg Tyr Asp Gly Leu Val Gly
        355                 360                 365

Met Phe Asp Pro Lys Gly Arg Lys Val Pro Cys Val Gly Leu Ser Ile
    370                 375                 380

Gly Val Glu Arg Ile Phe Ser Ile Val Glu Gln Arg Leu Glu Ala Ser
385                 390                 395                 400

Glu Glu Lys Val Arg Thr Thr Glu Thr Gln Val Leu Val Ala Ser Ala
                405                 410                 415

Gln Lys Lys Leu Leu Glu Glu Arg Leu Lys Leu Val Ser Glu Leu Trp
```

```
            420                 425                 430

Asp Ala Gly Ile Lys Ala Glu Leu Leu Tyr Lys Lys Asn Pro Lys Leu
        435                 440                 445

Leu Asn Gln Leu Gln Tyr Trp Glu Glu Ala Gly Ile Pro Leu Val Ala
    450                 455                 460

Ile Ile Gly Glu Gln Glu Leu Arg Asp Gly Val Ile Lys Leu Arg Ser
465                 470                 475                 480

Val Ala Ser Arg Glu Glu Val Asp Val Arg Arg Glu Asp Leu Val Glu
                485                 490                 495

Glu Ile Arg Arg Arg Thr Asn Gln Pro Leu Ser Thr Cys
            500                 505


<210> SEQ ID NO 20
<211> LENGTH: 509
<212> TYPE: PRT
<213> ORGANISM: Canis lupus familiaris

<400> SEQUENCE: 20

Met Ala Glu Arg Ala Ala Leu Glu Glu Leu Val Arg Leu Gln Gly Glu
1               5                   10                  15

Arg Val Arg Gly Leu Lys Gln Gln Lys Ala Ser Ala Glu Gln Ile Glu
            20                  25                  30

Glu Glu Val Ala Lys Leu Leu Lys Leu Lys Ala Gln Leu Gly Pro Asp
        35                  40                  45

Glu Gly Lys Gln Lys Phe Val Leu Lys Thr Pro Lys Gly Thr Arg Asp
    50                  55                  60

Tyr Ser Pro Arg Gln Met Ala Val Arg Glu Lys Val Phe Asp Val Ile
65                  70                  75                  80

Ile Ser Cys Phe Lys Arg His Gly Ala Glu Val Ile Asp Thr Pro Val
                85                  90                  95

Phe Glu Leu Lys Glu Thr Leu Thr Gly Lys Tyr Gly Glu Asp Ser Lys
            100                 105                 110

Leu Ile Tyr Asp Leu Lys Asp Gln Gly Gly Glu Leu Leu Ser Leu Arg
        115                 120                 125

Tyr Asp Leu Thr Val Pro Phe Ala Arg Tyr Leu Ala Met Asn Lys Leu
    130                 135                 140

Thr Asn Ile Lys Arg Tyr His Ile Ala Lys Val Tyr Arg Arg Asp Asn
145                 150                 155                 160

Pro Ala Met Thr Arg Gly Arg Tyr Arg Glu Phe Tyr Gln Cys Asp Phe
                165                 170                 175

Asp Ile Ala Gly Gln Phe Asp Pro Met Ile Pro Asp Ala Glu Cys Leu
            180                 185                 190

Glu Ile Met Cys Glu Ile Leu Arg Ser Leu Gln Ile Gly Asp Phe Leu
        195                 200                 205

Val Lys Val Asn Asp Arg Arg Ile Leu Asp Gly Met Phe Ala Ile Cys
    210                 215                 220

Gly Val Pro Asp Ser Lys Phe Arg Thr Ile Cys Ser Ser Val Asp Lys
225                 230                 235                 240

Leu Asp Lys Val Ser Trp Glu Glu Val Lys Asn Glu Met Val Gly Glu
                245                 250                 255

Lys Gly Leu Ala Pro Glu Val Ala Asp His Ile Gly Asp Tyr Val Gln
            260                 265                 270

Gln His Gly Gly Ile Ser Leu Val Glu Gln Leu Leu Gln Asp Pro Glu
        275                 280                 285
```

```
Leu Ser Gln Asn Lys Gln Ala Leu Glu Gly Leu Gly Asp Leu Lys Leu
    290                 295                 300

Leu Phe Glu Tyr Leu Thr Leu Phe Gly Ile Ala Asp Lys Ile Ser Phe
305                 310                 315                 320

Asp Leu Ser Leu Ala Arg Gly Leu Asp Tyr Tyr Thr Gly Val Ile Tyr
                325                 330                 335

Glu Ala Val Leu Leu Gln Thr Pro Val Gln Ala Gly Glu Glu Pro Leu
            340                 345                 350

Gly Val Gly Ser Val Ala Ala Gly Gly Arg Tyr Asp Gly Leu Val Gly
        355                 360                 365

Met Phe Asp Pro Lys Gly Arg Lys Val Pro Cys Val Gly Leu Ser Ile
    370                 375                 380

Gly Val Glu Arg Ile Phe Ser Ile Val Glu Gln Arg Leu Glu Ala Thr
385                 390                 395                 400

Glu Glu Lys Val Arg Thr Thr Glu Thr Gln Val Leu Val Ala Ser Ala
                405                 410                 415

Gln Lys Lys Leu Leu Glu Glu Arg Leu Lys Leu Val Ser Glu Leu Trp
            420                 425                 430

Asn Ala Gly Ile Lys Ala Glu Leu Leu Tyr Lys Lys Asn Pro Lys Leu
        435                 440                 445

Leu Asn Gln Leu Gln Tyr Cys Glu Glu Ala Gly Ile Pro Leu Val Ala
    450                 455                 460

Ile Ile Gly Glu Gln Glu Leu Lys Asp Gly Val Ile Lys Leu Arg Ser
465                 470                 475                 480

Val Ala Ser Arg Glu Glu Val Asp Val Pro Arg Glu Asp Leu Val Glu
                485                 490                 495

Glu Ile Lys Arg Arg Thr Ser Gln Pro Phe Cys Ile Cys
            500                 505
```

<210> SEQ ID NO 21
<211> LENGTH: 509
<212> TYPE: PRT
<213> ORGANISM: Bos taurus

<400> SEQUENCE: 21

```
Met Ala Asp Arg Ala Ala Leu Glu Asp Leu Val Arg Val Gln Gly Glu
1               5                   10                  15

Arg Val Arg Gly Leu Lys Gln Gln Lys Ala Ser Ala Glu Gln Ile Glu
            20                  25                  30

Glu Glu Val Ala Lys Leu Leu Lys Leu Lys Ala Gln Leu Gly Pro Asp
        35                  40                  45

Glu Gly Lys Pro Lys Phe Val Leu Lys Thr Pro Lys Gly Thr Arg Asp
    50                  55                  60

Tyr Ser Pro Arg Gln Met Ala Val Arg Glu Lys Val Phe Asp Val Ile
65                  70                  75                  80

Ile Ser Cys Phe Lys Arg His Gly Ala Glu Val Ile Asp Thr Pro Val
                85                  90                  95

Phe Glu Leu Lys Glu Thr Leu Thr Gly Lys Tyr Gly Glu Asp Ser Lys
            100                 105                 110

Leu Ile Tyr Asp Leu Lys Asp Gln Gly Gly Glu Leu Leu Ser Leu Arg
        115                 120                 125

Tyr Asp Leu Thr Val Pro Phe Ala Arg Tyr Leu Ala Met Asn Lys Leu
    130                 135                 140

Thr Asn Ile Lys Arg Tyr His Ile Ala Lys Val Tyr Arg Arg Asp Asn
145                 150                 155                 160
```

Pro Ala Met Thr Arg Gly Arg Tyr Arg Glu Phe Tyr Gln Cys Asp Phe
165 170 175

Asp Ile Ala Gly Gln Phe Asp Pro Met Leu Pro Asp Ala Glu Cys Leu
180 185 190

Lys Ile Met Cys Glu Ile Leu Ser Ser Leu Gln Ile Gly Asp Phe Leu
195 200 205

Val Lys Val Asn Asp Arg Arg Ile Leu Asp Gly Met Phe Ala Ile Cys
210 215 220

Gly Val Pro Asp Ser Lys Phe Arg Thr Ile Cys Ser Ser Val Asp Lys
225 230 235 240

Leu Asp Lys Val Ser Trp Glu Glu Val Lys Asn Glu Met Val Gly Glu
245 250 255

Lys Gly Leu Ala Pro Glu Val Ala Asp Arg Ile Gly Asp Tyr Val Gln
260 265 270

Gln His Gly Gly Val Ser Leu Val Glu Gln Leu Leu Gln Asp Pro Lys
275 280 285

Leu Ser Gln Asn Lys Gln Ala Leu Glu Gly Leu Gly Asp Leu Lys Leu
290 295 300

Leu Phe Glu Tyr Leu Thr Leu Phe Gly Ile Ala Asp Lys Ile Ser Phe
305 310 315 320

Asp Leu Ser Leu Ala Arg Gly Leu Asp Tyr Tyr Thr Gly Val Ile Tyr
325 330 335

Glu Ala Val Leu Leu Gln Pro Pro Ala Arg Ala Gly Glu Glu Pro Leu
340 345 350

Gly Val Gly Ser Val Ala Ala Gly Gly Arg Tyr Asp Gly Leu Val Gly
355 360 365

Met Phe Asp Pro Lys Gly Arg Lys Val Pro Cys Val Gly Leu Ser Ile
370 375 380

Gly Val Glu Arg Ile Phe Ser Ile Val Glu Gln Arg Leu Glu Ala Leu
385 390 395 400

Glu Glu Lys Val Arg Thr Thr Glu Thr Gln Val Leu Val Ala Ser Ala
405 410 415

Gln Lys Lys Leu Leu Glu Glu Arg Leu Lys Leu Ile Ser Glu Leu Trp
420 425 430

Asp Ala Gly Ile Lys Ala Glu Leu Leu Tyr Lys Lys Asn Pro Lys Leu
435 440 445

Leu Asn Gln Leu Gln Tyr Cys Glu Glu Thr Gly Ile Pro Leu Val Ala
450 455 460

Ile Ile Gly Glu Gln Glu Leu Lys Asp Gly Val Ile Lys Leu Arg Ser
465 470 475 480

Val Ala Ser Arg Glu Glu Val Asp Val Arg Arg Glu Asp Leu Val Glu
485 490 495

Glu Ile Lys Arg Arg Thr Ser Gln Pro Leu Cys Ile Cys
500 505

<210> SEQ ID NO 22
<211> LENGTH: 508
<212> TYPE: PRT
<213> ORGANISM: Rattus norvegicus

<400> SEQUENCE: 22

Met Ala Asp Arg Ala Ala Leu Glu Glu Leu Val Arg Leu Gln Gly Ala
1 5 10 15

His Val Arg Gly Leu Lys Glu Gln Lys Ala Ser Ala Glu Gln Ile Glu

-continued

```
            20                  25                  30

Glu Glu Val Thr Lys Leu Leu Lys Leu Lys Ala Gln Leu Gly His Asp
        35                  40                  45

Glu Gly Lys Gln Lys Phe Val Leu Lys Thr Pro Lys Gly Thr Arg Asp
    50                  55                  60

Tyr Ser Pro Arg Gln Met Ala Val Arg Glu Lys Val Phe Asp Val Ile
65                  70                  75                  80

Ile Arg Cys Phe Lys Arg His Gly Ala Glu Val Ile Asp Thr Pro Val
                85                  90                  95

Phe Glu Leu Lys Glu Thr Leu Thr Gly Lys Tyr Gly Glu Asp Ser Lys
            100                 105                 110

Leu Ile Tyr Asp Leu Lys Asp Gln Gly Gly Glu Leu Leu Ser Leu Arg
        115                 120                 125

Tyr Asp Leu Thr Val Pro Phe Ala Arg Tyr Leu Ala Met Asn Lys Leu
    130                 135                 140

Thr Asn Ile Lys Arg Tyr His Ile Ala Lys Val Tyr Arg Arg Asp Asn
145                 150                 155                 160

Pro Ala Met Thr Arg Gly Arg Tyr Arg Glu Phe Tyr Gln Cys Asp Phe
                165                 170                 175

Asp Ile Ala Gly Gln Phe Asp Pro Met Ile Pro Asp Ala Glu Cys Leu
            180                 185                 190

Lys Ile Met Cys Glu Ile Leu Ser Ser Leu Gln Ile Gly Asn Phe Gln
        195                 200                 205

Val Lys Val Asn Asp Arg Arg Ile Leu Asp Gly Met Phe Ala Val Cys
    210                 215                 220

Gly Val Pro Asp Ser Lys Phe Arg Thr Ile Cys Ser Ser Val Asp Lys
225                 230                 235                 240

Leu Asp Lys Val Ser Trp Glu Glu Val Lys Asn Glu Met Val Gly Glu
                245                 250                 255

Lys Gly Leu Ala Pro Glu Val Ala Asp Arg Ile Gly Asp Tyr Val Gln
            260                 265                 270

Gln His Gly Gly Val Ser Leu Val Glu Gln Leu Leu Gln Asp Pro Lys
        275                 280                 285

Leu Ser Gln Asn Lys Gln Ala Val Glu Gly Leu Gly Asp Leu Lys Leu
    290                 295                 300

Leu Phe Glu Tyr Leu Thr Leu Phe Gly Ile Asp Asp Lys Ile Ser Phe
305                 310                 315                 320

Asp Leu Ser Leu Ala Arg Gly Leu Asp Tyr Tyr Thr Gly Val Ile Tyr
                325                 330                 335

Glu Ala Val Leu Leu Gln Met Pro Thr Gln Ala Gly Glu Glu Pro Leu
            340                 345                 350

Gly Val Gly Ser Ile Ala Ala Gly Gly Arg Tyr Asp Gly Leu Val Gly
        355                 360                 365

Met Phe Asp Pro Lys Gly Arg Lys Val Pro Cys Val Gly Leu Ser Ile
    370                 375                 380

Gly Val Glu Arg Ile Phe Ser Ile Val Glu Gln Lys Leu Glu Ala Ser
385                 390                 395                 400

Glu Glu Lys Val Arg Thr Thr Glu Thr Gln Val Leu Val Ala Ser Ala
                405                 410                 415

Gln Lys Lys Leu Leu Glu Glu Arg Leu Lys Leu Ile Ser Glu Leu Trp
            420                 425                 430

Asp Ala Gly Ile Lys Ala Glu Leu Leu Tyr Lys Lys Asn Pro Lys Leu
        435                 440                 445
```

```
Leu Asn Gln Leu Gln Tyr Cys Glu Glu Ala Gly Ile Pro Leu Val Ala
    450                 455                 460

Ile Ile Gly Glu Gln Glu Leu Lys Asp Gly Val Ile Lys Leu Arg Ser
465                 470                 475                 480

Val Thr Ser Arg Glu Glu Val Asp Val Arg Arg Glu Asp Leu Val Glu
                485                 490                 495

Glu Ile Arg Arg Arg Thr Ser Gln Pro Leu Ser Met
            500                 505


<210> SEQ ID NO 23
<211> LENGTH: 500
<212> TYPE: PRT
<213> ORGANISM: Gallus gallus

<400> SEQUENCE: 23

Met Ala Asp Glu Ala Ala Val Arg Gln Gln Ala Glu Val Val Arg Arg
1               5                   10                  15

Leu Lys Gln Asp Lys Ala Glu Pro Asp Glu Ile Ala Lys Glu Val Ala
            20                  25                  30

Lys Leu Leu Glu Met Lys Ala His Leu Gly Gly Asp Glu Gly Lys His
        35                  40                  45

Lys Phe Val Leu Lys Thr Pro Lys Gly Thr Arg Asp Tyr Gly Pro Lys
    50                  55                  60

Gln Met Ala Ile Arg Glu Arg Val Phe Ser Ala Ile Ile Ala Cys Phe
65                  70                  75                  80

Lys Arg His Gly Ala Glu Val Ile Asp Thr Pro Val Phe Glu Leu Lys
                85                  90                  95

Glu Thr Leu Thr Gly Lys Tyr Gly Glu Asp Ser Lys Leu Ile Tyr Asp
            100                 105                 110

Leu Lys Asp Gln Gly Gly Glu Leu Leu Ser Leu Arg Tyr Asp Leu Thr
        115                 120                 125

Val Pro Phe Ala Arg Tyr Leu Ala Met Asn Lys Ile Thr Asn Ile Lys
    130                 135                 140

Arg Tyr His Ile Ala Lys Val Tyr Arg Arg Asp Asn Pro Ala Met Thr
145                 150                 155                 160

Arg Gly Arg Tyr Arg Glu Phe Tyr Gln Cys Asp Phe Asp Ile Ala Gly
                165                 170                 175

Gln Phe Asp Pro Met Ile Pro Asp Ala Glu Cys Leu Lys Ile Val Gln
            180                 185                 190

Glu Ile Leu Ser Asp Leu Gln Leu Gly Asp Phe Leu Ile Lys Val Asn
        195                 200                 205

Asp Arg Arg Ile Leu Asp Gly Met Phe Ala Val Cys Gly Val Pro Asp
    210                 215                 220

Ser Lys Phe Arg Thr Ile Cys Ser Ser Val Asp Lys Leu Asp Lys Met
225                 230                 235                 240

Pro Trp Glu Glu Val Arg Asn Glu Met Val Gly Glu Lys Gly Leu Ser
                245                 250                 255

Pro Glu Ala Ala Asp Arg Ile Gly Glu Tyr Val Gln Leu His Gly Gly
            260                 265                 270

Met Asp Leu Ile Glu Gln Leu Leu Gln Asp Pro Lys Leu Ser Gln Asn
        275                 280                 285

Lys Leu Val Lys Glu Gly Leu Gly Asp Met Lys Leu Leu Phe Glu Tyr
    290                 295                 300

Leu Thr Leu Phe Gly Ile Thr Gly Lys Ile Ser Phe Asp Leu Ser Leu
```

```
305                 310                 315                 320

Ala Arg Gly Leu Asp Tyr Tyr Thr Gly Val Ile Tyr Glu Ala Val Leu
                325                 330                 335

Leu Gln Gln Asn Asp His Gly Glu Glu Ser Val Ser Val Gly Ser Val
            340                 345                 350

Ala Gly Gly Gly Arg Tyr Asp Gly Leu Val Gly Met Phe Asp Pro Lys
        355                 360                 365

Gly Arg Lys Val Pro Cys Val Gly Ile Ser Ile Gly Ile Glu Arg Ile
    370                 375                 380

Phe Ser Ile Leu Glu Gln Arg Val Glu Ala Ser Glu Glu Lys Ile Arg
385                 390                 395                 400

Thr Thr Glu Thr Gln Val Leu Val Ala Ser Ala Gln Lys Lys Leu Leu
                405                 410                 415

Glu Glu Arg Leu Lys Leu Ile Ser Glu Leu Trp Asp Ala Gly Ile Lys
            420                 425                 430

Ala Glu Val Leu Tyr Lys Lys Asn Pro Lys Leu Leu Asn Gln Leu Gln
        435                 440                 445

Tyr Cys Glu Asp Thr Gly Ile Pro Leu Val Ala Ile Val Gly Glu Gln
    450                 455                 460

Glu Leu Lys Asp Gly Val Val Lys Leu Arg Val Val Ala Thr Gly Glu
465                 470                 475                 480

Glu Val Asn Ile Arg Arg Glu Ser Leu Val Glu Glu Ile Arg Arg Arg
                485                 490                 495

Thr Asn Gln Leu
            500


<210> SEQ ID NO 24
<211> LENGTH: 437
<212> TYPE: PRT
<213> ORGANISM: Danio rerio

<400> SEQUENCE: 24

Met Ala Ala Leu Gly Leu Val Ser Met Arg Leu Cys Ala Gly Leu Met
1               5                   10                  15

Gly Arg Arg Ser Ala Val Arg Leu His Ser Leu Arg Val Cys Ser Gly
            20                  25                  30

Met Thr Ile Ser Gln Ile Asp Glu Glu Val Ala Arg Leu Leu Gln Leu
        35                  40                  45

Lys Ala Gln Leu Gly Gly Asp Glu Gly Lys His Val Phe Val Leu Lys
    50                  55                  60

Thr Ala Lys Gly Thr Arg Asp Tyr Asn Pro Lys Gln Met Ala Ile Arg
65                  70                  75                  80

Glu Lys Val Phe Asn Ile Ile Ile Asn Cys Phe Lys Arg His Gly Ala
                85                  90                  95

Glu Thr Ile Asp Ser Pro Val Phe Glu Leu Lys Glu Thr Leu Thr Gly
            100                 105                 110

Lys Tyr Gly Glu Asp Ser Lys Leu Ile Tyr Asp Leu Lys Asp Gln Gly
        115                 120                 125

Gly Glu Leu Leu Ser Leu Arg Tyr Asp Leu Thr Val Pro Phe Ala Arg
    130                 135                 140

Tyr Leu Ala Met Asn Lys Ile Thr Asn Ile Lys Arg Tyr His Ile Ala
145                 150                 155                 160

Lys Val Tyr Arg Arg Asp Asn Pro Ala Met Thr Arg Gly Arg Tyr Arg
                165                 170                 175
```

```
Glu Phe Tyr Gln Cys Asp Phe Asp Ile Ala Gly Gln Tyr Asp Ala Met
            180                 185                 190

Ile Pro Asp Ala Glu Cys Leu Lys Leu Val Tyr Glu Ile Leu Ser Glu
        195                 200                 205

Leu Asp Leu Gly Asp Phe Arg Ile Lys Val Asn Asp Arg Arg Ile Leu
    210                 215                 220

Asp Gly Met Phe Ala Ile Cys Gly Val Pro Asp Glu Lys Phe Arg Thr
225                 230                 235                 240

Ile Cys Ser Thr Val Asp Lys Leu Asp Lys Leu Ala Trp Glu Glu Val
                245                 250                 255

Lys Lys Glu Met Val Asn Glu Lys Gly Leu Ser Glu Glu Val Ala Asp
            260                 265                 270

Arg Ile Arg Asp Tyr Val Ser Met Gln Gly Gly Lys Asp Leu Ala Glu
        275                 280                 285

Arg Leu Leu Gln Asp Pro Lys Leu Ser Gln Ser Lys Gln Ala Cys Ala
    290                 295                 300

Gly Ile Thr Asp Met Lys Leu Leu Phe Ser Tyr Leu Glu Leu Phe Gln
305                 310                 315                 320

Ile Thr Asp Lys Val Val Phe Asp Leu Ser Leu Ala Arg Gly Leu Asp
                325                 330                 335

Tyr Tyr Thr Gly Val Ile Tyr Glu Ala Ile Leu Thr Gln Ala Asn Pro
            340                 345                 350

Ala Pro Ala Ser Thr Pro Ala Glu Gln Asn Gly Ala Glu Asp Ala Gly
        355                 360                 365

Val Ser Val Gly Ser Val Ala Gly Gly Gly Arg Tyr Asp Gly Leu Val
    370                 375                 380

Gly Met Phe Asp Pro Lys Ala Gly Lys Cys Pro Val Trp Gly Ser Ala
385                 390                 395                 400

Leu Ala Leu Arg Gly Ser Ser Pro Ser Trp Ser Arg Arg Gln Ser Cys
                405                 410                 415

Leu Gln Arg Arg Cys Ala Pro Leu Lys Leu Lys Cys Leu Trp Leu Gln
            420                 425                 430

His Arg Arg Thr Phe
        435


<210> SEQ ID NO 25
<211> LENGTH: 506
<212> TYPE: PRT
<213> ORGANISM: Homo sapiens

<400> SEQUENCE: 25

Met Ala Glu Arg Ala Ala Leu Glu Glu Leu Val Lys Leu Gln Gly Glu
1               5                   10                  15

Arg Val Arg Gly Leu Lys Gln Gln Lys Ala Ser Ala Glu Leu Ile Glu
            20                  25                  30

Glu Glu Val Ala Lys Leu Leu Lys Leu Lys Ala Gln Leu Gly Pro Asp
        35                  40                  45

Glu Ser Lys Gln Lys Phe Val Leu Lys Thr Pro Lys Gly Thr Arg Asp
    50                  55                  60

Tyr Ser Pro Arg Gln Met Ala Val Arg Glu Lys Val Phe Asp Val Ile
65                  70                  75                  80

Ile Arg Cys Phe Lys Arg His Gly Ala Glu Val Ile Asp Thr Pro Val
                85                  90                  95

Phe Glu Leu Lys Glu Thr Leu Met Gly Lys Tyr Gly Glu Asp Ser Lys
            100                 105                 110
```

```
Leu Ile Tyr Asp Leu Lys Asp Gln Gly Gly Glu Leu Leu Ser Leu Arg
        115                 120                 125

Tyr Asp Leu Thr Val Pro Phe Ala Arg Tyr Leu Ala Met Asn Lys Leu
    130                 135                 140

Thr Asn Ile Lys Arg Tyr His Ile Ala Lys Val Tyr Arg Arg Asp Asn
145                 150                 155                 160

Pro Ala Met Thr Arg Gly Arg Tyr Arg Glu Phe Tyr Gln Cys Asp Phe
                165                 170                 175

Asp Ile Ala Gly Asn Phe Asp Pro Met Ile Pro Asp Ala Glu Cys Leu
            180                 185                 190

Lys Ile Met Cys Glu Ile Leu Ser Ser Leu Gln Ile Gly Asp Phe Leu
        195                 200                 205

Val Lys Val Asn Asp Arg Arg Ile Leu Asp Gly Met Phe Ala Ile Cys
    210                 215                 220

Gly Val Ser Asp Ser Lys Phe Arg Thr Ile Cys Ser Ser Val Asp Lys
225                 230                 235                 240

Leu Asp Lys Val Ser Trp Glu Glu Val Lys Asn Glu Met Val Gly Glu
                245                 250                 255

Lys Gly Leu Ala Pro Glu Val Ala Asp Arg Ile Gly Asp Tyr Val Gln
            260                 265                 270

Gln His Gly Gly Val Ser Leu Val Glu Gln Leu Leu Gln Asp Pro Lys
        275                 280                 285

Leu Ser Gln Asn Lys Gln Ala Leu Glu Gly Leu Gly Asp Leu Lys Leu
    290                 295                 300

Leu Phe Glu Tyr Leu Thr Leu Phe Gly Ile Asp Asp Lys Ile Ser Phe
305                 310                 315                 320

Asp Leu Ser Leu Ala Arg Gly Leu Asp Tyr Tyr Thr Gly Val Ile Tyr
                325                 330                 335

Glu Ala Val Leu Leu Gln Thr Pro Ala Gln Ala Gly Glu Glu Pro Leu
            340                 345                 350

Gly Val Gly Ser Val Ala Ala Gly Gly Arg Tyr Asp Gly Leu Val Gly
        355                 360                 365

Met Phe Asp Pro Lys Gly Arg Lys Val Pro Cys Val Gly Leu Ser Ile
    370                 375                 380

Gly Val Glu Arg Ile Phe Ser Ile Val Glu Gln Arg Leu Glu Ala Leu
385                 390                 395                 400

Glu Glu Lys Ile Arg Thr Thr Glu Thr Gln Val Leu Val Ala Ser Ala
                405                 410                 415

Gln Lys Lys Leu Leu Glu Glu Arg Leu Lys Leu Val Ser Glu Leu Trp
            420                 425                 430

Asp Ala Gly Ile Lys Ala Glu Leu Leu Tyr Lys Lys Asn Pro Lys Leu
        435                 440                 445

Leu Asn Gln Leu Gln Tyr Cys Glu Glu Ala Gly Ile Pro Leu Val Ala
    450                 455                 460

Ile Ile Gly Glu Gln Glu Leu Lys Asp Gly Val Ile Lys Leu Arg Ser
465                 470                 475                 480

Val Thr Ser Arg Glu Glu Val Asp Val Arg Arg Glu Asp Leu Val Glu
                485                 490                 495

Glu Ile Lys Arg Arg Thr Gly Gln Pro Leu
            500                 505
```

<210> SEQ ID NO 26
<211> LENGTH: 48

<212> TYPE: PRT
<213> ORGANISM: Homo sapiens

<400> SEQUENCE: 26

Met Ala Glu Arg Ala Ala Leu Glu Glu Leu Val Lys Leu Gln Gly Glu
1 5 10 15

Arg Val Arg Gly Leu Lys Gln Gln Lys Ala Ser Ala Glu Leu Ile Glu
20 25 30

Glu Glu Val Ala Lys Leu Leu Lys Leu Lys Ala Gln Leu Gly Pro Asp
35 40 45

<210> SEQ ID NO 27
<211> LENGTH: 80
<212> TYPE: PRT
<213> ORGANISM: Homo sapiens

<400> SEQUENCE: 27

Met Ala Glu Arg Ala Ala Leu Glu Glu Leu Val Lys Leu Gln Gly Glu
1 5 10 15

Arg Val Arg Gly Leu Lys Gln Gln Lys Ala Ser Ala Glu Leu Ile Glu
20 25 30

Glu Glu Val Ala Lys Leu Leu Lys Leu Lys Ala Gln Leu Gly Pro Asp
35 40 45

Glu Ser Lys Gln Lys Phe Val Leu Lys Thr Pro Lys Gly Thr Arg Asp
50 55 60

Tyr Ser Pro Arg Gln Met Ala Val Arg Glu Lys Val Phe Asp Val Ile
65 70 75 80

<210> SEQ ID NO 28
<211> LENGTH: 79
<212> TYPE: PRT
<213> ORGANISM: Homo sapiens

<400> SEQUENCE: 28

Met Ala Glu Arg Ala Ala Leu Glu Glu Leu Val Lys Leu Gln Gly Glu
1 5 10 15

Arg Val Arg Gly Leu Lys Gln Gln Lys Ala Ser Ala Glu Leu Ile Glu
20 25 30

Glu Glu Val Ala Lys Leu Leu Lys Leu Lys Ala Gln Leu Gly Pro Asp
35 40 45

Glu Ser Lys Gln Lys Phe Val Leu Lys Thr Pro Lys Gly Thr Arg Asp
50 55 60

Tyr Ser Pro Arg Gln Met Ala Val Arg Glu Lys Val Phe Asp Val
65 70 75

<210> SEQ ID NO 29
<211> LENGTH: 78
<212> TYPE: PRT
<213> ORGANISM: Homo sapiens

<400> SEQUENCE: 29

Met Ala Glu Arg Ala Ala Leu Glu Glu Leu Val Lys Leu Gln Gly Glu
1 5 10 15

Arg Val Arg Gly Leu Lys Gln Gln Lys Ala Ser Ala Glu Leu Ile Glu
20 25 30

Glu Glu Val Ala Lys Leu Leu Lys Leu Lys Ala Gln Leu Gly Pro Asp
35 40 45

Glu Ser Lys Gln Lys Phe Val Leu Lys Thr Pro Lys Gly Thr Arg Asp
50 55 60

```
Tyr Ser Pro Arg Gln Met Ala Val Arg Glu Lys Val Phe Asp
65                  70                  75


<210> SEQ ID NO 30
<211> LENGTH: 77
<212> TYPE: PRT
<213> ORGANISM: Homo sapiens

<400> SEQUENCE: 30

Met Ala Glu Arg Ala Ala Leu Glu Glu Leu Val Lys Leu Gln Gly Glu
1               5                   10                  15

Arg Val Arg Gly Leu Lys Gln Gln Lys Ala Ser Ala Glu Leu Ile Glu
            20                  25                  30

Glu Glu Val Ala Lys Leu Leu Lys Leu Lys Ala Gln Leu Gly Pro Asp
        35                  40                  45

Glu Ser Lys Gln Lys Phe Val Leu Lys Thr Pro Lys Gly Thr Arg Asp
    50                  55                  60

Tyr Ser Pro Arg Gln Met Ala Val Arg Glu Lys Val Phe
65                  70                  75


<210> SEQ ID NO 31
<211> LENGTH: 76
<212> TYPE: PRT
<213> ORGANISM: Homo sapiens

<400> SEQUENCE: 31

Met Ala Glu Arg Ala Ala Leu Glu Glu Leu Val Lys Leu Gln Gly Glu
1               5                   10                  15

Arg Val Arg Gly Leu Lys Gln Gln Lys Ala Ser Ala Glu Leu Ile Glu
            20                  25                  30

Glu Glu Val Ala Lys Leu Leu Lys Leu Lys Ala Gln Leu Gly Pro Asp
        35                  40                  45

Glu Ser Lys Gln Lys Phe Val Leu Lys Thr Pro Lys Gly Thr Arg Asp
    50                  55                  60

Tyr Ser Pro Arg Gln Met Ala Val Arg Glu Lys Val
65                  70                  75


<210> SEQ ID NO 32
<211> LENGTH: 75
<212> TYPE: PRT
<213> ORGANISM: Homo sapiens

<400> SEQUENCE: 32

Met Ala Glu Arg Ala Ala Leu Glu Glu Leu Val Lys Leu Gln Gly Glu
1               5                   10                  15

Arg Val Arg Gly Leu Lys Gln Gln Lys Ala Ser Ala Glu Leu Ile Glu
            20                  25                  30

Glu Glu Val Ala Lys Leu Leu Lys Leu Lys Ala Gln Leu Gly Pro Asp
        35                  40                  45

Glu Ser Lys Gln Lys Phe Val Leu Lys Thr Pro Lys Gly Thr Arg Asp
    50                  55                  60

Tyr Ser Pro Arg Gln Met Ala Val Arg Glu Lys
65                  70                  75


<210> SEQ ID NO 33
<211> LENGTH: 74
<212> TYPE: PRT
<213> ORGANISM: Homo sapiens
```

<400> SEQUENCE: 33

Met Ala Glu Arg Ala Ala Leu Glu Glu Leu Val Lys Leu Gln Gly Glu
1 5 10 15

Arg Val Arg Gly Leu Lys Gln Gln Lys Ala Ser Ala Glu Leu Ile Glu
20 25 30

Glu Glu Val Ala Lys Leu Leu Lys Leu Lys Ala Gln Leu Gly Pro Asp
35 40 45

Glu Ser Lys Gln Lys Phe Val Leu Lys Thr Pro Lys Gly Thr Arg Asp
50 55 60

Tyr Ser Pro Arg Gln Met Ala Val Arg Glu
65 70

<210> SEQ ID NO 34
<211> LENGTH: 73
<212> TYPE: PRT
<213> ORGANISM: Homo sapiens

<400> SEQUENCE: 34

Met Ala Glu Arg Ala Ala Leu Glu Glu Leu Val Lys Leu Gln Gly Glu
1 5 10 15

Arg Val Arg Gly Leu Lys Gln Gln Lys Ala Ser Ala Glu Leu Ile Glu
20 25 30

Glu Glu Val Ala Lys Leu Leu Lys Leu Lys Ala Gln Leu Gly Pro Asp
35 40 45

Glu Ser Lys Gln Lys Phe Val Leu Lys Thr Pro Lys Gly Thr Arg Asp
50 55 60

Tyr Ser Pro Arg Gln Met Ala Val Arg
65 70

<210> SEQ ID NO 35
<211> LENGTH: 72
<212> TYPE: PRT
<213> ORGANISM: Homo sapiens

<400> SEQUENCE: 35

Met Ala Glu Arg Ala Ala Leu Glu Glu Leu Val Lys Leu Gln Gly Glu
1 5 10 15

Arg Val Arg Gly Leu Lys Gln Gln Lys Ala Ser Ala Glu Leu Ile Glu
20 25 30

Glu Glu Val Ala Lys Leu Leu Lys Leu Lys Ala Gln Leu Gly Pro Asp
35 40 45

Glu Ser Lys Gln Lys Phe Val Leu Lys Thr Pro Lys Gly Thr Arg Asp
50 55 60

Tyr Ser Pro Arg Gln Met Ala Val
65 70

<210> SEQ ID NO 36
<211> LENGTH: 71
<212> TYPE: PRT
<213> ORGANISM: Homo sapiens

<400> SEQUENCE: 36

Met Ala Glu Arg Ala Ala Leu Glu Glu Leu Val Lys Leu Gln Gly Glu
1 5 10 15

Arg Val Arg Gly Leu Lys Gln Gln Lys Ala Ser Ala Glu Leu Ile Glu
20 25 30

Glu Glu Val Ala Lys Leu Leu Lys Leu Lys Ala Gln Leu Gly Pro Asp
35 40 45

```
Glu Ser Lys Gln Lys Phe Val Leu Lys Thr Pro Lys Gly Thr Arg Asp
    50                  55                  60

Tyr Ser Pro Arg Gln Met Ala
65                  70


<210> SEQ ID NO 37
<211> LENGTH: 70
<212> TYPE: PRT
<213> ORGANISM: Homo sapiens

<400> SEQUENCE: 37

Met Ala Glu Arg Ala Ala Leu Glu Glu Leu Val Lys Leu Gln Gly Glu
1               5                   10                  15

Arg Val Arg Gly Leu Lys Gln Gln Lys Ala Ser Ala Glu Leu Ile Glu
            20                  25                  30

Glu Glu Val Ala Lys Leu Leu Lys Leu Lys Ala Gln Leu Gly Pro Asp
        35                  40                  45

Glu Ser Lys Gln Lys Phe Val Leu Lys Thr Pro Lys Gly Thr Arg Asp
    50                  55                  60

Tyr Ser Pro Arg Gln Met
65                  70


<210> SEQ ID NO 38
<211> LENGTH: 69
<212> TYPE: PRT
<213> ORGANISM: Homo sapiens

<400> SEQUENCE: 38

Met Ala Glu Arg Ala Ala Leu Glu Glu Leu Val Lys Leu Gln Gly Glu
1               5                   10                  15

Arg Val Arg Gly Leu Lys Gln Gln Lys Ala Ser Ala Glu Leu Ile Glu
            20                  25                  30

Glu Glu Val Ala Lys Leu Leu Lys Leu Lys Ala Gln Leu Gly Pro Asp
        35                  40                  45

Glu Ser Lys Gln Lys Phe Val Leu Lys Thr Pro Lys Gly Thr Arg Asp
    50                  55                  60

Tyr Ser Pro Arg Gln
65


<210> SEQ ID NO 39
<211> LENGTH: 68
<212> TYPE: PRT
<213> ORGANISM: Homo sapiens

<400> SEQUENCE: 39

Met Ala Glu Arg Ala Ala Leu Glu Glu Leu Val Lys Leu Gln Gly Glu
1               5                   10                  15

Arg Val Arg Gly Leu Lys Gln Gln Lys Ala Ser Ala Glu Leu Ile Glu
            20                  25                  30

Glu Glu Val Ala Lys Leu Leu Lys Leu Lys Ala Gln Leu Gly Pro Asp
        35                  40                  45

Glu Ser Lys Gln Lys Phe Val Leu Lys Thr Pro Lys Gly Thr Arg Asp
    50                  55                  60

Tyr Ser Pro Arg
65


<210> SEQ ID NO 40
<211> LENGTH: 67
```

<212> TYPE: PRT
<213> ORGANISM: Homo sapiens

<400> SEQUENCE: 40

```
Met Ala Glu Arg Ala Ala Leu Glu Glu Leu Val Lys Leu Gln Gly Glu
1               5                   10                  15

Arg Val Arg Gly Leu Lys Gln Gln Lys Ala Ser Ala Glu Leu Ile Glu
            20                  25                  30

Glu Glu Val Ala Lys Leu Leu Lys Leu Lys Ala Gln Leu Gly Pro Asp
        35                  40                  45

Glu Ser Lys Gln Lys Phe Val Leu Lys Thr Pro Lys Gly Thr Arg Asp
    50                  55                  60

Tyr Ser Pro
65
```

<210> SEQ ID NO 41
<211> LENGTH: 66
<212> TYPE: PRT
<213> ORGANISM: Homo sapiens

<400> SEQUENCE: 41

```
Met Ala Glu Arg Ala Ala Leu Glu Glu Leu Val Lys Leu Gln Gly Glu
1               5                   10                  15

Arg Val Arg Gly Leu Lys Gln Gln Lys Ala Ser Ala Glu Leu Ile Glu
            20                  25                  30

Glu Glu Val Ala Lys Leu Leu Lys Leu Lys Ala Gln Leu Gly Pro Asp
        35                  40                  45

Glu Ser Lys Gln Lys Phe Val Leu Lys Thr Pro Lys Gly Thr Arg Asp
    50                  55                  60

Tyr Ser
65
```

<210> SEQ ID NO 42
<211> LENGTH: 65
<212> TYPE: PRT
<213> ORGANISM: Homo sapiens

<400> SEQUENCE: 42

```
Met Ala Glu Arg Ala Ala Leu Glu Glu Leu Val Lys Leu Gln Gly Glu
1               5                   10                  15

Arg Val Arg Gly Leu Lys Gln Gln Lys Ala Ser Ala Glu Leu Ile Glu
            20                  25                  30

Glu Glu Val Ala Lys Leu Leu Lys Leu Lys Ala Gln Leu Gly Pro Asp
        35                  40                  45

Glu Ser Lys Gln Lys Phe Val Leu Lys Thr Pro Lys Gly Thr Arg Asp
    50                  55                  60

Tyr
65
```

<210> SEQ ID NO 43
<211> LENGTH: 64
<212> TYPE: PRT
<213> ORGANISM: Homo sapiens

<400> SEQUENCE: 43

```
Met Ala Glu Arg Ala Ala Leu Glu Glu Leu Val Lys Leu Gln Gly Glu
1               5                   10                  15

Arg Val Arg Gly Leu Lys Gln Gln Lys Ala Ser Ala Glu Leu Ile Glu
            20                  25                  30
```

Glu Glu Val Ala Lys Leu Leu Lys Leu Lys Ala Gln Leu Gly Pro Asp
        35                  40                  45

Glu Ser Lys Gln Lys Phe Val Leu Lys Thr Pro Lys Gly Thr Arg Asp
    50                  55                  60

<210> SEQ ID NO 44
<211> LENGTH: 63
<212> TYPE: PRT
<213> ORGANISM: Homo sapiens

<400> SEQUENCE: 44

Met Ala Glu Arg Ala Ala Leu Glu Glu Leu Val Lys Leu Gln Gly Glu
1               5                   10                  15

Arg Val Arg Gly Leu Lys Gln Gln Lys Ala Ser Ala Glu Leu Ile Glu
            20                  25                  30

Glu Glu Val Ala Lys Leu Leu Lys Leu Lys Ala Gln Leu Gly Pro Asp
        35                  40                  45

Glu Ser Lys Gln Lys Phe Val Leu Lys Thr Pro Lys Gly Thr Arg
    50                  55                  60

<210> SEQ ID NO 45
<211> LENGTH: 62
<212> TYPE: PRT
<213> ORGANISM: Homo sapiens

<400> SEQUENCE: 45

Met Ala Glu Arg Ala Ala Leu Glu Glu Leu Val Lys Leu Gln Gly Glu
1               5                   10                  15

Arg Val Arg Gly Leu Lys Gln Gln Lys Ala Ser Ala Glu Leu Ile Glu
            20                  25                  30

Glu Glu Val Ala Lys Leu Leu Lys Leu Lys Ala Gln Leu Gly Pro Asp
        35                  40                  45

Glu Ser Lys Gln Lys Phe Val Leu Lys Thr Pro Lys Gly Thr
    50                  55                  60

<210> SEQ ID NO 46
<211> LENGTH: 61
<212> TYPE: PRT
<213> ORGANISM: Homo sapiens

<400> SEQUENCE: 46

Met Ala Glu Arg Ala Ala Leu Glu Glu Leu Val Lys Leu Gln Gly Glu
1               5                   10                  15

Arg Val Arg Gly Leu Lys Gln Gln Lys Ala Ser Ala Glu Leu Ile Glu
            20                  25                  30

Glu Glu Val Ala Lys Leu Leu Lys Leu Lys Ala Gln Leu Gly Pro Asp
        35                  40                  45

Glu Ser Lys Gln Lys Phe Val Leu Lys Thr Pro Lys Gly
    50                  55                  60

<210> SEQ ID NO 47
<211> LENGTH: 60
<212> TYPE: PRT
<213> ORGANISM: Homo sapiens

<400> SEQUENCE: 47

Met Ala Glu Arg Ala Ala Leu Glu Glu Leu Val Lys Leu Gln Gly Glu
1               5                   10                  15

Arg Val Arg Gly Leu Lys Gln Gln Lys Ala Ser Ala Glu Leu Ile Glu

```
            20                  25                  30

Glu Glu Val Ala Lys Leu Leu Lys Leu Lys Ala Gln Leu Gly Pro Asp
        35                  40                  45

Glu Ser Lys Gln Lys Phe Val Leu Lys Thr Pro Lys
    50                  55                  60


<210> SEQ ID NO 48
<211> LENGTH: 59
<212> TYPE: PRT
<213> ORGANISM: Homo sapiens

<400> SEQUENCE: 48

Met Ala Glu Arg Ala Ala Leu Glu Glu Leu Val Lys Leu Gln Gly Glu
1               5                   10                  15

Arg Val Arg Gly Leu Lys Gln Gln Lys Ala Ser Ala Glu Leu Ile Glu
            20                  25                  30

Glu Glu Val Ala Lys Leu Leu Lys Leu Lys Ala Gln Leu Gly Pro Asp
        35                  40                  45

Glu Ser Lys Gln Lys Phe Val Leu Lys Thr Pro
    50                  55


<210> SEQ ID NO 49
<211> LENGTH: 58
<212> TYPE: PRT
<213> ORGANISM: Homo sapiens

<400> SEQUENCE: 49

Met Ala Glu Arg Ala Ala Leu Glu Glu Leu Val Lys Leu Gln Gly Glu
1               5                   10                  15

Arg Val Arg Gly Leu Lys Gln Gln Lys Ala Ser Ala Glu Leu Ile Glu
            20                  25                  30

Glu Glu Val Ala Lys Leu Leu Lys Leu Lys Ala Gln Leu Gly Pro Asp
        35                  40                  45

Glu Ser Lys Gln Lys Phe Val Leu Lys Thr
    50                  55


<210> SEQ ID NO 50
<211> LENGTH: 57
<212> TYPE: PRT
<213> ORGANISM: Homo sapiens

<400> SEQUENCE: 50

Met Ala Glu Arg Ala Ala Leu Glu Glu Leu Val Lys Leu Gln Gly Glu
1               5                   10                  15

Arg Val Arg Gly Leu Lys Gln Gln Lys Ala Ser Ala Glu Leu Ile Glu
            20                  25                  30

Glu Glu Val Ala Lys Leu Leu Lys Leu Lys Ala Gln Leu Gly Pro Asp
        35                  40                  45

Glu Ser Lys Gln Lys Phe Val Leu Lys
    50                  55


<210> SEQ ID NO 51
<211> LENGTH: 56
<212> TYPE: PRT
<213> ORGANISM: Homo sapiens

<400> SEQUENCE: 51

Met Ala Glu Arg Ala Ala Leu Glu Glu Leu Val Lys Leu Gln Gly Glu
1               5                   10                  15
```

```
Arg Val Arg Gly Leu Lys Gln Gln Lys Ala Ser Ala Glu Leu Ile Glu
            20                  25                  30

Glu Glu Val Ala Lys Leu Leu Lys Leu Lys Ala Gln Leu Gly Pro Asp
        35                  40                  45

Glu Ser Lys Gln Lys Phe Val Leu
    50                  55


<210> SEQ ID NO 52
<211> LENGTH: 55
<212> TYPE: PRT
<213> ORGANISM: Homo sapiens

<400> SEQUENCE: 52

Met Ala Glu Arg Ala Ala Leu Glu Glu Leu Val Lys Leu Gln Gly Glu
1               5                   10                  15

Arg Val Arg Gly Leu Lys Gln Gln Lys Ala Ser Ala Glu Leu Ile Glu
            20                  25                  30

Glu Glu Val Ala Lys Leu Leu Lys Leu Lys Ala Gln Leu Gly Pro Asp
        35                  40                  45

Glu Ser Lys Gln Lys Phe Val
    50                  55


<210> SEQ ID NO 53
<211> LENGTH: 54
<212> TYPE: PRT
<213> ORGANISM: Homo sapiens

<400> SEQUENCE: 53

Met Ala Glu Arg Ala Ala Leu Glu Glu Leu Val Lys Leu Gln Gly Glu
1               5                   10                  15

Arg Val Arg Gly Leu Lys Gln Gln Lys Ala Ser Ala Glu Leu Ile Glu
            20                  25                  30

Glu Glu Val Ala Lys Leu Leu Lys Leu Lys Ala Gln Leu Gly Pro Asp
        35                  40                  45

Glu Ser Lys Gln Lys Phe
    50


<210> SEQ ID NO 54
<211> LENGTH: 53
<212> TYPE: PRT
<213> ORGANISM: Homo sapiens

<400> SEQUENCE: 54

Met Ala Glu Arg Ala Ala Leu Glu Glu Leu Val Lys Leu Gln Gly Glu
1               5                   10                  15

Arg Val Arg Gly Leu Lys Gln Gln Lys Ala Ser Ala Glu Leu Ile Glu
            20                  25                  30

Glu Glu Val Ala Lys Leu Leu Lys Leu Lys Ala Gln Leu Gly Pro Asp
        35                  40                  45

Glu Ser Lys Gln Lys
    50


<210> SEQ ID NO 55
<211> LENGTH: 52
<212> TYPE: PRT
<213> ORGANISM: Homo sapiens

<400> SEQUENCE: 55

Met Ala Glu Arg Ala Ala Leu Glu Glu Leu Val Lys Leu Gln Gly Glu
1               5                   10                  15
```

```
Arg Val Arg Gly Leu Lys Gln Gln Lys Ala Ser Ala Glu Leu Ile Glu
            20                  25                  30

Glu Glu Val Ala Lys Leu Leu Lys Leu Lys Ala Gln Leu Gly Pro Asp
        35                  40                  45

Glu Ser Lys Gln
    50


<210> SEQ ID NO 56
<211> LENGTH: 51
<212> TYPE: PRT
<213> ORGANISM: Homo sapiens

<400> SEQUENCE: 56

Met Ala Glu Arg Ala Ala Leu Glu Glu Leu Val Lys Leu Gln Gly Glu
1               5                   10                  15

Arg Val Arg Gly Leu Lys Gln Gln Lys Ala Ser Ala Glu Leu Ile Glu
            20                  25                  30

Glu Glu Val Ala Lys Leu Leu Lys Leu Lys Ala Gln Leu Gly Pro Asp
        35                  40                  45

Glu Ser Lys
    50


<210> SEQ ID NO 57
<211> LENGTH: 50
<212> TYPE: PRT
<213> ORGANISM: Homo sapiens

<400> SEQUENCE: 57

Met Ala Glu Arg Ala Ala Leu Glu Glu Leu Val Lys Leu Gln Gly Glu
1               5                   10                  15

Arg Val Arg Gly Leu Lys Gln Gln Lys Ala Ser Ala Glu Leu Ile Glu
            20                  25                  30

Glu Glu Val Ala Lys Leu Leu Lys Leu Lys Ala Gln Leu Gly Pro Asp
        35                  40                  45

Glu Ser
    50


<210> SEQ ID NO 58
<211> LENGTH: 49
<212> TYPE: PRT
<213> ORGANISM: Homo sapiens

<400> SEQUENCE: 58

Met Ala Glu Arg Ala Ala Leu Glu Glu Leu Val Lys Leu Gln Gly Glu
1               5                   10                  15

Arg Val Arg Gly Leu Lys Gln Gln Lys Ala Ser Ala Glu Leu Ile Glu
            20                  25                  30

Glu Glu Val Ala Lys Leu Leu Lys Leu Lys Ala Gln Leu Gly Pro Asp
        35                  40                  45

Glu


<210> SEQ ID NO 59
<211> LENGTH: 48
<212> TYPE: PRT
<213> ORGANISM: Homo sapiens

<400> SEQUENCE: 59

Met Ala Glu Arg Ala Ala Leu Glu Glu Leu Val Lys Leu Gln Gly Glu
1               5                   10                  15
```

```
Arg Val Arg Gly Leu Lys Gln Gln Lys Ala Ser Ala Glu Leu Ile Glu
            20                  25                  30

Glu Glu Val Ala Lys Leu Leu Lys Leu Lys Ala Gln Leu Gly Pro Asp
        35                  40                  45
```

<210> SEQ ID NO 60
<211> LENGTH: 47
<212> TYPE: PRT
<213> ORGANISM: Homo sapiens

<400> SEQUENCE: 60

```
Met Ala Glu Arg Ala Ala Leu Glu Glu Leu Val Lys Leu Gln Gly Glu
1               5                   10                  15

Arg Val Arg Gly Leu Lys Gln Gln Lys Ala Ser Ala Glu Leu Ile Glu
            20                  25                  30

Glu Glu Val Ala Lys Leu Leu Lys Leu Lys Ala Gln Leu Gly Pro
        35                  40                  45
```

<210> SEQ ID NO 61
<211> LENGTH: 46
<212> TYPE: PRT
<213> ORGANISM: Homo sapiens

<400> SEQUENCE: 61

```
Met Ala Glu Arg Ala Ala Leu Glu Glu Leu Val Lys Leu Gln Gly Glu
1               5                   10                  15

Arg Val Arg Gly Leu Lys Gln Gln Lys Ala Ser Ala Glu Leu Ile Glu
            20                  25                  30

Glu Glu Val Ala Lys Leu Leu Lys Leu Lys Ala Gln Leu Gly
        35                  40                  45
```

<210> SEQ ID NO 62
<211> LENGTH: 45
<212> TYPE: PRT
<213> ORGANISM: Homo sapiens

<400> SEQUENCE: 62

```
Met Ala Glu Arg Ala Ala Leu Glu Glu Leu Val Lys Leu Gln Gly Glu
1               5                   10                  15

Arg Val Arg Gly Leu Lys Gln Gln Lys Ala Ser Ala Glu Leu Ile Glu
            20                  25                  30

Glu Glu Val Ala Lys Leu Leu Lys Leu Lys Ala Gln Leu
        35                  40                  45
```

<210> SEQ ID NO 63
<211> LENGTH: 44
<212> TYPE: PRT
<213> ORGANISM: Homo sapiens

<400> SEQUENCE: 63

```
Met Ala Glu Arg Ala Ala Leu Glu Glu Leu Val Lys Leu Gln Gly Glu
1               5                   10                  15

Arg Val Arg Gly Leu Lys Gln Gln Lys Ala Ser Ala Glu Leu Ile Glu
            20                  25                  30

Glu Glu Val Ala Lys Leu Leu Lys Leu Lys Ala Gln
        35                  40
```

<210> SEQ ID NO 64
<211> LENGTH: 43
<212> TYPE: PRT

<213> ORGANISM: Homo sapiens

<400> SEQUENCE: 64

Met Ala Glu Arg Ala Ala Leu Glu Glu Leu Val Lys Leu Gln Gly Glu
1               5                   10                  15

Arg Val Arg Gly Leu Lys Gln Gln Lys Ala Ser Ala Glu Leu Ile Glu
            20                  25                  30

Glu Glu Val Ala Lys Leu Leu Lys Leu Lys Ala
        35                  40

<210> SEQ ID NO 65
<211> LENGTH: 42
<212> TYPE: PRT
<213> ORGANISM: Homo sapiens

<400> SEQUENCE: 65

Met Ala Glu Arg Ala Ala Leu Glu Glu Leu Val Lys Leu Gln Gly Glu
1               5                   10                  15

Arg Val Arg Gly Leu Lys Gln Gln Lys Ala Ser Ala Glu Leu Ile Glu
            20                  25                  30

Glu Glu Val Ala Lys Leu Leu Lys Leu Lys
        35                  40

<210> SEQ ID NO 66
<211> LENGTH: 41
<212> TYPE: PRT
<213> ORGANISM: Homo sapiens

<400> SEQUENCE: 66

Met Ala Glu Arg Ala Ala Leu Glu Glu Leu Val Lys Leu Gln Gly Glu
1               5                   10                  15

Arg Val Arg Gly Leu Lys Gln Gln Lys Ala Ser Ala Glu Leu Ile Glu
            20                  25                  30

Glu Glu Val Ala Lys Leu Leu Lys Leu
        35                  40

<210> SEQ ID NO 67
<211> LENGTH: 40
<212> TYPE: PRT
<213> ORGANISM: Homo sapiens

<400> SEQUENCE: 67

Met Ala Glu Arg Ala Ala Leu Glu Glu Leu Val Lys Leu Gln Gly Glu
1               5                   10                  15

Arg Val Arg Gly Leu Lys Gln Gln Lys Ala Ser Ala Glu Leu Ile Glu
            20                  25                  30

Glu Glu Val Ala Lys Leu Leu Lys
        35                  40

<210> SEQ ID NO 68
<211> LENGTH: 79
<212> TYPE: PRT
<213> ORGANISM: Homo sapiens

<400> SEQUENCE: 68

Ala Glu Arg Ala Ala Leu Glu Glu Leu Val Lys Leu Gln Gly Glu Arg
1               5                   10                  15

Val Arg Gly Leu Lys Gln Gln Lys Ala Ser Ala Glu Leu Ile Glu Glu
            20                  25                  30

Glu Val Ala Lys Leu Leu Lys Leu Lys Ala Gln Leu Gly Pro Asp Glu

```
        35                  40                  45

Ser Lys Gln Lys Phe Val Leu Lys Thr Pro Lys Gly Thr Arg Asp Tyr
    50                  55                  60

Ser Pro Arg Gln Met Ala Val Arg Glu Lys Val Phe Asp Val Ile
65                  70                  75


<210> SEQ ID NO 69
<211> LENGTH: 78
<212> TYPE: PRT
<213> ORGANISM: Homo sapiens

<400> SEQUENCE: 69

Glu Arg Ala Ala Leu Glu Glu Leu Val Lys Leu Gln Gly Glu Arg Val
1               5                   10                  15

Arg Gly Leu Lys Gln Gln Lys Ala Ser Ala Glu Leu Ile Glu Glu Glu
            20                  25                  30

Val Ala Lys Leu Leu Lys Leu Lys Ala Gln Leu Gly Pro Asp Glu Ser
        35                  40                  45

Lys Gln Lys Phe Val Leu Lys Thr Pro Lys Gly Thr Arg Asp Tyr Ser
    50                  55                  60

Pro Arg Gln Met Ala Val Arg Glu Lys Val Phe Asp Val Ile
65                  70                  75


<210> SEQ ID NO 70
<211> LENGTH: 77
<212> TYPE: PRT
<213> ORGANISM: Homo sapiens

<400> SEQUENCE: 70

Arg Ala Ala Leu Glu Glu Leu Val Lys Leu Gln Gly Glu Arg Val Arg
1               5                   10                  15

Gly Leu Lys Gln Gln Lys Ala Ser Ala Glu Leu Ile Glu Glu Glu Val
            20                  25                  30

Ala Lys Leu Leu Lys Leu Lys Ala Gln Leu Gly Pro Asp Glu Ser Lys
        35                  40                  45

Gln Lys Phe Val Leu Lys Thr Pro Lys Gly Thr Arg Asp Tyr Ser Pro
    50                  55                  60

Arg Gln Met Ala Val Arg Glu Lys Val Phe Asp Val Ile
65                  70                  75


<210> SEQ ID NO 71
<211> LENGTH: 76
<212> TYPE: PRT
<213> ORGANISM: Homo sapiens

<400> SEQUENCE: 71

Ala Ala Leu Glu Glu Leu Val Lys Leu Gln Gly Glu Arg Val Arg Gly
1               5                   10                  15

Leu Lys Gln Gln Lys Ala Ser Ala Glu Leu Ile Glu Glu Glu Val Ala
            20                  25                  30

Lys Leu Leu Lys Leu Lys Ala Gln Leu Gly Pro Asp Glu Ser Lys Gln
        35                  40                  45

Lys Phe Val Leu Lys Thr Pro Lys Gly Thr Arg Asp Tyr Ser Pro Arg
    50                  55                  60

Gln Met Ala Val Arg Glu Lys Val Phe Asp Val Ile
65                  70                  75


<210> SEQ ID NO 72
```

<211> LENGTH: 75
<212> TYPE: PRT
<213> ORGANISM: Homo sapiens

<400> SEQUENCE: 72

Ala Leu Glu Glu Leu Val Lys Leu Gln Gly Glu Arg Val Arg Gly Leu
1 5 10 15

Lys Gln Gln Lys Ala Ser Ala Glu Leu Ile Glu Glu Glu Val Ala Lys
20 25 30

Leu Leu Lys Leu Lys Ala Gln Leu Gly Pro Asp Glu Ser Lys Gln Lys
35 40 45

Phe Val Leu Lys Thr Pro Lys Gly Thr Arg Asp Tyr Ser Pro Arg Gln
50 55 60

Met Ala Val Arg Glu Lys Val Phe Asp Val Ile
65 70 75

<210> SEQ ID NO 73
<211> LENGTH: 74
<212> TYPE: PRT
<213> ORGANISM: Homo sapiens

<400> SEQUENCE: 73

Leu Glu Glu Leu Val Lys Leu Gln Gly Glu Arg Val Arg Gly Leu Lys
1 5 10 15

Gln Gln Lys Ala Ser Ala Glu Leu Ile Glu Glu Glu Val Ala Lys Leu
20 25 30

Leu Lys Leu Lys Ala Gln Leu Gly Pro Asp Glu Ser Lys Gln Lys Phe
35 40 45

Val Leu Lys Thr Pro Lys Gly Thr Arg Asp Tyr Ser Pro Arg Gln Met
50 55 60

Ala Val Arg Glu Lys Val Phe Asp Val Ile
65 70

<210> SEQ ID NO 74
<211> LENGTH: 73
<212> TYPE: PRT
<213> ORGANISM: Homo sapiens

<400> SEQUENCE: 74

Glu Glu Leu Val Lys Leu Gln Gly Glu Arg Val Arg Gly Leu Lys Gln
1 5 10 15

Gln Lys Ala Ser Ala Glu Leu Ile Glu Glu Glu Val Ala Lys Leu Leu
20 25 30

Lys Leu Lys Ala Gln Leu Gly Pro Asp Glu Ser Lys Gln Lys Phe Val
35 40 45

Leu Lys Thr Pro Lys Gly Thr Arg Asp Tyr Ser Pro Arg Gln Met Ala
50 55 60

Val Arg Glu Lys Val Phe Asp Val Ile
65 70

<210> SEQ ID NO 75
<211> LENGTH: 72
<212> TYPE: PRT
<213> ORGANISM: Homo sapiens

<400> SEQUENCE: 75

Glu Leu Val Lys Leu Gln Gly Glu Arg Val Arg Gly Leu Lys Gln Gln
1 5 10 15

Lys Ala Ser Ala Glu Leu Ile Glu Glu Glu Val Ala Lys Leu Leu Lys

```
            20                  25                  30

Leu Lys Ala Gln Leu Gly Pro Asp Glu Ser Lys Gln Lys Phe Val Leu
        35                  40                  45

Lys Thr Pro Lys Gly Thr Arg Asp Tyr Ser Pro Arg Gln Met Ala Val
    50                  55                  60

Arg Glu Lys Val Phe Asp Val Ile
65                  70


<210> SEQ ID NO 76
<211> LENGTH: 71
<212> TYPE: PRT
<213> ORGANISM: Homo sapiens

<400> SEQUENCE: 76

Leu Val Lys Leu Gln Gly Glu Arg Val Arg Gly Leu Lys Gln Gln Lys
1               5                   10                  15

Ala Ser Ala Glu Leu Ile Glu Glu Glu Val Ala Lys Leu Leu Lys Leu
            20                  25                  30

Lys Ala Gln Leu Gly Pro Asp Glu Ser Lys Gln Lys Phe Val Leu Lys
        35                  40                  45

Thr Pro Lys Gly Thr Arg Asp Tyr Ser Pro Arg Gln Met Ala Val Arg
    50                  55                  60

Glu Lys Val Phe Asp Val Ile
65                  70


<210> SEQ ID NO 77
<211> LENGTH: 70
<212> TYPE: PRT
<213> ORGANISM: Homo sapiens

<400> SEQUENCE: 77

Val Lys Leu Gln Gly Glu Arg Val Arg Gly Leu Lys Gln Gln Lys Ala
1               5                   10                  15

Ser Ala Glu Leu Ile Glu Glu Glu Val Ala Lys Leu Leu Lys Leu Lys
            20                  25                  30

Ala Gln Leu Gly Pro Asp Glu Ser Lys Gln Lys Phe Val Leu Lys Thr
        35                  40                  45

Pro Lys Gly Thr Arg Asp Tyr Ser Pro Arg Gln Met Ala Val Arg Glu
    50                  55                  60

Lys Val Phe Asp Val Ile
65                  70


<210> SEQ ID NO 78
<211> LENGTH: 69
<212> TYPE: PRT
<213> ORGANISM: Homo sapiens

<400> SEQUENCE: 78

Lys Leu Gln Gly Glu Arg Val Arg Gly Leu Lys Gln Gln Lys Ala Ser
1               5                   10                  15

Ala Glu Leu Ile Glu Glu Glu Val Ala Lys Leu Leu Lys Leu Lys Ala
            20                  25                  30

Gln Leu Gly Pro Asp Glu Ser Lys Gln Lys Phe Val Leu Lys Thr Pro
        35                  40                  45

Lys Gly Thr Arg Asp Tyr Ser Pro Arg Gln Met Ala Val Arg Glu Lys
    50                  55                  60

Val Phe Asp Val Ile
65
```

<210> SEQ ID NO 79
<211> LENGTH: 68
<212> TYPE: PRT
<213> ORGANISM: Homo sapiens

<400> SEQUENCE: 79

Leu Gln Gly Glu Arg Val Arg Gly Leu Lys Gln Gln Lys Ala Ser Ala
1 5 10 15

Glu Leu Ile Glu Glu Glu Val Ala Lys Leu Leu Lys Leu Lys Ala Gln
20 25 30

Leu Gly Pro Asp Glu Ser Lys Gln Lys Phe Val Leu Lys Thr Pro Lys
35 40 45

Gly Thr Arg Asp Tyr Ser Pro Arg Gln Met Ala Val Arg Glu Lys Val
50 55 60

Phe Asp Val Ile
65

<210> SEQ ID NO 80
<211> LENGTH: 67
<212> TYPE: PRT
<213> ORGANISM: Homo sapiens

<400> SEQUENCE: 80

Gln Gly Glu Arg Val Arg Gly Leu Lys Gln Gln Lys Ala Ser Ala Glu
1 5 10 15

Leu Ile Glu Glu Glu Val Ala Lys Leu Leu Lys Leu Lys Ala Gln Leu
20 25 30

Gly Pro Asp Glu Ser Lys Gln Lys Phe Val Leu Lys Thr Pro Lys Gly
35 40 45

Thr Arg Asp Tyr Ser Pro Arg Gln Met Ala Val Arg Glu Lys Val Phe
50 55 60

Asp Val Ile
65

<210> SEQ ID NO 81
<211> LENGTH: 66
<212> TYPE: PRT
<213> ORGANISM: Homo sapiens

<400> SEQUENCE: 81

Gly Glu Arg Val Arg Gly Leu Lys Gln Gln Lys Ala Ser Ala Glu Leu
1 5 10 15

Ile Glu Glu Glu Val Ala Lys Leu Leu Lys Leu Lys Ala Gln Leu Gly
20 25 30

Pro Asp Glu Ser Lys Gln Lys Phe Val Leu Lys Thr Pro Lys Gly Thr
35 40 45

Arg Asp Tyr Ser Pro Arg Gln Met Ala Val Arg Glu Lys Val Phe Asp
50 55 60

Val Ile
65

<210> SEQ ID NO 82
<211> LENGTH: 64
<212> TYPE: PRT
<213> ORGANISM: Homo sapiens

<400> SEQUENCE: 82

Arg Val Arg Gly Leu Lys Gln Gln Lys Ala Ser Ala Glu Leu Ile Glu

```
1               5                   10                  15

Glu Glu Val Ala Lys Leu Leu Lys Leu Lys Ala Gln Leu Gly Pro Asp
            20                  25                  30

Glu Ser Lys Gln Lys Phe Val Leu Lys Thr Pro Lys Gly Thr Arg Asp
        35                  40                  45

Tyr Ser Pro Arg Gln Met Ala Val Arg Glu Lys Val Phe Asp Val Ile
    50                  55                  60
```

<210> SEQ ID NO 83
<211> LENGTH: 63
<212> TYPE: PRT
<213> ORGANISM: Homo sapiens

<400> SEQUENCE: 83

```
Val Arg Gly Leu Lys Gln Gln Lys Ala Ser Ala Glu Leu Ile Glu Glu
1               5                   10                  15

Glu Val Ala Lys Leu Leu Lys Leu Lys Ala Gln Leu Gly Pro Asp Glu
            20                  25                  30

Ser Lys Gln Lys Phe Val Leu Lys Thr Pro Lys Gly Thr Arg Asp Tyr
        35                  40                  45

Ser Pro Arg Gln Met Ala Val Arg Glu Lys Val Phe Asp Val Ile
    50                  55                  60
```

<210> SEQ ID NO 84
<211> LENGTH: 62
<212> TYPE: PRT
<213> ORGANISM: Homo sapiens

<400> SEQUENCE: 84

```
Arg Gly Leu Lys Gln Gln Lys Ala Ser Ala Glu Leu Ile Glu Glu Glu
1               5                   10                  15

Val Ala Lys Leu Leu Lys Leu Lys Ala Gln Leu Gly Pro Asp Glu Ser
            20                  25                  30

Lys Gln Lys Phe Val Leu Lys Thr Pro Lys Gly Thr Arg Asp Tyr Ser
        35                  40                  45

Pro Arg Gln Met Ala Val Arg Glu Lys Val Phe Asp Val Ile
    50                  55                  60
```

<210> SEQ ID NO 85
<211> LENGTH: 61
<212> TYPE: PRT
<213> ORGANISM: Homo sapiens

<400> SEQUENCE: 85

```
Gly Leu Lys Gln Gln Lys Ala Ser Ala Glu Leu Ile Glu Glu Glu Val
1               5                   10                  15

Ala Lys Leu Leu Lys Leu Lys Ala Gln Leu Gly Pro Asp Glu Ser Lys
            20                  25                  30

Gln Lys Phe Val Leu Lys Thr Pro Lys Gly Thr Arg Asp Tyr Ser Pro
        35                  40                  45

Arg Gln Met Ala Val Arg Glu Lys Val Phe Asp Val Ile
    50                  55                  60
```

<210> SEQ ID NO 86
<211> LENGTH: 60
<212> TYPE: PRT
<213> ORGANISM: Homo sapiens

<400> SEQUENCE: 86

-continued

```
Leu Lys Gln Gln Lys Ala Ser Ala Glu Leu Ile Glu Glu Glu Val Ala
1               5                   10                  15

Lys Leu Leu Lys Leu Lys Ala Gln Leu Gly Pro Asp Glu Ser Lys Gln
            20                  25                  30

Lys Phe Val Leu Lys Thr Pro Lys Gly Thr Arg Asp Tyr Ser Pro Arg
        35                  40                  45

Gln Met Ala Val Arg Glu Lys Val Phe Asp Val Ile
    50                  55                  60


<210> SEQ ID NO 87
<211> LENGTH: 59
<212> TYPE: PRT
<213> ORGANISM: Homo sapiens

<400> SEQUENCE: 87

Lys Gln Gln Lys Ala Ser Ala Glu Leu Ile Glu Glu Glu Val Ala Lys
1               5                   10                  15

Leu Leu Lys Leu Lys Ala Gln Leu Gly Pro Asp Glu Ser Lys Gln Lys
            20                  25                  30

Phe Val Leu Lys Thr Pro Lys Gly Thr Arg Asp Tyr Ser Pro Arg Gln
        35                  40                  45

Met Ala Val Arg Glu Lys Val Phe Asp Val Ile
    50                  55


<210> SEQ ID NO 88
<211> LENGTH: 58
<212> TYPE: PRT
<213> ORGANISM: Homo sapiens

<400> SEQUENCE: 88

Gln Gln Lys Ala Ser Ala Glu Leu Ile Glu Glu Glu Val Ala Lys Leu
1               5                   10                  15

Leu Lys Leu Lys Ala Gln Leu Gly Pro Asp Glu Ser Lys Gln Lys Phe
            20                  25                  30

Val Leu Lys Thr Pro Lys Gly Thr Arg Asp Tyr Ser Pro Arg Gln Met
        35                  40                  45

Ala Val Arg Glu Lys Val Phe Asp Val Ile
    50                  55


<210> SEQ ID NO 89
<211> LENGTH: 57
<212> TYPE: PRT
<213> ORGANISM: Homo sapiens

<400> SEQUENCE: 89

Gln Lys Ala Ser Ala Glu Leu Ile Glu Glu Glu Val Ala Lys Leu Leu
1               5                   10                  15

Lys Leu Lys Ala Gln Leu Gly Pro Asp Glu Ser Lys Gln Lys Phe Val
            20                  25                  30

Leu Lys Thr Pro Lys Gly Thr Arg Asp Tyr Ser Pro Arg Gln Met Ala
        35                  40                  45

Val Arg Glu Lys Val Phe Asp Val Ile
    50                  55


<210> SEQ ID NO 90
<211> LENGTH: 56
<212> TYPE: PRT
<213> ORGANISM: Homo sapiens

<400> SEQUENCE: 90
```

```
Lys Ala Ser Ala Glu Leu Ile Glu Glu Glu Val Ala Lys Leu Leu Lys
1               5                   10                  15

Leu Lys Ala Gln Leu Gly Pro Asp Glu Ser Lys Gln Lys Phe Val Leu
            20                  25                  30

Lys Thr Pro Lys Gly Thr Arg Asp Tyr Ser Pro Arg Gln Met Ala Val
        35                  40                  45

Arg Glu Lys Val Phe Asp Val Ile
    50                  55


<210> SEQ ID NO 91
<211> LENGTH: 55
<212> TYPE: PRT
<213> ORGANISM: Homo sapiens

<400> SEQUENCE: 91

Ala Ser Ala Glu Leu Ile Glu Glu Glu Val Ala Lys Leu Leu Lys Leu
1               5                   10                  15

Lys Ala Gln Leu Gly Pro Asp Glu Ser Lys Gln Lys Phe Val Leu Lys
            20                  25                  30

Thr Pro Lys Gly Thr Arg Asp Tyr Ser Pro Arg Gln Met Ala Val Arg
        35                  40                  45

Glu Lys Val Phe Asp Val Ile
    50                  55


<210> SEQ ID NO 92
<211> LENGTH: 54
<212> TYPE: PRT
<213> ORGANISM: Homo sapiens

<400> SEQUENCE: 92

Ser Ala Glu Leu Ile Glu Glu Glu Val Ala Lys Leu Leu Lys Leu Lys
1               5                   10                  15

Ala Gln Leu Gly Pro Asp Glu Ser Lys Gln Lys Phe Val Leu Lys Thr
            20                  25                  30

Pro Lys Gly Thr Arg Asp Tyr Ser Pro Arg Gln Met Ala Val Arg Glu
        35                  40                  45

Lys Val Phe Asp Val Ile
    50


<210> SEQ ID NO 93
<211> LENGTH: 53
<212> TYPE: PRT
<213> ORGANISM: Homo sapiens

<400> SEQUENCE: 93

Ala Glu Leu Ile Glu Glu Glu Val Ala Lys Leu Leu Lys Leu Lys Ala
1               5                   10                  15

Gln Leu Gly Pro Asp Glu Ser Lys Gln Lys Phe Val Leu Lys Thr Pro
            20                  25                  30

Lys Gly Thr Arg Asp Tyr Ser Pro Arg Gln Met Ala Val Arg Glu Lys
        35                  40                  45

Val Phe Asp Val Ile
    50


<210> SEQ ID NO 94
<211> LENGTH: 52
<212> TYPE: PRT
<213> ORGANISM: Homo sapiens
```

<400> SEQUENCE: 94

Glu Leu Ile Glu Glu Glu Val Ala Lys Leu Leu Lys Leu Lys Ala Gln
1               5                   10                  15

Leu Gly Pro Asp Glu Ser Lys Gln Lys Phe Val Leu Lys Thr Pro Lys
            20                  25                  30

Gly Thr Arg Asp Tyr Ser Pro Arg Gln Met Ala Val Arg Glu Lys Val
        35                  40                  45

Phe Asp Val Ile
    50

<210> SEQ ID NO 95
<211> LENGTH: 51
<212> TYPE: PRT
<213> ORGANISM: Homo sapiens

<400> SEQUENCE: 95

Leu Ile Glu Glu Glu Val Ala Lys Leu Leu Lys Leu Lys Ala Gln Leu
1               5                   10                  15

Gly Pro Asp Glu Ser Lys Gln Lys Phe Val Leu Lys Thr Pro Lys Gly
            20                  25                  30

Thr Arg Asp Tyr Ser Pro Arg Gln Met Ala Val Arg Glu Lys Val Phe
        35                  40                  45

Asp Val Ile
    50

<210> SEQ ID NO 96
<211> LENGTH: 50
<212> TYPE: PRT
<213> ORGANISM: Homo sapiens

<400> SEQUENCE: 96

Ile Glu Glu Glu Val Ala Lys Leu Leu Lys Leu Lys Ala Gln Leu Gly
1               5                   10                  15

Pro Asp Glu Ser Lys Gln Lys Phe Val Leu Lys Thr Pro Lys Gly Thr
            20                  25                  30

Arg Asp Tyr Ser Pro Arg Gln Met Ala Val Arg Glu Lys Val Phe Asp
        35                  40                  45

Val Ile
    50

<210> SEQ ID NO 97
<211> LENGTH: 49
<212> TYPE: PRT
<213> ORGANISM: Homo sapiens

<400> SEQUENCE: 97

Glu Glu Glu Val Ala Lys Leu Leu Lys Leu Lys Ala Gln Leu Gly Pro
1               5                   10                  15

Asp Glu Ser Lys Gln Lys Phe Val Leu Lys Thr Pro Lys Gly Thr Arg
            20                  25                  30

Asp Tyr Ser Pro Arg Gln Met Ala Val Arg Glu Lys Val Phe Asp Val
        35                  40                  45

Ile

<210> SEQ ID NO 98
<211> LENGTH: 48
<212> TYPE: PRT
<213> ORGANISM: Homo sapiens

<400> SEQUENCE: 98

Glu Glu Val Ala Lys Leu Leu Lys Leu Lys Ala Gln Leu Gly Pro Asp
1 5 10 15

Glu Ser Lys Gln Lys Phe Val Leu Lys Thr Pro Lys Gly Thr Arg Asp
20 25 30

Tyr Ser Pro Arg Gln Met Ala Val Arg Glu Lys Val Phe Asp Val Ile
35 40 45

<210> SEQ ID NO 99
<211> LENGTH: 47
<212> TYPE: PRT
<213> ORGANISM: Homo sapiens

<400> SEQUENCE: 99

Glu Val Ala Lys Leu Leu Lys Leu Lys Ala Gln Leu Gly Pro Asp Glu
1 5 10 15

Ser Lys Gln Lys Phe Val Leu Lys Thr Pro Lys Gly Thr Arg Asp Tyr
20 25 30

Ser Pro Arg Gln Met Ala Val Arg Glu Lys Val Phe Asp Val Ile
35 40 45

<210> SEQ ID NO 100
<211> LENGTH: 46
<212> TYPE: PRT
<213> ORGANISM: Homo sapiens

<400> SEQUENCE: 100

Val Ala Lys Leu Leu Lys Leu Lys Ala Gln Leu Gly Pro Asp Glu Ser
1 5 10 15

Lys Gln Lys Phe Val Leu Lys Thr Pro Lys Gly Thr Arg Asp Tyr Ser
20 25 30

Pro Arg Gln Met Ala Val Arg Glu Lys Val Phe Asp Val Ile
35 40 45

<210> SEQ ID NO 101
<211> LENGTH: 45
<212> TYPE: PRT
<213> ORGANISM: Homo sapiens

<400> SEQUENCE: 101

Ala Lys Leu Leu Lys Leu Lys Ala Gln Leu Gly Pro Asp Glu Ser Lys
1 5 10 15

Gln Lys Phe Val Leu Lys Thr Pro Lys Gly Thr Arg Asp Tyr Ser Pro
20 25 30

Arg Gln Met Ala Val Arg Glu Lys Val Phe Asp Val Ile
35 40 45

<210> SEQ ID NO 102
<211> LENGTH: 44
<212> TYPE: PRT
<213> ORGANISM: Homo sapiens

<400> SEQUENCE: 102

Lys Leu Leu Lys Leu Lys Ala Gln Leu Gly Pro Asp Glu Ser Lys Gln
1 5 10 15

Lys Phe Val Leu Lys Thr Pro Lys Gly Thr Arg Asp Tyr Ser Pro Arg
20 25 30

Gln Met Ala Val Arg Glu Lys Val Phe Asp Val Ile
35 40

```
<210> SEQ ID NO 103
<211> LENGTH: 43
<212> TYPE: PRT
<213> ORGANISM: Homo sapiens

<400> SEQUENCE: 103

Leu Leu Lys Leu Lys Ala Gln Leu Gly Pro Asp Glu Ser Lys Gln Lys
1               5                   10                  15

Phe Val Leu Lys Thr Pro Lys Gly Thr Arg Asp Tyr Ser Pro Arg Gln
            20                  25                  30

Met Ala Val Arg Glu Lys Val Phe Asp Val Ile
        35                  40


<210> SEQ ID NO 104
<211> LENGTH: 42
<212> TYPE: PRT
<213> ORGANISM: Homo sapiens

<400> SEQUENCE: 104

Leu Lys Leu Lys Ala Gln Leu Gly Pro Asp Glu Ser Lys Gln Lys Phe
1               5                   10                  15

Val Leu Lys Thr Pro Lys Gly Thr Arg Asp Tyr Ser Pro Arg Gln Met
            20                  25                  30

Ala Val Arg Glu Lys Val Phe Asp Val Ile
        35                  40


<210> SEQ ID NO 105
<211> LENGTH: 41
<212> TYPE: PRT
<213> ORGANISM: Homo sapiens

<400> SEQUENCE: 105

Lys Leu Lys Ala Gln Leu Gly Pro Asp Glu Ser Lys Gln Lys Phe Val
1               5                   10                  15

Leu Lys Thr Pro Lys Gly Thr Arg Asp Tyr Ser Pro Arg Gln Met Ala
            20                  25                  30

Val Arg Glu Lys Val Phe Asp Val Ile
        35                  40


<210> SEQ ID NO 106
<211> LENGTH: 40
<212> TYPE: PRT
<213> ORGANISM: Homo sapiens

<400> SEQUENCE: 106

Leu Lys Ala Gln Leu Gly Pro Asp Glu Ser Lys Gln Lys Phe Val Leu
1               5                   10                  15

Lys Thr Pro Lys Gly Thr Arg Asp Tyr Ser Pro Arg Gln Met Ala Val
            20                  25                  30

Arg Glu Lys Val Phe Asp Val Ile
        35                  40


<210> SEQ ID NO 107
<211> LENGTH: 275
<212> TYPE: PRT
<213> ORGANISM: Artificial Sequence
<220> FEATURE:
<223> OTHER INFORMATION: HRS-Fc fusion protein (C-terminal Fc fusion)

<400> SEQUENCE: 107

Met Ala Glu Arg Ala Ala Leu Glu Glu Leu Val Lys Leu Gln Gly Glu
```

-continued

```
1               5                   10                  15

Arg Val Arg Gly Leu Lys Gln Gln Lys Ala Ser Ala Glu Leu Ile Glu
            20                  25                  30

Glu Glu Val Ala Lys Leu Leu Lys Leu Lys Ala Gln Leu Gly Pro Asp
        35                  40                  45

Asp Lys Thr His Thr Cys Pro Pro Cys Pro Ala Pro Glu Leu Leu Gly
    50                  55                  60

Gly Pro Ser Val Phe Leu Phe Pro Pro Lys Pro Lys Asp Thr Leu Met
65                  70                  75                  80

Ile Ser Arg Thr Pro Glu Val Thr Cys Val Val Val Asp Val Ser His
                85                  90                  95

Glu Asp Pro Glu Val Lys Phe Asn Trp Tyr Val Asp Gly Val Glu Val
            100                 105                 110

His Asn Ala Lys Thr Lys Pro Arg Glu Glu Gln Tyr Asn Ser Thr Tyr
        115                 120                 125

Arg Val Val Ser Val Leu Thr Val Leu His Gln Asp Trp Leu Asn Gly
    130                 135                 140

Lys Glu Tyr Lys Cys Lys Val Ser Asn Lys Ala Leu Pro Ala Pro Ile
145                 150                 155                 160

Glu Lys Thr Ile Ser Lys Ala Lys Gly Gln Pro Arg Glu Pro Gln Val
                165                 170                 175

Tyr Thr Leu Pro Pro Ser Arg Glu Glu Met Thr Lys Asn Gln Val Ser
            180                 185                 190

Leu Thr Cys Leu Val Lys Gly Phe Tyr Pro Ser Asp Ile Ala Val Glu
        195                 200                 205

Trp Glu Ser Asn Gly Gln Pro Glu Asn Asn Tyr Lys Thr Thr Pro Pro
    210                 215                 220

Val Leu Asp Ser Asp Gly Ser Phe Phe Leu Tyr Ser Lys Leu Thr Val
225                 230                 235                 240

Asp Lys Ser Arg Trp Gln Gln Gly Asn Val Phe Ser Cys Ser Val Met
                245                 250                 255

His Glu Ala Leu His Asn His Tyr Thr Gln Lys Ser Leu Ser Leu Ser
            260                 265                 270

Pro Gly Lys
        275


<210> SEQ ID NO 108
<211> LENGTH: 275
<212> TYPE: PRT
<213> ORGANISM: Artificial Sequence
<220> FEATURE:
<223> OTHER INFORMATION: HRS-Fc fusion protein (N-terminal Fc fusion)

<400> SEQUENCE: 108

Met Asp Lys Thr His Thr Cys Pro Pro Cys Pro Ala Pro Glu Leu Leu
1               5                   10                  15

Gly Gly Pro Ser Val Phe Leu Phe Pro Pro Lys Pro Lys Asp Thr Leu
            20                  25                  30

Met Ile Ser Arg Thr Pro Glu Val Thr Cys Val Val Val Asp Val Ser
        35                  40                  45

His Glu Asp Pro Glu Val Lys Phe Asn Trp Tyr Val Asp Gly Val Glu
    50                  55                  60

Val His Asn Ala Lys Thr Lys Pro Arg Glu Glu Gln Tyr Asn Ser Thr
65                  70                  75                  80

Tyr Arg Val Val Ser Val Leu Thr Val Leu His Gln Asp Trp Leu Asn
```

```
                85                  90                  95

Gly Lys Glu Tyr Lys Cys Lys Val Ser Asn Lys Ala Leu Pro Ala Pro
            100                 105                 110

Ile Glu Lys Thr Ile Ser Lys Ala Lys Gly Gln Pro Arg Glu Pro Gln
        115                 120                 125

Val Tyr Thr Leu Pro Pro Ser Arg Glu Glu Met Thr Lys Asn Gln Val
    130                 135                 140

Ser Leu Thr Cys Leu Val Lys Gly Phe Tyr Pro Ser Asp Ile Ala Val
145                 150                 155                 160

Glu Trp Glu Ser Asn Gly Gln Pro Glu Asn Asn Tyr Lys Thr Thr Pro
                165                 170                 175

Pro Val Leu Asp Ser Asp Gly Ser Phe Phe Leu Tyr Ser Lys Leu Thr
            180                 185                 190

Val Asp Lys Ser Arg Trp Gln Gln Gly Asn Val Phe Ser Cys Ser Val
        195                 200                 205

Met His Glu Ala Leu His Asn His Tyr Thr Gln Lys Ser Leu Ser Leu
    210                 215                 220

Ser Pro Gly Lys Ala Glu Arg Ala Ala Leu Glu Glu Leu Val Lys Leu
225                 230                 235                 240

Gln Gly Glu Arg Val Arg Gly Leu Lys Gln Gln Lys Ala Ser Ala Glu
                245                 250                 255

Leu Ile Glu Glu Glu Val Ala Lys Leu Leu Lys Leu Lys Ala Gln Leu
            260                 265                 270

Gly Pro Asp
        275


<210> SEQ ID NO 109
<211> LENGTH: 733
<212> TYPE: PRT
<213> ORGANISM: Artificial Sequence
<220> FEATURE:
<223> OTHER INFORMATION: HRS-Fc fusion protein (C-terminal Fc fusion)

<400> SEQUENCE: 109

Met Ala Glu Arg Ala Ala Leu Glu Glu Leu Val Lys Leu Gln Gly Glu
1               5                   10                  15

Arg Val Arg Gly Leu Lys Gln Gln Lys Ala Ser Ala Glu Leu Ile Glu
            20                  25                  30

Glu Glu Val Ala Lys Leu Leu Lys Leu Lys Ala Gln Leu Gly Pro Asp
        35                  40                  45

Glu Ser Lys Gln Lys Phe Val Leu Lys Thr Pro Lys Gly Thr Arg Asp
    50                  55                  60

Tyr Ser Pro Arg Gln Met Ala Val Arg Glu Lys Val Phe Asp Val Ile
65                  70                  75                  80

Ile Arg Cys Phe Lys Arg His Gly Ala Glu Val Ile Asp Thr Pro Val
                85                  90                  95

Phe Glu Leu Lys Glu Thr Leu Met Gly Lys Tyr Gly Glu Asp Ser Lys
            100                 105                 110

Leu Ile Tyr Asp Leu Lys Asp Gln Gly Gly Glu Leu Leu Ser Leu Arg
        115                 120                 125

Tyr Asp Leu Thr Val Pro Phe Ala Arg Tyr Leu Ala Met Asn Lys Leu
    130                 135                 140

Thr Asn Ile Lys Arg Tyr His Ile Ala Lys Val Tyr Arg Arg Asp Asn
145                 150                 155                 160

Pro Ala Met Thr Arg Gly Arg Tyr Arg Glu Phe Tyr Gln Cys Asp Phe
```

-continued

```
                165                 170                 175

Asp Ile Ala Gly Asn Phe Asp Pro Met Ile Pro Asp Ala Glu Cys Leu
            180                 185                 190

Lys Ile Met Cys Glu Ile Leu Ser Ser Leu Gln Ile Gly Asp Phe Leu
        195                 200                 205

Val Lys Val Asn Asp Arg Arg Ile Leu Asp Gly Met Phe Ala Ile Cys
    210                 215                 220

Gly Val Ser Asp Ser Lys Phe Arg Thr Ile Cys Ser Ser Val Asp Lys
225                 230                 235                 240

Leu Asp Lys Val Ser Trp Glu Glu Val Lys Asn Glu Met Val Gly Glu
                245                 250                 255

Lys Gly Leu Ala Pro Glu Val Ala Asp Arg Ile Gly Asp Tyr Val Gln
            260                 265                 270

Gln His Gly Gly Val Ser Leu Val Glu Gln Leu Leu Gln Asp Pro Lys
        275                 280                 285

Leu Ser Gln Asn Lys Gln Ala Leu Glu Gly Leu Gly Asp Leu Lys Leu
    290                 295                 300

Leu Phe Glu Tyr Leu Thr Leu Phe Gly Ile Asp Asp Lys Ile Ser Phe
305                 310                 315                 320

Asp Leu Ser Leu Ala Arg Gly Leu Asp Tyr Tyr Thr Gly Val Ile Tyr
                325                 330                 335

Glu Ala Val Leu Leu Gln Thr Pro Ala Gln Ala Gly Glu Glu Pro Leu
            340                 345                 350

Gly Val Gly Ser Val Ala Ala Gly Gly Arg Tyr Asp Gly Leu Val Gly
        355                 360                 365

Met Phe Asp Pro Lys Gly Arg Lys Val Pro Cys Val Gly Leu Ser Ile
    370                 375                 380

Gly Val Glu Arg Ile Phe Ser Ile Val Glu Gln Arg Leu Glu Ala Leu
385                 390                 395                 400

Glu Glu Lys Ile Arg Thr Thr Glu Thr Gln Val Leu Val Ala Ser Ala
                405                 410                 415

Gln Lys Lys Leu Leu Glu Glu Arg Leu Lys Leu Val Ser Glu Leu Trp
            420                 425                 430

Asp Ala Gly Ile Lys Ala Glu Leu Leu Tyr Lys Lys Asn Pro Lys Leu
        435                 440                 445

Leu Asn Gln Leu Gln Tyr Cys Glu Glu Ala Gly Ile Pro Leu Val Ala
    450                 455                 460

Ile Ile Gly Glu Gln Glu Leu Lys Asp Gly Val Ile Lys Leu Arg Ser
465                 470                 475                 480

Val Thr Ser Arg Glu Glu Val Asp Val Arg Arg Glu Asp Leu Val Glu
                485                 490                 495

Glu Ile Lys Arg Arg Thr Gly Gln Pro Leu Asp Lys Thr His Thr Cys
            500                 505                 510

Pro Pro Cys Pro Ala Pro Glu Leu Leu Gly Gly Pro Ser Val Phe Leu
        515                 520                 525

Phe Pro Pro Lys Pro Lys Asp Thr Leu Met Ile Ser Arg Thr Pro Glu
    530                 535                 540

Val Thr Cys Val Val Val Asp Val Ser His Glu Asp Pro Glu Val Lys
545                 550                 555                 560

Phe Asn Trp Tyr Val Asp Gly Val Glu Val His Asn Ala Lys Thr Lys
                565                 570                 575

Pro Arg Glu Glu Gln Tyr Asn Ser Thr Tyr Arg Val Val Ser Val Leu
            580                 585                 590
```

Thr Val Leu His Gln Asp Trp Leu Asn Gly Lys Glu Tyr Lys Cys Lys
595 600 605

Val Ser Asn Lys Ala Leu Pro Ala Pro Ile Glu Lys Thr Ile Ser Lys
610 615 620

Ala Lys Gly Gln Pro Arg Glu Pro Gln Val Tyr Thr Leu Pro Pro Ser
625 630 635 640

Arg Glu Glu Met Thr Lys Asn Gln Val Ser Leu Thr Cys Leu Val Lys
645 650 655

Gly Phe Tyr Pro Ser Asp Ile Ala Val Glu Trp Glu Ser Asn Gly Gln
660 665 670

Pro Glu Asn Asn Tyr Lys Thr Thr Pro Pro Val Leu Asp Ser Asp Gly
675 680 685

Ser Phe Phe Leu Tyr Ser Lys Leu Thr Val Asp Lys Ser Arg Trp Gln
690 695 700

Gln Gly Asn Val Phe Ser Cys Ser Val Met His Glu Ala Leu His Asn
705 710 715 720

His Tyr Thr Gln Lys Ser Leu Ser Leu Ser Pro Gly Lys
725 730

<210> SEQ ID NO 110
<211> LENGTH: 733
<212> TYPE: PRT
<213> ORGANISM: Artificial Sequence
<220> FEATURE:
<223> OTHER INFORMATION: HRS-Fc fusion protein (N-terminal Fc fusion)

<400> SEQUENCE: 110

Met Asp Lys Thr His Thr Cys Pro Pro Cys Pro Ala Pro Glu Leu Leu
1 5 10 15

Gly Gly Pro Ser Val Phe Leu Phe Pro Pro Lys Pro Lys Asp Thr Leu
20 25 30

Met Ile Ser Arg Thr Pro Glu Val Thr Cys Val Val Val Asp Val Ser
35 40 45

His Glu Asp Pro Glu Val Lys Phe Asn Trp Tyr Val Asp Gly Val Glu
50 55 60

Val His Asn Ala Lys Thr Lys Pro Arg Glu Glu Gln Tyr Asn Ser Thr
65 70 75 80

Tyr Arg Val Val Ser Val Leu Thr Val Leu His Gln Asp Trp Leu Asn
85 90 95

Gly Lys Glu Tyr Lys Cys Lys Val Ser Asn Lys Ala Leu Pro Ala Pro
100 105 110

Ile Glu Lys Thr Ile Ser Lys Ala Lys Gly Gln Pro Arg Glu Pro Gln
115 120 125

Val Tyr Thr Leu Pro Pro Ser Arg Glu Glu Met Thr Lys Asn Gln Val
130 135 140

Ser Leu Thr Cys Leu Val Lys Gly Phe Tyr Pro Ser Asp Ile Ala Val
145 150 155 160

Glu Trp Glu Ser Asn Gly Gln Pro Glu Asn Asn Tyr Lys Thr Thr Pro
165 170 175

Pro Val Leu Asp Ser Asp Gly Ser Phe Phe Leu Tyr Ser Lys Leu Thr
180 185 190

Val Asp Lys Ser Arg Trp Gln Gln Gly Asn Val Phe Ser Cys Ser Val
195 200 205

Met His Glu Ala Leu His Asn His Tyr Thr Gln Lys Ser Leu Ser Leu
210 215 220

```
Ser Pro Gly Lys Ala Glu Arg Ala Ala Leu Glu Glu Leu Val Lys Leu
225                 230                 235                 240

Gln Gly Glu Arg Val Arg Gly Leu Lys Gln Gln Lys Ala Ser Ala Glu
                245                 250                 255

Leu Ile Glu Glu Glu Val Ala Lys Leu Leu Lys Leu Lys Ala Gln Leu
            260                 265                 270

Gly Pro Asp Glu Ser Lys Gln Lys Phe Val Leu Lys Thr Pro Lys Gly
        275                 280                 285

Thr Arg Asp Tyr Ser Pro Arg Gln Met Ala Val Arg Glu Lys Val Phe
    290                 295                 300

Asp Val Ile Ile Arg Cys Phe Lys Arg His Gly Ala Glu Val Ile Asp
305                 310                 315                 320

Thr Pro Val Phe Glu Leu Lys Glu Thr Leu Met Gly Lys Tyr Gly Glu
                325                 330                 335

Asp Ser Lys Leu Ile Tyr Asp Leu Lys Asp Gln Gly Gly Glu Leu Leu
            340                 345                 350

Ser Leu Arg Tyr Asp Leu Thr Val Pro Phe Ala Arg Tyr Leu Ala Met
        355                 360                 365

Asn Lys Leu Thr Asn Ile Lys Arg Tyr His Ile Ala Lys Val Tyr Arg
    370                 375                 380

Arg Asp Asn Pro Ala Met Thr Arg Gly Arg Tyr Arg Glu Phe Tyr Gln
385                 390                 395                 400

Cys Asp Phe Asp Ile Ala Gly Asn Phe Asp Pro Met Ile Pro Asp Ala
                405                 410                 415

Glu Cys Leu Lys Ile Met Cys Glu Ile Leu Ser Ser Leu Gln Ile Gly
            420                 425                 430

Asp Phe Leu Val Lys Val Asn Asp Arg Arg Ile Leu Asp Gly Met Phe
        435                 440                 445

Ala Ile Cys Gly Val Ser Asp Ser Lys Phe Arg Thr Ile Cys Ser Ser
    450                 455                 460

Val Asp Lys Leu Asp Lys Val Ser Trp Glu Glu Val Lys Asn Glu Met
465                 470                 475                 480

Val Gly Glu Lys Gly Leu Ala Pro Glu Val Ala Asp Arg Ile Gly Asp
                485                 490                 495

Tyr Val Gln Gln His Gly Gly Val Ser Leu Val Glu Gln Leu Leu Gln
            500                 505                 510

Asp Pro Lys Leu Ser Gln Asn Lys Gln Ala Leu Glu Gly Leu Gly Asp
        515                 520                 525

Leu Lys Leu Leu Phe Glu Tyr Leu Thr Leu Phe Gly Ile Asp Asp Lys
    530                 535                 540

Ile Ser Phe Asp Leu Ser Leu Ala Arg Gly Leu Asp Tyr Tyr Thr Gly
545                 550                 555                 560

Val Ile Tyr Glu Ala Val Leu Leu Gln Thr Pro Ala Gln Ala Gly Glu
                565                 570                 575

Glu Pro Leu Gly Val Gly Ser Val Ala Ala Gly Gly Arg Tyr Asp Gly
            580                 585                 590

Leu Val Gly Met Phe Asp Pro Lys Gly Arg Lys Val Pro Cys Val Gly
        595                 600                 605

Leu Ser Ile Gly Val Glu Arg Ile Phe Ser Ile Val Glu Gln Arg Leu
    610                 615                 620

Glu Ala Leu Glu Glu Lys Ile Arg Thr Thr Glu Thr Gln Val Leu Val
625                 630                 635                 640
```

-continued

```
Ala Ser Ala Gln Lys Lys Leu Leu Glu Glu Arg Leu Lys Leu Val Ser
                645                 650                 655

Glu Leu Trp Asp Ala Gly Ile Lys Ala Glu Leu Leu Tyr Lys Lys Asn
            660                 665                 670

Pro Lys Leu Leu Asn Gln Leu Gln Tyr Cys Glu Glu Ala Gly Ile Pro
        675                 680                 685

Leu Val Ala Ile Ile Gly Glu Gln Glu Leu Lys Asp Gly Val Ile Lys
    690                 695                 700

Leu Arg Ser Val Thr Ser Arg Glu Glu Val Asp Val Arg Arg Glu Asp
705                 710                 715                 720

Leu Val Glu Glu Ile Lys Arg Arg Thr Gly Gln Pro Leu
                725                 730


<210> SEQ ID NO 111
<211> LENGTH: 1527
<212> TYPE: DNA
<213> ORGANISM: Artificial Sequence
<220> FEATURE:
<223> OTHER INFORMATION: Codon optimized version of HRS

<400> SEQUENCE: 111

atggcagagc gtgcggcgct ggaggagctg gtgaaacttc agggagagcg cgtgcgaggc      60

ctcaagcagc agaaggccag cgccgagctg atcgaggagg aggtggcgaa actcctgaaa     120

ctgaaggcac agctgggtcc tgatgaaagc aaacagaaat ttgtgctcaa aaccccccaag    180

ggcacaagag actatagtcc ccggcagatg gcagttcgcg agaaggtgtt tgacgtaatc     240

atccgttgct tcaagcgcca cggtgcagaa gtcattgata cacctgtatt tgaactaaag     300

gaaacactga tgggaaagta tggggaagac tccaagctta tctatgacct gaaggaccag     360

ggcggggagc tcctgtccct tcgctatgac ctcactgttc cttttgctcg gtatttggca     420

atgaataaac tgaccaacat taaacgctac cacatagcaa aggtatatcg gcgggataac     480

ccagccatga cccgtggccg ataccgggaa ttctaccagt gtgattttga cattgctggg     540

aactttgatc ccatgatccc tgatgcagag tgcctgaaga tcatgtgcga gatcctgagt     600

tcacttcaga taggcgactt cctggtcaag gtaaacgatc gacgcattct agatgggatg     660

tttgctatct gtggtgtttc tgacagcaag ttccgtacca tctgctcctc agtagacaag     720

ctggacaagg tgtcctggga agaggtgaag aatgagatgg tgggagagaa gggccttgca     780

cctgaggtgg ctgaccgcat tggggactat gtccagcaac atggtggggt atccctggtg     840

gaacagctgc tccaggatcc taaactatcc caaaacaagc aggccttgga gggcctggga     900

gacctgaagt tgctctttga gtacctgacc ctatttggca ttgatgacaa aatctccttt     960

gacctgagcc ttgctcgagg gctggattac tacactgggg tgatctatga ggcagtgctg    1020

ctacagaccc cagcccaggc aggggaagag cccctgggtg tgggcagtgt ggctgctgga    1080

ggacgctatg atgggctagt gggcatgttc gaccccaaag ggcgcaaggt gccatgtgtg    1140

gggctcagca ttggggtgga gcggattttc tccatcgtgg aacagagact agaggctttg    1200

gaggagaaga tacggaccac ggagacacag gtgcttgtgg catctgcaca gaagaagctg    1260

ctagaggaaa gactaaagct tgtctcagaa ctgtgggatg ctgggatcaa ggctgagctg    1320

ctgtacaaga agaacccaaa gctactgaac cagttacagt actgtgagga ggcaggcatc    1380

ccactggtgg ctatcatcgg cgagcaggaa ctcaaggatg gggtcatcaa gctccgttca    1440

gtgacgagca gggaagaggt ggatgtccga agagaagacc ttgtggagga aatcaaaagg    1500

agaacaggcc agcccctctg catctgc                                        1527
```

<210> SEQ ID NO 112
<211> LENGTH: 423
<212> TYPE: DNA
<213> ORGANISM: Artificial Sequence
<220> FEATURE:
<223> OTHER INFORMATION: Codon optimized version of HRS

<400> SEQUENCE: 112
atggcagaac gtgccgccct ggaagagctg gtaaaactgc aaggcgagcg tgttcgtggt 60
ctgaaacagc agaaagcaag cgctgaactg atcgaagaag aagtggcgaa actgctgaaa 120
ctgaaagcac agctgggtcc tgatgaatca aaacaaaaat tcgtcctgaa aactccgaaa 180
ggaacccgtg actattctcc tcgtcaaatg gccgtccgtg aaaaagtgtt cgacgtgatc 240
attcgctgct ttaaacgcca tggtgccgaa gtgattgata ccccggtgtt tgagctgaaa 300
gagacactga tgggcaaata tggtgaggac agcaaactga tttatgacct gaaagatcag 360
ggtggtgaac tgctgagtct gcgctatgat ctgacagttc cgtttgcccg ttatctggca 420
atg 423

<210> SEQ ID NO 113
<211> LENGTH: 1224
<212> TYPE: DNA
<213> ORGANISM: Artificial Sequence
<220> FEATURE:
<223> OTHER INFORMATION: Codon optimized version of HRS

<400> SEQUENCE: 113
atggcagaac gtgccgccct ggaagagctg gtaaaactgc aaggcgagcg tgttcgtggt 60
ctgaaacagc agaaagcaag cgctgaactg atcgaagaag aagtggcgaa actgctgaaa 120
ctgaaagcac agctgggtcc tgatgaatca aaacaaaaat tcgtcctgaa aactccgaaa 180
ggaacccgtg actattctcc tcgtcaaatg gccgtccgtg aaaaagtgtt cgacgtgatc 240
attcgctgct ttaaacgcca tggtgccgaa gtgattgata ccccggtgtt tgagctgaaa 300
gagacactga tgggcaaata tggtgaggac agcaaactga tttatgacct gaaagatcag 360
ggtggtgaac tgctgagtct gcgctatgat ctgacagttc cgtttgcccg ttatctggca 420
atgaataaac tgaccaacat taaacgctat cacattgcta aagtctatcg ccgtgacaat 480
cctgctatga cccgtggtcg ttatcgtgag ttctatcagt gtgacttcga tattgccggc 540
aactttgatc cgatgatccc ggatgctgaa tgcctgaaaa tcatgtgtga gatcctgagc 600
agtctgcaga ttggcgattt cctggtgaaa gtcaacgatc gccgtattct ggatggcatg 660
ttcgccatct gtggtgttag cgactccaaa ttccgtacca tctgtagtag tgtggacaaa 720
ctggataaag tgagctggga ggaggtgaaa aacgaaatgg tgggcgagaa aggtctggct 780
cctgaagtgg ctgaccgtat tggtgattat gtccagcagc acggtggagt atcactggtt 840
gagcaactgc tgcaagaccc taaactgagt cagaataaac aggccctgga gggactggga 900
gatctgaaac tgctgttcga gtatctgacc ctgttcggta tcgatgacaa aatctccttt 960
gacctgtcac tggctcgtgg actggactat tataccggcg tgatctatga agctgtactg 1020
ctgcaaactc cagcacaagc aggtgaagag cctctgggtg tgggtagtgt agccgctggg 1080
ggacgttatg atggactggt ggggatgttc gaccctaaag gccgtaaagt tccgtgtgtg 1140
ggtctgagta tcggtgttga gcgtatcttt tccatcgtcg agcaacgtct ggaagcactg 1200
gaggaaaaaa tccgtacgac cgaa 1224

<210> SEQ ID NO 114
<211> LENGTH: 339
<212> TYPE: DNA
<213> ORGANISM: Artificial Sequence
<220> FEATURE:
<223> OTHER INFORMATION: Codon optimized version of HRS

<400> SEQUENCE: 114
atggcagaac gtgccgccct ggaagagctg gtaaaactgc aaggcgagcg tgttcgtggt 60
ctgaaacagc agaaagcaag cgctgaactg atcgaagaag aagtggcgaa actgctgaaa 120
ctgaaagcac agctgggtcc tgatgaatca aaacaaaaat tcgtcctgaa aactccgaaa 180
ggaacccgtg actattctcc tcgtcaaatg gccgtccgtg aaaaagtgtt cgacgtgatc 240
attcgctgct ttaaacgcca tggtgccgaa gtgattgata ccccggtgtt tgagctgaaa 300
gagacactga tgggcaaata tggtgaggac agcaaactg 339

<210> SEQ ID NO 115
<211> LENGTH: 180
<212> TYPE: DNA
<213> ORGANISM: Artificial Sequence
<220> FEATURE:
<223> OTHER INFORMATION: Codon optimized version of HRS

<400> SEQUENCE: 115
atggcagaac gtgccgccct ggaagagctg gtaaaactgc aaggcgagcg tgttcgtggt 60
ctgaaacagc agaaagcaag cgctgaactg atcgaagaag aagtggcgaa actgctgaaa 120
ctgaaagcac agctgggtcc tgatgaatca aaacaaaaat tcgtcctgaa aactccgaag 180

<210> SEQ ID NO 116
<211> LENGTH: 1518
<212> TYPE: DNA
<213> ORGANISM: Artificial Sequence
<220> FEATURE:
<223> OTHER INFORMATION: Codon optimized version of HRS

<400> SEQUENCE: 116
atggcagagc gtgcggcgct ggaggagctg gtgaaacttc agggagagcg cgtgcgaggc 60
ctcaagcagc agaaggccag cgccgagctg atcgaggagg aggtggcgaa actcctgaaa 120
ctgaaggcac agctgggtcc tgatgaaagc aaacagaaat ttgtgctcaa aacccccaag 180
ggcacaagag actatagtcc ccggcagatg gcagttcgcg agaaggtgtt tgacgtaatc 240
atccgttgct tcaagcgcca cggtgcagaa gtcattgata cacctgtatt tgaactaaag 300
gaaacactga tgggaaagta tggggaagac tccaagctta tctatgacct gaaggaccag 360
ggcggggagc tcctgtccct tcgctatgac ctcactgttc cttttgctcg gtatttggca 420
atgaataaac tgaccaacat taaacgctac cacatagcaa aggtatatcg gcgggataac 480
ccagccatga cccgtggccg ataccgggaa ttctaccagt gtgattttga cattgctggg 540
aactttgatc ccatgatccc tgatgcagag tgcctgaaga tcatgtgcga gatcctgagt 600
tcacttcaga taggcgactt cctggtcaag gtaaacgatc gacgcattct agatgggatg 660
tttgctatct gtggtgtttc tgacagcaag ttccgtacca tctgctcctc agtagacaag 720
ctggacaagg tgtcctggga agaggtgaag aatgagatgg tgggagagaa gggccttgca 780
cctgaggtgg ctgaccgcat tggggactat gtccagcaac atggtggggt atccctggtg 840
gaacagctgc tccaggatcc taaactatcc caaaacaagc aggccttgga gggcctggga 900
gacctgaagt tgctctttga gtacctgacc ctatttggca ttgatgacaa aatctccttt 960

-continued gacctgagcc ttgctcgagg gctggattac tacactgggg tgatctatga ggcagtgctg 1020
ctacagaccc cagcccaggc aggggaagag cccctgggtg tgggcagtgt ggctgctgga 1080
ggacgctatg atgggctagt gggcatgttc gaccccaaag ggcgcaaggt gccatgtgtg 1140
gggctcagca ttggggtgga gcggattttc tccatcgtgg aacagagact agaggctttg 1200
gaggagaaga tacggaccac ggagacacag gtgcttgtgg catctgcaca gaagaagctg 1260
ctagaggaaa gactaaagct tgtctcagaa ctgtgggatg ctgggatcaa ggctgagctg 1320
ctgtacaaga agaacccaaa gctactgaac cagttacagt actgtgagga ggcaggcatc 1380
ccactggtgg ctatcatcgg cgagcaggaa ctcaaggatg gggtcatcaa gctccgttca 1440
gtgacgagca gggaagaggt ggatgtccga agagaagacc ttgtggagga aatcaaaagg 1500
agaacaggcc agcccctc 1518

<210> SEQ ID NO 117
<211> LENGTH: 144
<212> TYPE: DNA
<213> ORGANISM: Artificial Sequence
<220> FEATURE:
<223> OTHER INFORMATION: Codon Optimized version of HRS

<400> SEQUENCE: 117
atggcagaac gtgccgccct ggaagagctg gtaaaactgc aaggcgagcg tgttcgtggt 60
ctgaaacagc agaaagcaag cgctgaactg atcgaagaag aagtggcgaa actgctgaaa 120
ctgaaagcac agctgggtcc tgat 144

<210> SEQ ID NO 118
<211> LENGTH: 429
<212> TYPE: DNA
<213> ORGANISM: Artificial Sequence
<220> FEATURE:
<223> OTHER INFORMATION: Codon optimized version of HRS

<400> SEQUENCE: 118
tgcctgaaaa tcatgtgtga gatcctgagt agtctgcaaa ttggcgactt tctggtcaaa 60
gtgaacgatc gccgtattct ggatggcatg ttcgccatct gtggtgttag cgactccaaa 120
ttccgtacaa tctgtagcag cgtggacaaa ctggataaag tgtcctggga agaggtgaaa 180
aacgaaatgg tgggtgaaaa aggtctggct ccggaggttg ctgaccgtat cggtgattat 240
gttcagcagc acggcggtgt tagtctggtt gaacaactgc tgcaagaccc gaaactgtct 300
cagaacaaac aggccctgga aggactggga gatctgaaac tgctgttcga gtatctgacg 360
ctgttcggca ttgatgacaa aatttctttc gacctgtcac tggcacgtgg actggactat 420
tataccggt 429

<210> SEQ ID NO 119
<211> LENGTH: 315
<212> TYPE: DNA
<213> ORGANISM: Artificial Sequence
<220> FEATURE:
<223> OTHER INFORMATION: Codon optimized version of HRS

<400> SEQUENCE: 119
cgtaccaccg aaacccaagt tctggttgcc tcagctcaga aaaaactgct ggaagaacgc 60
ctgaaactgg ttagcgaact gtgggatgct ggcattaaag ccgaactgct gtataaaaaa 120
aacccgaaac tgctgaatca gctgcagtat tgtgaggaag cgggtattcc tctggtggcc 180

```
attatcggag aacaggaact gaaagacggc gttattaaac tgcgtagcgt gacctctcgt    240

gaagaagttg acgttcgccg tgaagatctg gtcgaggaaa tcaaacgtcg taccggtcaa    300

cctctgtgta tttgc                                                     315
```

<210> SEQ ID NO 120
<211> LENGTH: 810
<212> TYPE: DNA
<213> ORGANISM: Artificial Sequence
<220> FEATURE:
<223> OTHER INFORMATION: Codon optimized version of HRS

<400> SEQUENCE: 120

```
atggcagaac gtgccgccct ggaagagctg gtaaaactgc aaggcgagcg tgttcgtggt     60

ctgaaacagc agaaagcaag cgctgaactg atcgaagaag aagtggcgaa actgctgaaa    120

ctgaaagcac agctgggtcc tgatgaatca aaacaaaaat tcgtcctgaa aactccgaaa    180

ggaacccgtg actattctcc tcgtcaaatg gccgtccgtg aaaaagtgtt cgacgtgatc    240

attcgctgct ttaaacgcca tggtgccgaa gtgattgata ccccggtgtt tgagctgaaa    300

gagacactga tgggcaaata tggtgaggac agcaaactga tctatgacct gaaagaccaa    360

ggcggtgaac tgctgtccct gcgttatgat ctgactgtgc cgtttgcccg ttatctggcc    420

atgaataaac tgacgaacat taaacgctat cacattgcca aagtgtatcg ccgtgacaat    480

cctgctatga ctcgtggacg ttatcgtgaa ttctatcagt gtgacttcga tattgccggc    540

aacttcgacc ctatgattcc ggatgctgaa tgcctgaaaa tcatgtgtga gatcctgagc    600

agcctgcaaa ttggtgactt cctggtgaaa gtgaatgacc gtcgtatcct ggatggcatg    660

tttgccattt gtggtgtgag cgattccaaa ttccgtacca tctgtagtag tgtggacaaa    720

ctggataaag tgggctatcc gtggtggaac tcttgtagcc gtattctgaa ctatcctaaa    780

accagccgcc cgtggcgtgc ttgggaaact                                     810
```

<210> SEQ ID NO 121
<211> LENGTH: 1185
<212> TYPE: DNA
<213> ORGANISM: Artificial Sequence
<220> FEATURE:
<223> OTHER INFORMATION: Codon optimized version of HRS

<400> SEQUENCE: 121

```
atggcagaac gtgccgccct ggaagagctg gtaaaactgc aaggcgagcg tgttcgtggt     60

ctgaaacagc agaaagcaag cgctgaactg atcgaagaag aagtggcgaa actgctgaaa    120

ctgaaagcac agctgggtcc tgatgaatca aaacaaaaat tcgtcctgaa aactccgaaa    180

gacttcgata ttgccgggaa ttttgaccct atgatccctg atgccgaatg tctgaaaatc    240

atgtgtgaga tcctgagcag tctgcagatt ggtgacttcc tggtgaaagt gaacgatcgc    300

cgtattctgg atggaatgtt tgccatttgt ggcgtgtctg acagcaaatt tcgtacgatc    360

tgtagcagcg tggataaact ggataaagtg agctgggagg aggtgaaaaa tgagatggtg    420

ggcgaaaaag gtctggcacc tgaagtggct gaccgtatcg gtgattatgt tcagcaacat    480

ggcggtgttt ctctggtcga acagctgctg caagacccaa aactgagcca gaacaaacag    540

gcactggaag gactgggtga tctgaaactg ctgtttgagt atctgacgct gtttggcatc    600

gatgacaaaa tctcgtttga cctgagcctg gcacgtggtc tggattatta taccggcgtg    660

atctatgaag ccgtcctgct gcaaactcca gcacaagcag gtgaagaacc tctgggtgtt    720

ggtagtgtag cggcaggcgg acgttatgat ggactggtgg ggatgtttga tccgaaaggc    780
```

-continued cgtaaagttc cgtgtgtcgg tctgagtatc ggggttgagc gtatctttag cattgtggag 840
caacgtctgg aagctctgga ggaaaaaatc cgtaccaccg aaacccaagt tctggttgcc 900
tcagctcaga aaaaactgct ggaagaacgc ctgaaactgg ttagcgaact gtgggatgct 960
ggcattaaag ccgaactgct gtataaaaaa aacccgaaac tgctgaatca gctgcagtat 1020
tgtgaggaag cgggtattcc tctggtggcc attatcggag aacaggaact gaaagacggc 1080
gttattaaac tgcgtagcgt gacctctcgt gaagaagttg acgttcgccg tgaagatctg 1140
gtcgaggaaa tcaaacgtcg taccggtcaa cctctgtgta tttgc 1185

<210> SEQ ID NO 122
<211> LENGTH: 1077
<212> TYPE: DNA
<213> ORGANISM: Artificial Sequence
<220> FEATURE:
<223> OTHER INFORMATION: Codon optimized version of HRS

<400> SEQUENCE: 122
atggcagaac gtgccgccct ggaagagctg gtaaaactgc aaggcgagcg tgttcgtggt 60
ctgaaacagc agaaagcaag cgctgaactg atcgaagaag aagtggcgaa actgctgaaa 120
ctgaaagcac agctgggtcc tgatgaatca aaacaaaaat tcgtcctgaa aactccgaaa 180
gtgaatgatc gccgtatcct ggatggcatg tttgccattt gtggtgtgag cgactcgaaa 240
ttccgtacga tttgctctag cgtcgataaa ctggacaaag tgtcctggga agaggtgaaa 300
aacgagatgg tgggtgagaa aggtctggct cctgaagttg ccgaccgtat tggtgattat 360
gttcagcagc atggcggtgt ttcactggtt gaacaactgc tgcaagaccc gaaactgtct 420
cagaataaac aggcgctgga aggactggga gatctgaaac tgctgtttga gtatctgacc 480
ctgttcggca ttgatgacaa aatcagcttc gacctgagcc tggcacgtgg tctggattat 540
tataccggcg tgatctatga agccgttctg ctgcagacac cagcacaagc aggcgaagaa 600
cctctgggtg ttggttctgt ggcagccggt ggtcgttatg atggactggt aggcatgttc 660
gatccgaaag gccgtaaagt tccgtgtgtg ggactgagta tcggtgttga gcgtatcttt 720
agcatcgtgg aacaacgtct ggaagcgctg gaggagaaaa ttcgtaccac cgaaacccaa 780
gttctggttg cctcagctca gaaaaaactg ctggaagaac gcctgaaact ggttagcgaa 840
ctgtgggatg ctggcattaa agccgaactg ctgtataaaa aaaacccgaa actgctgaat 900
cagctgcagt attgtgagga agcgggtatt cctctggtgg ccattatcgg agaacaggaa 960
ctgaaagacg gcgttattaa actgcgtagc gtgacctctc gtgaagaagt tgacgttcgc 1020
cgtgaagatc tggtcgagga aatcaaacgt cgtaccggtc aacctctgtg tatttgc 1077

<210> SEQ ID NO 123
<211> LENGTH: 1197
<212> TYPE: DNA
<213> ORGANISM: Artificial Sequence
<220> FEATURE:
<223> OTHER INFORMATION: Codon optimized version of HRS

<400> SEQUENCE: 123
atggcagaac gtgccgccct ggaagagctg gtaaaactgc aaggcgagcg tgttcgtggt 60
ctgaaacagc agaaagcaag cgctgaactg atcgaagaag aagtggcgaa actgctgaaa 120
ctgaaagcac agctgggtcc tgatgaatca aaacaaaaat tcgtcctgaa aactccgaaa 180
ggaactcgtg attatagccc tcgccagatg gctgtccgtg aaaaagtgtt cgatgtgatc 240

-continued

```
attcgctgct tcaaacgtca tggtgccgaa gtcattgata ccccggtgtt cgagctgaaa    300

gtgaacgatc gccgtattct ggatggcatg ttcgccattt gtggtgttag cgatagcaaa    360

ttccgtacaa tctgctctag cgtggacaaa ctggacaaag tgagctggga agaggtgaaa    420

aacgagatgg tgggtgagaa aggcctggct cctgaagttg ccgaccgtat cggagattat    480

gttcagcagc atggcggagt ttcactggtt gaacaactgc tgcaagaccc gaaactgtct    540

cagaacaaac aggcactgga aggtctggga gatctgaaac tgctgttcga gtatctgacg    600

ctgttcggta ttgacgacaa aatttccttc gacctgtcgc tggcacgtgg tctggattat    660

tatacaggcg tgatctatga ggctgtactg ctgcagacac cagcacaagc aggtgaagag    720

cctctgggtg ttggttcagt tgctgccggt ggacgttatg acggactggt agggatgttt    780

gacccaaaag gccgtaaagt cccgtgtgta ggactgtcta ttggcgttga gcgtatcttt    840

agcatcgtgg agcaacgtct ggaagctctg gaggagaaaa tccgtaccac cgaaacccaa    900

gttctggttg cctcagctca gaaaaaactg ctggaagaac gcctgaaact ggttagcgaa    960

ctgtgggatg ctggcattaa agccgaactg ctgtataaaa aaaacccgaa actgctgaat   1020

cagctgcagt attgtgagga agcgggtatt cctctggtgg ccattatcgg agaacaggaa   1080

ctgaaagacg gcgttattaa actgcgtagc gtgacctctc gtgaagaagt tgacgttcgc   1140

cgtgaagatc tggtcgagga aatcaaacgt cgtaccggtc aacctctgtg tatttgc      1197
```

<210> SEQ ID NO 124
<211> LENGTH: 1419
<212> TYPE: DNA
<213> ORGANISM: Artificial Sequence
<220> FEATURE:
<223> OTHER INFORMATION: Codon optimized version of HRS

<400> SEQUENCE: 124

```
atggcagaac gtgccgccct ggaagagctg gtaaaactgc aaggcgagcg tgttcgtggt     60

ctgaaacagc agaaagcaag cgctgaactg atcgaagaag aagtggcgaa actgctgaaa    120

ctgaaagcac agctgggtcc tgatgaatca aaacaaaaat tcgtcctgaa aactccgaaa    180

ggaactcgtg attatagccc tcgccagatg gctgtccgtg aaaaagtgtt cgatgtgatc    240

attcgctgct tcaaacgtca tggtgccgaa gtcattgata ccccggtgtt cgagctgaaa    300

gaaaccctga tgggcaaata tggggaagat tccaaactga tctatgacct gaaagaccag    360

ggaggtgaac tgctgtctct gcgctatgac ctgactgttc cttttgctcg ctatctggcc    420

atgaataaac tgaccaacat caaacgctat catatcgcca aagtgtatcg ccgtgacaat    480

ccagcaatga cccgtggtcg ttatcgtgaa ttttatcagt gtgtgaacga tcgccgtatt    540

ctggacggca tgttcgccat ttgtggtgtg tctgactcca aatttcgtac gatctgctca    600

agcgtggaca aactggacaa agtgagctgg gaagaggtga aaaacgagat ggtgggtgag    660

aaaggcctgg ctcctgaagt tgccgaccgt atcggagatt atgttcagca gcatggcgga    720

gtttcactgg ttgaacaact gctgcaagac ccgaaactgt cacagaacaa acaggcactg    780

gaaggtctgg gggatctgaa actgctgttc gagtatctga cgctgttcgg tattgacgac    840

aaaatcagct tcgatctgag cctggcacgt ggtctggact attataccgg cgtgatttat    900

gaagccgttc tgctgcagac tccagcacaa gcaggtgaag agcctctggg tgttggaagt    960

gtggcagccg gtggccgtta tgatggtctg gttggcatgt ttgacccgaa aggccgtaaa   1020

gtcccgtgtg taggactgtc tatcggcgtg gagcgtattt ttagcatcgt ggaacaacgc   1080

ctggaagctc tggaagagaa aatccgtacc accgaaaccc aagttctggt tgcctcagct   1140
```

```
cagaaaaaac tgctggaaga acgcctgaaa ctggttagcg aactgtggga tgctggcatt   1200

aaagccgaac tgctgtataa aaaaaacccg aaactgctga atcagctgca gtattgtgag   1260

gaagcgggta ttcctctggt ggccattatc ggagaacagg aactgaaaga cggcgttatt   1320

aaactgcgta gcgtgacctc tcgtgaagaa gttgacgttc gccgtgaaga tctggtcgag   1380

gaaatcaaac gtcgtaccgg tcaacctctg tgtatttgc                          1419
```

<210> SEQ ID NO 125
<211> LENGTH: 1407
<212> TYPE: DNA
<213> ORGANISM: Artificial Sequence
<220> FEATURE:
<223> OTHER INFORMATION: Codon optimized version of HRS

<400> SEQUENCE: 125

```
atggcagaac gtgccgccct ggaagagctg gtaaaactgc aaggcgagcg tgttcgtggt     60

ctgaaacagc agaaagcaag cgctgaactg atcgaagaag aagtggcgaa actgctgaaa    120

ctgaaagcac agctgggtcc tgatgaatca aaacaaaaat tcgtcctgaa aactccgaaa    180

gaaaccctga tgggcaaata tggcgaagat tccaaactga tctatgacct gaaagaccaa    240

ggcggtgaac tgctgtccct gcgttatgac ctgactgttc cgtttgctcg ttatctggcc    300

atgaataaac tgaccaacat taaacgctat cacattgcca aagtgtatcg ccgtgacaat    360

cctgctatga ctcgtggacg ttatcgtgaa ttctatcagt gtgacttcga tattgccggc    420

aacttcgacc ctatgattcc ggatgctgaa tgcctgaaaa tcatgtgtga gatcctgagc    480

agcctgcaaa ttggtgactt cctggtgaaa gtgaatgacc gtcgtatcct ggatggcatg    540

ttcgccattt gtggtgttag cgattccaaa ttccgtacca tctgtagtag tgtggacaaa    600

ctggataaag tgagctggga agaggtgaaa aacgaaatgg tgggcgaaaa aggtctggca    660

cctgaggttg ctgatcgtat cggtgactat gtccagcagc atggaggtgt ttcactggtt    720

gagcaactgc tgcaagatcc gaaactgtct cagaacaaac aggccctgga aggactgggt    780

gatctgaaac tgctgttcga gtatctgacg ctgttcggta ttgatgacaa aatctcgttc    840

gacctgtctc tggctcgtgg actggattat tatacgggcg taatctatga agctgtcctg    900

ctgcagacac cagcacaagc aggtgaagag cctctgggtg ttggaagtgt tgctgccggt    960

ggtcgctatg acggactggt tggcatgttc gatccgaaag gccgtaaagt tccgtgtgta   1020

ggactgagca ttggcgttga gcgtatcttt tccatcgttg agcaacgtct ggaagcactg   1080

gaagagaaaa tccgtaccac cgaaacccaa gttctggttg cctcagctca gaaaaaactg   1140

ctggaagaac gcctgaaact ggttagcgaa ctgtgggatg ctggcattaa agccgaactg   1200

ctgtataaaa aaaacccgaa actgctgaat cagctgcagt attgtgagga agcgggtatt   1260

cctctggtgg ccattatcgg agaacaggaa ctgaaagacg gcgttattaa actgcgtagc   1320

gtgacctctc gtgaagaagt tgacgttcgc cgtgaagatc tggtcgagga aatcaaacgt   1380

cgtaccggtc aacctctgtg tatttgc                                       1407
```

<210> SEQ ID NO 126
<211> LENGTH: 1305
<212> TYPE: DNA
<213> ORGANISM: Artificial Sequence
<220> FEATURE:
<223> OTHER INFORMATION: Codon optimized version of HRS

<400> SEQUENCE: 126

-continued

```
atggcagaac gtgccgccct ggaagagctg gtaaaactgc aaggcgagcg tgttcgtggt     60

ctgaaacagc agaaagcaag cgctgaactg atcgaagaag aagtggcgaa actgctgaaa    120

ctgaaagcac agctgggtcc tgatgaatca aaacaaaaat tcgtcctgaa aactccgaaa    180

ggaactcgtg attatagccc tcgccagatg gctgtccgtg aaaaagtgtt cgatgtgatc    240

attcgctgct tcaaacgtca tggtgccgaa gtcattgata ccccggtgtt cgagctgaaa    300

gatttcgata ttgccggcaa ctttgatccg atgattccgg atgctgagtg tctgaaaatc    360

atgtgtgaga tcctgagtag tctgcagatt ggggatttcc tggtgaaagt gaacgatcgc    420

cgtattctgg acggcatgtt tgccatttgt ggcgttagcg atagcaaatt ccgtacgatc    480

tgtagcagtg tggacaaact ggataaagtc tcttgggaag aggtcaaaaa cgagatggtt    540

ggtgagaaag gcctggctcc tgaagtggct gaccgtattg gtgattatgt ccagcagcat    600

ggtggtgttt cactggttga acaactgctg caagacccga aactgtctca gaacaaacag    660

gcactggaag gtctgggtga tctgaaactg ctgttcgagt atctgacgct gttcggtatt    720

gacgacaaaa tttccttcga cctgtcactg gcacgtggtc tggattatta tacaggcgta    780

atctatgagg ctgtactgct gcaaactcca gcacaagcag gtgaagaacc tctgggagtt    840

ggtagtgtag cggcaggggg tcgttatgat gggctggtcg ggatgttcga tccaaaaggc    900

cgtaaagtcc cgtgtgttgg tctgtctatt ggcgttgagc gtatcttctc catcgtggag    960

caacgtctgg aagctctgga agaaaaaatc cgtaccaccg aaacccaagt tctggttgcc   1020

tcagctcaga aaaaactgct ggaagaacgc ctgaaactgg ttagcgaact gtgggatgct   1080

ggcattaaag ccgaactgct gtataaaaaa aacccgaaac tgctgaatca gctgcagtat   1140

tgtgaggaag cgggtattcc tctggtggcc attatcggag aacaggaact gaaagacggc   1200

gttattaaac tgcgtagcgt gacctctcgt gaagaagttg acgttcgccg tgaagatctg   1260

gtcgaggaaa tcaaacgtcg taccggtcaa cctctgtgta tttgc                   1305
```

<210> SEQ ID NO 127
<211> LENGTH: 423
<212> TYPE: DNA
<213> ORGANISM: Artificial Sequence
<220> FEATURE:
<223> OTHER INFORMATION: Codon optimized version of HRS

<400> SEQUENCE: 127

```
atgttcgacc caaaaggccg taaagttccg tgtgtagggc tgtctatcgg tgttgagcgt     60

atcttctcca tcgttgagca gcgtctggaa gcactggagg aaaaaatccg tacgaccgag    120

actcaagtcc tggttgctag tgcccagaaa aaactgctgg aagagcgcct gaaactggtt    180

agtgagctgt gggatgccgg tattaaagcc gaactgctgt ataaaaaaaa cccgaaactg    240

ctgaatcagc tgcagtattg tgaagaagcg ggcattccgc tggtagcgat tatcggggaa    300

caagaactga aagatggcgt gatcaaactg cgtagcgtta caagccgtga ggaagtggac    360

gtccgccgtg aggatctggt tgaagagatt aaacgccgta caggtcagcc tctgtgtatt    420

tgc                                                                  423
```

<210> SEQ ID NO 128
<211> LENGTH: 19
<212> TYPE: PRT
<213> ORGANISM: Homo sapiens
<220> FEATURE:
<221> NAME/KEY: MISC_FEATURE
<222> LOCATION: (1)..(19)
<223> OTHER INFORMATION: Human IgA1 hinge region

<400> SEQUENCE: 128

Val Pro Ser Thr Pro Pro Thr Pro Ser Pro Ser Thr Pro Pro Thr Pro
1 5 10 15

Ser Pro Ser

<210> SEQ ID NO 129
<211> LENGTH: 101
<212> TYPE: PRT
<213> ORGANISM: Homo sapiens
<220> FEATURE:
<221> NAME/KEY: MISC_FEATURE
<222> LOCATION: (1)..(101)
<223> OTHER INFORMATION: Human IgA1 CH2 region

<400> SEQUENCE: 129

Cys Cys His Pro Arg Leu Ser Leu His Arg Pro Ala Leu Glu Asp Leu
1 5 10 15

Leu Leu Gly Ser Glu Ala Asn Leu Thr Cys Thr Leu Thr Gly Leu Arg
20 25 30

Asp Ala Ser Gly Val Thr Phe Thr Trp Thr Pro Ser Ser Gly Lys Ser
35 40 45

Ala Val Gln Gly Pro Pro Glu Arg Asp Leu Cys Gly Cys Tyr Ser Val
50 55 60

Ser Ser Val Leu Pro Gly Cys Ala Glu Pro Trp Asn His Gly Lys Thr
65 70 75 80

Phe Thr Cys Thr Ala Ala Tyr Pro Glu Ser Lys Thr Pro Leu Thr Ala
85 90 95

Thr Leu Ser Lys Ser
100

<210> SEQ ID NO 130
<211> LENGTH: 131
<212> TYPE: PRT
<213> ORGANISM: Homo sapiens
<220> FEATURE:
<221> NAME/KEY: MISC_FEATURE
<222> LOCATION: (1)..(131)
<223> OTHER INFORMATION: human IgA1 CH3 region

<400> SEQUENCE: 130

Gly Asn Thr Phe Arg Pro Glu Val His Leu Leu Pro Pro Pro Ser Glu
1 5 10 15

Glu Leu Ala Leu Asn Glu Leu Val Thr Leu Thr Cys Leu Ala Arg Gly
20 25 30

Phe Ser Pro Lys Asp Val Leu Val Arg Trp Leu Gln Gly Ser Gln Glu
35 40 45

Leu Pro Arg Glu Lys Tyr Leu Thr Trp Ala Ser Arg Gln Glu Pro Ser
50 55 60

Gln Gly Thr Thr Thr Phe Ala Val Thr Ser Ile Leu Arg Val Ala Ala
65 70 75 80

Glu Asp Trp Lys Lys Gly Asp Thr Phe Ser Cys Met Val Gly His Glu
85 90 95

Ala Leu Pro Leu Ala Phe Thr Gln Lys Thr Ile Asp Arg Leu Ala Gly
100 105 110

Lys Pro Thr His Val Asn Val Ser Val Val Met Ala Glu Val Asp Gly
115 120 125

Thr Cys Tyr
130

```
<210> SEQ ID NO 131
<211> LENGTH: 6
<212> TYPE: PRT
<213> ORGANISM: Homo sapiens
<220> FEATURE:
<221> NAME/KEY: MISC_FEATURE
<222> LOCATION: (1)..(6)
<223> OTHER INFORMATION: human IgA2 hinge region

<400> SEQUENCE: 131

Val Pro Pro Pro Pro Pro
1               5


<210> SEQ ID NO 132
<211> LENGTH: 101
<212> TYPE: PRT
<213> ORGANISM: Homo sapiens
<220> FEATURE:
<221> NAME/KEY: MISC_FEATURE
<222> LOCATION: (1)..(101)
<223> OTHER INFORMATION: human IgA2 CH2

<400> SEQUENCE: 132

Cys Cys His Pro Arg Leu Ser Leu His Arg Pro Ala Leu Glu Asp Leu
1               5                   10                  15

Leu Leu Gly Ser Glu Ala Asn Leu Thr Cys Thr Leu Thr Gly Leu Arg
            20                  25                  30

Asp Ala Ser Gly Ala Thr Phe Thr Trp Thr Pro Ser Ser Gly Lys Ser
        35                  40                  45

Ala Val Gln Gly Pro Pro Glu Arg Asp Leu Cys Gly Cys Tyr Ser Val
    50                  55                  60

Ser Ser Val Leu Pro Gly Cys Ala Gln Pro Trp Asn His Gly Glu Thr
65                  70                  75                  80

Phe Thr Cys Thr Ala Ala His Pro Glu Leu Lys Thr Pro Leu Thr Ala
                85                  90                  95

Asn Ile Thr Lys Ser
            100


<210> SEQ ID NO 133
<211> LENGTH: 131
<212> TYPE: PRT
<213> ORGANISM: Homo sapiens
<220> FEATURE:
<221> NAME/KEY: MISC_FEATURE
<222> LOCATION: (1)..(131)
<223> OTHER INFORMATION: human IgA2 CH3 region

<400> SEQUENCE: 133

Gly Asn Thr Phe Arg Pro Glu Val His Leu Leu Pro Pro Pro Ser Glu
1               5                   10                  15

Glu Leu Ala Leu Asn Glu Leu Val Thr Leu Thr Cys Leu Ala Arg Gly
            20                  25                  30

Phe Ser Pro Lys Asp Val Leu Val Arg Trp Leu Gln Gly Ser Gln Glu
        35                  40                  45

Leu Pro Arg Glu Lys Tyr Leu Thr Trp Ala Ser Arg Gln Glu Pro Ser
    50                  55                  60

Gln Gly Thr Thr Thr Phe Ala Val Thr Ser Ile Leu Arg Val Ala Ala
65                  70                  75                  80

Glu Asp Trp Lys Lys Gly Asp Thr Phe Ser Cys Met Val Gly His Glu
                85                  90                  95
```

```
Ala Leu Pro Leu Ala Phe Thr Gln Lys Thr Ile Asp Arg Leu Ala Gly
            100                 105                 110

Lys Pro Thr His Val Asn Val Ser Val Val Met Ala Glu Val Asp Gly
        115                 120                 125

Thr Cys Tyr
    130


<210> SEQ ID NO 134
<211> LENGTH: 58
<212> TYPE: PRT
<213> ORGANISM: Homo sapiens
<220> FEATURE:
<221> NAME/KEY: MISC_FEATURE
<222> LOCATION: (1)..(58)
<223> OTHER INFORMATION: human IgD hinge region

<400> SEQUENCE: 134

Glu Ser Pro Lys Ala Gln Ala Ser Ser Val Pro Thr Ala Gln Pro Gln
1               5                   10                  15

Ala Glu Gly Ser Leu Ala Lys Ala Thr Thr Ala Pro Ala Thr Thr Arg
            20                  25                  30

Asn Thr Gly Arg Gly Gly Glu Glu Lys Lys Lys Glu Lys Glu Lys Glu
        35                  40                  45

Glu Gln Glu Glu Arg Glu Thr Lys Thr Pro
    50                  55


<210> SEQ ID NO 135
<211> LENGTH: 108
<212> TYPE: PRT
<213> ORGANISM: Homo sapiens
<220> FEATURE:
<221> NAME/KEY: MISC_FEATURE
<222> LOCATION: (1)..(108)
<223> OTHER INFORMATION: human IgD CH2 region

<400> SEQUENCE: 135

Glu Cys Pro Ser His Thr Gln Pro Leu Gly Val Tyr Leu Leu Thr Pro
1               5                   10                  15

Ala Val Gln Asp Leu Trp Leu Arg Asp Lys Ala Thr Phe Thr Cys Phe
            20                  25                  30

Val Val Gly Ser Asp Leu Lys Asp Ala His Leu Thr Trp Glu Val Ala
        35                  40                  45

Gly Lys Val Pro Thr Gly Gly Val Glu Glu Gly Leu Leu Glu Arg His
    50                  55                  60

Ser Asn Gly Ser Gln Ser Gln His Ser Arg Leu Thr Leu Pro Arg Ser
65                  70                  75                  80

Leu Trp Asn Ala Gly Thr Ser Val Thr Cys Thr Leu Asn His Pro Ser
                85                  90                  95

Leu Pro Pro Gln Arg Leu Met Ala Leu Arg Glu Pro
            100                 105


<210> SEQ ID NO 136
<211> LENGTH: 117
<212> TYPE: PRT
<213> ORGANISM: Homo sapiens
<220> FEATURE:
<221> NAME/KEY: MISC_FEATURE
<222> LOCATION: (1)..(117)
<223> OTHER INFORMATION: human IgD CH3 region

<400> SEQUENCE: 136

Ala Ala Gln Ala Pro Val Lys Leu Ser Leu Asn Leu Leu Ala Ser Ser
```

```
1               5                   10                  15

Asp Pro Pro Glu Ala Ala Ser Trp Leu Leu Cys Glu Val Ser Gly Phe
            20                  25                  30

Ser Pro Pro Asn Ile Leu Leu Met Trp Leu Glu Asp Gln Arg Glu Val
        35                  40                  45

Asn Thr Ser Gly Phe Ala Pro Ala Arg Pro Pro Pro Gln Pro Arg Ser
    50                  55                  60

Thr Thr Phe Trp Ala Trp Ser Val Leu Arg Val Pro Ala Pro Pro Ser
65                  70                  75                  80

Pro Gln Pro Ala Thr Tyr Thr Cys Val Val Ser His Glu Asp Ser Arg
                85                  90                  95

Thr Leu Leu Asn Ala Ser Arg Ser Leu Glu Val Ser Tyr Val Thr Asp
            100                 105                 110

His Gly Pro Met Lys
        115


<210> SEQ ID NO 137
<211> LENGTH: 107
<212> TYPE: PRT
<213> ORGANISM: Homo sapiens
<220> FEATURE:
<221> NAME/KEY: MISC_FEATURE
<222> LOCATION: (1)..(107)
<223> OTHER INFORMATION: human IgE CH2 region

<400> SEQUENCE: 137

Val Cys Ser Arg Asp Phe Thr Pro Pro Thr Val Lys Ile Leu Gln Ser
1               5                   10                  15

Ser Cys Asp Gly Gly Gly His Phe Pro Pro Thr Ile Gln Leu Leu Cys
            20                  25                  30

Leu Val Ser Gly Tyr Thr Pro Gly Thr Ile Asn Ile Thr Trp Leu Glu
        35                  40                  45

Asp Gly Gln Val Met Asp Val Asp Leu Ser Thr Ala Ser Thr Thr Gln
    50                  55                  60

Glu Gly Glu Leu Ala Ser Thr Gln Ser Glu Leu Thr Leu Ser Gln Lys
65                  70                  75                  80

His Trp Leu Ser Asp Arg Thr Tyr Thr Cys Gln Val Thr Tyr Gln Gly
                85                  90                  95

His Thr Phe Glu Asp Ser Thr Lys Lys Cys Ala
            100                 105


<210> SEQ ID NO 138
<211> LENGTH: 108
<212> TYPE: PRT
<213> ORGANISM: Homo sapiens
<220> FEATURE:
<221> NAME/KEY: MISC_FEATURE
<222> LOCATION: (1)..(108)
<223> OTHER INFORMATION: human IgE CH3 region

<400> SEQUENCE: 138

Asp Ser Asn Pro Arg Gly Val Ser Ala Tyr Leu Ser Arg Pro Ser Pro
1               5                   10                  15

Phe Asp Leu Phe Ile Arg Lys Ser Pro Thr Ile Thr Cys Leu Val Val
            20                  25                  30

Asp Leu Ala Pro Ser Lys Gly Thr Val Asn Leu Thr Trp Ser Arg Ala
        35                  40                  45

Ser Gly Lys Pro Val Asn His Ser Thr Arg Lys Glu Glu Lys Gln Arg
    50                  55                  60
```

```
Asn Gly Thr Leu Thr Val Thr Ser Thr Leu Pro Val Gly Thr Arg Asp
65                  70                  75                  80

Trp Ile Glu Gly Glu Thr Tyr Gln Cys Arg Val Thr His Pro His Leu
                85                  90                  95

Pro Arg Ala Leu Met Arg Ser Thr Thr Lys Thr Ser
            100                 105


<210> SEQ ID NO 139
<211> LENGTH: 110
<212> TYPE: PRT
<213> ORGANISM: Homo sapiens
<220> FEATURE:
<221> NAME/KEY: MISC_FEATURE
<222> LOCATION: (1)..(110)
<223> OTHER INFORMATION: human IgE CH4 region

<400> SEQUENCE: 139

Gly Pro Arg Ala Ala Pro Glu Val Tyr Ala Phe Ala Thr Pro Glu Trp
1               5                   10                  15

Pro Gly Ser Arg Asp Lys Arg Thr Leu Ala Cys Leu Ile Gln Asn Phe
            20                  25                  30

Met Pro Glu Asp Ile Ser Val Gln Trp Leu His Asn Glu Val Gln Leu
        35                  40                  45

Pro Asp Ala Arg His Ser Thr Thr Gln Pro Arg Lys Thr Lys Gly Ser
    50                  55                  60

Gly Phe Phe Val Phe Ser Arg Leu Glu Val Thr Arg Ala Glu Trp Glu
65                  70                  75                  80

Gln Lys Asp Glu Phe Ile Cys Arg Ala Val His Glu Ala Ala Ser Pro
                85                  90                  95

Ser Gln Thr Val Gln Arg Ala Val Ser Val Asn Pro Gly Lys
            100                 105                 110


<210> SEQ ID NO 140
<211> LENGTH: 15
<212> TYPE: PRT
<213> ORGANISM: Homo sapiens
<220> FEATURE:
<221> NAME/KEY: MISC_FEATURE
<222> LOCATION: (1)..(15)
<223> OTHER INFORMATION: human IgG1 hinge region

<400> SEQUENCE: 140

Glu Pro Lys Ser Cys Asp Lys Thr His Thr Cys Pro Pro Cys Pro
1               5                   10                  15


<210> SEQ ID NO 141
<211> LENGTH: 110
<212> TYPE: PRT
<213> ORGANISM: Homo sapiens
<220> FEATURE:
<221> NAME/KEY: MISC_FEATURE
<222> LOCATION: (1)..(110)
<223> OTHER INFORMATION: human IgG1 CH2 region

<400> SEQUENCE: 141

Ala Pro Glu Leu Leu Gly Gly Pro Ser Val Phe Leu Phe Pro Pro Lys
1               5                   10                  15

Pro Lys Asp Thr Leu Met Ile Ser Arg Thr Pro Glu Val Thr Cys Val
            20                  25                  30

Val Val Asp Val Ser His Glu Asp Pro Glu Val Lys Phe Asn Trp Tyr
        35                  40                  45
```

-continued

```
Val Asp Gly Val Glu Val His Asn Ala Lys Thr Lys Pro Arg Glu Glu
    50                  55                  60

Gln Tyr Asn Ser Thr Tyr Arg Val Val Ser Val Leu Thr Val Leu His
65                  70                  75                  80

Gln Asp Trp Leu Asn Gly Lys Glu Tyr Lys Cys Lys Val Ser Asn Lys
                85                  90                  95

Ala Leu Pro Ala Pro Ile Glu Lys Thr Ile Ser Lys Ala Lys
            100                 105                 110


<210> SEQ ID NO 142
<211> LENGTH: 107
<212> TYPE: PRT
<213> ORGANISM: Homo sapiens
<220> FEATURE:
<221> NAME/KEY: MISC_FEATURE
<222> LOCATION: (1)..(107)
<223> OTHER INFORMATION: human IgG1 CH3 region

<400> SEQUENCE: 142

Gly Gln Pro Arg Glu Pro Gln Val Tyr Thr Leu Pro Pro Ser Arg Asp
1               5                   10                  15

Glu Leu Thr Lys Asn Gln Val Ser Leu Thr Cys Leu Val Lys Gly Phe
            20                  25                  30

Tyr Pro Ser Asp Ile Ala Val Glu Trp Glu Ser Asn Gly Gln Pro Glu
        35                  40                  45

Asn Asn Tyr Lys Thr Thr Pro Pro Val Leu Asp Ser Asp Gly Ser Phe
    50                  55                  60

Phe Leu Tyr Ser Lys Leu Thr Val Asp Lys Ser Arg Trp Gln Gln Gly
65                  70                  75                  80

Asn Val Phe Ser Cys Ser Val Met His Glu Ala Leu His Asn His Tyr
                85                  90                  95

Thr Gln Lys Ser Leu Ser Leu Ser Pro Gly Lys
            100                 105


<210> SEQ ID NO 143
<211> LENGTH: 12
<212> TYPE: PRT
<213> ORGANISM: Homo sapiens
<220> FEATURE:
<221> NAME/KEY: MISC_FEATURE
<222> LOCATION: (1)..(12)
<223> OTHER INFORMATION: human IgG2 hinge region

<400> SEQUENCE: 143

Glu Arg Lys Cys Cys Val Glu Cys Pro Pro Cys Pro
1               5                   10


<210> SEQ ID NO 144
<211> LENGTH: 109
<212> TYPE: PRT
<213> ORGANISM: Homo sapiens
<220> FEATURE:
<221> NAME/KEY: MISC_FEATURE
<222> LOCATION: (1)..(109)
<223> OTHER INFORMATION: human IgG2 CH2 region

<400> SEQUENCE: 144

Ala Pro Pro Val Ala Gly Pro Ser Val Phe Leu Phe Pro Pro Lys Pro
1               5                   10                  15

Lys Asp Thr Leu Met Ile Ser Arg Thr Pro Glu Val Thr Cys Val Val
            20                  25                  30

Val Asp Val Ser His Glu Asp Pro Glu Val Gln Phe Asn Trp Tyr Val
```

```
        35                  40                  45

Asp Gly Val Glu Val His Asn Ala Lys Thr Lys Pro Arg Glu Glu Gln
    50                  55                  60

Phe Asn Ser Thr Phe Arg Val Val Ser Val Leu Thr Val Val His Gln
65                  70                  75                  80

Asp Trp Leu Asn Gly Lys Glu Tyr Lys Cys Lys Val Ser Asn Lys Gly
                85                  90                  95

Leu Pro Ala Pro Ile Glu Lys Thr Ile Ser Lys Thr Lys
            100                 105


<210> SEQ ID NO 145
<211> LENGTH: 107
<212> TYPE: PRT
<213> ORGANISM: Homo sapiens
<220> FEATURE:
<221> NAME/KEY: MISC_FEATURE
<222> LOCATION: (1)..(107)
<223> OTHER INFORMATION: human IgG2 CH3 region

<400> SEQUENCE: 145

Gly Gln Pro Arg Glu Pro Gln Val Tyr Thr Leu Pro Pro Ser Arg Glu
1               5                   10                  15

Glu Met Thr Lys Asn Gln Val Ser Leu Thr Cys Leu Val Lys Gly Phe
            20                  25                  30

Tyr Pro Ser Asp Ile Ala Val Glu Trp Glu Ser Asn Gly Gln Pro Glu
        35                  40                  45

Asn Asn Tyr Lys Thr Thr Pro Pro Met Leu Asp Ser Asp Gly Ser Phe
    50                  55                  60

Phe Leu Tyr Ser Lys Leu Thr Val Asp Lys Ser Arg Trp Gln Gln Gly
65                  70                  75                  80

Asn Val Phe Ser Cys Ser Val Met His Glu Ala Leu His Asn His Tyr
                85                  90                  95

Thr Gln Lys Ser Leu Ser Leu Ser Pro Gly Lys
            100                 105


<210> SEQ ID NO 146
<211> LENGTH: 62
<212> TYPE: PRT
<213> ORGANISM: Homo sapiens
<220> FEATURE:
<221> NAME/KEY: MISC_FEATURE
<222> LOCATION: (1)..(62)
<223> OTHER INFORMATION: human IgG3 hinge region

<400> SEQUENCE: 146

Glu Leu Lys Thr Pro Leu Gly Asp Thr Thr His Thr Cys Pro Arg Cys
1               5                   10                  15

Pro Glu Pro Lys Ser Cys Asp Thr Pro Pro Pro Cys Pro Arg Cys Pro
            20                  25                  30

Glu Pro Lys Ser Cys Asp Thr Pro Pro Pro Cys Pro Arg Cys Pro Glu
        35                  40                  45

Pro Lys Ser Cys Asp Thr Pro Pro Pro Cys Pro Arg Cys Pro
    50                  55                  60


<210> SEQ ID NO 147
<211> LENGTH: 110
<212> TYPE: PRT
<213> ORGANISM: Homo sapiens
<220> FEATURE:
<221> NAME/KEY: MISC_FEATURE
<222> LOCATION: (1)..(110)
```

<223> OTHER INFORMATION: human IgG3 CH2 region

<400> SEQUENCE: 147

Ala Pro Glu Leu Leu Gly Gly Pro Ser Val Phe Leu Phe Pro Pro Lys
1 5 10 15

Pro Lys Asp Thr Leu Met Ile Ser Arg Thr Pro Glu Val Thr Cys Val
20 25 30

Val Val Asp Val Ser His Glu Asp Pro Glu Val Gln Phe Lys Trp Tyr
35 40 45

Val Asp Gly Val Glu Val His Asn Ala Lys Thr Lys Pro Arg Glu Glu
50 55 60

Gln Tyr Asn Ser Thr Phe Arg Val Val Ser Val Leu Thr Val Leu His
65 70 75 80

Gln Asp Trp Leu Asn Gly Lys Glu Tyr Lys Cys Lys Val Ser Asn Lys
85 90 95

Ala Leu Pro Ala Pro Ile Glu Lys Thr Ile Ser Lys Thr Lys
100 105 110

<210> SEQ ID NO 148
<211> LENGTH: 107
<212> TYPE: PRT
<213> ORGANISM: Homo sapiens
<220> FEATURE:
<221> NAME/KEY: MISC_FEATURE
<222> LOCATION: (1)..(107)
<223> OTHER INFORMATION: human IgG3 CH3 region

<400> SEQUENCE: 148

Gly Gln Pro Arg Glu Pro Gln Val Tyr Thr Leu Pro Pro Ser Arg Glu
1 5 10 15

Glu Met Thr Lys Asn Gln Val Ser Leu Thr Cys Leu Val Lys Gly Phe
20 25 30

Tyr Pro Ser Asp Ile Ala Val Glu Trp Glu Ser Ser Gly Gln Pro Glu
35 40 45

Asn Asn Tyr Asn Thr Thr Pro Pro Met Leu Asp Ser Asp Gly Ser Phe
50 55 60

Phe Leu Tyr Ser Lys Leu Thr Val Asp Lys Ser Arg Trp Gln Gln Gly
65 70 75 80

Asn Ile Phe Ser Cys Ser Val Met His Glu Ala Leu His Asn Arg Phe
85 90 95

Thr Gln Lys Ser Leu Ser Leu Ser Pro Gly Lys
100 105

<210> SEQ ID NO 149
<211> LENGTH: 12
<212> TYPE: PRT
<213> ORGANISM: Homo sapiens
<220> FEATURE:
<221> NAME/KEY: MISC_FEATURE
<222> LOCATION: (1)..(12)
<223> OTHER INFORMATION: human IgG4 hinge region

<400> SEQUENCE: 149

Glu Ser Lys Tyr Gly Pro Pro Cys Pro Ser Cys Pro
1 5 10

<210> SEQ ID NO 150
<211> LENGTH: 110
<212> TYPE: PRT
<213> ORGANISM: Homo sapiens
<220> FEATURE:

<221> NAME/KEY: MISC_FEATURE
<222> LOCATION: (1)..(110)
<223> OTHER INFORMATION: human IgG4 CH2 region

<400> SEQUENCE: 150

Ala Pro Glu Phe Leu Gly Gly Pro Ser Val Phe Leu Phe Pro Pro Lys
1 5 10 15

Pro Lys Asp Thr Leu Met Ile Ser Arg Thr Pro Glu Val Thr Cys Val
20 25 30

Val Val Asp Val Ser Gln Glu Asp Pro Glu Val Gln Phe Asn Trp Tyr
35 40 45

Val Asp Gly Val Glu Val His Asn Ala Lys Thr Lys Pro Arg Glu Glu
50 55 60

Gln Phe Asn Ser Thr Tyr Arg Val Val Ser Val Leu Thr Val Leu His
65 70 75 80

Gln Asp Trp Leu Asn Gly Lys Glu Tyr Lys Cys Lys Val Ser Asn Lys
85 90 95

Gly Leu Pro Ser Ser Ile Glu Lys Thr Ile Ser Lys Ala Lys
100 105 110

<210> SEQ ID NO 151
<211> LENGTH: 107
<212> TYPE: PRT
<213> ORGANISM: Homo sapiens
<220> FEATURE:
<221> NAME/KEY: MISC_FEATURE
<222> LOCATION: (1)..(107)
<223> OTHER INFORMATION: human IgG4 CH3 region

<400> SEQUENCE: 151

Gly Gln Pro Arg Glu Pro Gln Val Tyr Thr Leu Pro Pro Ser Gln Glu
1 5 10 15

Glu Met Thr Lys Asn Gln Val Ser Leu Thr Cys Leu Val Lys Gly Phe
20 25 30

Tyr Pro Ser Asp Ile Ala Val Glu Trp Glu Ser Asn Gly Gln Pro Glu
35 40 45

Asn Asn Tyr Lys Thr Thr Pro Pro Val Leu Asp Ser Asp Gly Ser Phe
50 55 60

Phe Leu Tyr Ser Arg Leu Thr Val Asp Lys Ser Arg Trp Gln Glu Gly
65 70 75 80

Asn Val Phe Ser Cys Ser Val Met His Glu Ala Leu His Asn His Tyr
85 90 95

Thr Gln Lys Ser Leu Ser Leu Ser Leu Gly Lys
100 105

<210> SEQ ID NO 152
<211> LENGTH: 112
<212> TYPE: PRT
<213> ORGANISM: Homo sapiens
<220> FEATURE:
<221> NAME/KEY: MISC_FEATURE
<222> LOCATION: (1)..(112)
<223> OTHER INFORMATION: human IgM CH2 region

<400> SEQUENCE: 152

Val Ile Ala Glu Leu Pro Pro Lys Val Ser Val Phe Val Pro Pro Arg
1 5 10 15

Asp Gly Phe Phe Gly Asn Pro Arg Lys Ser Lys Leu Ile Cys Gln Ala
20 25 30

Thr Gly Phe Ser Pro Arg Gln Ile Gln Val Ser Trp Leu Arg Glu Gly

```
        35                  40                  45

Lys Gln Val Gly Ser Gly Val Thr Thr Asp Gln Val Gln Ala Glu Ala
    50                  55                  60

Lys Glu Ser Gly Pro Thr Thr Tyr Lys Val Thr Ser Thr Leu Thr Ile
65                  70                  75                  80

Lys Glu Ser Asp Trp Leu Gly Gln Ser Met Phe Thr Cys Arg Val Asp
                85                  90                  95

His Arg Gly Leu Thr Phe Gln Gln Asn Ala Ser Ser Met Cys Val Pro
            100                 105                 110
```

<210> SEQ ID NO 153
<211> LENGTH: 106
<212> TYPE: PRT
<213> ORGANISM: Homo sapiens
<220> FEATURE:
<221> NAME/KEY: MISC_FEATURE
<222> LOCATION: (1)..(106)
<223> OTHER INFORMATION: human IgM CH3 region

<400> SEQUENCE: 153

```
Asp Gln Asp Thr Ala Ile Arg Val Phe Ala Ile Pro Pro Ser Phe Ala
1               5                   10                  15

Ser Ile Phe Leu Thr Lys Ser Thr Lys Leu Thr Cys Leu Val Thr Asp
            20                  25                  30

Leu Thr Thr Tyr Asp Ser Val Thr Ile Ser Trp Thr Arg Gln Asn Gly
        35                  40                  45

Glu Ala Val Lys Thr His Thr Asn Ile Ser Glu Ser His Pro Asn Ala
    50                  55                  60

Thr Phe Ser Ala Val Gly Glu Ala Ser Ile Cys Glu Asp Asp Trp Asn
65                  70                  75                  80

Ser Gly Glu Arg Phe Thr Cys Thr Val Thr His Thr Asp Leu Pro Ser
                85                  90                  95

Pro Leu Lys Gln Thr Ile Ser Arg Pro Lys
            100                 105
```

<210> SEQ ID NO 154
<211> LENGTH: 131
<212> TYPE: PRT
<213> ORGANISM: Homo sapiens
<220> FEATURE:
<221> NAME/KEY: MISC_FEATURE
<222> LOCATION: (1)..(131)
<223> OTHER INFORMATION: human IgM CH4 region

<400> SEQUENCE: 154

```
Gly Val Ala Leu His Arg Pro Asp Val Tyr Leu Leu Pro Pro Ala Arg
1               5                   10                  15

Glu Gln Leu Asn Leu Arg Glu Ser Ala Thr Ile Thr Cys Leu Val Thr
            20                  25                  30

Gly Phe Ser Pro Ala Asp Val Phe Val Gln Trp Met Gln Arg Gly Gln
        35                  40                  45

Pro Leu Ser Pro Glu Lys Tyr Val Thr Ser Ala Pro Met Pro Glu Pro
    50                  55                  60

Gln Ala Pro Gly Arg Tyr Phe Ala His Ser Ile Leu Thr Val Ser Glu
65                  70                  75                  80

Glu Glu Trp Asn Thr Gly Glu Thr Tyr Thr Cys Val Val Ala His Glu
                85                  90                  95

Ala Leu Pro Asn Arg Val Thr Glu Arg Thr Val Asp Lys Ser Thr Gly
            100                 105                 110
```

```
Lys Pro Thr Leu Tyr Asn Val Ser Leu Val Met Ser Asp Thr Ala Gly
        115                 120                 125

Thr Cys Tyr
    130


<210> SEQ ID NO 155
<211> LENGTH: 230
<212> TYPE: PRT
<213> ORGANISM: Artificial Sequence
<220> FEATURE:
<223> OTHER INFORMATION: Fc variant
<220> FEATURE:
<221> NAME/KEY: VARIANT
<222> LOCATION: (1)..(1)
<223> OTHER INFORMATION: Xaa is Ala or absent
<220> FEATURE:
<221> NAME/KEY: VARIANT
<222> LOCATION: (16)..(16)
<223> OTHER INFORMATION: Xaa is Pro or Glu
<220> FEATURE:
<221> NAME/KEY: VARIANT
<222> LOCATION: (17)..(17)
<223> OTHER INFORMATION: Xaa is Phe, Val or Ala
<220> FEATURE:
<221> NAME/KEY: VARIANT
<222> LOCATION: (18)..(18)
<223> OTHER INFORMATION: Xaa is Leu, Glu or Ala
<220> FEATURE:
<221> NAME/KEY: VARIANT
<222> LOCATION: (80)..(80)
<223> OTHER INFORMATION: Xaa is Asn or Ala
<220> FEATURE:
<221> NAME/KEY: VARIANT
<222> LOCATION: (230)..(230)
<223> OTHER INFORMATION: Xaa is Lys or absent

<400> SEQUENCE: 155

Xaa Glu Ser Lys Tyr Gly Pro Pro Cys Pro Pro Cys Pro Ala Pro Xaa
1               5                   10                  15

Xaa Xaa Gly Gly Pro Ser Val Phe Leu Phe Pro Pro Lys Pro Lys Asp
            20                  25                  30

Thr Leu Met Ile Ser Arg Thr Pro Glu Val Thr Cys Val Val Val Asp
        35                  40                  45

Val Ser Gln Glu Asp Pro Glu Val Gln Phe Asn Trp Tyr Val Asp Gly
    50                  55                  60

Val Glu Val His Asn Ala Lys Thr Lys Pro Arg Glu Glu Gln Phe Xaa
65                  70                  75                  80

Ser Thr Tyr Arg Val Val Ser Val Leu Thr Val Leu His Gln Asp Trp
                85                  90                  95

Leu Asn Gly Lys Glu Tyr Lys Cys Lys Val Ser Asn Lys Gly Leu Pro
            100                 105                 110

Ser Ser Ile Glu Lys Thr Ile Ser Lys Ala Lys Gly Gln Pro Arg Glu
        115                 120                 125

Pro Gln Val Tyr Thr Leu Pro Pro Ser Gln Glu Glu Met Thr Lys Asn
    130                 135                 140

Gln Val Ser Leu Thr Cys Leu Val Lys Gly Phe Tyr Pro Ser Asp Ile
145                 150                 155                 160

Ala Val Glu Trp Glu Ser Asn Gly Gln Pro Glu Asn Asn Tyr Lys Thr
                165                 170                 175

Thr Pro Pro Val Leu Asp Ser Asp Gly Ser Phe Phe Leu Tyr Ser Arg
            180                 185                 190

Leu Thr Val Asp Lys Ser Arg Trp Gln Glu Gly Asn Val Phe Ser Cys
        195                 200                 205
```

```
Ser Val Met His Glu Ala Leu His Asn His Tyr Thr Gln Lys Ser Leu
    210                 215                 220

Ser Leu Ser Leu Gly Xaa
225                 230


<210> SEQ ID NO 156
<211> LENGTH: 209
<212> TYPE: PRT
<213> ORGANISM: Homo sapiens

<400> SEQUENCE: 156

Cys His Pro Arg Leu Ser Leu His Arg Pro Ala Leu Glu Asp Leu Leu
1               5                   10                  15

Leu Gly Ser Glu Ala Asn Leu Thr Cys Thr Leu Thr Gly Leu Arg Asp
            20                  25                  30

Ala Ser Gly Val Thr Phe Thr Trp Thr Pro Ser Ser Gly Lys Ser Ala
        35                  40                  45

Val Gln Gly Pro Pro Glu Arg Asp Leu Cys Gly Cys Tyr Ser Val Ser
    50                  55                  60

Ser Val Leu Pro Gly Cys Ala Glu Pro Trp Asn His Gly Lys Thr Phe
65                  70                  75                  80

Thr Cys Thr Ala Ala Tyr Pro Glu Ser Lys Thr Pro Leu Thr Ala Thr
                85                  90                  95

Leu Ser Lys Ser Gly Asn Thr Phe Arg Pro Glu Val His Leu Leu Pro
            100                 105                 110

Pro Pro Ser Glu Glu Leu Ala Leu Asn Glu Leu Val Thr Leu Thr Cys
        115                 120                 125

Leu Ala Arg Gly Phe Ser Pro Lys Asp Val Leu Val Arg Trp Leu Gln
    130                 135                 140

Gly Ser Gln Glu Leu Pro Arg Glu Lys Tyr Leu Thr Trp Ala Ser Arg
145                 150                 155                 160

Gln Glu Pro Ser Gln Gly Thr Thr Thr Phe Ala Val Thr Ser Ile Leu
                165                 170                 175

Arg Val Ala Ala Glu Asp Trp Lys Lys Gly Asp Thr Phe Ser Cys Met
            180                 185                 190

Val Gly His Glu Ala Leu Pro Leu Ala Phe Thr Gln Lys Thr Ile Asp
        195                 200                 205

Arg


<210> SEQ ID NO 157
<211> LENGTH: 209
<212> TYPE: PRT
<213> ORGANISM: Homo sapiens

<400> SEQUENCE: 157

Cys His Pro Arg Leu Ser Leu His Arg Pro Ala Leu Glu Asp Leu Leu
1               5                   10                  15

Leu Gly Ser Glu Ala Asn Leu Thr Cys Thr Leu Thr Gly Leu Arg Asp
            20                  25                  30

Ala Ser Gly Ala Thr Phe Thr Trp Thr Pro Ser Ser Gly Lys Ser Ala
        35                  40                  45

Val Gln Gly Pro Pro Glu Arg Asp Leu Cys Gly Cys Tyr Ser Val Ser
    50                  55                  60

Ser Val Leu Pro Gly Cys Ala Gln Pro Trp Asn His Gly Glu Thr Phe
65                  70                  75                  80
```

Thr Cys Thr Ala Ala His Pro Glu Leu Lys Thr Pro Leu Thr Ala Asn
85 90 95

Ile Thr Lys Ser Gly Asn Thr Phe Arg Pro Glu Val His Leu Leu Pro
100 105 110

Pro Pro Ser Glu Glu Leu Ala Leu Asn Glu Leu Val Thr Leu Thr Cys
115 120 125

Leu Ala Arg Gly Phe Ser Pro Lys Asp Val Leu Val Arg Trp Leu Gln
130 135 140

Gly Ser Gln Glu Leu Pro Arg Glu Lys Tyr Leu Thr Trp Ala Ser Arg
145 150 155 160

Gln Glu Pro Ser Gln Gly Thr Thr Thr Phe Ala Val Thr Ser Ile Leu
165 170 175

Arg Val Ala Ala Glu Asp Trp Lys Lys Gly Asp Thr Phe Ser Cys Met
180 185 190

Val Gly His Glu Ala Leu Pro Leu Ala Phe Thr Gln Lys Thr Ile Asp
195 200 205

Arg

<210> SEQ ID NO 158
<211> LENGTH: 212
<212> TYPE: PRT
<213> ORGANISM: Homo sapiens

<400> SEQUENCE: 158

Thr Ala Ile Arg Val Phe Ala Ile Pro Pro Ser Phe Ala Ser Ile Phe
1 5 10 15

Leu Thr Lys Ser Thr Lys Leu Thr Cys Leu Val Thr Asp Leu Thr Thr
20 25 30

Tyr Asp Ser Val Thr Ile Ser Trp Thr Arg Gln Asn Gly Glu Ala Val
35 40 45

Lys Thr His Thr Asn Ile Ser Glu Ser His Pro Asn Ala Thr Phe Ser
50 55 60

Ala Val Gly Glu Ala Ser Ile Cys Glu Asp Asp Trp Asn Ser Gly Glu
65 70 75 80

Arg Phe Thr Cys Thr Val Thr His Thr Asp Leu Pro Ser Pro Leu Lys
85 90 95

Gln Thr Ile Ser Arg Pro Lys Gly Val Ala Leu His Arg Pro Asp Val
100 105 110

Tyr Leu Leu Pro Pro Ala Arg Glu Gln Leu Asn Leu Arg Glu Ser Ala
115 120 125

Thr Ile Thr Cys Leu Val Thr Gly Phe Ser Pro Ala Asp Val Phe Val
130 135 140

Gln Trp Met Gln Arg Gly Gln Pro Leu Ser Pro Glu Lys Tyr Val Thr
145 150 155 160

Ser Ala Pro Met Pro Glu Pro Gln Ala Pro Gly Arg Tyr Phe Ala His
165 170 175

Ser Ile Leu Thr Val Ser Glu Glu Glu Trp Asn Thr Gly Glu Thr Tyr
180 185 190

Thr Cys Val Val Ala His Glu Ala Leu Pro Asn Arg Val Thr Glu Arg
195 200 205

Thr Val Asp Lys
210

<210> SEQ ID NO 159
<211> LENGTH: 208

<212> TYPE: PRT
<213> ORGANISM: Homo sapiens

<400> SEQUENCE: 159

Ala Gly Pro Ser Val Phe Leu Phe Pro Pro Lys Pro Lys Asp Thr Leu
1               5                   10                  15

Met Ile Ser Arg Thr Pro Glu Val Thr Cys Val Val Val Asp Val Ser
            20                  25                  30

His Glu Asp Pro Glu Val Gln Phe Asn Trp Tyr Val Asp Gly Met Glu
        35                  40                  45

Val His Asn Ala Lys Thr Lys Pro Arg Glu Glu Gln Phe Asn Ser Thr
    50                  55                  60

Phe Arg Val Val Ser Val Leu Thr Val Val His Gln Asp Trp Leu Asn
65                  70                  75                  80

Gly Lys Glu Tyr Lys Cys Lys Val Ser Asn Lys Gly Leu Pro Ala Pro
                85                  90                  95

Ile Glu Lys Thr Ile Ser Lys Thr Lys Gly Gln Pro Arg Glu Pro Gln
            100                 105                 110

Val Tyr Thr Leu Pro Pro Ser Arg Glu Glu Met Thr Lys Asn Gln Val
        115                 120                 125

Ser Leu Thr Cys Leu Val Lys Gly Phe Tyr Pro Ser Asp Ile Ala Val
    130                 135                 140

Glu Trp Glu Ser Asn Gly Gln Pro Glu Asn Asn Tyr Lys Thr Thr Pro
145                 150                 155                 160

Pro Met Leu Asp Ser Asp Gly Ser Phe Phe Leu Tyr Ser Lys Leu Thr
                165                 170                 175

Val Asp Lys Ser Arg Trp Gln Gln Gly Asn Val Phe Ser Cys Ser Val
            180                 185                 190

Met His Glu Ala Leu His Asn His Tyr Thr Gln Lys Ser Leu Ser Leu
        195                 200                 205

<210> SEQ ID NO 160
<211> LENGTH: 208
<212> TYPE: PRT
<213> ORGANISM: Homo sapiens

<400> SEQUENCE: 160

Gly Gly Pro Ser Val Phe Leu Phe Pro Pro Lys Pro Lys Asp Thr Leu
1               5                   10                  15

Met Ile Ser Arg Thr Pro Glu Val Thr Cys Val Val Val Asp Val Ser
            20                  25                  30

His Glu Asp Pro Glu Val Lys Phe Asn Trp Tyr Val Asp Gly Val Glu
        35                  40                  45

Val His Asn Ala Lys Thr Lys Pro Arg Glu Glu Gln Tyr Asn Ser Thr
    50                  55                  60

Tyr Arg Val Val Ser Val Leu Thr Val Leu His Gln Asp Trp Leu Asn
65                  70                  75                  80

Gly Lys Glu Tyr Lys Cys Lys Val Ser Asn Lys Ala Leu Pro Ala Pro
                85                  90                  95

Ile Glu Lys Thr Ile Ser Lys Ala Lys Gly Gln Pro Arg Glu Pro Gln
            100                 105                 110

Val Tyr Thr Leu Pro Pro Ser Arg Asp Glu Leu Thr Lys Asn Gln Val
        115                 120                 125

Ser Leu Thr Cys Leu Val Lys Gly Phe Tyr Pro Ser Asp Ile Ala Val
    130                 135                 140

-continued

```
Glu Trp Glu Ser Asn Gly Gln Pro Glu Asn Asn Tyr Lys Thr Thr Pro
145                 150                 155                 160

Pro Val Leu Asp Ser Asp Gly Ser Phe Phe Leu Tyr Ser Lys Leu Thr
                165                 170                 175

Val Asp Lys Ser Arg Trp Gln Gln Gly Asn Val Phe Ser Cys Ser Val
            180                 185                 190

Met His Glu Ala Leu His Asn His Tyr Thr Gln Lys Ser Leu Ser Leu
        195                 200                 205


<210> SEQ ID NO 161
<211> LENGTH: 208
<212> TYPE: PRT
<213> ORGANISM: Homo sapiens

<400> SEQUENCE: 161

Gly Gly Pro Ser Val Phe Leu Phe Pro Pro Lys Pro Lys Asp Thr Leu
1               5                   10                  15

Met Ile Ser Arg Thr Pro Glu Val Thr Cys Val Val Val Asp Val Ser
            20                  25                  30

His Glu Asp Pro Glu Val Lys Phe Asn Trp Tyr Val Asp Gly Val Glu
        35                  40                  45

Val His Asn Ala Lys Thr Lys Pro Arg Glu Glu Gln Tyr Asn Ser Thr
    50                  55                  60

Tyr Arg Val Val Ser Val Leu Thr Val Leu His Gln Asp Trp Leu Asn
65                  70                  75                  80

Gly Lys Glu Tyr Lys Cys Lys Val Ser Asn Lys Ala Leu Pro Ala Pro
                85                  90                  95

Ile Glu Lys Thr Ile Ser Lys Ala Lys Gly Gln Pro Arg Glu Pro Gln
            100                 105                 110

Val Tyr Thr Leu Pro Pro Ser Arg Glu Glu Met Thr Lys Asn Gln Val
        115                 120                 125

Ser Leu Thr Cys Leu Val Lys Gly Phe Tyr Pro Ser Asp Ile Ala Val
    130                 135                 140

Glu Trp Glu Ser Asn Gly Gln Pro Glu Asn Asn Tyr Lys Thr Thr Pro
145                 150                 155                 160

Pro Val Leu Asp Ser Asp Gly Ser Phe Phe Leu Tyr Ser Lys Leu Thr
                165                 170                 175

Val Asp Lys Ser Arg Trp Gln Gln Gly Asn Val Phe Ser Cys Ser Val
            180                 185                 190

Met His Glu Ala Leu His Asn His Tyr Thr Gln Lys Ser Leu Ser Leu
        195                 200                 205


<210> SEQ ID NO 162
<211> LENGTH: 208
<212> TYPE: PRT
<213> ORGANISM: Homo sapiens
<220> FEATURE:
<221> NAME/KEY: VARIANT
<222> LOCATION: (80)..(80)
<223> OTHER INFORMATION: Xaa = any amino acid
<220> FEATURE:
<221> NAME/KEY: VARIANT
<222> LOCATION: (90)..(90)
<223> OTHER INFORMATION: Xaa = any amino acid
<220> FEATURE:
<221> NAME/KEY: VARIANT
<222> LOCATION: (103)..(103)
<223> OTHER INFORMATION: Xaa = any amino acid
<220> FEATURE:
<221> NAME/KEY: VARIANT
<222> LOCATION: (105)..(105)
```

```
<223> OTHER INFORMATION: Xaa = any amino acid
<220> FEATURE:
<221> NAME/KEY: VARIANT
<222> LOCATION: (181)..(181)
<223> OTHER INFORMATION: Xaa = any amino acid

<400> SEQUENCE: 162

Gly Gly Pro Ser Val Phe Leu Phe Pro Pro Lys Pro Lys Asp Thr Leu
1               5                   10                  15

Met Ile Ser Arg Thr Pro Glu Val Thr Cys Val Val Val Asp Val Ser
            20                  25                  30

Gln Glu Asp Pro Glu Val Gln Phe Asn Trp Tyr Val Asp Gly Val Glu
        35                  40                  45

Val His Asn Ala Lys Thr Lys Pro Arg Glu Glu Gln Phe Asn Ser Thr
    50                  55                  60

Tyr Arg Val Val Ser Val Leu Thr Val Leu His Gln Asp Trp Leu Xaa
65                  70                  75                  80

Gly Lys Glu Tyr Lys Cys Lys Val Ser Xaa Lys Gly Leu Pro Ser Ser
                85                  90                  95

Ile Glu Lys Thr Ile Ser Xaa Ala Xaa Gly Gln Pro Arg Glu Pro Gln
            100                 105                 110

Val Tyr Thr Leu Pro Pro Ser Gln Glu Glu Met Thr Lys Asn Gln Val
        115                 120                 125

Ser Leu Thr Cys Leu Val Lys Gly Phe Tyr Pro Ser Asp Ile Ala Val
    130                 135                 140

Glu Trp Glu Ser Asn Gly Gln Pro Glu Asn Asn Tyr Lys Thr Thr Pro
145                 150                 155                 160

Pro Val Leu Asp Ser Asp Gly Ser Phe Phe Leu Tyr Ser Arg Leu Thr
                165                 170                 175

Val Asp Lys Ser Xaa Trp Gln Glu Gly Asn Val Phe Ser Cys Ser Val
            180                 185                 190

Met His Glu Ala Leu His Asn His Tyr Thr Gln Lys Ser Leu Ser Leu
        195                 200                 205


<210> SEQ ID NO 163
<211> LENGTH: 210
<212> TYPE: PRT
<213> ORGANISM: Homo sapiens

<400> SEQUENCE: 163

Arg Gly Val Ser Ala Tyr Leu Ser Arg Pro Ser Pro Phe Asp Leu Phe
1               5                   10                  15

Ile Arg Lys Ser Pro Thr Ile Thr Cys Leu Val Val Asp Leu Ala Pro
            20                  25                  30

Ser Lys Gly Thr Val Gln Leu Thr Trp Ser Arg Ala Ser Gly Lys Pro
        35                  40                  45

Val Asn His Ser Thr Arg Lys Glu Glu Lys Gln Arg Asn Gly Thr Leu
    50                  55                  60

Thr Val Thr Ser Thr Leu Pro Val Gly Thr Arg Asp Trp Ile Glu Gly
65                  70                  75                  80

Glu Thr Tyr Gln Cys Arg Val Thr His Pro His Leu Pro Arg Ala Leu
                85                  90                  95

Met Arg Ser Thr Thr Lys Thr Ser Gly Pro Arg Ala Ala Pro Glu Val
            100                 105                 110

Tyr Ala Phe Ala Thr Pro Glu Trp Pro Gly Ser Arg Asp Lys Arg Thr
        115                 120                 125
```

```
Leu Ala Cys Leu Ile Gln Asn Phe Met Pro Glu Asp Ile Ser Val Gln
    130                 135                 140

Trp Leu His Asn Glu Val Gln Leu Pro Asp Ala Arg His Ser Thr Thr
145                 150                 155                 160

Gln Pro Arg Lys Thr Lys Gly Ser Gly Phe Phe Val Phe Ser Arg Leu
                165                 170                 175

Glu Val Thr Arg Ala Glu Trp Glu Gln Lys Asp Glu Phe Ile Cys Arg
            180                 185                 190

Ala Val His Glu Ala Ala Ser Pro Ser Gln Thr Val Gln Arg Ala Val
        195                 200                 205

Ser Val
    210


<210> SEQ ID NO 164
<211> LENGTH: 15
<212> TYPE: DNA
<213> ORGANISM: Homo sapiens

<400> SEQUENCE: 164

aaacaaaaca aaaca                                                    15


<210> SEQ ID NO 165
<211> LENGTH: 10
<212> TYPE: DNA
<213> ORGANISM: Homo sapiens

<400> SEQUENCE: 165

aaacaaaaca                                                          10


<210> SEQ ID NO 166
<211> LENGTH: 10
<212> TYPE: DNA
<213> ORGANISM: Homo sapiens

<400> SEQUENCE: 166

caaaacaaaa                                                          10


<210> SEQ ID NO 167
<211> LENGTH: 15
<212> TYPE: DNA
<213> ORGANISM: Homo sapiens

<400> SEQUENCE: 167

caaaacaaaa caaaa                                                    15


<210> SEQ ID NO 168
<211> LENGTH: 10
<212> TYPE: DNA
<213> ORGANISM: Homo sapiens

<400> SEQUENCE: 168

aaacaaaaca                                                          10


<210> SEQ ID NO 169
<211> LENGTH: 10
<212> TYPE: DNA
<213> ORGANISM: Homo sapiens

<400> SEQUENCE: 169

acaaaacaaa                                                          10
```

<210> SEQ ID NO 170
<211> LENGTH: 500
<212> TYPE: PRT
<213> ORGANISM: Homo sapiens

<400> SEQUENCE: 170

```
Met Ala Glu Arg Ala Ala Leu Glu Glu Leu Val Lys Leu Gln Gly Glu
1               5                   10                  15

Arg Val Arg Gly Leu Lys Gln Gln Lys Ala Ser Ala Glu Leu Ile Glu
            20                  25                  30

Glu Glu Val Ala Lys Leu Leu Lys Leu Lys Ala Gln Leu Gly Pro Asp
        35                  40                  45

Glu Ser Lys Gln Lys Phe Val Leu Lys Thr Pro Lys Gly Thr Arg Asp
    50                  55                  60

Tyr Ser Pro Arg Gln Met Ala Val Arg Glu Lys Val Phe Asp Val Ile
65                  70                  75                  80

Ile Arg Cys Phe Lys Arg His Gly Ala Glu Val Ile Asp Thr Pro Val
                85                  90                  95

Phe Glu Leu Lys Glu Thr Leu Met Gly Lys Tyr Gly Glu Asp Ser Lys
            100                 105                 110

Leu Ile Tyr Asp Leu Lys Asp Gln Gly Gly Glu Leu Leu Ser Leu Arg
        115                 120                 125

Tyr Asp Leu Thr Val Pro Phe Ala Arg Tyr Leu Ala Met Asn Lys Leu
    130                 135                 140

Thr Asn Ile Lys Arg Tyr His Ile Ala Lys Val Tyr Arg Arg Asp Asn
145                 150                 155                 160

Pro Ala Met Thr Arg Gly Arg Tyr Arg Glu Phe Tyr Gln Cys Asp Phe
                165                 170                 175

Asp Ile Ala Gly Asn Phe Asp Pro Met Ile Pro Asp Ala Glu Cys Leu
            180                 185                 190

Lys Ile Met Cys Glu Ile Leu Ser Ser Leu Gln Ile Gly Asp Phe Leu
        195                 200                 205

Val Lys Val Asn Asp Arg Arg Ile Leu Asp Gly Met Phe Ala Ile Cys
    210                 215                 220

Gly Val Ser Asp Ser Lys Phe Arg Thr Ile Cys Ser Ser Val Asp Lys
225                 230                 235                 240

Leu Asp Lys Val Ser Trp Glu Glu Val Lys Asn Glu Met Val Gly Glu
                245                 250                 255

Lys Gly Leu Ala Pro Glu Val Ala Asp Arg Ile Gly Asp Tyr Val Gln
            260                 265                 270

Gln His Gly Gly Val Ser Leu Val Glu Gln Leu Leu Gln Asp Pro Lys
        275                 280                 285

Leu Ser Gln Asn Lys Gln Ala Leu Glu Gly Leu Gly Asp Leu Lys Leu
    290                 295                 300

Leu Phe Glu Tyr Leu Thr Leu Phe Gly Ile Asp Asp Lys Ile Ser Phe
305                 310                 315                 320

Asp Leu Ser Leu Ala Arg Gly Leu Asp Tyr Tyr Thr Gly Val Ile Tyr
                325                 330                 335

Glu Ala Val Leu Leu Gln Thr Pro Ala Gln Ala Gly Glu Glu Pro Leu
            340                 345                 350

Gly Val Gly Ser Val Ala Ala Gly Gly Arg Tyr Asp Gly Leu Val Gly
        355                 360                 365

Met Phe Asp Pro Lys Gly Arg Lys Val Pro Cys Val Gly Leu Ser Ile
    370                 375                 380
```

```
Gly Val Glu Arg Ile Phe Ser Ile Val Glu Gln Arg Leu Glu Ala Leu
385                 390                 395                 400

Glu Glu Lys Ile Arg Thr Thr Glu Thr Gln Val Leu Val Ala Ser Ala
                405                 410                 415

Gln Lys Lys Leu Leu Glu Glu Arg Leu Lys Leu Val Ser Glu Leu Trp
            420                 425                 430

Asp Ala Gly Ile Lys Ala Glu Leu Leu Tyr Lys Lys Asn Pro Lys Leu
        435                 440                 445

Leu Asn Gln Leu Gln Tyr Cys Glu Glu Ala Gly Ile Pro Leu Val Ala
    450                 455                 460

Ile Ile Gly Glu Gln Glu Leu Lys Asp Gly Val Ile Lys Leu Arg Ser
465                 470                 475                 480

Val Thr Ser Arg Glu Glu Val Asp Val Arg Arg Glu Asp Leu Val Glu
                485                 490                 495

Glu Ile Lys Arg
            500


<210> SEQ ID NO 171
<211> LENGTH: 501
<212> TYPE: PRT
<213> ORGANISM: Homo sapiens

<400> SEQUENCE: 171

Met Ala Glu Arg Ala Ala Leu Glu Glu Leu Val Lys Leu Gln Gly Glu
1               5                   10                  15

Arg Val Arg Gly Leu Lys Gln Gln Lys Ala Ser Ala Glu Leu Ile Glu
            20                  25                  30

Glu Glu Val Ala Lys Leu Leu Lys Leu Lys Ala Gln Leu Gly Pro Asp
        35                  40                  45

Glu Ser Lys Gln Lys Phe Val Leu Lys Thr Pro Lys Gly Thr Arg Asp
    50                  55                  60

Tyr Ser Pro Arg Gln Met Ala Val Arg Glu Lys Val Phe Asp Val Ile
65                  70                  75                  80

Ile Arg Cys Phe Lys Arg His Gly Ala Glu Val Ile Asp Thr Pro Val
                85                  90                  95

Phe Glu Leu Lys Glu Thr Leu Met Gly Lys Tyr Gly Glu Asp Ser Lys
            100                 105                 110

Leu Ile Tyr Asp Leu Lys Asp Gln Gly Gly Glu Leu Leu Ser Leu Arg
        115                 120                 125

Tyr Asp Leu Thr Val Pro Phe Ala Arg Tyr Leu Ala Met Asn Lys Leu
    130                 135                 140

Thr Asn Ile Lys Arg Tyr His Ile Ala Lys Val Tyr Arg Arg Asp Asn
145                 150                 155                 160

Pro Ala Met Thr Arg Gly Arg Tyr Arg Glu Phe Tyr Gln Cys Asp Phe
                165                 170                 175

Asp Ile Ala Gly Asn Phe Asp Pro Met Ile Pro Asp Ala Glu Cys Leu
            180                 185                 190

Lys Ile Met Cys Glu Ile Leu Ser Ser Leu Gln Ile Gly Asp Phe Leu
        195                 200                 205

Val Lys Val Asn Asp Arg Arg Ile Leu Asp Gly Met Phe Ala Ile Cys
    210                 215                 220

Gly Val Ser Asp Ser Lys Phe Arg Thr Ile Cys Ser Ser Val Asp Lys
225                 230                 235                 240

Leu Asp Lys Val Ser Trp Glu Glu Val Lys Asn Glu Met Val Gly Glu
                245                 250                 255
```

```
Lys Gly Leu Ala Pro Glu Val Ala Asp Arg Ile Gly Asp Tyr Val Gln
            260                 265                 270

Gln His Gly Gly Val Ser Leu Val Glu Gln Leu Leu Gln Asp Pro Lys
        275                 280                 285

Leu Ser Gln Asn Lys Gln Ala Leu Glu Gly Leu Gly Asp Leu Lys Leu
    290                 295                 300

Leu Phe Glu Tyr Leu Thr Leu Phe Gly Ile Asp Asp Lys Ile Ser Phe
305                 310                 315                 320

Asp Leu Ser Leu Ala Arg Gly Leu Asp Tyr Tyr Thr Gly Val Ile Tyr
                325                 330                 335

Glu Ala Val Leu Leu Gln Thr Pro Ala Gln Ala Gly Glu Glu Pro Leu
            340                 345                 350

Gly Val Gly Ser Val Ala Ala Gly Gly Arg Tyr Asp Gly Leu Val Gly
        355                 360                 365

Met Phe Asp Pro Lys Gly Arg Lys Val Pro Cys Val Gly Leu Ser Ile
    370                 375                 380

Gly Val Glu Arg Ile Phe Ser Ile Val Glu Gln Arg Leu Glu Ala Leu
385                 390                 395                 400

Glu Glu Lys Ile Arg Thr Thr Glu Thr Gln Val Leu Val Ala Ser Ala
                405                 410                 415

Gln Lys Lys Leu Leu Glu Glu Arg Leu Lys Leu Val Ser Glu Leu Trp
            420                 425                 430

Asp Ala Gly Ile Lys Ala Glu Leu Leu Tyr Lys Lys Asn Pro Lys Leu
        435                 440                 445

Leu Asn Gln Leu Gln Tyr Cys Glu Glu Ala Gly Ile Pro Leu Val Ala
    450                 455                 460

Ile Ile Gly Glu Gln Glu Leu Lys Asp Gly Val Ile Lys Leu Arg Ser
465                 470                 475                 480

Val Thr Ser Arg Glu Glu Val Asp Val Arg Arg Glu Asp Leu Val Glu
                485                 490                 495

Glu Ile Lys Arg Arg
            500


<210> SEQ ID NO 172
<211> LENGTH: 502
<212> TYPE: PRT
<213> ORGANISM: Homo sapiens

<400> SEQUENCE: 172

Met Ala Glu Arg Ala Ala Leu Glu Glu Leu Val Lys Leu Gln Gly Glu
1               5                   10                  15

Arg Val Arg Gly Leu Lys Gln Gln Lys Ala Ser Ala Glu Leu Ile Glu
            20                  25                  30

Glu Glu Val Ala Lys Leu Leu Lys Leu Lys Ala Gln Leu Gly Pro Asp
        35                  40                  45

Glu Ser Lys Gln Lys Phe Val Leu Lys Thr Pro Lys Gly Thr Arg Asp
    50                  55                  60

Tyr Ser Pro Arg Gln Met Ala Val Arg Glu Lys Val Phe Asp Val Ile
65                  70                  75                  80

Ile Arg Cys Phe Lys Arg His Gly Ala Glu Val Ile Asp Thr Pro Val
                85                  90                  95

Phe Glu Leu Lys Glu Thr Leu Met Gly Lys Tyr Gly Glu Asp Ser Lys
            100                 105                 110

Leu Ile Tyr Asp Leu Lys Asp Gln Gly Gly Glu Leu Leu Ser Leu Arg
```

```
        115                 120                 125

Tyr Asp Leu Thr Val Pro Phe Ala Arg Tyr Leu Ala Met Asn Lys Leu
    130                 135                 140

Thr Asn Ile Lys Arg Tyr His Ile Ala Lys Val Tyr Arg Arg Asp Asn
145                 150                 155                 160

Pro Ala Met Thr Arg Gly Arg Tyr Arg Glu Phe Tyr Gln Cys Asp Phe
                165                 170                 175

Asp Ile Ala Gly Asn Phe Asp Pro Met Ile Pro Asp Ala Glu Cys Leu
            180                 185                 190

Lys Ile Met Cys Glu Ile Leu Ser Ser Leu Gln Ile Gly Asp Phe Leu
        195                 200                 205

Val Lys Val Asn Asp Arg Arg Ile Leu Asp Gly Met Phe Ala Ile Cys
    210                 215                 220

Gly Val Ser Asp Ser Lys Phe Arg Thr Ile Cys Ser Ser Val Asp Lys
225                 230                 235                 240

Leu Asp Lys Val Ser Trp Glu Glu Val Lys Asn Glu Met Val Gly Glu
                245                 250                 255

Lys Gly Leu Ala Pro Glu Val Ala Asp Arg Ile Gly Asp Tyr Val Gln
            260                 265                 270

Gln His Gly Gly Val Ser Leu Val Glu Gln Leu Leu Gln Asp Pro Lys
        275                 280                 285

Leu Ser Gln Asn Lys Gln Ala Leu Glu Gly Leu Gly Asp Leu Lys Leu
    290                 295                 300

Leu Phe Glu Tyr Leu Thr Leu Phe Gly Ile Asp Asp Lys Ile Ser Phe
305                 310                 315                 320

Asp Leu Ser Leu Ala Arg Gly Leu Asp Tyr Tyr Thr Gly Val Ile Tyr
                325                 330                 335

Glu Ala Val Leu Leu Gln Thr Pro Ala Gln Ala Gly Glu Glu Pro Leu
            340                 345                 350

Gly Val Gly Ser Val Ala Ala Gly Gly Arg Tyr Asp Gly Leu Val Gly
        355                 360                 365

Met Phe Asp Pro Lys Gly Arg Lys Val Pro Cys Val Gly Leu Ser Ile
    370                 375                 380

Gly Val Glu Arg Ile Phe Ser Ile Val Glu Gln Arg Leu Glu Ala Leu
385                 390                 395                 400

Glu Glu Lys Ile Arg Thr Thr Glu Thr Gln Val Leu Val Ala Ser Ala
                405                 410                 415

Gln Lys Lys Leu Leu Glu Glu Arg Leu Lys Leu Val Ser Glu Leu Trp
            420                 425                 430

Asp Ala Gly Ile Lys Ala Glu Leu Leu Tyr Lys Lys Asn Pro Lys Leu
        435                 440                 445

Leu Asn Gln Leu Gln Tyr Cys Glu Glu Ala Gly Ile Pro Leu Val Ala
    450                 455                 460

Ile Ile Gly Glu Gln Glu Leu Lys Asp Gly Val Ile Lys Leu Arg Ser
465                 470                 475                 480

Val Thr Ser Arg Glu Glu Val Asp Val Arg Arg Glu Asp Leu Val Glu
                485                 490                 495

Glu Ile Lys Arg Arg Thr
            500
```

<210> SEQ ID NO 173
<211> LENGTH: 503
<212> TYPE: PRT
<213> ORGANISM: Homo sapiens

<400> SEQUENCE: 173

Met Ala Glu Arg Ala Ala Leu Glu Glu Leu Val Lys Leu Gln Gly Glu
1 5 10 15

Arg Val Arg Gly Leu Lys Gln Gln Lys Ala Ser Ala Glu Leu Ile Glu
20 25 30

Glu Glu Val Ala Lys Leu Leu Lys Leu Lys Ala Gln Leu Gly Pro Asp
35 40 45

Glu Ser Lys Gln Lys Phe Val Leu Lys Thr Pro Lys Gly Thr Arg Asp
50 55 60

Tyr Ser Pro Arg Gln Met Ala Val Arg Glu Lys Val Phe Asp Val Ile
65 70 75 80

Ile Arg Cys Phe Lys Arg His Gly Ala Glu Val Ile Asp Thr Pro Val
85 90 95

Phe Glu Leu Lys Glu Thr Leu Met Gly Lys Tyr Gly Glu Asp Ser Lys
100 105 110

Leu Ile Tyr Asp Leu Lys Asp Gln Gly Gly Glu Leu Leu Ser Leu Arg
115 120 125

Tyr Asp Leu Thr Val Pro Phe Ala Arg Tyr Leu Ala Met Asn Lys Leu
130 135 140

Thr Asn Ile Lys Arg Tyr His Ile Ala Lys Val Tyr Arg Arg Asp Asn
145 150 155 160

Pro Ala Met Thr Arg Gly Arg Tyr Arg Glu Phe Tyr Gln Cys Asp Phe
165 170 175

Asp Ile Ala Gly Asn Phe Asp Pro Met Ile Pro Asp Ala Glu Cys Leu
180 185 190

Lys Ile Met Cys Glu Ile Leu Ser Ser Leu Gln Ile Gly Asp Phe Leu
195 200 205

Val Lys Val Asn Asp Arg Arg Ile Leu Asp Gly Met Phe Ala Ile Cys
210 215 220

Gly Val Ser Asp Ser Lys Phe Arg Thr Ile Cys Ser Ser Val Asp Lys
225 230 235 240

Leu Asp Lys Val Ser Trp Glu Glu Val Lys Asn Glu Met Val Gly Glu
245 250 255

Lys Gly Leu Ala Pro Glu Val Ala Asp Arg Ile Gly Asp Tyr Val Gln
260 265 270

Gln His Gly Gly Val Ser Leu Val Glu Gln Leu Leu Gln Asp Pro Lys
275 280 285

Leu Ser Gln Asn Lys Gln Ala Leu Glu Gly Leu Gly Asp Leu Lys Leu
290 295 300

Leu Phe Glu Tyr Leu Thr Leu Phe Gly Ile Asp Asp Lys Ile Ser Phe
305 310 315 320

Asp Leu Ser Leu Ala Arg Gly Leu Asp Tyr Tyr Thr Gly Val Ile Tyr
325 330 335

Glu Ala Val Leu Leu Gln Thr Pro Ala Gln Ala Gly Glu Glu Pro Leu
340 345 350

Gly Val Gly Ser Val Ala Ala Gly Gly Arg Tyr Asp Gly Leu Val Gly
355 360 365

Met Phe Asp Pro Lys Gly Arg Lys Val Pro Cys Val Gly Leu Ser Ile
370 375 380

Gly Val Glu Arg Ile Phe Ser Ile Val Glu Gln Arg Leu Glu Ala Leu
385 390 395 400

Glu Glu Lys Ile Arg Thr Thr Glu Thr Gln Val Leu Val Ala Ser Ala

```
                405                 410                 415

Gln Lys Lys Leu Leu Glu Glu Arg Leu Lys Leu Val Ser Glu Leu Trp
            420                 425                 430

Asp Ala Gly Ile Lys Ala Glu Leu Leu Tyr Lys Lys Asn Pro Lys Leu
        435                 440                 445

Leu Asn Gln Leu Gln Tyr Cys Glu Glu Ala Gly Ile Pro Leu Val Ala
    450                 455                 460

Ile Ile Gly Glu Gln Glu Leu Lys Asp Gly Val Ile Lys Leu Arg Ser
465                 470                 475                 480

Val Thr Ser Arg Glu Glu Val Asp Val Arg Arg Glu Asp Leu Val Glu
            485                 490                 495

Glu Ile Lys Arg Arg Thr Gly
            500


<210> SEQ ID NO 174
<211> LENGTH: 504
<212> TYPE: PRT
<213> ORGANISM: Homo sapiens

<400> SEQUENCE: 174

Met Ala Glu Arg Ala Ala Leu Glu Glu Leu Val Lys Leu Gln Gly Glu
1               5                   10                  15

Arg Val Arg Gly Leu Lys Gln Gln Lys Ala Ser Ala Glu Leu Ile Glu
            20                  25                  30

Glu Glu Val Ala Lys Leu Leu Lys Leu Lys Ala Gln Leu Gly Pro Asp
        35                  40                  45

Glu Ser Lys Gln Lys Phe Val Leu Lys Thr Pro Lys Gly Thr Arg Asp
    50                  55                  60

Tyr Ser Pro Arg Gln Met Ala Val Arg Glu Lys Val Phe Asp Val Ile
65                  70                  75                  80

Ile Arg Cys Phe Lys Arg His Gly Ala Glu Val Ile Asp Thr Pro Val
                85                  90                  95

Phe Glu Leu Lys Glu Thr Leu Met Gly Lys Tyr Gly Glu Asp Ser Lys
            100                 105                 110

Leu Ile Tyr Asp Leu Lys Asp Gln Gly Gly Glu Leu Leu Ser Leu Arg
        115                 120                 125

Tyr Asp Leu Thr Val Pro Phe Ala Arg Tyr Leu Ala Met Asn Lys Leu
    130                 135                 140

Thr Asn Ile Lys Arg Tyr His Ile Ala Lys Val Tyr Arg Arg Asp Asn
145                 150                 155                 160

Pro Ala Met Thr Arg Gly Arg Tyr Arg Glu Phe Tyr Gln Cys Asp Phe
                165                 170                 175

Asp Ile Ala Gly Asn Phe Asp Pro Met Ile Pro Asp Ala Glu Cys Leu
            180                 185                 190

Lys Ile Met Cys Glu Ile Leu Ser Ser Leu Gln Ile Gly Asp Phe Leu
        195                 200                 205

Val Lys Val Asn Asp Arg Arg Ile Leu Asp Gly Met Phe Ala Ile Cys
    210                 215                 220

Gly Val Ser Asp Ser Lys Phe Arg Thr Ile Cys Ser Ser Val Asp Lys
225                 230                 235                 240

Leu Asp Lys Val Ser Trp Glu Glu Val Lys Asn Glu Met Val Gly Glu
                245                 250                 255

Lys Gly Leu Ala Pro Glu Val Ala Asp Arg Ile Gly Asp Tyr Val Gln
            260                 265                 270
```

-continued

```
Gln His Gly Gly Val Ser Leu Val Glu Gln Leu Leu Gln Asp Pro Lys
        275                 280                 285

Leu Ser Gln Asn Lys Gln Ala Leu Glu Gly Leu Gly Asp Leu Lys Leu
    290                 295                 300

Leu Phe Glu Tyr Leu Thr Leu Phe Gly Ile Asp Asp Lys Ile Ser Phe
305                 310                 315                 320

Asp Leu Ser Leu Ala Arg Gly Leu Asp Tyr Tyr Thr Gly Val Ile Tyr
                325                 330                 335

Glu Ala Val Leu Leu Gln Thr Pro Ala Gln Ala Gly Glu Glu Pro Leu
            340                 345                 350

Gly Val Gly Ser Val Ala Ala Gly Gly Arg Tyr Asp Gly Leu Val Gly
        355                 360                 365

Met Phe Asp Pro Lys Gly Arg Lys Val Pro Cys Val Gly Leu Ser Ile
    370                 375                 380

Gly Val Glu Arg Ile Phe Ser Ile Val Glu Gln Arg Leu Glu Ala Leu
385                 390                 395                 400

Glu Glu Lys Ile Arg Thr Thr Glu Thr Gln Val Leu Val Ala Ser Ala
                405                 410                 415

Gln Lys Lys Leu Leu Glu Glu Arg Leu Lys Leu Val Ser Glu Leu Trp
            420                 425                 430

Asp Ala Gly Ile Lys Ala Glu Leu Leu Tyr Lys Lys Asn Pro Lys Leu
        435                 440                 445

Leu Asn Gln Leu Gln Tyr Cys Glu Glu Ala Gly Ile Pro Leu Val Ala
    450                 455                 460

Ile Ile Gly Glu Gln Glu Leu Lys Asp Gly Val Ile Lys Leu Arg Ser
465                 470                 475                 480

Val Thr Ser Arg Glu Glu Val Asp Val Arg Arg Glu Asp Leu Val Glu
                485                 490                 495

Glu Ile Lys Arg Arg Thr Gly Gln
            500


<210> SEQ ID NO 175
<211> LENGTH: 505
<212> TYPE: PRT
<213> ORGANISM: Homo sapiens

<400> SEQUENCE: 175

Met Ala Glu Arg Ala Ala Leu Glu Glu Leu Val Lys Leu Gln Gly Glu
1               5                   10                  15

Arg Val Arg Gly Leu Lys Gln Gln Lys Ala Ser Ala Glu Leu Ile Glu
            20                  25                  30

Glu Glu Val Ala Lys Leu Leu Lys Leu Lys Ala Gln Leu Gly Pro Asp
        35                  40                  45

Glu Ser Lys Gln Lys Phe Val Leu Lys Thr Pro Lys Gly Thr Arg Asp
    50                  55                  60

Tyr Ser Pro Arg Gln Met Ala Val Arg Glu Lys Val Phe Asp Val Ile
65                  70                  75                  80

Ile Arg Cys Phe Lys Arg His Gly Ala Glu Val Ile Asp Thr Pro Val
                85                  90                  95

Phe Glu Leu Lys Glu Thr Leu Met Gly Lys Tyr Gly Glu Asp Ser Lys
            100                 105                 110

Leu Ile Tyr Asp Leu Lys Asp Gln Gly Gly Glu Leu Leu Ser Leu Arg
        115                 120                 125

Tyr Asp Leu Thr Val Pro Phe Ala Arg Tyr Leu Ala Met Asn Lys Leu
    130                 135                 140
```

```
Thr Asn Ile Lys Arg Tyr His Ile Ala Lys Val Tyr Arg Arg Asp Asn
145                 150                 155                 160

Pro Ala Met Thr Arg Gly Arg Tyr Arg Glu Phe Tyr Gln Cys Asp Phe
                165                 170                 175

Asp Ile Ala Gly Asn Phe Asp Pro Met Ile Pro Asp Ala Glu Cys Leu
            180                 185                 190

Lys Ile Met Cys Glu Ile Leu Ser Ser Leu Gln Ile Gly Asp Phe Leu
        195                 200                 205

Val Lys Val Asn Asp Arg Arg Ile Leu Asp Gly Met Phe Ala Ile Cys
    210                 215                 220

Gly Val Ser Asp Ser Lys Phe Arg Thr Ile Cys Ser Ser Val Asp Lys
225                 230                 235                 240

Leu Asp Lys Val Ser Trp Glu Glu Val Lys Asn Glu Met Val Gly Glu
                245                 250                 255

Lys Gly Leu Ala Pro Glu Val Ala Asp Arg Ile Gly Asp Tyr Val Gln
            260                 265                 270

Gln His Gly Gly Val Ser Leu Val Glu Gln Leu Leu Gln Asp Pro Lys
        275                 280                 285

Leu Ser Gln Asn Lys Gln Ala Leu Glu Gly Leu Gly Asp Leu Lys Leu
    290                 295                 300

Leu Phe Glu Tyr Leu Thr Leu Phe Gly Ile Asp Asp Lys Ile Ser Phe
305                 310                 315                 320

Asp Leu Ser Leu Ala Arg Gly Leu Asp Tyr Tyr Thr Gly Val Ile Tyr
                325                 330                 335

Glu Ala Val Leu Leu Gln Thr Pro Ala Gln Ala Gly Glu Glu Pro Leu
            340                 345                 350

Gly Val Gly Ser Val Ala Ala Gly Gly Arg Tyr Asp Gly Leu Val Gly
        355                 360                 365

Met Phe Asp Pro Lys Gly Arg Lys Val Pro Cys Val Gly Leu Ser Ile
    370                 375                 380

Gly Val Glu Arg Ile Phe Ser Ile Val Glu Gln Arg Leu Glu Ala Leu
385                 390                 395                 400

Glu Glu Lys Ile Arg Thr Thr Glu Thr Gln Val Leu Val Ala Ser Ala
                405                 410                 415

Gln Lys Lys Leu Leu Glu Glu Arg Leu Lys Leu Val Ser Glu Leu Trp
            420                 425                 430

Asp Ala Gly Ile Lys Ala Glu Leu Leu Tyr Lys Lys Asn Pro Lys Leu
        435                 440                 445

Leu Asn Gln Leu Gln Tyr Cys Glu Glu Ala Gly Ile Pro Leu Val Ala
    450                 455                 460

Ile Ile Gly Glu Gln Glu Leu Lys Asp Gly Val Ile Lys Leu Arg Ser
465                 470                 475                 480

Val Thr Ser Arg Glu Glu Val Asp Val Arg Arg Glu Asp Leu Val Glu
                485                 490                 495

Glu Ile Lys Arg Arg Thr Gly Gln Pro
            500                 505


<210> SEQ ID NO 176
<211> LENGTH: 507
<212> TYPE: PRT
<213> ORGANISM: Homo sapiens

<400> SEQUENCE: 176

Met Ala Glu Arg Ala Ala Leu Glu Glu Leu Val Lys Leu Gln Gly Glu
```

-continued

```
1               5                   10                  15

Arg Val Arg Gly Leu Lys Gln Gln Lys Ala Ser Ala Glu Leu Ile Glu
            20                  25                  30

Glu Glu Val Ala Lys Leu Leu Lys Leu Lys Ala Gln Leu Gly Pro Asp
        35                  40                  45

Glu Ser Lys Gln Lys Phe Val Leu Lys Thr Pro Lys Gly Thr Arg Asp
    50                  55                  60

Tyr Ser Pro Arg Gln Met Ala Val Arg Glu Lys Val Phe Asp Val Ile
65                  70                  75                  80

Ile Arg Cys Phe Lys Arg His Gly Ala Glu Val Ile Asp Thr Pro Val
                85                  90                  95

Phe Glu Leu Lys Glu Thr Leu Met Gly Lys Tyr Gly Glu Asp Ser Lys
            100                 105                 110

Leu Ile Tyr Asp Leu Lys Asp Gln Gly Gly Glu Leu Leu Ser Leu Arg
        115                 120                 125

Tyr Asp Leu Thr Val Pro Phe Ala Arg Tyr Leu Ala Met Asn Lys Leu
    130                 135                 140

Thr Asn Ile Lys Arg Tyr His Ile Ala Lys Val Tyr Arg Arg Asp Asn
145                 150                 155                 160

Pro Ala Met Thr Arg Gly Arg Tyr Arg Glu Phe Tyr Gln Cys Asp Phe
                165                 170                 175

Asp Ile Ala Gly Asn Phe Asp Pro Met Ile Pro Asp Ala Glu Cys Leu
            180                 185                 190

Lys Ile Met Cys Glu Ile Leu Ser Ser Leu Gln Ile Gly Asp Phe Leu
        195                 200                 205

Val Lys Val Asn Asp Arg Arg Ile Leu Asp Gly Met Phe Ala Ile Cys
    210                 215                 220

Gly Val Ser Asp Ser Lys Phe Arg Thr Ile Cys Ser Ser Val Asp Lys
225                 230                 235                 240

Leu Asp Lys Val Ser Trp Glu Glu Val Lys Asn Glu Met Val Gly Glu
                245                 250                 255

Lys Gly Leu Ala Pro Glu Val Ala Asp Arg Ile Gly Asp Tyr Val Gln
            260                 265                 270

Gln His Gly Gly Val Ser Leu Val Glu Gln Leu Leu Gln Asp Pro Lys
        275                 280                 285

Leu Ser Gln Asn Lys Gln Ala Leu Glu Gly Leu Gly Asp Leu Lys Leu
    290                 295                 300

Leu Phe Glu Tyr Leu Thr Leu Phe Gly Ile Asp Asp Lys Ile Ser Phe
305                 310                 315                 320

Asp Leu Ser Leu Ala Arg Gly Leu Asp Tyr Tyr Thr Gly Val Ile Tyr
                325                 330                 335

Glu Ala Val Leu Leu Gln Thr Pro Ala Gln Ala Gly Glu Glu Pro Leu
            340                 345                 350

Gly Val Gly Ser Val Ala Ala Gly Gly Arg Tyr Asp Gly Leu Val Gly
        355                 360                 365

Met Phe Asp Pro Lys Gly Arg Lys Val Pro Cys Val Gly Leu Ser Ile
    370                 375                 380

Gly Val Glu Arg Ile Phe Ser Ile Val Glu Gln Arg Leu Glu Ala Leu
385                 390                 395                 400

Glu Glu Lys Ile Arg Thr Thr Glu Thr Gln Val Leu Val Ala Ser Ala
                405                 410                 415

Gln Lys Lys Leu Leu Glu Glu Arg Leu Lys Leu Val Ser Glu Leu Trp
            420                 425                 430
```

```
Asp Ala Gly Ile Lys Ala Glu Leu Leu Tyr Lys Lys Asn Pro Lys Leu
        435                 440                 445

Leu Asn Gln Leu Gln Tyr Cys Glu Glu Ala Gly Ile Pro Leu Val Ala
    450                 455                 460

Ile Ile Gly Glu Gln Glu Leu Lys Asp Gly Val Ile Lys Leu Arg Ser
465                 470                 475                 480

Val Thr Ser Arg Glu Glu Val Asp Val Arg Arg Glu Asp Leu Val Glu
                485                 490                 495

Glu Ile Lys Arg Arg Thr Gly Gln Pro Leu Cys
            500                 505


<210> SEQ ID NO 177
<211> LENGTH: 508
<212> TYPE: PRT
<213> ORGANISM: Homo sapiens

<400> SEQUENCE: 177

Met Ala Glu Arg Ala Ala Leu Glu Glu Leu Val Lys Leu Gln Gly Glu
1               5                   10                  15

Arg Val Arg Gly Leu Lys Gln Gln Lys Ala Ser Ala Glu Leu Ile Glu
            20                  25                  30

Glu Glu Val Ala Lys Leu Leu Lys Leu Lys Ala Gln Leu Gly Pro Asp
        35                  40                  45

Glu Ser Lys Gln Lys Phe Val Leu Lys Thr Pro Lys Gly Thr Arg Asp
    50                  55                  60

Tyr Ser Pro Arg Gln Met Ala Val Arg Glu Lys Val Phe Asp Val Ile
65                  70                  75                  80

Ile Arg Cys Phe Lys Arg His Gly Ala Glu Val Ile Asp Thr Pro Val
                85                  90                  95

Phe Glu Leu Lys Glu Thr Leu Met Gly Lys Tyr Gly Glu Asp Ser Lys
            100                 105                 110

Leu Ile Tyr Asp Leu Lys Asp Gln Gly Gly Glu Leu Leu Ser Leu Arg
        115                 120                 125

Tyr Asp Leu Thr Val Pro Phe Ala Arg Tyr Leu Ala Met Asn Lys Leu
    130                 135                 140

Thr Asn Ile Lys Arg Tyr His Ile Ala Lys Val Tyr Arg Arg Asp Asn
145                 150                 155                 160

Pro Ala Met Thr Arg Gly Arg Tyr Arg Glu Phe Tyr Gln Cys Asp Phe
                165                 170                 175

Asp Ile Ala Gly Asn Phe Asp Pro Met Ile Pro Asp Ala Glu Cys Leu
            180                 185                 190

Lys Ile Met Cys Glu Ile Leu Ser Ser Leu Gln Ile Gly Asp Phe Leu
        195                 200                 205

Val Lys Val Asn Asp Arg Arg Ile Leu Asp Gly Met Phe Ala Ile Cys
    210                 215                 220

Gly Val Ser Asp Ser Lys Phe Arg Thr Ile Cys Ser Ser Val Asp Lys
225                 230                 235                 240

Leu Asp Lys Val Ser Trp Glu Glu Val Lys Asn Glu Met Val Gly Glu
                245                 250                 255

Lys Gly Leu Ala Pro Glu Val Ala Asp Arg Ile Gly Asp Tyr Val Gln
            260                 265                 270

Gln His Gly Gly Val Ser Leu Val Glu Gln Leu Leu Gln Asp Pro Lys
        275                 280                 285

Leu Ser Gln Asn Lys Gln Ala Leu Glu Gly Leu Gly Asp Leu Lys Leu
```

-continued

```
    290                 295                 300

Leu Phe Glu Tyr Leu Thr Leu Phe Gly Ile Asp Asp Lys Ile Ser Phe
305                 310                 315                 320

Asp Leu Ser Leu Ala Arg Gly Leu Asp Tyr Tyr Thr Gly Val Ile Tyr
                325                 330                 335

Glu Ala Val Leu Leu Gln Thr Pro Ala Gln Ala Gly Glu Glu Pro Leu
            340                 345                 350

Gly Val Gly Ser Val Ala Ala Gly Gly Arg Tyr Asp Gly Leu Val Gly
        355                 360                 365

Met Phe Asp Pro Lys Gly Arg Lys Val Pro Cys Val Gly Leu Ser Ile
    370                 375                 380

Gly Val Glu Arg Ile Phe Ser Ile Val Glu Gln Arg Leu Glu Ala Leu
385                 390                 395                 400

Glu Glu Lys Ile Arg Thr Thr Glu Thr Gln Val Leu Val Ala Ser Ala
                405                 410                 415

Gln Lys Lys Leu Leu Glu Glu Arg Leu Lys Leu Val Ser Glu Leu Trp
            420                 425                 430

Asp Ala Gly Ile Lys Ala Glu Leu Leu Tyr Lys Lys Asn Pro Lys Leu
        435                 440                 445

Leu Asn Gln Leu Gln Tyr Cys Glu Glu Ala Gly Ile Pro Leu Val Ala
    450                 455                 460

Ile Ile Gly Glu Gln Glu Leu Lys Asp Gly Val Ile Lys Leu Arg Ser
465                 470                 475                 480

Val Thr Ser Arg Glu Glu Val Asp Val Arg Arg Glu Asp Leu Val Glu
                485                 490                 495

Glu Ile Lys Arg Arg Thr Gly Gln Pro Leu Cys Ile
            500                 505


<210> SEQ ID NO 178
<211> LENGTH: 509
<212> TYPE: PRT
<213> ORGANISM: Homo sapiens

<400> SEQUENCE: 178

Met Ala Glu Arg Ala Ala Leu Glu Glu Leu Val Lys Leu Gln Gly Glu
1               5                   10                  15

Arg Val Arg Gly Leu Lys Gln Gln Lys Ala Ser Ala Glu Leu Ile Glu
            20                  25                  30

Glu Glu Val Ala Lys Leu Leu Lys Leu Lys Ala Gln Leu Gly Pro Asp
        35                  40                  45

Glu Ser Lys Gln Lys Phe Val Leu Lys Thr Pro Lys Gly Thr Arg Asp
    50                  55                  60

Tyr Ser Pro Arg Gln Met Ala Val Arg Glu Lys Val Phe Asp Val Ile
65                  70                  75                  80

Ile Arg Cys Phe Lys Arg His Gly Ala Glu Val Ile Asp Thr Pro Val
                85                  90                  95

Phe Glu Leu Lys Glu Thr Leu Met Gly Lys Tyr Gly Glu Asp Ser Lys
            100                 105                 110

Leu Ile Tyr Asp Leu Lys Asp Gln Gly Gly Glu Leu Leu Ser Leu Arg
        115                 120                 125

Tyr Asp Leu Thr Val Pro Phe Ala Arg Tyr Leu Ala Met Asn Lys Leu
    130                 135                 140

Thr Asn Ile Lys Arg Tyr His Ile Ala Lys Val Tyr Arg Arg Asp Asn
145                 150                 155                 160
```

-continued

```
Pro Ala Met Thr Arg Gly Arg Tyr Arg Glu Phe Tyr Gln Cys Asp Phe
                165                 170                 175

Asp Ile Ala Gly Asn Phe Asp Pro Met Ile Pro Asp Ala Glu Cys Leu
            180                 185                 190

Lys Ile Met Cys Glu Ile Leu Ser Ser Leu Gln Ile Gly Asp Phe Leu
        195                 200                 205

Val Lys Val Asn Asp Arg Arg Ile Leu Asp Gly Met Phe Ala Ile Cys
    210                 215                 220

Gly Val Ser Asp Ser Lys Phe Arg Thr Ile Cys Ser Ser Val Asp Lys
225                 230                 235                 240

Leu Asp Lys Val Ser Trp Glu Glu Val Lys Asn Glu Met Val Gly Glu
                245                 250                 255

Lys Gly Leu Ala Pro Glu Val Ala Asp Arg Ile Gly Asp Tyr Val Gln
            260                 265                 270

Gln His Gly Gly Val Ser Leu Val Glu Gln Leu Leu Gln Asp Pro Lys
        275                 280                 285

Leu Ser Gln Asn Lys Gln Ala Leu Glu Gly Leu Gly Asp Leu Lys Leu
    290                 295                 300

Leu Phe Glu Tyr Leu Thr Leu Phe Gly Ile Asp Asp Lys Ile Ser Phe
305                 310                 315                 320

Asp Leu Ser Leu Ala Arg Gly Leu Asp Tyr Tyr Thr Gly Val Ile Tyr
                325                 330                 335

Glu Ala Val Leu Leu Gln Thr Pro Ala Gln Ala Gly Glu Glu Pro Leu
            340                 345                 350

Gly Val Gly Ser Val Ala Ala Gly Gly Arg Tyr Asp Gly Leu Val Gly
        355                 360                 365

Met Phe Asp Pro Lys Gly Arg Lys Val Pro Cys Val Gly Leu Ser Ile
    370                 375                 380

Gly Val Glu Arg Ile Phe Ser Ile Val Glu Gln Arg Leu Glu Ala Leu
385                 390                 395                 400

Glu Glu Lys Ile Arg Thr Thr Glu Thr Gln Val Leu Val Ala Ser Ala
                405                 410                 415

Gln Lys Lys Leu Leu Glu Glu Arg Leu Lys Leu Val Ser Glu Leu Trp
            420                 425                 430

Asp Ala Gly Ile Lys Ala Glu Leu Leu Tyr Lys Lys Asn Pro Lys Leu
        435                 440                 445

Leu Asn Gln Leu Gln Tyr Cys Glu Glu Ala Gly Ile Pro Leu Val Ala
    450                 455                 460

Ile Ile Gly Glu Gln Glu Leu Lys Asp Gly Val Ile Lys Leu Arg Ser
465                 470                 475                 480

Val Thr Ser Arg Glu Glu Val Asp Val Arg Arg Glu Asp Leu Val Glu
                485                 490                 495

Glu Ile Lys Arg Arg Thr Gly Gln Pro Leu Cys Ile Cys
            500                 505


<210> SEQ ID NO 179
<211> LENGTH: 61
<212> TYPE: PRT
<213> ORGANISM: Artificial Sequence
<220> FEATURE:
<223> OTHER INFORMATION: Cysteine modified HRS polypeptide

<400> SEQUENCE: 179

Met Cys Ala Glu Arg Ala Ala Leu Glu Glu Leu Val Lys Leu Gln Gly
1               5                   10                  15
```

```
Glu Arg Val Arg Gly Leu Lys Gln Gln Lys Ala Ser Ala Glu Leu Ile
            20                  25                  30

Glu Glu Glu Val Ala Lys Leu Leu Lys Leu Lys Ala Gln Leu Gly Pro
        35                  40                  45

Asp Glu Ser Lys Gln Lys Phe Val Leu Lys Thr Pro Lys
    50                  55                  60


<210> SEQ ID NO 180
<211> LENGTH: 60
<212> TYPE: PRT
<213> ORGANISM: Artificial Sequence
<220> FEATURE:
<223> OTHER INFORMATION: Cysteine modified HRS polypeptide

<400> SEQUENCE: 180

Met Ala Glu Arg Ala Ala Leu Glu Glu Leu Val Lys Leu Gln Gly Glu
1               5                   10                  15

Arg Val Arg Gly Leu Lys Gln Gln Lys Cys Ser Ala Glu Leu Ile Glu
            20                  25                  30

Glu Glu Val Ala Lys Leu Leu Lys Leu Lys Ala Gln Leu Gly Pro Asp
        35                  40                  45

Glu Ser Lys Gln Lys Phe Val Leu Lys Thr Pro Lys
    50                  55                  60


<210> SEQ ID NO 181
<211> LENGTH: 61
<212> TYPE: PRT
<213> ORGANISM: Artificial Sequence
<220> FEATURE:
<223> OTHER INFORMATION: Cysteine modified HRS polypeptide

<400> SEQUENCE: 181

Met Ala Glu Arg Ala Ala Leu Glu Glu Leu Val Lys Leu Gln Gly Glu
1               5                   10                  15

Arg Val Arg Gly Leu Lys Gln Gln Lys Ala Ser Ala Glu Leu Ile Glu
            20                  25                  30

Glu Glu Val Ala Lys Leu Leu Lys Leu Lys Ala Gln Leu Gly Pro Asp
        35                  40                  45

Glu Ser Lys Gln Lys Phe Val Leu Lys Thr Pro Lys Cys
    50                  55                  60


<210> SEQ ID NO 182
<211> LENGTH: 183
<212> TYPE: DNA
<213> ORGANISM: Artificial Sequence
<220> FEATURE:
<223> OTHER INFORMATION: Polynucleotide encoding cyteine modified HRS

<400> SEQUENCE: 182

atgtgtgcag aaagagccgc cctggaagag ttagttaagt tgcaaggtga acgtgtccgt      60

ggtctgaagc agcagaaggc tagcgcggag ctgatcgaag aagaggtggc caaactgctg     120

aagctgaagg cgcagctggg cccggacgag agcaaacaaa agttcgtcct gaaaaccccg     180

aaa                                                                   183


<210> SEQ ID NO 183
<211> LENGTH: 180
<212> TYPE: DNA
<213> ORGANISM: Artificial Sequence
<220> FEATURE:
<223> OTHER INFORMATION: Polynucleotide encoding cyteine modified HRS
```

<400> SEQUENCE: 183
atggcagaac gtgcggcatt ggaagaattg gttaaactgc aaggtgaacg tgttcgtggt 60
ctgaagcagc agaagtgcag cgcggagctg atcgaagaag aggtggccaa actgctgaag 120
ctgaaggcgc agctgggccc ggacgagagc aaacaaaagt tcgtcctgaa aaccccgaaa 180

<210> SEQ ID NO 184
<211> LENGTH: 183
<212> TYPE: DNA
<213> ORGANISM: Artificial Sequence
<220> FEATURE:
<223> OTHER INFORMATION: Polynucleotide encoding cyteine modified HRS

<400> SEQUENCE: 184
atggcagaac gtgcggcatt ggaagaattg gttaaactgc aaggtgaacg tgttcgtggt 60
ctgaagcagc agaaggctag cgcggagctg atcgaagaag aggtggccaa actgctgaag 120
ctgaaggcgc agctgggccc ggacgagagc aaacaaaagt tcgtcctgaa aaccccgaaa 180
tgc 183

<210> SEQ ID NO 185
<211> LENGTH: 506
<212> TYPE: PRT
<213> ORGANISM: Artificial Sequence
<220> FEATURE:
<223> OTHER INFORMATION: Cysteine mutated HRS polypeptide

<400> SEQUENCE: 185

Met Ala Glu Arg Ala Ala Leu Glu Glu Leu Val Lys Leu Gln Gly Glu
1 5 10 15

Arg Val Arg Gly Leu Lys Gln Gln Lys Ala Ser Ala Glu Leu Ile Glu
20 25 30

Glu Glu Val Ala Lys Leu Leu Lys Leu Lys Ala Gln Leu Gly Pro Asp
35 40 45

Glu Ser Lys Gln Lys Phe Val Leu Lys Thr Pro Lys Gly Thr Arg Asp
50 55 60

Tyr Ser Pro Arg Gln Met Ala Val Arg Glu Lys Val Phe Asp Val Ile
65 70 75 80

Ile Arg Cys Phe Lys Arg His Gly Ala Glu Val Ile Asp Thr Pro Val
85 90 95

Phe Glu Leu Lys Glu Thr Leu Met Gly Lys Tyr Gly Glu Asp Ser Lys
100 105 110

Leu Ile Tyr Asp Leu Lys Asp Gln Gly Gly Glu Leu Leu Ser Leu Arg
115 120 125

Tyr Asp Leu Thr Val Pro Phe Ala Arg Tyr Leu Ala Met Asn Lys Leu
130 135 140

Thr Asn Ile Lys Arg Tyr His Ile Ala Lys Val Tyr Arg Arg Asp Asn
145 150 155 160

Pro Ala Met Thr Arg Gly Arg Tyr Arg Glu Phe Tyr Gln Ala Asp Phe
165 170 175

Asp Ile Ala Gly Asn Phe Asp Pro Met Ile Pro Asp Ala Glu Cys Leu
180 185 190

Lys Ile Met Cys Glu Ile Leu Ser Ser Leu Gln Ile Gly Asp Phe Leu
195 200 205

Val Lys Val Asn Asp Arg Arg Ile Leu Asp Gly Met Phe Ala Ile Cys
210 215 220

Gly Val Ser Asp Ser Lys Phe Arg Thr Ile Cys Ser Ser Val Asp Lys

```
225                 230                 235                 240

Leu Asp Lys Val Ser Trp Glu Glu Val Lys Asn Glu Met Val Gly Glu
                245                 250                 255

Lys Gly Leu Ala Pro Glu Val Ala Asp Arg Ile Gly Asp Tyr Val Gln
            260                 265                 270

Gln His Gly Gly Val Ser Leu Val Glu Gln Leu Leu Gln Asp Pro Lys
        275                 280                 285

Leu Ser Gln Asn Lys Gln Ala Leu Glu Gly Leu Gly Asp Leu Lys Leu
    290                 295                 300

Leu Phe Glu Tyr Leu Thr Leu Phe Gly Ile Asp Asp Lys Ile Ser Phe
305                 310                 315                 320

Asp Leu Ser Leu Ala Arg Gly Leu Asp Tyr Tyr Thr Gly Val Ile Tyr
                325                 330                 335

Glu Ala Val Leu Leu Gln Thr Pro Ala Gln Ala Gly Glu Glu Pro Leu
            340                 345                 350

Gly Val Gly Ser Val Ala Ala Gly Gly Arg Tyr Asp Gly Leu Val Gly
        355                 360                 365

Met Phe Asp Pro Lys Gly Arg Lys Val Pro Cys Val Gly Leu Ser Ile
    370                 375                 380

Gly Val Glu Arg Ile Phe Ser Ile Val Glu Gln Arg Leu Glu Ala Leu
385                 390                 395                 400

Glu Glu Lys Ile Arg Thr Thr Glu Thr Gln Val Leu Val Ala Ser Ala
                405                 410                 415

Gln Lys Lys Leu Leu Glu Glu Arg Leu Lys Leu Val Ser Glu Leu Trp
            420                 425                 430

Asp Ala Gly Ile Lys Ala Glu Leu Leu Tyr Lys Lys Asn Pro Lys Leu
        435                 440                 445

Leu Asn Gln Leu Gln Tyr Cys Glu Glu Ala Gly Ile Pro Leu Val Ala
    450                 455                 460

Ile Ile Gly Glu Gln Glu Leu Lys Asp Gly Val Ile Lys Leu Arg Ser
465                 470                 475                 480

Val Thr Ser Arg Glu Glu Val Asp Val Arg Arg Glu Asp Leu Val Glu
                485                 490                 495

Glu Ile Lys Arg Arg Thr Gly Gln Pro Leu
            500                 505


<210> SEQ ID NO 186
<211> LENGTH: 506
<212> TYPE: PRT
<213> ORGANISM: Artificial Sequence
<220> FEATURE:
<223> OTHER INFORMATION: Cysteine mutated HRS polypeptide

<400> SEQUENCE: 186

Met Ala Glu Arg Ala Ala Leu Glu Glu Leu Val Lys Leu Gln Gly Glu
1               5                   10                  15

Arg Val Arg Gly Leu Lys Gln Gln Lys Ala Ser Ala Glu Leu Ile Glu
            20                  25                  30

Glu Glu Val Ala Lys Leu Leu Lys Leu Lys Ala Gln Leu Gly Pro Asp
        35                  40                  45

Glu Ser Lys Gln Lys Phe Val Leu Lys Thr Pro Lys Gly Thr Arg Asp
    50                  55                  60

Tyr Ser Pro Arg Gln Met Ala Val Arg Glu Lys Val Phe Asp Val Ile
65                  70                  75                  80

Ile Arg Cys Phe Lys Arg His Gly Ala Glu Val Ile Asp Thr Pro Val
```

```
                85                  90                  95

Phe Glu Leu Lys Glu Thr Leu Met Gly Lys Tyr Gly Glu Asp Ser Lys
            100                 105                 110

Leu Ile Tyr Asp Leu Lys Asp Gln Gly Gly Glu Leu Leu Ser Leu Arg
        115                 120                 125

Tyr Asp Leu Thr Val Pro Phe Ala Arg Tyr Leu Ala Met Asn Lys Leu
    130                 135                 140

Thr Asn Ile Lys Arg Tyr His Ile Ala Lys Val Tyr Arg Arg Asp Asn
145                 150                 155                 160

Pro Ala Met Thr Arg Gly Arg Tyr Arg Glu Phe Tyr Gln Val Asp Phe
                165                 170                 175

Asp Ile Ala Gly Asn Phe Asp Pro Met Ile Pro Asp Ala Glu Cys Leu
            180                 185                 190

Lys Ile Met Cys Glu Ile Leu Ser Ser Leu Gln Ile Gly Asp Phe Leu
        195                 200                 205

Val Lys Val Asn Asp Arg Arg Ile Leu Asp Gly Met Phe Ala Ile Cys
    210                 215                 220

Gly Val Ser Asp Ser Lys Phe Arg Thr Ile Cys Ser Ser Val Asp Lys
225                 230                 235                 240

Leu Asp Lys Val Ser Trp Glu Glu Val Lys Asn Glu Met Val Gly Glu
                245                 250                 255

Lys Gly Leu Ala Pro Glu Val Ala Asp Arg Ile Gly Asp Tyr Val Gln
            260                 265                 270

Gln His Gly Gly Val Ser Leu Val Glu Gln Leu Leu Gln Asp Pro Lys
        275                 280                 285

Leu Ser Gln Asn Lys Gln Ala Leu Glu Gly Leu Gly Asp Leu Lys Leu
    290                 295                 300

Leu Phe Glu Tyr Leu Thr Leu Phe Gly Ile Asp Asp Lys Ile Ser Phe
305                 310                 315                 320

Asp Leu Ser Leu Ala Arg Gly Leu Asp Tyr Tyr Thr Gly Val Ile Tyr
                325                 330                 335

Glu Ala Val Leu Leu Gln Thr Pro Ala Gln Ala Gly Glu Glu Pro Leu
            340                 345                 350

Gly Val Gly Ser Val Ala Ala Gly Gly Arg Tyr Asp Gly Leu Val Gly
        355                 360                 365

Met Phe Asp Pro Lys Gly Arg Lys Val Pro Cys Val Gly Leu Ser Ile
    370                 375                 380

Gly Val Glu Arg Ile Phe Ser Ile Val Glu Gln Arg Leu Glu Ala Leu
385                 390                 395                 400

Glu Glu Lys Ile Arg Thr Thr Glu Thr Gln Val Leu Val Ala Ser Ala
                405                 410                 415

Gln Lys Lys Leu Leu Glu Glu Arg Leu Lys Leu Val Ser Glu Leu Trp
            420                 425                 430

Asp Ala Gly Ile Lys Ala Glu Leu Leu Tyr Lys Lys Asn Pro Lys Leu
        435                 440                 445

Leu Asn Gln Leu Gln Tyr Cys Glu Glu Ala Gly Ile Pro Leu Val Ala
    450                 455                 460

Ile Ile Gly Glu Gln Glu Leu Lys Asp Gly Val Ile Lys Leu Arg Ser
465                 470                 475                 480

Val Thr Ser Arg Glu Glu Val Asp Val Arg Arg Glu Asp Leu Val Glu
                485                 490                 495

Glu Ile Lys Arg Arg Thr Gly Gln Pro Leu
            500                 505
```

<210> SEQ ID NO 187
<211> LENGTH: 506
<212> TYPE: PRT
<213> ORGANISM: Artificial Sequence
<220> FEATURE:
<223> OTHER INFORMATION: Cysteine mutated HRS polypeptide

<400> SEQUENCE: 187

```
Met Ala Glu Arg Ala Ala Leu Glu Glu Leu Val Lys Leu Gln Gly Glu
1               5                   10                  15

Arg Val Arg Gly Leu Lys Gln Gln Lys Ala Ser Ala Glu Leu Ile Glu
            20                  25                  30

Glu Glu Val Ala Lys Leu Leu Lys Leu Lys Ala Gln Leu Gly Pro Asp
        35                  40                  45

Glu Ser Lys Gln Lys Phe Val Leu Lys Thr Pro Lys Gly Thr Arg Asp
    50                  55                  60

Tyr Ser Pro Arg Gln Met Ala Val Arg Glu Lys Val Phe Asp Val Ile
65                  70                  75                  80

Ile Arg Cys Phe Lys Arg His Gly Ala Glu Val Ile Asp Thr Pro Val
                85                  90                  95

Phe Glu Leu Lys Glu Thr Leu Met Gly Lys Tyr Gly Glu Asp Ser Lys
            100                 105                 110

Leu Ile Tyr Asp Leu Lys Asp Gln Gly Gly Glu Leu Leu Ser Leu Arg
        115                 120                 125

Tyr Asp Leu Thr Val Pro Phe Ala Arg Tyr Leu Ala Met Asn Lys Leu
    130                 135                 140

Thr Asn Ile Lys Arg Tyr His Ile Ala Lys Val Tyr Arg Arg Asp Asn
145                 150                 155                 160

Pro Ala Met Thr Arg Gly Arg Tyr Arg Glu Phe Tyr Gln Cys Asp Phe
                165                 170                 175

Asp Ile Ala Gly Asn Phe Asp Pro Met Ile Pro Asp Ala Glu Ala Leu
            180                 185                 190

Lys Ile Met Cys Glu Ile Leu Ser Ser Leu Gln Ile Gly Asp Phe Leu
        195                 200                 205

Val Lys Val Asn Asp Arg Arg Ile Leu Asp Gly Met Phe Ala Ile Cys
    210                 215                 220

Gly Val Ser Asp Ser Lys Phe Arg Thr Ile Cys Ser Ser Val Asp Lys
225                 230                 235                 240

Leu Asp Lys Val Ser Trp Glu Glu Val Lys Asn Glu Met Val Gly Glu
                245                 250                 255

Lys Gly Leu Ala Pro Glu Val Ala Asp Arg Ile Gly Asp Tyr Val Gln
            260                 265                 270

Gln His Gly Gly Val Ser Leu Val Glu Gln Leu Leu Gln Asp Pro Lys
        275                 280                 285

Leu Ser Gln Asn Lys Gln Ala Leu Glu Gly Leu Gly Asp Leu Lys Leu
    290                 295                 300

Leu Phe Glu Tyr Leu Thr Leu Phe Gly Ile Asp Asp Lys Ile Ser Phe
305                 310                 315                 320

Asp Leu Ser Leu Ala Arg Gly Leu Asp Tyr Tyr Thr Gly Val Ile Tyr
                325                 330                 335

Glu Ala Val Leu Leu Gln Thr Pro Ala Gln Ala Gly Glu Glu Pro Leu
            340                 345                 350

Gly Val Gly Ser Val Ala Ala Gly Gly Arg Tyr Asp Gly Leu Val Gly
        355                 360                 365
```

```
Met Phe Asp Pro Lys Gly Arg Lys Val Pro Cys Val Gly Leu Ser Ile
    370                 375                 380

Gly Val Glu Arg Ile Phe Ser Ile Val Glu Gln Arg Leu Glu Ala Leu
385                 390                 395                 400

Glu Glu Lys Ile Arg Thr Thr Glu Thr Gln Val Leu Val Ala Ser Ala
                405                 410                 415

Gln Lys Lys Leu Leu Glu Glu Arg Leu Lys Leu Val Ser Glu Leu Trp
            420                 425                 430

Asp Ala Gly Ile Lys Ala Glu Leu Leu Tyr Lys Lys Asn Pro Lys Leu
        435                 440                 445

Leu Asn Gln Leu Gln Tyr Cys Glu Glu Ala Gly Ile Pro Leu Val Ala
    450                 455                 460

Ile Ile Gly Glu Gln Glu Leu Lys Asp Gly Val Ile Lys Leu Arg Ser
465                 470                 475                 480

Val Thr Ser Arg Glu Glu Val Asp Val Arg Arg Glu Asp Leu Val Glu
                485                 490                 495

Glu Ile Lys Arg Arg Thr Gly Gln Pro Leu
            500                 505
```

<210> SEQ ID NO 188
<211> LENGTH: 506
<212> TYPE: PRT
<213> ORGANISM: Artificial Sequence
<220> FEATURE:
<223> OTHER INFORMATION: Cysteine mutated HRS polypeptide

<400> SEQUENCE: 188

```
Met Ala Glu Arg Ala Ala Leu Glu Glu Leu Val Lys Leu Gln Gly Glu
1               5                   10                  15

Arg Val Arg Gly Leu Lys Gln Gln Lys Ala Ser Ala Glu Leu Ile Glu
            20                  25                  30

Glu Glu Val Ala Lys Leu Leu Lys Leu Lys Ala Gln Leu Gly Pro Asp
        35                  40                  45

Glu Ser Lys Gln Lys Phe Val Leu Lys Thr Pro Lys Gly Thr Arg Asp
    50                  55                  60

Tyr Ser Pro Arg Gln Met Ala Val Arg Glu Lys Val Phe Asp Val Ile
65                  70                  75                  80

Ile Arg Cys Phe Lys Arg His Gly Ala Glu Val Ile Asp Thr Pro Val
                85                  90                  95

Phe Glu Leu Lys Glu Thr Leu Met Gly Lys Tyr Gly Glu Asp Ser Lys
            100                 105                 110

Leu Ile Tyr Asp Leu Lys Asp Gln Gly Gly Glu Leu Leu Ser Leu Arg
        115                 120                 125

Tyr Asp Leu Thr Val Pro Phe Ala Arg Tyr Leu Ala Met Asn Lys Leu
    130                 135                 140

Thr Asn Ile Lys Arg Tyr His Ile Ala Lys Val Tyr Arg Arg Asp Asn
145                 150                 155                 160

Pro Ala Met Thr Arg Gly Arg Tyr Arg Glu Phe Tyr Gln Cys Asp Phe
                165                 170                 175

Asp Ile Ala Gly Asn Phe Asp Pro Met Ile Pro Asp Ala Glu Ser Leu
            180                 185                 190

Lys Ile Met Cys Glu Ile Leu Ser Ser Leu Gln Ile Gly Asp Phe Leu
        195                 200                 205

Val Lys Val Asn Asp Arg Arg Ile Leu Asp Gly Met Phe Ala Ile Cys
    210                 215                 220
```

Gly Val Ser Asp Ser Lys Phe Arg Thr Ile Cys Ser Ser Val Asp Lys
225 230 235 240

Leu Asp Lys Val Ser Trp Glu Glu Val Lys Asn Glu Met Val Gly Glu
245 250 255

Lys Gly Leu Ala Pro Glu Val Ala Asp Arg Ile Gly Asp Tyr Val Gln
260 265 270

Gln His Gly Gly Val Ser Leu Val Glu Gln Leu Leu Gln Asp Pro Lys
275 280 285

Leu Ser Gln Asn Lys Gln Ala Leu Glu Gly Leu Gly Asp Leu Lys Leu
290 295 300

Leu Phe Glu Tyr Leu Thr Leu Phe Gly Ile Asp Asp Lys Ile Ser Phe
305 310 315 320

Asp Leu Ser Leu Ala Arg Gly Leu Asp Tyr Tyr Thr Gly Val Ile Tyr
325 330 335

Glu Ala Val Leu Leu Gln Thr Pro Ala Gln Ala Gly Glu Glu Pro Leu
340 345 350

Gly Val Gly Ser Val Ala Ala Gly Gly Arg Tyr Asp Gly Leu Val Gly
355 360 365

Met Phe Asp Pro Lys Gly Arg Lys Val Pro Cys Val Gly Leu Ser Ile
370 375 380

Gly Val Glu Arg Ile Phe Ser Ile Val Glu Gln Arg Leu Glu Ala Leu
385 390 395 400

Glu Glu Lys Ile Arg Thr Thr Glu Thr Gln Val Leu Val Ala Ser Ala
405 410 415

Gln Lys Lys Leu Leu Glu Glu Arg Leu Lys Leu Val Ser Glu Leu Trp
420 425 430

Asp Ala Gly Ile Lys Ala Glu Leu Leu Tyr Lys Lys Asn Pro Lys Leu
435 440 445

Leu Asn Gln Leu Gln Tyr Cys Glu Glu Ala Gly Ile Pro Leu Val Ala
450 455 460

Ile Ile Gly Glu Gln Glu Leu Lys Asp Gly Val Ile Lys Leu Arg Ser
465 470 475 480

Val Thr Ser Arg Glu Glu Val Asp Val Arg Arg Glu Asp Leu Val Glu
485 490 495

Glu Ile Lys Arg Arg Thr Gly Gln Pro Leu
500 505

<210> SEQ ID NO 189
<211> LENGTH: 506
<212> TYPE: PRT
<213> ORGANISM: Artificial Sequence
<220> FEATURE:
<223> OTHER INFORMATION: Cysteine mutated HRS polypeptide

<400> SEQUENCE: 189

Met Ala Glu Arg Ala Ala Leu Glu Glu Leu Val Lys Leu Gln Gly Glu
1 5 10 15

Arg Val Arg Gly Leu Lys Gln Gln Lys Ala Ser Ala Glu Leu Ile Glu
20 25 30

Glu Glu Val Ala Lys Leu Leu Lys Leu Lys Ala Gln Leu Gly Pro Asp
35 40 45

Glu Ser Lys Gln Lys Phe Val Leu Lys Thr Pro Lys Gly Thr Arg Asp
50 55 60

Tyr Ser Pro Arg Gln Met Ala Val Arg Glu Lys Val Phe Asp Val Ile
65 70 75 80

```
Ile Arg Cys Phe Lys Arg His Gly Ala Glu Val Ile Asp Thr Pro Val
                85                  90                  95

Phe Glu Leu Lys Glu Thr Leu Met Gly Lys Tyr Gly Glu Asp Ser Lys
            100                 105                 110

Leu Ile Tyr Asp Leu Lys Asp Gln Gly Gly Glu Leu Leu Ser Leu Arg
        115                 120                 125

Tyr Asp Leu Thr Val Pro Phe Ala Arg Tyr Leu Ala Met Asn Lys Leu
    130                 135                 140

Thr Asn Ile Lys Arg Tyr His Ile Ala Lys Val Tyr Arg Arg Asp Asn
145                 150                 155                 160

Pro Ala Met Thr Arg Gly Arg Tyr Arg Glu Phe Tyr Gln Cys Asp Phe
                165                 170                 175

Asp Ile Ala Gly Asn Phe Asp Pro Met Ile Pro Asp Ala Glu Val Leu
            180                 185                 190

Lys Ile Met Cys Glu Ile Leu Ser Ser Leu Gln Ile Gly Asp Phe Leu
        195                 200                 205

Val Lys Val Asn Asp Arg Arg Ile Leu Asp Gly Met Phe Ala Ile Cys
    210                 215                 220

Gly Val Ser Asp Ser Lys Phe Arg Thr Ile Cys Ser Ser Val Asp Lys
225                 230                 235                 240

Leu Asp Lys Val Ser Trp Glu Glu Val Lys Asn Glu Met Val Gly Glu
                245                 250                 255

Lys Gly Leu Ala Pro Glu Val Ala Asp Arg Ile Gly Asp Tyr Val Gln
            260                 265                 270

Gln His Gly Gly Val Ser Leu Val Glu Gln Leu Leu Gln Asp Pro Lys
        275                 280                 285

Leu Ser Gln Asn Lys Gln Ala Leu Glu Gly Leu Gly Asp Leu Lys Leu
    290                 295                 300

Leu Phe Glu Tyr Leu Thr Leu Phe Gly Ile Asp Asp Lys Ile Ser Phe
305                 310                 315                 320

Asp Leu Ser Leu Ala Arg Gly Leu Asp Tyr Tyr Thr Gly Val Ile Tyr
                325                 330                 335

Glu Ala Val Leu Leu Gln Thr Pro Ala Gln Ala Gly Glu Glu Pro Leu
            340                 345                 350

Gly Val Gly Ser Val Ala Ala Gly Gly Arg Tyr Asp Gly Leu Val Gly
        355                 360                 365

Met Phe Asp Pro Lys Gly Arg Lys Val Pro Cys Val Gly Leu Ser Ile
    370                 375                 380

Gly Val Glu Arg Ile Phe Ser Ile Val Glu Gln Arg Leu Glu Ala Leu
385                 390                 395                 400

Glu Glu Lys Ile Arg Thr Thr Glu Thr Gln Val Leu Val Ala Ser Ala
                405                 410                 415

Gln Lys Lys Leu Leu Glu Glu Arg Leu Lys Leu Val Ser Glu Leu Trp
            420                 425                 430

Asp Ala Gly Ile Lys Ala Glu Leu Leu Tyr Lys Lys Asn Pro Lys Leu
        435                 440                 445

Leu Asn Gln Leu Gln Tyr Cys Glu Glu Ala Gly Ile Pro Leu Val Ala
    450                 455                 460

Ile Ile Gly Glu Gln Glu Leu Lys Asp Gly Val Ile Lys Leu Arg Ser
465                 470                 475                 480

Val Thr Ser Arg Glu Glu Val Asp Val Arg Arg Glu Asp Leu Val Glu
                485                 490                 495
```

```
Glu Ile Lys Arg Arg Thr Gly Gln Pro Leu
            500                 505


<210> SEQ ID NO 190
<211> LENGTH: 506
<212> TYPE: PRT
<213> ORGANISM: Artificial Sequence
<220> FEATURE:
<223> OTHER INFORMATION: Cysteine mutated HRS polypeptide

<400> SEQUENCE: 190

Met Ala Glu Arg Ala Ala Leu Glu Glu Leu Val Lys Leu Gln Gly Glu
1               5                   10                  15

Arg Val Arg Gly Leu Lys Gln Gln Lys Ala Ser Ala Glu Leu Ile Glu
            20                  25                  30

Glu Glu Val Ala Lys Leu Leu Lys Leu Lys Ala Gln Leu Gly Pro Asp
        35                  40                  45

Glu Ser Lys Gln Lys Phe Val Leu Lys Thr Pro Lys Gly Thr Arg Asp
    50                  55                  60

Tyr Ser Pro Arg Gln Met Ala Val Arg Glu Lys Val Phe Asp Val Ile
65                  70                  75                  80

Ile Arg Cys Phe Lys Arg His Gly Ala Glu Val Ile Asp Thr Pro Val
                85                  90                  95

Phe Glu Leu Lys Glu Thr Leu Met Gly Lys Tyr Gly Glu Asp Ser Lys
            100                 105                 110

Leu Ile Tyr Asp Leu Lys Asp Gln Gly Gly Glu Leu Leu Ser Leu Arg
        115                 120                 125

Tyr Asp Leu Thr Val Pro Phe Ala Arg Tyr Leu Ala Met Asn Lys Leu
    130                 135                 140

Thr Asn Ile Lys Arg Tyr His Ile Ala Lys Val Tyr Arg Arg Asp Asn
145                 150                 155                 160

Pro Ala Met Thr Arg Gly Arg Tyr Arg Glu Phe Tyr Gln Cys Asp Phe
                165                 170                 175

Asp Ile Ala Gly Asn Phe Asp Pro Met Ile Pro Asp Ala Glu Cys Leu
            180                 185                 190

Lys Ile Met Cys Glu Ile Leu Ser Ser Leu Gln Ile Gly Asp Phe Leu
        195                 200                 205

Val Lys Val Asn Asp Arg Arg Ile Leu Asp Gly Met Phe Ala Ile Ser
    210                 215                 220

Gly Val Ser Asp Ser Lys Phe Arg Thr Ile Cys Ser Ser Val Asp Lys
225                 230                 235                 240

Leu Asp Lys Val Ser Trp Glu Glu Val Lys Asn Glu Met Val Gly Glu
                245                 250                 255

Lys Gly Leu Ala Pro Glu Val Ala Asp Arg Ile Gly Asp Tyr Val Gln
            260                 265                 270

Gln His Gly Gly Val Ser Leu Val Glu Gln Leu Leu Gln Asp Pro Lys
        275                 280                 285

Leu Ser Gln Asn Lys Gln Ala Leu Glu Gly Leu Gly Asp Leu Lys Leu
    290                 295                 300

Leu Phe Glu Tyr Leu Thr Leu Phe Gly Ile Asp Asp Lys Ile Ser Phe
305                 310                 315                 320

Asp Leu Ser Leu Ala Arg Gly Leu Asp Tyr Tyr Thr Gly Val Ile Tyr
                325                 330                 335

Glu Ala Val Leu Leu Gln Thr Pro Ala Gln Ala Gly Glu Glu Pro Leu
            340                 345                 350
```

-continued

Gly Val Gly Ser Val Ala Ala Gly Gly Arg Tyr Asp Gly Leu Val Gly
355 360 365

Met Phe Asp Pro Lys Gly Arg Lys Val Pro Cys Val Gly Leu Ser Ile
370 375 380

Gly Val Glu Arg Ile Phe Ser Ile Val Glu Gln Arg Leu Glu Ala Leu
385 390 395 400

Glu Glu Lys Ile Arg Thr Thr Glu Thr Gln Val Leu Val Ala Ser Ala
405 410 415

Gln Lys Lys Leu Leu Glu Glu Arg Leu Lys Leu Val Ser Glu Leu Trp
420 425 430

Asp Ala Gly Ile Lys Ala Glu Leu Leu Tyr Lys Lys Asn Pro Lys Leu
435 440 445

Leu Asn Gln Leu Gln Tyr Cys Glu Glu Ala Gly Ile Pro Leu Val Ala
450 455 460

Ile Ile Gly Glu Gln Glu Leu Lys Asp Gly Val Ile Lys Leu Arg Ser
465 470 475 480

Val Thr Ser Arg Glu Glu Val Asp Val Arg Arg Glu Asp Leu Val Glu
485 490 495

Glu Ile Lys Arg Arg Thr Gly Gln Pro Leu
500 505

<210> SEQ ID NO 191
<211> LENGTH: 506
<212> TYPE: PRT
<213> ORGANISM: Artificial Sequence
<220> FEATURE:
<223> OTHER INFORMATION: Cysteine mutated HRS polypeptide

<400> SEQUENCE: 191

Met Ala Glu Arg Ala Ala Leu Glu Glu Leu Val Lys Leu Gln Gly Glu
1 5 10 15

Arg Val Arg Gly Leu Lys Gln Gln Lys Ala Ser Ala Glu Leu Ile Glu
20 25 30

Glu Glu Val Ala Lys Leu Leu Lys Leu Lys Ala Gln Leu Gly Pro Asp
35 40 45

Glu Ser Lys Gln Lys Phe Val Leu Lys Thr Pro Lys Gly Thr Arg Asp
50 55 60

Tyr Ser Pro Arg Gln Met Ala Val Arg Glu Lys Val Phe Asp Val Ile
65 70 75 80

Ile Arg Cys Phe Lys Arg His Gly Ala Glu Val Ile Asp Thr Pro Val
85 90 95

Phe Glu Leu Lys Glu Thr Leu Met Gly Lys Tyr Gly Glu Asp Ser Lys
100 105 110

Leu Ile Tyr Asp Leu Lys Asp Gln Gly Gly Glu Leu Leu Ser Leu Arg
115 120 125

Tyr Asp Leu Thr Val Pro Phe Ala Arg Tyr Leu Ala Met Asn Lys Leu
130 135 140

Thr Asn Ile Lys Arg Tyr His Ile Ala Lys Val Tyr Arg Arg Asp Asn
145 150 155 160

Pro Ala Met Thr Arg Gly Arg Tyr Arg Glu Phe Tyr Gln Cys Asp Phe
165 170 175

Asp Ile Ala Gly Asn Phe Asp Pro Met Ile Pro Asp Ala Glu Cys Leu
180 185 190

Lys Ile Met Cys Glu Ile Leu Ser Ser Leu Gln Ile Gly Asp Phe Leu
195 200 205

```
Val Lys Val Asn Asp Arg Arg Ile Leu Asp Gly Met Phe Ala Ile Cys
    210                 215                 220

Gly Val Ser Asp Ser Lys Phe Arg Thr Ile Ser Ser Ser Val Asp Lys
225                 230                 235                 240

Leu Asp Lys Val Ser Trp Glu Glu Val Lys Asn Glu Met Val Gly Glu
                245                 250                 255

Lys Gly Leu Ala Pro Glu Val Ala Asp Arg Ile Gly Asp Tyr Val Gln
            260                 265                 270

Gln His Gly Gly Val Ser Leu Val Glu Gln Leu Leu Gln Asp Pro Lys
        275                 280                 285

Leu Ser Gln Asn Lys Gln Ala Leu Glu Gly Leu Gly Asp Leu Lys Leu
    290                 295                 300

Leu Phe Glu Tyr Leu Thr Leu Phe Gly Ile Asp Asp Lys Ile Ser Phe
305                 310                 315                 320

Asp Leu Ser Leu Ala Arg Gly Leu Asp Tyr Tyr Thr Gly Val Ile Tyr
                325                 330                 335

Glu Ala Val Leu Leu Gln Thr Pro Ala Gln Ala Gly Glu Glu Pro Leu
            340                 345                 350

Gly Val Gly Ser Val Ala Ala Gly Gly Arg Tyr Asp Gly Leu Val Gly
        355                 360                 365

Met Phe Asp Pro Lys Gly Arg Lys Val Pro Cys Val Gly Leu Ser Ile
    370                 375                 380

Gly Val Glu Arg Ile Phe Ser Ile Val Glu Gln Arg Leu Glu Ala Leu
385                 390                 395                 400

Glu Glu Lys Ile Arg Thr Thr Glu Thr Gln Val Leu Val Ala Ser Ala
                405                 410                 415

Gln Lys Lys Leu Leu Glu Glu Arg Leu Lys Leu Val Ser Glu Leu Trp
            420                 425                 430

Asp Ala Gly Ile Lys Ala Glu Leu Leu Tyr Lys Lys Asn Pro Lys Leu
        435                 440                 445

Leu Asn Gln Leu Gln Tyr Cys Glu Glu Ala Gly Ile Pro Leu Val Ala
    450                 455                 460

Ile Ile Gly Glu Gln Glu Leu Lys Asp Gly Val Ile Lys Leu Arg Ser
465                 470                 475                 480

Val Thr Ser Arg Glu Glu Val Asp Val Arg Arg Glu Asp Leu Val Glu
                485                 490                 495

Glu Ile Lys Arg Arg Thr Gly Gln Pro Leu
            500                 505
```

<210> SEQ ID NO 192
<211> LENGTH: 1518
<212> TYPE: DNA
<213> ORGANISM: Artificial Sequence
<220> FEATURE:
<223> OTHER INFORMATION: Polynucleotide encoding cysteine mutated HRS protein

<400> SEQUENCE: 192

```
atggcggaac gtgccgcact ggaagaattg gttaaattac agggagaacg cgtacgtggt     60

cttaaacaac aaaaagcctc tgcggaattg attgaagaag aagttgccaa attactgaaa    120

ctgaaagctc aacttggacc cgatgaaagt aaacaaaaat ttgtgttgaa aacgcccaaa    180

ggaacccgtg attatagtcc acgtcaaatg gccgttcgtg aaaaagtgtt cgacgttatt    240

attcgctgtt ttaaacgtca cggtgctgaa gtaatcgata cccccgtatt tgaattgaaa    300

gagactctga tgggcaaata tggtgaagat tctaaactga tttatgattt gaaagaccaa    360
```

```
ggaggtgaac tgctgagcct gcgctacgac ttaactgtgc cttttgcccg ttacttagcc    420

atgaataaat taaccaacat caaacgttac catattgcaa aagtatatcg ccgcgacaac    480

cctgcaatga ctcgtggacg ctatcgcgaa ttctatcagg ctgattttga tattgccgga    540

aatttcgacc cgatgatccc ggatgccgag tgtttgaaaa ttatgtgtga aattctgagt    600

tcgttgcaga tcggagactt tcttgtaaaa gttaatgacc gccgtattct ggatggtatg    660

tttgctattt gcggtgtttc tgattccaaa ttccgtacaa tctgctcaag cgtggacaaa    720

ttggataaag tgtcttggga agaagtaaaa aatgaaatgg tgggagaaaa aggcctggct    780

ccagaagtag cagaccgtat tggtgactat gttcaacaac atggcggtgt gtccttagtc    840

gaacagttat tacaggatcc taaactgagc caaaataaac aagcacttga aggactggga    900

gatctgaaat tactctttga atatctgacc ttatttggga ttgatgataa aattagcttt    960

gatctgagct tggcccgcgg tcttgattat tataccggcg tgatttacga agctgttctc   1020

ttgcaaaccc cagcccaggc gggcgaagag cctttgggag tcggcagtgt ggcagccggt   1080

ggtcgttatg atggtttggt aggaatgttt gaccctaaag gccgtaaagt accatgtgtg   1140

gggctttcta tcggtgtcga acgtatcttt tctattgttg aacaacgtct tgaagctttg   1200

gaggaaaaga tccgtaccac ggaaacccaa gtcttagttg caagtgccca aaaaaaactg   1260

ttagaagaac gcctgaaact cgtatcagaa ctttgggacg ccggcatcaa ggccgaactg   1320

ctgtataaaa agaacccgaa attgttaaac caactccagt attgtgaaga agctgggatc   1380

ccactcgtag ctattattgg tgagcaagaa ttaaaagatg gcgtgattaa actgcgttca   1440

gtaacaagcc gtgaagaggt agatgtacgt cgcgaagact tagtggaaga aattaaacgc   1500

cgcaccggtc aaccgtta                                                 1518
```

<210> SEQ ID NO 193
<211> LENGTH: 1518
<212> TYPE: DNA
<213> ORGANISM: Artificial Sequence
<220> FEATURE:
<223> OTHER INFORMATION: Polynucleotide encoding cysteine mutated HRS protein

<400> SEQUENCE: 193

```
atggcggaac gtgccgcact ggaagaattg gttaaattac agggagaacg cgtacgtggt     60

cttaaacaac aaaaagcctc tgcggaattg attgaagaag aagttgccaa attactgaaa    120

ctgaaagctc aacttggacc cgatgaaagt aaacaaaaat ttgtgttgaa aacgcccaaa    180

ggaacccgtg attatagtcc acgtcaaatg gccgttcgtg aaaaagtgtt cgacgttatt    240

attcgctgtt ttaaacgtca cggtgctgaa gtaatcgata cccccgtatt tgaattgaaa    300

gagactctga tgggcaaata tggtgaagat tctaaactga tttatgattt gaaagaccaa    360

ggaggtgaac tgctgagcct gcgctacgac ttaactgtgc cttttgcccg ttacttagcc    420

atgaataaat taaccaacat caaacgttac catattgcaa aagtatatcg ccgcgacaac    480

cctgcaatga ctcgtggacg ctatcgcgaa ttctatcagg ttgattttga tattgccgga    540

aatttcgacc cgatgatccc ggatgccgag tgtttgaaaa ttatgtgtga aattctgagt    600

tcgttgcaga tcggagactt tcttgtaaaa gttaatgacc gccgtattct ggatggtatg    660

tttgctattt gcggtgtttc tgattccaaa ttccgtacaa tctgctcaag cgtggacaaa    720

ttggataaag tgtcttggga agaagtaaaa aatgaaatgg tgggagaaaa aggcctggct    780

ccagaagtag cagaccgtat tggtgactat gttcaacaac atggcggtgt gtccttagtc    840
```

gaacagttat tacaggatcc taaactgagc caaaataaac aagcacttga aggactggga 900
gatctgaaat tactctttga atatctgacc ttatttggga ttgatgataa aattagcttt 960
gatctgagct tggcccgcgg tcttgattat tataccggcg tgatttacga agctgttctc 1020
ttgcaaaccc cagcccaggc gggcgaagag cctttgggag tcggcagtgt ggcagccggt 1080
ggtcgttatg atggtttggt aggaatgttt gaccctaaag gccgtaaagt accatgtgtg 1140
gggctttcta tcggtgtcga acgtatcttt tctattgttg aacaacgtct tgaagctttg 1200
gaggaaaaga tccgtaccac ggaaacccaa gtcttagttg caagtgccca aaaaaaactg 1260
ttagaagaac gcctgaaact cgtatcagaa ctttgggacg ccggcatcaa ggccgaactg 1320
ctgtataaaa agaacccgaa attgttaaac caactccagt attgtgaaga agctgggatc 1380
ccactcgtag ctattattgg tgagcaagaa ttaaaagatg gcgtgattaa actgcgttca 1440
gtaacaagcc gtgaagaggt agatgtacgt cgcgaagact tagtggaaga aattaaacgc 1500
cgcaccggtc aaccgtta 1518

<210> SEQ ID NO 194
<211> LENGTH: 1518
<212> TYPE: DNA
<213> ORGANISM: Artificial Sequence
<220> FEATURE:
<223> OTHER INFORMATION: Polynucleotide encoding cysteine mutated HRS protein

<400> SEQUENCE: 194
atggcggaac gtgccgcact ggaagaattg gttaaattac agggagaacg cgtacgtggt 60
cttaaacaac aaaaagcctc tgcggaattg attgaagaag aagttgccaa attactgaaa 120
ctgaaagctc aacttggacc cgatgaaagt aaacaaaaat ttgtgttgaa aacgcccaaa 180
ggaacccgtg attatagtcc acgtcaaatg gccgttcgtg aaaaagtgtt cgacgttatt 240
attcgctgtt ttaaacgtca cggtgctgaa gtaatcgata cccccgtatt tgaattgaaa 300
gagactctga tgggcaaata tggtgaagat tctaaactga tttatgattt gaaagaccaa 360
ggaggtgaac tgctgagcct gcgctacgac ttaactgtgc cttttgcccg ttacttagcc 420
atgaataaat taaccaacat caaacgttac catattgcaa aagtatatcg ccgcgacaac 480
cctgcaatga ctcgtggacg ctatcgcgaa ttctatcagt gtgattttga tattgccgga 540
aatttcgacc cgatgatccc ggatgccgag gctttgaaaa ttatgtgtga aattctgagt 600
tcgttgcaga tcggagactt tcttgtaaaa gttaatgacc gccgtattct ggatggtatg 660
tttgctattt gcggtgtttc tgattccaaa ttccgtacaa tctgctcaag cgtggacaaa 720
ttggataaag tgtcttggga agaagtaaaa aatgaaatgg tgggagaaaa aggcctggct 780
ccagaagtag cagaccgtat tggtgactat gttcaacaac atggcggtgt gtccttagtc 840
gaacagttat tacaggatcc taaactgagc caaaataaac aagcacttga aggactggga 900
gatctgaaat tactctttga atatctgacc ttatttggga ttgatgataa aattagcttt 960
gatctgagct tggcccgcgg tcttgattat tataccggcg tgatttacga agctgttctc 1020
ttgcaaaccc cagcccaggc gggcgaagag cctttgggag tcggcagtgt ggcagccggt 1080
ggtcgttatg atggtttggt aggaatgttt gaccctaaag gccgtaaagt accatgtgtg 1140
gggctttcta tcggtgtcga acgtatcttt tctattgttg aacaacgtct tgaagctttg 1200
gaggaaaaga tccgtaccac ggaaacccaa gtcttagttg caagtgccca aaaaaaactg 1260
ttagaagaac gcctgaaact cgtatcagaa ctttgggacg ccggcatcaa ggccgaactg 1320
ctgtataaaa agaacccgaa attgttaaac caactccagt attgtgaaga agctgggatc 1380
ccactcgtag ctattattgg tgagcaagaa ttaaaagatg gcgtgattaa actgcgttca 1440
gtaacaagcc gtgaagaggt agatgtacgt cgcgaagact tagtggaaga aattaaacgc 1500
cgcaccggtc aaccgtta 1518

<210> SEQ ID NO 195
<211> LENGTH: 1518
<212> TYPE: DNA
<213> ORGANISM: Artificial Sequence
<220> FEATURE:
<223> OTHER INFORMATION: Polynucleotide encoding cysteine mutated HRS
protein

<400> SEQUENCE: 195
atggcggaac gtgccgcact ggaagaattg gttaaattac agggagaacg cgtacgtggt 60
cttaaacaac aaaaagcctc tgcggaattg attgaagaag aagttgccaa attactgaaa 120
ctgaaagctc aacttggacc cgatgaaagt aaacaaaaat ttgtgttgaa aacgcccaaa 180
ggaacccgtg attatagtcc acgtcaaatg gccgttcgtg aaaaagtgtt cgacgttatt 240
attcgctgtt ttaaacgtca cggtgctgaa gtaatcgata cccccgtatt tgaattgaaa 300
gagactctga tgggcaaata tggtgaagat tctaaactga tttatgattt gaaagaccaa 360
ggaggtgaac tgctgagcct gcgctacgac ttaactgtgc cttttgcccg ttacttagcc 420
atgaataaat taaccaacat caaacgttac catattgcaa aagtatatcg ccgcgacaac 480
cctgcaatga ctcgtggacg ctatcgcgaa ttctatcagt gtgattttga tattgccgga 540
aatttcgacc cgatgatccc ggatgccgag agtttgaaaa ttatgtgtga aattctgagt 600
tcgttgcaga tcggagactt tcttgtaaaa gttaatgacc gccgtattct ggatggtatg 660
tttgctattt gcggtgtttc tgattccaaa ttccgtacaa tctgctcaag cgtggacaaa 720
ttggataaag tgtcttggga agaagtaaaa aatgaaatgg tgggagaaaa aggcctggct 780
ccagaagtag cagaccgtat tggtgactat gttcaacaac atggcggtgt gtccttagtc 840
gaacagttat tacaggatcc taaactgagc caaaataaac aagcacttga aggactggga 900
gatctgaaat tactctttga atatctgacc ttatttggga ttgatgataa aattagcttt 960
gatctgagct tggcccgcgg tcttgattat tataccggcg tgatttacga agctgttctc 1020
ttgcaaaccc cagcccaggc gggcgaagag cctttgggag tcggcagtgt ggcagccggt 1080
ggtcgttatg atggtttggt aggaatgttt gaccctaaag gccgtaaagt accatgtgtg 1140
gggctttcta tcggtgtcga acgtatcttt tctattgttg aacaacgtct tgaagctttg 1200
gaggaaaaga tccgtaccac ggaaacccaa gtcttagttg caagtgccca aaaaaaactg 1260
ttagaagaac gcctgaaact cgtatcagaa ctttgggacg ccggcatcaa ggccgaactg 1320
ctgtataaaa agaacccgaa attgttaaac caactccagt attgtgaaga agctgggatc 1380
ccactcgtag ctattattgg tgagcaagaa ttaaaagatg gcgtgattaa actgcgttca 1440
gtaacaagcc gtgaagaggt agatgtacgt cgcgaagact tagtggaaga aattaaacgc 1500
cgcaccggtc aaccgtta 1518

<210> SEQ ID NO 196
<211> LENGTH: 1518
<212> TYPE: DNA
<213> ORGANISM: Artificial Sequence
<220> FEATURE:
<223> OTHER INFORMATION: Polynucleotide encoding cysteine mutated HRS protein

<400> SEQUENCE: 196

```
atggcggaac gtgccgcact ggaagaattg gttaaattac agggagaacg cgtacgtggt      60
cttaaacaac aaaaagcctc tgcggaattg attgaagaag aagttgccaa attactgaaa     120
ctgaaagctc aacttggacc cgatgaaagt aaacaaaaat ttgtgttgaa aacgcccaaa     180
ggaacccgtg attatagtcc acgtcaaatg gccgttcgtg aaaaagtgtt cgacgttatt     240
attcgctgtt ttaaacgtca cggtgctgaa gtaatcgata cccccgtatt tgaattgaaa     300
gagactctga tgggcaaata tggtgaagat tctaaactga tttatgattt gaaagaccaa     360
ggaggtgaac tgctgagcct gcgctacgac ttaactgtgc cttttgcccg ttacttagcc     420
atgaataaat taaccaacat caaacgttac catattgcaa aagtatatcg ccgcgacaac     480
cctgcaatga ctcgtggacg ctatcgcgaa ttctatcagt gtgattttga tattgccgga     540
aatttcgacc cgatgatccc ggatgccgag gttttgaaaa ttatgtgtga aattctgagt     600
tcgttgcaga tcggagactt tcttgtaaaa gttaatgacc gccgtattct ggatggtatg     660
tttgctattt gcggtgtttc tgattccaaa ttccgtacaa tctgctcaag cgtggacaaa     720
ttggataaag tgtcttggga agaagtaaaa aatgaaatgg tgggagaaaa aggcctggct     780
ccagaagtag cagaccgtat tggtgactat gttcaacaac atggcggtgt gtccttagtc     840
gaacagttat tacaggatcc taaactgagc caaaataaac aagcacttga aggactggga     900
gatctgaaat tactctttga atatctgacc ttatttggga ttgatgataa aattagcttt     960
gatctgagct tggcccgcgg tcttgattat tataccggcg tgatttacga agctgttctc    1020
ttgcaaaccc cagcccaggc gggcgaagag cctttgggag tcggcagtgt ggcagccggt    1080
ggtcgttatg atggtttggt aggaatgttt gaccctaaag gccgtaaagt accatgtgtg    1140
gggctttcta tcggtgtcga acgtatcttt tctattgttg aacaacgtct tgaagctttg    1200
gaggaaaaga tccgtaccac ggaaacccaa gtcttagttg caagtgccca aaaaaaactg    1260
ttagaagaac gcctgaaact cgtatcagaa ctttgggacg ccggcatcaa ggccgaactg    1320
ctgtataaaa agaacccgaa attgttaaac caactccagt attgtgaaga agctgggatc    1380
ccactcgtag ctattattgg tgagcaagaa ttaaaagatg gcgtgattaa actgcgttca    1440
gtaacaagcc gtgaagaggt agatgtacgt cgcgaagact tagtggaaga aattaaacgc    1500
cgcaccggtc aaccgtta                                                  1518
```

<210> SEQ ID NO 197
<211> LENGTH: 1518
<212> TYPE: DNA
<213> ORGANISM: Artificial Sequence
<220> FEATURE:
<223> OTHER INFORMATION: Polynucleotide encoding cysteine mutated HRS
protein

<400> SEQUENCE: 197

```
atggcggaac gtgccgcact ggaagaattg gttaaattac agggagaacg cgtacgtggt      60
cttaaacaac aaaaagcctc tgcggaattg attgaagaag aagttgccaa attactgaaa     120
ctgaaagctc aacttggacc cgatgaaagt aaacaaaaat ttgtgttgaa aacgcccaaa     180
ggaacccgtg attatagtcc acgtcaaatg gccgttcgtg aaaaagtgtt cgacgttatt     240
attcgctgtt ttaaacgtca cggtgctgaa gtaatcgata cccccgtatt tgaattgaaa     300
gagactctga tgggcaaata tggtgaagat tctaaactga tttatgattt gaaagaccaa     360
```

```
ggaggtgaac tgctgagcct gcgctacgac ttaactgtgc cttttgcccg ttacttagcc    420

atgaataaat taaccaacat caaacgttac catattgcaa aagtatatcg ccgcgacaac    480

cctgcaatga ctcgtggacg ctatcgcgaa ttctatcagt gtgattttga tattgccgga    540

aatttcgacc cgatgatccc ggatgccgag tgtttgaaaa ttatgtgtga aattctgagt    600

tcgttgcaga tcggagactt tcttgtaaaa gttaatgacc gccgtattct ggatggtatg    660

tttgctattt ccggtgtttc tgattccaaa ttccgtacaa tctgctcaag cgtggacaaa    720

ttggataaag tgtcttggga agaagtaaaa aatgaaatgg tgggagaaaa aggcctggct    780

ccagaagtag cagaccgtat tggtgactat gttcaacaac atggcggtgt gtccttagtc    840

gaacagttat tacaggatcc taaactgagc caaaataaac aagcacttga aggactggga    900

gatctgaaat tactctttga atatctgacc ttatttggga ttgatgataa aattagcttt    960

gatctgagct tggcccgcgg tcttgattat tataccggcg tgatttacga agctgttctc   1020

ttgcaaaccc cagcccaggc gggcgaagag cctttgggag tcggcagtgt ggcagccggt   1080

ggtcgttatg atggtttggt aggaatgttt gaccctaaag gccgtaaagt accatgtgtg   1140

gggctttcta tcggtgtcga acgtatcttt tctattgttg aacaacgtct tgaagctttg   1200

gaggaaaaga tccgtaccac ggaaacccaa gtcttagttg caagtgccca aaaaaaactg   1260

ttagaagaac gcctgaaact cgtatcagaa ctttgggacg ccggcatcaa ggccgaactg   1320

ctgtataaaa agaacccgaa attgttaaac caactccagt attgtgaaga agctgggatc   1380

ccactcgtag ctattattgg tgagcaagaa ttaaaagatg gcgtgattaa actgcgttca   1440

gtaacaagcc gtgaagaggt agatgtacgt cgcgaagact tagtggaaga aattaaacgc   1500

cgcaccggtc aaccgtta                                                 1518
```

```
<210> SEQ ID NO 198
<211> LENGTH: 1518
<212> TYPE: DNA
<213> ORGANISM: Artificial Sequence
<220> FEATURE:
<223> OTHER INFORMATION: Polynucleotide encoding cysteine mutated HRS
      protein

<400> SEQUENCE: 198
```

```
atggcggaac gtgccgcact ggaagaattg gttaaattac agggagaacg cgtacgtggt     60

cttaaacaac aaaaagcctc tgcggaattg attgaagaag aagttgccaa attactgaaa    120

ctgaaagctc aacttggacc cgatgaaagt aaacaaaaat ttgtgttgaa aacgccccaaa    180

ggaacccgtg attatagtcc acgtcaaatg gccgttcgtg aaaaagtgtt cgacgttatt    240

attcgctgtt ttaaacgtca cggtgctgaa gtaatcgata cccccgtatt tgaattgaaa    300

gagactctga tgggcaaata tggtgaagat tctaaactga tttatgattt gaaagaccaa    360

ggaggtgaac tgctgagcct gcgctacgac ttaactgtgc cttttgcccg ttacttagcc    420

atgaataaat taaccaacat caaacgttac catattgcaa aagtatatcg ccgcgacaac    480

cctgcaatga ctcgtggacg ctatcgcgaa ttctatcagt gtgattttga tattgccgga    540

aatttcgacc cgatgatccc ggatgccgag tgtttgaaaa ttatgtgtga aattctgagt    600

tcgttgcaga tcggagactt tcttgtaaaa gttaatgacc gccgtattct ggatggtatg    660

tttgctattt gcggtgtttc tgattccaaa ttccgtacaa tctcctcaag cgtggacaaa    720

ttggataaag tgtcttggga agaagtaaaa aatgaaatgg tgggagaaaa aggcctggct    780

ccagaagtag cagaccgtat tggtgactat gttcaacaac atggcggtgt gtccttagtc    840
```

gaacagttat tacaggatcc taaactgagc caaaataaac aagcacttga aggactggga 900
gatctgaaat tactctttga atatctgacc ttatttggga ttgatgataa aattagcttt 960
gatctgagct tggcccgcgg tcttgattat tataccggcg tgatttacga agctgttctc 1020
ttgcaaaccc cagcccaggc gggcgaagag cctttgggag tcggcagtgt ggcagccggt 1080
ggtcgttatg atggtttggt aggaatgttt gaccctaaag gccgtaaagt accatgtgtg 1140
gggctttcta tcggtgtcga acgtatcttt tctattgttg aacaacgtct tgaagctttg 1200
gaggaaaaga tccgtaccac ggaaacccaa gtcttagttg caagtgccca aaaaaaactg 1260
ttagaagaac gcctgaaact cgtatcagaa ctttgggacg ccggcatcaa ggccgaactg 1320
ctgtataaaa agaacccgaa attgttaaac caactccagt attgtgaaga agctgggatc 1380
ccactcgtag ctattattgg tgagcaagaa ttaaaagatg gcgtgattaa actgcgttca 1440
gtaacaagcc gtgaagaggt agatgtacgt cgcgaagact tagtggaaga aattaaacgc 1500
cgcaccggtc aaccgtta 1518

<210> SEQ ID NO 199
<211> LENGTH: 10
<212> TYPE: DNA
<213> ORGANISM: Artificial Sequence
<220> FEATURE:
<223> OTHER INFORMATION: Kozak consensus sequence

<400> SEQUENCE: 199 rccrccatgg 10

<210> SEQ ID NO 200
<211> LENGTH: 4
<212> TYPE: PRT
<213> ORGANISM: Artificial Sequence
<220> FEATURE:
<223> OTHER INFORMATION: Exemplary peptide linker sequence

<400> SEQUENCE: 200

Gly Ser Gly Ser
1

<210> SEQ ID NO 201
<211> LENGTH: 4
<212> TYPE: PRT
<213> ORGANISM: Artificial Sequence
<220> FEATURE:
<223> OTHER INFORMATION: Exemplary peptide linker sequence

<400> SEQUENCE: 201

Gly Gly Ser Gly
1

<210> SEQ ID NO 202
<211> LENGTH: 4
<212> TYPE: PRT
<213> ORGANISM: Artificial Sequence
<220> FEATURE:
<223> OTHER INFORMATION: Exemplary peptide linker sequence

<400> SEQUENCE: 202

Gly Gly Gly Ser
1

<210> SEQ ID NO 203
<211> LENGTH: 5
<212> TYPE: PRT

<213> ORGANISM: Artificial Sequence
<220> FEATURE:
<223> OTHER INFORMATION: Exemplary peptide linker sequence

<400> SEQUENCE: 203

Gly Gly Gly Gly Ser
1 5

<210> SEQ ID NO 204
<211> LENGTH: 4
<212> TYPE: PRT
<213> ORGANISM: Artificial Sequence
<220> FEATURE:
<223> OTHER INFORMATION: Exemplary peptide linker sequence

<400> SEQUENCE: 204

Gly Asn Gly Asn
1

<210> SEQ ID NO 205
<211> LENGTH: 4
<212> TYPE: PRT
<213> ORGANISM: Artificial Sequence
<220> FEATURE:
<223> OTHER INFORMATION: Exemplary peptide linker sequence

<400> SEQUENCE: 205

Gly Gly Asn Gly
1

<210> SEQ ID NO 206
<211> LENGTH: 4
<212> TYPE: PRT
<213> ORGANISM: Artificial Sequence
<220> FEATURE:
<223> OTHER INFORMATION: Exemplary peptide linker sequence

<400> SEQUENCE: 206

Gly Gly Gly Asn
1

<210> SEQ ID NO 207
<211> LENGTH: 5
<212> TYPE: PRT
<213> ORGANISM: Artificial Sequence
<220> FEATURE:
<223> OTHER INFORMATION: Exemplary peptide linker sequence

<400> SEQUENCE: 207

Gly Gly Gly Gly Asn
1 5

<210> SEQ ID NO 208
<211> LENGTH: 15
<212> TYPE: PRT
<213> ORGANISM: Artificial Sequence
<220> FEATURE:
<223> OTHER INFORMATION: Exemplary peptide linker sequence

<400> SEQUENCE: 208

Gly Gly Gly Gly Ser Gly Gly Gly Gly Ser Gly Gly Gly Gly Ser
1 5 10 15

<210> SEQ ID NO 209
<211> LENGTH: 22
<212> TYPE: PRT
<213> ORGANISM: Artificial Sequence
<220> FEATURE:
<223> OTHER INFORMATION: Exemplary peptide linker sequence

<400> SEQUENCE: 209

Gly Ser Gly Gly Gly Gly Ser Gly Gly Gly Gly Ser Gly Gly Gly Gly
1               5                   10                  15

Ser Gly Gly Gly Gly Ser
            20

<210> SEQ ID NO 210
<211> LENGTH: 30
<212> TYPE: PRT
<213> ORGANISM: Artificial Sequence
<220> FEATURE:
<223> OTHER INFORMATION: Exemplary peptide linker sequence

<400> SEQUENCE: 210

Gly Gly Gly Gly Ser Gly Gly Gly Gly Ser Gly Gly Gly Gly Ser Gly
1               5                   10                  15

Gly Gly Gly Ser Gly Gly Gly Gly Ser Gly Gly Gly Gly Ser
            20                  25                  30

<210> SEQ ID NO 211
<211> LENGTH: 25
<212> TYPE: PRT
<213> ORGANISM: Artificial Sequence
<220> FEATURE:
<223> OTHER INFORMATION: Exemplary peptide linker sequence

<400> SEQUENCE: 211

Asp Ala Ala Ala Lys Glu Ala Ala Ala Lys Asp Ala Ala Ala Arg Glu
1               5                   10                  15

Ala Ala Ala Arg Asp Ala Ala Ala Lys
            20                  25

<210> SEQ ID NO 212
<211> LENGTH: 14
<212> TYPE: PRT
<213> ORGANISM: Artificial Sequence
<220> FEATURE:
<223> OTHER INFORMATION: Exemplary peptide linker sequence

<400> SEQUENCE: 212

Asn Val Asp His Lys Pro Ser Asn Thr Lys Val Asp Lys Arg
1               5                   10

<210> SEQ ID NO 213
<211> LENGTH: 5
<212> TYPE: PRT
<213> ORGANISM: Artificial Sequence
<220> FEATURE:
<223> OTHER INFORMATION: Peptide linker sequence

<400> SEQUENCE: 213

Asp Gly Gly Gly Ser
1               5

<210> SEQ ID NO 214
<211> LENGTH: 5
<212> TYPE: PRT
<213> ORGANISM: Artificial Sequence
<220> FEATURE:
<223> OTHER INFORMATION: Peptide linker sequence

<400> SEQUENCE: 214

Thr Gly Glu Lys Pro
1 5

<210> SEQ ID NO 215
<211> LENGTH: 4
<212> TYPE: PRT
<213> ORGANISM: Artificial Sequence
<220> FEATURE:
<223> OTHER INFORMATION: Peptide linker sequence

<400> SEQUENCE: 215

Gly Gly Arg Arg
1

<210> SEQ ID NO 216
<211> LENGTH: 14
<212> TYPE: PRT
<213> ORGANISM: Artificial Sequence
<220> FEATURE:
<223> OTHER INFORMATION: Peptide linker sequence

<400> SEQUENCE: 216

Glu Gly Lys Ser Ser Gly Ser Gly Ser Glu Ser Lys Val Asp
1 5 10

<210> SEQ ID NO 217
<211> LENGTH: 18
<212> TYPE: PRT
<213> ORGANISM: Artificial Sequence
<220> FEATURE:
<223> OTHER INFORMATION: Peptide linker sequence

<400> SEQUENCE: 217

Lys Glu Ser Gly Ser Val Ser Ser Glu Gln Leu Ala Gln Phe Arg Ser
1 5 10 15

Leu Asp

<210> SEQ ID NO 218
<211> LENGTH: 8
<212> TYPE: PRT
<213> ORGANISM: Artificial Sequence
<220> FEATURE:
<223> OTHER INFORMATION: Peptide linker sequence

<400> SEQUENCE: 218

Gly Gly Arg Arg Gly Gly Gly Ser
1 5

<210> SEQ ID NO 219
<211> LENGTH: 9
<212> TYPE: PRT
<213> ORGANISM: Artificial Sequence
<220> FEATURE:
<223> OTHER INFORMATION: Peptide linker sequence

<400> SEQUENCE: 219

Leu Arg Gln Arg Asp Gly Glu Arg Pro
1 5

<210> SEQ ID NO 220
<211> LENGTH: 12
<212> TYPE: PRT
<213> ORGANISM: Artificial Sequence
<220> FEATURE:
<223> OTHER INFORMATION: Peptide linker sequence

<400> SEQUENCE: 220

```
Leu Arg Gln Lys Asp Gly Gly Gly Ser Glu Arg Pro
1               5                   10


<210> SEQ ID NO 221
<211> LENGTH: 16
<212> TYPE: PRT
<213> ORGANISM: Artificial Sequence
<220> FEATURE:
<223> OTHER INFORMATION: Peptide linker sequence

<400> SEQUENCE: 221

Leu Arg Gln Lys Asp Gly Gly Gly Ser Gly Gly Gly Ser Glu Arg Pro
1               5                   10                  15


<210> SEQ ID NO 222
<211> LENGTH: 19
<212> TYPE: PRT
<213> ORGANISM: Unknown
<220> FEATURE:
<223> OTHER INFORMATION: Naturally occurring 2A or 2A-like self cleaving
      peptide

<400> SEQUENCE: 222

Leu Leu Asn Phe Asp Leu Leu Lys Leu Ala Gly Asp Val Glu Ser Asn
1               5                   10                  15

Pro Gly Pro


<210> SEQ ID NO 223
<211> LENGTH: 19
<212> TYPE: PRT
<213> ORGANISM: Unknown
<220> FEATURE:
<223> OTHER INFORMATION: Naturally occurring 2A or 2A-like self cleaving
      peptide

<400> SEQUENCE: 223

Thr Leu Asn Phe Asp Leu Leu Lys Leu Ala Gly Asp Val Glu Ser Asn
1               5                   10                  15

Pro Gly Pro


<210> SEQ ID NO 224
<211> LENGTH: 14
<212> TYPE: PRT
<213> ORGANISM: Unknown
<220> FEATURE:
<223> OTHER INFORMATION: Naturally occurring 2A or 2A-like self cleaving
      peptide

<400> SEQUENCE: 224

Leu Leu Lys Leu Ala Gly Asp Val Glu Ser Asn Pro Gly Pro
1               5                   10


<210> SEQ ID NO 225
<211> LENGTH: 17
<212> TYPE: PRT
<213> ORGANISM: Unknown
<220> FEATURE:
<223> OTHER INFORMATION: Naturally occurring 2A or 2A-like self cleaving
      peptide

<400> SEQUENCE: 225

Asn Phe Asp Leu Leu Lys Leu Ala Gly Asp Val Glu Ser Asn Pro Gly
1               5                   10                  15

Pro
```

<210> SEQ ID NO 226
<211> LENGTH: 20
<212> TYPE: PRT
<213> ORGANISM: Unknown
<220> FEATURE:
<223> OTHER INFORMATION: Naturally occurring 2A or 2A-like self cleaving peptide

<400> SEQUENCE: 226

```
Gln Leu Leu Asn Phe Asp Leu Leu Lys Leu Ala Gly Asp Val Glu Ser
1               5                   10                  15

Asn Pro Gly Pro
            20
```

<210> SEQ ID NO 227
<211> LENGTH: 24
<212> TYPE: PRT
<213> ORGANISM: Unknown
<220> FEATURE:
<223> OTHER INFORMATION: Naturally occurring 2A or 2A-like self cleaving peptide

<400> SEQUENCE: 227

```
Ala Pro Val Lys Gln Thr Leu Asn Phe Asp Leu Leu Lys Leu Ala Gly
1               5                   10                  15

Asp Val Glu Ser Asn Pro Gly Pro
            20
```

<210> SEQ ID NO 228
<211> LENGTH: 40
<212> TYPE: PRT
<213> ORGANISM: Unknown
<220> FEATURE:
<223> OTHER INFORMATION: Naturally occurring 2A or 2A-like self cleaving peptide

<400> SEQUENCE: 228

```
Val Thr Glu Leu Leu Tyr Arg Met Lys Arg Ala Glu Thr Tyr Cys Pro
1               5                   10                  15

Arg Pro Leu Leu Ala Ile His Pro Thr Glu Ala Arg His Lys Gln Lys
            20                  25                  30

Ile Val Ala Pro Val Lys Gln Thr
        35                  40
```

<210> SEQ ID NO 229
<211> LENGTH: 18
<212> TYPE: PRT
<213> ORGANISM: Unknown
<220> FEATURE:
<223> OTHER INFORMATION: Naturally occurring 2A or 2A-like self cleaving peptide

<400> SEQUENCE: 229

```
Leu Asn Phe Asp Leu Leu Lys Leu Ala Gly Asp Val Glu Ser Asn Pro
1               5                   10                  15

Gly Pro
```

<210> SEQ ID NO 230
<211> LENGTH: 40
<212> TYPE: PRT
<213> ORGANISM: Unknown
<220> FEATURE:
<223> OTHER INFORMATION: Naturally occurring 2A or 2A-like self cleaving peptide

<400> SEQUENCE: 230

Leu Leu Ala Ile His Pro Thr Glu Ala Arg His Lys Gln Lys Ile Val
1 5 10 15

Ala Pro Val Lys Gln Thr Leu Asn Phe Asp Leu Leu Lys Leu Ala Gly
20 25 30

Asp Val Glu Ser Asn Pro Gly Pro
35 40

<210> SEQ ID NO 231
<211> LENGTH: 33
<212> TYPE: PRT
<213> ORGANISM: Unknown
<220> FEATURE:
<223> OTHER INFORMATION: Naturally occurring 2A or 2A-like self cleaving peptide

<400> SEQUENCE: 231

Glu Ala Arg His Lys Gln Lys Ile Val Ala Pro Val Lys Gln Thr Leu
1 5 10 15

Asn Phe Asp Leu Leu Lys Leu Ala Gly Asp Val Glu Ser Asn Pro Gly
20 25 30

Pro

<210> SEQ ID NO 232
<211> LENGTH: 7
<212> TYPE: PRT
<213> ORGANISM: Tobacco etch virus
<220> FEATURE:
<221> NAME/KEY: VARIANT
<222> LOCATION: (2)..(2)
<223> OTHER INFORMATION: Xaa = any amino acid
<220> FEATURE:
<221> NAME/KEY: VARIANT
<222> LOCATION: (3)..(3)
<223> OTHER INFORMATION: Xaa = any amino acid
<220> FEATURE:
<221> NAME/KEY: VARIANT
<222> LOCATION: (5)..(5)
<223> OTHER INFORMATION: Xaa = any amino acid
<220> FEATURE:
<221> NAME/KEY: VARIANT
<222> LOCATION: (7)..(7)
<223> OTHER INFORMATION: Xaa is either Gly or Ser

<400> SEQUENCE: 232

Glu Xaa Xaa Tyr Xaa Gln Xaa
1 5

<210> SEQ ID NO 233
<211> LENGTH: 7
<212> TYPE: PRT
<213> ORGANISM: Tobacco etch virus

<400> SEQUENCE: 233

Glu Asn Leu Tyr Phe Gln Gly
1 5

<210> SEQ ID NO 234
<211> LENGTH: 7
<212> TYPE: PRT
<213> ORGANISM: Tabacco etch virus

<400> SEQUENCE: 234

Glu Asn Leu Tyr Phe Gln Ser
1 5

<210> SEQ ID NO 235
<211> LENGTH: 4
<212> TYPE: PRT
<213> ORGANISM: Artificial Sequence
<220> FEATURE:
<223> OTHER INFORMATION: Thrombin cleavable linker

<400> SEQUENCE: 235

Gly Arg Gly Asp
1

<210> SEQ ID NO 236
<211> LENGTH: 6
<212> TYPE: PRT
<213> ORGANISM: Artificial Sequence
<220> FEATURE:
<223> OTHER INFORMATION: Thrombin cleavable linker

<400> SEQUENCE: 236

Gly Arg Gly Asp Asn Pro
1 5

<210> SEQ ID NO 237
<211> LENGTH: 5
<212> TYPE: PRT
<213> ORGANISM: Artificial Sequence
<220> FEATURE:
<223> OTHER INFORMATION: Thrombin cleavable linker

<400> SEQUENCE: 237

Gly Arg Gly Asp Ser
1 5

<210> SEQ ID NO 238
<211> LENGTH: 7
<212> TYPE: PRT
<213> ORGANISM: Artificial Sequence
<220> FEATURE:
<223> OTHER INFORMATION: Thrombin cleavable linker

<400> SEQUENCE: 238

Gly Arg Gly Asp Ser Pro Lys
1 5

<210> SEQ ID NO 239
<211> LENGTH: 4
<212> TYPE: PRT
<213> ORGANISM: Artificial Sequence
<220> FEATURE:
<223> OTHER INFORMATION: Elastase cleavable linker

<400> SEQUENCE: 239

Ala Ala Pro Val
1

<210> SEQ ID NO 240
<211> LENGTH: 4
<212> TYPE: PRT
<213> ORGANISM: Artificial Sequence
<220> FEATURE:
<223> OTHER INFORMATION: Elastase cleavable linker

<400> SEQUENCE: 240

Ala Ala Pro Leu
1

<210> SEQ ID NO 241
<211> LENGTH: 4
<212> TYPE: PRT
<213> ORGANISM: Artificial Sequence
<220> FEATURE:
<223> OTHER INFORMATION: Elastase cleavable linker

<400> SEQUENCE: 241

Ala Ala Pro Phe
1

<210> SEQ ID NO 242
<211> LENGTH: 4
<212> TYPE: PRT
<213> ORGANISM: Artificial Sequence
<220> FEATURE:
<223> OTHER INFORMATION: Elastase cleavable linker

<400> SEQUENCE: 242

Ala Ala Pro Ala
1

<210> SEQ ID NO 243
<211> LENGTH: 4
<212> TYPE: PRT
<213> ORGANISM: Artificial Sequence
<220> FEATURE:
<223> OTHER INFORMATION: Elastase cleavable linker

<400> SEQUENCE: 243

Ala Tyr Leu Val
1

<210> SEQ ID NO 244
<211> LENGTH: 6
<212> TYPE: PRT
<213> ORGANISM: Artificial Sequence
<220> FEATURE:
<223> OTHER INFORMATION: Matrix metalloproteinase cleavable linker
<220> FEATURE:
<221> NAME/KEY: VARIANT
<222> LOCATION: (3)..(3)
<223> OTHER INFORMATION: Xaa = Any amino acid
<220> FEATURE:
<221> NAME/KEY: VARIANT
<222> LOCATION: (6)..(6)
<223> OTHER INFORMATION: Xaa = Any amino acid

<400> SEQUENCE: 244

Gly Pro Xaa Gly Pro Xaa
1               5

<210> SEQ ID NO 245
<211> LENGTH: 4
<212> TYPE: PRT
<213> ORGANISM: Artificial Sequence
<220> FEATURE:
<223> OTHER INFORMATION: Matrix metalloproteinase cleavable linker
<220> FEATURE:
<221> NAME/KEY: VARIANT
<222> LOCATION: (4)..(4)
<223> OTHER INFORMATION: Xaa = Any amino acid

<400> SEQUENCE: 245

Leu Gly Pro Xaa
1

<210> SEQ ID NO 246
<211> LENGTH: 6

<212> TYPE: PRT
<213> ORGANISM: Artificial Sequence
<220> FEATURE:
<223> OTHER INFORMATION: Matrix metalloproteinase cleavable linker
<220> FEATURE:
<221> NAME/KEY: VARIANT
<222> LOCATION: (6)..(6)
<223> OTHER INFORMATION: Xaa = Any amino acid

<400> SEQUENCE: 246

Gly Pro Ile Gly Pro Xaa
1               5

<210> SEQ ID NO 247
<211> LENGTH: 5
<212> TYPE: PRT
<213> ORGANISM: Artificial Sequence
<220> FEATURE:
<223> OTHER INFORMATION: Matrix metalloproteinase cleavable linker
<220> FEATURE:
<221> NAME/KEY: VARIANT
<222> LOCATION: (5)..(5)
<223> OTHER INFORMATION: Xaa = Any amino acid

<400> SEQUENCE: 247

Ala Pro Gly Leu Xaa
1               5

<210> SEQ ID NO 248
<211> LENGTH: 7
<212> TYPE: PRT
<213> ORGANISM: Artificial Sequence
<220> FEATURE:
<223> OTHER INFORMATION: Collagenase cleavable linker
<220> FEATURE:
<221> NAME/KEY: VARIANT
<222> LOCATION: (7)..(7)
<223> OTHER INFORMATION: Xaa = Any amino acid

<400> SEQUENCE: 248

Pro Leu Gly Pro Asp Arg Xaa
1               5

<210> SEQ ID NO 249
<211> LENGTH: 7
<212> TYPE: PRT
<213> ORGANISM: Artificial Sequence
<220> FEATURE:
<223> OTHER INFORMATION: Collagenase cleavable linker
<220> FEATURE:
<221> NAME/KEY: VARIANT
<222> LOCATION: (7)..(7)
<223> OTHER INFORMATION: Xaa = Any amino acid

<400> SEQUENCE: 249

Pro Leu Gly Leu Leu Gly Xaa
1               5

<210> SEQ ID NO 250
<211> LENGTH: 7
<212> TYPE: PRT
<213> ORGANISM: Artificial Sequence
<220> FEATURE:
<223> OTHER INFORMATION: Collagenase cleavable linker

<400> SEQUENCE: 250

Pro Gln Gly Ile Ala Gly Trp
1               5

-continued

<210> SEQ ID NO 251
<211> LENGTH: 5
<212> TYPE: PRT
<213> ORGANISM: Artificial Sequence
<220> FEATURE:
<223> OTHER INFORMATION: Collagenase cleavable linker

<400> SEQUENCE: 251

Pro Leu Gly Cys His
1               5

<210> SEQ ID NO 252
<211> LENGTH: 6
<212> TYPE: PRT
<213> ORGANISM: Artificial Sequence
<220> FEATURE:
<223> OTHER INFORMATION: Collagenase cleavable linker

<400> SEQUENCE: 252

Pro Leu Gly Leu Tyr Ala
1               5

<210> SEQ ID NO 253
<211> LENGTH: 7
<212> TYPE: PRT
<213> ORGANISM: Artificial Sequence
<220> FEATURE:
<223> OTHER INFORMATION: Collagenase cleavable linker

<400> SEQUENCE: 253

Pro Leu Ala Leu Trp Ala Arg
1               5

<210> SEQ ID NO 254
<211> LENGTH: 7
<212> TYPE: PRT
<213> ORGANISM: Artificial Sequence
<220> FEATURE:
<223> OTHER INFORMATION: Collagenase cleavable linker

<400> SEQUENCE: 254

Pro Leu Ala Tyr Trp Ala Arg
1               5

<210> SEQ ID NO 255
<211> LENGTH: 7
<212> TYPE: PRT
<213> ORGANISM: Artificial Sequence
<220> FEATURE:
<223> OTHER INFORMATION: Stromelysin cleavable linker

<400> SEQUENCE: 255

Pro Tyr Ala Tyr Tyr Met Arg
1               5

<210> SEQ ID NO 256
<211> LENGTH: 7
<212> TYPE: PRT
<213> ORGANISM: Artificial Sequence
<220> FEATURE:
<223> OTHER INFORMATION: Gelatinase cleavable linker

<400> SEQUENCE: 256

Pro Leu Gly Met Tyr Ser Arg
1               5

<210> SEQ ID NO 257

```
<211> LENGTH: 4
<212> TYPE: PRT
<213> ORGANISM: Artificial Sequence
<220> FEATURE:
<223> OTHER INFORMATION: Angiotensin converting enzyme cleavable linker

<400> SEQUENCE: 257

Gly Asp Lys Pro
1


<210> SEQ ID NO 258
<211> LENGTH: 5
<212> TYPE: PRT
<213> ORGANISM: Artificial Sequence
<220> FEATURE:
<223> OTHER INFORMATION: Angiotensin converting enzyme cleavable linker

<400> SEQUENCE: 258

Gly Ser Asp Lys Pro
1               5


<210> SEQ ID NO 259
<211> LENGTH: 4
<212> TYPE: PRT
<213> ORGANISM: Artificial Sequence
<220> FEATURE:
<223> OTHER INFORMATION: Cathepsin B cleavable linker

<400> SEQUENCE: 259

Ala Leu Ala Leu
1


<210> SEQ ID NO 260
<211> LENGTH: 4
<212> TYPE: PRT
<213> ORGANISM: Artificial Sequence
<220> FEATURE:
<223> OTHER INFORMATION: Cathepsin B cleavable linker

<400> SEQUENCE: 260

Gly Phe Leu Gly
1


<210> SEQ ID NO 261
<211> LENGTH: 198
<212> TYPE: DNA
<213> ORGANISM: Artificial Sequence
<220> FEATURE:
<223> OTHER INFORMATION: Codon optimized DNA sequence for HRS
      polypeptide with 6xHis tag

<400> SEQUENCE: 261

atggcagaac gtgcggcatt ggaagaattg gttaaactgc aaggtgaacg tgttcgtggt      60

ctgaagcagc agaaggctag cgcggagctg atcgaagaag aggtggccaa actgctgaag     120

ctgaaggcgc agctgggccc ggacgagagc aaacaaaagt tcgtcctgaa aaccccgaaa     180

caccaccatc accatcac                                                   198


<210> SEQ ID NO 262
<211> LENGTH: 66
<212> TYPE: PRT
<213> ORGANISM: Artificial Sequence
<220> FEATURE:
<223> OTHER INFORMATION: HRS polypeptide with 6xHis tag

<400> SEQUENCE: 262
```

```
Met Ala Glu Arg Ala Ala Leu Glu Glu Leu Val Lys Leu Gln Gly Glu
1               5                   10                  15

Arg Val Arg Gly Leu Lys Gln Gln Lys Ala Ser Ala Glu Leu Ile Glu
            20                  25                  30

Glu Glu Val Ala Lys Leu Leu Lys Leu Lys Ala Gln Leu Gly Pro Asp
        35                  40                  45

Glu Ser Lys Gln Lys Phe Val Leu Lys Thr Pro Lys His His His His
    50                  55                  60

His His
65


<210> SEQ ID NO 263
<211> LENGTH: 201
<212> TYPE: DNA
<213> ORGANISM: Artificial Sequence
<220> FEATURE:
<223> OTHER INFORMATION: Codon optimized DNA sequence for HRS
      polypeptide with 6xHis tag

<400> SEQUENCE: 263

atgtgtgcag aaagagccgc cctggaagag ttagttaagt tgcaaggtga acgtgtccgt      60

ggtctgaagc agcagaaggc tagcgcggag ctgatcgaag aagaggtggc caaactgctg     120

aagctgaagg cgcagctggg cccggacgag agcaaacaaa agttcgtcct gaaaaccccg     180

aaacaccacc atcaccatca c                                               201


<210> SEQ ID NO 264
<211> LENGTH: 67
<212> TYPE: PRT
<213> ORGANISM: Artificial Sequence
<220> FEATURE:
<223> OTHER INFORMATION: HRS polypeptide with 6xHis tag

<400> SEQUENCE: 264

Met Cys Ala Glu Arg Ala Ala Leu Glu Glu Leu Val Lys Leu Gln Gly
1               5                   10                  15

Glu Arg Val Arg Gly Leu Lys Gln Gln Lys Ala Ser Ala Glu Leu Ile
            20                  25                  30

Glu Glu Glu Val Ala Lys Leu Leu Lys Leu Lys Ala Gln Leu Gly Pro
        35                  40                  45

Asp Glu Ser Lys Gln Lys Phe Val Leu Lys Thr Pro Lys His His His
    50                  55                  60

His His His
65


<210> SEQ ID NO 265
<211> LENGTH: 198
<212> TYPE: DNA
<213> ORGANISM: Artificial Sequence
<220> FEATURE:
<223> OTHER INFORMATION: Codon optimized DNA sequence for HRS
      polypeptide with 6xHis tag

<400> SEQUENCE: 265

atggcagaac gtgcggcatt ggaagaattg gttaaactgc aaggtgaacg tgttcgtggt      60

ctgaagcagc agaagtgcag cgcggagctg atcgaagaag aggtggccaa actgctgaag     120

ctgaaggcgc agctgggccc ggacgagagc aaacaaaagt tcgtcctgaa aaccccgaaa     180

caccaccatc accatcac                                                   198
```

<210> SEQ ID NO 266
<211> LENGTH: 66
<212> TYPE: PRT
<213> ORGANISM: Artificial Sequence
<220> FEATURE:
<223> OTHER INFORMATION: HRS polypeptide with 6xHis tag

<400> SEQUENCE: 266

```
Met Ala Glu Arg Ala Ala Leu Glu Glu Leu Val Lys Leu Gln Gly Glu
1               5                   10                  15

Arg Val Arg Gly Leu Lys Gln Gln Lys Cys Ser Ala Glu Leu Ile Glu
            20                  25                  30

Glu Glu Val Ala Lys Leu Leu Lys Leu Lys Ala Gln Leu Gly Pro Asp
        35                  40                  45

Glu Ser Lys Gln Lys Phe Val Leu Lys Thr Pro Lys His His His His
    50                  55                  60

His His
65
```

<210> SEQ ID NO 267
<211> LENGTH: 201
<212> TYPE: DNA
<213> ORGANISM: Artificial Sequence
<220> FEATURE:
<223> OTHER INFORMATION: Codon optimized DNA sequence for HRS
polypeptide with 6xHis tag

<400> SEQUENCE: 267

```
atggcagaac gtgcggcatt ggaagaattg gttaaactgc aaggtgaacg tgttcgtggt      60

ctgaagcagc agaaggctag cgcggagctg atcgaagaag aggtggccaa actgctgaag     120

ctgaaggcgc agctgggccc ggacgagagc aaacaaaagt tcgtcctgaa aaccccgaaa     180

tgccaccacc atcaccatca c                                               201
```

<210> SEQ ID NO 268
<211> LENGTH: 67
<212> TYPE: PRT
<213> ORGANISM: Artificial Sequence
<220> FEATURE:
<223> OTHER INFORMATION: HRS polypeptide with 6xHis tag

<400> SEQUENCE: 268

```
Met Ala Glu Arg Ala Ala Leu Glu Glu Leu Val Lys Leu Gln Gly Glu
1               5                   10                  15

Arg Val Arg Gly Leu Lys Gln Gln Lys Ala Ser Ala Glu Leu Ile Glu
            20                  25                  30

Glu Glu Val Ala Lys Leu Leu Lys Leu Lys Ala Gln Leu Gly Pro Asp
        35                  40                  45

Glu Ser Lys Gln Lys Phe Val Leu Lys Thr Pro Lys Cys His His His
    50                  55                  60

His His His
65
```

<210> SEQ ID NO 269
<211> LENGTH: 1563
<212> TYPE: DNA
<213> ORGANISM: Artificial Sequence
<220> FEATURE:
<223> OTHER INFORMATION: Codon optimized DNA for HRS full length protein
with 6xHis tag

<400> SEQUENCE: 269

-continued

```
atggcggaac gtgccgcact ggaagaattg gttaaattac agggagaacg cgtacgtggt     60
cttaaacaac aaaaagcctc tgcggaattg attgaagaag aagttgccaa attactgaaa    120
ctgaaagctc aacttggacc cgatgaaagt aaacaaaaat ttgtgttgaa aacgcccaaa    180
ggaacccgtg attatagtcc acgtcaaatg gccgttcgtg aaaaagtgtt cgacgttatt    240
attcgctgtt ttaaacgtca cggtgctgaa gtaatcgata cccccgtatt tgaattgaaa    300
gagactctga tgggcaaata tggtgaagat tctaaactga tttatgattt gaaagaccaa    360
ggaggtgaac tgctgagcct gcgctacgac ttaactgtgc cttttgcccg ttacttagcc    420
atgaataaat taaccaacat caaacgttac catattgcaa aagtatatcg ccgcgacaac    480
cctgcaatga ctcgtggacg ctatcgcgaa ttctatcagt gtgattttga tattgccgga    540
aatttcgacc cgatgatccc ggatgccgag tgtttgaaaa ttatgtgtga aattctgagt    600
tcgttgcaga tcggagactt tcttgtaaaa gttaatgacc gccgtattct ggatggtatg    660
tttgctattt gcggtgtttc tgattccaaa ttccgtacaa tctgctcaag cgtggacaaa    720
ttggataaag tgtcttggga agaagtaaaa aatgaaatgg tgggagaaaa aggcctggct    780
ccagaagtag cagaccgtat tggtgactat gttcaacaac atggcggtgt gtccttagtc    840
gaacagttat tacaggatcc taaactgagc caaaataaac aagcacttga aggactggga    900
gatctgaaat tactctttga atatctgacc ttatttggga ttgatgataa aattagcttt    960
gatctgagct tggcccgcgg tcttgattat tataccggcg tgatttacga agctgttctc   1020
ttgcaaaccc cagcccaggc gggcgaagag cctttgggag tcggcagtgt ggcagccggt   1080
ggtcgttatg atggtttggt aggaatgttt gaccctaaag gccgtaaagt accatgtgtg   1140
gggctttcta tcggtgtcga acgtatcttt tctattgttg aacaacgtct tgaagctttg   1200
gaggaaaaga tccgtaccac ggaaacccaa gtcttagttg caagtgccca aaaaaaactg   1260
ttagaagaac gcctgaaact cgtatcagaa ctttgggacg ccggcatcaa ggccgaactg   1320
ctgtataaaa agaacccgaa attgttaaac caactccagt attgtgaaga agctgggatc   1380
ccactcgtag ctattattgg tgagcaagaa ttaaaagatg gcgtgattaa actgcgttca   1440
gtaacaagcc gtgaagaggt agatgtacgt cgcgaagact tagtggaaga aattaaacgc   1500
cgcaccggtc aaccgttatg tatttgcgcg gccgcactcg agcaccacca ccaccaccac   1560
tga                                                                 1563
```

<210> SEQ ID NO 270
<211> LENGTH: 520
<212> TYPE: PRT
<213> ORGANISM: Artificial Sequence
<220> FEATURE:
<223> OTHER INFORMATION: HRS full length protein with 6xHis tag

<400> SEQUENCE: 270

```
Met Ala Glu Arg Ala Ala Leu Glu Glu Leu Val Lys Leu Gln Gly Glu
1               5                   10                  15

Arg Val Arg Gly Leu Lys Gln Gln Lys Ala Ser Ala Glu Leu Ile Glu
            20                  25                  30

Glu Glu Val Ala Lys Leu Leu Lys Leu Lys Ala Gln Leu Gly Pro Asp
        35                  40                  45

Glu Ser Lys Gln Lys Phe Val Leu Lys Thr Pro Lys Gly Thr Arg Asp
    50                  55                  60

Tyr Ser Pro Arg Gln Met Ala Val Arg Glu Lys Val Phe Asp Val Ile
65                  70                  75                  80
```

Ile Arg Cys Phe Lys Arg His Gly Ala Glu Val Ile Asp Thr Pro Val
85 90 95

Phe Glu Leu Lys Glu Thr Leu Met Gly Lys Tyr Gly Glu Asp Ser Lys
100 105 110

Leu Ile Tyr Asp Leu Lys Asp Gln Gly Gly Glu Leu Leu Ser Leu Arg
115 120 125

Tyr Asp Leu Thr Val Pro Phe Ala Arg Tyr Leu Ala Met Asn Lys Leu
130 135 140

Thr Asn Ile Lys Arg Tyr His Ile Ala Lys Val Tyr Arg Arg Asp Asn
145 150 155 160

Pro Ala Met Thr Arg Gly Arg Tyr Arg Glu Phe Tyr Gln Cys Asp Phe
165 170 175

Asp Ile Ala Gly Asn Phe Asp Pro Met Ile Pro Asp Ala Glu Cys Leu
180 185 190

Lys Ile Met Cys Glu Ile Leu Ser Ser Leu Gln Ile Gly Asp Phe Leu
195 200 205

Val Lys Val Asn Asp Arg Arg Ile Leu Asp Gly Met Phe Ala Ile Cys
210 215 220

Gly Val Ser Asp Ser Lys Phe Arg Thr Ile Cys Ser Ser Val Asp Lys
225 230 235 240

Leu Asp Lys Val Ser Trp Glu Glu Val Lys Asn Glu Met Val Gly Glu
245 250 255

Lys Gly Leu Ala Pro Glu Val Ala Asp Arg Ile Gly Asp Tyr Val Gln
260 265 270

Gln His Gly Gly Val Ser Leu Val Glu Gln Leu Leu Gln Asp Pro Lys
275 280 285

Leu Ser Gln Asn Lys Gln Ala Leu Glu Gly Leu Gly Asp Leu Lys Leu
290 295 300

Leu Phe Glu Tyr Leu Thr Leu Phe Gly Ile Asp Asp Lys Ile Ser Phe
305 310 315 320

Asp Leu Ser Leu Ala Arg Gly Leu Asp Tyr Tyr Thr Gly Val Ile Tyr
325 330 335

Glu Ala Val Leu Leu Gln Thr Pro Ala Gln Ala Gly Glu Glu Pro Leu
340 345 350

Gly Val Gly Ser Val Ala Ala Gly Gly Arg Tyr Asp Gly Leu Val Gly
355 360 365

Met Phe Asp Pro Lys Gly Arg Lys Val Pro Cys Val Gly Leu Ser Ile
370 375 380

Gly Val Glu Arg Ile Phe Ser Ile Val Glu Gln Arg Leu Glu Ala Leu
385 390 395 400

Glu Glu Lys Ile Arg Thr Thr Glu Thr Gln Val Leu Val Ala Ser Ala
405 410 415

Gln Lys Lys Leu Leu Glu Glu Arg Leu Lys Leu Val Ser Glu Leu Trp
420 425 430

Asp Ala Gly Ile Lys Ala Glu Leu Leu Tyr Lys Lys Asn Pro Lys Leu
435 440 445

Leu Asn Gln Leu Gln Tyr Cys Glu Glu Ala Gly Ile Pro Leu Val Ala
450 455 460

Ile Ile Gly Glu Gln Glu Leu Lys Asp Gly Val Ile Lys Leu Arg Ser
465 470 475 480

Val Thr Ser Arg Glu Glu Val Asp Val Arg Arg Glu Asp Leu Val Glu
485 490 495

Glu Ile Lys Arg Arg Thr Gly Gln Pro Leu Cys Ile Cys Ala Ala Ala 500 505 510

Leu Glu His His His His His His
515 520

<210> SEQ ID NO 271
<211> LENGTH: 10
<212> TYPE: PRT
<213> ORGANISM: Artificial Sequence
<220> FEATURE:
<223> OTHER INFORMATION: Cysteine modified HARS peptide fragment

<400> SEQUENCE: 271

Val Phe Asp Val Ile Ile Arg Cys Phe Lys
1 5 10

<210> SEQ ID NO 272
<211> LENGTH: 39
<212> TYPE: PRT
<213> ORGANISM: Artificial Sequence
<220> FEATURE:
<223> OTHER INFORMATION: Cysteine modified HARS peptide fragment

<400> SEQUENCE: 272

Val Tyr Arg Arg Asp Asn Pro Ala Met Thr Arg Gly Arg Tyr Arg Glu
1 5 10 15

Phe Tyr Gln Cys Asp Phe Asp Ile Ala Gly Asn Phe Asp Pro Met Ile
20 25 30

Pro Asp Ala Glu Cys Leu Lys
35

<210> SEQ ID NO 273
<211> LENGTH: 17
<212> TYPE: PRT
<213> ORGANISM: Artificial Sequence
<220> FEATURE:
<223> OTHER INFORMATION: Cysteine modified HARS peptide fragment

<400> SEQUENCE: 273

Ile Met Cys Glu Ile Leu Ser Ser Leu Gln Ile Gly Asp Phe Leu Val
1 5 10 15

Lys

<210> SEQ ID NO 274
<211> LENGTH: 20
<212> TYPE: PRT
<213> ORGANISM: Artificial Sequence
<220> FEATURE:
<223> OTHER INFORMATION: Cysteine modified HARS peptide fragment

<400> SEQUENCE: 274

Val Asn Asp Arg Arg Ile Leu Asp Gly Met Phe Ala Ile Cys Gly Val
1 5 10 15

Ser Asp Ser Lys
20

<210> SEQ ID NO 275
<211> LENGTH: 10
<212> TYPE: PRT
<213> ORGANISM: Artificial Sequence
<220> FEATURE:
<223> OTHER INFORMATION: Cysteine modified HARS peptide fragment

<400> SEQUENCE: 275

Phe Arg Thr Ile Cys Ser Ser Val Asp Lys 1 5 10

<210> SEQ ID NO 276
<211> LENGTH: 13
<212> TYPE: PRT
<213> ORGANISM: Artificial Sequence
<220> FEATURE:
<223> OTHER INFORMATION: Cysteine modified HARS peptide fragment

<400> SEQUENCE: 276

Phe Arg Thr Ile Cys Ser Ser Val Asp Lys Leu Asp Lys
1 5 10

<210> SEQ ID NO 277
<211> LENGTH: 27
<212> TYPE: PRT
<213> ORGANISM: Artificial Sequence
<220> FEATURE:
<223> OTHER INFORMATION: Cysteine modified HARS peptide fragment

<400> SEQUENCE: 277

Val Pro Cys Val Gly Leu Ser Ile Gly Val Glu Arg Ile Phe Ser Ile
1 5 10 15

Val Glu Gln Arg Leu Glu Ala Leu Glu Glu Lys
20 25

<210> SEQ ID NO 278
<211> LENGTH: 25
<212> TYPE: PRT
<213> ORGANISM: Artificial Sequence
<220> FEATURE:
<223> OTHER INFORMATION: Cysteine modified HARS peptide fragment

<400> SEQUENCE: 278

Leu Leu Asn Gln Leu Gln Tyr Cys Glu Glu Ala Gly Ile Pro Leu Val
1 5 10 15

Ala Ile Ile Gly Glu Gln Glu Leu Lys
20 25

<210> SEQ ID NO 279
<211> LENGTH: 10
<212> TYPE: PRT
<213> ORGANISM: Artificial Sequence
<220> FEATURE:
<223> OTHER INFORMATION: Cysteine modified HARS peptide fragment

<400> SEQUENCE: 279

Arg Arg Thr Gly Gln Pro Leu Cys Ile Cys
1 5 10

<210> SEQ ID NO 280
<211> LENGTH: 41
<212> TYPE: DNA
<213> ORGANISM: Artificial Sequence
<220> FEATURE:
<223> OTHER INFORMATION: Primer to selectively mutate cysteine residue

<400> SEQUENCE: 280
gtttgacgta atcatccgtt gcttcaagcg ccacggtgca g 41

<210> SEQ ID NO 281
<211> LENGTH: 41
<212> TYPE: DNA
<213> ORGANISM: Artificial Sequence
<220> FEATURE:
<223> OTHER INFORMATION: Primer to selectively mutate cysteine residue

<400> SEQUENCE: 281
ctgcaccgtg gcgcttgaag caacggatga ttacgtcaaa c 41

<210> SEQ ID NO 282
<211> LENGTH: 44
<212> TYPE: DNA
<213> ORGANISM: Artificial Sequence
<220> FEATURE:
<223> OTHER INFORMATION: Primer to selectively mutate cysteine residue

<400> SEQUENCE: 282
gccgataccg ggaattctac cagtgtgatt ttgacattgc tggg 44

<210> SEQ ID NO 283
<211> LENGTH: 44
<212> TYPE: DNA
<213> ORGANISM: Artificial Sequence
<220> FEATURE:
<223> OTHER INFORMATION: Primer to selectively mutate cysteine residue

<400> SEQUENCE: 283
cccagcaatg tcaaaatcac actggtagaa ttcccggtat cggc 44

<210> SEQ ID NO 284
<211> LENGTH: 41
<212> TYPE: DNA
<213> ORGANISM: Artificial Sequence
<220> FEATURE:
<223> OTHER INFORMATION: Primer to selectively mutate cysteine residue

<400> SEQUENCE: 284
ccatgatccc tgatgcagag tgcctgaaga tcatgtgcga g 41

<210> SEQ ID NO 285
<211> LENGTH: 41
<212> TYPE: DNA
<213> ORGANISM: Artificial Sequence
<220> FEATURE:
<223> OTHER INFORMATION: Primer to selectively mutate cysteine residue

<400> SEQUENCE: 285
ctcgcacatg atcttcaggc actctgcatc agggatcatg g 41

<210> SEQ ID NO 286
<211> LENGTH: 43
<212> TYPE: DNA
<213> ORGANISM: Artificial Sequence
<220> FEATURE:
<223> OTHER INFORMATION: Primer to selectively mutate cysteine residue

<400> SEQUENCE: 286
gcagagtgcc tgaagatcat gtgcgagatc ctgagttcac ttc 43

<210> SEQ ID NO 287
<211> LENGTH: 43
<212> TYPE: DNA
<213> ORGANISM: Artificial Sequence
<220> FEATURE:
<223> OTHER INFORMATION: Primer to selectively mutate cysteine residue

<400> SEQUENCE: 287
gaagtgaact caggatctcg cacatgatct tcaggcactc tgc 43

<210> SEQ ID NO 288

-continued

<211> LENGTH: 45
<212> TYPE: DNA
<213> ORGANISM: Artificial Sequence
<220> FEATURE:
<223> OTHER INFORMATION: Primer to selectively mutate cysteine residue

<400> SEQUENCE: 288
ctagatggga tgtttgctat ctgtggtgtt tctgacagca agttc 45

<210> SEQ ID NO 289
<211> LENGTH: 45
<212> TYPE: DNA
<213> ORGANISM: Artificial Sequence
<220> FEATURE:
<223> OTHER INFORMATION: Primer to selectively mutate cysteine residue

<400> SEQUENCE: 289
gaacttgctg tcagaaacac cacagatagc aaacatccca tctag 45

<210> SEQ ID NO 290
<211> LENGTH: 41
<212> TYPE: DNA
<213> ORGANISM: Artificial Sequence
<220> FEATURE:
<223> OTHER INFORMATION: Primer to selectively mutate cysteine residue

<400> SEQUENCE: 290
cagcaagttc cgtaccatct gctcctcagt agacaagctg g 41

<210> SEQ ID NO 291
<211> LENGTH: 41
<212> TYPE: DNA
<213> ORGANISM: Artificial Sequence
<220> FEATURE:
<223> OTHER INFORMATION: Primer to selectively mutate cysteine residue

<400> SEQUENCE: 291
ccagcttgtc tactgaggag cagatggtac ggaacttgct g 41

<210> SEQ ID NO 292
<211> LENGTH: 37
<212> TYPE: DNA
<213> ORGANISM: Artificial Sequence
<220> FEATURE:
<223> OTHER INFORMATION: Primer to selectively mutate cysteine residue

<400> SEQUENCE: 292
gggcgcaagg tgccatgtgt ggggctcagc attgggg 37

<210> SEQ ID NO 293
<211> LENGTH: 37
<212> TYPE: DNA
<213> ORGANISM: Artificial Sequence
<220> FEATURE:
<223> OTHER INFORMATION: Primer to selectively mutate cysteine residue

<400> SEQUENCE: 293
ccccaatgct gagccccaca catggcacct tgcgccc 37

<210> SEQ ID NO 294
<211> LENGTH: 38
<212> TYPE: DNA
<213> ORGANISM: Artificial Sequence
<220> FEATURE:
<223> OTHER INFORMATION: Primer to selectively mutate cysteine residue

<400> SEQUENCE: 294
ctgaaccagt tacagtactg tgaggaggca ggcatccc 38

<210> SEQ ID NO 295
<211> LENGTH: 38
<212> TYPE: DNA
<213> ORGANISM: Artificial Sequence
<220> FEATURE:
<223> OTHER INFORMATION: Primer to selectively mutate cysteine residue

<400> SEQUENCE: 295
gggatgcctg cctcctcaca gtactgtaac tggttcag 38

<210> SEQ ID NO 296
<211> LENGTH: 39
<212> TYPE: DNA
<213> ORGANISM: Artificial Sequence
<220> FEATURE:
<223> OTHER INFORMATION: Primer to selectively mutate cysteine residue

<400> SEQUENCE: 296
gagaacaggc cagcccctct gcatctgcta gaacccagc 39

<210> SEQ ID NO 297
<211> LENGTH: 39
<212> TYPE: DNA
<213> ORGANISM: Artificial Sequence
<220> FEATURE:
<223> OTHER INFORMATION: Primer to selectively mutate cysteine residue

<400> SEQUENCE: 297
gctgggttct agcagatgca gaggggctgg cctgttctc 39

<210> SEQ ID NO 298
<211> LENGTH: 37
<212> TYPE: DNA
<213> ORGANISM: Artificial Sequence
<220> FEATURE:
<223> OTHER INFORMATION: Primer to selectively mutate cysteine residue

<400> SEQUENCE: 298
ccagcccctc tgcatctgct agaacccagc tttcttg 37

<210> SEQ ID NO 299
<211> LENGTH: 37
<212> TYPE: DNA
<213> ORGANISM: Artificial Sequence
<220> FEATURE:
<223> OTHER INFORMATION: Primer to selectively mutate cysteine residue

<400> SEQUENCE: 299
caagaaagct gggttctagc agatgcagag gggctgg 37

<210> SEQ ID NO 300
<211> LENGTH: 35
<212> TYPE: DNA
<213> ORGANISM: Artificial Sequence
<220> FEATURE:
<223> OTHER INFORMATION: Primer to selectively mutate cysteine residue

<400> SEQUENCE: 300
gaacaggcca gcccctctag aacccagctt tcttg 35

<210> SEQ ID NO 301
<211> LENGTH: 35
<212> TYPE: DNA

<213> ORGANISM: Artificial Sequence
<220> FEATURE:
<223> OTHER INFORMATION: Primer to selectively mutate cysteine residue

<400> SEQUENCE: 301
caagaaagct gggttctaga ggggctggcc tgttc 35

<210> SEQ ID NO 302
<211> LENGTH: 30
<212> TYPE: DNA
<213> ORGANISM: Artificial Sequence
<220> FEATURE:
<223> OTHER INFORMATION: Primer to selectively mutate cysteine residue

<400> SEQUENCE: 302
cccggatgcc gaggctttga aaattatgtg 30

<210> SEQ ID NO 303
<211> LENGTH: 30
<212> TYPE: DNA
<213> ORGANISM: Artificial Sequence
<220> FEATURE:
<223> OTHER INFORMATION: Primer to selectively mutate cysteine residue

<400> SEQUENCE: 303
cacataattt tcaaagcctc ggcatccggg 30

<210> SEQ ID NO 304
<211> LENGTH: 35
<212> TYPE: DNA
<213> ORGANISM: Artificial Sequence
<220> FEATURE:
<223> OTHER INFORMATION: Primer to selectively mutate cysteine residue

<400> SEQUENCE: 304
gatcccggat gccgagagtt tgaaaattat gtgtg 35

<210> SEQ ID NO 305
<211> LENGTH: 35
<212> TYPE: DNA
<213> ORGANISM: Artificial Sequence
<220> FEATURE:
<223> OTHER INFORMATION: Primer to selectively mutate cysteine residue

<400> SEQUENCE: 305
cacacataat tttcaaactc tcggcatccg ggatc 35

<210> SEQ ID NO 306
<211> LENGTH: 35
<212> TYPE: DNA
<213> ORGANISM: Artificial Sequence
<220> FEATURE:
<223> OTHER INFORMATION: Primer to selectively mutate cysteine residue

<400> SEQUENCE: 306
gatcccggat gccgaggttt tgaaaattat gtgtg 35

<210> SEQ ID NO 307
<211> LENGTH: 35
<212> TYPE: DNA
<213> ORGANISM: Artificial Sequence
<220> FEATURE:
<223> OTHER INFORMATION: Primer to selectively mutate cysteine residue

<400> SEQUENCE: 307
cacacataat tttcaaaacc tcggcatccg ggatc 35

-continued

<210> SEQ ID NO 308
<211> LENGTH: 35
<212> TYPE: DNA
<213> ORGANISM: Artificial Sequence
<220> FEATURE:
<223> OTHER INFORMATION: Primer to selectively mutate cysteine residue

<400> SEQUENCE: 308
cgcgaattct atcaggctga ttttgatatt gccgg 35

<210> SEQ ID NO 309
<211> LENGTH: 35
<212> TYPE: DNA
<213> ORGANISM: Artificial Sequence
<220> FEATURE:
<223> OTHER INFORMATION: Primer to selectively mutate cysteine residue

<400> SEQUENCE: 309
ccggcaatat caaaatcagc ctgatagaat tcgcg 35

<210> SEQ ID NO 310
<211> LENGTH: 34
<212> TYPE: DNA
<213> ORGANISM: Artificial Sequence
<220> FEATURE:
<223> OTHER INFORMATION: Primer to selectively mutate cysteine residue

<400> SEQUENCE: 310
cgcgaattct atcaggttga ttttgatatt gccg 34

<210> SEQ ID NO 311
<211> LENGTH: 34
<212> TYPE: DNA
<213> ORGANISM: Artificial Sequence
<220> FEATURE:
<223> OTHER INFORMATION: Primer to selectively mutate cysteine residue

<400> SEQUENCE: 311
cggcaatatc aaaatcaacc tgatagaatt cgcg 34

<210> SEQ ID NO 312
<211> LENGTH: 33
<212> TYPE: DNA
<213> ORGANISM: Artificial Sequence
<220> FEATURE:
<223> OTHER INFORMATION: Primer to selectively mutate cysteine residue

<400> SEQUENCE: 312
ggtatgtttg ctatttccgg tgtttctgat tcc 33

<210> SEQ ID NO 313
<211> LENGTH: 33
<212> TYPE: DNA
<213> ORGANISM: Artificial Sequence
<220> FEATURE:
<223> OTHER INFORMATION: Primer to selectively mutate cysteine residue

<400> SEQUENCE: 313
ggaatcagaa acaccggaaa tagcaaacat acc 33

<210> SEQ ID NO 314
<211> LENGTH: 39
<212> TYPE: DNA
<213> ORGANISM: Artificial Sequence
<220> FEATURE:

<223> OTHER INFORMATION: Primer to selectively mutate cysteine residue

<400> SEQUENCE: 314
ccaaattccg tacaatctcc tcaagcgtgg acaaattgg 39

<210> SEQ ID NO 315
<211> LENGTH: 39
<212> TYPE: DNA
<213> ORGANISM: Artificial Sequence
<220> FEATURE:
<223> OTHER INFORMATION: Primer to selectively mutate cysteine residue

<400> SEQUENCE: 315
ccaatttgtc cacgcttgag gagattgtac ggaatttgg 39

<210> SEQ ID NO 316
<211> LENGTH: 30
<212> TYPE: DNA
<213> ORGANISM: Artificial Sequence
<220> FEATURE:
<223> OTHER INFORMATION: Primer to selectively mutate cysteine residue

<400> SEQUENCE: 316
cccggatgcc gaggctttga aaattatgtg 30

<210> SEQ ID NO 317
<211> LENGTH: 30
<212> TYPE: DNA
<213> ORGANISM: Artificial Sequence
<220> FEATURE:
<223> OTHER INFORMATION: Primer to selectively mutate cysteine residue

<400> SEQUENCE: 317
cacataattt tcaaagcctc ggcatccggg 30

<210> SEQ ID NO 318
<211> LENGTH: 41
<212> TYPE: DNA
<213> ORGANISM: Artificial Sequence
<220> FEATURE:
<223> OTHER INFORMATION: Primer for tag free HRS polypeptide

<400> SEQUENCE: 318
cgccgcaccg gtcaaccgtt acaccaccac caccaccact g 41

<210> SEQ ID NO 319
<211> LENGTH: 41
<212> TYPE: DNA
<213> ORGANISM: Artificial Sequence
<220> FEATURE:
<223> OTHER INFORMATION: Primer for tag free HRS polypeptide

<400> SEQUENCE: 319
cagtggtggt ggtggtggtg taacggttga ccggtgcggc g 41

<210> SEQ ID NO 320
<211> LENGTH: 39
<212> TYPE: DNA
<213> ORGANISM: Artificial Sequence
<220> FEATURE:
<223> OTHER INFORMATION: Primer for tag free HRS polypeptide

<400> SEQUENCE: 320
cgccgcaccg gtcaaccgtt atgagatccg gctgctaac 39

<210> SEQ ID NO 321
<211> LENGTH: 39
<212> TYPE: DNA
<213> ORGANISM: Artificial Sequence
<220> FEATURE:
<223> OTHER INFORMATION: Primer for tag free HRS polypeptide

<400> SEQUENCE: 321
gttagcagcc ggatctcata acggttgacc ggtgcggcg 39

<210> SEQ ID NO 322
<211> LENGTH: 38
<212> TYPE: PRT
<213> ORGANISM: Artificial Sequence
<220> FEATURE:
<223> OTHER INFORMATION: HRS WHEP consensus sequence
<220> FEATURE:
<221> NAME/KEY: MISC_FEATURE
<222> LOCATION: (2)..(6)
<223> OTHER INFORMATION: Xaa = Any Amino Acid
<220> FEATURE:
<221> NAME/KEY: MISC_FEATURE
<222> LOCATION: (7)..(8)
<223> OTHER INFORMATION: Xaa = Any Amino Acid or absent
<220> FEATURE:
<221> NAME/KEY: MISC_FEATURE
<222> LOCATION: (11)..(12)
<223> OTHER INFORMATION: Xaa = Any Amino Acid
<220> FEATURE:
<221> NAME/KEY: MISC_FEATURE
<222> LOCATION: (15)..(15)
<223> OTHER INFORMATION: Xaa = Any Amino Acid
<220> FEATURE:
<221> NAME/KEY: MISC_FEATURE
<222> LOCATION: (18)..(19)
<223> OTHER INFORMATION: Xaa = Any Amino Acid
<220> FEATURE:
<221> NAME/KEY: MISC_FEATURE
<222> LOCATION: (22)..(28)
<223> OTHER INFORMATION: Xaa = Any Amino Acid
<220> FEATURE:
<221> NAME/KEY: MISC_FEATURE
<222> LOCATION: (29)..(30)
<223> OTHER INFORMATION: Xaa = Any Amino Acid or Absent
<220> FEATURE:
<221> NAME/KEY: MISC_FEATURE
<222> LOCATION: (32)..(33)
<223> OTHER INFORMATION: Xaa = Any Amino Acid
<220> FEATURE:
<221> NAME/KEY: MISC_FEATURE
<222> LOCATION: (36)..(36)
<223> OTHER INFORMATION: Xaa = Any Amino Acid

<400> SEQUENCE: 322

```
Leu Xaa Xaa Xaa Xaa Xaa Xaa Xaa Gln Gly Xaa Xaa Val Arg Xaa Leu
1               5                   10                  15

Lys Xaa Xaa Lys Ala Xaa Xaa Xaa Xaa Xaa Xaa Xaa Xaa Xaa Val Xaa
            20                  25                  30

Xaa Leu Leu Xaa Leu Lys
        35
```

<210> SEQ ID NO 323
<211> LENGTH: 60
<212> TYPE: DNA
<213> ORGANISM: Artificial Sequence
<220> FEATURE:
<223> OTHER INFORMATION: Primer used to create the N-terminally fused
HRS(1-60) Fc fusion protein

<400> SEQUENCE: 323
taattttgtt taactttaag aaggagatat acatatgtct gacaaaactc acacatgccc 60

<210> SEQ ID NO 324
<211> LENGTH: 43
<212> TYPE: DNA
<213> ORGANISM: Artificial Sequence
<220> FEATURE:
<223> OTHER INFORMATION: Primer used to create the N-terminally fused
HRS(1-60) Fc fusion protein

<400> SEQUENCE: 324
agcctctccc tgtctccggg taaagcagag cgtgcggcgc tgg 43

<210> SEQ ID NO 325
<211> LENGTH: 43
<212> TYPE: DNA
<213> ORGANISM: Artificial Sequence
<220> FEATURE:
<223> OTHER INFORMATION: Primer used to create the N-terminally fused
HRS(1-60) Fc fusion protein

<400> SEQUENCE: 325
ccagcgccgc acgctctgct ttacccggag acagggagag gct 43

<210> SEQ ID NO 326
<211> LENGTH: 57
<212> TYPE: DNA
<213> ORGANISM: Artificial Sequence
<220> FEATURE:
<223> OTHER INFORMATION: Primer used to create the N-terminally fused
HRS(1-60) Fc fusion protein

<400> SEQUENCE: 326
ttttgtttaa ctttaagaag gagatataca tatgtctgac aaaactcaca catgccc 57

<210> SEQ ID NO 327
<211> LENGTH: 37
<212> TYPE: DNA
<213> ORGANISM: Artificial Sequence
<220> FEATURE:
<223> OTHER INFORMATION: Primer used to create the N-terminally fused
HRS(1-60) Fc fusion protein

<400> SEQUENCE: 327
ctctccctgt ctccgggtaa agcagagcgt gcggcgc 37

<210> SEQ ID NO 328
<211> LENGTH: 37
<212> TYPE: DNA
<213> ORGANISM: Artificial Sequence
<220> FEATURE:
<223> OTHER INFORMATION: Primer used to create the N-terminally fused
HRS(1-60) Fc fusion protein

<400> SEQUENCE: 328
gcgccgcacg ctctgcttta cccggagaca gggagag 37

<210> SEQ ID NO 329
<211> LENGTH: 58
<212> TYPE: DNA
<213> ORGANISM: Artificial Sequence
<220> FEATURE:
<223> OTHER INFORMATION: Primer used to create the C-terminally fused
HRS(1-60) Fc fusion protein

<400> SEQUENCE: 329
caaacagaaa tttgtgctca aaacccccaa gtctgacaaa actcacacat gcccaccg 58

```
<210> SEQ ID NO 330
<211> LENGTH: 49
<212> TYPE: DNA
<213> ORGANISM: Artificial Sequence
<220> FEATURE:
<223> OTHER INFORMATION: Primer used to create the C-terminally fused
      HRS(1-60) Fc fusion protein

<400> SEQUENCE: 330

agcctctccc tgtctccggg taaatgagat ccggctgcta acaaagccc                    49

<210> SEQ ID NO 331
<211> LENGTH: 49
<212> TYPE: DNA
<213> ORGANISM: Artificial Sequence
<220> FEATURE:
<223> OTHER INFORMATION: Primer used to create the C-terminally fused
      HRS(1-60) Fc fusion protein

<400> SEQUENCE: 331

gggctttgtt agcagccgga tctcatttac ccggagacag ggagaggct                    49

<210> SEQ ID NO 332
<211> LENGTH: 50
<212> TYPE: DNA
<213> ORGANISM: Artificial Sequence
<220> FEATURE:
<223> OTHER INFORMATION: Primer used to create the C-terminally fused
      HRS(1-60) Fc fusion protein

<400> SEQUENCE: 332

cagaaatttg tgctcaaaac ccccaagtct gacaaaactc acacatgccc                   50

<210> SEQ ID NO 333
<211> LENGTH: 43
<212> TYPE: DNA
<213> ORGANISM: Artificial Sequence
<220> FEATURE:
<223> OTHER INFORMATION: Primer used to create the C-terminally fused
      HRS(1-60) Fc fusion protein

<400> SEQUENCE: 333

ctctccctgt ctccgggtaa atgagatccg gctgctaaca aag                          43

<210> SEQ ID NO 334
<211> LENGTH: 43
<212> TYPE: DNA
<213> ORGANISM: Artificial Sequence
<220> FEATURE:
<223> OTHER INFORMATION: Primer used to create the C-terminally fused
      HRS(1-60) Fc fusion protein

<400> SEQUENCE: 334

ctttgttagc agccggatct catttacccg gagacaggga gag                          43

<210> SEQ ID NO 335
<211> LENGTH: 867
<212> TYPE: DNA
<213> ORGANISM: Artificial Sequence
<220> FEATURE:
<223> OTHER INFORMATION: DNA sequence of FC-HRS(1-60) (N-terminal Fc
      fusion)

<400> SEQUENCE: 335

atgtctgaca aaactcacac atgcccaccg tgcccagcac ctgaactcct ggggggaccg        60

tcagtcttcc tcttcccccc aaaacccaag gacaccctca tgatctcccg gacccctgag      120
```

-continued

```
gtcacatgcg tggtggtgga cgtgagccac gaagaccctg aggtcaagtt caactggtac    180

gtggacggcg tggaggtgca taatgccaag acaaagccgc gggaggagca gtacaacagc    240

acgtaccgtg tggtcagcgt cctcaccgtc ctgcaccagg actggctgaa tggcaaggag    300

tacaagtgca aggtctccaa caaagccctc ccagccccca tcgagaaaac catctccaaa    360

gccaaagggc agccccgaga accacaggtg tacaccctgc ccccatcccg ggaggagatg    420

accaagaacc aggtcagcct gacctgcctg gtcaaaggct tctatcccag cgacatcgcc    480

gtggagtggg agagcaatgg gcagccggag aacaactaca agaccacgcc tcccgtgctg    540

gactccgacg gctccttctt cctctacagc aagctcaccg tggacaagag caggtggcag    600

caggggaacg tcttctcatg ctccgtgatg cacgaggctc tgcacaacca ctacacgcag    660

aagagcctct ccctgtctcc gggtaaagca gagcgtgcgg cgctggagga gctggtgaaa    720

cttcagggag agcgcgtgcg aggcctcaag cagcagaagg ccagcgccga gctgatcgag    780

gaggaggtgg cgaaactcct gaaactgaag gcacagctgg gtcctgatga aagcaaacag    840

aaatttgtgc tcaaaacccc caagtga                                        867
```

<210> SEQ ID NO 336
<211> LENGTH: 866
<212> TYPE: DNA
<213> ORGANISM: Artificial Sequence
<220> FEATURE:
<223> OTHER INFORMATION: DNA sequence of HRS(1-60)-Fc (C-terminal Fc fusion)

<400> SEQUENCE: 336

```
atggcagagc gtgcggcgct ggaggagctg gtgaaacttc agggagagcg cgtgcgaggc     60

ctcaagcagc agaaggccag cgccgagctg atcgaggagg aggtggcgaa actcctgaaa    120

ctgaaggcac agctgggtcc tgatgaagca aacagaaatt tgtgctcaaa acccccaagt    180

ctgacaaaac tcacacatgc ccaccgtgcc cagcacctga actcctgggg ggaccgtcag    240

tcttcctctt ccccccaaaa cccaaggaca ccctcatgat ctcccggacc cctgaggtca    300

catgcgtggt ggtggacgtg agccacgaag accctgaggt caagttcaac tggtacgtgg    360

acggcgtgga ggtgcataat gccaagacaa agccgcggga ggagcagtac aacagcacgt    420

accgtgtggt cagcgtcctc accgtcctgc accaggactg gctgaatggc aaggagtaca    480

agtgcaaggt ctccaacaaa gccctcccag cccccatcga gaaaaccatc tccaaagcca    540

aagggcagcc ccgagaacca caggtgtaca ccctgccccc atcccgggag gagatgacca    600

agaaccaggt cagcctgacc tgcctggtca aaggcttcta tcccagcgac atcgccgtgg    660

agtgggagag caatgggcag ccggagaaca actacaagac cacgcctccc gtgctggact    720

ccgacggctc cttcttcctc tacagcaagc tcaccgtgga caagagcagg tggcagcagg    780

ggaacgtctt ctcatgctcc gtgatgcacg aggctctgca caaccactac acgcagaaga    840

gcctctccct gtctccgggt aaatga                                         866
```

<210> SEQ ID NO 337
<211> LENGTH: 288
<212> TYPE: PRT
<213> ORGANISM: Artificial Sequence
<220> FEATURE:
<223> OTHER INFORMATION: Protein sequence of Fc-HRS(1-60) (N-terminal Fc fusion)

<400> SEQUENCE: 337

Met Ser Asp Lys Thr His Thr Cys Pro Pro Cys Pro Ala Pro Glu Leu

-continued

```
1               5                   10                  15

Leu Gly Gly Pro Ser Val Phe Leu Phe Pro Pro Lys Pro Lys Asp Thr
            20                  25                  30

Leu Met Ile Ser Arg Thr Pro Glu Val Thr Cys Val Val Val Asp Val
        35                  40                  45

Ser His Glu Asp Pro Glu Val Lys Phe Asn Trp Tyr Val Asp Gly Val
    50                  55                  60

Glu Val His Asn Ala Lys Thr Lys Pro Arg Glu Glu Gln Tyr Asn Ser
65                  70                  75                  80

Thr Tyr Arg Val Val Ser Val Leu Thr Val Leu His Gln Asp Trp Leu
                85                  90                  95

Asn Gly Lys Glu Tyr Lys Cys Lys Val Ser Asn Lys Ala Leu Pro Ala
            100                 105                 110

Pro Ile Glu Lys Thr Ile Ser Lys Ala Lys Gly Gln Pro Arg Glu Pro
        115                 120                 125

Gln Val Tyr Thr Leu Pro Pro Ser Arg Glu Glu Met Thr Lys Asn Gln
    130                 135                 140

Val Ser Leu Thr Cys Leu Val Lys Gly Phe Tyr Pro Ser Asp Ile Ala
145                 150                 155                 160

Val Glu Trp Glu Ser Asn Gly Gln Pro Glu Asn Asn Tyr Lys Thr Thr
                165                 170                 175

Pro Pro Val Leu Asp Ser Asp Gly Ser Phe Phe Leu Tyr Ser Lys Leu
            180                 185                 190

Thr Val Asp Lys Ser Arg Trp Gln Gln Gly Asn Val Phe Ser Cys Ser
        195                 200                 205

Val Met His Glu Ala Leu His Asn His Tyr Thr Gln Lys Ser Leu Ser
    210                 215                 220

Leu Ser Pro Gly Lys Ala Glu Arg Ala Ala Leu Glu Glu Leu Val Lys
225                 230                 235                 240

Leu Gln Gly Glu Arg Val Arg Gly Leu Lys Gln Gln Lys Ala Ser Ala
                245                 250                 255

Glu Leu Ile Glu Glu Glu Val Ala Lys Leu Leu Lys Leu Lys Ala Gln
            260                 265                 270

Leu Gly Pro Asp Glu Ser Lys Gln Lys Phe Val Leu Lys Thr Pro Lys
        275                 280                 285


<210> SEQ ID NO 338
<211> LENGTH: 288
<212> TYPE: PRT
<213> ORGANISM: Artificial Sequence
<220> FEATURE:
<223> OTHER INFORMATION: Protein sequence of HRS(1-60)-Fc (C-terminal Fc
      fusion)

<400> SEQUENCE: 338

Met Ala Glu Arg Ala Ala Leu Glu Glu Leu Val Lys Leu Gln Gly Glu
1               5                   10                  15

Arg Val Arg Gly Leu Lys Gln Gln Lys Ala Ser Ala Glu Leu Ile Glu
            20                  25                  30

Glu Glu Val Ala Lys Leu Leu Lys Leu Lys Ala Gln Leu Gly Pro Asp
        35                  40                  45

Glu Ser Lys Gln Lys Phe Val Leu Lys Thr Pro Lys Ser Asp Lys Thr
    50                  55                  60

His Thr Cys Pro Pro Cys Pro Ala Pro Glu Leu Leu Gly Gly Pro Ser
65                  70                  75                  80
```

```
Val Phe Leu Phe Pro Pro Lys Pro Lys Asp Thr Leu Met Ile Ser Arg
                85                  90                  95

Thr Pro Glu Val Thr Cys Val Val Val Asp Val Ser His Glu Asp Pro
            100                 105                 110

Glu Val Lys Phe Asn Trp Tyr Val Asp Gly Val Glu Val His Asn Ala
        115                 120                 125

Lys Thr Lys Pro Arg Glu Glu Gln Tyr Asn Ser Thr Tyr Arg Val Val
    130                 135                 140

Ser Val Leu Thr Val Leu His Gln Asp Trp Leu Asn Gly Lys Glu Tyr
145                 150                 155                 160

Lys Cys Lys Val Ser Asn Lys Ala Leu Pro Ala Pro Ile Glu Lys Thr
                165                 170                 175

Ile Ser Lys Ala Lys Gly Gln Pro Arg Glu Pro Gln Val Tyr Thr Leu
            180                 185                 190

Pro Pro Ser Arg Glu Glu Met Thr Lys Asn Gln Val Ser Leu Thr Cys
        195                 200                 205

Leu Val Lys Gly Phe Tyr Pro Ser Asp Ile Ala Val Glu Trp Glu Ser
    210                 215                 220

Asn Gly Gln Pro Glu Asn Asn Tyr Lys Thr Thr Pro Pro Val Leu Asp
225                 230                 235                 240

Ser Asp Gly Ser Phe Phe Leu Tyr Ser Lys Leu Thr Val Asp Lys Ser
                245                 250                 255

Arg Trp Gln Gln Gly Asn Val Phe Ser Cys Ser Val Met His Glu Ala
            260                 265                 270

Leu His Asn His Tyr Thr Gln Lys Ser Leu Ser Leu Ser Pro Gly Lys
        275                 280                 285


<210> SEQ ID NO 339
<211> LENGTH: 229
<212> TYPE: PRT
<213> ORGANISM: Homo sapiens

<400> SEQUENCE: 339

Met Ser Asp Lys Thr His Thr Cys Pro Pro Cys Pro Ala Pro Glu Leu
1               5                   10                  15

Leu Gly Gly Pro Ser Val Phe Leu Phe Pro Pro Lys Pro Lys Asp Thr
            20                  25                  30

Leu Met Ile Ser Arg Thr Pro Glu Val Thr Cys Val Val Val Asp Val
        35                  40                  45

Ser His Glu Asp Pro Glu Val Lys Phe Asn Trp Tyr Val Asp Gly Val
    50                  55                  60

Glu Val His Asn Ala Lys Thr Lys Pro Arg Glu Glu Gln Tyr Asn Ser
65                  70                  75                  80

Thr Tyr Arg Val Val Ser Val Leu Thr Val Leu His Gln Asp Trp Leu
                85                  90                  95

Asn Gly Lys Glu Tyr Lys Cys Lys Val Ser Asn Lys Ala Leu Pro Ala
            100                 105                 110

Pro Ile Glu Lys Thr Ile Ser Lys Ala Lys Gly Gln Pro Arg Glu Pro
        115                 120                 125

Gln Val Tyr Thr Leu Pro Pro Ser Arg Glu Glu Met Thr Lys Asn Gln
    130                 135                 140

Val Ser Leu Thr Cys Leu Val Lys Gly Phe Tyr Pro Ser Asp Ile Ala
145                 150                 155                 160

Val Glu Trp Glu Ser Asn Gly Gln Pro Glu Asn Asn Tyr Lys Thr Thr
                165                 170                 175
```

Pro Pro Val Leu Asp Ser Asp Gly Ser Phe Phe Leu Tyr Ser Lys Leu
180 185 190

Thr Val Asp Lys Ser Arg Trp Gln Gln Gly Asn Val Phe Ser Cys Ser
195 200 205

Val Met His Glu Ala Leu His Asn His Tyr Thr Gln Lys Ser Leu Ser
210 215 220

Leu Ser Pro Gly Lys
225

<210> SEQ ID NO 340
<211> LENGTH: 228
<212> TYPE: PRT
<213> ORGANISM: Homo sapiens

<400> SEQUENCE: 340

Ser Asp Lys Thr His Thr Cys Pro Pro Cys Pro Ala Pro Glu Leu Leu
1 5 10 15

Gly Gly Pro Ser Val Phe Leu Phe Pro Pro Lys Pro Lys Asp Thr Leu
20 25 30

Met Ile Ser Arg Thr Pro Glu Val Thr Cys Val Val Val Asp Val Ser
35 40 45

His Glu Asp Pro Glu Val Lys Phe Asn Trp Tyr Val Asp Gly Val Glu
50 55 60

Val His Asn Ala Lys Thr Lys Pro Arg Glu Glu Gln Tyr Asn Ser Thr
65 70 75 80

Tyr Arg Val Val Ser Val Leu Thr Val Leu His Gln Asp Trp Leu Asn
85 90 95

Gly Lys Glu Tyr Lys Cys Lys Val Ser Asn Lys Ala Leu Pro Ala Pro
100 105 110

Ile Glu Lys Thr Ile Ser Lys Ala Lys Gly Gln Pro Arg Glu Pro Gln
115 120 125

Val Tyr Thr Leu Pro Pro Ser Arg Glu Glu Met Thr Lys Asn Gln Val
130 135 140

Ser Leu Thr Cys Leu Val Lys Gly Phe Tyr Pro Ser Asp Ile Ala Val
145 150 155 160

Glu Trp Glu Ser Asn Gly Gln Pro Glu Asn Asn Tyr Lys Thr Thr Pro
165 170 175

Pro Val Leu Asp Ser Asp Gly Ser Phe Phe Leu Tyr Ser Lys Leu Thr
180 185 190

Val Asp Lys Ser Arg Trp Gln Gln Gly Asn Val Phe Ser Cys Ser Val
195 200 205

Met His Glu Ala Leu His Asn His Tyr Thr Gln Lys Ser Leu Ser Leu
210 215 220

Ser Pro Gly Lys
225

<210> SEQ ID NO 341
<211> LENGTH: 11
<212> TYPE: PRT
<213> ORGANISM: Artificial Sequence
<220> FEATURE:
<223> OTHER INFORMATION: modified human IgG1 hinge region

<400> SEQUENCE: 341

Ser Asp Lys Thr His Thr Cys Pro Pro Cys Pro
1 5 10

<210> SEQ ID NO 342
<211> LENGTH: 229
<212> TYPE: PRT
<213> ORGANISM: Homo sapiens

<400> SEQUENCE: 342

```
Met Ser Asp Lys Thr His Thr Cys Pro Pro Cys Pro Ala Pro Glu Leu
1               5                   10                  15

Leu Gly Gly Pro Ser Val Phe Leu Phe Pro Pro Lys Pro Lys Asp Thr
            20                  25                  30

Leu Met Ile Ser Arg Thr Pro Glu Val Thr Cys Val Val Val Asp Val
        35                  40                  45

Ser His Glu Asp Pro Glu Val Lys Phe Asn Trp Tyr Val Asp Gly Val
    50                  55                  60

Glu Val His Asn Ala Lys Thr Lys Pro Arg Glu Glu Gln Tyr Asn Ser
65                  70                  75                  80

Thr Tyr Arg Val Val Ser Val Leu Thr Val Leu His Gln Asp Trp Leu
                85                  90                  95

Asn Gly Lys Glu Tyr Lys Cys Lys Val Ser Asn Lys Ala Leu Pro Ala
            100                 105                 110

Pro Ile Glu Lys Thr Ile Ser Lys Ala Lys Gly Gln Pro Arg Glu Pro
        115                 120                 125

Gln Val Tyr Thr Leu Pro Pro Ser Arg Glu Glu Met Thr Lys Asn Gln
    130                 135                 140

Val Ser Leu Thr Cys Leu Val Lys Gly Phe Tyr Pro Ser Asp Ile Ala
145                 150                 155                 160

Val Glu Trp Glu Ser Asn Gly Gln Pro Glu Asn Asn Tyr Lys Thr Thr
                165                 170                 175

Pro Pro Val Leu Asp Ser Asp Gly Ser Phe Phe Leu Tyr Ser Lys Leu
            180                 185                 190

Thr Val Asp Lys Ser Arg Trp Gln Gln Gly Asn Val Phe Ser Cys Ser
        195                 200                 205

Val Met His Glu Ala Leu His Asn His Tyr Thr Gln Lys Ser Leu Ser
    210                 215                 220

Leu Ser Pro Gly Lys
225
```

<210> SEQ ID NO 343
<211> LENGTH: 34
<212> TYPE: DNA
<213> ORGANISM: Artificial Sequence
<220> FEATURE:
<223> OTHER INFORMATION: primer to amplify Fc-HRS (2-60)

<400> SEQUENCE: 343

```
gatatacata tgtctgacaa aactcacaca tgcc                                 34
```

<210> SEQ ID NO 344
<211> LENGTH: 26
<212> TYPE: DNA
<213> ORGANISM: Artificial Sequence
<220> FEATURE:
<223> OTHER INFORMATION: primer to amplify Fc-HRS (2-60)

<400> SEQUENCE: 344

```
gatcctcgag tcacttgggg gttttg                                          26
```

<210> SEQ ID NO 345

<211> LENGTH: 25
<212> TYPE: DNA
<213> ORGANISM: Artificial Sequence
<220> FEATURE:
<223> OTHER INFORMATION: primer to amplify HRS (1-60)-Fc

<400> SEQUENCE: 345
gatatacata tggcagagcg tgcgg 25

<210> SEQ ID NO 346
<211> LENGTH: 26
<212> TYPE: DNA
<213> ORGANISM: Artificial Sequence
<220> FEATURE:
<223> OTHER INFORMATION: primer to amplify HRS (1-60)-Fc

<400> SEQUENCE: 346
gatcctcgag tcatttaccc ggagac 26

<210> SEQ ID NO 347
<211> LENGTH: 867
<212> TYPE: DNA
<213> ORGANISM: Artificial Sequence
<220> FEATURE:
<223> OTHER INFORMATION: DNA sequence of Fc-HRS(2-60)

<400> SEQUENCE: 347
atgtctgaca aaactcacac atgcccaccg tgcccagcac ctgaactcct ggggggaccg 60
tcagtcttcc tcttcccccc aaaacccaag gacaccctca tgatctcccg gacccctgag 120
gtcacatgcg tggtggtgga cgtgagccac gaagaccctg aggtcaagtt caactggtac 180
gtggacggcg tggaggtgca taatgccaag acaaagccgc gggaggagca gtacaacagc 240
acgtaccgtg tggtcagcgt cctcaccgtc ctgcaccagg actggctgaa tggcaaggag 300
tacaagtgca aggtctccaa caaagccctc ccagccccca tcgagaaaac catctccaaa 360
gccaaagggc agccccgaga accacaggtg tacaccctgc ccccatcccg ggaggagatg 420
accaagaacc aggtcagcct gacctgcctg gtcaaaggct tctatcccag cgacatcgcc 480
gtggagtggg agagcaatgg gcagccggag aacaactaca agaccacgcc tcccgtgctg 540
gactccgacg gctccttctt cctctacagc aagctcaccg tggacaagag caggtggcag 600
caggggaacg tcttctcatg ctccgtgatg cacgaggctc tgcacaacca ctacacgcag 660
aagagcctct ccctgtctcc gggtaaagca gagcgtgcgg cgctggagga gctggtgaaa 720
cttcagggag agcgcgtgcg aggcctcaag cagcagaagg ccagcgccga gctgatcgag 780
gaggaggtgg cgaaactcct gaaactgaag gcacagctgg gtcctgatga aagcaaacag 840
aaatttgtgc tcaaaacccc caagtga 867

<210> SEQ ID NO 348
<211> LENGTH: 867
<212> TYPE: DNA
<213> ORGANISM: Artificial Sequence
<220> FEATURE:
<223> OTHER INFORMATION: DNA sequence of HRS(1-60)-Fc (C-terminal Fc
fusion)

<400> SEQUENCE: 348
atggcagagc gtgcggcgct ggaggagctg gtgaaacttc agggagagcg cgtgcgaggc 60
ctcaagcagc agaaggccag cgccgagctg atcgaggagg aggtggcgaa actcctgaaa 120
ctgaaggcac agctgggtcc tgatgaaagc aaacagaaat ttgtgctcaa aacccccaag 180

```
tctgacaaaa ctcacacatg cccaccgtgc ccagcacctg aactcctggg gggaccgtca    240

gtcttcctct tccccccaaa acccaaggac accctcatga tctcccggac ccctgaggtc    300

acatgcgtgg tggtggacgt gagccacgaa gaccctgagg tcaagttcaa ctggtacgtg    360

gacggcgtgg aggtgcataa tgccaagaca aagccgcggg aggagcagta caacagcacg    420

taccgtgtgg tcagcgtcct caccgtcctg caccaggact ggctgaatgg caaggagtac    480

aagtgcaagg tctccaacaa agccctccca gcccccatcg agaaaaccat ctccaaagcc    540

aaagggcagc cccgagaacc acaggtgtac accctgcccc catcccggga ggagatgacc    600

aagaaccagg tcagcctgac ctgcctggtc aaaggcttct atcccagcga catcgccgtg    660

gagtgggaga gcaatgggca gccggagaac aactacaaga ccacgcctcc cgtgctggac    720

tccgacggct ccttcttcct ctacagcaag ctcaccgtgg acaagagcag gtggcagcag    780

gggaacgtct tctcatgctc cgtgatgcac gaggctctgc acaaccacta cacgcagaag    840

agcctctccc tgtctccggg taaatga                                        867
```

<210> SEQ ID NO 349
<211> LENGTH: 288
<212> TYPE: PRT
<213> ORGANISM: Artificial Sequence
<220> FEATURE:
<223> OTHER INFORMATION: Protein sequence of Fc-HRS(2-60) (N-terminal Fc fusion)

<400> SEQUENCE: 349

```
Met Ser Asp Lys Thr His Thr Cys Pro Pro Cys Pro Ala Pro Glu Leu
1               5                   10                  15

Leu Gly Gly Pro Ser Val Phe Leu Phe Pro Pro Lys Pro Lys Asp Thr
            20                  25                  30

Leu Met Ile Ser Arg Thr Pro Glu Val Thr Cys Val Val Val Asp Val
        35                  40                  45

Ser His Glu Asp Pro Glu Val Lys Phe Asn Trp Tyr Val Asp Gly Val
    50                  55                  60

Glu Val His Asn Ala Lys Thr Lys Pro Arg Glu Glu Gln Tyr Asn Ser
65                  70                  75                  80

Thr Tyr Arg Val Val Ser Val Leu Thr Val Leu His Gln Asp Trp Leu
                85                  90                  95

Asn Gly Lys Glu Tyr Lys Cys Lys Val Ser Asn Lys Ala Leu Pro Ala
            100                 105                 110

Pro Ile Glu Lys Thr Ile Ser Lys Ala Lys Gly Gln Pro Arg Glu Pro
        115                 120                 125

Gln Val Tyr Thr Leu Pro Pro Ser Arg Glu Glu Met Thr Lys Asn Gln
    130                 135                 140

Val Ser Leu Thr Cys Leu Val Lys Gly Phe Tyr Pro Ser Asp Ile Ala
145                 150                 155                 160

Val Glu Trp Glu Ser Asn Gly Gln Pro Glu Asn Asn Tyr Lys Thr Thr
                165                 170                 175

Pro Pro Val Leu Asp Ser Asp Gly Ser Phe Phe Leu Tyr Ser Lys Leu
            180                 185                 190

Thr Val Asp Lys Ser Arg Trp Gln Gln Gly Asn Val Phe Ser Cys Ser
        195                 200                 205

Val Met His Glu Ala Leu His Asn His Tyr Thr Gln Lys Ser Leu Ser
    210                 215                 220

Leu Ser Pro Gly Lys Ala Glu Arg Ala Ala Leu Glu Glu Leu Val Lys
225                 230                 235                 240
```

```
Leu Gln Gly Glu Arg Val Arg Gly Leu Lys Gln Gln Lys Ala Ser Ala
                245                 250                 255

Glu Leu Ile Glu Glu Glu Val Ala Lys Leu Leu Lys Leu Lys Ala Gln
            260                 265                 270

Leu Gly Pro Asp Glu Ser Lys Gln Lys Phe Val Leu Lys Thr Pro Lys
        275                 280                 285


<210> SEQ ID NO 350
<211> LENGTH: 288
<212> TYPE: PRT
<213> ORGANISM: Artificial Sequence
<220> FEATURE:
<223> OTHER INFORMATION: Protein sequence of HRS(1-60)-Fc (C-terminal Fc
      fusion)

<400> SEQUENCE: 350

Met Ala Glu Arg Ala Ala Leu Glu Glu Leu Val Lys Leu Gln Gly Glu
1               5                   10                  15

Arg Val Arg Gly Leu Lys Gln Gln Lys Ala Ser Ala Glu Leu Ile Glu
            20                  25                  30

Glu Glu Val Ala Lys Leu Leu Lys Leu Lys Ala Gln Leu Gly Pro Asp
        35                  40                  45

Glu Ser Lys Gln Lys Phe Val Leu Lys Thr Pro Lys Ser Asp Lys Thr
    50                  55                  60

His Thr Cys Pro Pro Cys Pro Ala Pro Glu Leu Leu Gly Gly Pro Ser
65                  70                  75                  80

Val Phe Leu Phe Pro Pro Lys Pro Lys Asp Thr Leu Met Ile Ser Arg
                85                  90                  95

Thr Pro Glu Val Thr Cys Val Val Val Asp Val Ser His Glu Asp Pro
            100                 105                 110

Glu Val Lys Phe Asn Trp Tyr Val Asp Gly Val Glu Val His Asn Ala
        115                 120                 125

Lys Thr Lys Pro Arg Glu Glu Gln Tyr Asn Ser Thr Tyr Arg Val Val
    130                 135                 140

Ser Val Leu Thr Val Leu His Gln Asp Trp Leu Asn Gly Lys Glu Tyr
145                 150                 155                 160

Lys Cys Lys Val Ser Asn Lys Ala Leu Pro Ala Pro Ile Glu Lys Thr
                165                 170                 175

Ile Ser Lys Ala Lys Gly Gln Pro Arg Glu Pro Gln Val Tyr Thr Leu
            180                 185                 190

Pro Pro Ser Arg Glu Glu Met Thr Lys Asn Gln Val Ser Leu Thr Cys
        195                 200                 205

Leu Val Lys Gly Phe Tyr Pro Ser Asp Ile Ala Val Glu Trp Glu Ser
    210                 215                 220

Asn Gly Gln Pro Glu Asn Asn Tyr Lys Thr Thr Pro Pro Val Leu Asp
225                 230                 235                 240

Ser Asp Gly Ser Phe Phe Leu Tyr Ser Lys Leu Thr Val Asp Lys Ser
                245                 250                 255

Arg Trp Gln Gln Gly Asn Val Phe Ser Cys Ser Val Met His Glu Ala
            260                 265                 270

Leu His Asn His Tyr Thr Gln Lys Ser Leu Ser Leu Ser Pro Gly Lys
        275                 280                 285


<210> SEQ ID NO 351
<211> LENGTH: 39
<212> TYPE: DNA
```

<213> ORGANISM: Artificial Sequence
<220> FEATURE:
<223> OTHER INFORMATION: primer to amplify Fc-HRS polypeptides

<400> SEQUENCE: 351
ggtggcgaaa ctcctgaaat gactcgagga tccggctgc 39

<210> SEQ ID NO 352
<211> LENGTH: 39
<212> TYPE: DNA
<213> ORGANISM: Artificial Sequence
<220> FEATURE:
<223> OTHER INFORMATION: primer to amplify Fc-HRS polypeptides

<400> SEQUENCE: 352
gcagccggat cctcgagtca tttcaggagt ttcgccacc 39

<210> SEQ ID NO 353
<211> LENGTH: 35
<212> TYPE: DNA
<213> ORGANISM: Artificial Sequence
<220> FEATURE:
<223> OTHER INFORMATION: primer to amplify Fc-HRS polypeptides

<400> SEQUENCE: 353
ctgaaggcac agctgtgact cgaggatccg gctgc 35

<210> SEQ ID NO 354
<211> LENGTH: 35
<212> TYPE: DNA
<213> ORGANISM: Artificial Sequence
<220> FEATURE:
<223> OTHER INFORMATION: primer to amplify Fc-HRS polypeptides

<400> SEQUENCE: 354
gcagccggat cctcgagtca cagctgtgcc ttcag 35

<210> SEQ ID NO 355
<211> LENGTH: 36
<212> TYPE: DNA
<213> ORGANISM: Artificial Sequence
<220> FEATURE:
<223> OTHER INFORMATION: primer to amplify Fc-HRS polypeptides

<400> SEQUENCE: 355
gggtcctgat gaaagctgac tcgaggatcc ggctgc 36

<210> SEQ ID NO 356
<211> LENGTH: 36
<212> TYPE: DNA
<213> ORGANISM: Artificial Sequence
<220> FEATURE:
<223> OTHER INFORMATION: primer to amplify Fc-HRS polypeptides

<400> SEQUENCE: 356
gcagccggat cctcgagtca gctttcatca ggaccc 36

<210> SEQ ID NO 357
<211> LENGTH: 37
<212> TYPE: DNA
<213> ORGANISM: Artificial Sequence
<220> FEATURE:
<223> OTHER INFORMATION: primer to amplify Fc-HRS polypeptides

<400> SEQUENCE: 357
gcaaacagaa atttgtgtga ctcgaggatc cggctgc 37

<210> SEQ ID NO 358
<211> LENGTH: 37
<212> TYPE: DNA
<213> ORGANISM: Artificial Sequence
<220> FEATURE:
<223> OTHER INFORMATION: primer to amplify Fc-HRS polypeptides

<400> SEQUENCE: 358
gcagccggat cctcgagtca cacaaatttc tgtttgc 37

<210> SEQ ID NO 359
<211> LENGTH: 50
<212> TYPE: DNA
<213> ORGANISM: Artificial Sequence
<220> FEATURE:
<223> OTHER INFORMATION: primer to amplify Fc-HRS polypeptides

<400> SEQUENCE: 359
gctcaaaacc cccaagggaa cccgtgatta tagttgactc gaggatccgg 50

<210> SEQ ID NO 360
<211> LENGTH: 50
<212> TYPE: DNA
<213> ORGANISM: Artificial Sequence
<220> FEATURE:
<223> OTHER INFORMATION: primer to amplify Fc-HRS polypeptides

<400> SEQUENCE: 360
ccggatcctc gagtcaacta taatcacggg ttcccttggg ggttttgagc 50

<210> SEQ ID NO 361
<211> LENGTH: 40
<212> TYPE: DNA
<213> ORGANISM: Artificial Sequence
<220> FEATURE:
<223> OTHER INFORMATION: primer to amplify HRS-Fc polypeptides

<400> SEQUENCE: 361
ggtggcgaaa ctcctgaaat ctgacaaaac tcacacatgc 40

<210> SEQ ID NO 362
<211> LENGTH: 40
<212> TYPE: DNA
<213> ORGANISM: Artificial Sequence
<220> FEATURE:
<223> OTHER INFORMATION: primer to amplify HRS-Fc polypeptides

<400> SEQUENCE: 362
gcatgtgtga gttttgtcag atttcaggag tttcgccacc 40

<210> SEQ ID NO 363
<211> LENGTH: 42
<212> TYPE: DNA
<213> ORGANISM: Artificial Sequence
<220> FEATURE:
<223> OTHER INFORMATION: primer to amplify HRS-Fc polypeptides

<400> SEQUENCE: 363
ctgaaactga aggcacagct gtctgacaaa actcacacat gc 42

<210> SEQ ID NO 364
<211> LENGTH: 42
<212> TYPE: DNA
<213> ORGANISM: Artificial Sequence
<220> FEATURE:

-continued

<223> OTHER INFORMATION: primer to amplify HRS-Fc polypeptides

<400> SEQUENCE: 364
gcatgtgtga gttttgtcag acagctgtgc cttcagtttc ag 42

<210> SEQ ID NO 365
<211> LENGTH: 40
<212> TYPE: DNA
<213> ORGANISM: Artificial Sequence
<220> FEATURE:
<223> OTHER INFORMATION: primer to amplify HRS-Fc polypeptides

<400> SEQUENCE: 365
gctgggtcct gatgaaagct ctgacaaaac tcacacatgc 40

<210> SEQ ID NO 366
<211> LENGTH: 40
<212> TYPE: DNA
<213> ORGANISM: Artificial Sequence
<220> FEATURE:
<223> OTHER INFORMATION: primer to amplify HRS-Fc polypeptides

<400> SEQUENCE: 366
gcatgtgtga gttttgtcag agctttcatc aggacccagc 40

<210> SEQ ID NO 367
<211> LENGTH: 42
<212> TYPE: DNA
<213> ORGANISM: Artificial Sequence
<220> FEATURE:
<223> OTHER INFORMATION: primer to amplify HRS-Fc polypeptides

<400> SEQUENCE: 367
gaaagcaaac agaaatttgt gtctgacaaa actcacacat gc 42

<210> SEQ ID NO 368
<211> LENGTH: 42
<212> TYPE: DNA
<213> ORGANISM: Artificial Sequence
<220> FEATURE:
<223> OTHER INFORMATION: primer to amplify HRS-Fc polypeptides

<400> SEQUENCE: 368
gcatgtgtga gttttgtcag acacaaattt ctgtttgctt tc 42

<210> SEQ ID NO 369
<211> LENGTH: 49
<212> TYPE: DNA
<213> ORGANISM: Artificial Sequenc
<220> FEATURE:
<223> OTHER INFORMATION: primer to amplify HRS-Fc polypeptides

<400> SEQUENCE: 369
gctcaaaacc cccaagggaa cccgtgatta tagttctgac aaaactcac 49

<210> SEQ ID NO 370
<211> LENGTH: 49
<212> TYPE: DNA
<213> ORGANISM: Artificial Sequence
<220> FEATURE:
<223> OTHER INFORMATION: primer to amplify HRS-Fc polypeptides

<400> SEQUENCE: 370
gtgagttttg tcagaactat aatcacgggt tcccttgggg gttttgagc 49

<210> SEQ ID NO 371
<211> LENGTH: 807
<212> TYPE: DNA
<213> ORGANISM: Artificial Sequence
<220> FEATURE:
<223> OTHER INFORMATION: DNA sequence of Fc-HRS (2-40) (N-terminal Fc fusion)

<400> SEQUENCE: 371
atgtctgaca aaactcacac atgcccaccg tgcccagcac ctgaactcct gggggggaccg 60 tcagtcttcc tcttcccccc aaaacccaag gacaccctca tgatctcccg gacccctgag 120
gtcacatgcg tggtggtgga cgtgagccac gaagaccctg aggtcaagtt caactggtac 180
gtggacggcg tggaggtgca taatgccaag acaaagccgc gggaggagca gtacaacagc 240
acgtaccgtg tggtcagcgt cctcaccgtc ctgcaccagg actggctgaa tggcaaggag 300
tacaagtgca aggtctccaa caaagccctc ccagccccca tcgagaaaac catctccaaa 360
gccaaagggc agccccgaga accacaggtg tacaccctgc ccccatcccg ggaggagatg 420
accaagaacc aggtcagcct gacctgcctg gtcaaaggct tctatcccag cgacatcgcc 480
gtggagtggg agagcaatgg gcagccggag aacaactaca agaccacgcc tcccgtgctg 540
gactccgacg gctccttctt cctctacagc aagctcaccg tggacaagag caggtggcag 600
caggggaacg tcttctcatg ctccgtgatg cacgaggctc tgcacaacca ctacacgcag 660
aagagcctct ccctgtctcc gggtaaagca gagcgtgcgg cgctggagga gctggtgaaa 720
cttcagggag agcgcgtgcg aggcctcaag cagcagaagg ccagcgccga gctgatcgag 780
gaggaggtgg cgaaactcct gaaatga 807

<210> SEQ ID NO 372
<211> LENGTH: 822
<212> TYPE: DNA
<213> ORGANISM: Artificial Sequence
<220> FEATURE:
<223> OTHER INFORMATION: DNA sequence of Fc-HRS (2-45) (N-terminal Fc fusion)

<400> SEQUENCE: 372
atgtctgaca aaactcacac atgcccaccg tgcccagcac ctgaactcct gggggggaccg 60 tcagtcttcc tcttcccccc aaaacccaag gacaccctca tgatctcccg gacccctgag 120
gtcacatgcg tggtggtgga cgtgagccac gaagaccctg aggtcaagtt caactggtac 180
gtggacggcg tggaggtgca taatgccaag acaaagccgc gggaggagca gtacaacagc 240
acgtaccgtg tggtcagcgt cctcaccgtc ctgcaccagg actggctgaa tggcaaggag 300
tacaagtgca aggtctccaa caaagccctc ccagccccca tcgagaaaac catctccaaa 360
gccaaagggc agccccgaga accacaggtg tacaccctgc ccccatcccg ggaggagatg 420
accaagaacc aggtcagcct gacctgcctg gtcaaaggct tctatcccag cgacatcgcc 480
gtggagtggg agagcaatgg gcagccggag aacaactaca agaccacgcc tcccgtgctg 540
gactccgacg gctccttctt cctctacagc aagctcaccg tggacaagag caggtggcag 600
caggggaacg tcttctcatg ctccgtgatg cacgaggctc tgcacaacca ctacacgcag 660
aagagcctct ccctgtctcc gggtaaagca gagcgtgcgg cgctggagga gctggtgaaa 720
cttcagggag agcgcgtgcg aggcctcaag cagcagaagg ccagcgccga gctgatcgag 780
gaggaggtgg cgaaactcct gaaactgaag gcacagctgt ga 822

<210> SEQ ID NO 373

<211> LENGTH: 837
<212> TYPE: DNA
<213> ORGANISM: Artificial Sequence
<220> FEATURE:
<223> OTHER INFORMATION: DNA sequence of Fc-HRS (2-50) (N-terminal Fc fusion)

<400> SEQUENCE: 373
atgtctgaca aaactcacac atgcccaccg tgcccagcac ctgaactcct ggggggaccg 60
tcagtcttcc tcttcccccc aaaacccaag gacaccctca tgatctcccg gacccctgag 120
gtcacatgcg tggtggtgga cgtgagccac gaagaccctg aggtcaagtt caactggtac 180
gtggacggcg tggaggtgca taatgccaag acaaagccgc gggaggagca gtacaacagc 240
acgtaccgtg tggtcagcgt cctcaccgtc ctgcaccagg actggctgaa tggcaaggag 300
tacaagtgca aggtctccaa caaagccctc ccagccccca tcgagaaaac catctccaaa 360
gccaaagggc agccccgaga accacaggtg tacaccctgc ccccatcccg ggaggagatg 420
accaagaacc aggtcagcct gacctgcctg gtcaaaggct tctatcccag cgacatcgcc 480
gtggagtggg agagcaatgg gcagccggag aacaactaca agaccacgcc tcccgtgctg 540
gactccgacg gctccttctt cctctacagc aagctcaccg tggacaagag caggtggcag 600
caggggaacg tcttctcatg ctccgtgatg cacgaggctc tgcacaacca ctacacgcag 660
aagagcctct ccctgtctcc gggtaaagca gagcgtgcgg cgctggagga gctggtgaaa 720
cttcagggag agcgcgtgcg aggcctcaag cagcagaagg ccagcgccga gctgatcgag 780
gaggaggtgg cgaaactcct gaaactgaag gcacagctgg gtcctgatga aagctga 837

<210> SEQ ID NO 374
<211> LENGTH: 852
<212> TYPE: DNA
<213> ORGANISM: Artificial Sequence
<220> FEATURE:
<223> OTHER INFORMATION: DNA sequence of Fc-HRS (2-55) (N-terminal Fc fusion)

<400> SEQUENCE: 374
atgtctgaca aaactcacac atgcccaccg tgcccagcac ctgaactcct ggggggaccg 60
tcagtcttcc tcttcccccc aaaacccaag gacaccctca tgatctcccg gacccctgag 120
gtcacatgcg tggtggtgga cgtgagccac gaagaccctg aggtcaagtt caactggtac 180
gtggacggcg tggaggtgca taatgccaag acaaagccgc gggaggagca gtacaacagc 240
acgtaccgtg tggtcagcgt cctcaccgtc ctgcaccagg actggctgaa tggcaaggag 300
tacaagtgca aggtctccaa caaagccctc ccagccccca tcgagaaaac catctccaaa 360
gccaaagggc agccccgaga accacaggtg tacaccctgc ccccatcccg ggaggagatg 420
accaagaacc aggtcagcct gacctgcctg gtcaaaggct tctatcccag cgacatcgcc 480
gtggagtggg agagcaatgg gcagccggag aacaactaca agaccacgcc tcccgtgctg 540
gactccgacg gctccttctt cctctacagc aagctcaccg tggacaagag caggtggcag 600
caggggaacg tcttctcatg ctccgtgatg cacgaggctc tgcacaacca ctacacgcag 660
aagagcctct ccctgtctcc gggtaaagca gagcgtgcgg cgctggagga gctggtgaaa 720
cttcagggag agcgcgtgcg aggcctcaag cagcagaagg ccagcgccga gctgatcgag 780
gaggaggtgg cgaaactcct gaaactgaag gcacagctgg gtcctgatga aagcaaacag 840
aaatttgtgt ga 852

<210> SEQ ID NO 375
<211> LENGTH: 885
<212> TYPE: DNA
<213> ORGANISM: Artificial Sequence
<220> FEATURE:
<223> OTHER INFORMATION: DNA sequence of Fc-HRS (2-66) (N-terminal Fc fusion)

<400> SEQUENCE: 375
atgtctgaca aaactcacac atgcccaccg tgcccagcac ctgaactcct gggggggaccg 60 tcagtcttcc tcttcccccc aaaacccaag gacaccctca tgatctcccg gacccctgag 120
gtcacatgcg tggtggtgga cgtgagccac gaagaccctg aggtcaagtt caactggtac 180
gtggacggcg tggaggtgca taatgccaag acaaagccgc gggaggagca gtacaacagc 240
acgtaccgtg tggtcagcgt cctcaccgtc ctgcaccagg actggctgaa tggcaaggag 300
tacaagtgca aggtctccaa caaagccctc ccagccccca tcgagaaaac catctccaaa 360
gccaaagggc agccccgaga accacaggtg tacaccctgc ccccatcccg ggaggagatg 420
accaagaacc aggtcagcct gacctgcctg gtcaaaggct tctatcccag cgacatcgcc 480
gtggagtggg agagcaatgg gcagccggag aacaactaca agaccacgcc tcccgtgctg 540
gactccgacg gctccttctt cctctacagc aagctcaccg tggacaagag caggtggcag 600
caggggaacg tcttctcatg ctccgtgatg cacgaggctc tgcacaacca ctacacgcag 660
aagagcctct ccctgtctcc gggtaaagca gagcgtgcgg cgctggagga gctggtgaaa 720
cttcagggag agcgcgtgcg aggcctcaag cagcagaagg ccagcgccga gctgatcgag 780
gaggaggtgg cgaaactcct gaaactgaag gcacagctgg gtcctgatga aagcaaacag 840
aaatttgtgc tcaaaacccc caagggaacc cgtgattata gttga 885

<210> SEQ ID NO 376
<211> LENGTH: 807
<212> TYPE: DNA
<213> ORGANISM: Artificial Sequence
<220> FEATURE:
<223> OTHER INFORMATION: DNA sequence of HRS(1-40)-Fc (C-terminal Fc fusion)

<400> SEQUENCE: 376
atggcagagc gtgcggcgct ggaggagctg gtgaaacttc agggagagcg cgtgcgaggc 60
ctcaagcagc agaaggccag cgccgagctg atcgaggagg aggtggcgaa actcctgaaa 120
tctgacaaaa ctcacacatg cccaccgtgc ccagcacctg aactcctggg gggaccgtca 180
gtcttcctct tccccccaaa acccaaggac accctcatga tctcccggac ccctgaggtc 240
acatgcgtgg tggtggacgt gagccacgaa gaccctgagg tcaagttcaa ctggtacgtg 300
gacggcgtgg aggtgcataa tgccaagaca aagccgcggg aggagcagta caacagcacg 360
taccgtgtgg tcagcgtcct caccgtcctg caccaggact ggctgaatgg caaggagtac 420
aagtgcaagg tctccaacaa agccctccca gcccccatcg agaaaaccat ctccaaagcc 480
aaagggcagc cccgagaacc acaggtgtac accctgcccc catcccggga ggagatgacc 540
aagaaccagg tcagcctgac ctgcctggtc aaaggcttct atcccagcga catcgccgtg 600
gagtgggaga gcaatgggca gccggagaac aactacaaga ccacgcctcc cgtgctggac 660
tccgacggct ccttcttcct ctacagcaag ctcaccgtgg acaagagcag gtggcagcag 720
gggaacgtct tctcatgctc cgtgatgcac gaggctctgc acaaccacta cacgcagaag 780
agcctctccc tgtctccggg taaatga 807

<210> SEQ ID NO 377
<211> LENGTH: 822
<212> TYPE: DNA
<213> ORGANISM: Artificial Sequence
<220> FEATURE:
<223> OTHER INFORMATION: DNA sequence of HRS(1-45)-Fc (C-terminal Fc fusion)

<400> SEQUENCE: 377
atggcagagc gtgcggcgct ggaggagctg gtgaaacttc agggagagcg cgtgcgaggc 60
ctcaagcagc agaaggccag cgccgagctg atcgaggagg aggtggcgaa actcctgaaa 120
ctgaaggcac agctgtctga caaaactcac acatgcccac cgtgcccagc acctgaactc 180
ctggggggac cgtcagtctt cctcttcccc ccaaaaccca aggacaccct catgatctcc 240
cggacccctg aggtcacatg cgtggtggtg gacgtgagcc acgaagaccc tgaggtcaag 300
ttcaactggt acgtggacgg cgtggaggtg cataatgcca agacaaagcc gcgggaggag 360
cagtacaaca gcacgtaccg tgtggtcagc gtcctcaccg tcctgcacca ggactggctg 420
aatggcaagg agtacaagtg caaggtctcc aacaaagccc tcccagcccc catcgagaaa 480
accatctcca aagccaaagg gcagccccga gaaccacagg tgtacaccct gcccccatcc 540
cgggaggaga tgaccaagaa ccaggtcagc ctgacctgcc tggtcaaagg cttctatccc 600
agcgacatcg ccgtggagtg ggagagcaat gggcagccgg agaacaacta caagaccacg 660
cctcccgtgc tggactccga cggctccttc ttcctctaca gcaagctcac cgtggacaag 720
agcaggtggc agcaggggaa cgtcttctca tgctccgtga tgcacgaggc tctgcacaac 780
cactacacgc agaagagcct ctccctgtct ccgggtaaat ga 822

<210> SEQ ID NO 378
<211> LENGTH: 837
<212> TYPE: DNA
<213> ORGANISM: Artificial Sequence
<220> FEATURE:
<223> OTHER INFORMATION: DNA sequence of HRS(1-50)-Fc (C-terminal Fc fusion)

<400> SEQUENCE: 378
atggcagagc gtgcggcgct ggaggagctg gtgaaacttc agggagagcg cgtgcgaggc 60
ctcaagcagc agaaggccag cgccgagctg atcgaggagg aggtggcgaa actcctgaaa 120
ctgaaggcac agctgggtcc tgatgaaagc tctgacaaaa ctcacacatg cccaccgtgc 180
ccagcacctg aactcctggg gggaccgtca gtcttcctct tccccccaaa acccaaggac 240
accctcatga tctcccggac ccctgaggtc acatgcgtgg tggtggacgt gagccacgaa 300
gaccctgagg tcaagttcaa ctggtacgtg gacggcgtgg aggtgcataa tgccaagaca 360
aagccgcggg aggagcagta caacagcacg taccgtgtgg tcagcgtcct caccgtcctg 420
caccaggact ggctgaatgg caaggagtac aagtgcaagg tctccaacaa agccctccca 480
gcccccatcg agaaaaccat ctccaaagcc aaagggcagc cccgagaacc acaggtgtac 540
accctgcccc catcccggga ggagatgacc aagaaccagg tcagcctgac ctgcctggtc 600
aaaggcttct atcccagcga catcgccgtg gagtgggaga gcaatgggca gccggagaac 660
aactacaaga ccacgcctcc cgtgctggac tccgacggct ccttcttcct ctacagcaag 720
ctcaccgtgg acaagagcag gtggcagcag gggaacgtct tctcatgctc cgtgatgcac 780
gaggctctgc acaaccacta cacgcagaag agcctctccc tgtctccggg taaatga 837

<210> SEQ ID NO 379
<211> LENGTH: 852
<212> TYPE: DNA
<213> ORGANISM: Artificial Sequence
<220> FEATURE:
<223> OTHER INFORMATION: DNA sequence of HRS(1-55)-Fc (C-terminal Fc fusion)

<400> SEQUENCE: 379

```
atggcagagc gtgcggcgct ggaggagctg gtgaaacttc agggagagcg cgtgcgaggc      60
ctcaagcagc agaaggccag cgccgagctg atcgaggagg aggtggcgaa actcctgaaa     120
ctgaaggcac agctgggtcc tgatgaaagc aaacagaaat ttgtgtctga caaaactcac     180
acatgcccac cgtgcccagc acctgaactc ctggggggac cgtcagtctt cctcttcccc     240
ccaaaaccca aggacaccct catgatctcc cggacccctg aggtcacatg cgtggtggtg     300
gacgtgagcc acgaagaccc tgaggtcaag ttcaactggt acgtggacgg cgtggaggtg     360
cataatgcca agacaaagcc gcgggaggag cagtacaaca gcacgtaccg tgtggtcagc     420
gtcctcaccg tcctgcacca ggactggctg aatggcaagg agtacaagtg caaggtctcc     480
aacaaagccc tcccagcccc catcgagaaa accatctcca aagccaaagg gcagccccga     540
gaaccacagg tgtacaccct gcccccatcc cgggaggaga tgaccaagaa ccaggtcagc     600
ctgacctgcc tggtcaaagg cttctatccc agcgacatcg ccgtggagtg ggagagcaat     660
gggcagccgg agaacaacta caagaccacg cctcccgtgc tggactccga cggctccttc     720
ttcctctaca gcaagctcac cgtggacaag agcaggtggc agcaggggaa cgtcttctca     780
tgctccgtga tgcacgaggc tctgcacaac cactacacgc agaagagcct ctccctgtct     840
ccgggtaaat ga                                                         852
```

<210> SEQ ID NO 380
<211> LENGTH: 885
<212> TYPE: DNA
<213> ORGANISM: Artificial Sequence
<220> FEATURE:
<223> OTHER INFORMATION: DNA sequence of HRS(1-66)-Fc (C-terminal Fc fusion)

<400> SEQUENCE: 380

```
atggcagagc gtgcggcgct ggaggagctg gtgaaacttc agggagagcg cgtgcgaggc      60
ctcaagcagc agaaggccag cgccgagctg atcgaggagg aggtggcgaa actcctgaaa     120
ctgaaggcac agctgggtcc tgatgaaagc aaacagaaat ttgtgctcaa aacccccaag     180
ggaacccgtg attatagttc tgacaaaact cacacatgcc caccgtgccc agcacctgaa     240
ctcctggggg gaccgtcagt cttcctcttc cccccaaaac ccaaggacac cctcatgatc     300
tcccggaccc ctgaggtcac atgcgtggtg gtggacgtga gccacgaaga ccctgaggtc     360
aagttcaact ggtacgtgga cggcgtggag gtgcataatg ccaagacaaa gccgcgggag     420
gagcagtaca acagcacgta ccgtgtggtc agcgtcctca ccgtcctgca ccaggactgg     480
ctgaatggca aggagtacaa gtgcaaggtc tccaacaaag ccctcccagc ccccatcgag     540
aaaaccatct ccaaagccaa agggcagccc cgagaaccac aggtgtacac cctgccccca     600
tcccgggagg agatgaccaa gaaccaggtc agcctgacct gcctggtcaa aggcttctat     660
cccagcgaca tcgccgtgga gtgggagagc aatgggcagc cggagaacaa ctacaagacc     720
acgcctcccg tgctggactc cgacggctcc ttcttcctct acagcaagct caccgtggac     780
aagagcaggt ggcagcaggg gaacgtcttc tcatgctccg tgatgcacga ggctctgcac     840
```

aaccactaca cgcagaagag cctctccctg tctccgggta aatga 885

<210> SEQ ID NO 381
<211> LENGTH: 268
<212> TYPE: PRT
<213> ORGANISM: Artificial Sequence
<220> FEATURE:
<223> OTHER INFORMATION: Protein sequence of Fc-HRS (2-40) (N-terminal Fc fusion)

<400> SEQUENCE: 381

Met Ser Asp Lys Thr His Thr Cys Pro Pro Cys Pro Ala Pro Glu Leu
1 5 10 15

Leu Gly Gly Pro Ser Val Phe Leu Phe Pro Pro Lys Pro Lys Asp Thr
20 25 30

Leu Met Ile Ser Arg Thr Pro Glu Val Thr Cys Val Val Val Asp Val
35 40 45

Ser His Glu Asp Pro Glu Val Lys Phe Asn Trp Tyr Val Asp Gly Val
50 55 60

Glu Val His Asn Ala Lys Thr Lys Pro Arg Glu Glu Gln Tyr Asn Ser
65 70 75 80

Thr Tyr Arg Val Val Ser Val Leu Thr Val Leu His Gln Asp Trp Leu
85 90 95

Asn Gly Lys Glu Tyr Lys Cys Lys Val Ser Asn Lys Ala Leu Pro Ala
100 105 110

Pro Ile Glu Lys Thr Ile Ser Lys Ala Lys Gly Gln Pro Arg Glu Pro
115 120 125

Gln Val Tyr Thr Leu Pro Pro Ser Arg Glu Glu Met Thr Lys Asn Gln
130 135 140

Val Ser Leu Thr Cys Leu Val Lys Gly Phe Tyr Pro Ser Asp Ile Ala
145 150 155 160

Val Glu Trp Glu Ser Asn Gly Gln Pro Glu Asn Asn Tyr Lys Thr Thr
165 170 175

Pro Pro Val Leu Asp Ser Asp Gly Ser Phe Phe Leu Tyr Ser Lys Leu
180 185 190

Thr Val Asp Lys Ser Arg Trp Gln Gln Gly Asn Val Phe Ser Cys Ser
195 200 205

Val Met His Glu Ala Leu His Asn His Tyr Thr Gln Lys Ser Leu Ser
210 215 220

Leu Ser Pro Gly Lys Ala Glu Arg Ala Ala Leu Glu Glu Leu Val Lys
225 230 235 240

Leu Gln Gly Glu Arg Val Arg Gly Leu Lys Gln Gln Lys Ala Ser Ala
245 250 255

Glu Leu Ile Glu Glu Glu Val Ala Lys Leu Leu Lys
260 265

<210> SEQ ID NO 382
<211> LENGTH: 273
<212> TYPE: PRT
<213> ORGANISM: Artificial Sequence
<220> FEATURE:
<223> OTHER INFORMATION: Protein sequence of Fc-HRS (2-45) (N-terminal Fc fusion)

<400> SEQUENCE: 382

Met Ser Asp Lys Thr His Thr Cys Pro Pro Cys Pro Ala Pro Glu Leu
1 5 10 15

Leu Gly Gly Pro Ser Val Phe Leu Phe Pro Pro Lys Pro Lys Asp Thr

```
            20                  25                  30

Leu Met Ile Ser Arg Thr Pro Glu Val Thr Cys Val Val Val Asp Val
        35                  40                  45

Ser His Glu Asp Pro Glu Val Lys Phe Asn Trp Tyr Val Asp Gly Val
    50                  55                  60

Glu Val His Asn Ala Lys Thr Lys Pro Arg Glu Glu Gln Tyr Asn Ser
65                  70                  75                  80

Thr Tyr Arg Val Val Ser Val Leu Thr Val Leu His Gln Asp Trp Leu
                85                  90                  95

Asn Gly Lys Glu Tyr Lys Cys Lys Val Ser Asn Lys Ala Leu Pro Ala
            100                 105                 110

Pro Ile Glu Lys Thr Ile Ser Lys Ala Lys Gly Gln Pro Arg Glu Pro
        115                 120                 125

Gln Val Tyr Thr Leu Pro Pro Ser Arg Glu Glu Met Thr Lys Asn Gln
    130                 135                 140

Val Ser Leu Thr Cys Leu Val Lys Gly Phe Tyr Pro Ser Asp Ile Ala
145                 150                 155                 160

Val Glu Trp Glu Ser Asn Gly Gln Pro Glu Asn Asn Tyr Lys Thr Thr
                165                 170                 175

Pro Pro Val Leu Asp Ser Asp Gly Ser Phe Phe Leu Tyr Ser Lys Leu
            180                 185                 190

Thr Val Asp Lys Ser Arg Trp Gln Gln Gly Asn Val Phe Ser Cys Ser
        195                 200                 205

Val Met His Glu Ala Leu His Asn His Tyr Thr Gln Lys Ser Leu Ser
    210                 215                 220

Leu Ser Pro Gly Lys Ala Glu Arg Ala Ala Leu Glu Glu Leu Val Lys
225                 230                 235                 240

Leu Gln Gly Glu Arg Val Arg Gly Leu Lys Gln Gln Lys Ala Ser Ala
                245                 250                 255

Glu Leu Ile Glu Glu Glu Val Ala Lys Leu Leu Lys Leu Lys Ala Gln
            260                 265                 270

Leu


<210> SEQ ID NO 383
<211> LENGTH: 278
<212> TYPE: PRT
<213> ORGANISM: Artificial Sequence
<220> FEATURE:
<223> OTHER INFORMATION: Protein sequence of Fc-HRS (2-50) (N-terminal
      Fc fusion)

<400> SEQUENCE: 383

Met Ser Asp Lys Thr His Thr Cys Pro Pro Cys Pro Ala Pro Glu Leu
1               5                   10                  15

Leu Gly Gly Pro Ser Val Phe Leu Phe Pro Pro Lys Pro Lys Asp Thr
            20                  25                  30

Leu Met Ile Ser Arg Thr Pro Glu Val Thr Cys Val Val Val Asp Val
        35                  40                  45

Ser His Glu Asp Pro Glu Val Lys Phe Asn Trp Tyr Val Asp Gly Val
    50                  55                  60

Glu Val His Asn Ala Lys Thr Lys Pro Arg Glu Glu Gln Tyr Asn Ser
65                  70                  75                  80

Thr Tyr Arg Val Val Ser Val Leu Thr Val Leu His Gln Asp Trp Leu
                85                  90                  95

Asn Gly Lys Glu Tyr Lys Cys Lys Val Ser Asn Lys Ala Leu Pro Ala
```

100 105 110

Pro Ile Glu Lys Thr Ile Ser Lys Ala Lys Gly Gln Pro Arg Glu Pro
115 120 125

Gln Val Tyr Thr Leu Pro Pro Ser Arg Glu Glu Met Thr Lys Asn Gln
130 135 140

Val Ser Leu Thr Cys Leu Val Lys Gly Phe Tyr Pro Ser Asp Ile Ala
145 150 155 160

Val Glu Trp Glu Ser Asn Gly Gln Pro Glu Asn Asn Tyr Lys Thr Thr
165 170 175

Pro Pro Val Leu Asp Ser Asp Gly Ser Phe Phe Leu Tyr Ser Lys Leu
180 185 190

Thr Val Asp Lys Ser Arg Trp Gln Gln Gly Asn Val Phe Ser Cys Ser
195 200 205

Val Met His Glu Ala Leu His Asn His Tyr Thr Gln Lys Ser Leu Ser
210 215 220

Leu Ser Pro Gly Lys Ala Glu Arg Ala Ala Leu Glu Glu Leu Val Lys
225 230 235 240

Leu Gln Gly Glu Arg Val Arg Gly Leu Lys Gln Gln Lys Ala Ser Ala
245 250 255

Glu Leu Ile Glu Glu Glu Val Ala Lys Leu Leu Lys Leu Lys Ala Gln
260 265 270

Leu Gly Pro Asp Glu Ser
275

<210> SEQ ID NO 384
<211> LENGTH: 283
<212> TYPE: PRT
<213> ORGANISM: Artificial Sequence
<220> FEATURE:
<223> OTHER INFORMATION: Protein sequence of Fc-HRS (2-55) (N-terminal
Fc fusion)

<400> SEQUENCE: 384

Met Ser Asp Lys Thr His Thr Cys Pro Pro Cys Pro Ala Pro Glu Leu
1 5 10 15

Leu Gly Gly Pro Ser Val Phe Leu Phe Pro Pro Lys Pro Lys Asp Thr
20 25 30

Leu Met Ile Ser Arg Thr Pro Glu Val Thr Cys Val Val Val Asp Val
35 40 45

Ser His Glu Asp Pro Glu Val Lys Phe Asn Trp Tyr Val Asp Gly Val
50 55 60

Glu Val His Asn Ala Lys Thr Lys Pro Arg Glu Glu Gln Tyr Asn Ser
65 70 75 80

Thr Tyr Arg Val Val Ser Val Leu Thr Val Leu His Gln Asp Trp Leu
85 90 95

Asn Gly Lys Glu Tyr Lys Cys Lys Val Ser Asn Lys Ala Leu Pro Ala
100 105 110

Pro Ile Glu Lys Thr Ile Ser Lys Ala Lys Gly Gln Pro Arg Glu Pro
115 120 125

Gln Val Tyr Thr Leu Pro Pro Ser Arg Glu Glu Met Thr Lys Asn Gln
130 135 140

Val Ser Leu Thr Cys Leu Val Lys Gly Phe Tyr Pro Ser Asp Ile Ala
145 150 155 160

Val Glu Trp Glu Ser Asn Gly Gln Pro Glu Asn Asn Tyr Lys Thr Thr
165 170 175

```
Pro Pro Val Leu Asp Ser Asp Gly Ser Phe Phe Leu Tyr Ser Lys Leu
            180                 185                 190

Thr Val Asp Lys Ser Arg Trp Gln Gln Gly Asn Val Phe Ser Cys Ser
        195                 200                 205

Val Met His Glu Ala Leu His Asn His Tyr Thr Gln Lys Ser Leu Ser
    210                 215                 220

Leu Ser Pro Gly Lys Ala Glu Arg Ala Ala Leu Glu Glu Leu Val Lys
225                 230                 235                 240

Leu Gln Gly Glu Arg Val Arg Gly Leu Lys Gln Gln Lys Ala Ser Ala
                245                 250                 255

Glu Leu Ile Glu Glu Glu Val Ala Lys Leu Leu Lys Leu Lys Ala Gln
            260                 265                 270

Leu Gly Pro Asp Glu Ser Lys Gln Lys Phe Val
        275                 280


<210> SEQ ID NO 385
<211> LENGTH: 294
<212> TYPE: PRT
<213> ORGANISM: Artificial Sequence
<220> FEATURE:
<223> OTHER INFORMATION: Protein sequence of Fc-HRS (2-66) (N-terminal
      Fc fusion)

<400> SEQUENCE: 385

Met Ser Asp Lys Thr His Thr Cys Pro Pro Cys Pro Ala Pro Glu Leu
1               5                   10                  15

Leu Gly Gly Pro Ser Val Phe Leu Phe Pro Pro Lys Pro Lys Asp Thr
            20                  25                  30

Leu Met Ile Ser Arg Thr Pro Glu Val Thr Cys Val Val Val Asp Val
        35                  40                  45

Ser His Glu Asp Pro Glu Val Lys Phe Asn Trp Tyr Val Asp Gly Val
    50                  55                  60

Glu Val His Asn Ala Lys Thr Lys Pro Arg Glu Glu Gln Tyr Asn Ser
65                  70                  75                  80

Thr Tyr Arg Val Val Ser Val Leu Thr Val Leu His Gln Asp Trp Leu
                85                  90                  95

Asn Gly Lys Glu Tyr Lys Cys Lys Val Ser Asn Lys Ala Leu Pro Ala
            100                 105                 110

Pro Ile Glu Lys Thr Ile Ser Lys Ala Lys Gly Gln Pro Arg Glu Pro
        115                 120                 125

Gln Val Tyr Thr Leu Pro Pro Ser Arg Glu Glu Met Thr Lys Asn Gln
    130                 135                 140

Val Ser Leu Thr Cys Leu Val Lys Gly Phe Tyr Pro Ser Asp Ile Ala
145                 150                 155                 160

Val Glu Trp Glu Ser Asn Gly Gln Pro Glu Asn Asn Tyr Lys Thr Thr
                165                 170                 175

Pro Pro Val Leu Asp Ser Asp Gly Ser Phe Phe Leu Tyr Ser Lys Leu
            180                 185                 190

Thr Val Asp Lys Ser Arg Trp Gln Gln Gly Asn Val Phe Ser Cys Ser
        195                 200                 205

Val Met His Glu Ala Leu His Asn His Tyr Thr Gln Lys Ser Leu Ser
    210                 215                 220

Leu Ser Pro Gly Lys Ala Glu Arg Ala Ala Leu Glu Glu Leu Val Lys
225                 230                 235                 240

Leu Gln Gly Glu Arg Val Arg Gly Leu Lys Gln Gln Lys Ala Ser Ala
                245                 250                 255
```

Glu Leu Ile Glu Glu Glu Val Ala Lys Leu Leu Lys Leu Lys Ala Gln
            260                 265                 270

Leu Gly Pro Asp Glu Ser Lys Gln Lys Phe Val Leu Lys Thr Pro Lys
        275                 280                 285

Gly Thr Arg Asp Tyr Ser
    290

<210> SEQ ID NO 386
<211> LENGTH: 268
<212> TYPE: PRT
<213> ORGANISM: Artificial Sequence
<220> FEATURE:
<223> OTHER INFORMATION: Protein sequence of HRS(1-40)-Fc (C-terminal Fc fusion)

<400> SEQUENCE: 386

Met Ala Glu Arg Ala Ala Leu Glu Glu Leu Val Lys Leu Gln Gly Glu
1               5                   10                  15

Arg Val Arg Gly Leu Lys Gln Gln Lys Ala Ser Ala Glu Leu Ile Glu
            20                  25                  30

Glu Glu Val Ala Lys Leu Leu Lys Ser Asp Lys Thr His Thr Cys Pro
        35                  40                  45

Pro Cys Pro Ala Pro Glu Leu Leu Gly Gly Pro Ser Val Phe Leu Phe
    50                  55                  60

Pro Pro Lys Pro Lys Asp Thr Leu Met Ile Ser Arg Thr Pro Glu Val
65                  70                  75                  80

Thr Cys Val Val Val Asp Val Ser His Glu Asp Pro Glu Val Lys Phe
                85                  90                  95

Asn Trp Tyr Val Asp Gly Val Glu Val His Asn Ala Lys Thr Lys Pro
            100                 105                 110

Arg Glu Glu Gln Tyr Asn Ser Thr Tyr Arg Val Val Ser Val Leu Thr
        115                 120                 125

Val Leu His Gln Asp Trp Leu Asn Gly Lys Glu Tyr Lys Cys Lys Val
    130                 135                 140

Ser Asn Lys Ala Leu Pro Ala Pro Ile Glu Lys Thr Ile Ser Lys Ala
145                 150                 155                 160

Lys Gly Gln Pro Arg Glu Pro Gln Val Tyr Thr Leu Pro Pro Ser Arg
                165                 170                 175

Glu Glu Met Thr Lys Asn Gln Val Ser Leu Thr Cys Leu Val Lys Gly
            180                 185                 190

Phe Tyr Pro Ser Asp Ile Ala Val Glu Trp Glu Ser Asn Gly Gln Pro
        195                 200                 205

Glu Asn Asn Tyr Lys Thr Thr Pro Pro Val Leu Asp Ser Asp Gly Ser
    210                 215                 220

Phe Phe Leu Tyr Ser Lys Leu Thr Val Asp Lys Ser Arg Trp Gln Gln
225                 230                 235                 240

Gly Asn Val Phe Ser Cys Ser Val Met His Glu Ala Leu His Asn His
                245                 250                 255

Tyr Thr Gln Lys Ser Leu Ser Leu Ser Pro Gly Lys
            260                 265

<210> SEQ ID NO 387
<211> LENGTH: 273
<212> TYPE: PRT
<213> ORGANISM: Artificial Sequence
<220> FEATURE:
<223> OTHER INFORMATION: Protein sequence of HRS(1-45)-Fc (C-terminal Fc fusion)

<400> SEQUENCE: 387

Met Ala Glu Arg Ala Ala Leu Glu Glu Leu Val Lys Leu Gln Gly Glu
1 5 10 15

Arg Val Arg Gly Leu Lys Gln Gln Lys Ala Ser Ala Glu Leu Ile Glu
20 25 30

Glu Glu Val Ala Lys Leu Leu Lys Leu Lys Ala Gln Leu Ser Asp Lys
35 40 45

Thr His Thr Cys Pro Pro Cys Pro Ala Pro Glu Leu Leu Gly Gly Pro
50 55 60

Ser Val Phe Leu Phe Pro Pro Lys Pro Lys Asp Thr Leu Met Ile Ser
65 70 75 80

Arg Thr Pro Glu Val Thr Cys Val Val Val Asp Val Ser His Glu Asp
85 90 95

Pro Glu Val Lys Phe Asn Trp Tyr Val Asp Gly Val Glu Val His Asn
100 105 110

Ala Lys Thr Lys Pro Arg Glu Glu Gln Tyr Asn Ser Thr Tyr Arg Val
115 120 125

Val Ser Val Leu Thr Val Leu His Gln Asp Trp Leu Asn Gly Lys Glu
130 135 140

Tyr Lys Cys Lys Val Ser Asn Lys Ala Leu Pro Ala Pro Ile Glu Lys
145 150 155 160

Thr Ile Ser Lys Ala Lys Gly Gln Pro Arg Glu Pro Gln Val Tyr Thr
165 170 175

Leu Pro Pro Ser Arg Glu Glu Met Thr Lys Asn Gln Val Ser Leu Thr
180 185 190

Cys Leu Val Lys Gly Phe Tyr Pro Ser Asp Ile Ala Val Glu Trp Glu
195 200 205

Ser Asn Gly Gln Pro Glu Asn Asn Tyr Lys Thr Thr Pro Pro Val Leu
210 215 220

Asp Ser Asp Gly Ser Phe Phe Leu Tyr Ser Lys Leu Thr Val Asp Lys
225 230 235 240

Ser Arg Trp Gln Gln Gly Asn Val Phe Ser Cys Ser Val Met His Glu
245 250 255

Ala Leu His Asn His Tyr Thr Gln Lys Ser Leu Ser Leu Ser Pro Gly
260 265 270

Lys

<210> SEQ ID NO 388
<211> LENGTH: 278
<212> TYPE: PRT
<213> ORGANISM: Artificial Sequence
<220> FEATURE:
<223> OTHER INFORMATION: Protein sequence of HRS(1-50)-Fc (C-terminal Fc fusion)

<400> SEQUENCE: 388

Met Ala Glu Arg Ala Ala Leu Glu Glu Leu Val Lys Leu Gln Gly Glu
1 5 10 15

Arg Val Arg Gly Leu Lys Gln Gln Lys Ala Ser Ala Glu Leu Ile Glu
20 25 30

Glu Glu Val Ala Lys Leu Leu Lys Leu Lys Ala Gln Leu Gly Pro Asp
35 40 45

Glu Ser Ser Asp Lys Thr His Thr Cys Pro Pro Cys Pro Ala Pro Glu
50 55 60

```
Leu Leu Gly Gly Pro Ser Val Phe Leu Phe Pro Pro Lys Pro Lys Asp
65                  70                  75                  80

Thr Leu Met Ile Ser Arg Thr Pro Glu Val Thr Cys Val Val Val Asp
                85                  90                  95

Val Ser His Glu Asp Pro Glu Val Lys Phe Asn Trp Tyr Val Asp Gly
            100                 105                 110

Val Glu Val His Asn Ala Lys Thr Lys Pro Arg Glu Glu Gln Tyr Asn
        115                 120                 125

Ser Thr Tyr Arg Val Val Ser Val Leu Thr Val Leu His Gln Asp Trp
    130                 135                 140

Leu Asn Gly Lys Glu Tyr Lys Cys Lys Val Ser Asn Lys Ala Leu Pro
145                 150                 155                 160

Ala Pro Ile Glu Lys Thr Ile Ser Lys Ala Lys Gly Gln Pro Arg Glu
                165                 170                 175

Pro Gln Val Tyr Thr Leu Pro Pro Ser Arg Glu Glu Met Thr Lys Asn
            180                 185                 190

Gln Val Ser Leu Thr Cys Leu Val Lys Gly Phe Tyr Pro Ser Asp Ile
        195                 200                 205

Ala Val Glu Trp Glu Ser Asn Gly Gln Pro Glu Asn Asn Tyr Lys Thr
    210                 215                 220

Thr Pro Pro Val Leu Asp Ser Asp Gly Ser Phe Phe Leu Tyr Ser Lys
225                 230                 235                 240

Leu Thr Val Asp Lys Ser Arg Trp Gln Gln Gly Asn Val Phe Ser Cys
                245                 250                 255

Ser Val Met His Glu Ala Leu His Asn His Tyr Thr Gln Lys Ser Leu
            260                 265                 270

Ser Leu Ser Pro Gly Lys
        275


<210> SEQ ID NO 389
<211> LENGTH: 283
<212> TYPE: PRT
<213> ORGANISM: Artificial Sequence
<220> FEATURE:
<223> OTHER INFORMATION: Protein sequence of HRS(1-55)-Fc (C-terminal Fc
      fusion)

<400> SEQUENCE: 389

Met Ala Glu Arg Ala Ala Leu Glu Glu Leu Val Lys Leu Gln Gly Glu
1               5                   10                  15

Arg Val Arg Gly Leu Lys Gln Gln Lys Ala Ser Ala Glu Leu Ile Glu
            20                  25                  30

Glu Glu Val Ala Lys Leu Leu Lys Leu Lys Ala Gln Leu Gly Pro Asp
        35                  40                  45

Glu Ser Lys Gln Lys Phe Val Ser Asp Lys Thr His Thr Cys Pro Pro
    50                  55                  60

Cys Pro Ala Pro Glu Leu Leu Gly Gly Pro Ser Val Phe Leu Phe Pro
65                  70                  75                  80

Pro Lys Pro Lys Asp Thr Leu Met Ile Ser Arg Thr Pro Glu Val Thr
                85                  90                  95

Cys Val Val Val Asp Val Ser His Glu Asp Pro Glu Val Lys Phe Asn
            100                 105                 110

Trp Tyr Val Asp Gly Val Glu Val His Asn Ala Lys Thr Lys Pro Arg
        115                 120                 125

Glu Glu Gln Tyr Asn Ser Thr Tyr Arg Val Val Ser Val Leu Thr Val
```

```
    130                 135                 140

Leu His Gln Asp Trp Leu Asn Gly Lys Glu Tyr Lys Cys Lys Val Ser
145                 150                 155                 160

Asn Lys Ala Leu Pro Ala Pro Ile Glu Lys Thr Ile Ser Lys Ala Lys
                165                 170                 175

Gly Gln Pro Arg Glu Pro Gln Val Tyr Thr Leu Pro Pro Ser Arg Glu
            180                 185                 190

Glu Met Thr Lys Asn Gln Val Ser Leu Thr Cys Leu Val Lys Gly Phe
        195                 200                 205

Tyr Pro Ser Asp Ile Ala Val Glu Trp Glu Ser Asn Gly Gln Pro Glu
    210                 215                 220

Asn Asn Tyr Lys Thr Thr Pro Pro Val Leu Asp Ser Asp Gly Ser Phe
225                 230                 235                 240

Phe Leu Tyr Ser Lys Leu Thr Val Asp Lys Ser Arg Trp Gln Gln Gly
                245                 250                 255

Asn Val Phe Ser Cys Ser Val Met His Glu Ala Leu His Asn His Tyr
            260                 265                 270

Thr Gln Lys Ser Leu Ser Leu Ser Pro Gly Lys
        275                 280


<210> SEQ ID NO 390
<211> LENGTH: 294
<212> TYPE: PRT
<213> ORGANISM: Artificial Sequence
<220> FEATURE:
<223> OTHER INFORMATION: Protein sequence of HRS(1-66)-Fc (C-terminal Fc
      fusion)

<400> SEQUENCE: 390

Met Ala Glu Arg Ala Ala Leu Glu Glu Leu Val Lys Leu Gln Gly Glu
1               5                   10                  15

Arg Val Arg Gly Leu Lys Gln Gln Lys Ala Ser Ala Glu Leu Ile Glu
            20                  25                  30

Glu Glu Val Ala Lys Leu Leu Lys Leu Lys Ala Gln Leu Gly Pro Asp
        35                  40                  45

Glu Ser Lys Gln Lys Phe Val Leu Lys Thr Pro Lys Gly Thr Arg Asp
    50                  55                  60

Tyr Ser Ser Asp Lys Thr His Thr Cys Pro Pro Cys Pro Ala Pro Glu
65                  70                  75                  80

Leu Leu Gly Gly Pro Ser Val Phe Leu Phe Pro Pro Lys Pro Lys Asp
                85                  90                  95

Thr Leu Met Ile Ser Arg Thr Pro Glu Val Thr Cys Val Val Val Asp
            100                 105                 110

Val Ser His Glu Asp Pro Glu Val Lys Phe Asn Trp Tyr Val Asp Gly
        115                 120                 125

Val Glu Val His Asn Ala Lys Thr Lys Pro Arg Glu Glu Gln Tyr Asn
    130                 135                 140

Ser Thr Tyr Arg Val Val Ser Val Leu Thr Val Leu His Gln Asp Trp
145                 150                 155                 160

Leu Asn Gly Lys Glu Tyr Lys Cys Lys Val Ser Asn Lys Ala Leu Pro
                165                 170                 175

Ala Pro Ile Glu Lys Thr Ile Ser Lys Ala Lys Gly Gln Pro Arg Glu
            180                 185                 190

Pro Gln Val Tyr Thr Leu Pro Pro Ser Arg Glu Glu Met Thr Lys Asn
        195                 200                 205
```

-continued

```
Gln Val Ser Leu Thr Cys Leu Val Lys Gly Phe Tyr Pro Ser Asp Ile
    210                 215                 220

Ala Val Glu Trp Glu Ser Asn Gly Gln Pro Glu Asn Asn Tyr Lys Thr
225                 230                 235                 240

Thr Pro Pro Val Leu Asp Ser Asp Gly Ser Phe Phe Leu Tyr Ser Lys
                245                 250                 255

Leu Thr Val Asp Lys Ser Arg Trp Gln Gln Gly Asn Val Phe Ser Cys
            260                 265                 270

Ser Val Met His Glu Ala Leu His Asn His Tyr Thr Gln Lys Ser Leu
        275                 280                 285

Ser Leu Ser Pro Gly Lys
    290


<210> SEQ ID NO 391
<211> LENGTH: 24
<212> TYPE: DNA
<213> ORGANISM: Artificial Sequence
<220> FEATURE:
<223> OTHER INFORMATION: primer used to amplify Fc-HRS (2-60)

<400> SEQUENCE: 391

tattctcgag gcagagcgtg cggc                                              24


<210> SEQ ID NO 392
<211> LENGTH: 26
<212> TYPE: DNA
<213> ORGANISM: Artificial Sequence
<220> FEATURE:
<223> OTHER INFORMATION: primer used to amplify Fc-HRS (2-60)

<400> SEQUENCE: 392

gcgcctcgag tcacttgggg gttttg                                            26


<210> SEQ ID NO 393
<211> LENGTH: 37
<212> TYPE: DNA
<213> ORGANISM: Artificial Sequence
<220> FEATURE:
<223> OTHER INFORMATION: primer used to amplify Fc-HRS (2-60)

<400> SEQUENCE: 393

gtgctcaaaa cccccaaggc agagcgtgcg gcgctgg                                37


<210> SEQ ID NO 394
<211> LENGTH: 37
<212> TYPE: DNA
<213> ORGANISM: Artificial Sequence
<220> FEATURE:
<223> OTHER INFORMATION: primer used to amplify Fc-HRS (2-60)

<400> SEQUENCE: 394

ccagcgccgc acgctctgcc ttgggggttt tgagcac                                37


<210> SEQ ID NO 395
<211> LENGTH: 1044
<212> TYPE: DNA
<213> ORGANISM: Artificial Sequence
<220> FEATURE:
<223> OTHER INFORMATION: DNA sequence of Fc-HRS(2-60) HRS(2-60)
      (N-terminal Fc fusion)

<400> SEQUENCE: 395

atgtctgaca aaactcacac atgcccaccg tgcccagcac ctgaactcct ggggggaccg      60
```

-continued

```
tcagtcttcc tcttcccccc aaaacccaag gacaccctca tgatctcccg gacccctgag    120
gtcacatgcg tggtggtgga cgtgagccac gaagaccctg aggtcaagtt caactggtac    180
gtggacggcg tggaggtgca taatgccaag acaaagccgc gggaggagca gtacaacagc    240
acgtaccgtg tggtcagcgt cctcaccgtc ctgcaccagg actggctgaa tggcaaggag    300
tacaagtgca aggtctccaa caaagccctc ccagccccca tcgagaaaac catctccaaa    360
gccaaagggc agccccgaga accacaggtg tacaccctgc ccccatcccg ggaggagatg    420
accaagaacc aggtcagcct gacctgcctg gtcaaaggct tctatcccag cgacatcgcc    480
gtggagtggg agagcaatgg gcagccggag aacaactaca agaccacgcc tcccgtgctg    540
gactccgacg gctccttctt cctctacagc aagctcaccg tggacaagag caggtggcag    600
caggggaacg tcttctcatg ctccgtgatg cacgaggctc tgcacaacca ctacacgcag    660
aagagcctct ccctgtctcc gggtaaagca gagcgtgcgg cgctggagga gctggtgaaa    720
cttcagggag agcgcgtgcg aggcctcaag cagcagaagg ccagcgccga gctgatcgag    780
gaggaggtgg cgaaactcct gaaactgaag gcacagctgg gtcctgatga aagcaaacag    840
aaatttgtgc tcaaaacccc caaggcagag cgtgcggcgc tggaggagct ggtgaaactt    900
cagggagagc gcgtgcgagg cctcaagcag cagaaggcca gcgccgagct gatcgaggag    960
gaggtggcga aactcctgaa actgaaggca cagctgggtc ctgatgaaag caaacagaaa   1020
tttgtgctca aaacccccaa gtga                                          1044
```

```
<210> SEQ ID NO 396
<211> LENGTH: 347
<212> TYPE: PRT
<213> ORGANISM: Artificial Sequence
<220> FEATURE:
<223> OTHER INFORMATION: Protein sequence of Fc-HRS(2-60) HRS(2-60)
      (N-terminal Fc fusion)

<400> SEQUENCE: 396

Met Ser Asp Lys Thr His Thr Cys Pro Pro Cys Pro Ala Pro Glu Leu
1               5                   10                  15

Leu Gly Gly Pro Ser Val Phe Leu Phe Pro Pro Lys Pro Lys Asp Thr
            20                  25                  30

Leu Met Ile Ser Arg Thr Pro Glu Val Thr Cys Val Val Val Asp Val
        35                  40                  45

Ser His Glu Asp Pro Glu Val Lys Phe Asn Trp Tyr Val Asp Gly Val
    50                  55                  60

Glu Val His Asn Ala Lys Thr Lys Pro Arg Glu Glu Gln Tyr Asn Ser
65                  70                  75                  80

Thr Tyr Arg Val Val Ser Val Leu Thr Val Leu His Gln Asp Trp Leu
                85                  90                  95

Asn Gly Lys Glu Tyr Lys Cys Lys Val Ser Asn Lys Ala Leu Pro Ala
            100                 105                 110

Pro Ile Glu Lys Thr Ile Ser Lys Ala Lys Gly Gln Pro Arg Glu Pro
        115                 120                 125

Gln Val Tyr Thr Leu Pro Pro Ser Arg Glu Glu Met Thr Lys Asn Gln
    130                 135                 140

Val Ser Leu Thr Cys Leu Val Lys Gly Phe Tyr Pro Ser Asp Ile Ala
145                 150                 155                 160

Val Glu Trp Glu Ser Asn Gly Gln Pro Glu Asn Asn Tyr Lys Thr Thr
                165                 170                 175

Pro Pro Val Leu Asp Ser Asp Gly Ser Phe Phe Leu Tyr Ser Lys Leu
```

-continued

```
            180                 185                 190

Thr Val Asp Lys Ser Arg Trp Gln Gln Gly Asn Val Phe Ser Cys Ser
        195                 200                 205

Val Met His Glu Ala Leu His Asn His Tyr Thr Gln Lys Ser Leu Ser
    210                 215                 220

Leu Ser Pro Gly Lys Ala Glu Arg Ala Ala Leu Glu Glu Leu Val Lys
225                 230                 235                 240

Leu Gln Gly Glu Arg Val Arg Gly Leu Lys Gln Gln Lys Ala Ser Ala
                245                 250                 255

Glu Leu Ile Glu Glu Glu Val Ala Lys Leu Leu Lys Leu Lys Ala Gln
            260                 265                 270

Leu Gly Pro Asp Glu Ser Lys Gln Lys Phe Val Leu Lys Thr Pro Lys
        275                 280                 285

Ala Glu Arg Ala Ala Leu Glu Glu Leu Val Lys Leu Gln Gly Glu Arg
    290                 295                 300

Val Arg Gly Leu Lys Gln Gln Lys Ala Ser Ala Glu Leu Ile Glu Glu
305                 310                 315                 320

Glu Val Ala Lys Leu Leu Lys Leu Lys Ala Gln Leu Gly Pro Asp Glu
                325                 330                 335

Ser Lys Gln Lys Phe Val Leu Lys Thr Pro Lys
            340                 345
```